(12) United States Patent
Lee et al.

(10) Patent No.: US 11,069,858 B2
(45) Date of Patent: Jul. 20, 2021

(54) AMINE-BASED COMPOUND AND ORGANIC LIGHT EMITTING DEVICE COMPRISING SAME

(71) Applicant: LG CHEM, LTD., Seoul (KR)

(72) Inventors: Sung Jae Lee, Daejeon (KR); Jae Seung Ha, Daejeon (KR); Sung Kil Hong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 238 days.

(21) Appl. No.: 16/322,730

(22) PCT Filed: Sep. 25, 2017

(86) PCT No.: PCT/KR2017/010533
§ 371 (c)(1),
(2) Date: Feb. 1, 2019

(87) PCT Pub. No.: WO2018/056773
PCT Pub. Date: Mar. 29, 2018

(65) Prior Publication Data
US 2019/0198763 A1  Jun. 27, 2019

(30) Foreign Application Priority Data

Sep. 23, 2016 (KR) .................. 10-2016-0122409
Sep. 22, 2017 (KR) .................. 10-2017-0122421

(51) Int. Cl.
*H01L 51/00* (2006.01)
*C07C 211/61* (2006.01)
(Continued)

(52) U.S. Cl.
CPC .......... *H01L 51/006* (2013.01); *C07C 211/61* (2013.01); *C07D 209/88* (2013.01); *C07D 307/91* (2013.01); *C07D 333/76* (2013.01); *H01L 51/0061* (2013.01); *C07C 2603/18* (2017.05); *C07C 2603/26* (2017.05); *C07C 2603/42* (2017.05); *C07C 2603/94* (2017.05); *H01L 51/0054* (2013.01); *H01L 51/0058* (2013.01); *H01L 51/0073* (2013.01); *H01L 51/5016* (2013.01); *H01L 51/5056* (2013.01); *H01L 51/5072* (2013.01);
(Continued)

(58) Field of Classification Search
None
See application file for complete search history.

(56) References Cited

U.S. PATENT DOCUMENTS

2010/0108997 A1  5/2010  Kim et al.
2016/0351816 A1* 12/2016  Kim .................. C09K 11/06
(Continued)

FOREIGN PATENT DOCUMENTS

CN  109314189 A  2/2019
JP  2017-001979 A  1/2017
(Continued)

*Primary Examiner* — Robert S Loewe
(74) *Attorney, Agent, or Firm* — Dentons US LLP

(57) ABSTRACT

The present specification provides a compound of Chemical Formula 1, and an organic light emitting device including the same. The compound of Chemical Formula 1 used in one or more organic material layers of an organic light emitting device provides enhanced efficiency, lowered driving voltage, and increased lifetime of the device.

15 Claims, 1 Drawing Sheet

(51) Int. Cl.
  *C07D 307/91*  (2006.01)
  *C07D 333/76*  (2006.01)
  *C07D 209/88*  (2006.01)
  *H01L 51/50*   (2006.01)

(52) U.S. Cl.
  CPC ...... *H01L 51/5088* (2013.01); *H01L 51/5092* (2013.01); *H01L 51/5096* (2013.01)

(56) References Cited

U.S. PATENT DOCUMENTS

| | | | |
|---|---|---|---|
| 2016/0351817 A1* | 12/2016 | Kim | H01L 51/006 |
| 2016/0351818 A1* | 12/2016 | Kim | H01L 51/0052 |
| 2017/0229649 A1 | 8/2017 | Kato et al. | |
| 2018/0248119 A1 | 8/2018 | Cha et al. | |
| 2019/0296238 A1 | 9/2019 | Cha et al. | |

FOREIGN PATENT DOCUMENTS

| | | | |
|---|---|---|---|
| KR | 10-2010-0041043 A | 4/2010 | |
| KR | 10-2013-0078749 A | 7/2013 | |
| KR | 10-2013-0125575 A | 11/2013 | |
| KR | 10-2015-0012488 A | 2/2015 | |
| KR | 10-1614740 B1 | 4/2016 | |
| KR | 10-2017-0028859 A | 3/2017 | |
| KR | 10-2017-0088313 A | 8/2017 | |

\* cited by examiner

[FIG. 1]
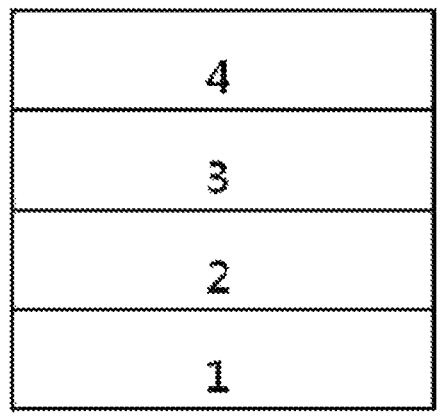
[FIG. 2]
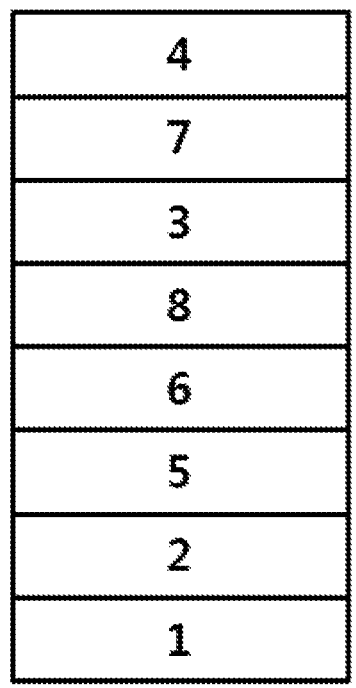

AMINE-BASED COMPOUND AND ORGANIC LIGHT EMITTING DEVICE COMPRISING SAME

This application is a National Stage Application of International Application No. PCT/KR2017/010533 filed on Dec. 21, 2017, and claims priority to and the benefits of Korean Patent Application No. 10-2016-0122409, filed on Sep. 23, 2016, and Korean Patent Application No. 10-2017-0122421, filed on Sep. 25, 2017, the disclosures of which are incorporated herein by reference in their entirety.

TECHNICAL FIELD

This application claims priority to and the benefits of Korean Patent Application No. 10-2016-0122409, filed with the Korean Intellectual Property Office on Sep. 23, 2016, and Korean Patent Application No. 10-2017-0122421, filed with the Korean Intellectual Property Office on Sep. 22, 2017, the entire contents of which are incorporated herein by reference.

The present specification relates to a compound, and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification describes an amine-based compound, and an organic light emitting device including the same.

Technical Solution

One embodiment of the present specification provides a compound represented by the following Chemical Formula 1.

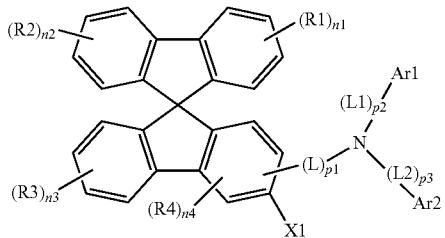

[Chemical Formula 1]

In Chemical Formula 1,

R1 to R4 are the same as or different from each other, and each independently hydrogen; deuterium; a halogen group; a cyano group; a silyl group; a substituted or unsubstituted alkyl group; a substituted or unsubstituted alkoxy group; a substituted or unsubstituted thioalkyl group; a substituted or unsubstituted cycloalkyl group; a substituted or unsubstituted aryl group; or a substituted or unsubstituted heterocyclic group, n1 to n3 are each an integer of 0 to 4, when n1 to n3 are each 2 or greater, substituents in the parentheses are the same as or different from each other, n4 is an integer of 0 to 2, when n4 is 2 or greater, substituents in the parentheses are the same as or different from each other, p1 to p3 are each an integer of 0 to 3, when p1 to p3 are each 2 or greater, substituents in the parentheses are the same as or different from each other, L, L1 and L2 are the same as or different from each other, and each independently a direct bond; a substituted or unsubstituted arylene group; or a substituted or unsubstituted divalent heterocyclic group, Ar1 is triphenylene, Ar2 is hydrogen; deuterium; a substituted or unsubstituted aryl group; a substituted or unsubstituted arylalkyl group; a substituted or unsubstituted arylalkenyl group; or a substituted or unsubstituted heterocyclic group, and X1 is a substituted or unsubstituted aryl group; a substituted or unsubstituted arylalkyl group; a substituted or unsubstituted arylalkenyl group; or a substituted or unsubstituted heterocyclic group.

Another embodiment of the present specification provides an organic light emitting device including a first electrode, a second electrode, and one or more organic material layers disposed between the first electrode and the second electrode, wherein one or more layers of the one or more organic material layers include the compound of Chemical Formula 1.

Advantageous Effects

A compound described in the present specification can be used as a material of an organic material layer of an organic light emitting device. A compound according to at least one embodiment is capable of enhancing efficiency, obtaining a low a driving voltage and/or enhancing a lifetime property in an organic light emitting device. A compound described in the present specification can be used as a material of hole injection, hole transfer, hole injection and hole transfer, electron blocking, light emission, hole blocking, electron transfer or electron injection.

Particularly, when using the compound described in the present specification in a hole injection layer or a hole transfer layer of an organic light emitting device, effects of enhancing efficiency of the organic light emitting device, lowering a driving voltage, and increasing a lifetime of the device can be obtained.

DESCRIPTION OF DRAWINGS

FIG. 1 illustrates an example of an organic light emitting device formed with a substrate (1), an anode (2), a light emitting layer (3) and a cathode (4).

FIG. 2 illustrates an example of an organic light emitting device formed with a substrate (1), an anode (2), a hole injection layer (5), a hole transfer layer (6), an electron blocking layer (8), a light emitting layer (3), a layer carrying out electron transfer and electron injection at the same time (7) and a cathode (4).

1: Substrate
2: Anode
3: Light Emitting Layer
4: Cathode
5: Hole Injection Layer
6: Hole Transfer Layer
7: Layer Carrying Out Electron Transfer and Electron Injection at The Same Time
8: Electron Blocking Layer

MODE FOR DISCLOSURE

Hereinafter, the present specification will be described in more detail.

One embodiment of the present specification provides a compound represented by the following Chemical Formula 1.

[Chemical Formula 1]

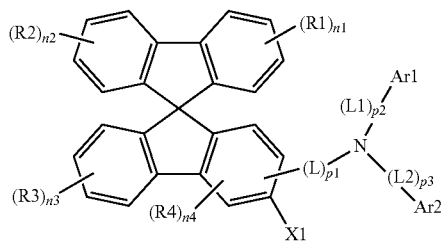

In Chemical Formula 1,

R1 to R4 are the same as or different from each other, and each independently hydrogen; deuterium; a halogen group; a cyano group; a silyl group; a substituted or unsubstituted alkyl group; a substituted or unsubstituted alkoxy group; a substituted or unsubstituted thioalkyl group; a substituted or unsubstituted cycloalkyl group; a substituted or unsubstituted aryl group; or a substituted or unsubstituted heterocyclic group, n1 to n3 are each an integer of 0 to 4, when n1 to n3 are each 2 or greater, substituents in the parentheses are the same as or different from each other, n4 is an integer of 0 to 2, when n4 is 2 or greater, substituents in the parentheses are the same as or different from each other, p1 to p3 are each an integer of 0 to 3, when p1 to p3 are each 2 or greater, substituents in the parentheses are the same as or different from each other, L, L1 and L2 are the same as or different from each other, and each independently a direct bond; a substituted or unsubstituted arylene group; or a substituted or unsubstituted divalent heterocyclic group, Ar1 is triphenylene, Ar2 is hydrogen; deuterium; a substituted or unsubstituted aryl group; a substituted or unsubstituted arylalkyl group; a substituted or unsubstituted arylalkenyl group; or a substituted or unsubstituted heterocyclic group, and X1 is a substituted or unsubstituted aryl group; a substituted or unsubstituted arylalkyl group; a substituted or unsubstituted arylalkenyl group; or a substituted or unsubstituted heterocyclic group.

Examples of the substituents are described below, however, the substituents are not limited thereto.

In the present specification, "------" and

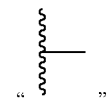

means a bonding site.

In the present specification, the term "substituted or unsubstituted" means being substituted with one or more substituents selected from the group consisting of deuterium; a halogen group; a nitrile group; a nitro group; a hydroxyl group; a carbonyl group; an ester group; an imide group; an amino group; a phosphine oxide group; an alkoxy group; a silyl group; a boron group; an alkyl group; an arylalkyl group; a cycloalkyl group; an alkenyl group; an arylalkenyl group; an aryl group; an amine group; and a heterocyclic group, or being unsubstituted, or being substituted with a substituent linking two or more substituents among the substituents illustrated above, or being unsubstituted. For example, "a substituent linking two or more substituents" may include a biphenyl group.

In other words, a biphenyl group may be an aryl group, or may be interpreted as a substituent linking two phenyl groups.

In the present specification, examples of the halogen group include fluorine, chlorine, bromine or iodine.

In the present specification, the number of carbon atoms of the carbonyl group is not particularly limited, but is preferably from 1 to 40. Specifically, compounds having structures as below may be included, however, the carbonyl group is not limited thereto.

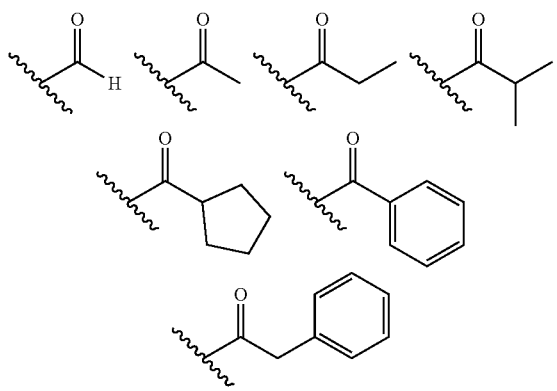

In the present specification, in the ester group, the oxygen of the ester group may be substituted with a linear, branched or cyclic alkyl group having 1 to 40 carbon atoms or an aryl group having 6 to 30 carbon atoms. Specifically, compounds having the following structural formulae may be included, however, the ester group is not limited thereto.

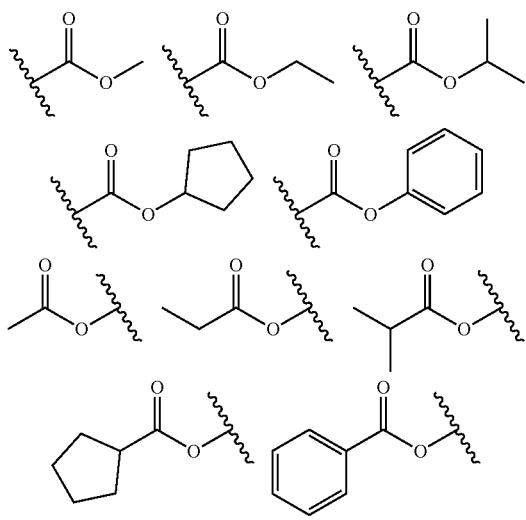

In the present specification, the number of carbon atoms of the imide group is not particularly limited, but is preferably from 1 to 25. Specifically, compounds having structures as below may be included, however, the imide group is not limited thereto.

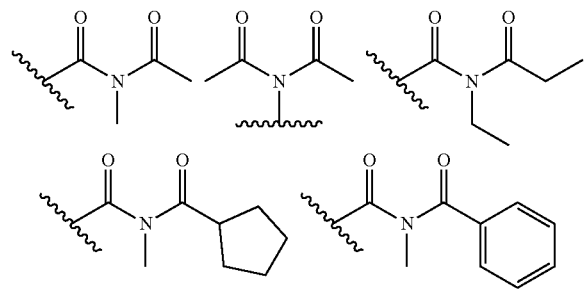

In the present specification, the silyl group may be represented by the chemical formula of —$SiR_aR_bR_c$, and $R_a$, $R_b$ and $R_c$ may each be hydrogen; a substituted or unsubstituted alkyl group; or a substituted or unsubstituted aryl group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by the chemical formula of —$BR_aR_b$, and $R_a$ and $R_b$ may each be hydrogen; a substituted or unsubstituted alkyl group; or a substituted or unsubstituted aryl group. Specific examples of the boron group may include a trimethylboron group, a triethylboron group, a t-butyldimethylboron group, a triphenylboron group, a phenylboron group and the like, but are not limited thereto.

In the present specification, the alkyl group may be linear or branched, and although not particularly limited thereto, the number of carbon atoms is preferably from 1 to 40. According to one embodiment, the number of carbon atoms of the alkyl group is from 1 to 20. According to another embodiment, the number of carbon atoms of the alkyl group is from 1 to 10. According to another embodiment, the number of carbon atoms of the alkyl group is from 1 to 6. Specific examples of the alkyl group may include a methyl group, an ethyl group, a propyl group, an n-propyl group, an isopropyl group, a butyl group, an n-butyl group, an isobutyl group, a tert-butyl group, a sec-butyl group, a pentyl group, an n-pentyl group, an isopentyl group, a neopentyl group, a tert-pentyl group, a hexyl group, an n-hexyl group, heptyl, n-heptyl, cyclopentylmethyl, cyclohexylmethyl, octyl, n-octyl, tert-octyl, n-nonyl and the like, but are not limited thereto.

In the present specification, the alkoxy group may be linear, branched or cyclic. The number of carbon atoms of the alkoxy group is not particularly limited, but is preferably from 1 to 40. Specific examples thereof may include a methoxy group, an ethoxy group, an n-propoxy group, an isopropoxy group, an i-propyloxy group, an n-butoxy group, an isobutoxy group, a tert-butoxy group, a sec-butoxy group, an n-pentyloxy group, a neopentyloxy group, an isopentyloxy group, an n-hexyloxy group, a 3,3-dimethylbutyloxy group, a 2-ethylbutyloxy group, an n-octyloxy group, an n-nonyloxy group, an n-decyloxy group and the like, but are not limited thereto.

The alkyl group, the alkoxy group and other substituents including an alkyl group part described in the present specification include both a linear or a branched form.

In the present specification, the alkenyl group may be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to another embodiment, the number of carbon atoms of the alkenyl group is from 2 to 6. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 40. According to another embodiment, the number of the carbon atoms of the cycloalkyl group is from 3 to 20. According to another embodiment, the number of carbon atoms of the cycloalkyl group is from 3 to 6. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the number of carbon atoms of the amine group is not particularly limited, but is preferably from 1 to 30. The amine group may be substituted with the above-described alkyl group, aryl group, heterocyclic group, alkenyl group, cycloalkyl group, a combination thereof, and the like. Specific examples of the amine group may include a methylamine group, a dimethylamine group, an ethylamine group, a diethylamine group, a phenylamine group, a 9,9-dimethylfluorenylphenylamine group, a pyridylphenylamine group, a diphenylamine group, a phenylpyridylamine group, a naphthylamine group, a biphenylamine group, an nthracenylamine group, a dibenzofuranylphenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, the aryl group is not particularly limited, but preferably has 6 to 60 carbon atoms, and may be a monocyclic aryl group or a multicyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof may include a phenyl group, a biphenyl group, a terphenyl group, a tetraphenyl and the like, but are not limited thereto. Examples of the multicyclic aryl group may include a naphthyl group, an anthracenyl group, a phenanthryl group, a pyrenyl group, a perylenyl group, a chrysenyl group, a triphenylenyl group, a fluorenyl group and the like, but are not limited thereto.

In the present specification, the fluorenyl group may be substituted, and two substituents may bond to each other to form a spiro structure. When the fluorenyl group is substituted,

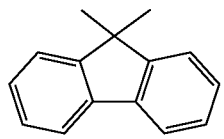

(9,9-dimethylfluorenyl group),

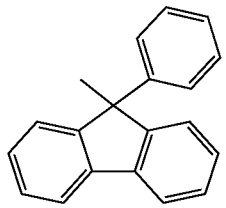 [SMILES: CC1(c2ccccc2)c2ccccc2-c2ccccc21]

(9-methyl-9-phenylfluorenyl group),

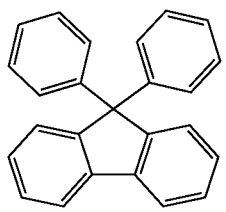 [SMILES: c1ccc(C2(c3ccccc3)c3ccccc3-c3ccccc32)cc1]

(9,9-diphenylfluorenyl group),

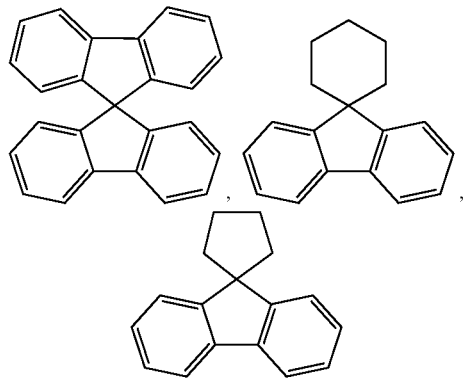

and the like may be included. However, the structure is not limited thereto.

In the present specification, the heterocyclic group is a heterocyclic group including one or more of N, O, P, S, Si and Se as a heteroatom, and although not particularly limited thereto, the number of carbon atoms is preferably from 1 to 60. According to one embodiment, the number of carbon atoms of the heterocyclic group is from 1 to 30. Examples of the heterocyclic group may include a pyridyl group, a pyrrole group, a pyrimidyl group, a pyridazinyl group, a furanyl group, a thiophenyl group, an imidazole group, a pyrazole group, an oxazole group, an isoxazole group, a triazole group, an isothiazole group, a triazole group, an oxadiazole group, a thiadiazole group, dithiazole group, a tetrazole group, a pyranyl group, a thiopyranyl group, a pyrazinyl group, an oxazinyl group, a triazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzothiazole group, a benzoxazole group, a benzimidazole group, a phenazinyl group, an imidazopyridine group, a phenoxazinyl group, a phenanthridine group, a phenanthroline group, a phenothiazine group, an imidazopyridine group, an imidazophenanthridine group, a benzimidazoquinazoline group, a benzimidazophenanthridine group or the like, but are not limited thereto.

In the present specification, the heterocyclic group has 2 to 60 elements forming the ring. In another embodiment, the heterocyclic group has 2 to 40 elements forming the ring. In one embodiment, the heterocyclic group has 2 to 20 elements forming the ring.

In the present specification, descriptions on the aryl group provided above may be applied to the aryl group in the arylalkyl group and the arylalkenyl group.

In the present specification, descriptions on the alkyl group provided above may be applied to the alkyl group in the arylalkyl group and the thioalkyl group.

In the present specification, descriptions on the alkenyl group provided above may be applied to the alkenyl group in the arylalkenyl group.

In the present specification, the meaning of bonding to adjacent groups to form a ring means bonding to adjacent groups to form a substituted or unsubstituted aliphatic hydrocarbon ring; a substituted or unsubstituted aromatic hydrocarbon ring; a substituted or unsubstituted aliphatic heterocyclic group; a substituted or unsubstituted aromatic heterocyclic group; or a fused ring thereof.

In the present specification, the aliphatic hydrocarbon ring means a ring formed only with carbon and hydrogen atoms as a ring that is not aromatic. Specifically, examples of the aliphatic hydrocarbon ring may include cyclopropane, cyclobutane, cyclobutene, cyclopentane, cyclopentene, cyclohexane, cyclohexene, 1,4-cyclohexadiene, cycloheptane, cycloheptene, cyclooctane, cyclooctene and the like, but are not limited thereto.

In one embodiment of the present specification, the compound represented by Chemical Formula 1 may be represented by any one of the following Chemical Formulae 2 to 4.

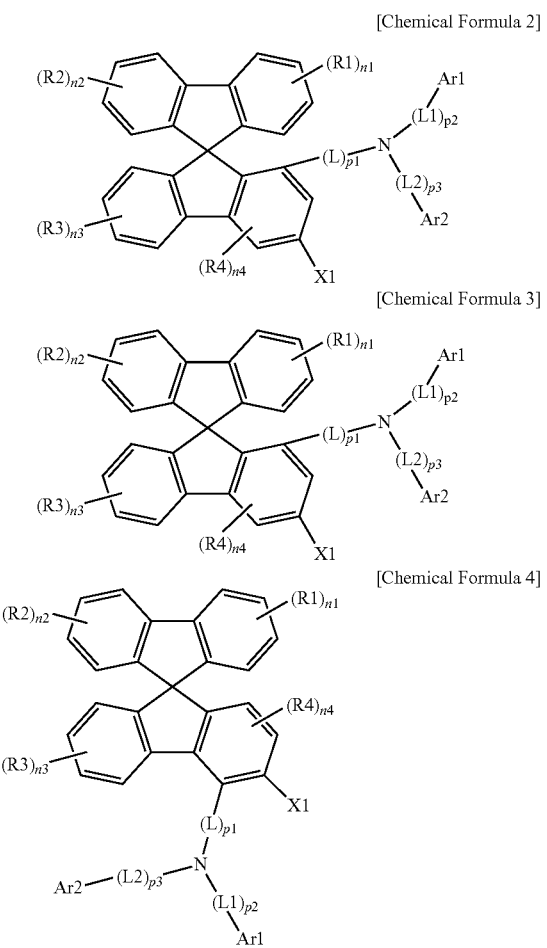

In Chemical Formulae 2 to 4,

R1 to R4, X1, L, L1, L2, n1 to n4, p1 to p3, Ar1 and Ar2 have the same definitions as in Chemical Formula 1.

In one embodiment of the present specification, L1 and L2 are the same as or different from each other, and each independently a direct bond; a substituted or unsubstituted arylene group having 6 to 60 carbon atoms; or a substituted or unsubstituted divalent heterocyclic group having 2 to 60 carbon atoms.

In another embodiment, L1 and L2 are the same as or different from each other, and each independently a direct bond; a substituted or unsubstituted arylene group having 6 to 30 carbon atoms; or a substituted or unsubstituted heterocyclic group having 2 to 30 carbon atoms.

In one embodiment of the present specification, L1 and L2 are the same as or different from each other, and may be each independently a direct bond; or selected from the group consisting of the following structures.

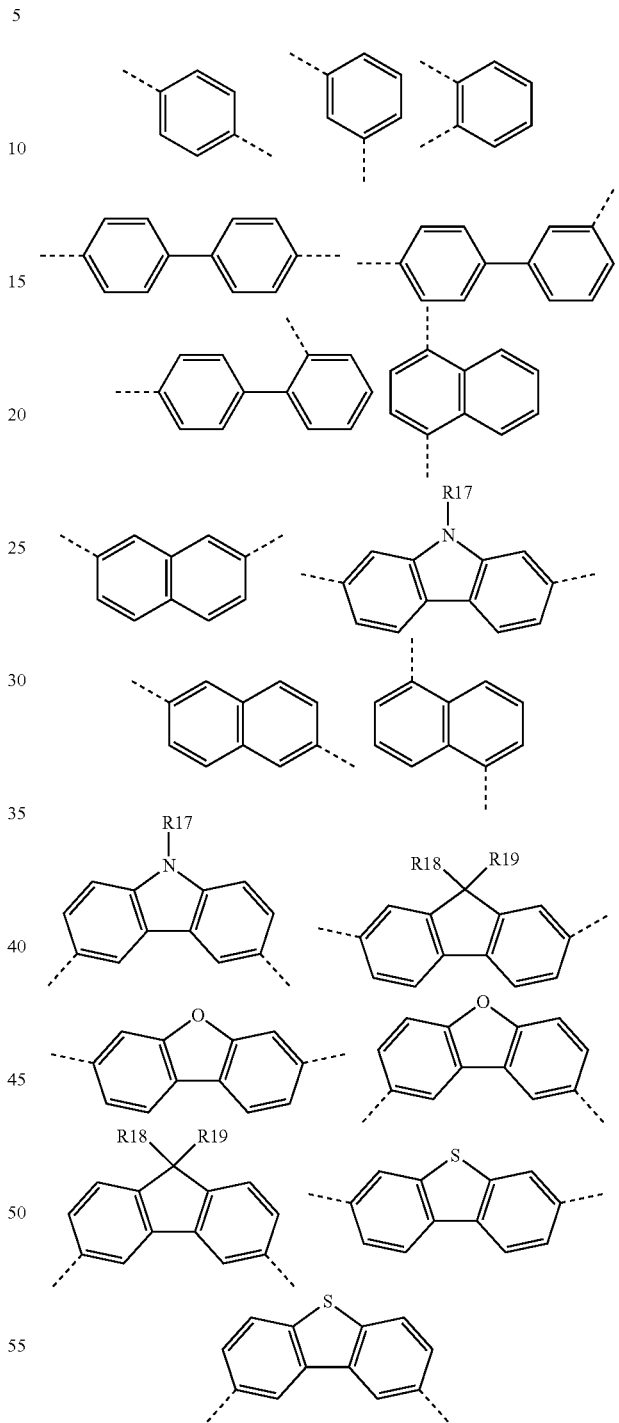

In the structures,

R17 to R19 are the same as or different from each other, and each independently hydrogen; deuterium; a halogen group; a cyano group; a silyl group; a substituted or unsubstituted alkyl group; a substituted or unsubstituted cycloalkyl group; a substituted or unsubstituted alkoxy group; a substituted or unsubstituted alkenyl group; a substituted or unsubstituted boron group; a substituted or unsubstituted amine group; a substituted or unsubstituted aryl group; or a substituted or unsubstituted heterocyclic group.

According to an embodiment of the present specification, L1 and L2 are the same as or different from each other, and each independently a direct bond; or a substituted or unsubstituted phenylene group.

In one embodiment of the present specification, L1 and L2 are the same as or different from each other, and each independently a direct bond; or a phenylene group.

According to one embodiment of the present specification, in Chemical Formula 1, —(L)$_{p1}$—N[(L1)$_{p2}$Ar1][(L2)$_{p3}$Ar2] may be represented by the following Chemical Formula 5.

[Chemical Formula 5]

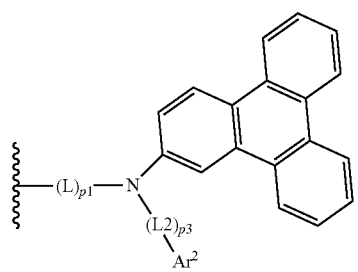

In Chemical Formula 5,
L, L2, p1, p3 and Ar2 have the same definitions as in Chemical Formula 1.

In one embodiment of the present specification, R1 to R4 are the same as or different from each other, and each independently hydrogen; deuterium; a substituted or unsubstituted alkyl group; a substituted or unsubstituted cycloalkyl group; a substituted or unsubstituted aryl group; or a substituted or unsubstituted heterocyclic group.

In one embodiment of the present specification, R1 to R4 are the same as or different from each other, and each independently hydrogen; deuterium; a substituted or unsubstituted alkyl group having 1 to 40 carbon atoms; a substituted or unsubstituted cycloalkyl group having 3 to 60 carbon atoms; a substituted or unsubstituted aryl group having 6 to 60 carbon atoms; or a substituted or unsubstituted heterocyclic group having 2 to 60 carbon atoms.

In one embodiment of the present specification, R1 to R4 are the same as or different from each other, and each independently hydrogen; deuterium; a substituted or unsubstituted alkyl group having 1 to 20 carbon atoms; a substituted or unsubstituted cycloalkyl group having 3 to 30 carbon atoms; a substituted or unsubstituted aryl group having 6 to 30 carbon atoms; or a substituted or unsubstituted heterocyclic group having 2 to 30 carbon atoms.

In one embodiment of the present specification, R1 to R4 are the same as or different from each other, and each independently hydrogen; deuterium; an alkyl group having 1 to 20 carbon atoms unsubstituted or substituted with an aryl group or a heterocyclic group; a cycloalkyl group having 3 to 30 carbon atoms unsubstituted or substituted with an alkyl group, an aryl group or a heterocyclic group; an aryl group having 6 to 30 carbon atoms unsubstituted or substituted with an alkyl group or a heterocyclic group; or a heterocyclic group having 2 to 30 carbon atoms unsubstituted or substituted with an alkyl group or an aryl group.

In one embodiment of the present specification, L is a direct bond or any one selected from the following structures.

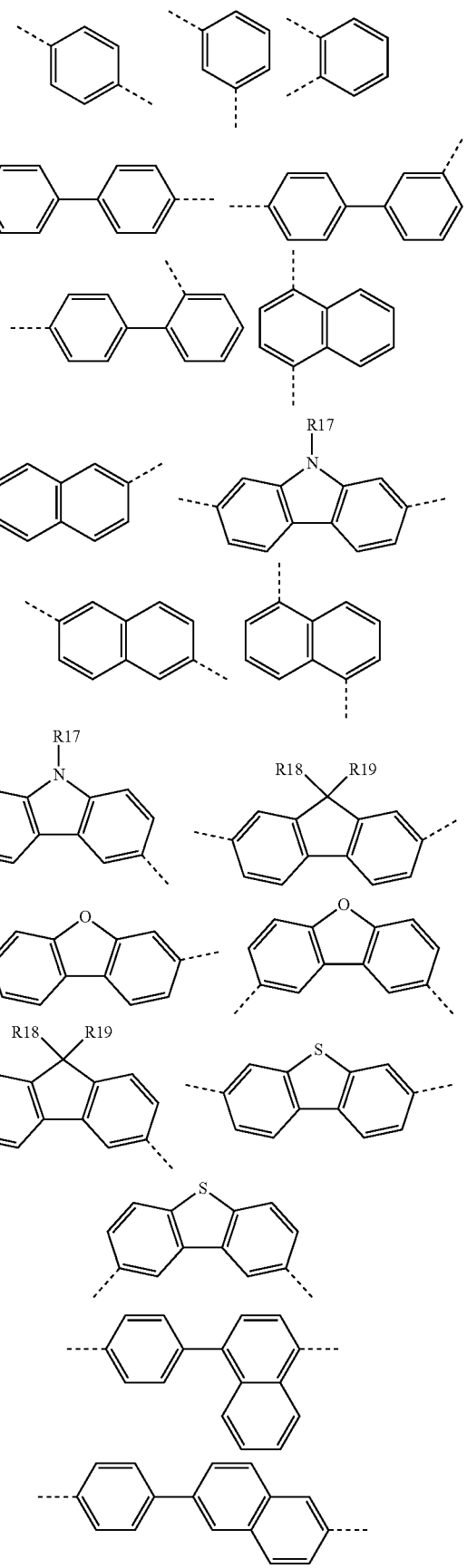

-continued

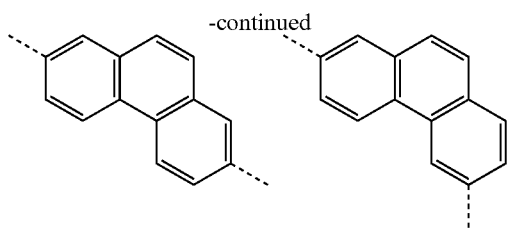

In the structures,

R17 to R19 are the same as or different from each other, and each independently hydrogen; deuterium; a halogen group; a cyano group; a silyl group; a substituted or unsubstituted alkyl group; a substituted or unsubstituted cycloalkyl group; a substituted or unsubstituted alkoxy group; a substituted or unsubstituted alkenyl group; a substituted or unsubstituted boron group; a substituted or unsubstituted amine group; a substituted or unsubstituted aryl group; or a substituted or unsubstituted heterocyclic group.

In one embodiment of the present specification, R17 to R19 are the same as or different from each other, and each independently hydrogen; deuterium; a substituted or unsubstituted alkyl group; a substituted or unsubstituted cycloalkyl group; a substituted or unsubstituted aryl group; or a substituted or unsubstituted heterocyclic group.

In one embodiment of the present specification, R17 to R19 are the same as or different from each other, and each independently hydrogen; deuterium; a substituted or unsubstituted alkyl group having 1 to 40 carbon atoms; a substituted or unsubstituted cycloalkyl group having 3 to 60 carbon atoms; a substituted or unsubstituted aryl group having 6 to 60 carbon atoms; or a substituted or unsubstituted heterocyclic group having 2 to 60 carbon atoms.

In one embodiment of the present specification, R17 to R19 are the same as or different from each other, and each independently hydrogen; deuterium; a substituted or unsubstituted alkyl group having 1 to 20 carbon atoms; a substituted or unsubstituted cycloalkyl group having 3 to 30 carbon atoms; a substituted or unsubstituted aryl group having 6 to 30 carbon atoms; or a substituted or unsubstituted heterocyclic group having 2 to 30 carbon atoms.

In one embodiment of the present specification, R17 to R19 are the same as or different from each other, and each independently hydrogen; deuterium; an alkyl group having 1 to 20 carbon atoms unsubstituted or substituted with an aryl group or a heterocyclic group; a cycloalkyl group having 3 to 30 carbon atoms unsubstituted or substituted with an alkyl group, an aryl group or a heterocyclic group; an aryl group having 6 to 30 carbon atoms unsubstituted or substituted with an alkyl group or a heterocyclic group; or a heterocyclic group having 2 to 30 carbon atoms unsubstituted or substituted with an alkyl group or an aryl group.

According to one embodiment of the present specification, X1 is a substituted or unsubstituted aryl group; or a substituted or unsubstituted heterocyclic group.

In another embodiment, X1 is a substituted or unsubstituted aryl group having 6 to 60 carbon atoms; or a substituted or unsubstituted heterocyclic group having 2 to 60 carbon atoms.

In one embodiment of the present specification, X1 is an aryl group having 6 to 60 carbon atoms unsubstituted or substituted with an aryl group; or a heterocyclic group having 2 to 60 carbon atoms unsubstituted or substituted with an aryl group.

In one embodiment of the present specification, X1 is an aryl group having 6 to 30 carbon atoms unsubstituted or substituted with a phenyl group; or a heterocyclic group having 2 to 40 carbon atoms unsubstituted or substituted with a phenyl group.

According to one embodiment of the present specification, X1 is a phenyl group unsubstituted or substituted with a phenyl group; a biphenyl group unsubstituted or substituted with a phenyl group; a naphthyl group unsubstituted or substituted with a phenyl group; a phenanthrenyl group unsubstituted or substituted with a phenyl group; a triphenylene group unsubstituted or substituted with a phenyl group; a dibenzothiophene group unsubstituted or substituted with a phenyl group; a dibenzofuran group unsubstituted or substituted with a phenyl group; a carbazolyl group unsubstituted or substituted with a phenyl group; or a benzocarbazolyl group unsubstituted or substituted with a phenyl group.

In one embodiment of the present specification, X1 may be selected from the following structures.

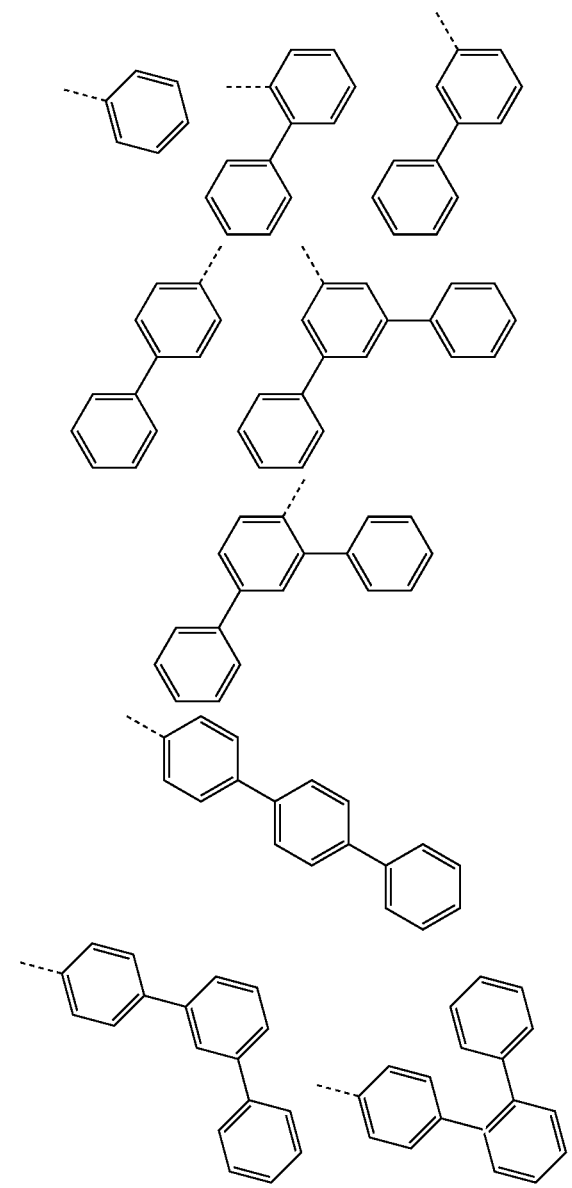

-continued
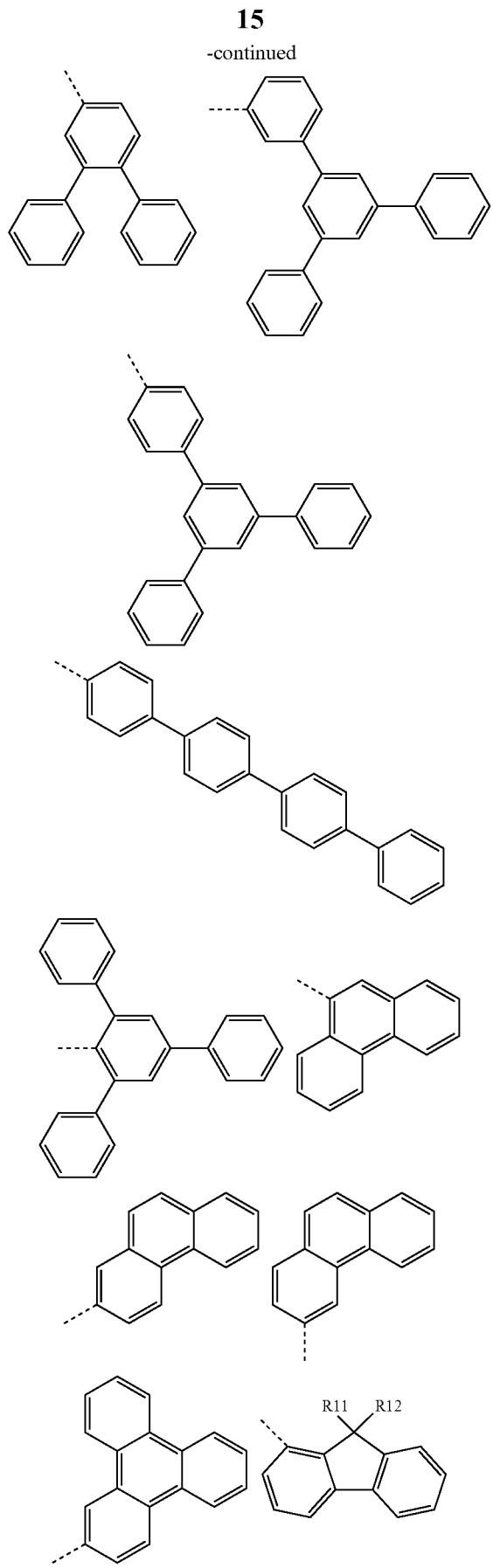
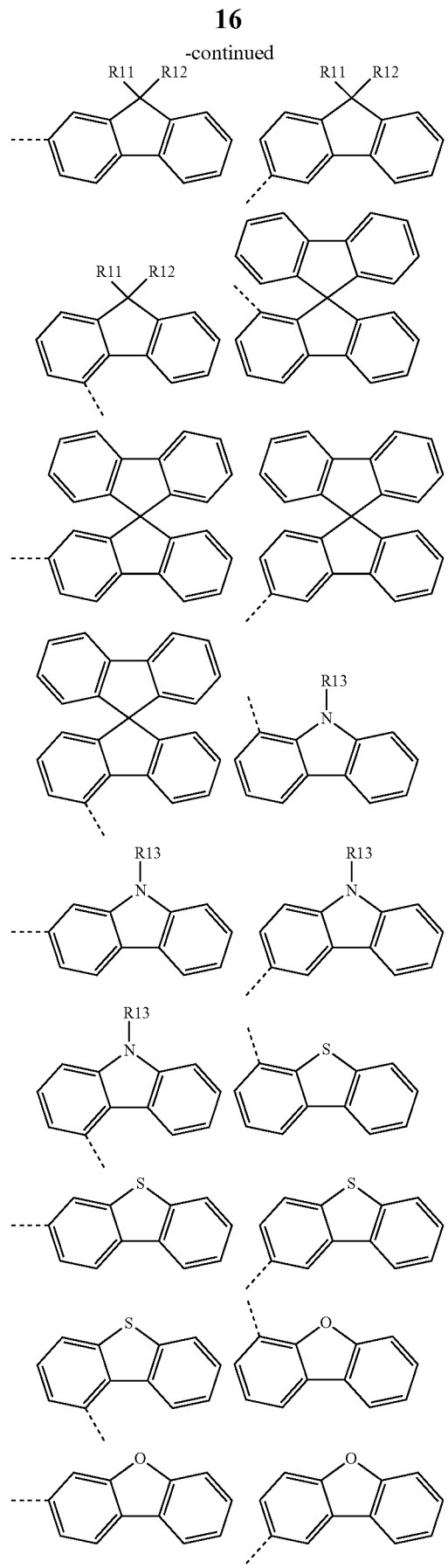

-continued

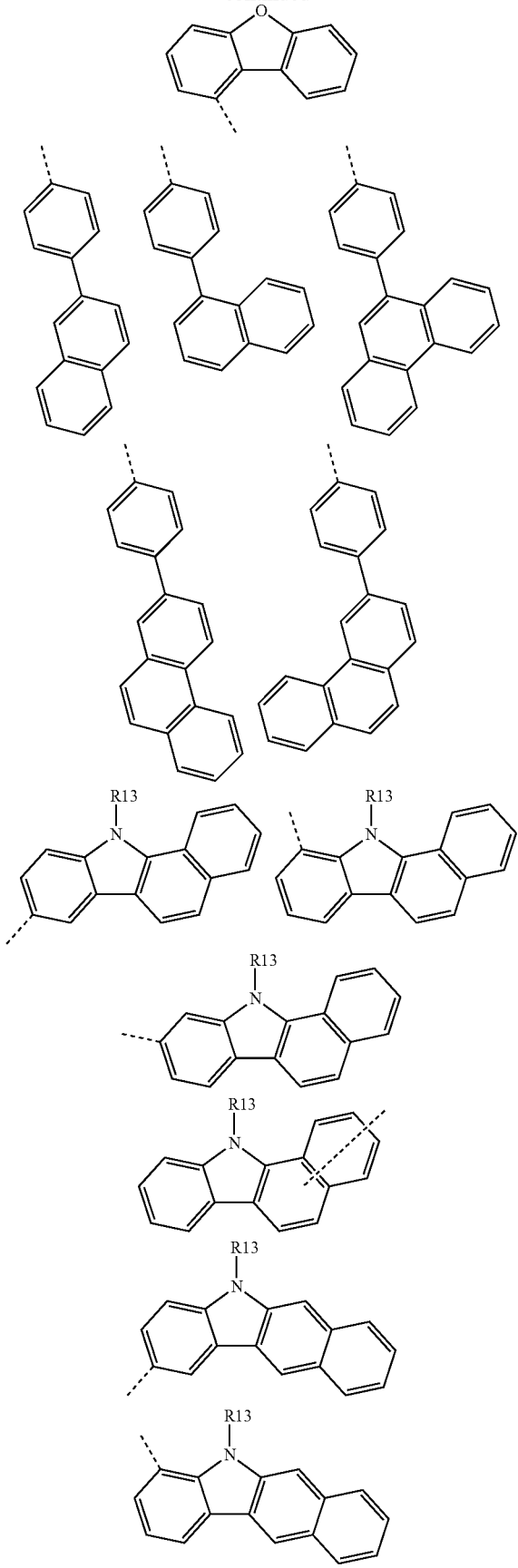

-continued

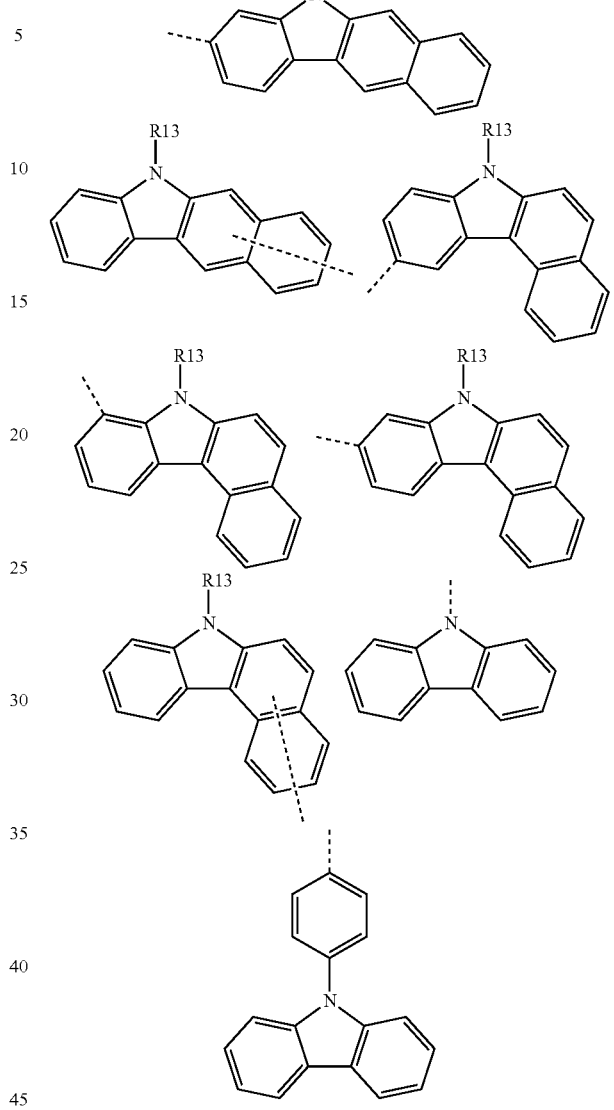

In the structures,

R11 to R13 are the same as or different from each other, and each independently hydrogen; deuterium; a halogen group; a cyano group; a silyl group; a substituted or unsubstituted alkyl group; a substituted or unsubstituted cycloalkyl group; a substituted or unsubstituted alkoxy group; a substituted or unsubstituted alkenyl group; a substituted or unsubstituted boron group; a substituted or unsubstituted amine group; a substituted or unsubstituted aryl group; or a substituted or unsubstituted heterocyclic group, or adjacent substituents bond to each other to form a substituted or unsubstituted ring.

In one embodiment of the present specification, R11 to R13 are the same as or different from each other, and each independently hydrogen; deuterium; a substituted or unsubstituted alkyl group; a substituted or unsubstituted cycloalkyl group; a substituted or unsubstituted aryl group; or a substituted or unsubstituted heterocyclic group.

In one embodiment of the present specification, R11 to R13 are the same as or different from each other, and each independently hydrogen; deuterium; a substituted or unsubstituted alkyl group having 1 to 40 carbon atoms; a substituted or unsubstituted cycloalkyl group having 3 to 60 carbon atoms; a substituted or unsubstituted aryl group having 6 to 60 carbon atoms; or a substituted or unsubstituted heterocyclic group having 2 to 60 carbon atoms.

In one embodiment of the present specification, R11 to R13 are the same as or different from each other, and each independently hydrogen; deuterium; a substituted or unsubstituted alkyl group having 1 to 20 carbon atoms; a substituted or unsubstituted cycloalkyl group having 3 to 30 carbon atoms; a substituted or unsubstituted aryl group having 6 to 30 carbon atoms; or a substituted or unsubstituted heterocyclic group having 2 to 30 carbon atoms.

In one embodiment of the present specification, R11 to R13 are the same as or different from each other, and each independently hydrogen; deuterium; an alkyl group having 1 to 20 carbon atoms unsubstituted or substituted with an aryl group or a heterocyclic group; a cycloalkyl group having 3 to 30 carbon atoms unsubstituted or substituted with an alkyl group, an aryl group or a heterocyclic group; an aryl group having 6 to 30 carbon atoms unsubstituted or substituted with an alkyl group or a heterocyclic group; or a heterocyclic group having 2 to 30 carbon atoms unsubstituted or substituted with an alkyl group or an aryl group.

In one embodiment of the present specification, R11 and R12 may bond to each other to form a substituted or unsubstituted ring.

According to one embodiment of the present specification, R11 and R12 may bond to each other to form a substituted or unsubstituted hydrocarbon ring.

According to another embodiment, R11 and R12 may bond to each other to form cyclopentane or cyclohexane.

In one embodiment of the present specification, Ar2 is hydrogen; deuterium; a substituted or unsubstituted aryl group; or a substituted or unsubstituted heterocyclic group.

According to one embodiment of the present specification, Ar2 is hydrogen; deuterium; a substituted or unsubstituted aryl group having 6 to 60 carbon atoms; or a substituted or unsubstituted heterocyclic group having 2 to 40 carbon atoms.

In one embodiment of the present specification, Ar2 is hydrogen; deuterium; a substituted or unsubstituted phenyl group; a substituted or unsubstituted biphenyl group; a substituted or unsubstituted terphenyl group; a substituted or unsubstituted naphthyl group; a substituted or unsubstituted phenanthrenyl group; a substituted or unsubstituted triphenyl group; a substituted or unsubstituted fluorenyl group; a substituted or unsubstituted carbazolyl group; or a substituted or unsubstituted benzocarbazolyl group.

In one embodiment of the present specification, Ar2 may be selected from the following structures.

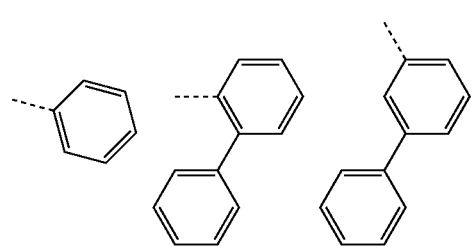

-continued

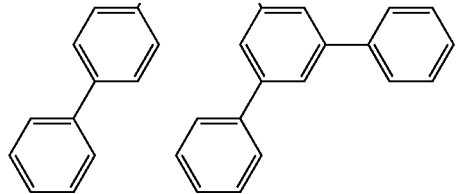

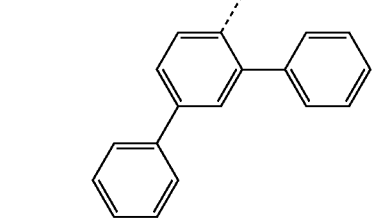

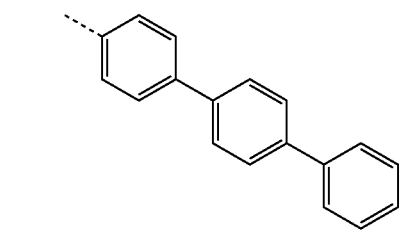

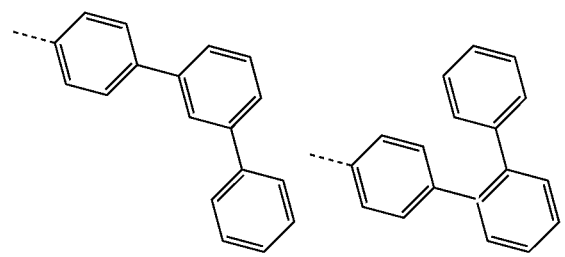

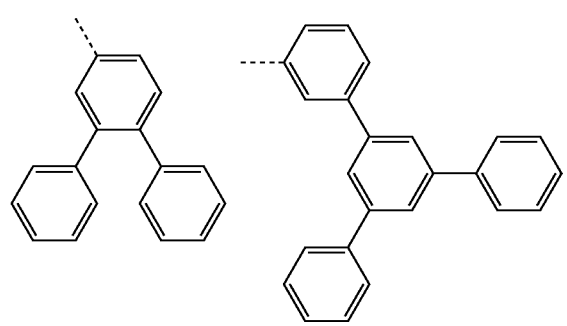

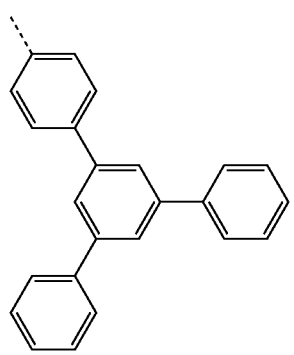

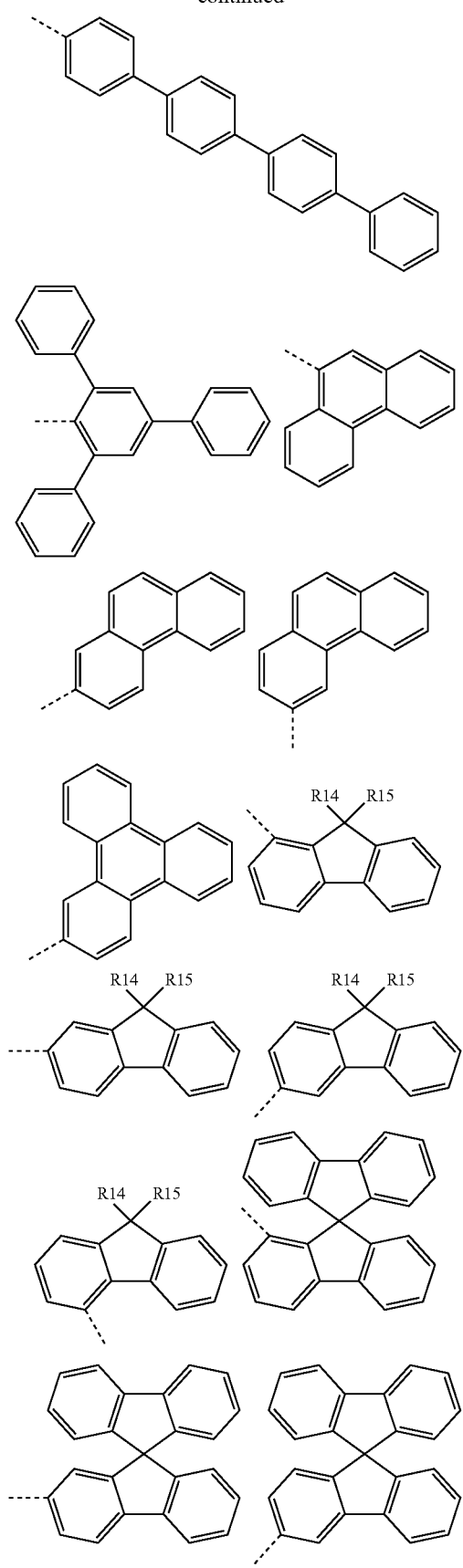
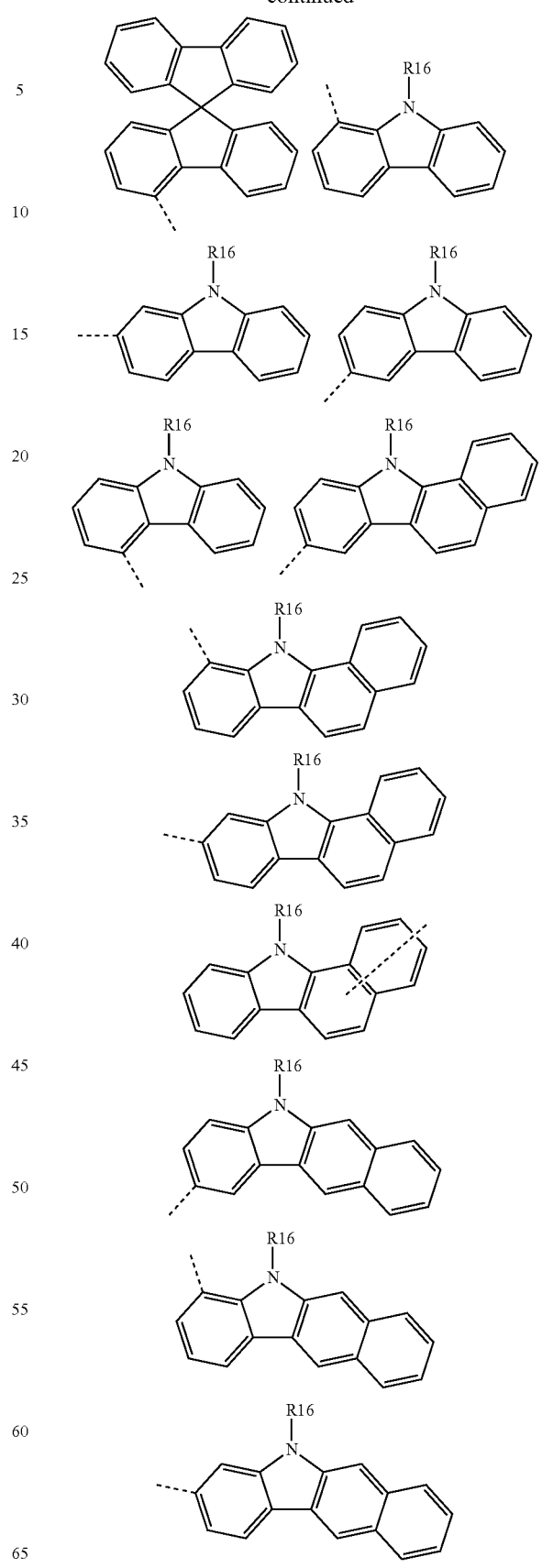

-continued

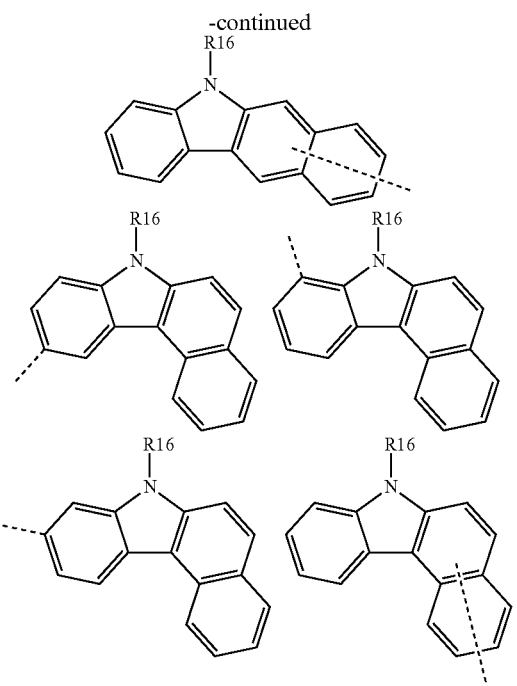

In the structures,

R14 to R16 are the same as or different from each other, and each independently hydrogen; deuterium; a halogen group; a cyano group; a silyl group; a substituted or unsubstituted alkyl group; a substituted or unsubstituted cycloalkyl group; a substituted or unsubstituted alkoxy group; a substituted or unsubstituted alkenyl group; a substituted or unsubstituted boron group; a substituted or unsubstituted amine group; a substituted or unsubstituted aryl group; or a substituted or unsubstituted heterocyclic group, or adjacent substituents bond to each other to form a substituted or unsubstituted ring.

In one embodiment of the present specification, R14 to R16 are the same as or different from each other, and each independently hydrogen; deuterium; a substituted or unsubstituted alkyl group; a substituted or unsubstituted cycloalkyl group; a substituted or unsubstituted aryl group; or a substituted or unsubstituted heterocyclic group.

In one embodiment of the present specification, R14 to R16 are the same as or different from each other, and each independently hydrogen; deuterium; a substituted or unsubstituted alkyl group having 1 to 40 carbon atoms; a substituted or unsubstituted cycloalkyl group having 3 to 60 carbon atoms; a substituted or unsubstituted aryl group having 6 to 60 carbon atoms; or a substituted or unsubstituted heterocyclic group having 2 to 60 carbon atoms.

In one embodiment of the present specification, R14 to R16 are the same as or different from each other, and each independently hydrogen; deuterium; a substituted or unsubstituted alkyl group having 1 to 20 carbon atoms; a substituted or unsubstituted cycloalkyl group having 3 to 30 carbon atoms; a substituted or unsubstituted aryl group having 6 to 30 carbon atoms; or a substituted or unsubstituted heterocyclic group having 2 to 30 carbon atoms.

In one embodiment of the present specification, R14 to R16 are the same as or different from each other, and each independently hydrogen; deuterium; an alkyl group having 1 to 20 carbon atoms unsubstituted or substituted with an aryl group or a heterocyclic group; a cycloalkyl group having 3 to 30 carbon atoms unsubstituted or substituted with an alkyl group, an aryl group or a heterocyclic group; an aryl group having 6 to 30 carbon atoms unsubstituted or substituted with an alkyl group or a heterocyclic group; or a heterocyclic group having 2 to 30 carbon atoms unsubstituted or substituted with an alkyl group or an aryl group.

In one embodiment of the present specification, R14 and R15 may bond to each other to form a substituted or unsubstituted hydrocarbon ring.

According to one embodiment of the present specification, R14 and R15 may bond to each other to form cyclopentane or cyclohexane.

In one embodiment of the present specification, the compound of Chemical Formula 1 may be selected from the following structures.

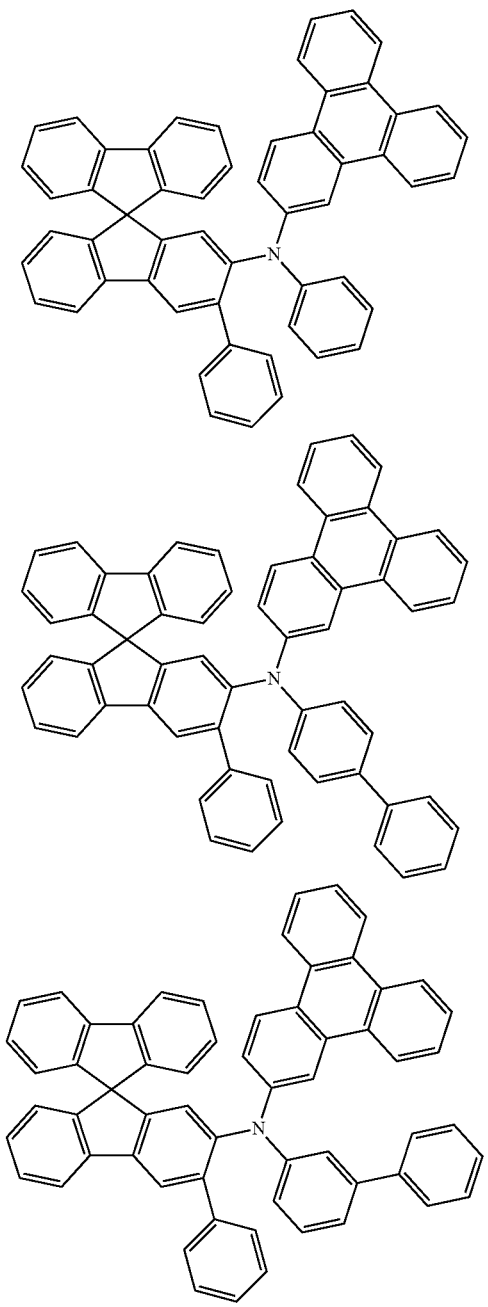

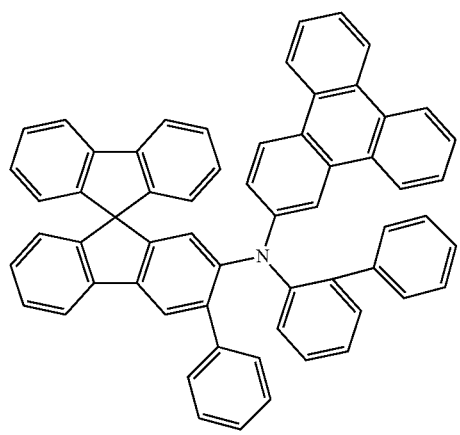
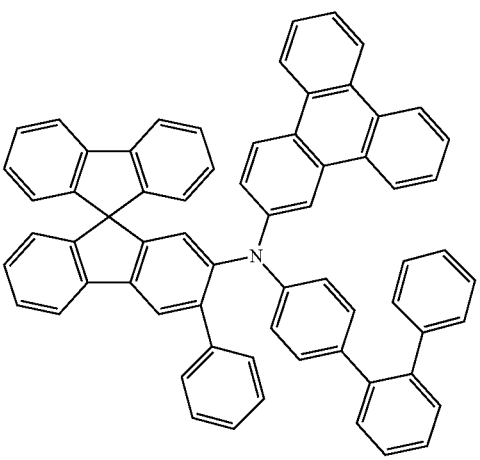
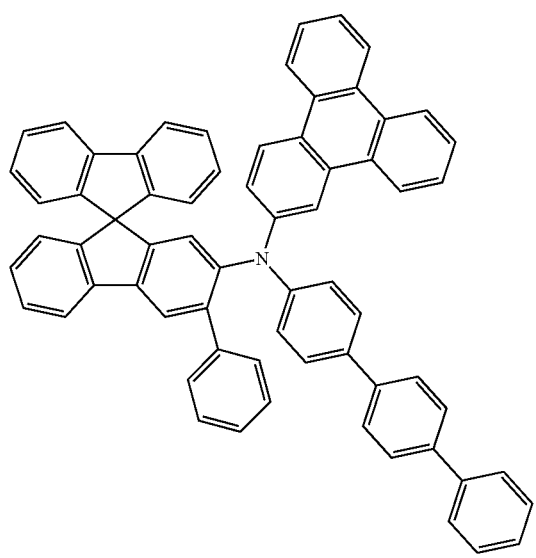
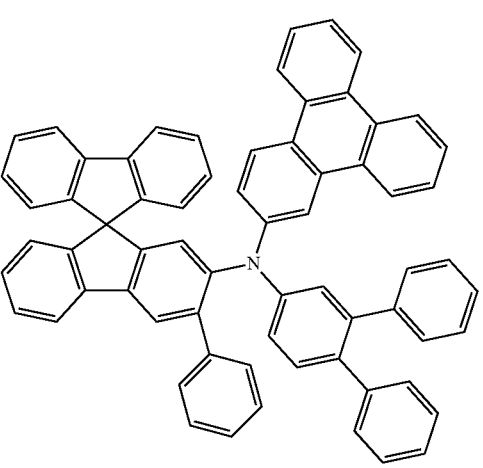
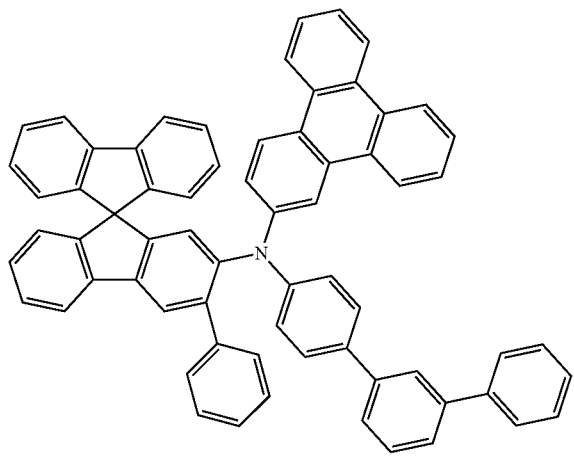
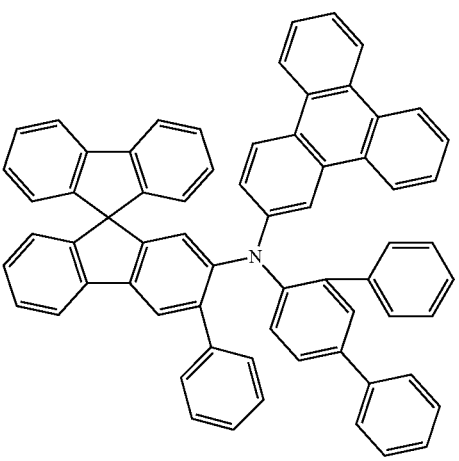

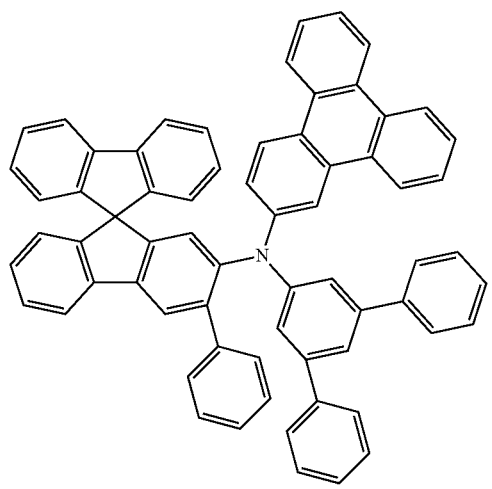
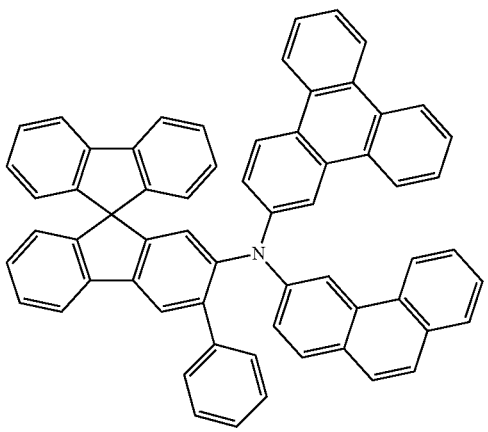
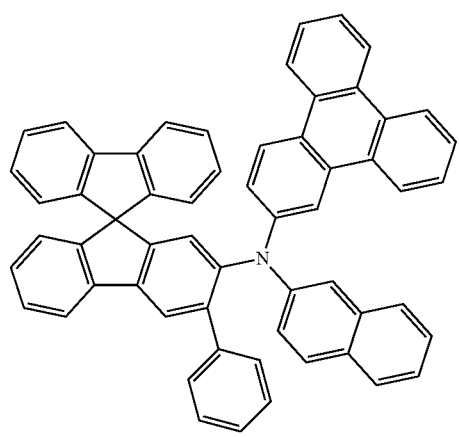
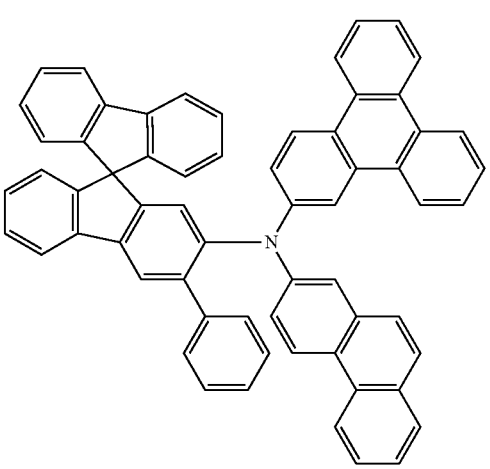
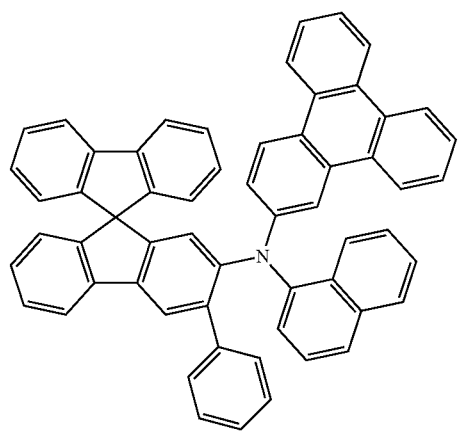
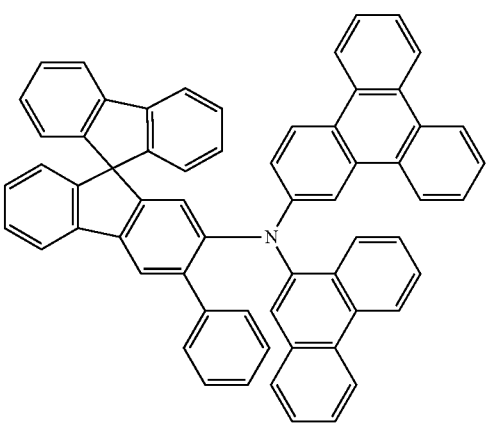

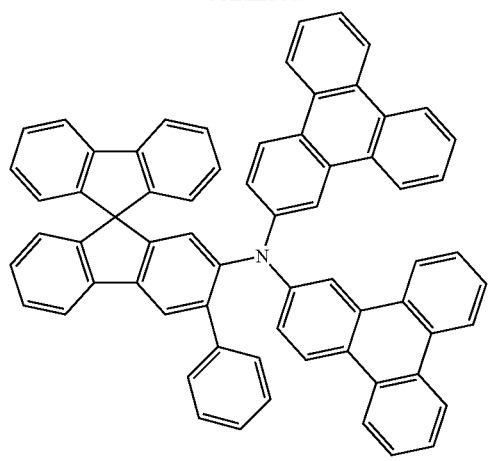
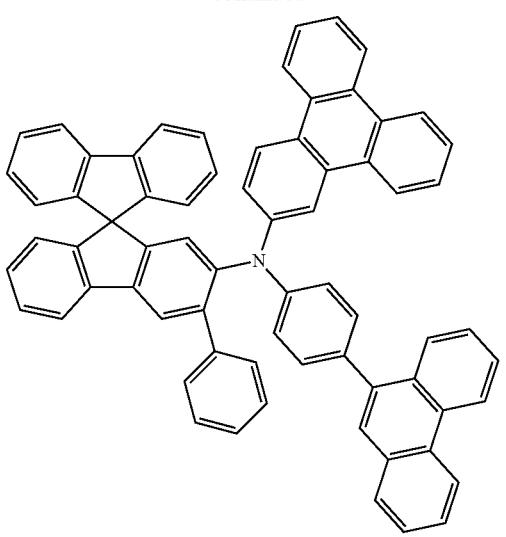
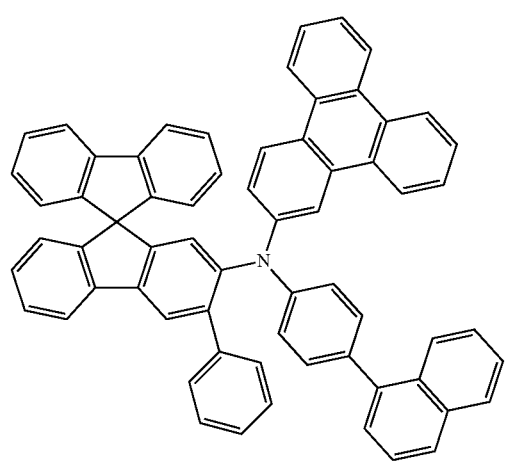
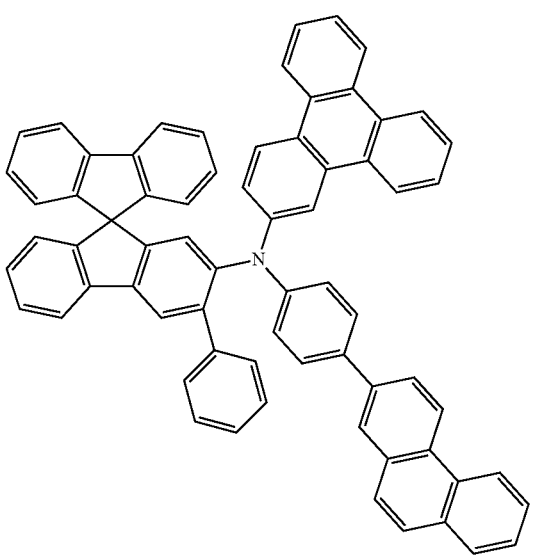
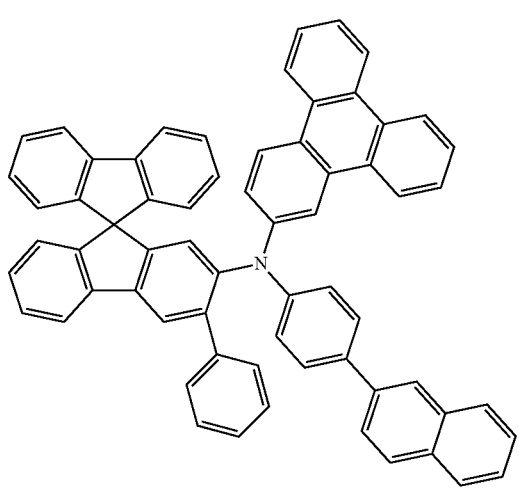
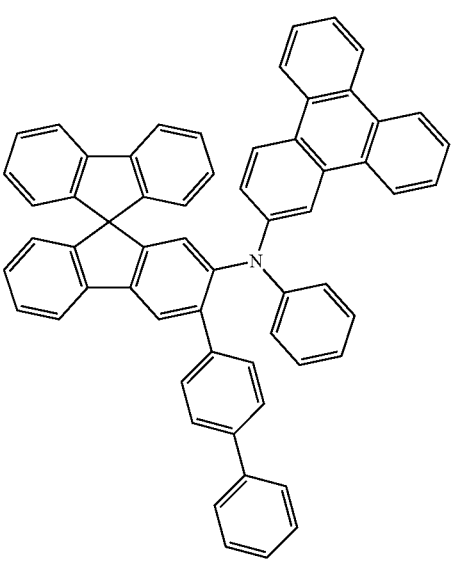

-continued
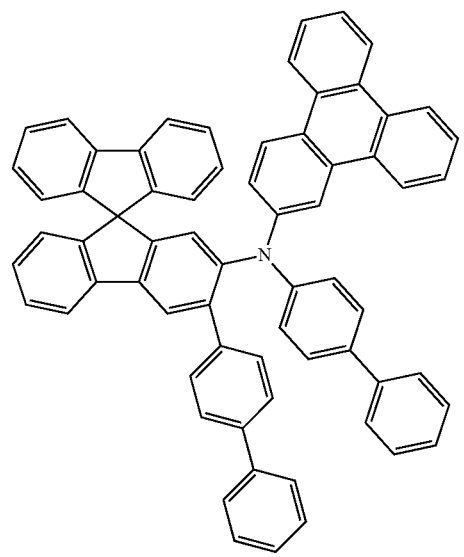
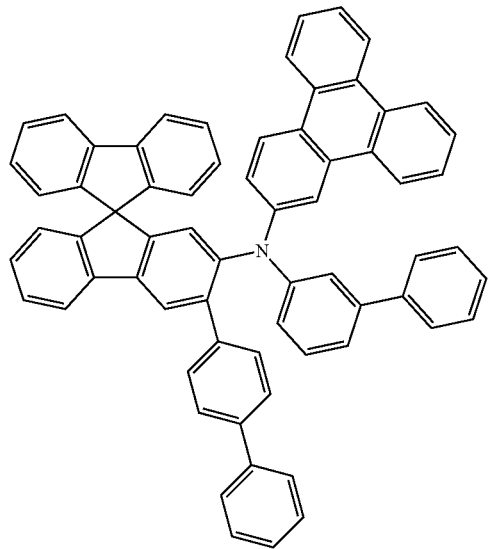
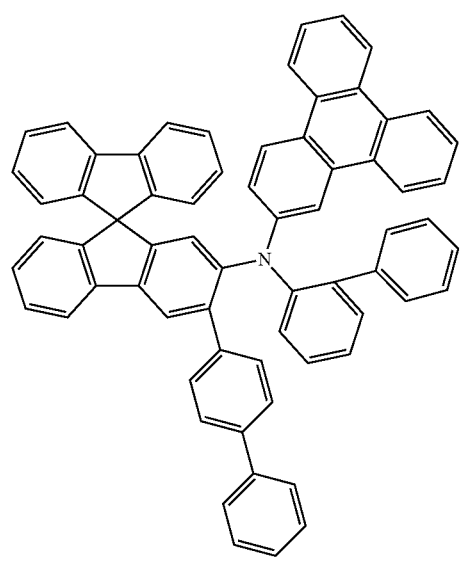
-continued

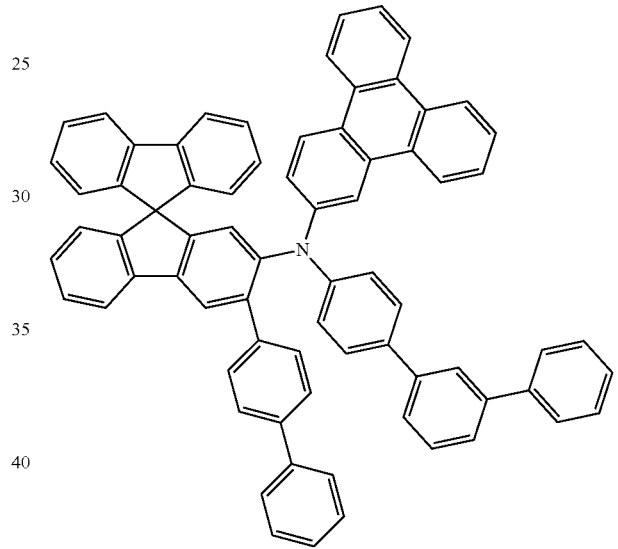
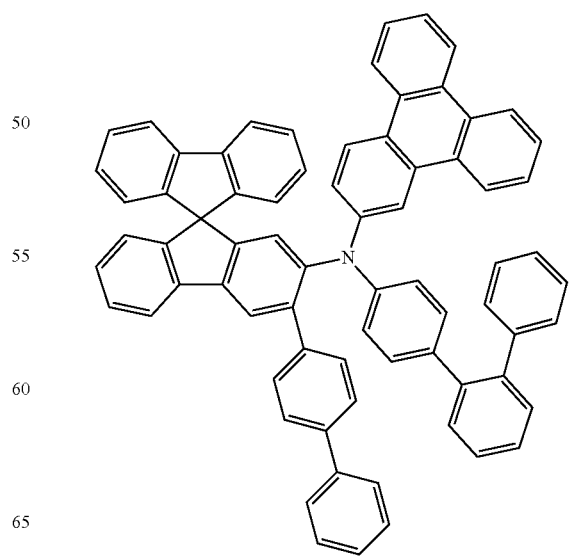

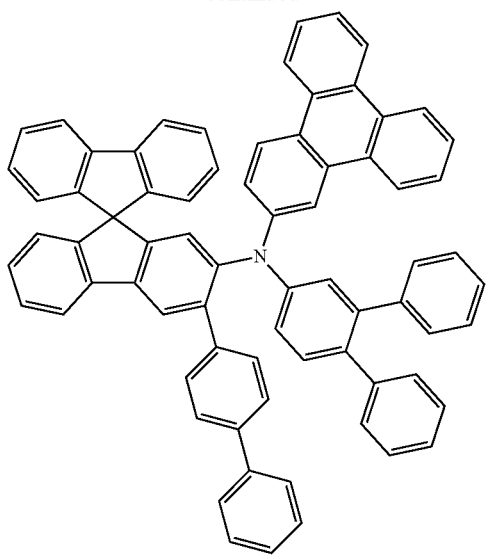
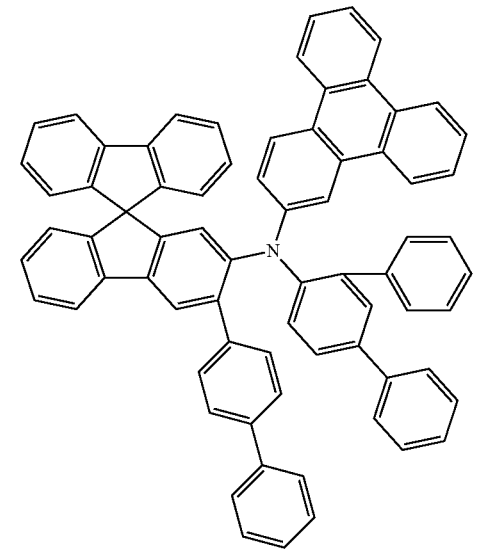
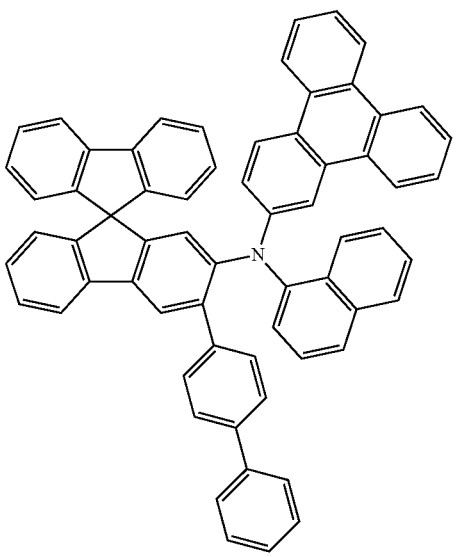
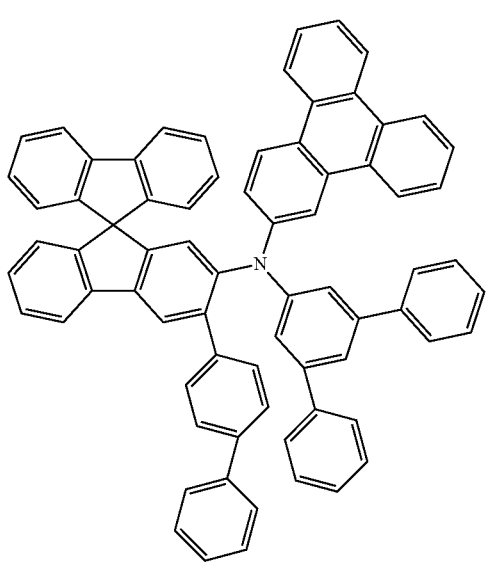
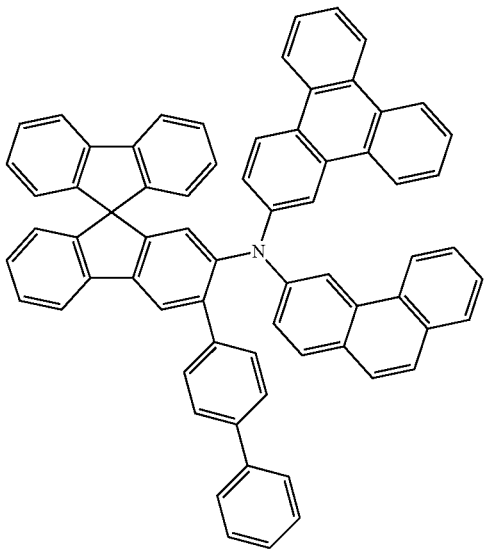

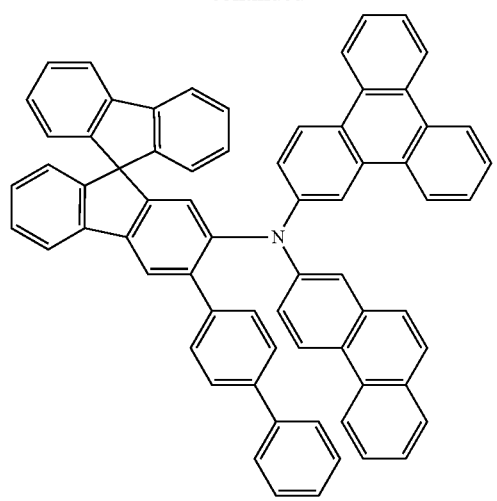
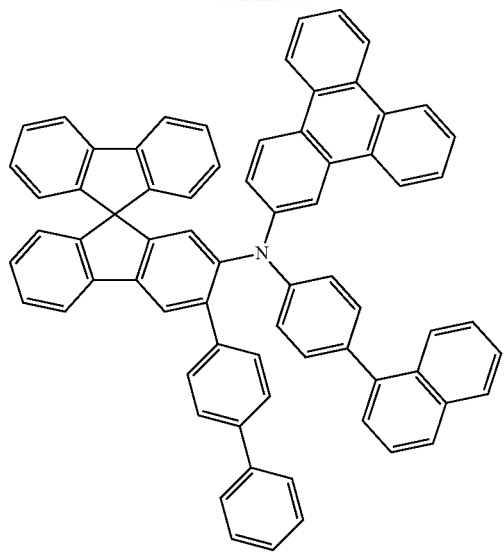
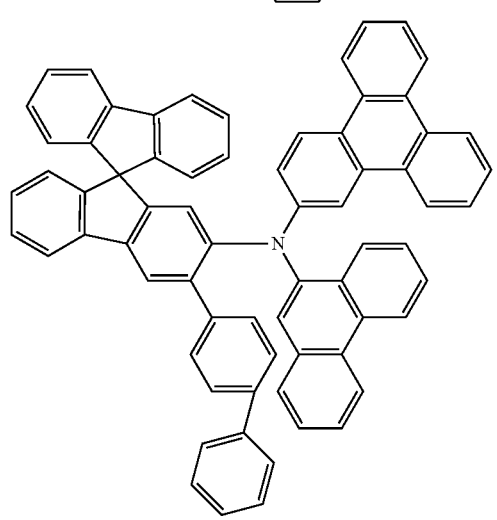
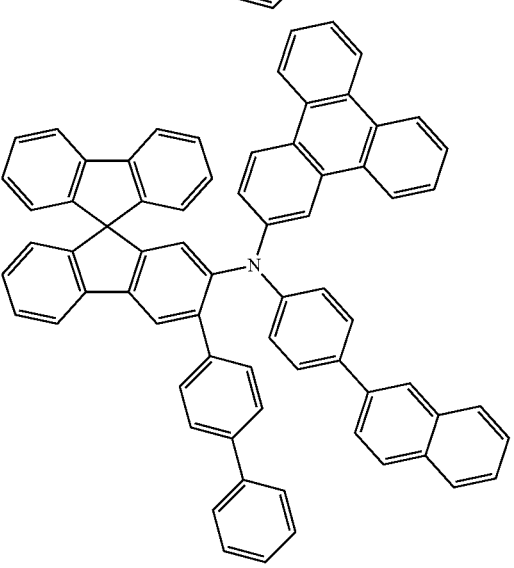
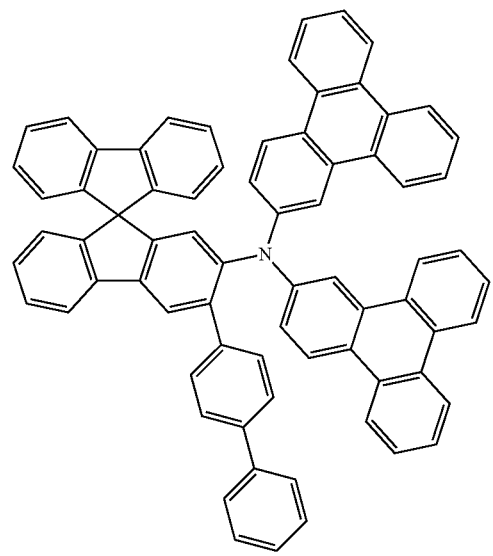
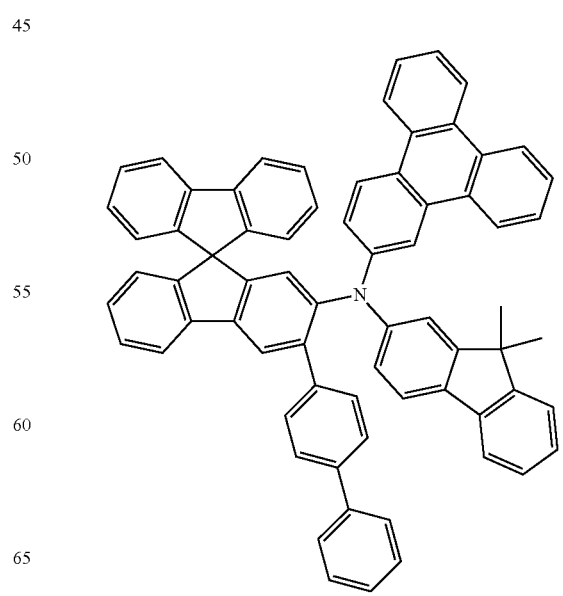

37
-continued
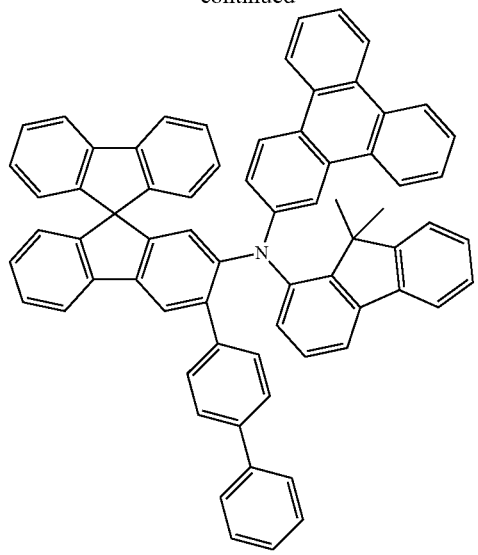
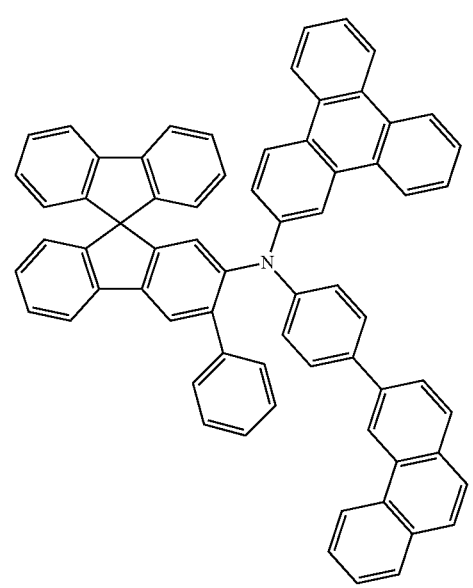
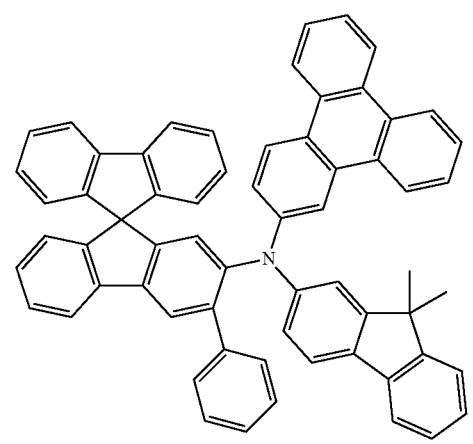
38
-continued
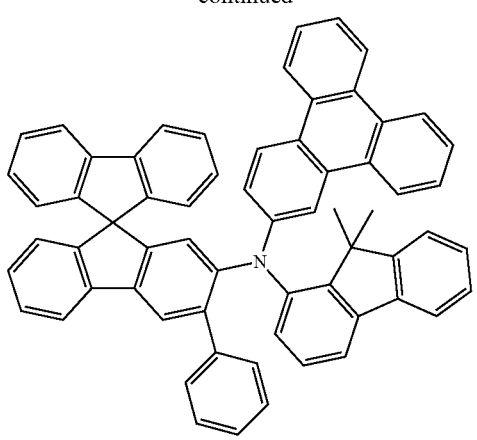
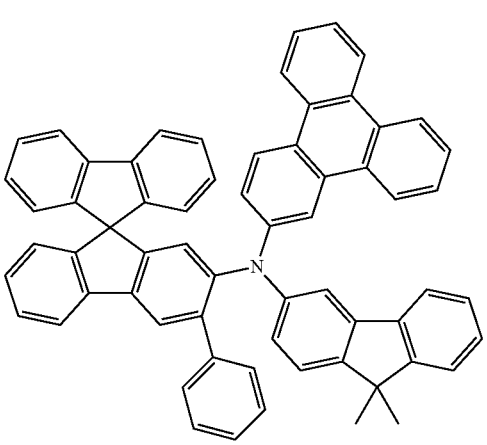
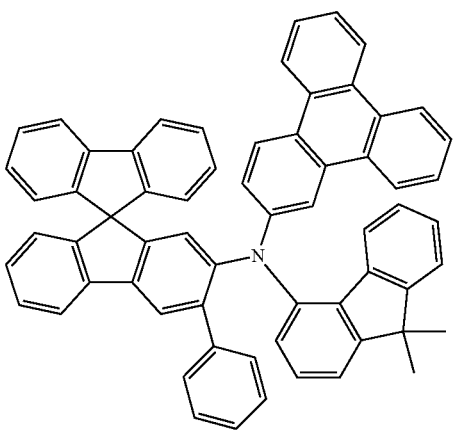

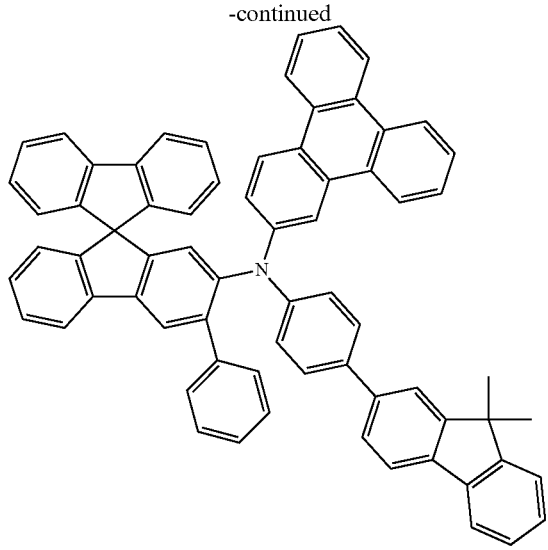
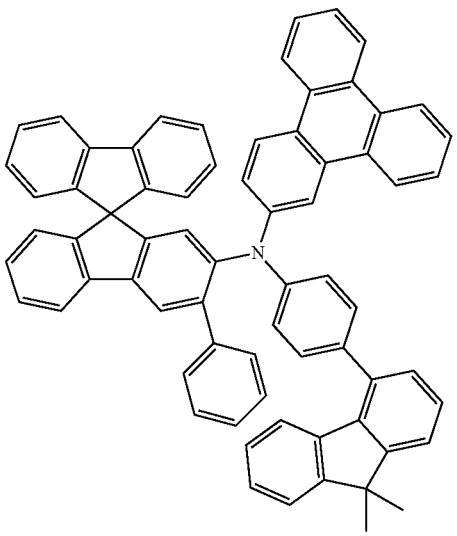
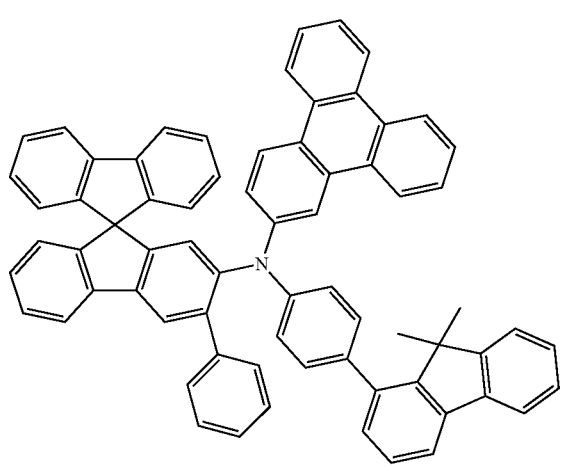
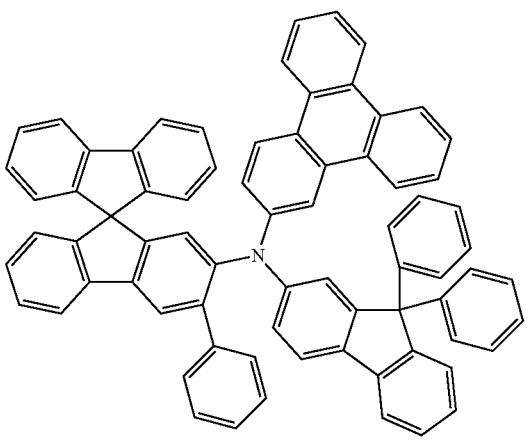
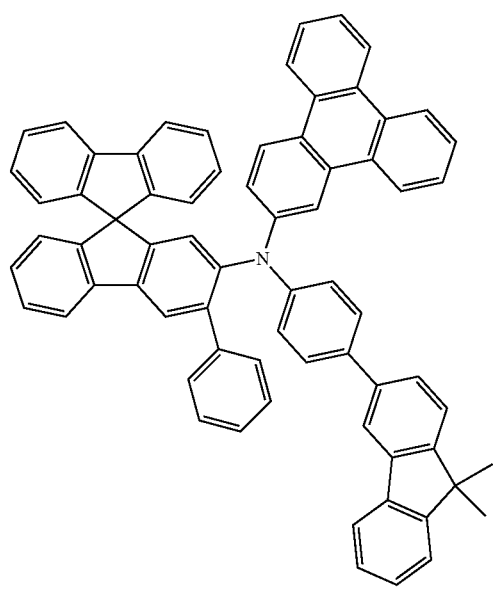
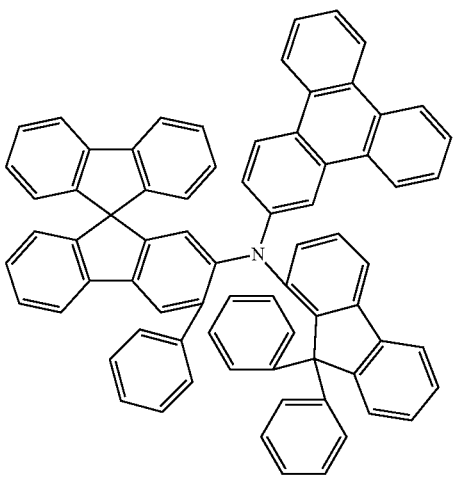

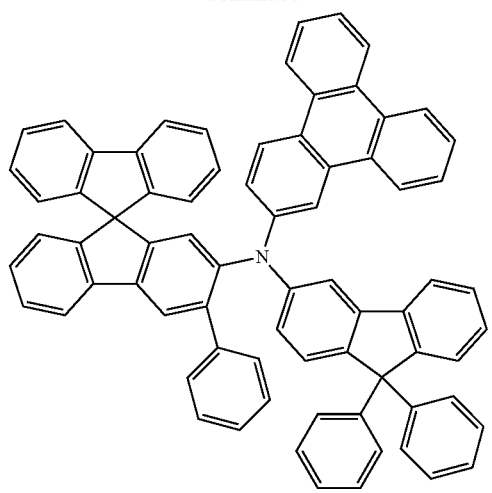
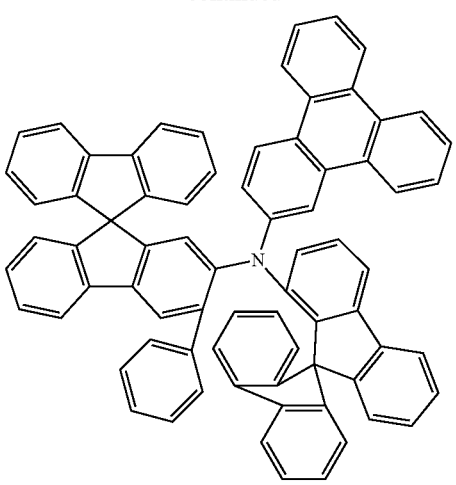
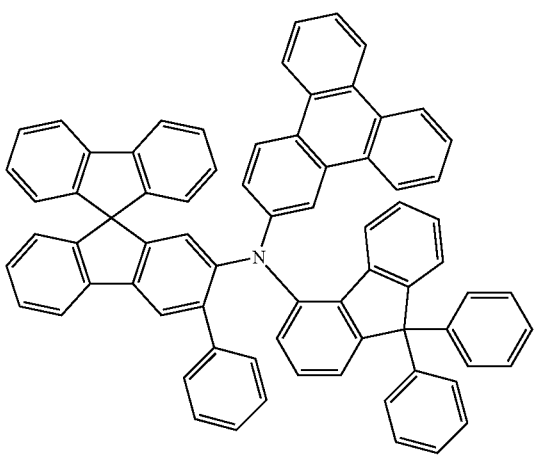
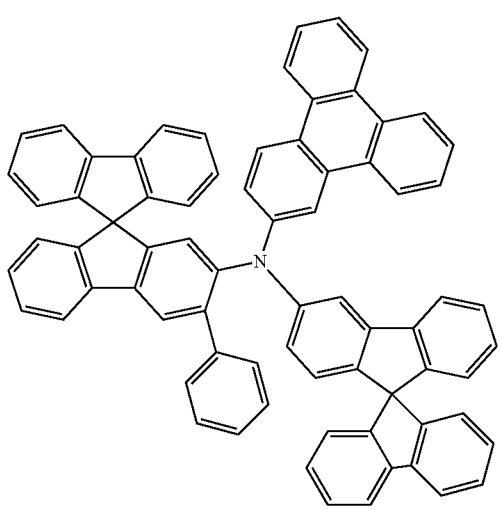
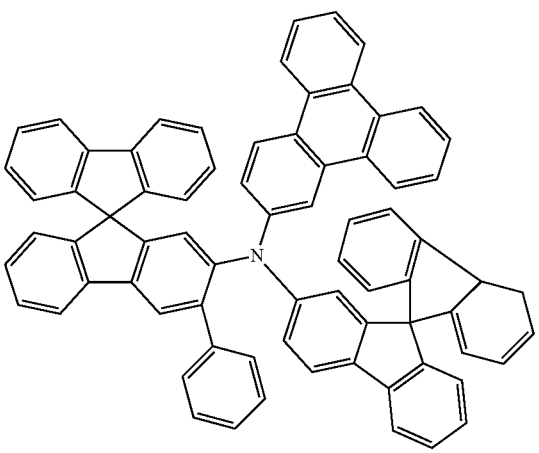
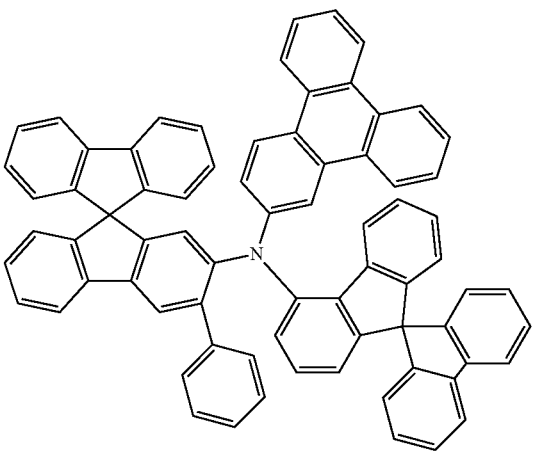

43
-continued
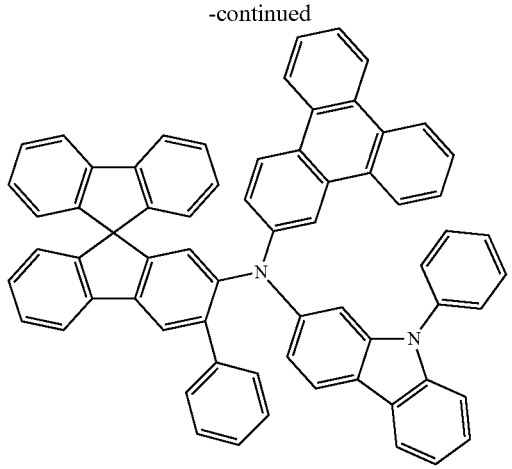
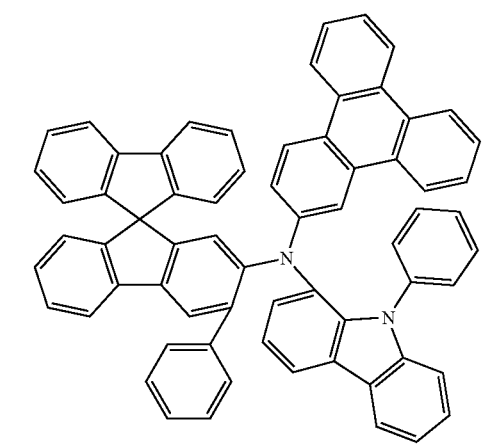
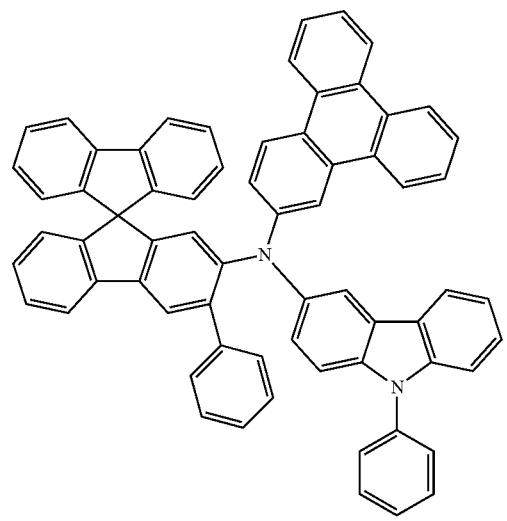
44
-continued
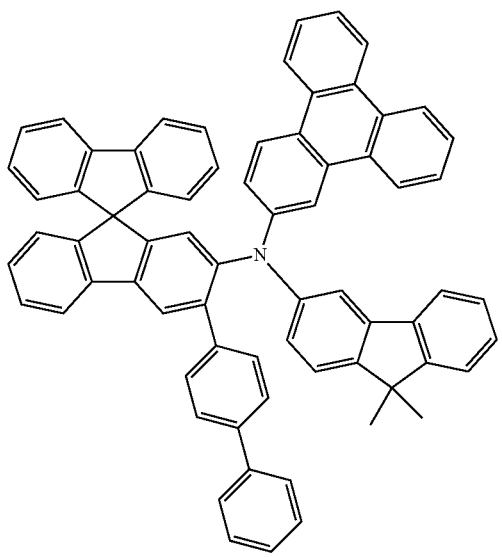
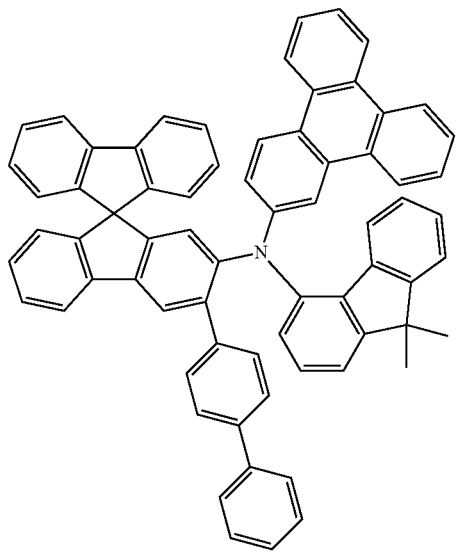
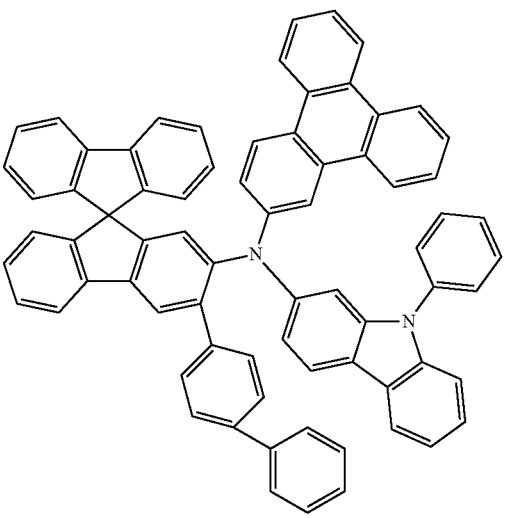

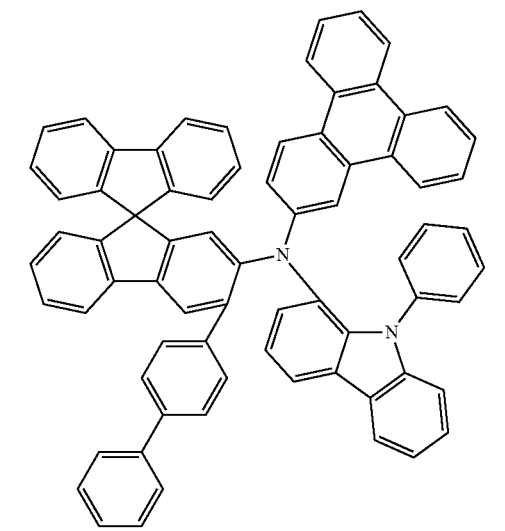
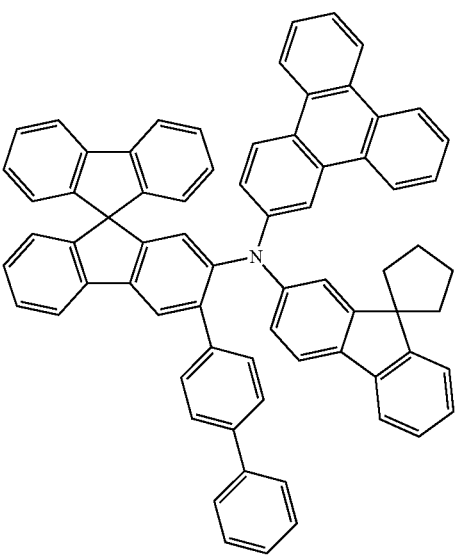
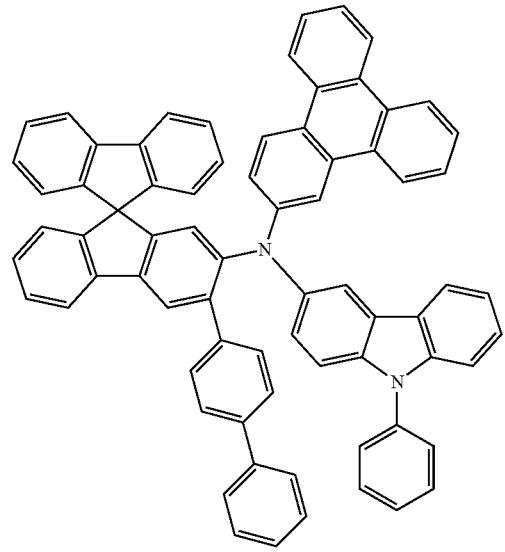

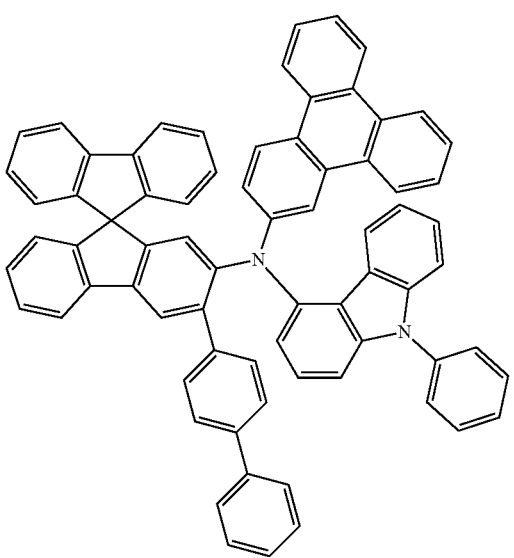
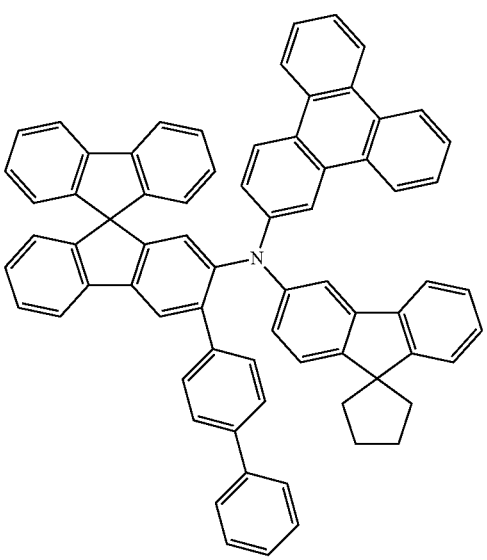

-continued
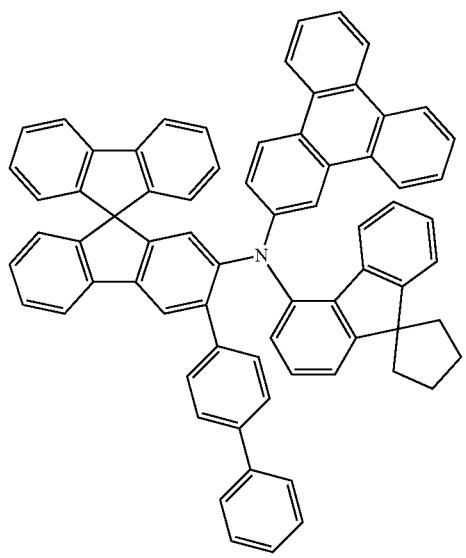
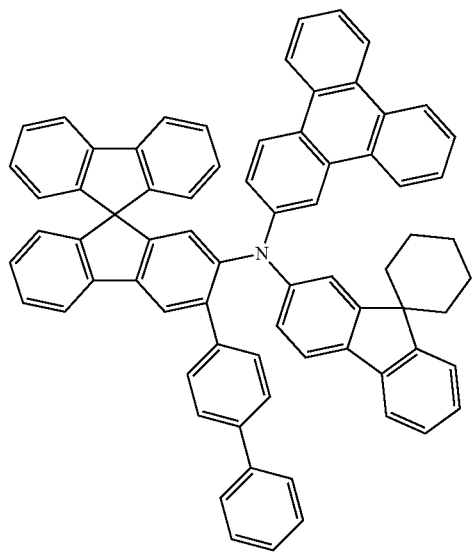
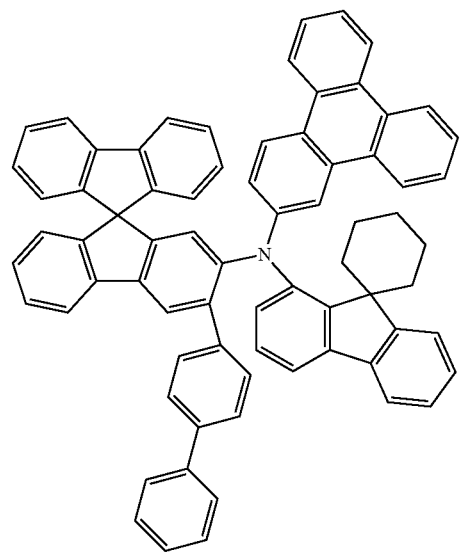
-continued
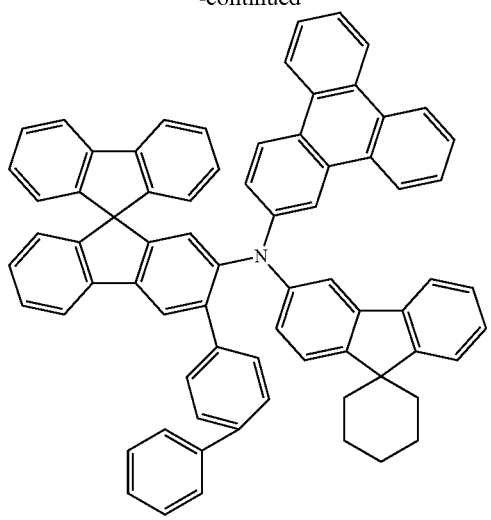
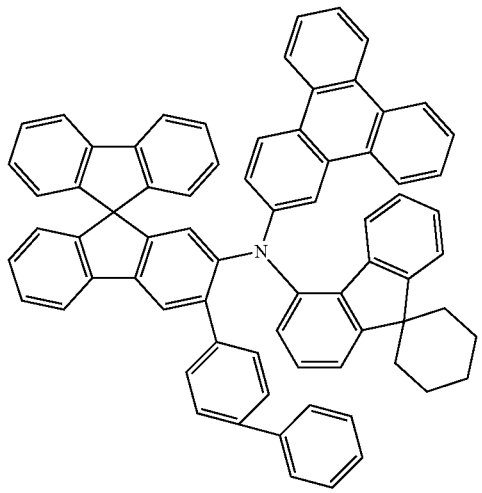
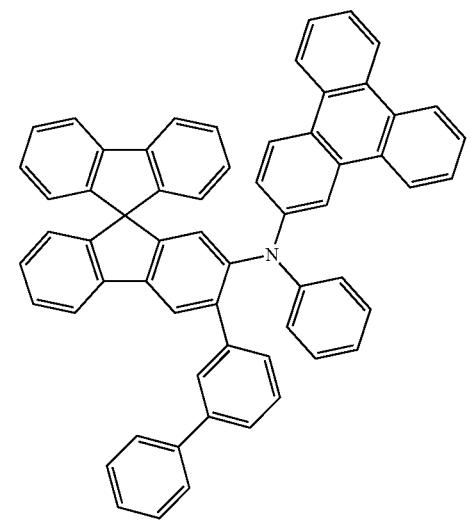

49
-continued
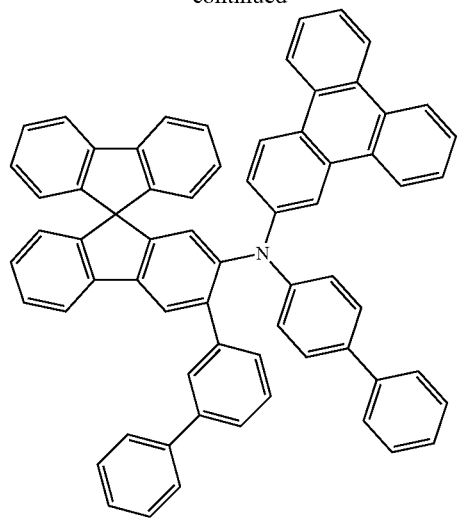
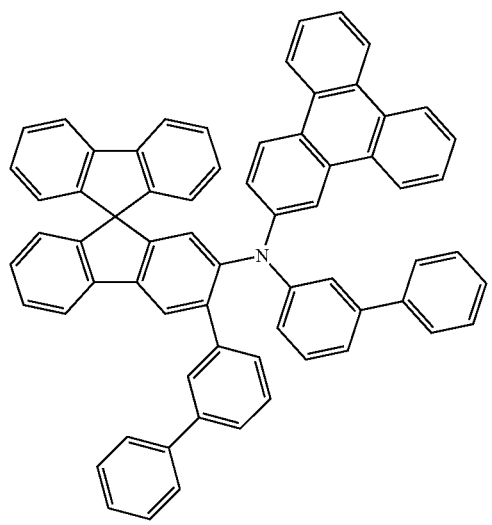
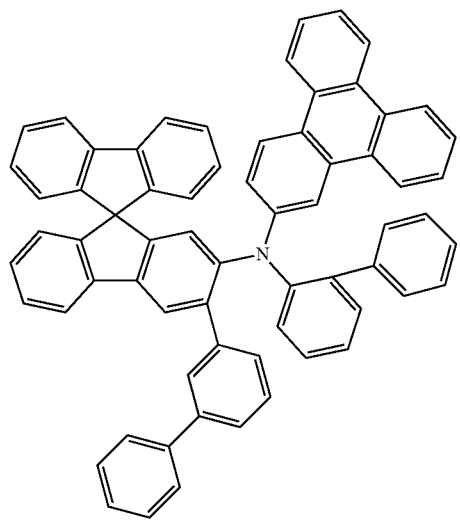
50
-continued
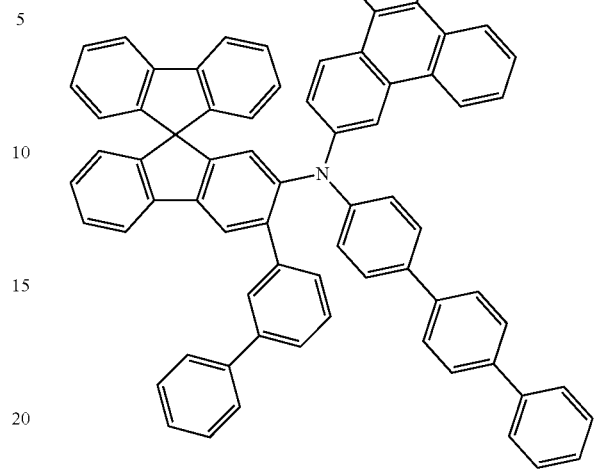
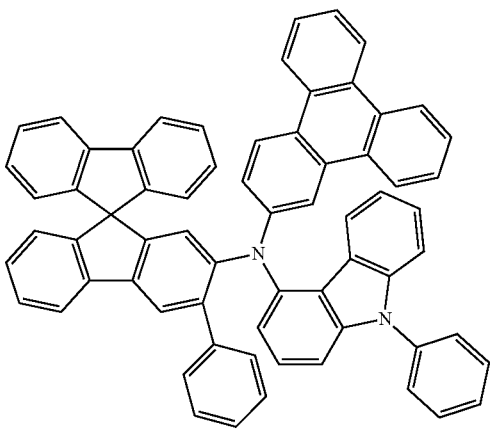
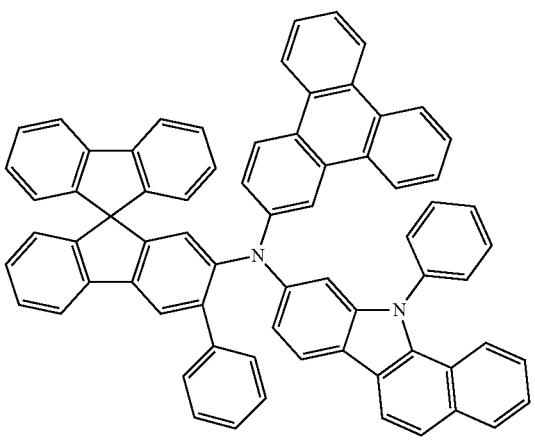

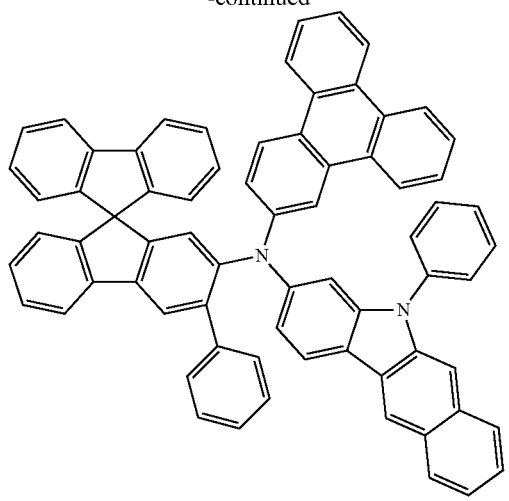
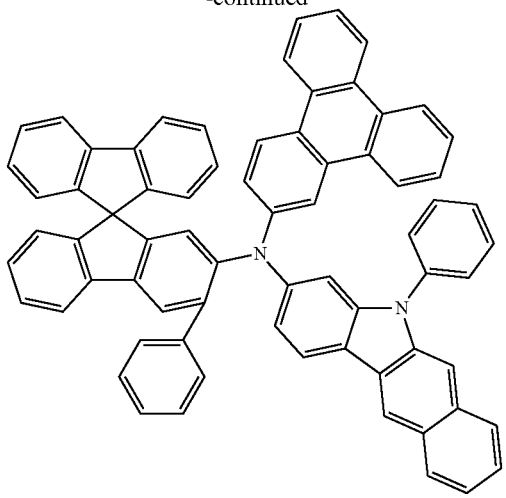
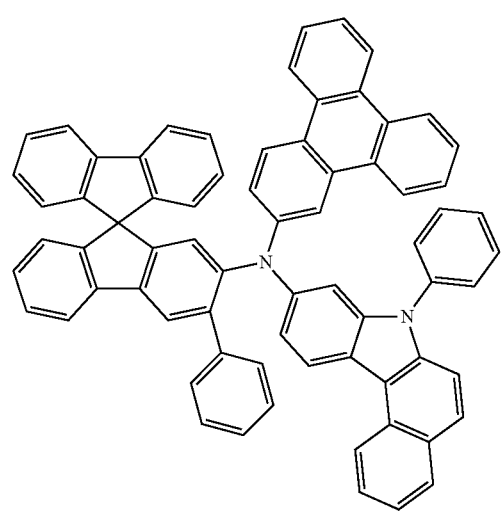
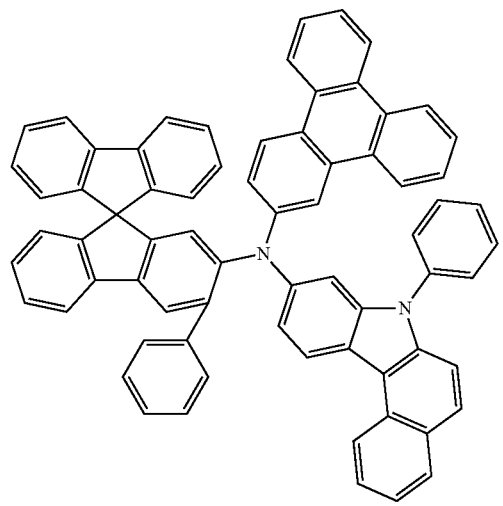
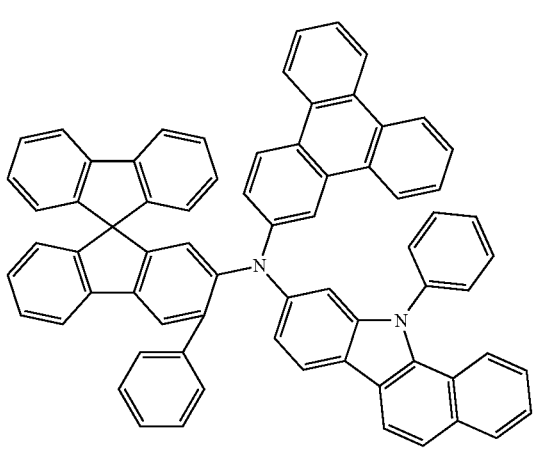
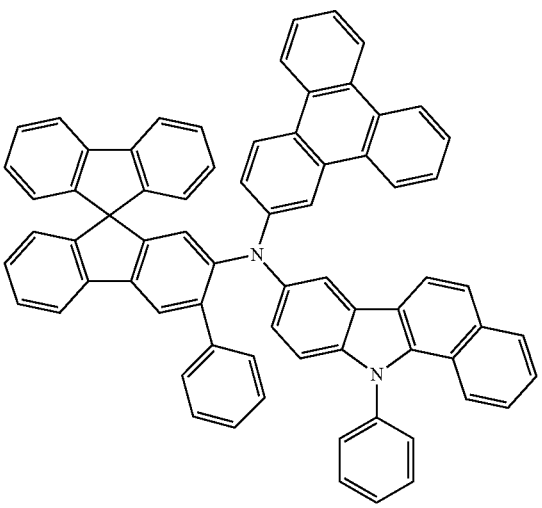

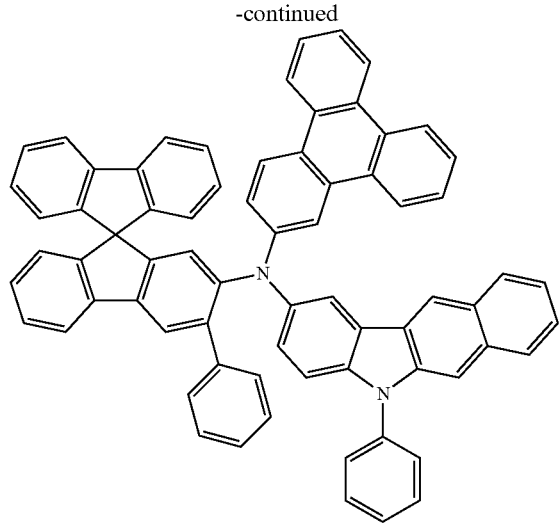
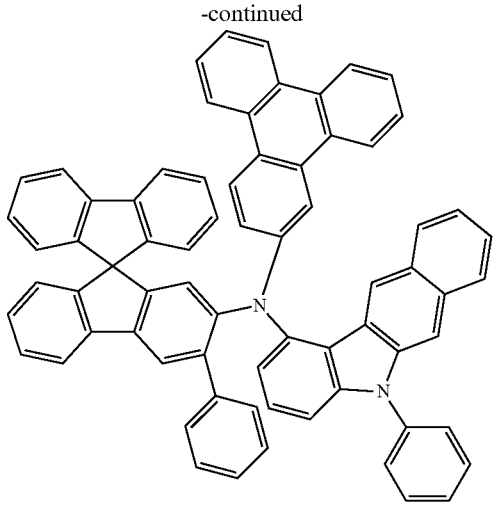
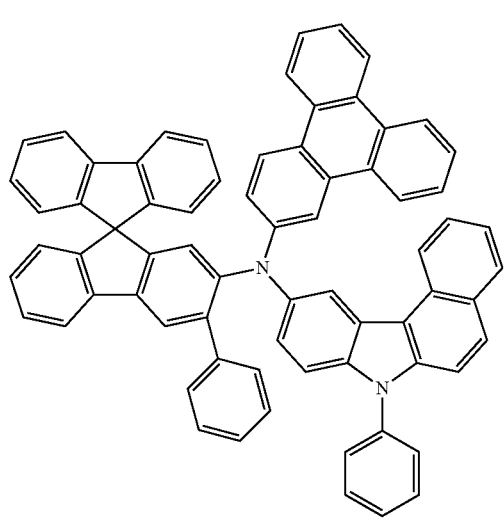
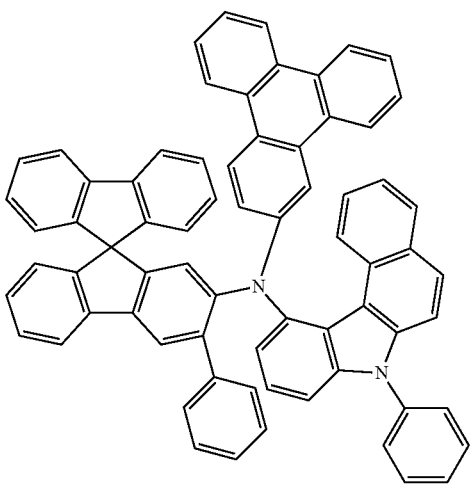
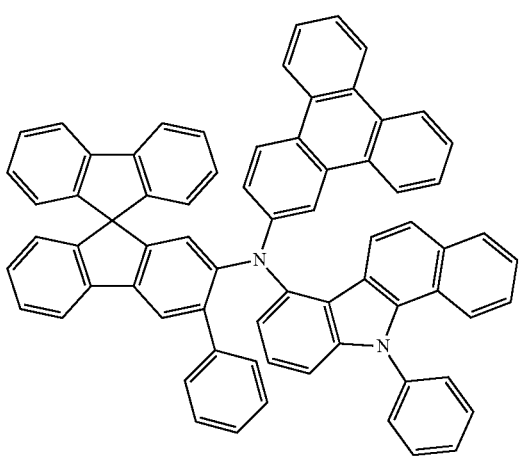
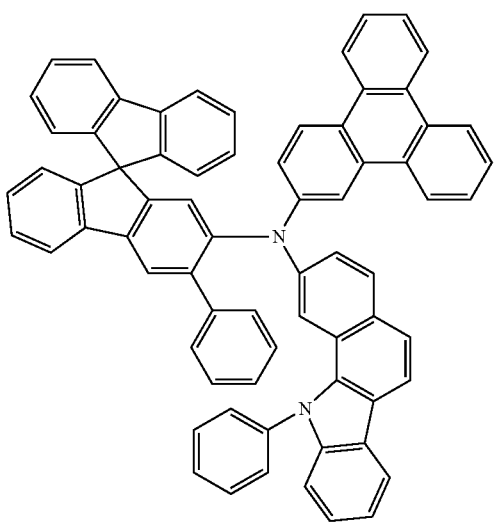

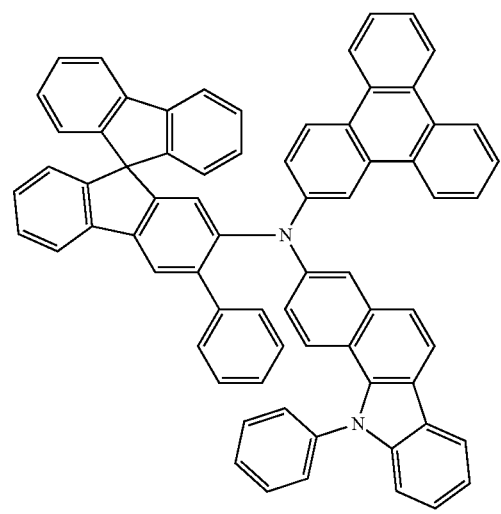
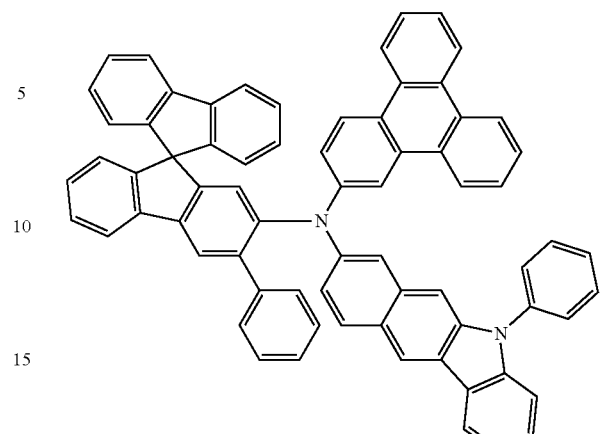
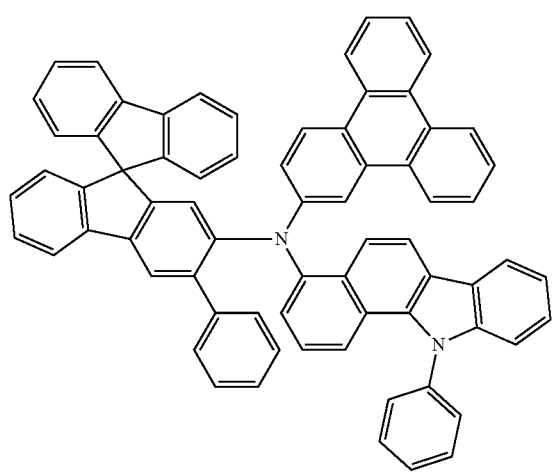
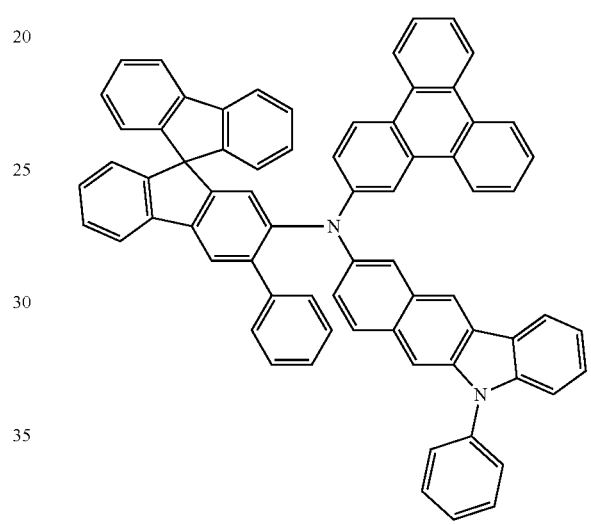
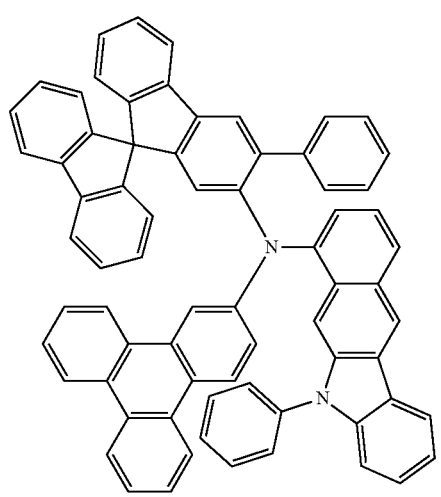
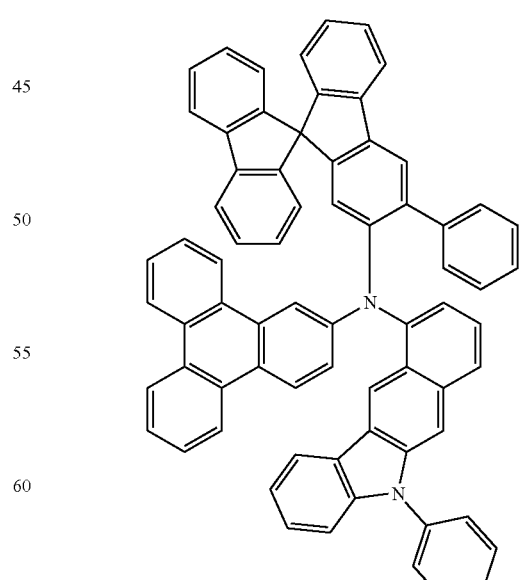

-continued
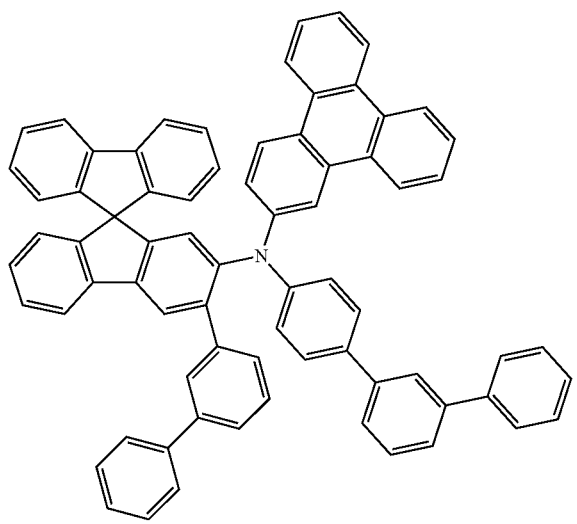
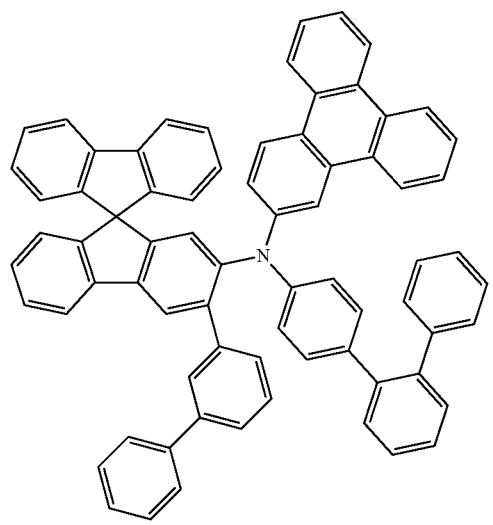
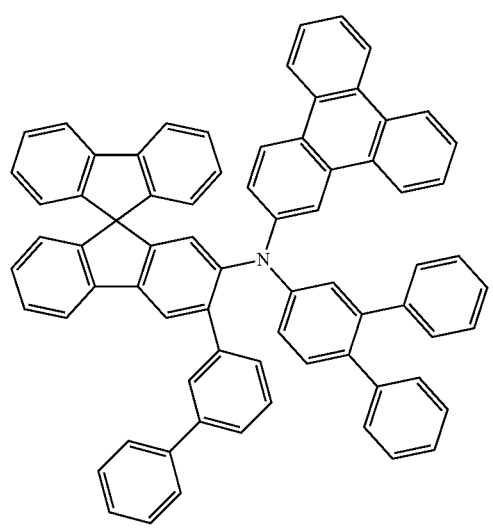
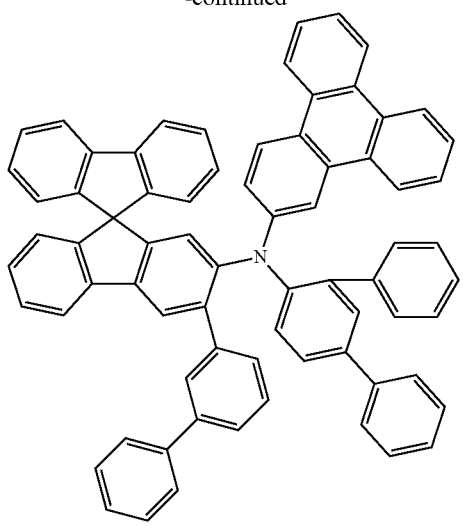
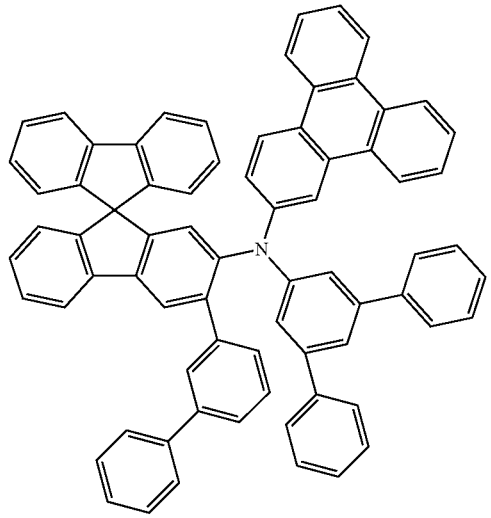
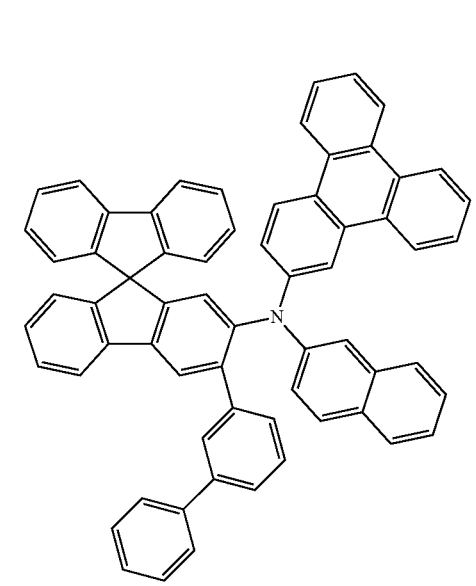

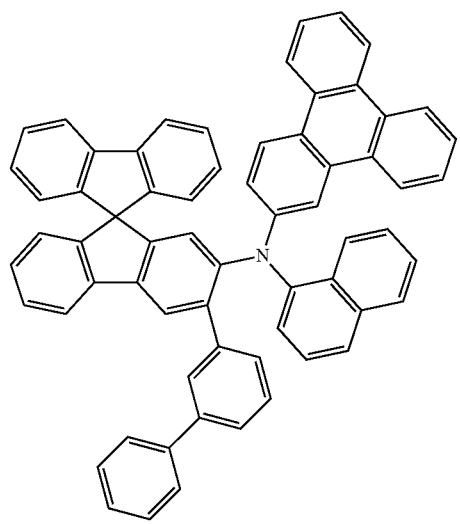
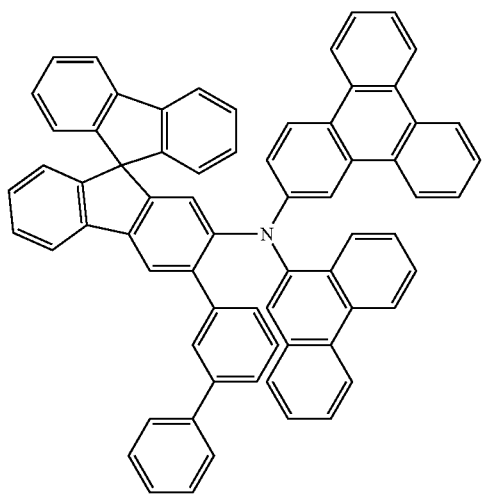
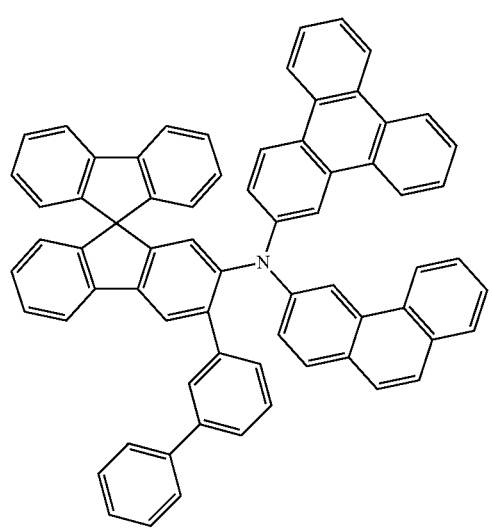
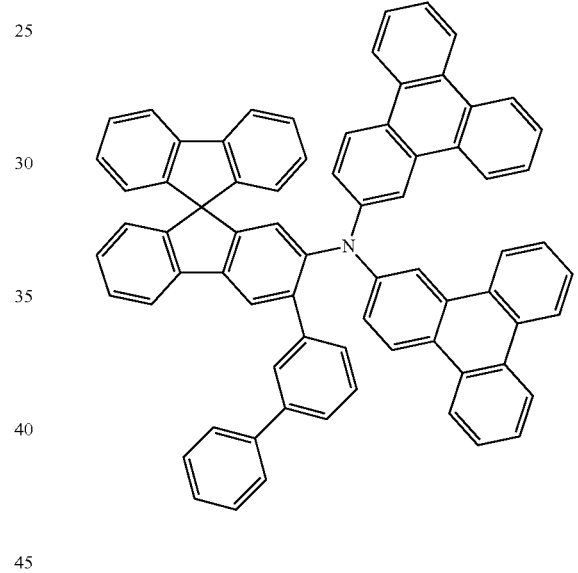
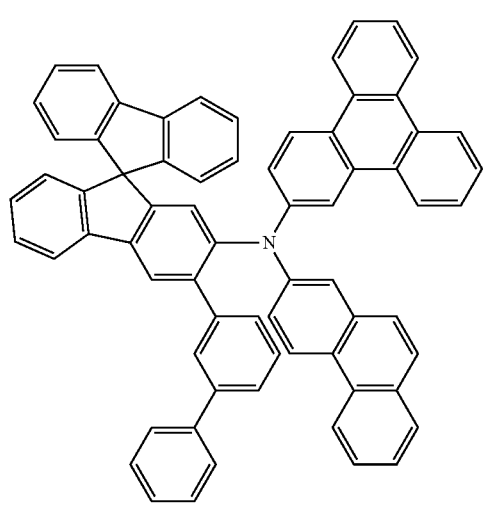
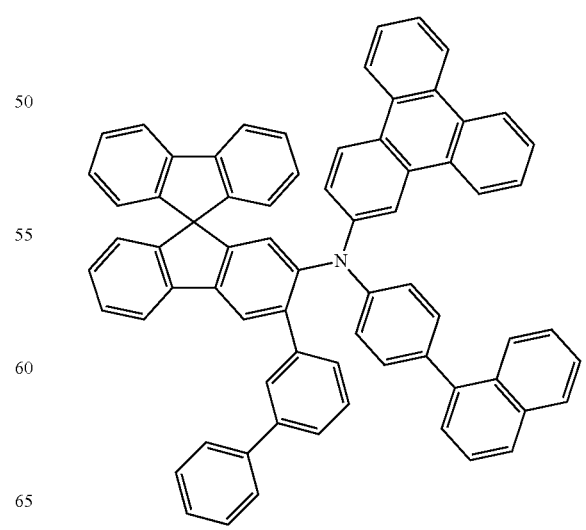

61
-continued
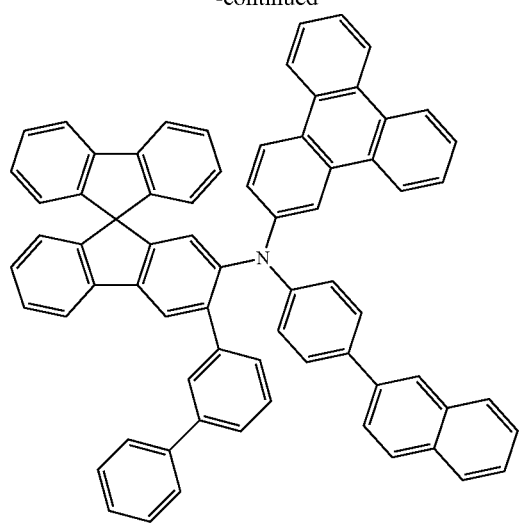
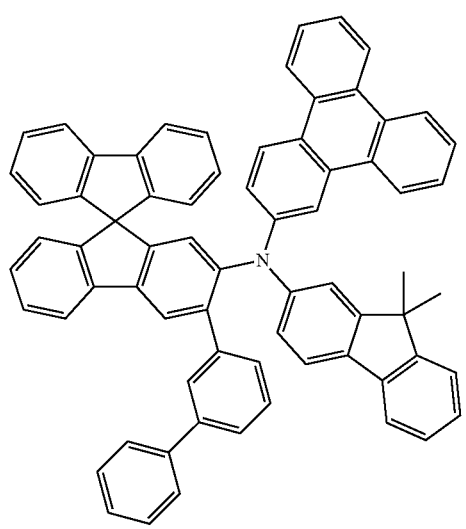
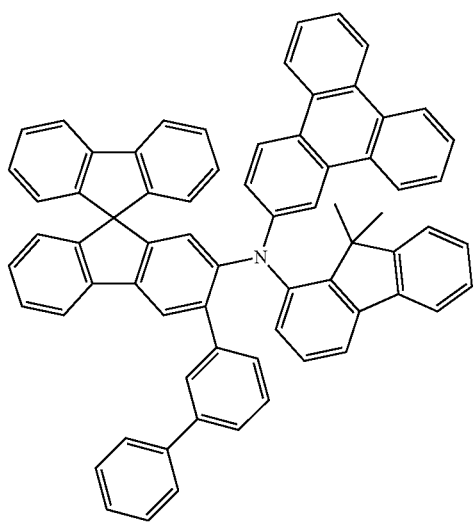
62
-continued
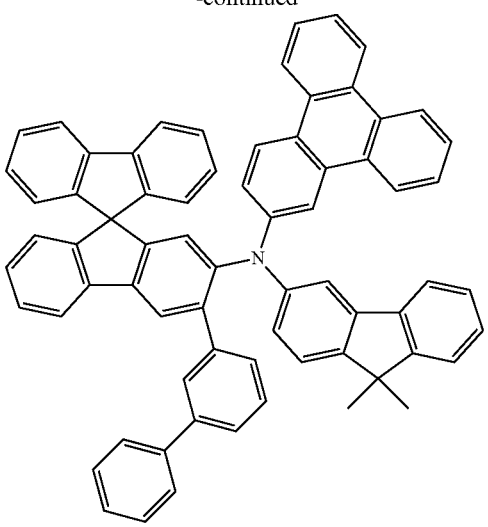
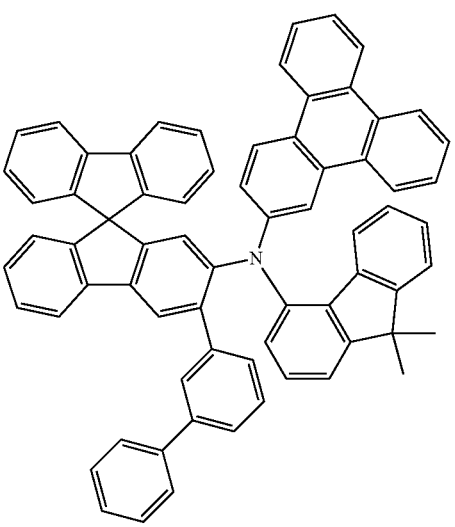
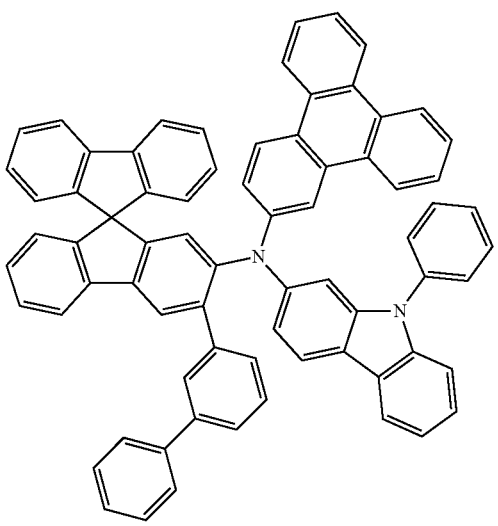

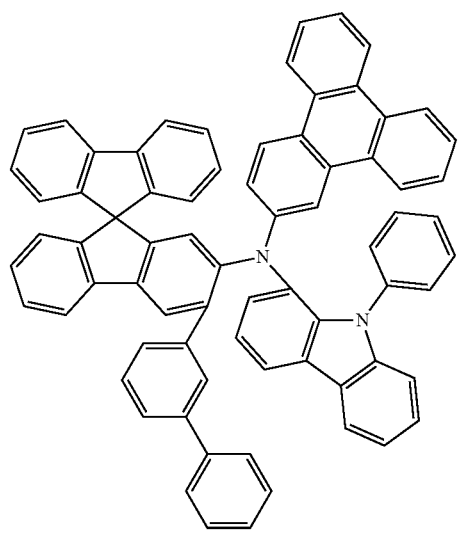 [SMILES: c1ccc(-c2cccc(-c3cc4c(cc3N(c3ccc5c6ccccc6c6ccccc6c5c3)c3cccc5c6ccccc6n(-c6ccccc6)c35)C3(c5ccccc5-c5ccccc53)c3ccccc3-4)c2)cc1]
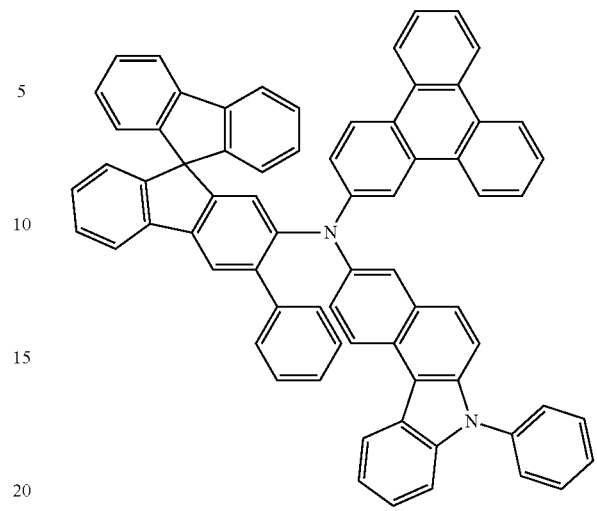
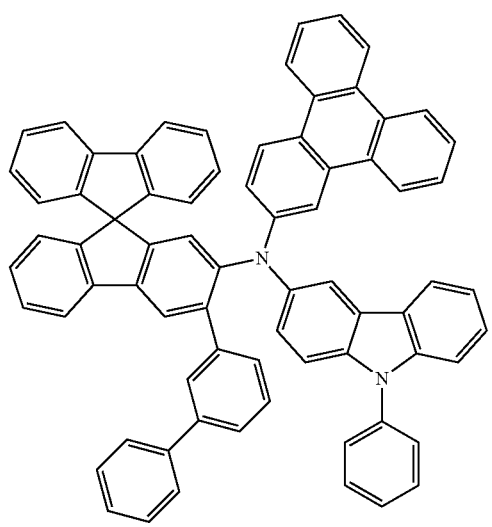
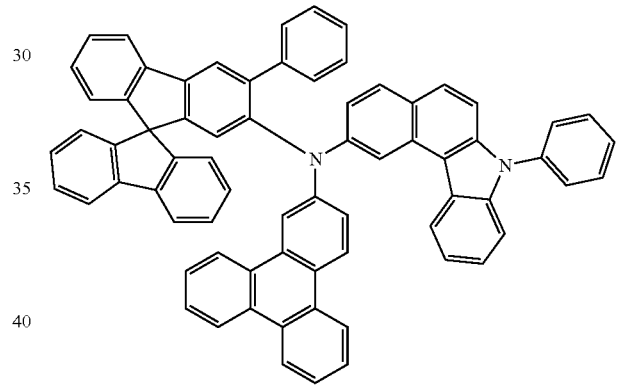
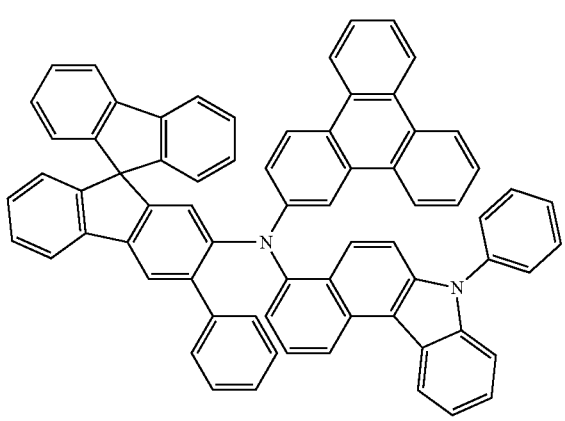
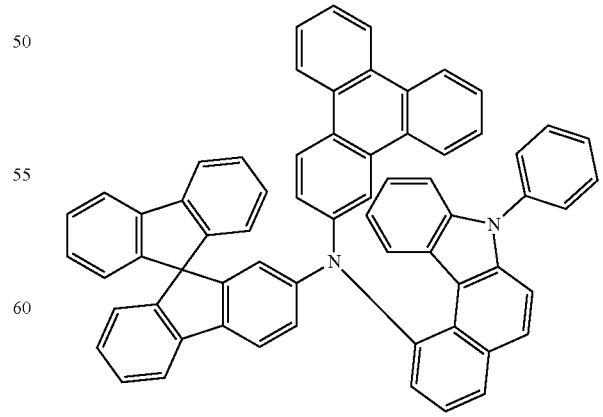

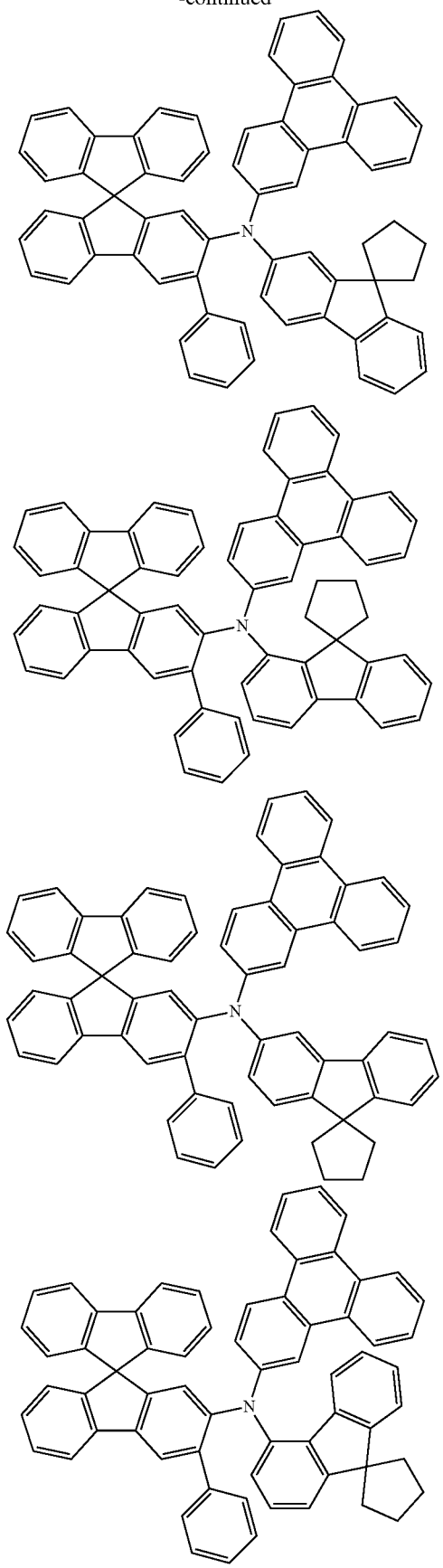
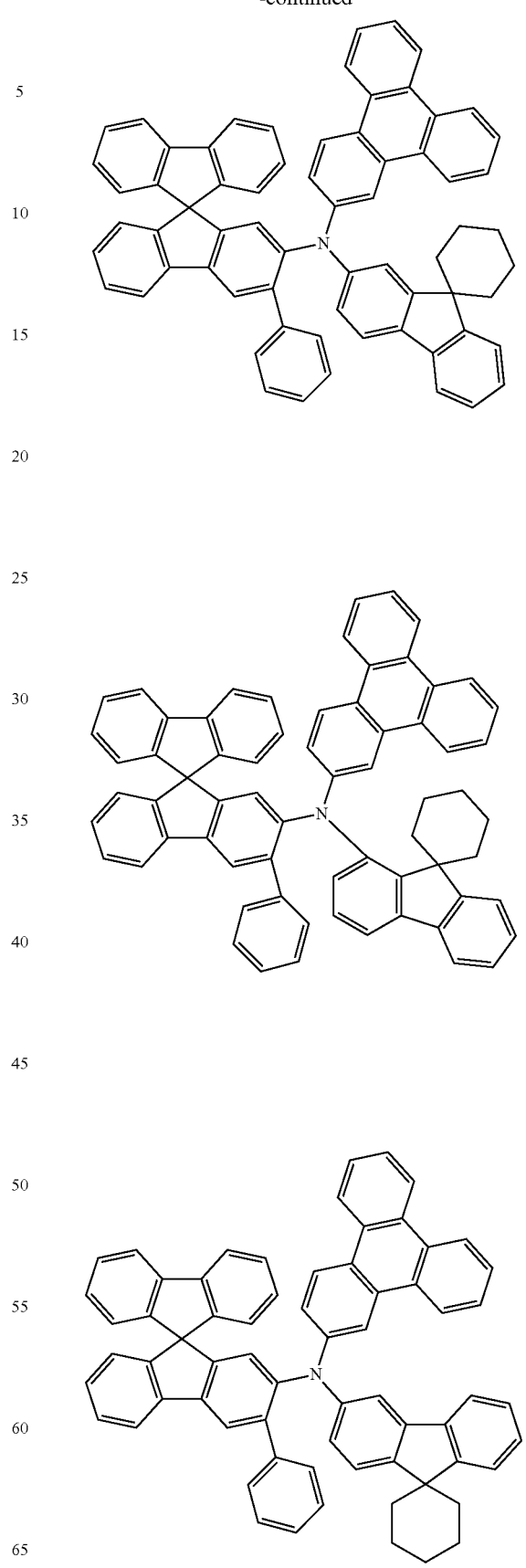

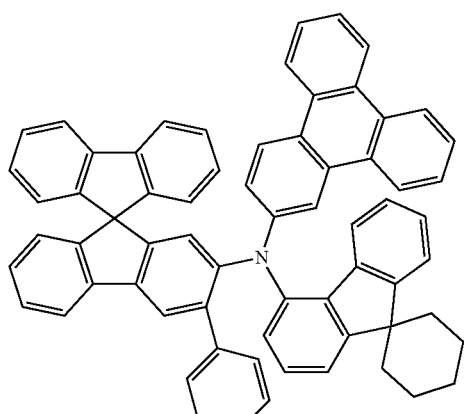
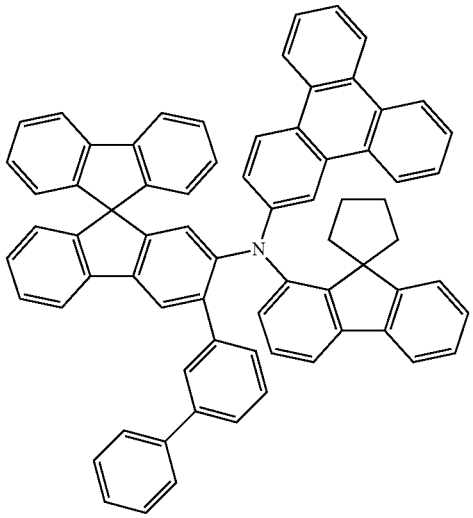
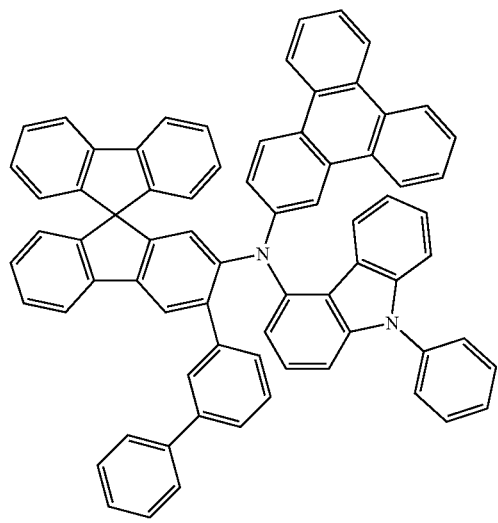
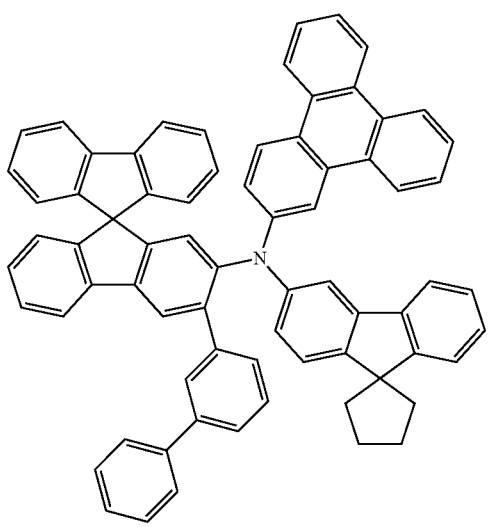
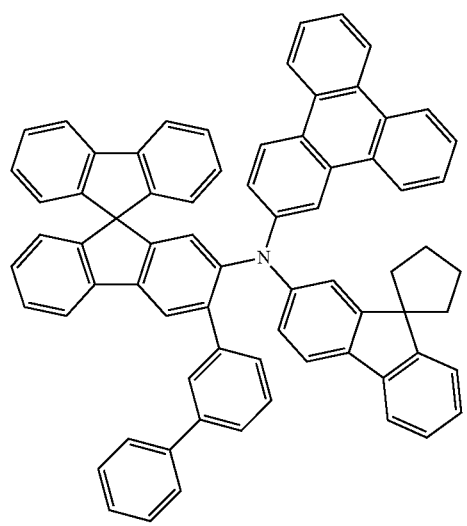
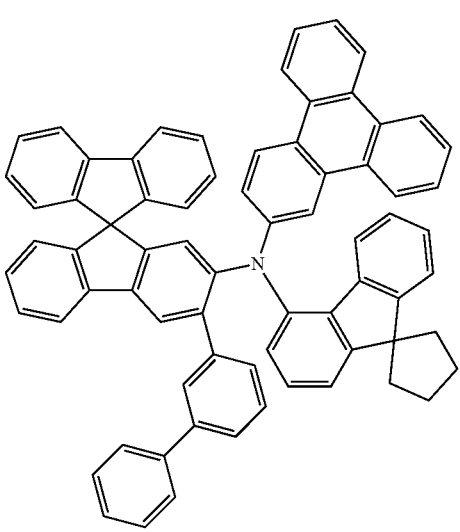

69
-continued
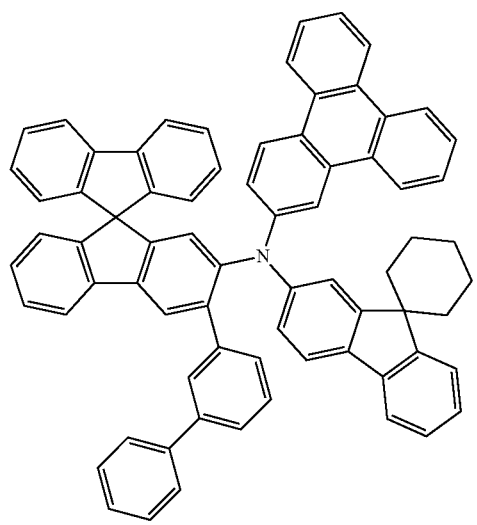
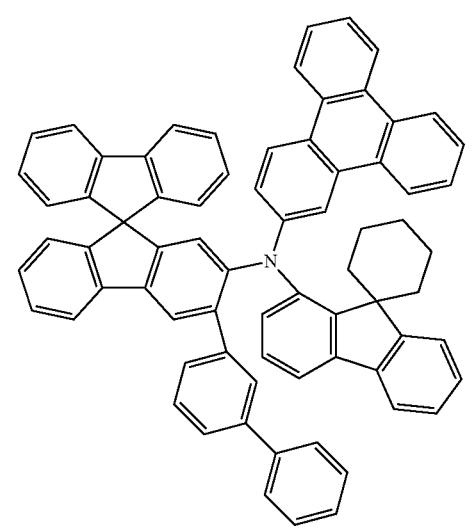
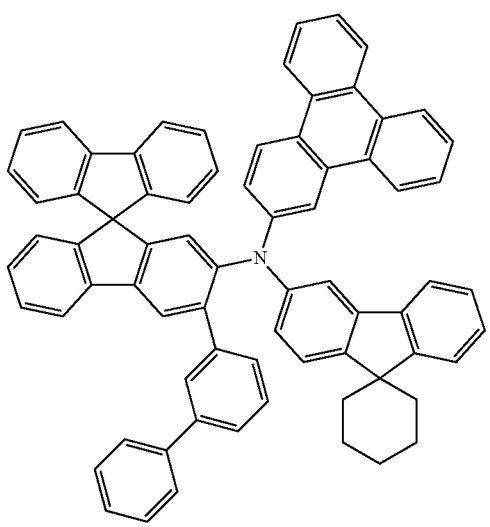
70
-continued
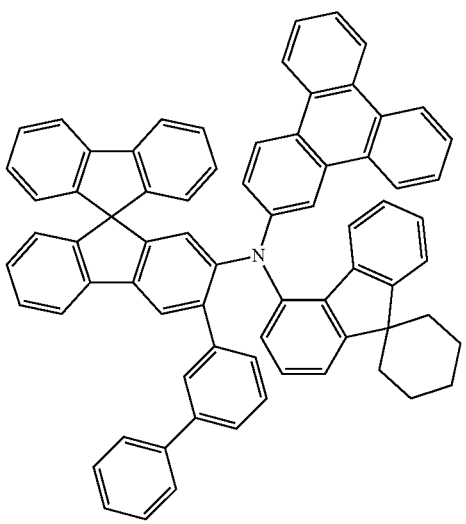 [SMILES: c1ccc(-c2cccc(-c3cc4c(cc3N(c3ccc5c6ccccc6c6ccccc6c5c3)c3cccc5c3-c3ccccc3C53CCCCC3)C3(c5ccccc5-c5ccccc53)c3ccccc3-4)c2)cc1]
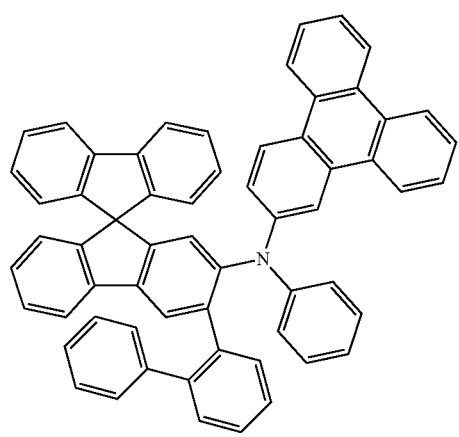
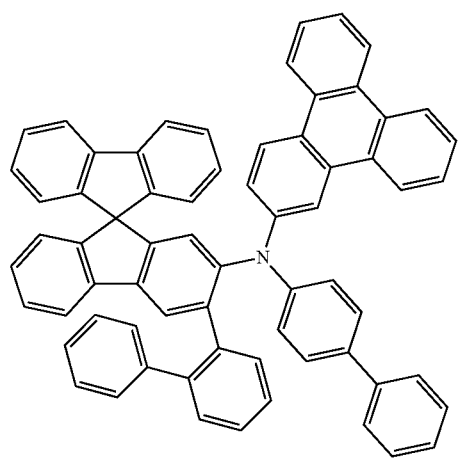

71
-continued
72
-continued
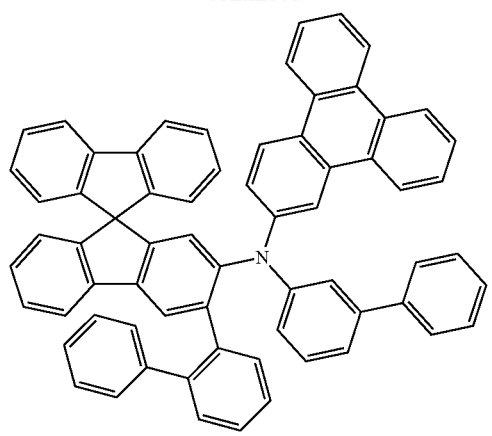
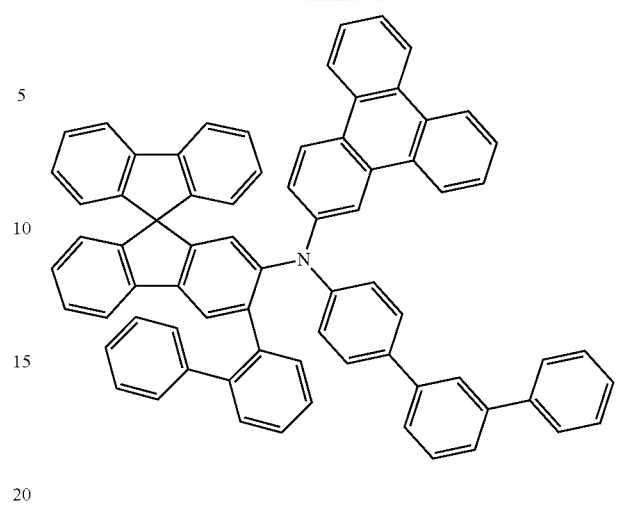
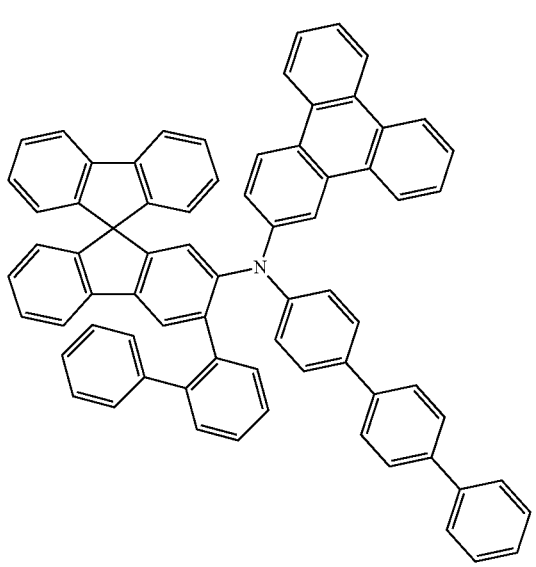
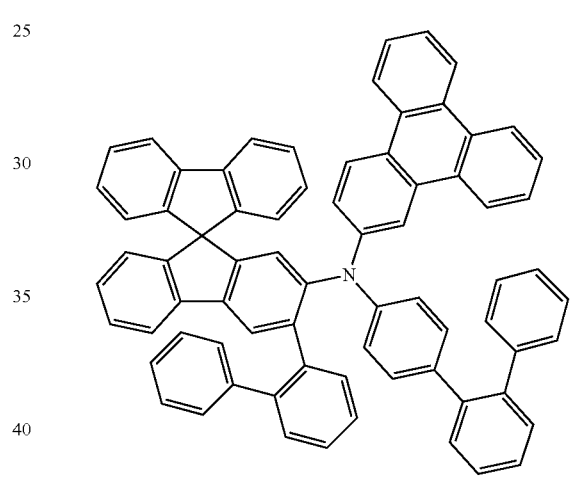
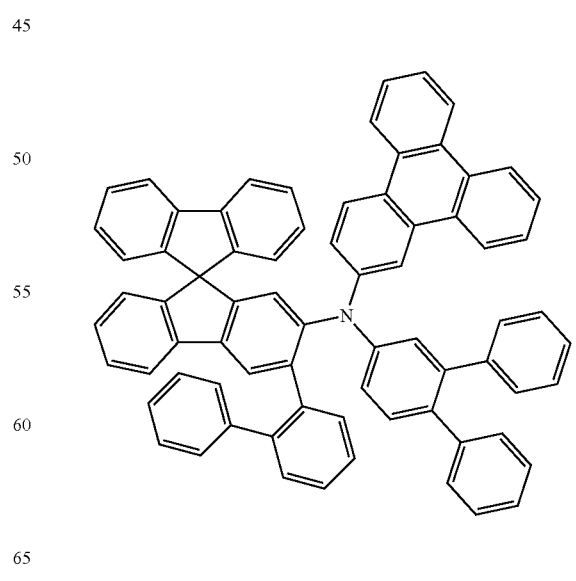

73
-continued
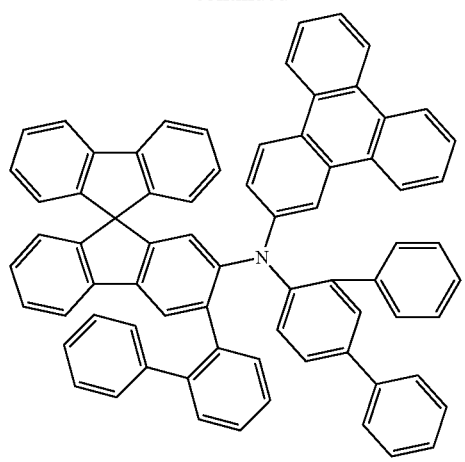
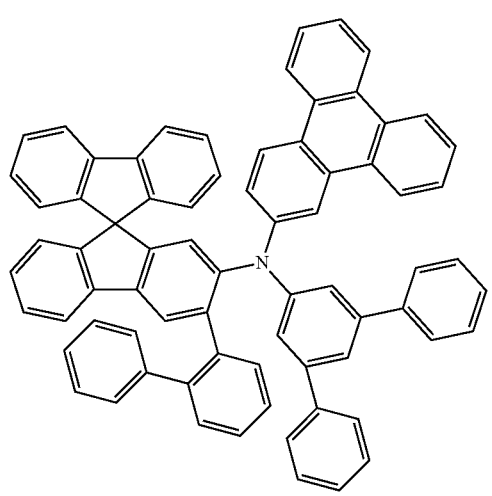
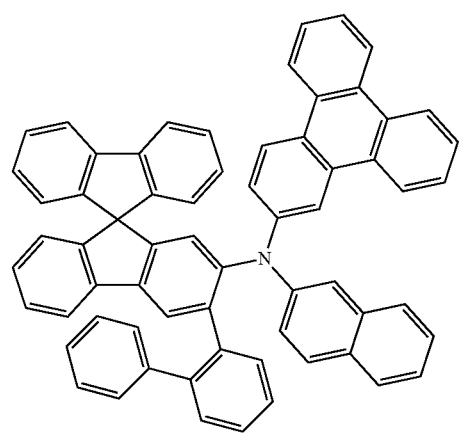
74
-continued
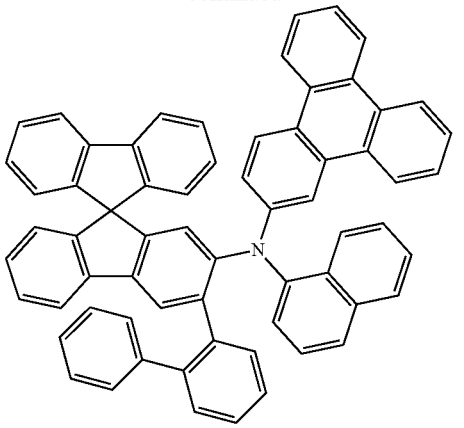
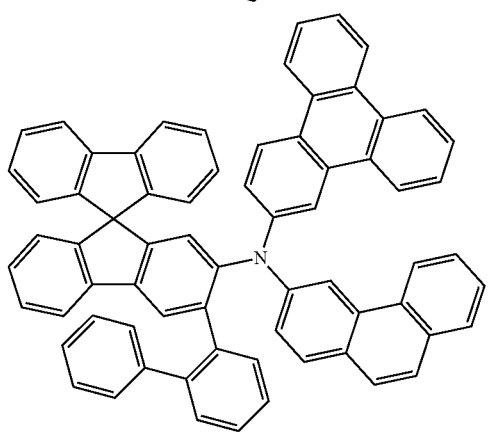
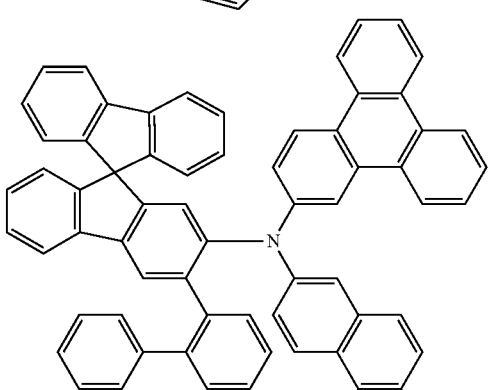
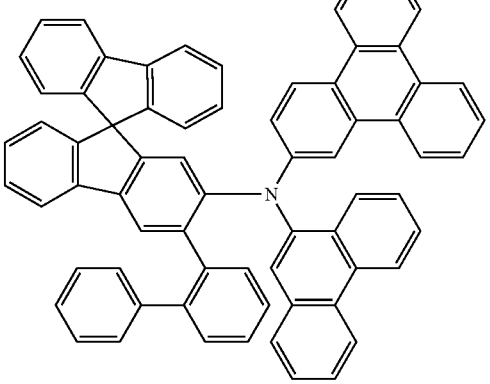

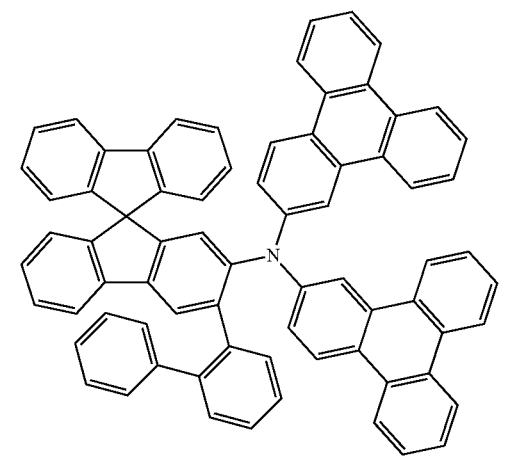
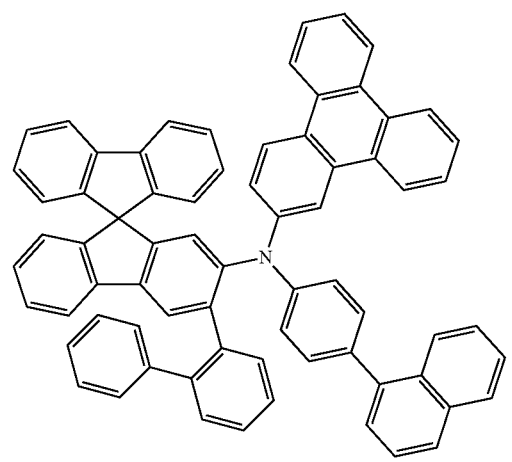
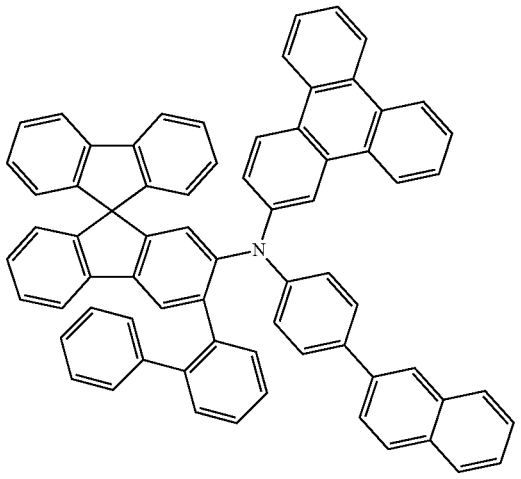
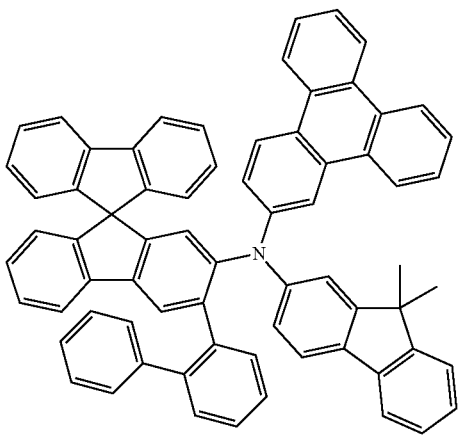
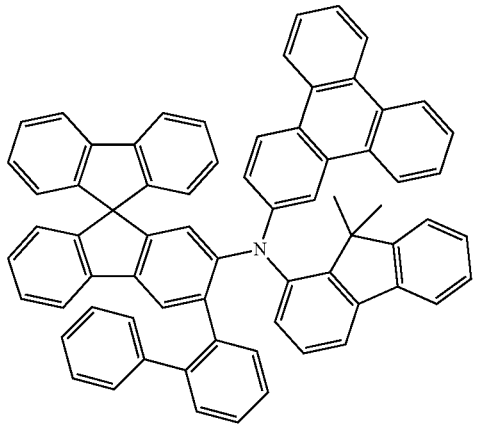
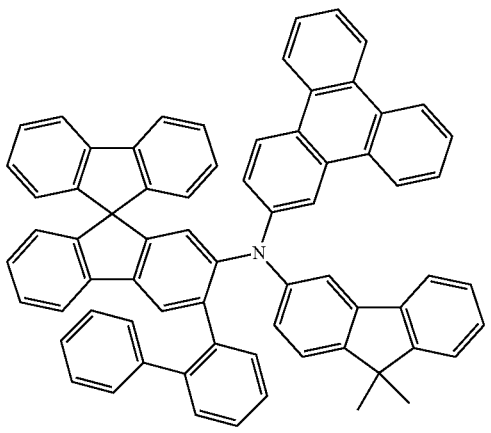
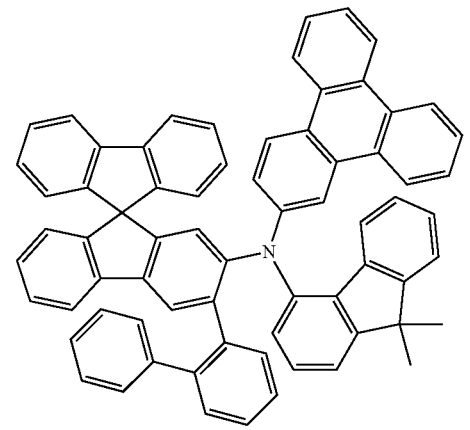

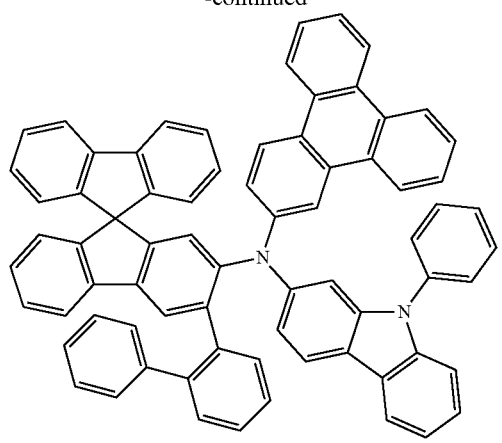
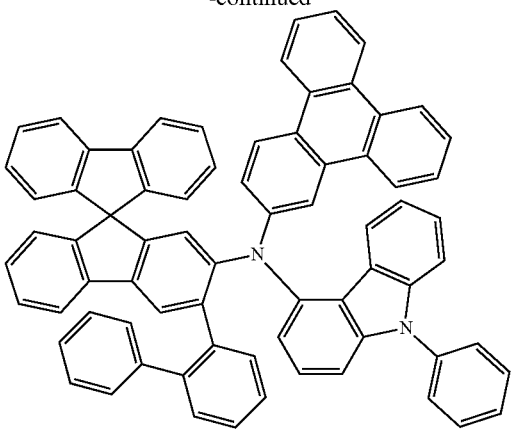
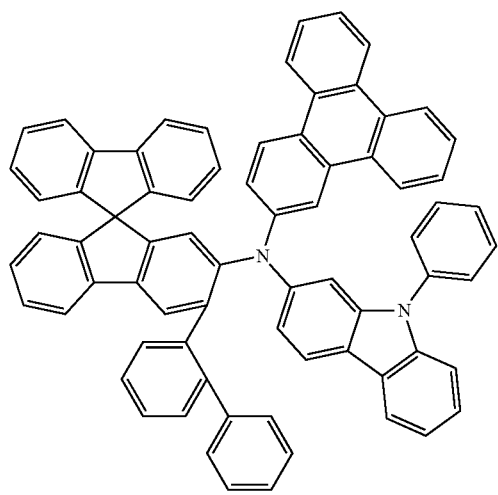
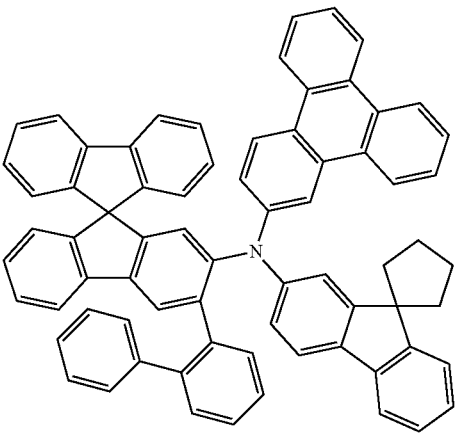
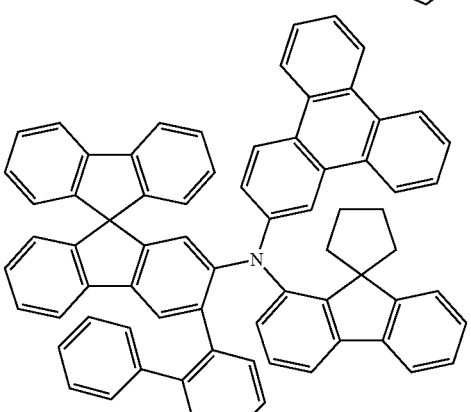
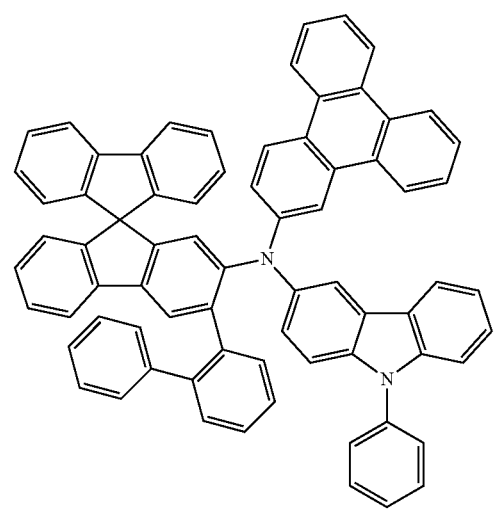
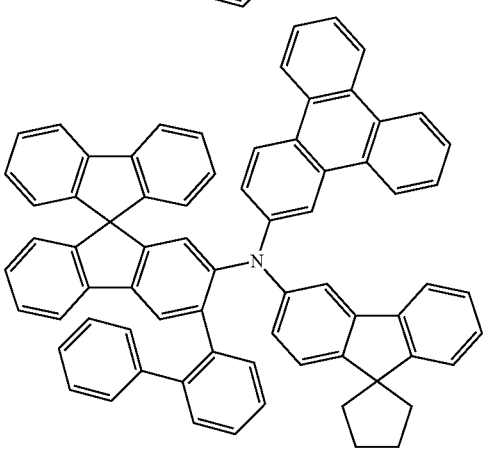

-continued
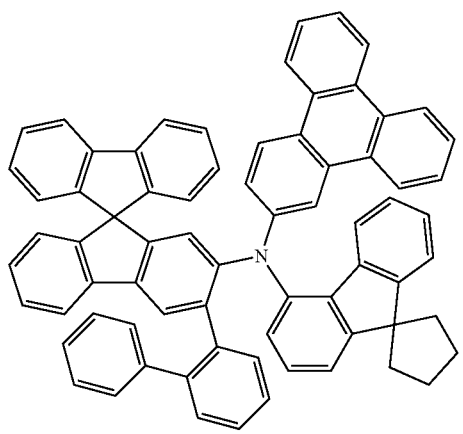
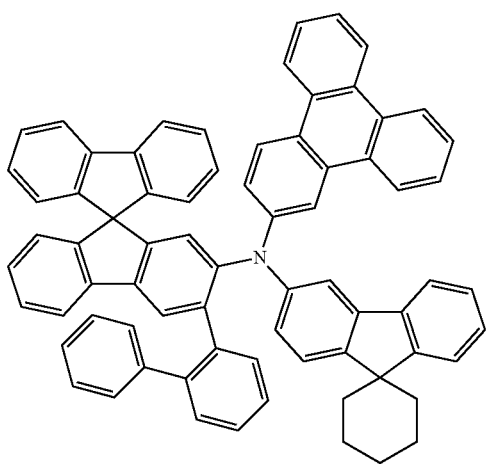
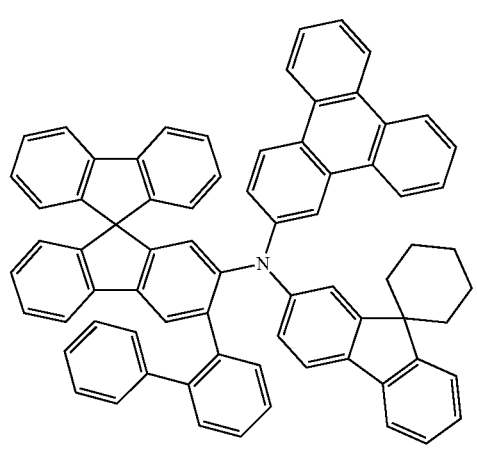
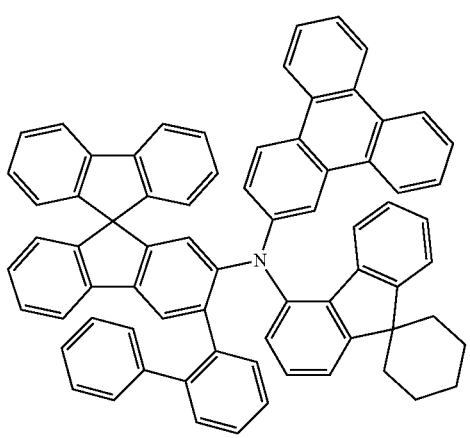 [SMILES: c1ccc(-c2ccccc2-c2cc3c(cc2N(c2ccc4c5ccccc5c5ccccc5c4c2)c2cccc4c2-c2ccccc2C42CCCCC2)C2(c4ccccc4-c4ccccc42)c2ccccc2-3)cc1]
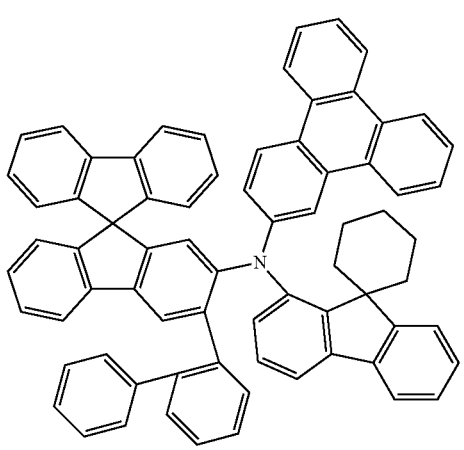
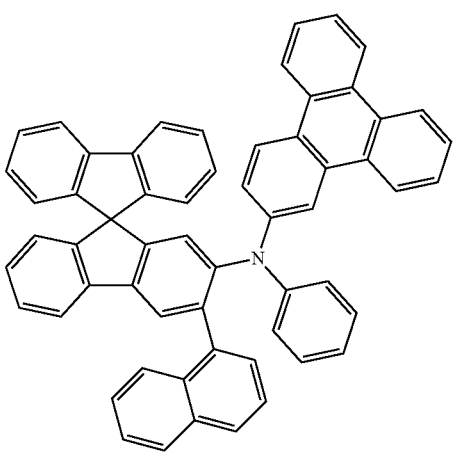

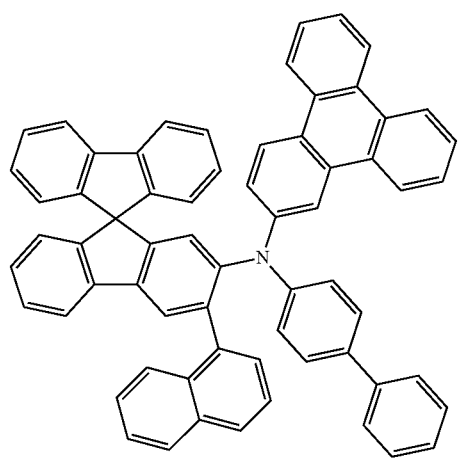
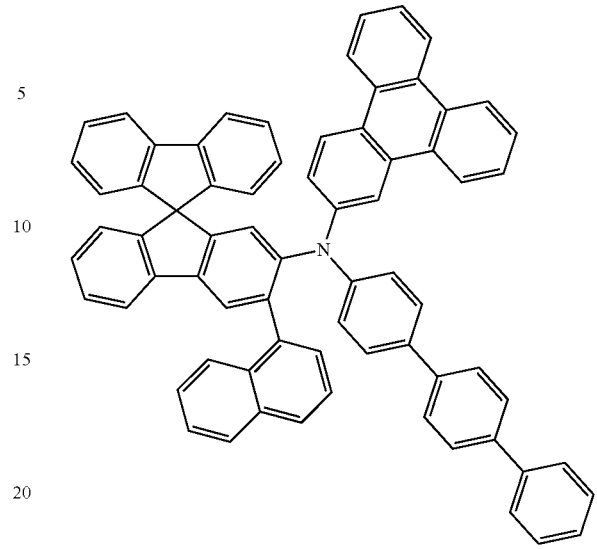
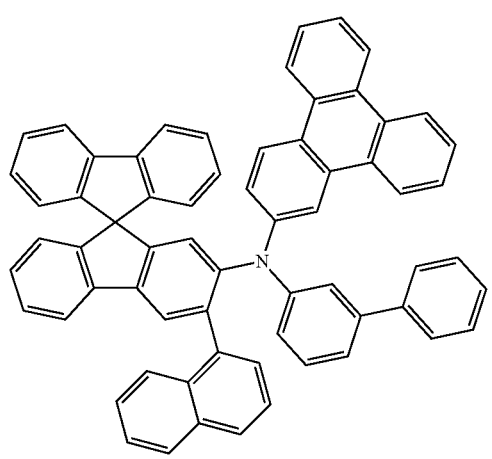
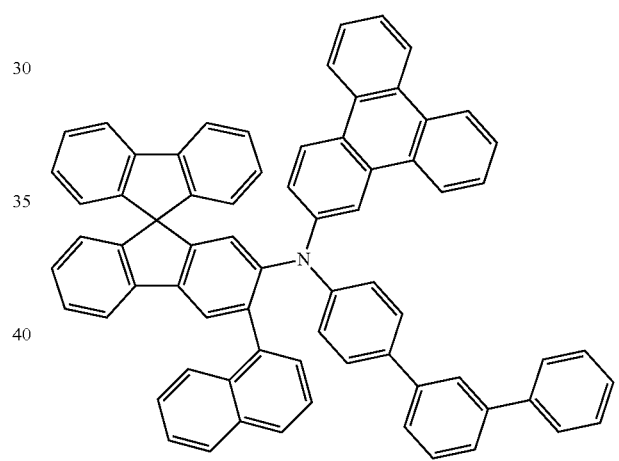
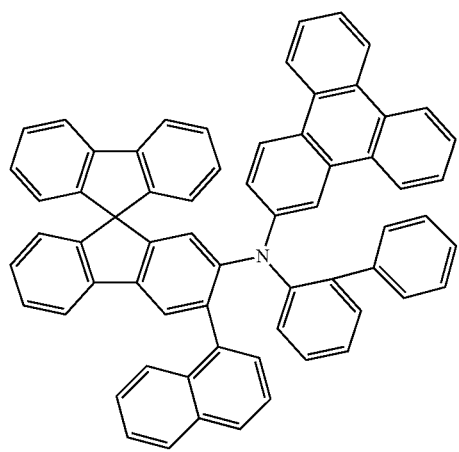
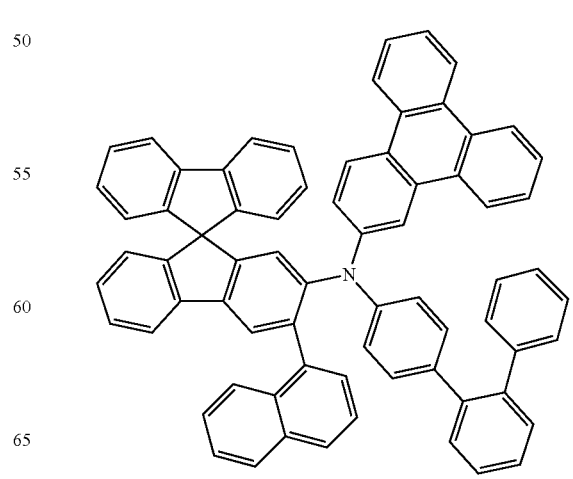

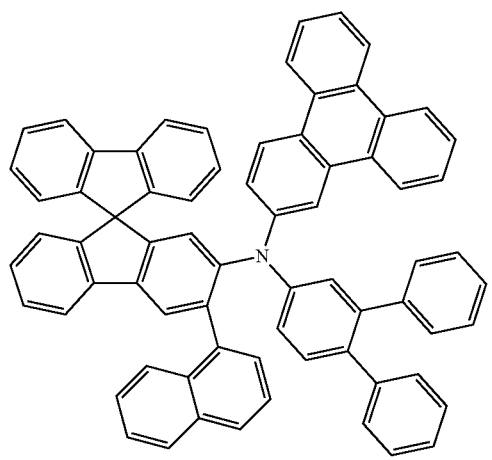
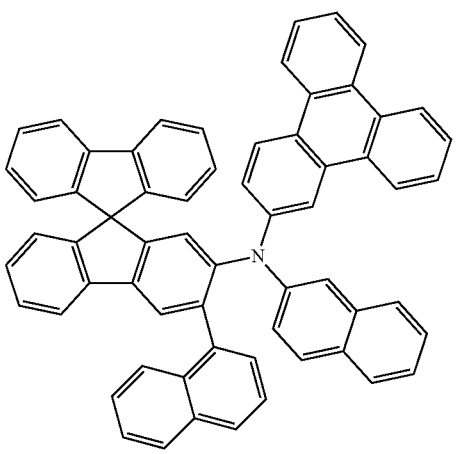
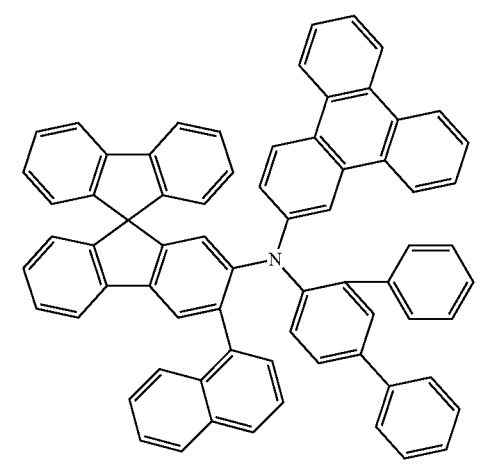
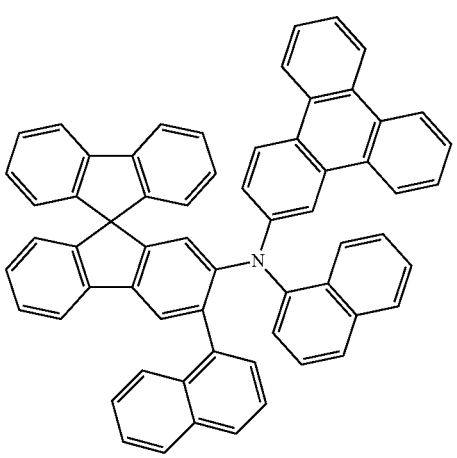
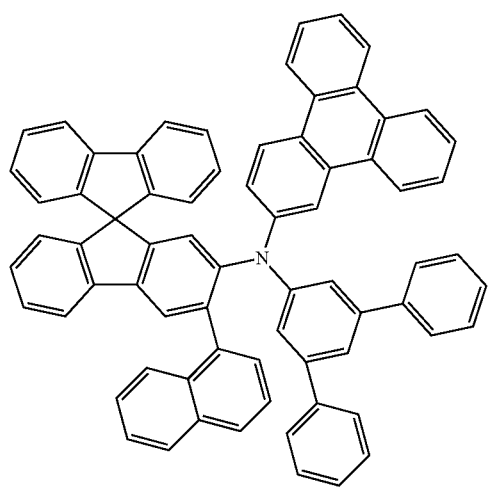
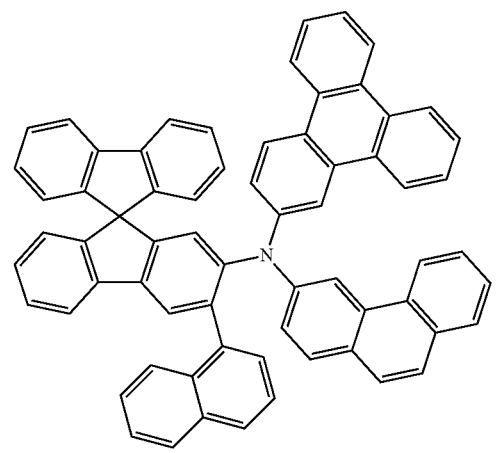

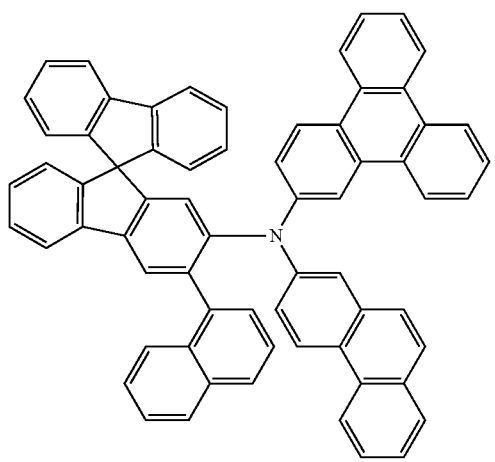
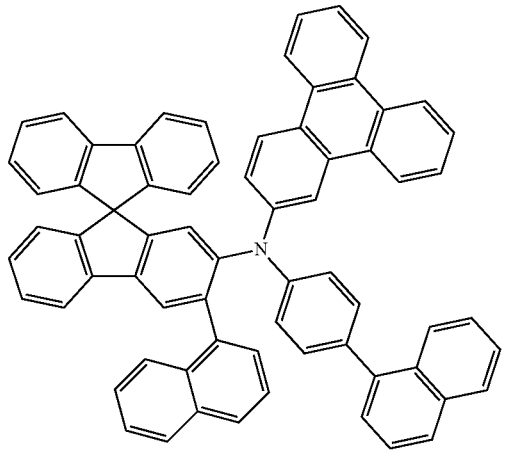
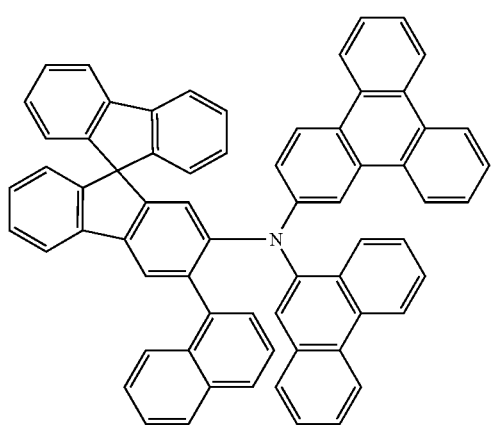
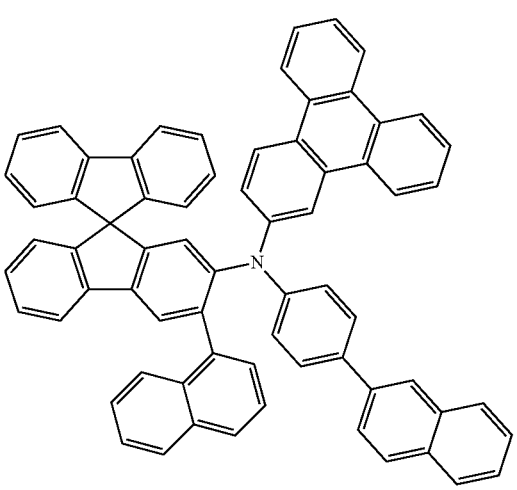
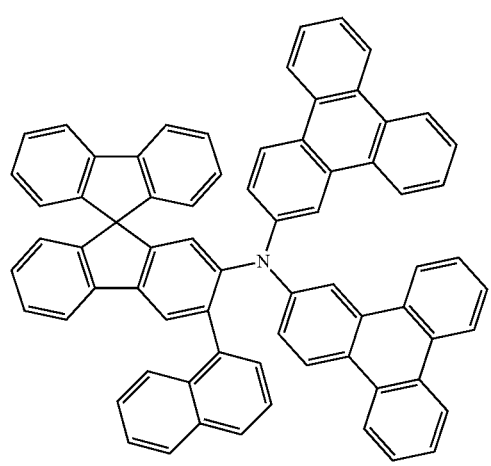
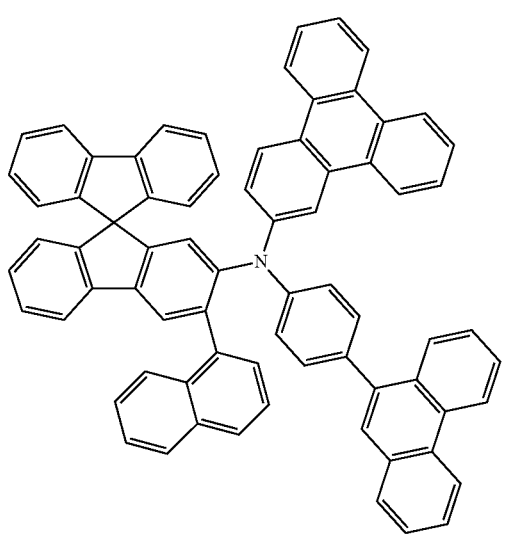

87
-continued
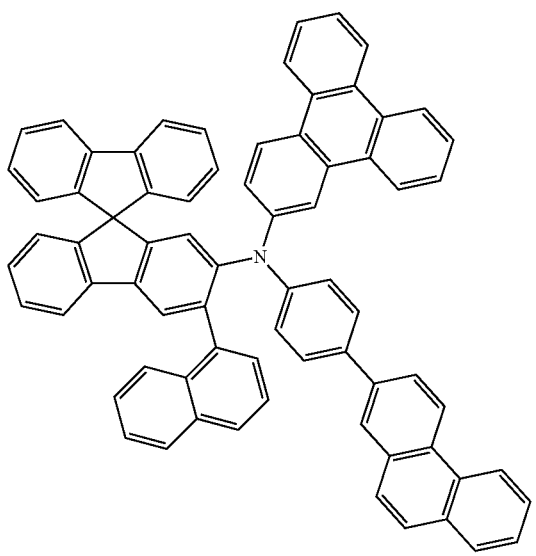
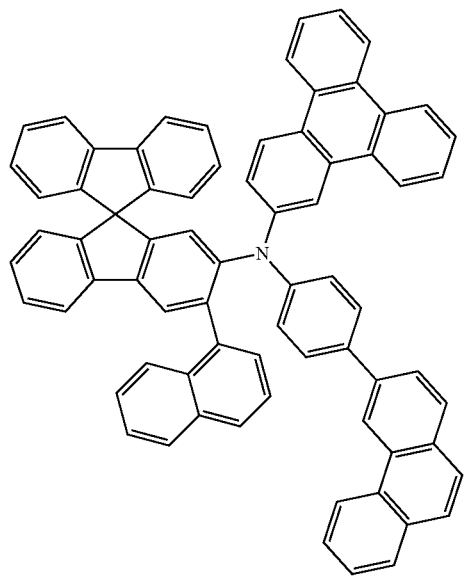
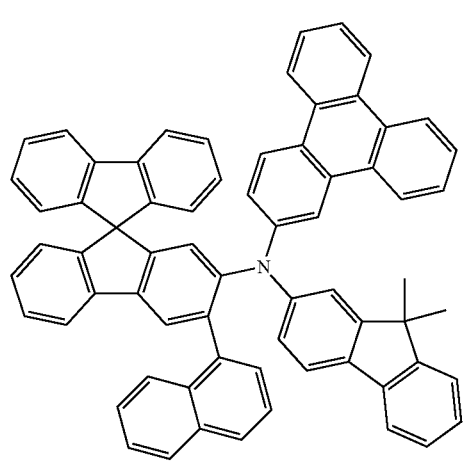
88
-continued
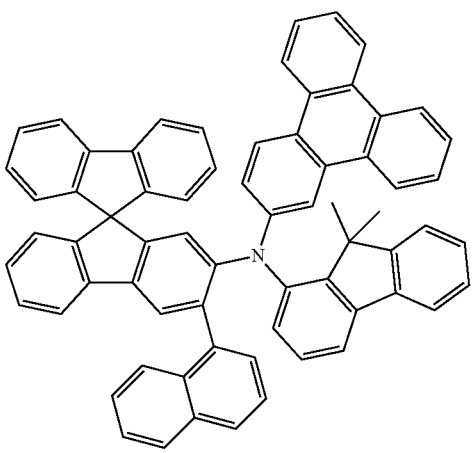
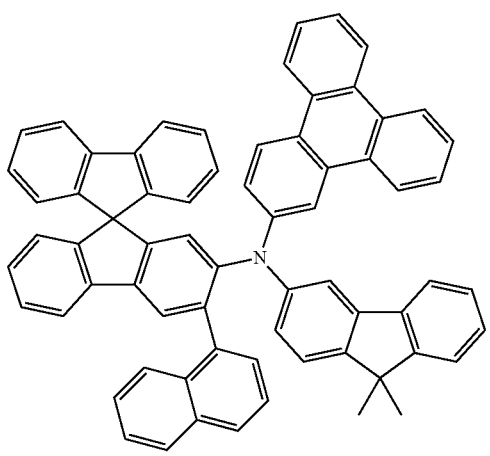
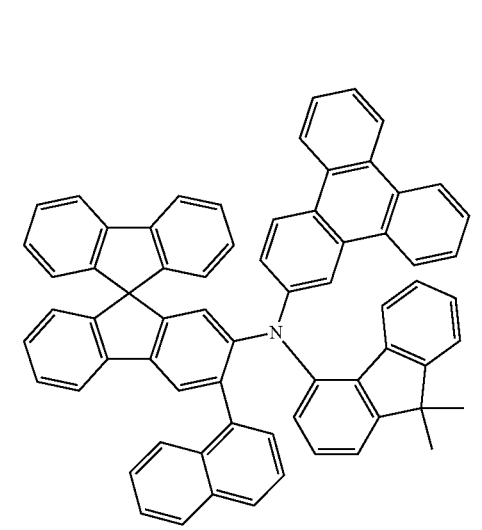

89
-continued
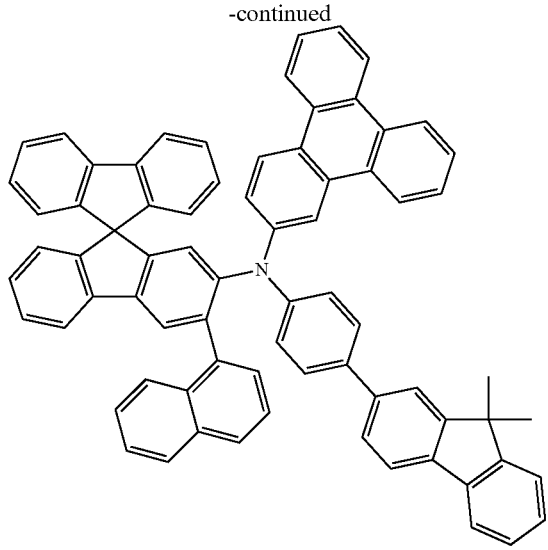
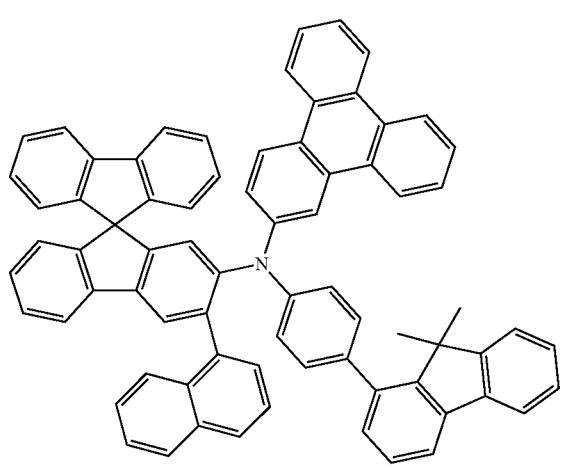
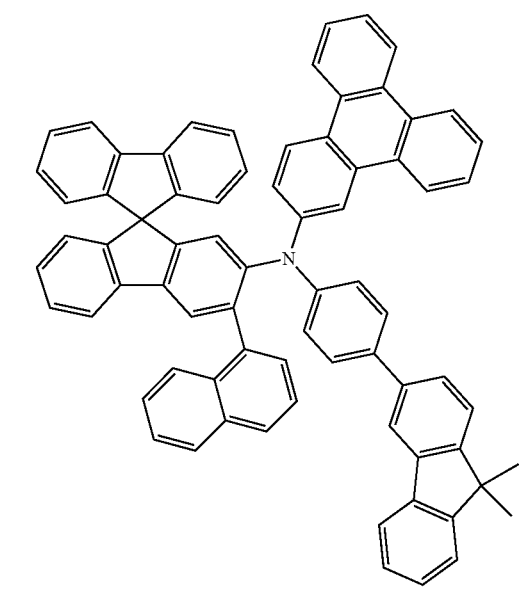
90
-continued
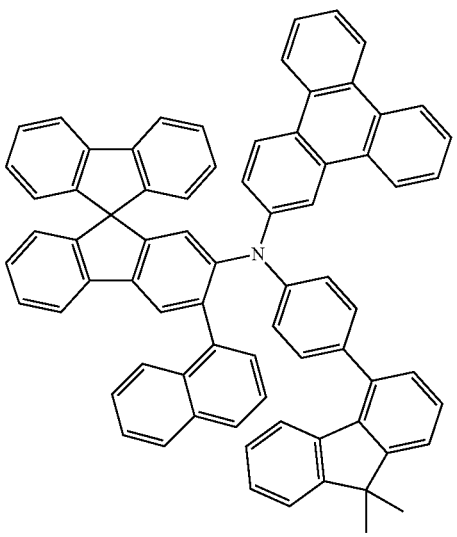
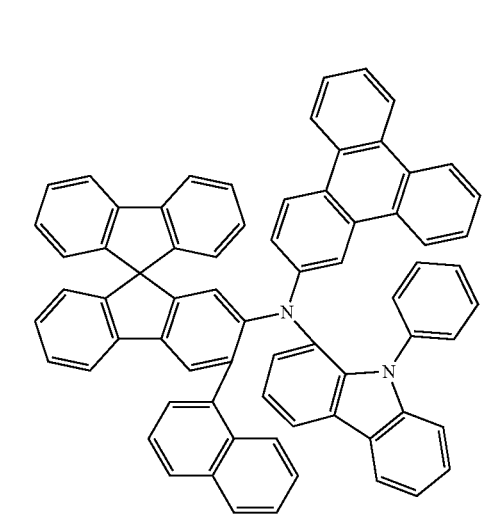

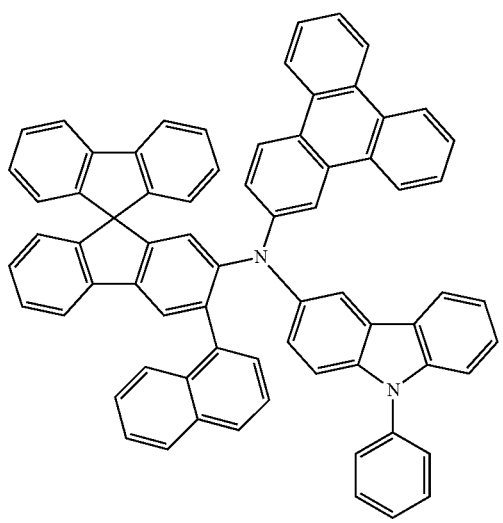
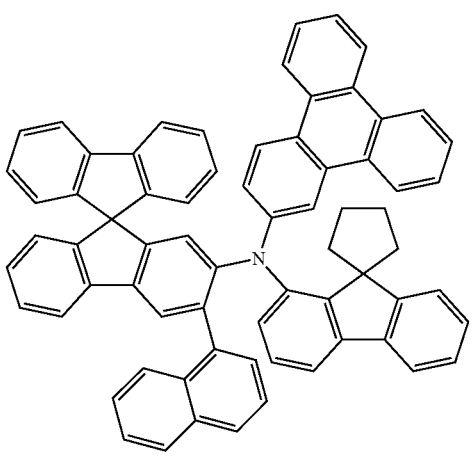
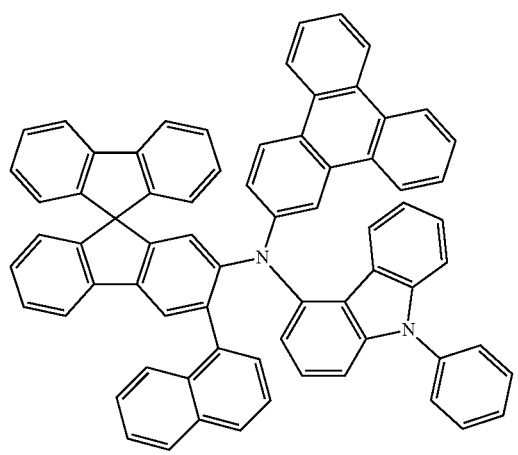
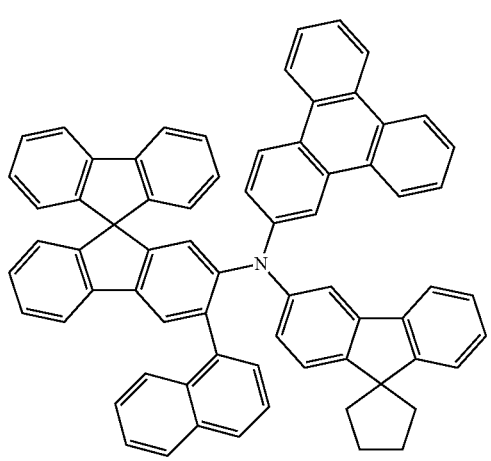
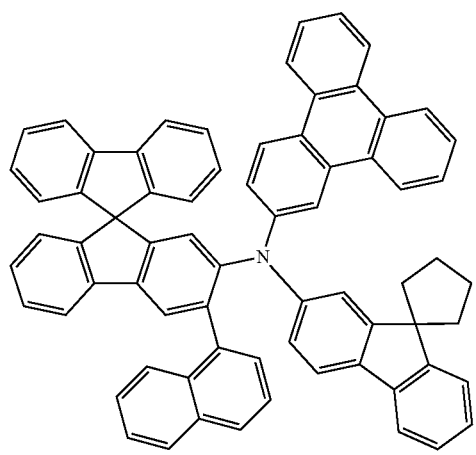
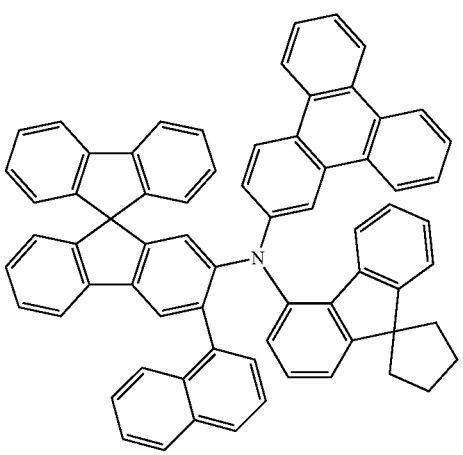

93
-continued
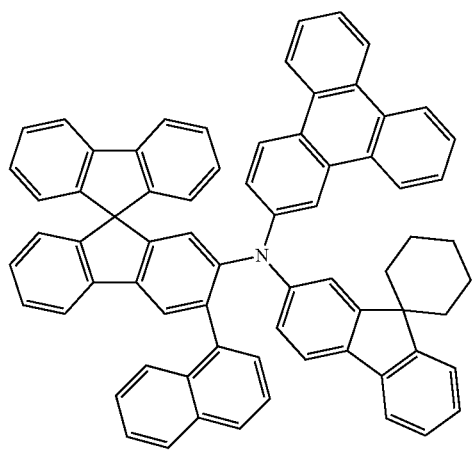
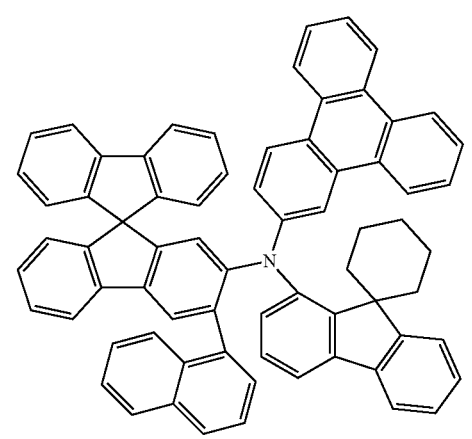
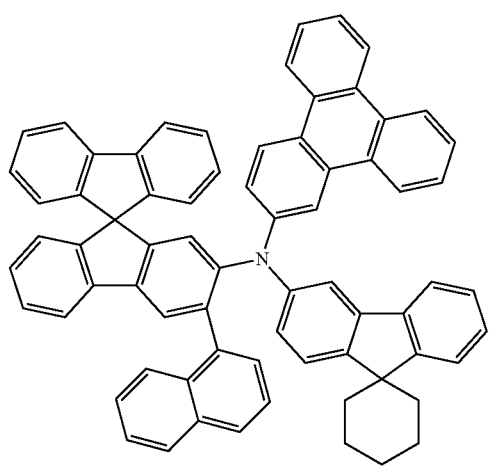
94
-continued
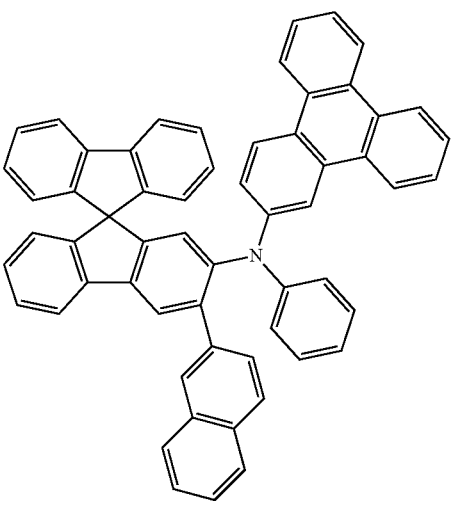
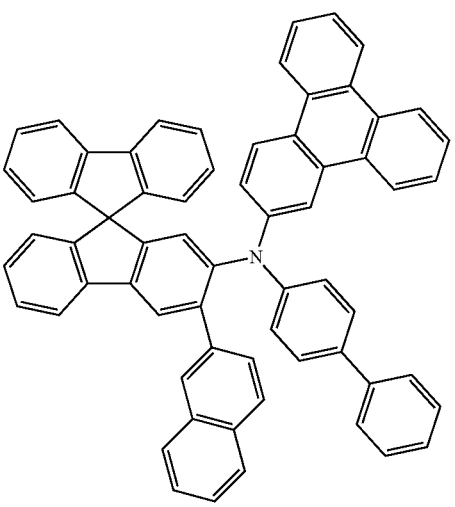
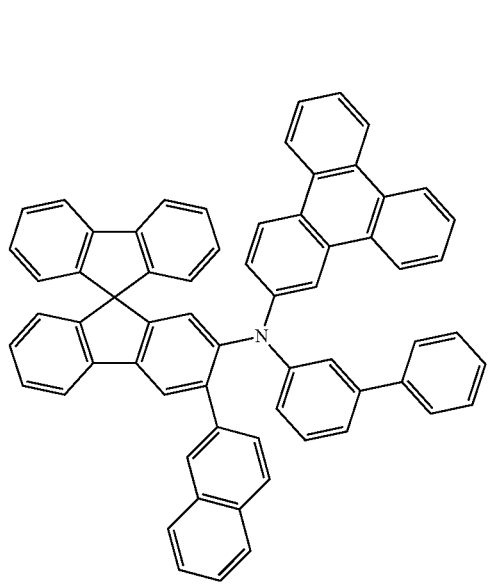

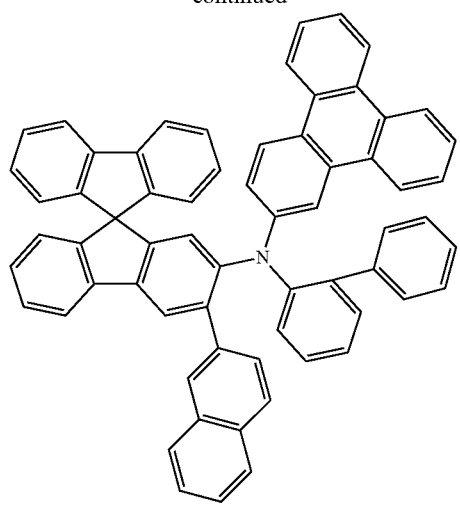
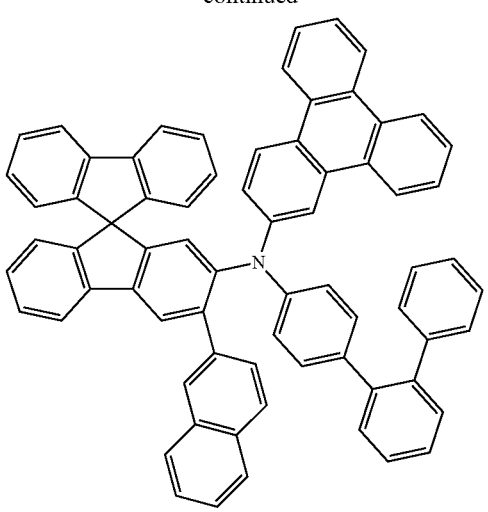
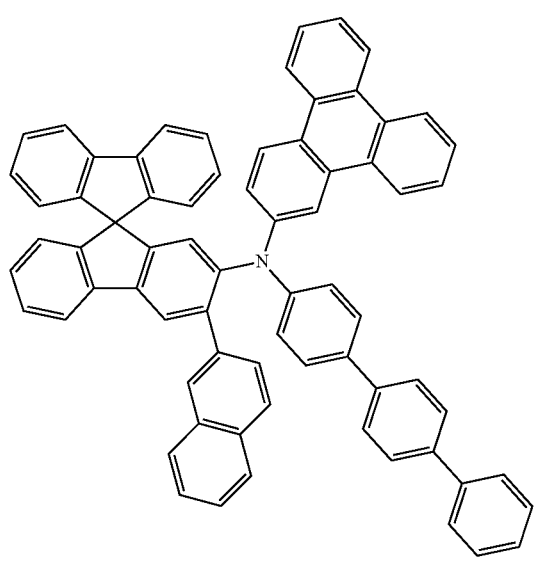
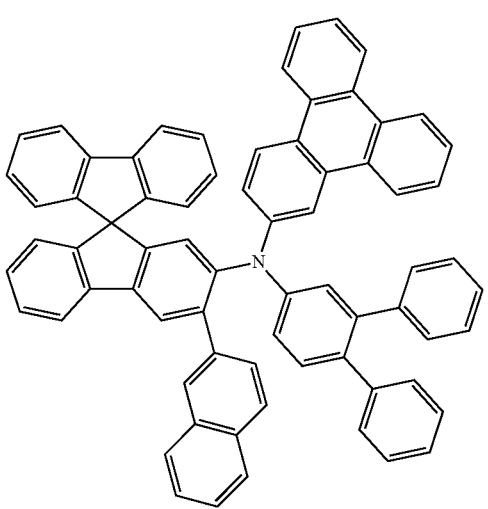
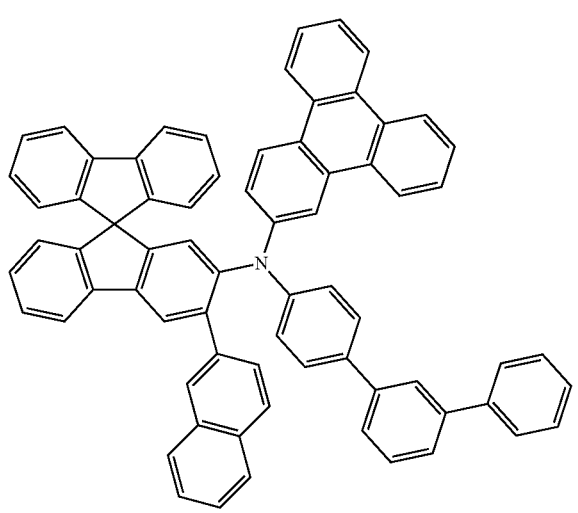
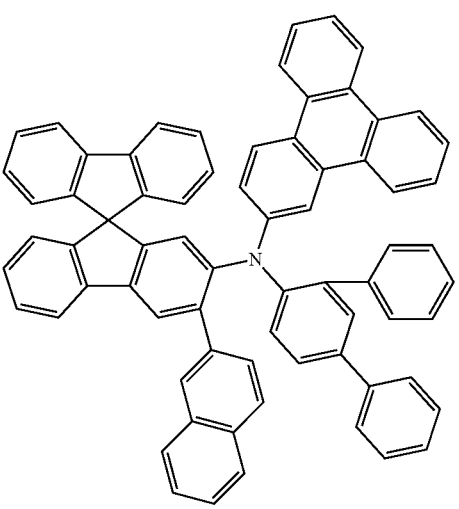

97
-continued
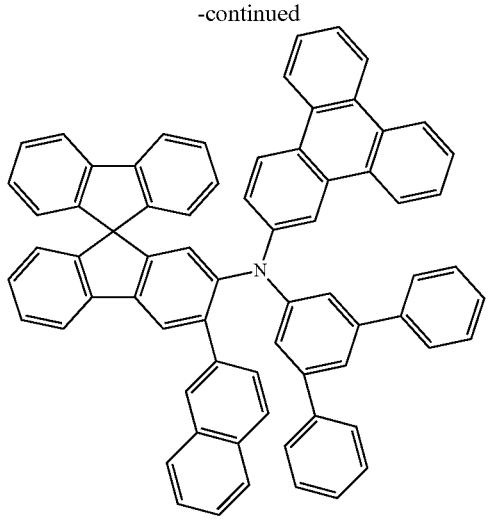
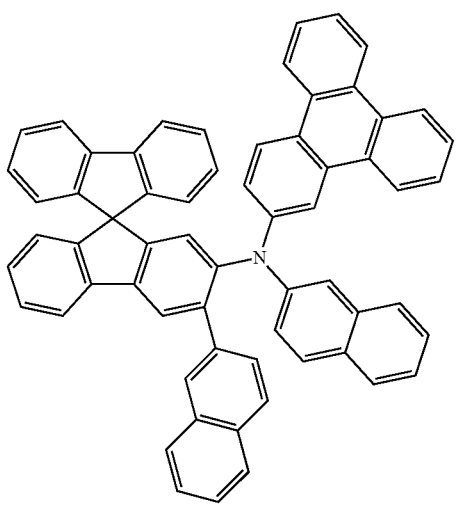
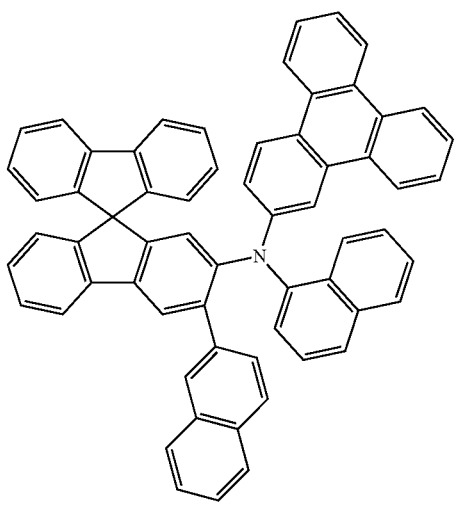
98
-continued
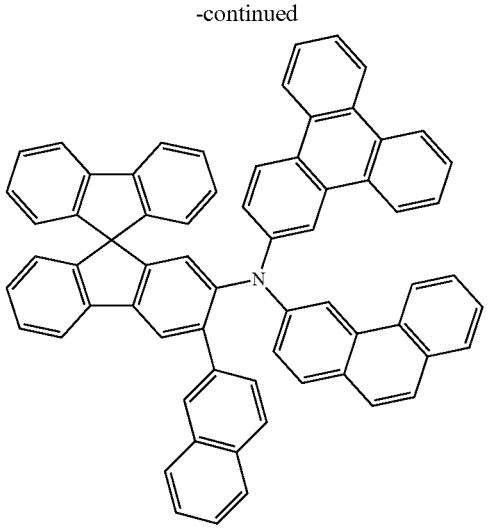
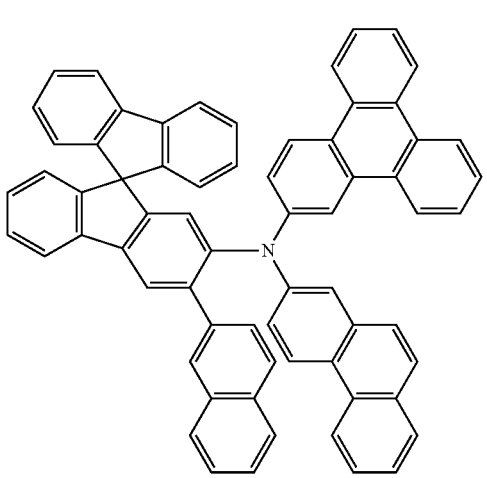
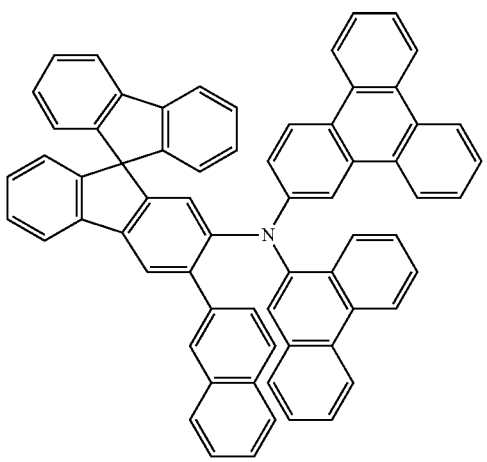

-continued
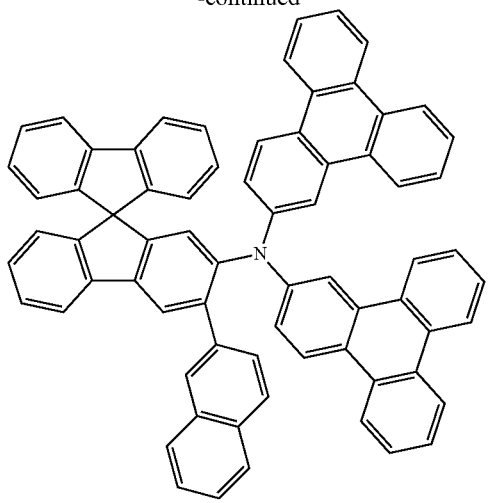
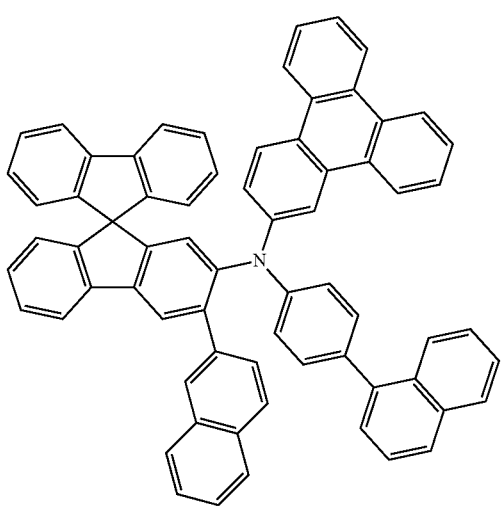
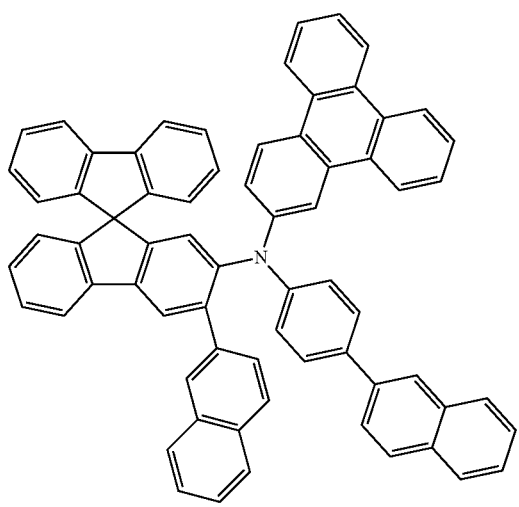
-continued
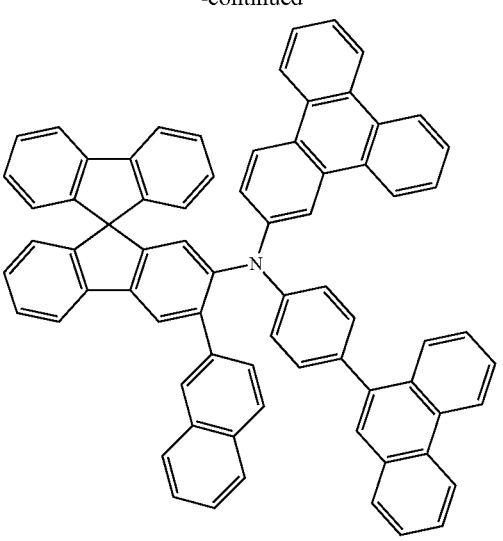
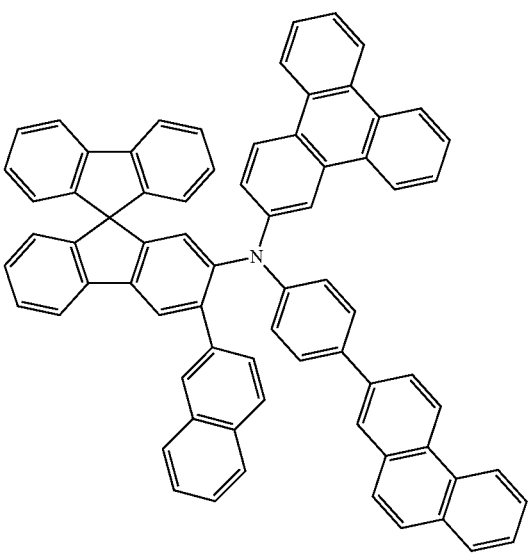

101
-continued
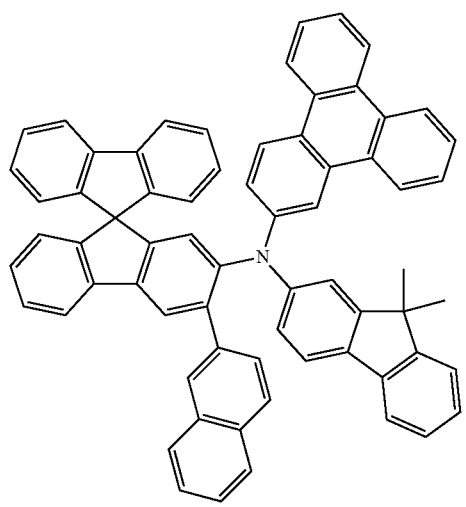
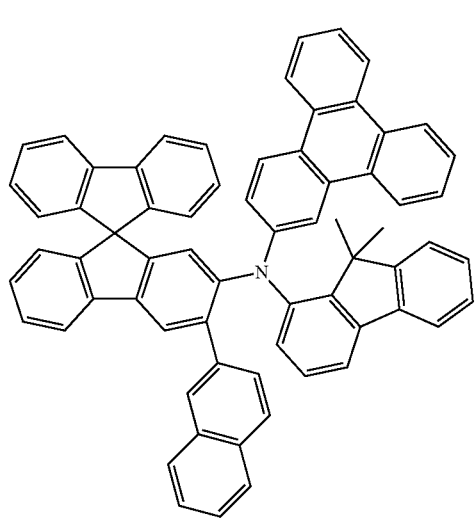
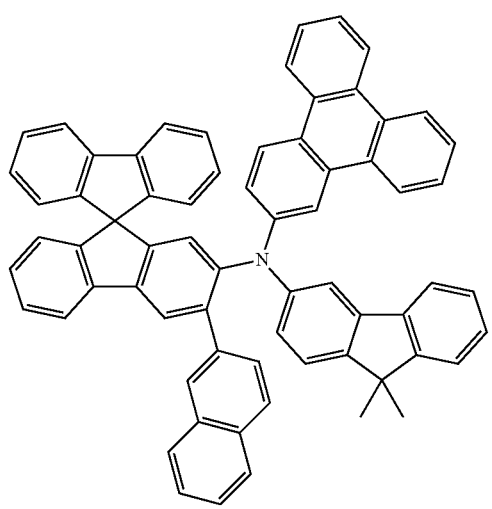
102
-continued
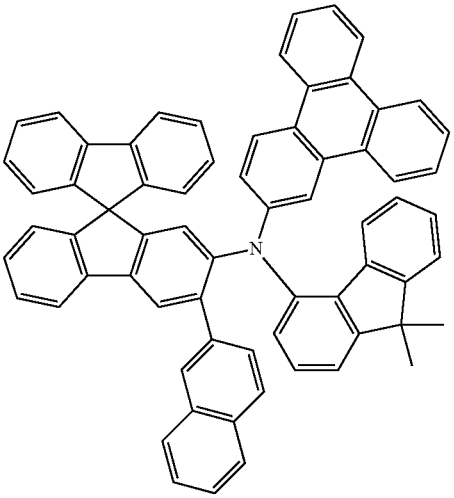
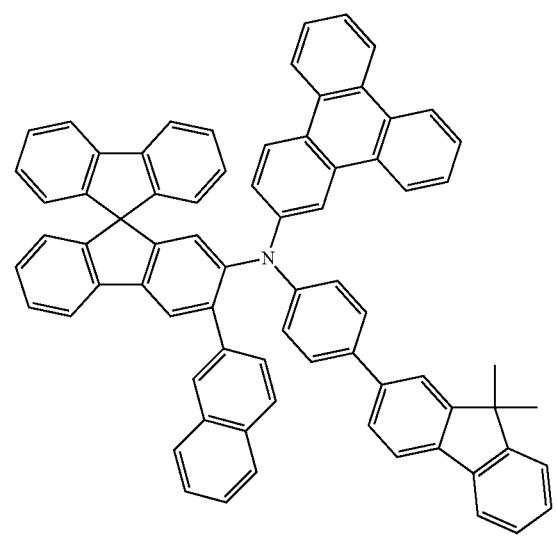
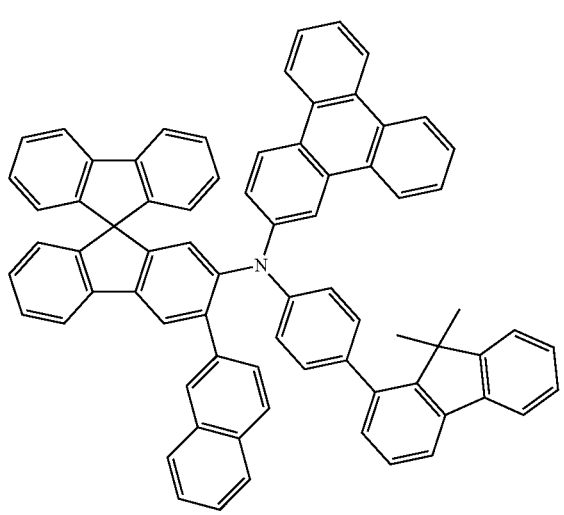

103
-continued
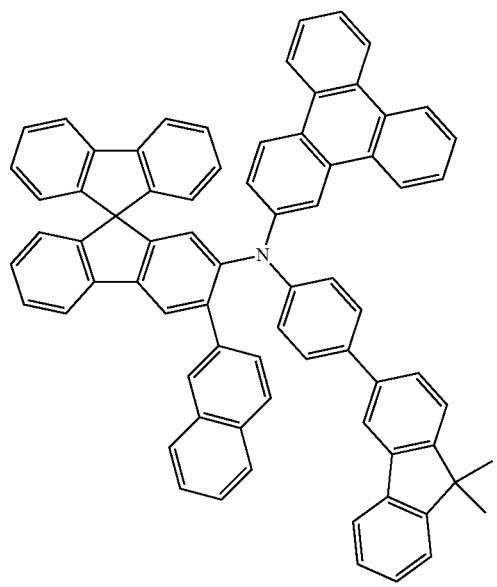
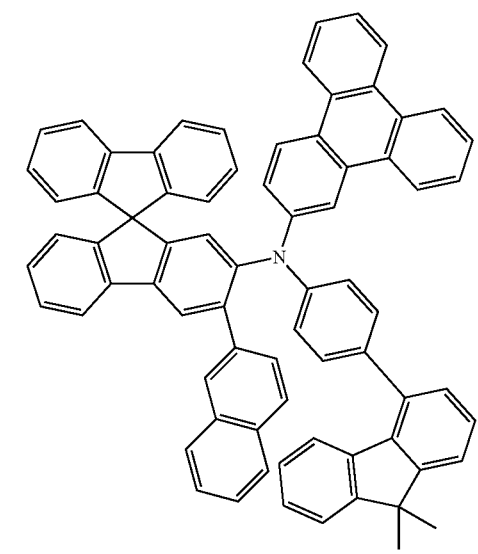
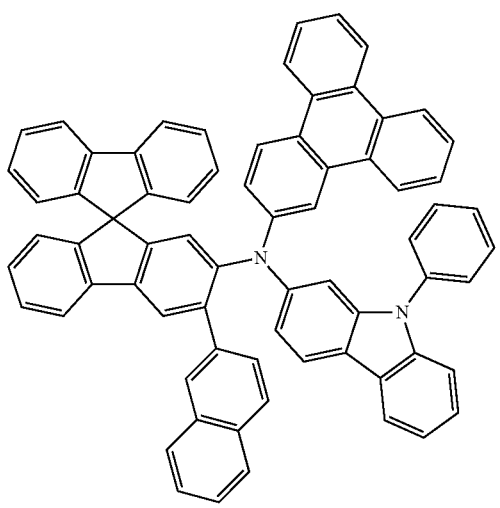
104
-continued
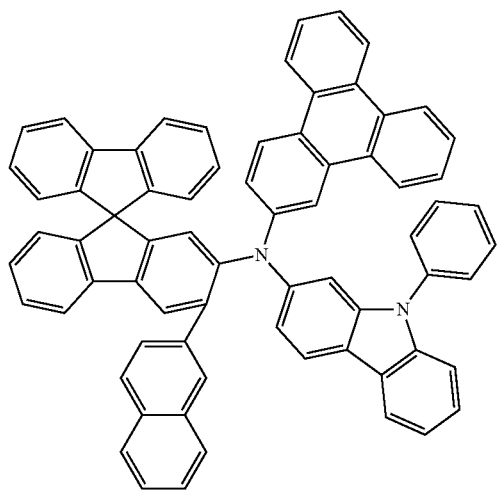
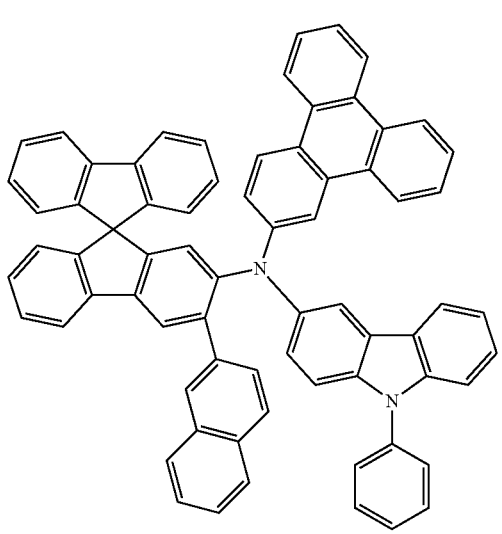
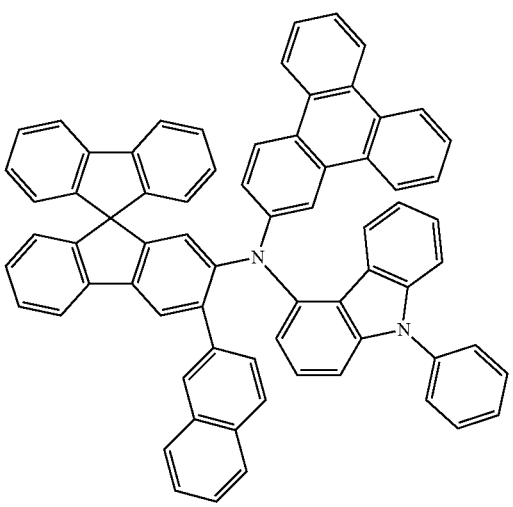

105
-continued
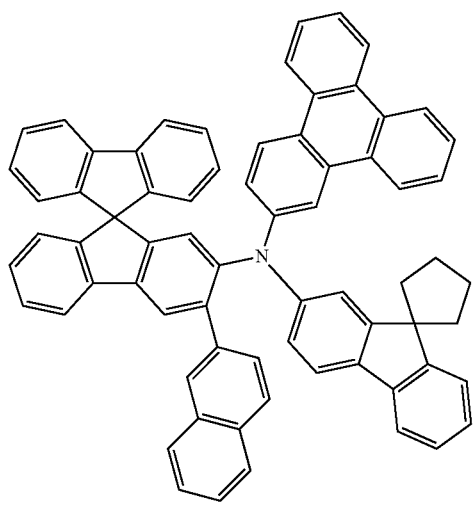
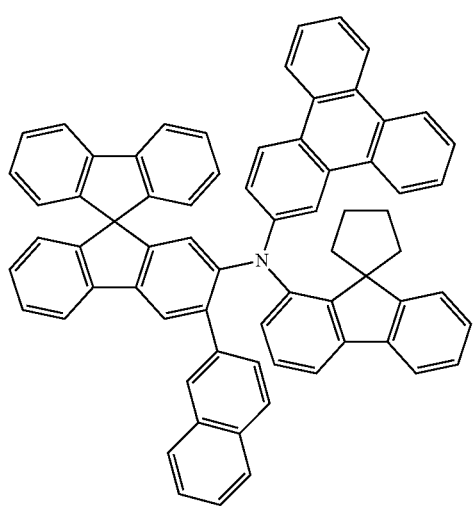
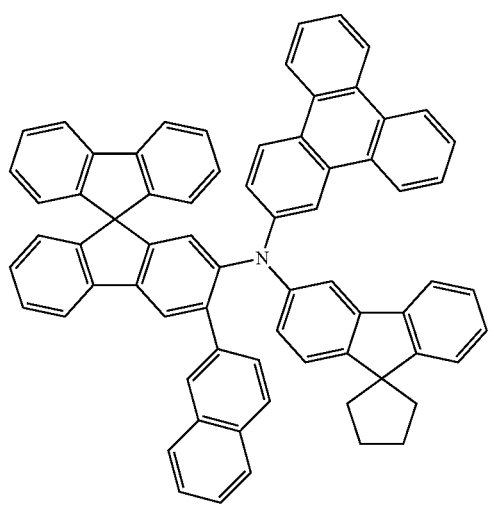
106
-continued
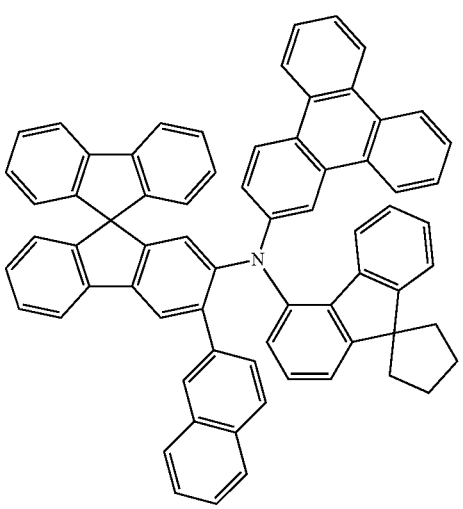
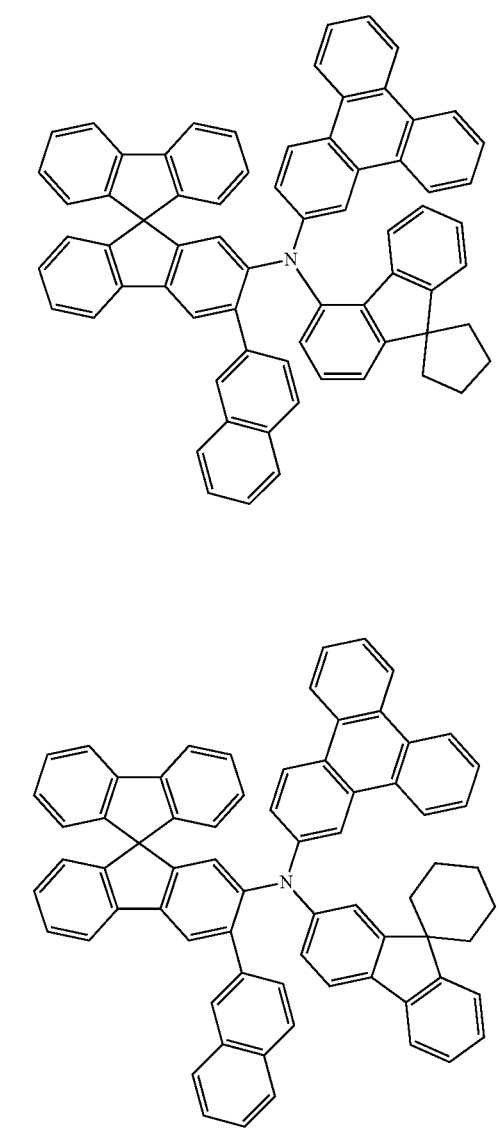
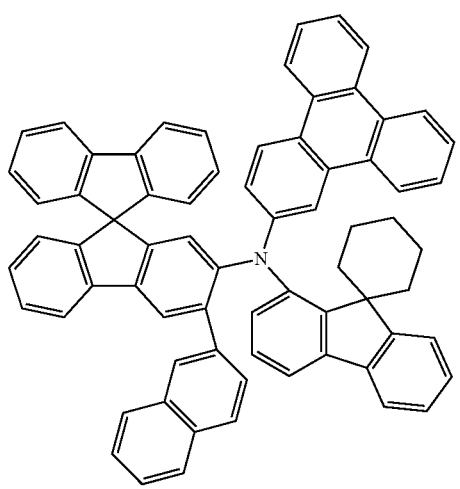

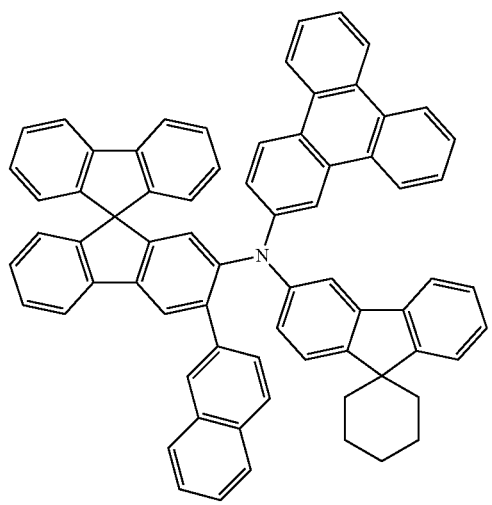
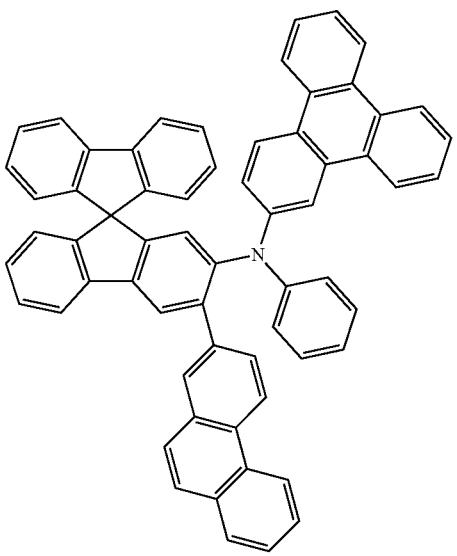
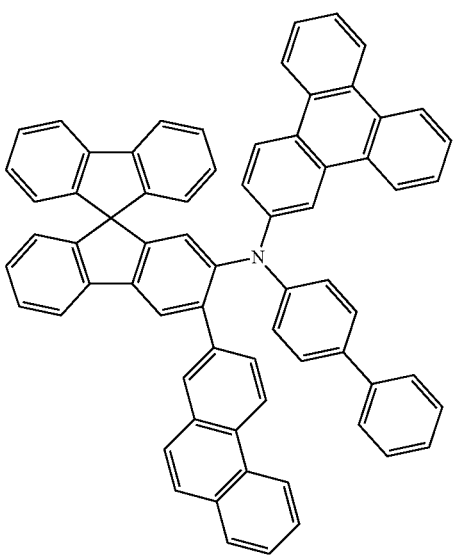
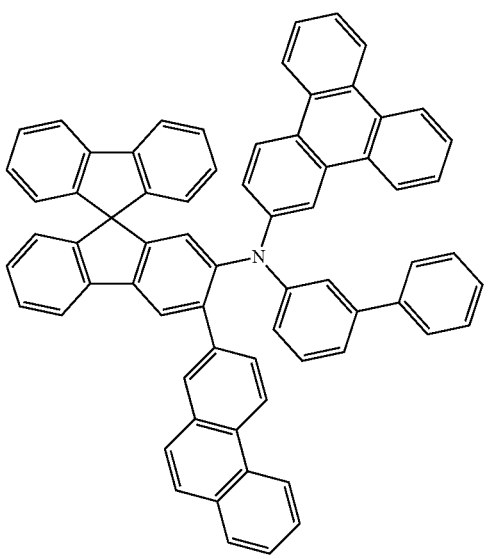
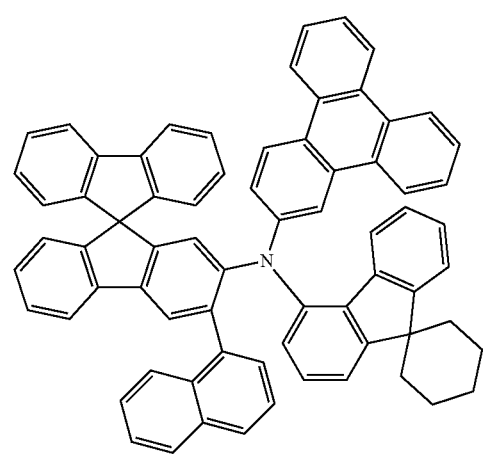

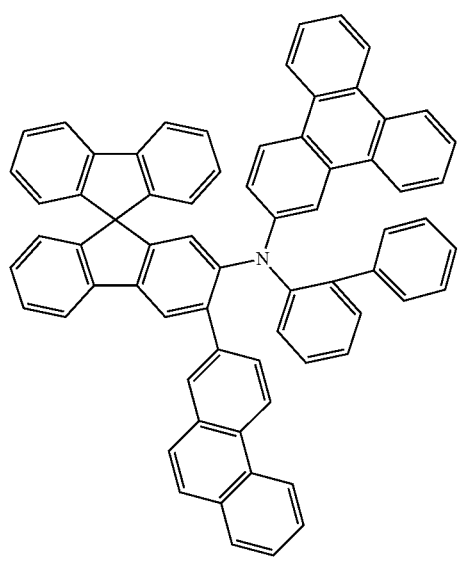
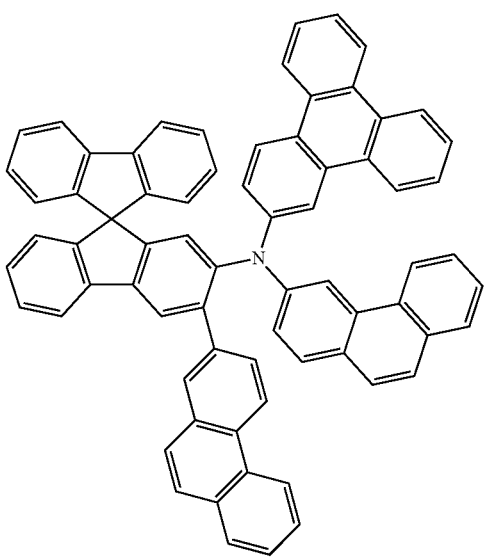
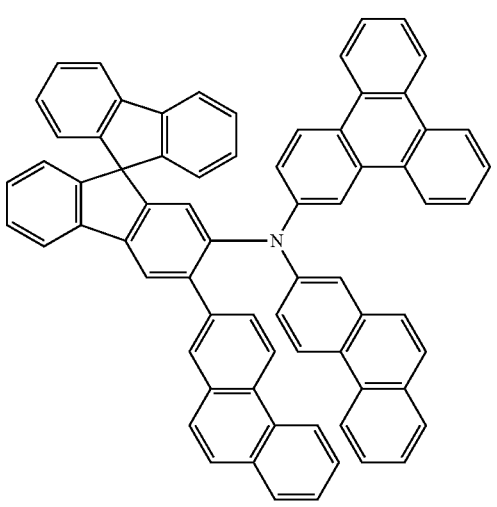
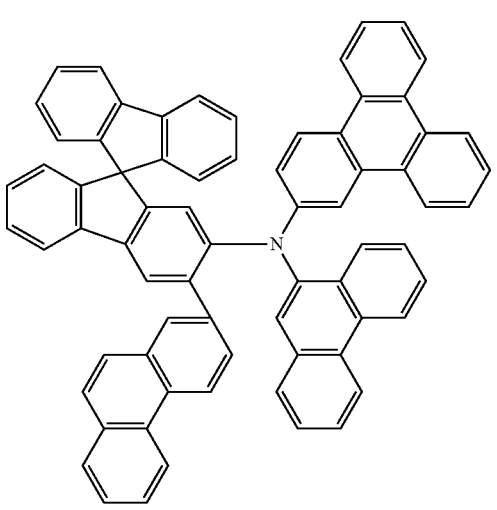

111 -continued
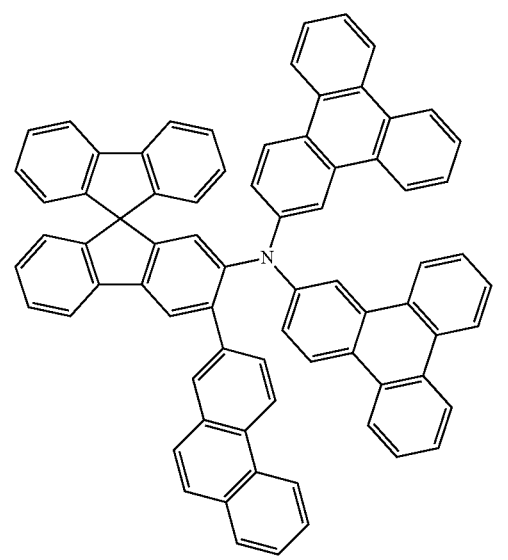
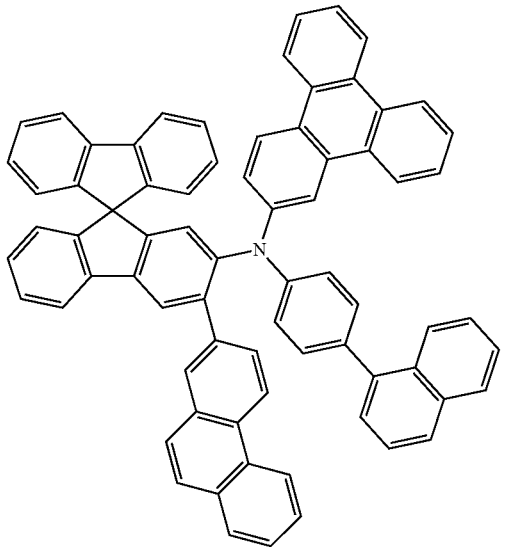
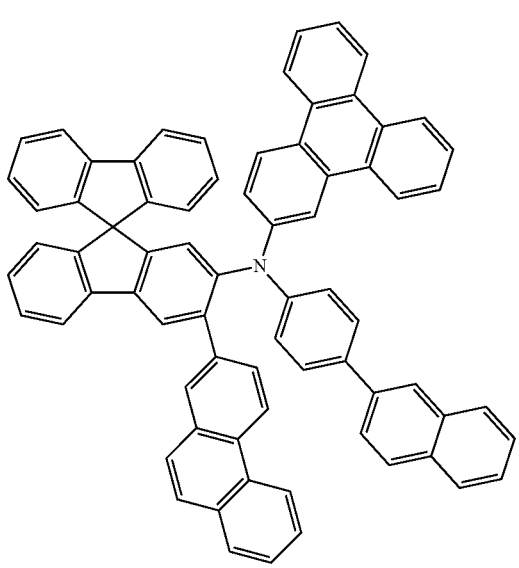
112 -continued
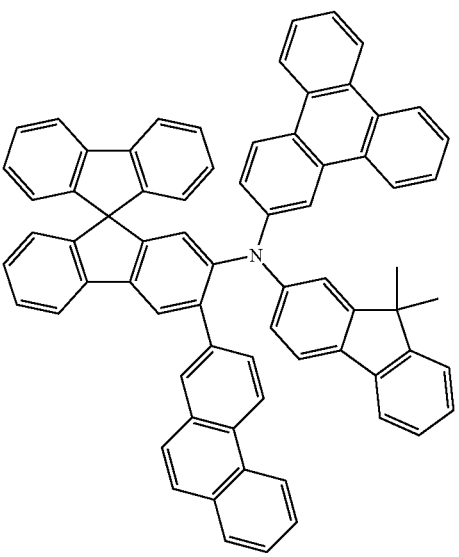
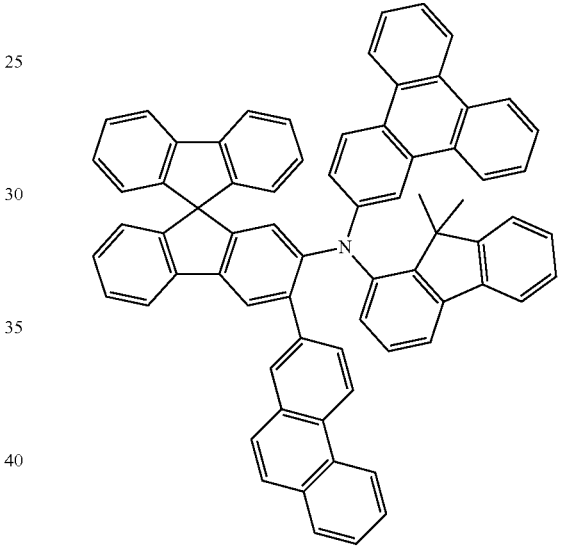
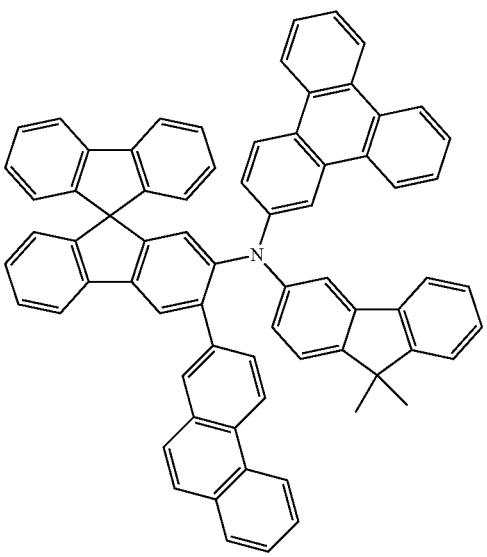

113
-continued
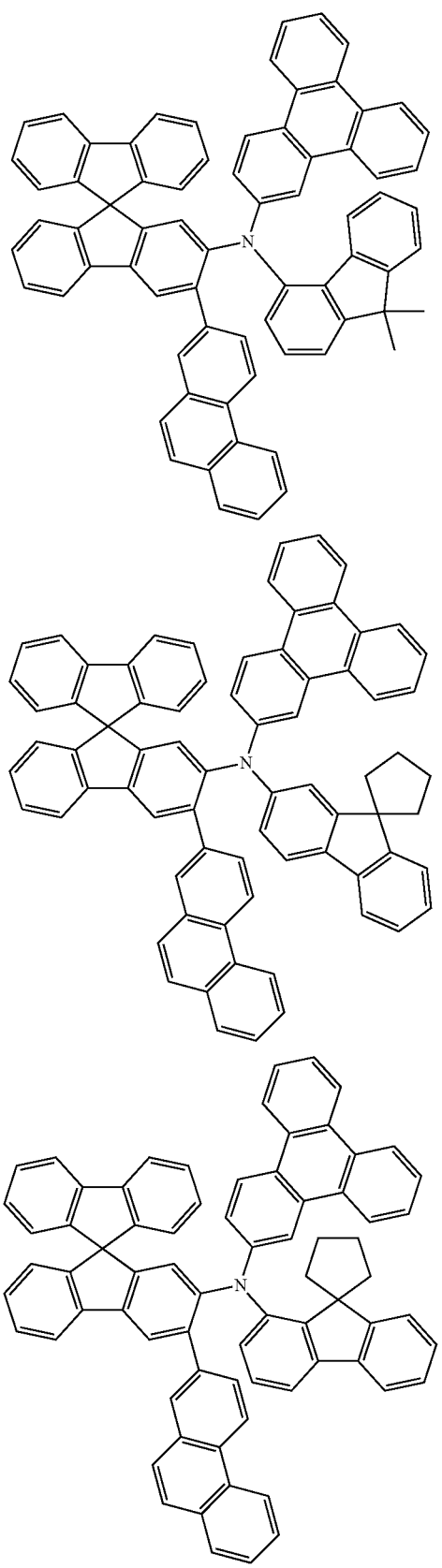
114
-continued
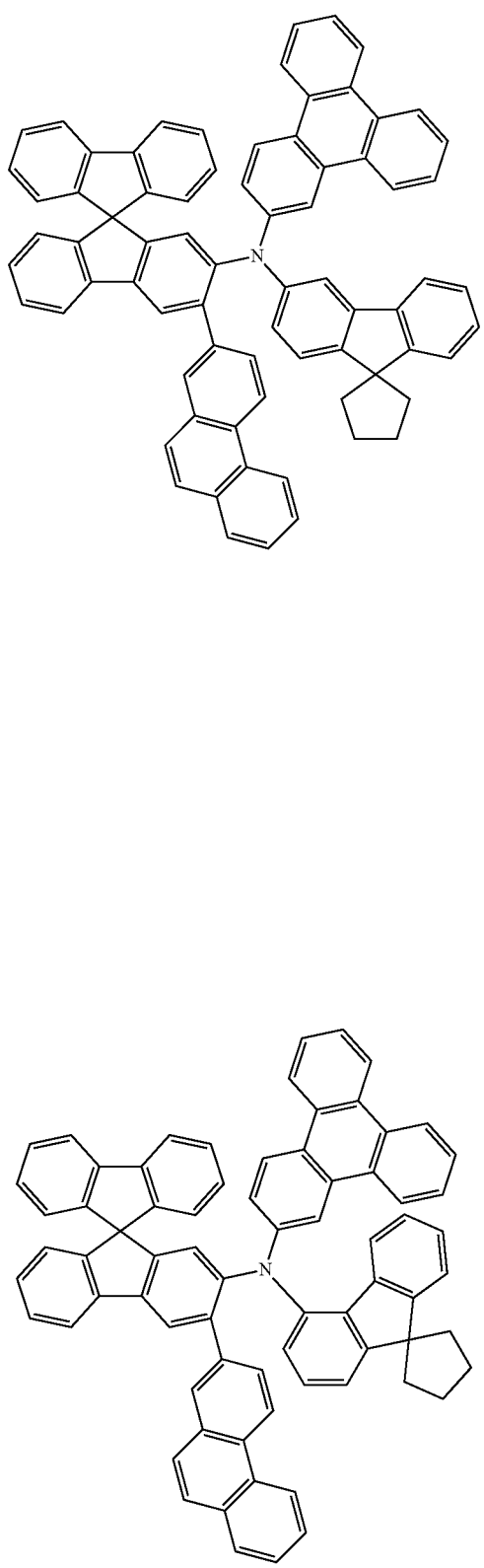

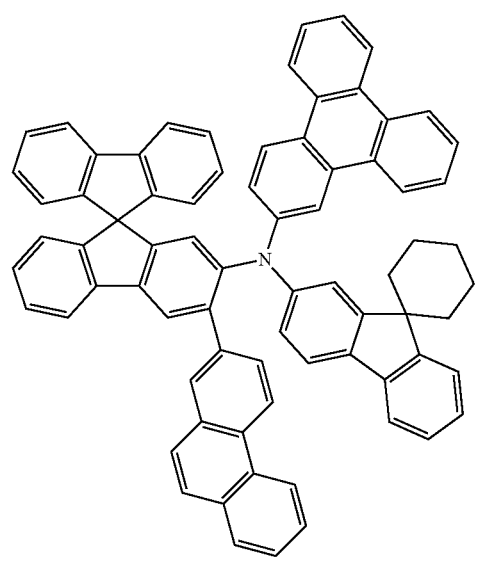
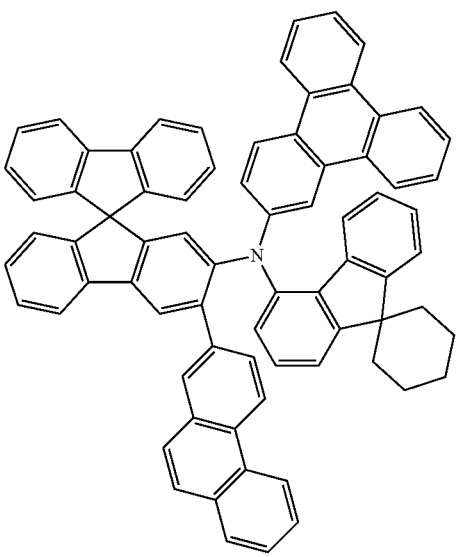
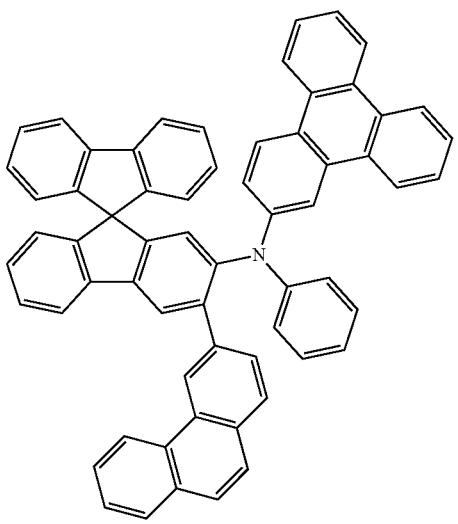
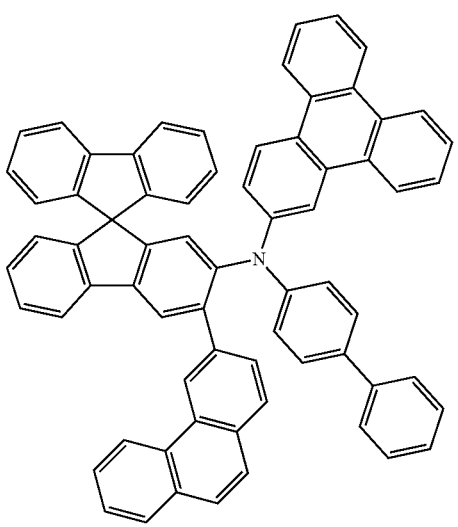

117
-continued
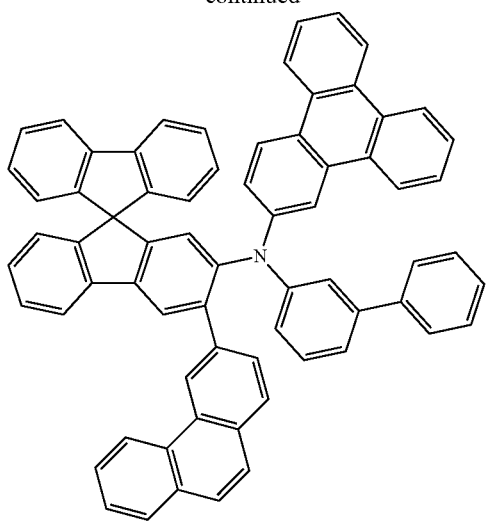
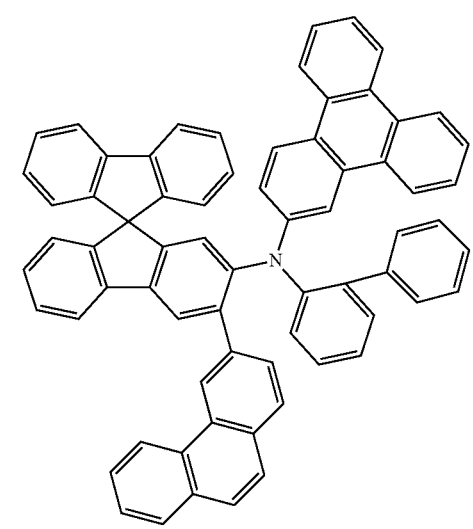
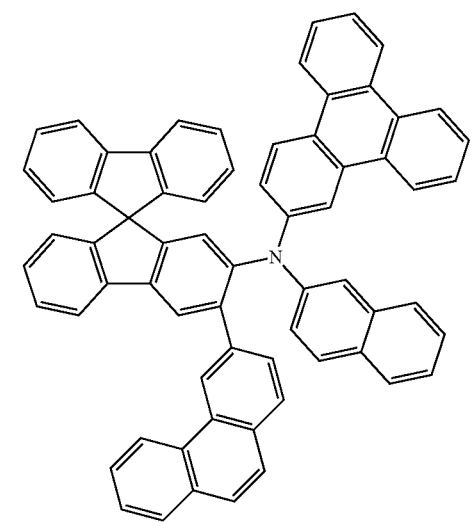
118
-continued
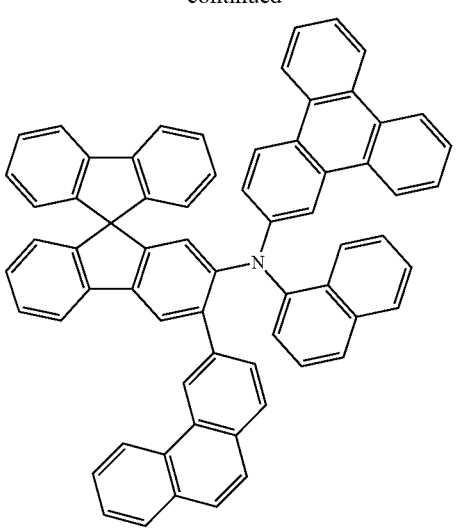
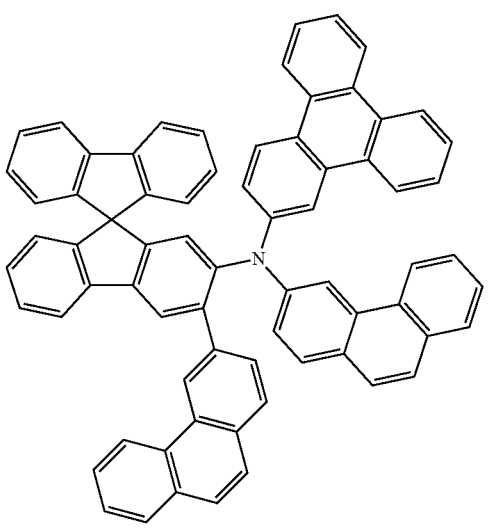
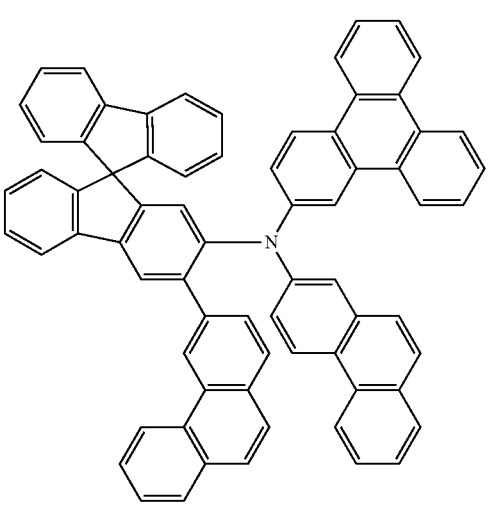

119
-continued
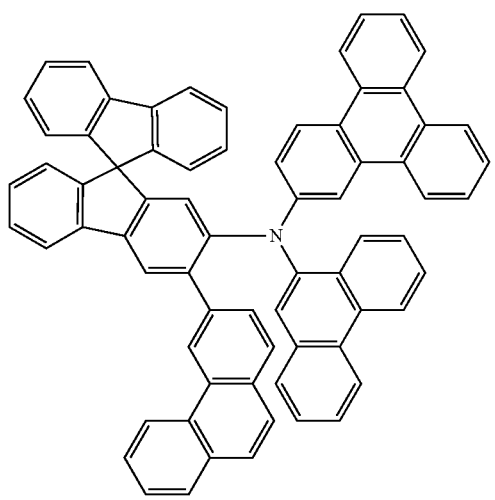
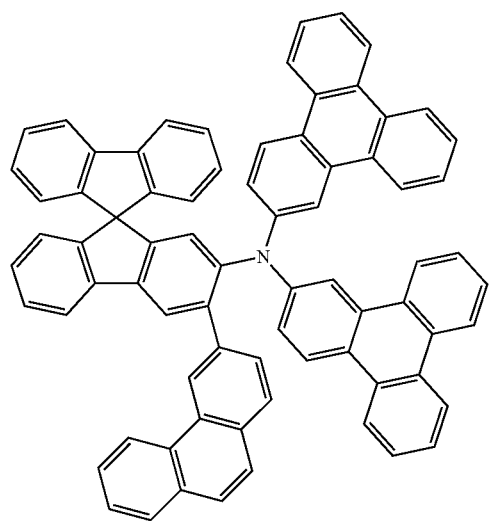
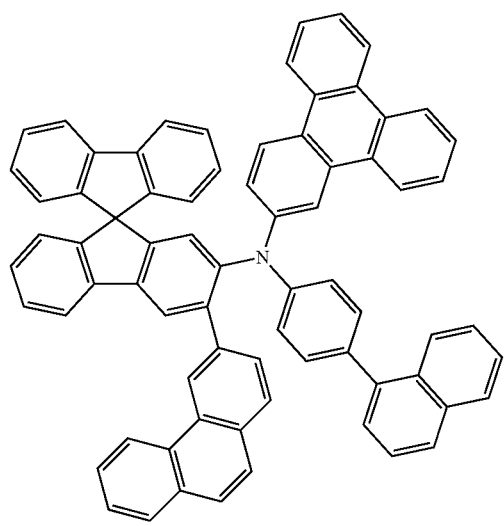
120
-continued
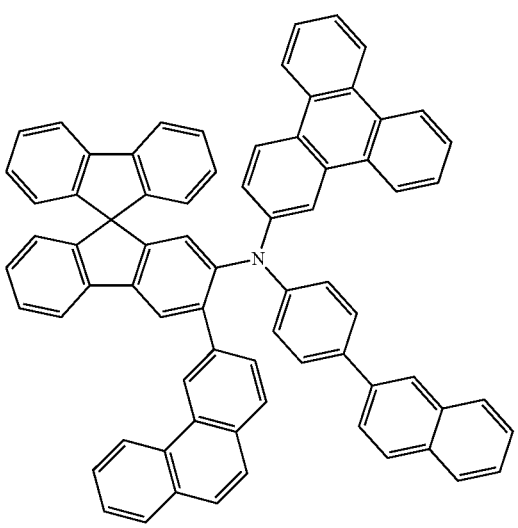
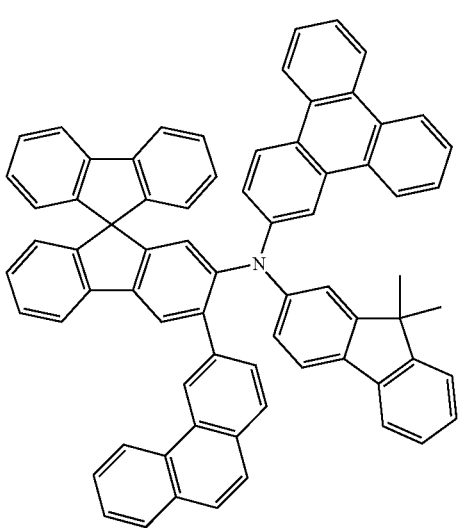
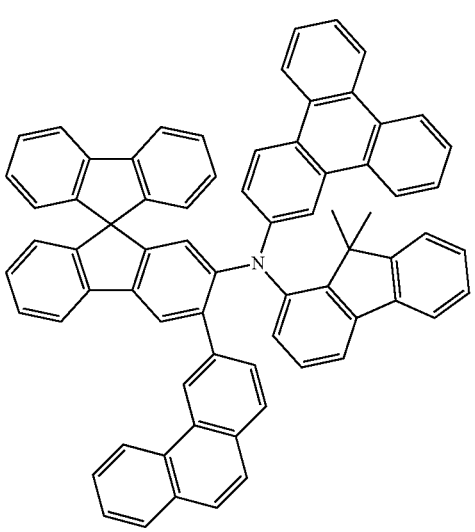

121
-continued
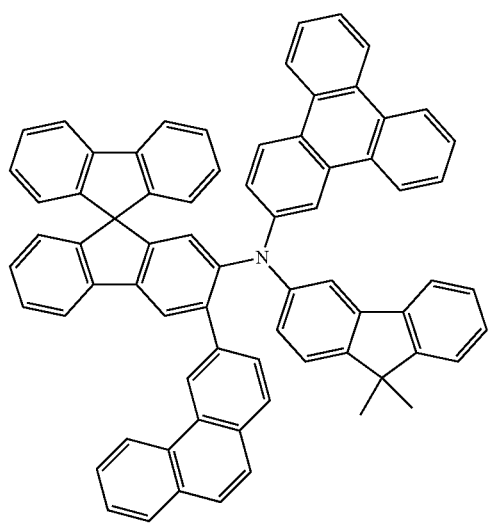
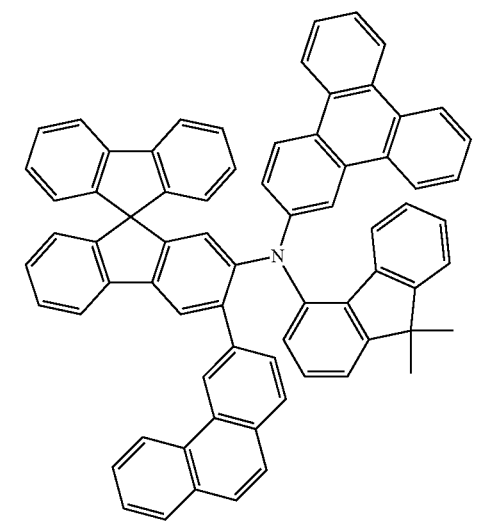
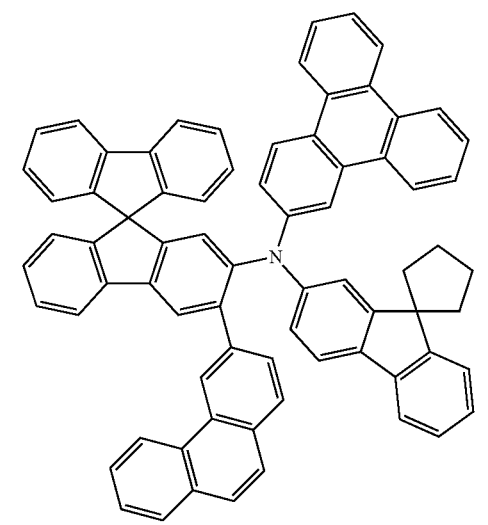
122
-continued
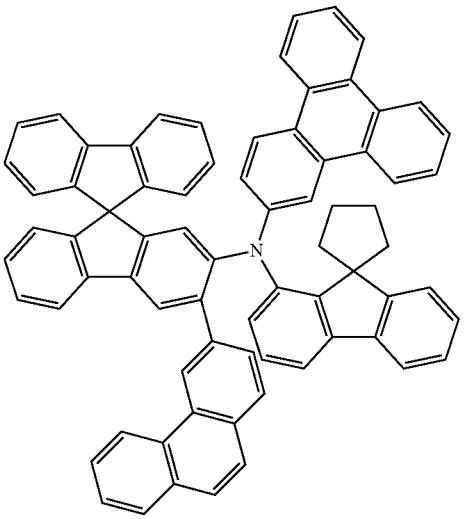
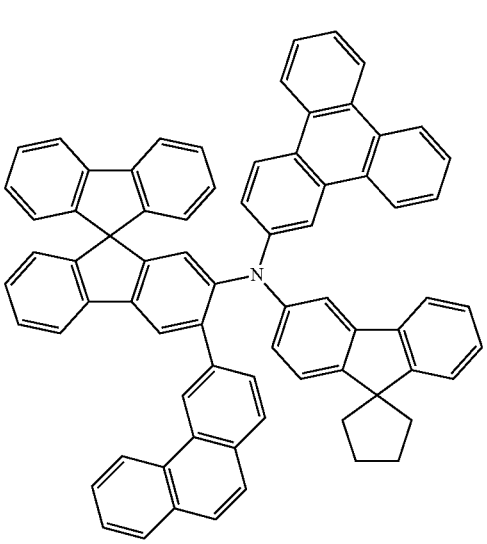
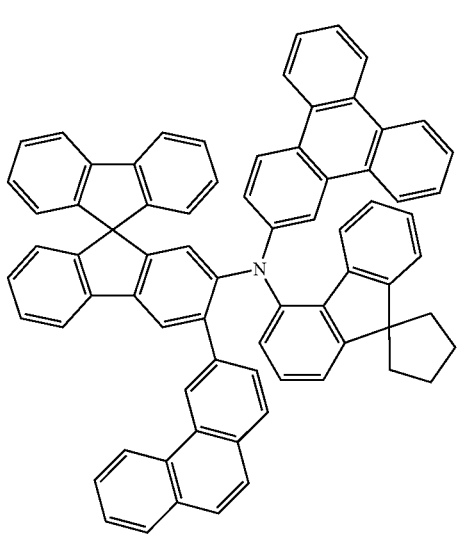

123
-continued
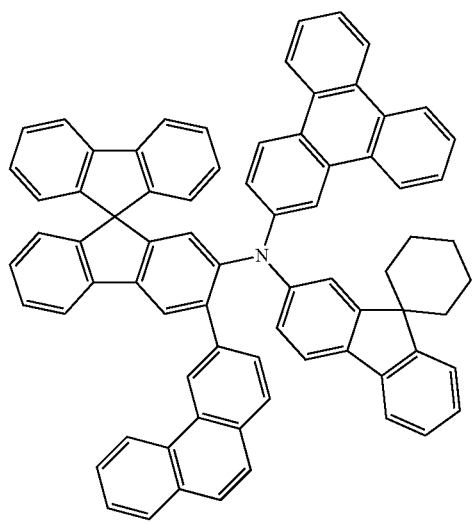
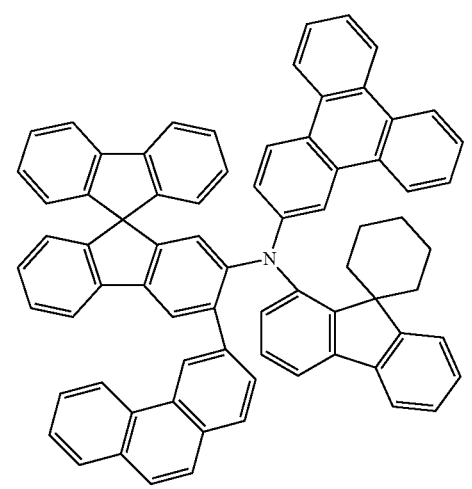
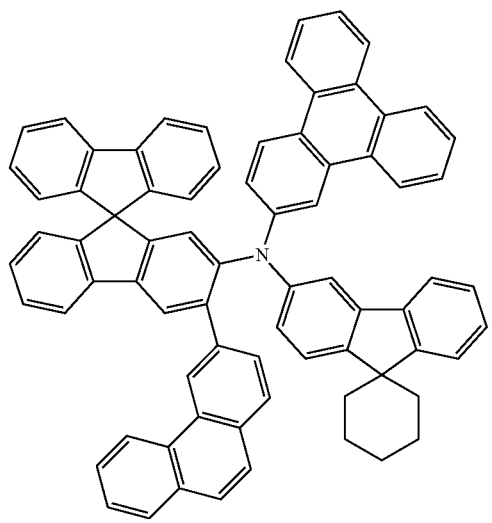
124
-continued
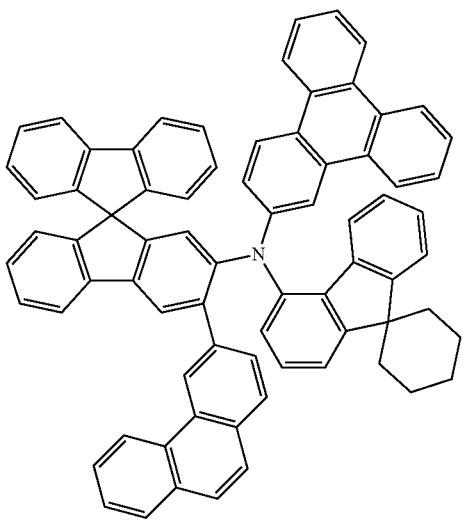
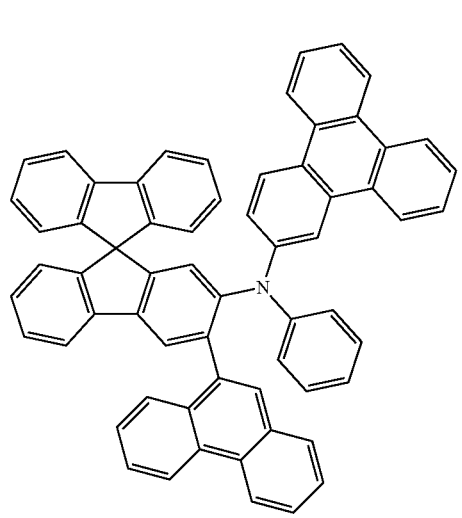
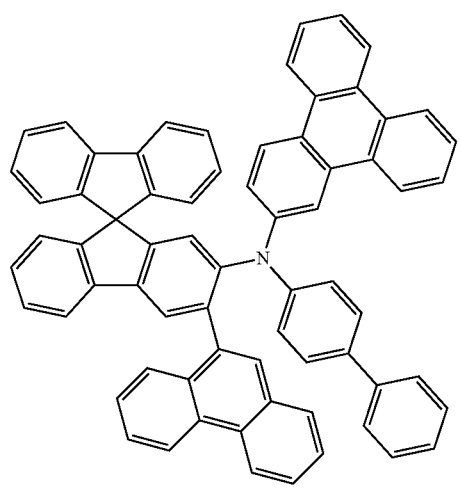

125
-continued
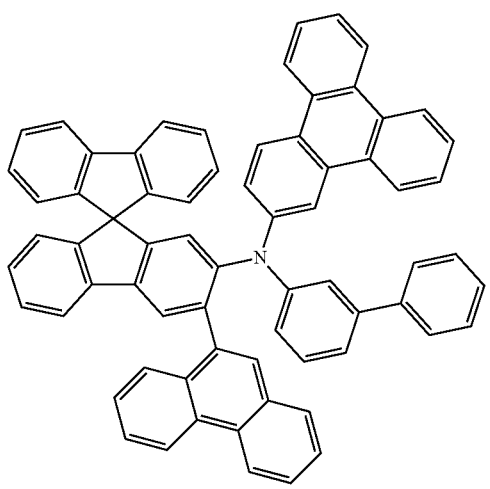
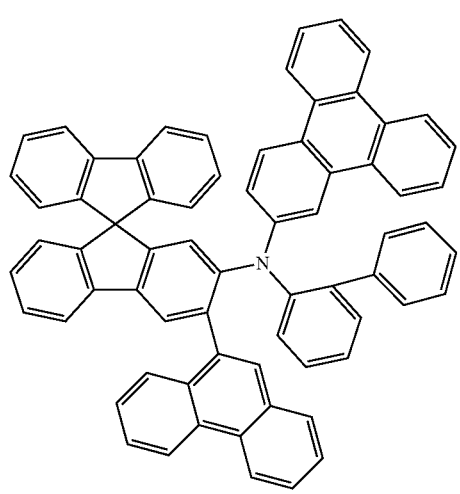
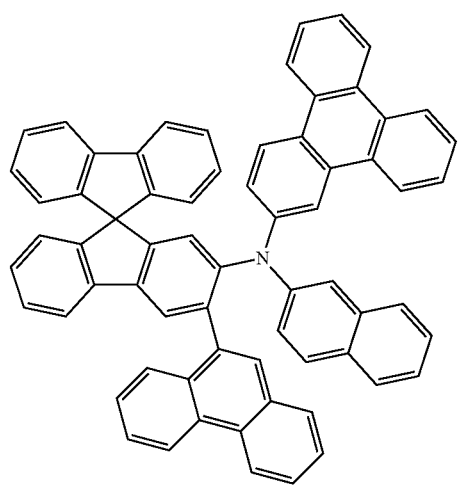
126
-continued
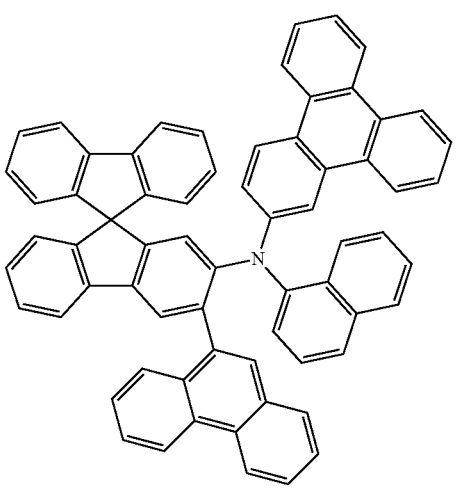
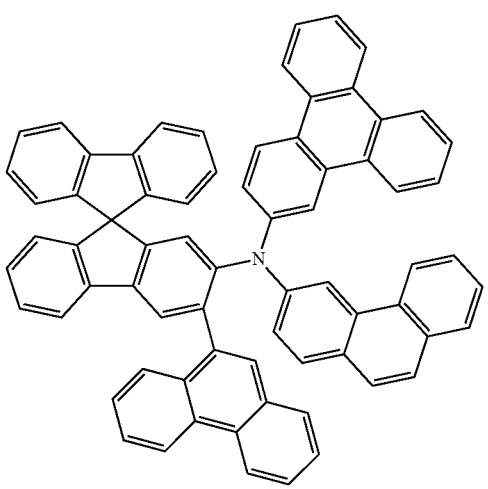
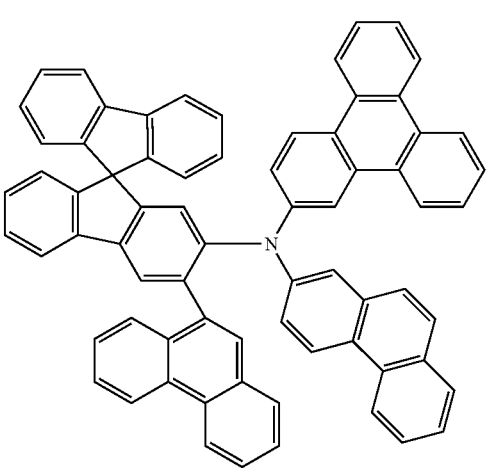

127
-continued
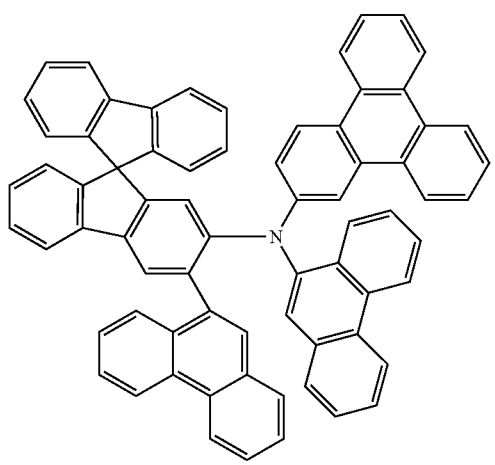
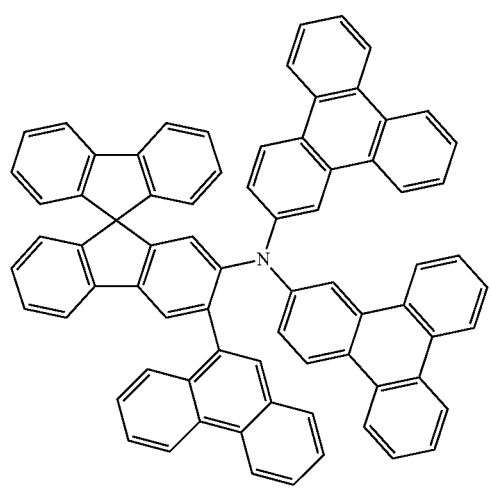
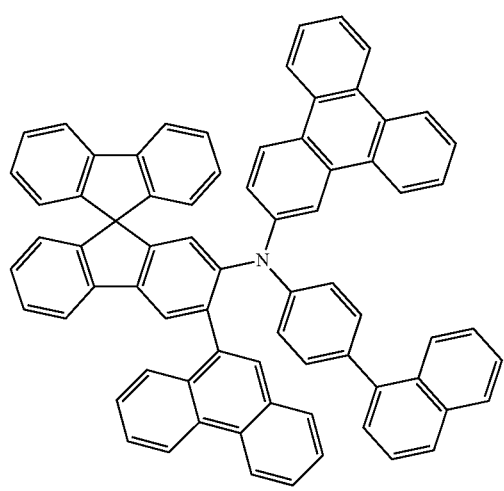
128
-continued
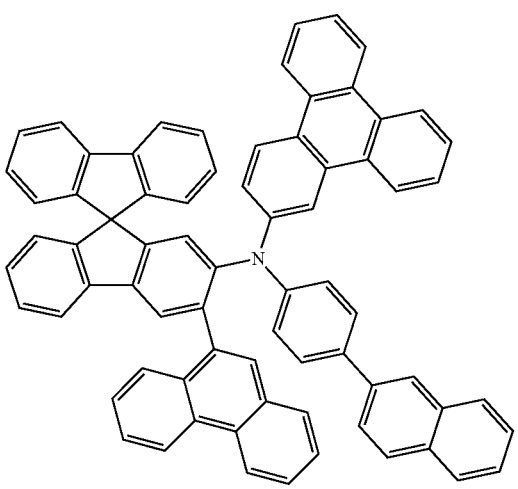
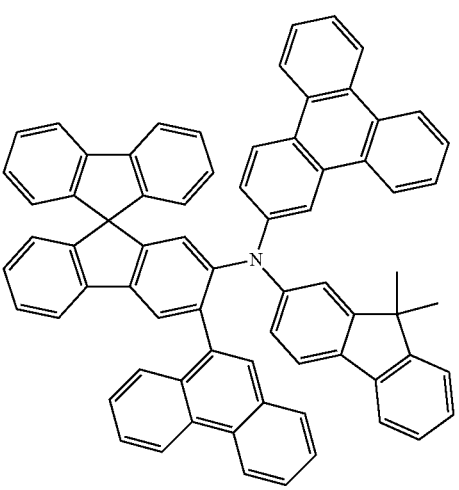
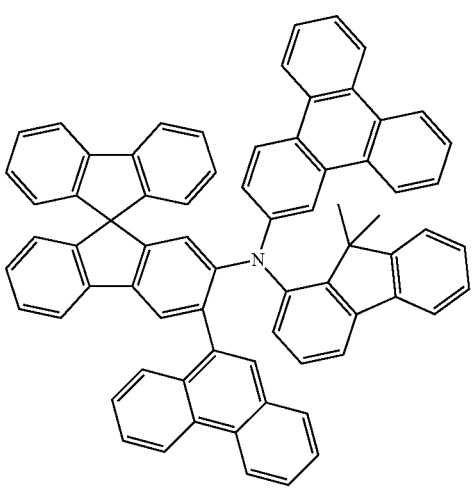

129
-continued
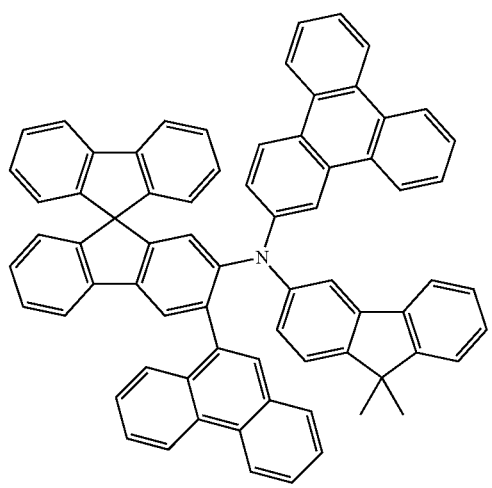
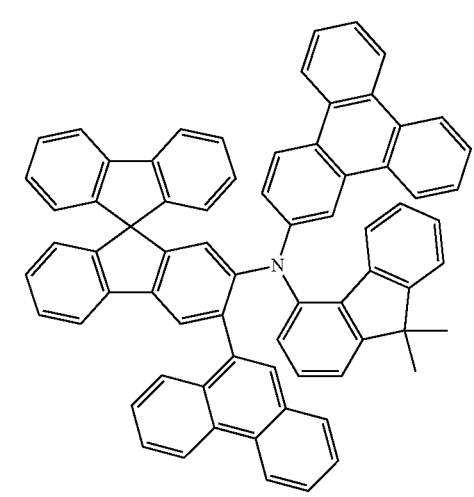
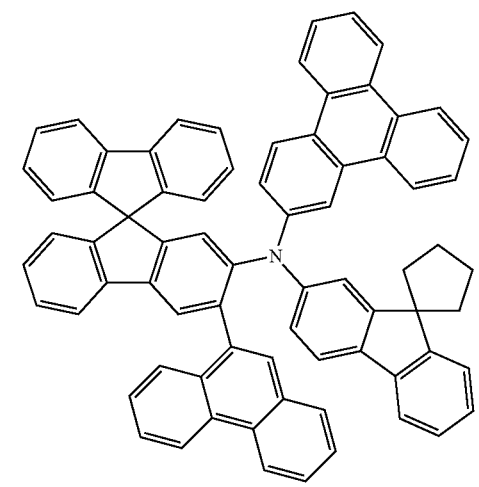
130
-continued
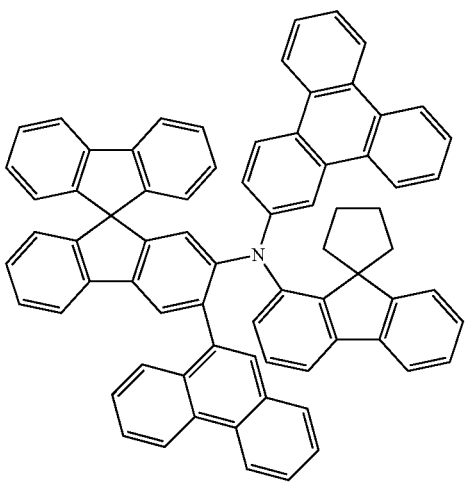
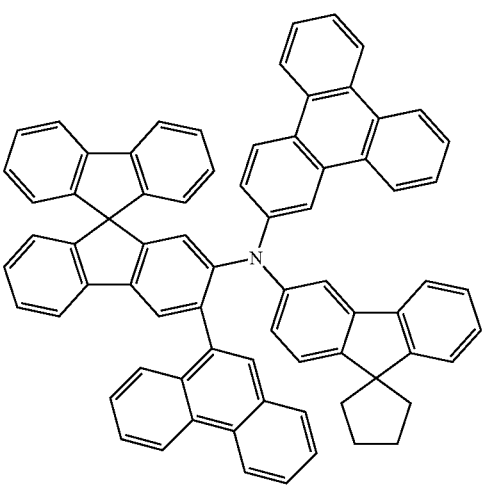
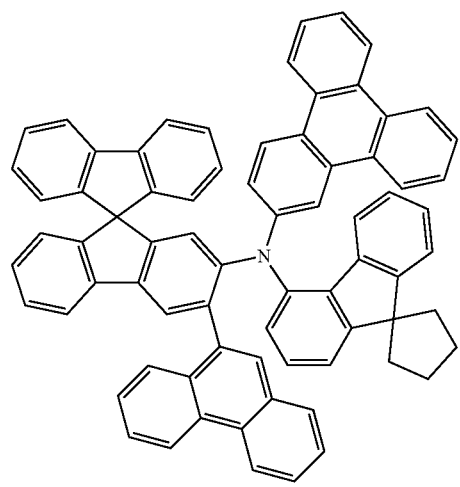

131
-continued
132
-continued
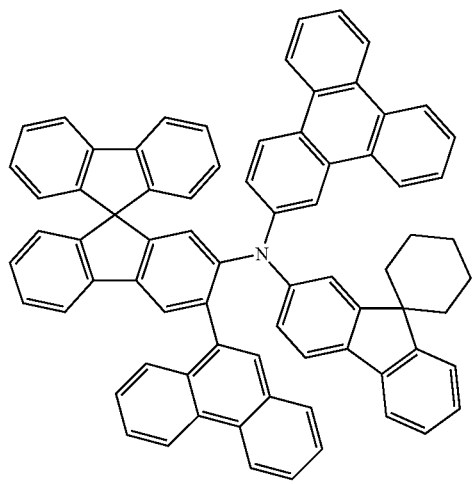
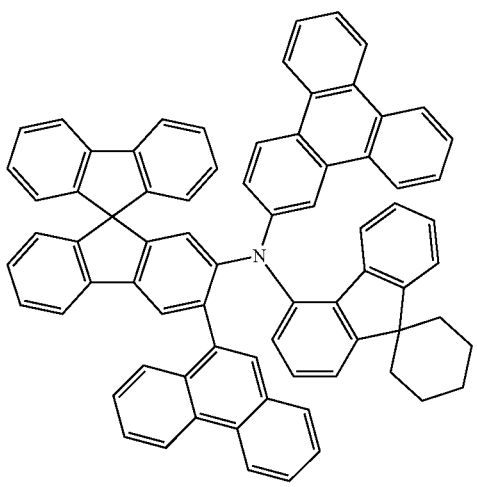

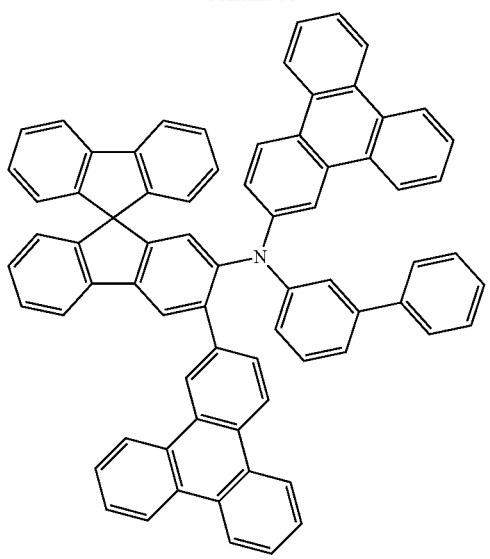
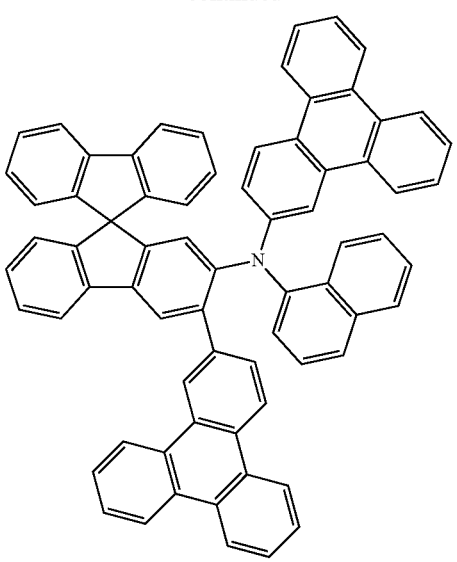
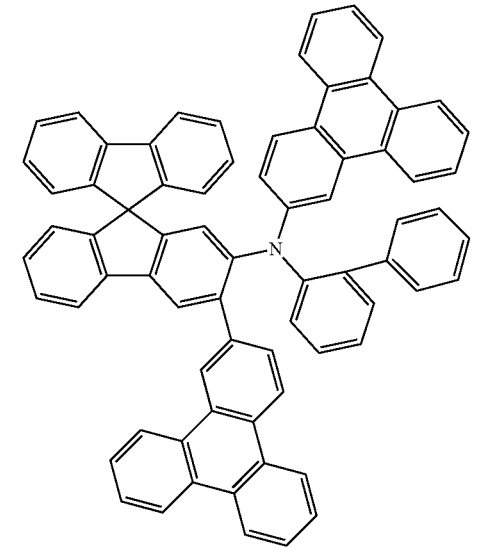
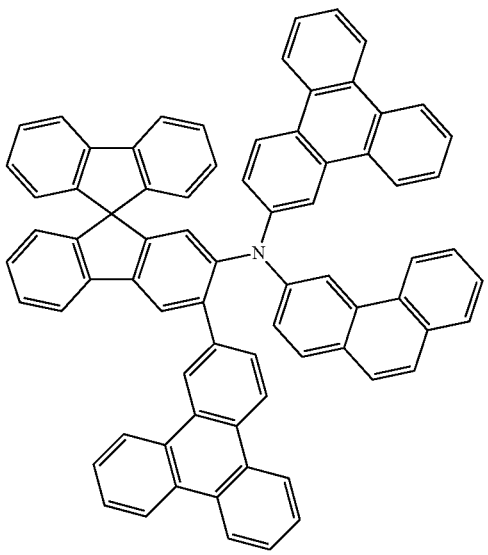
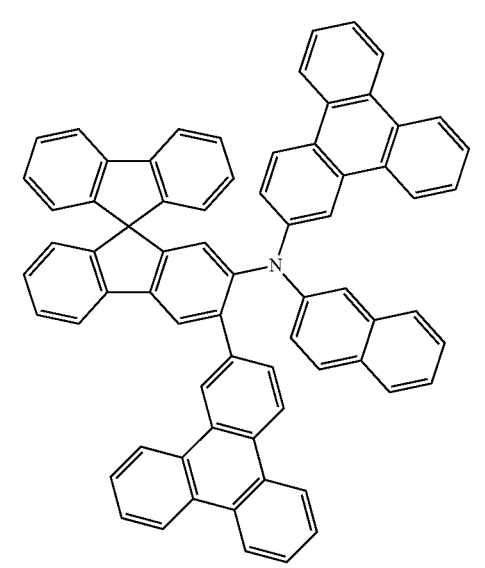
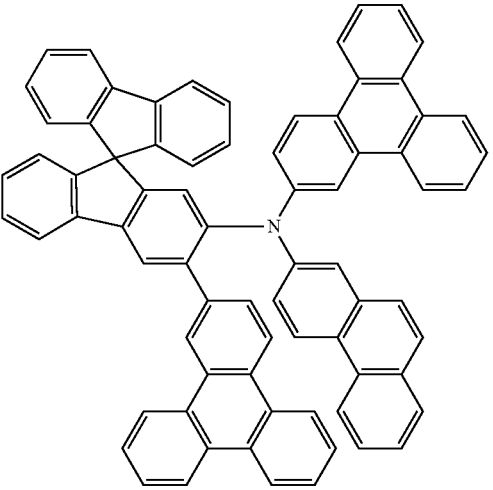

135
-continued
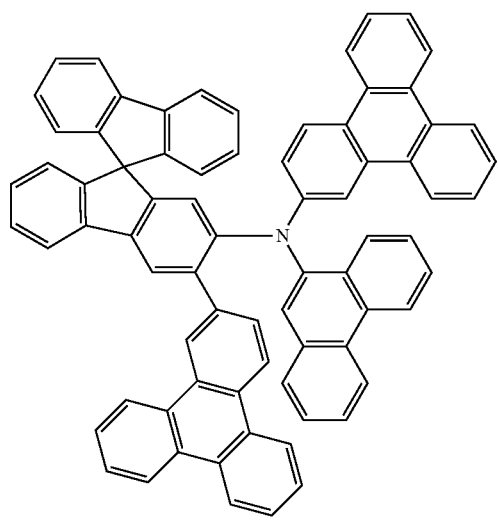
136
-continued
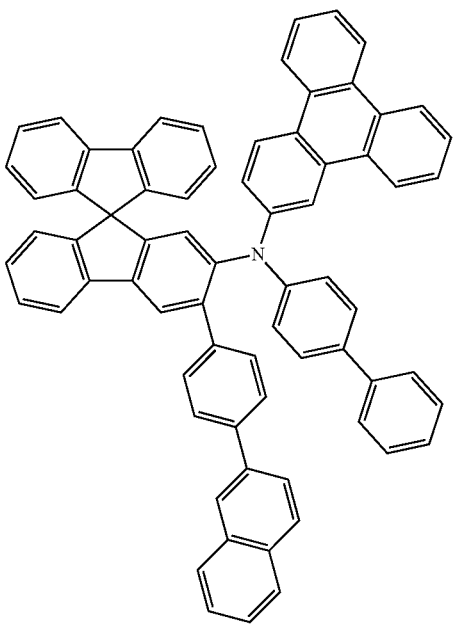
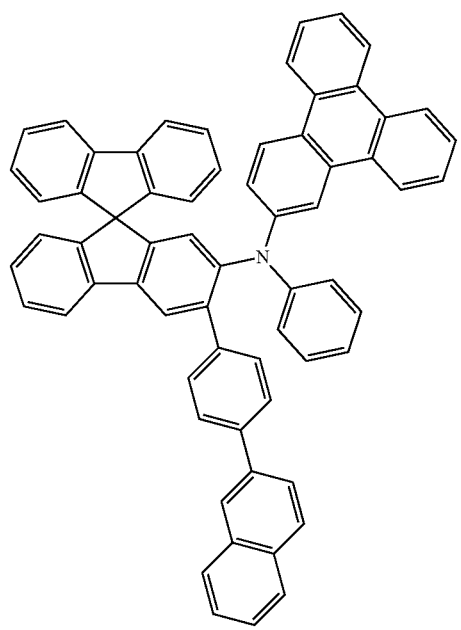
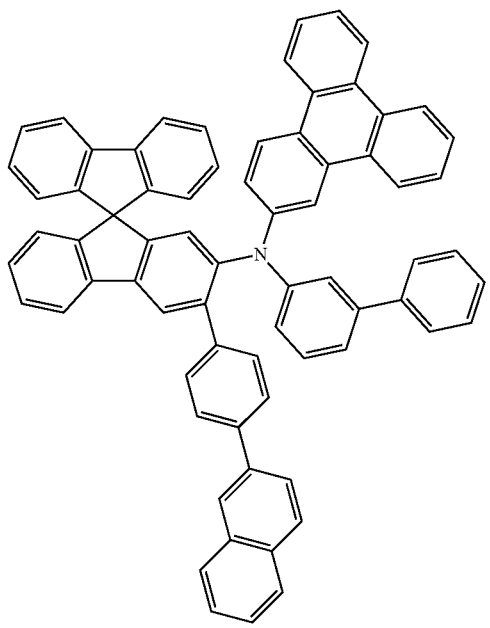

137
-continued
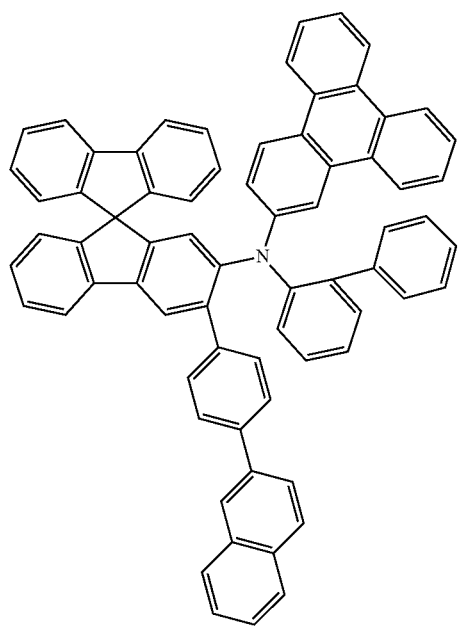
138
-continued
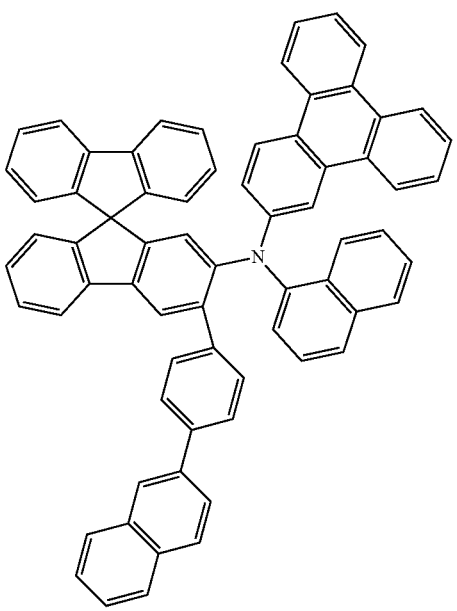
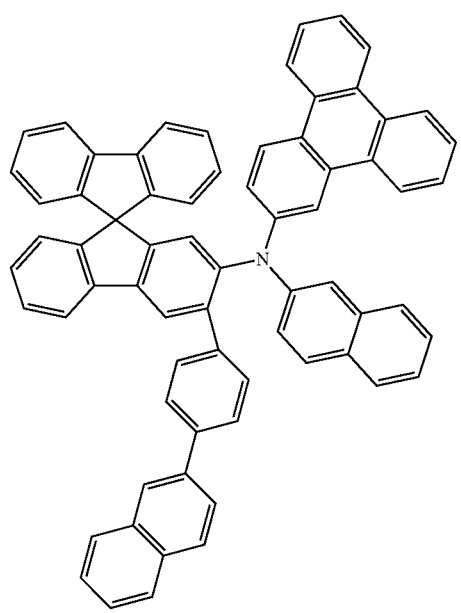
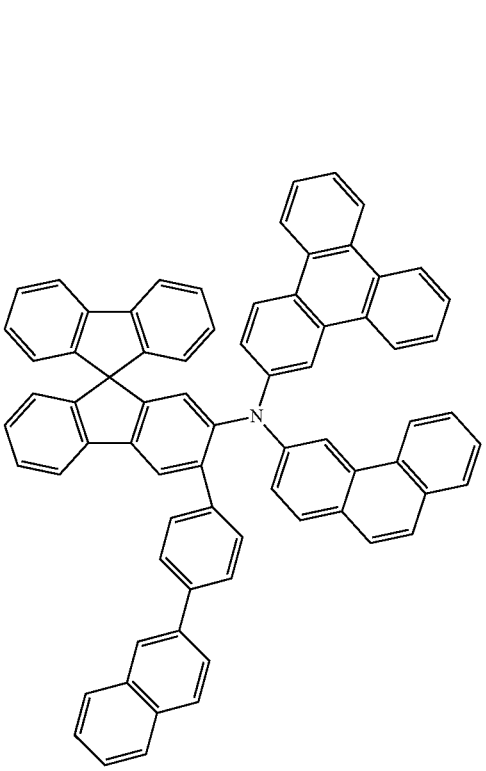

139
-continued
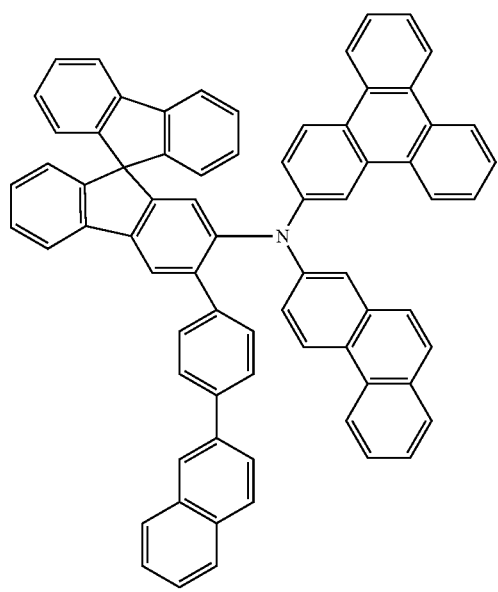
140
-continued
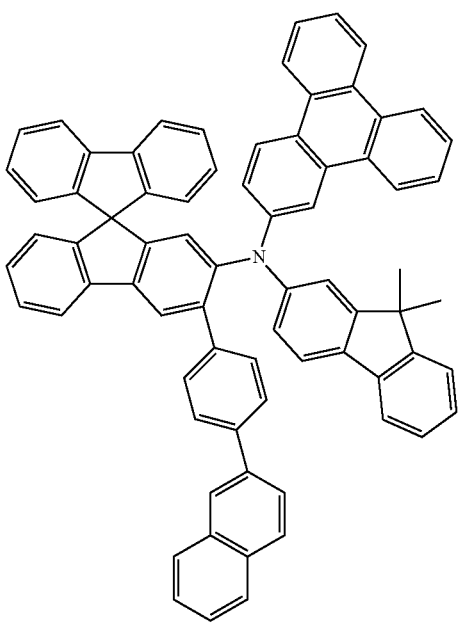
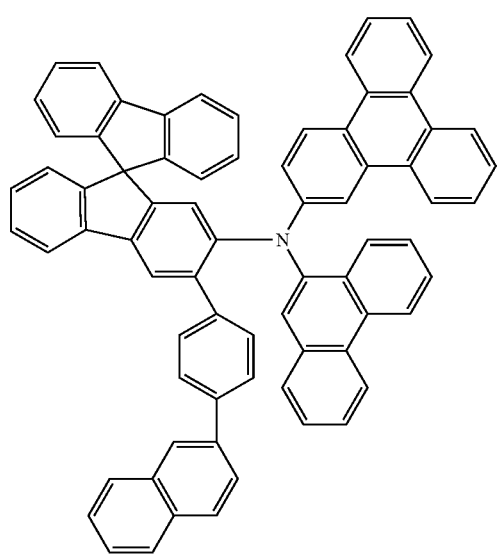
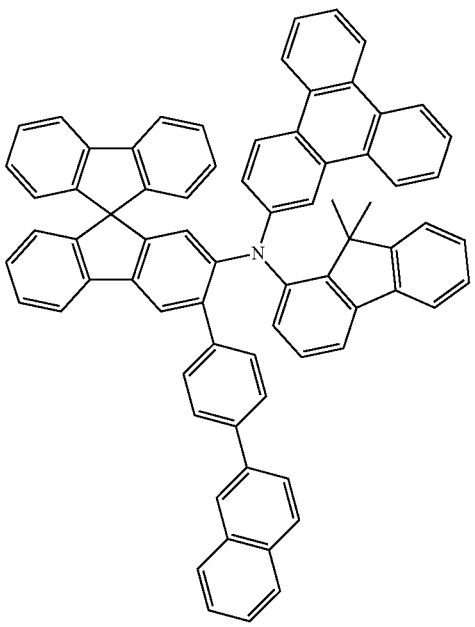

141
-continued
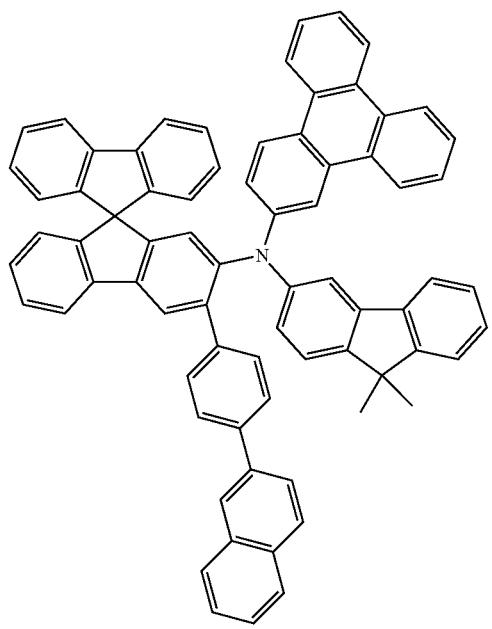
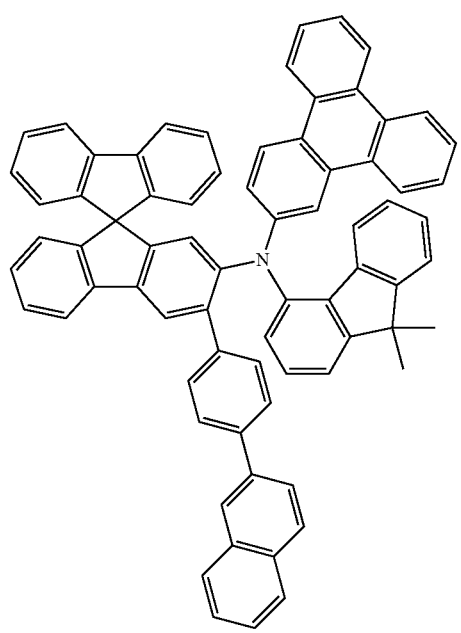
142
-continued
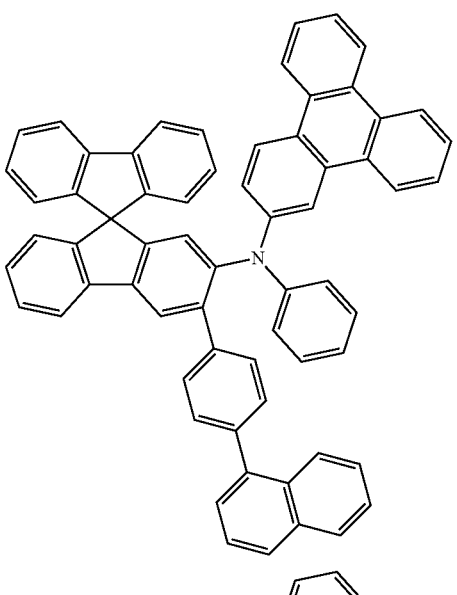
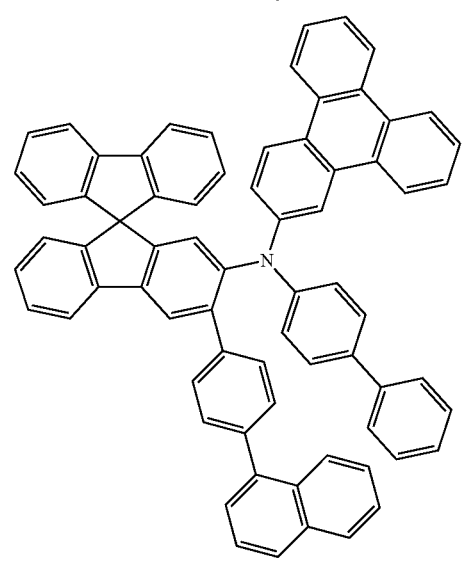
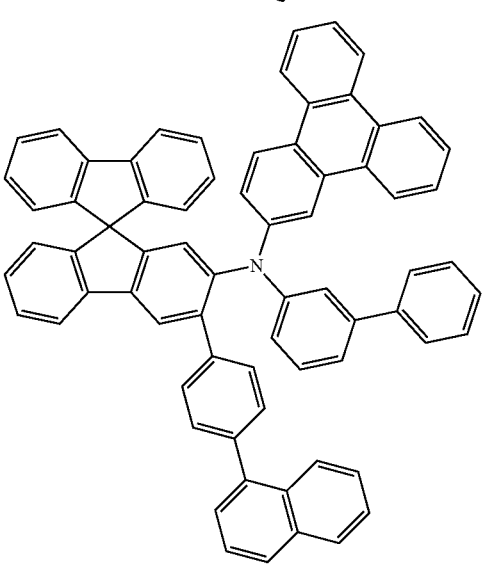

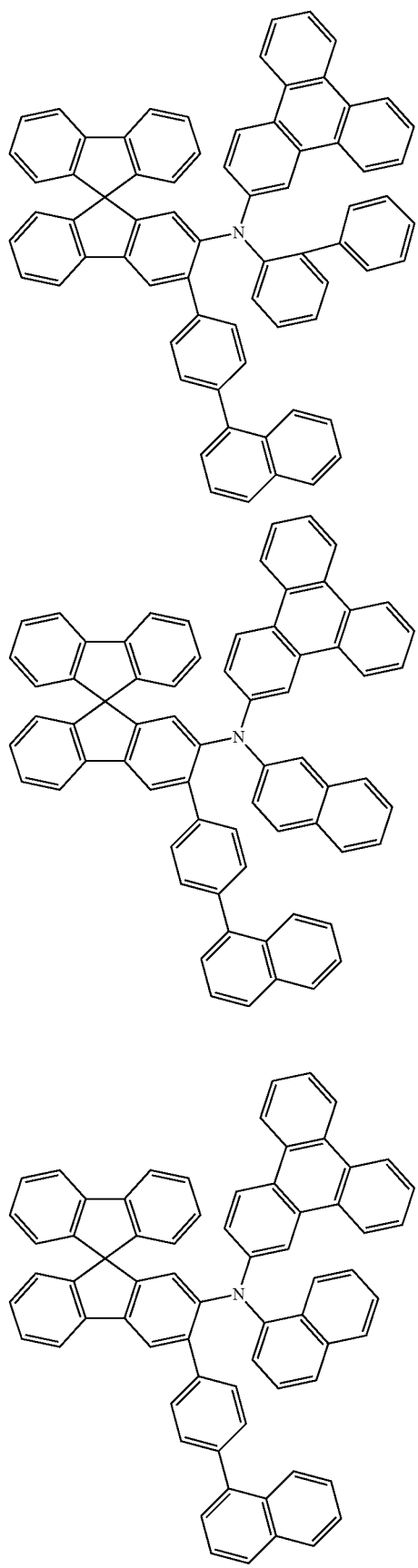
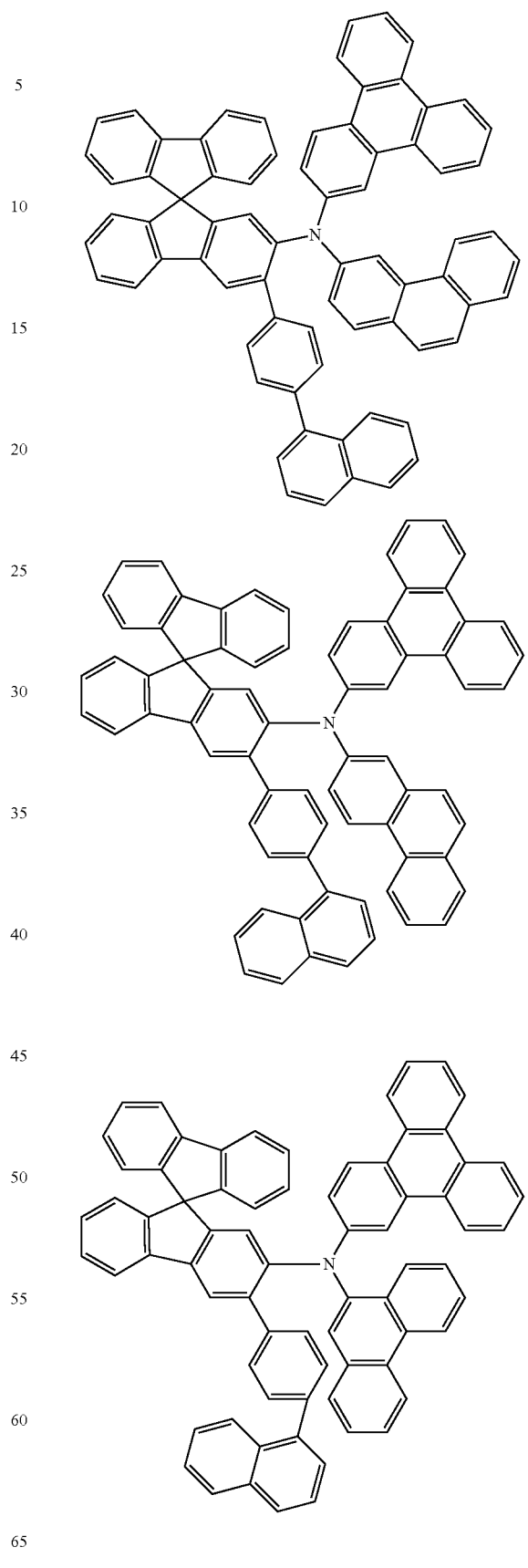

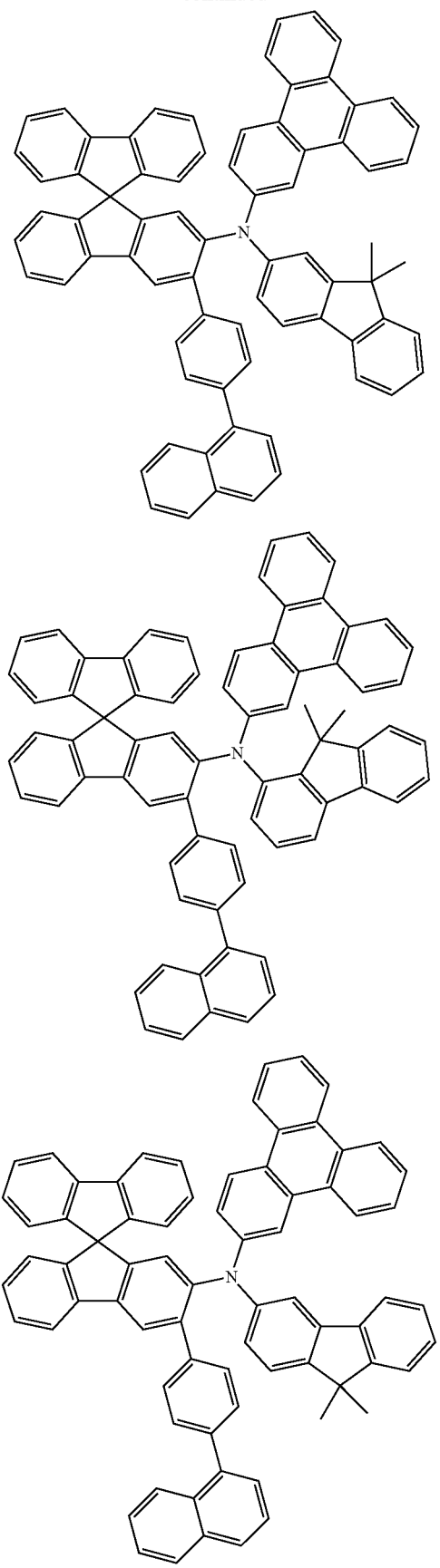

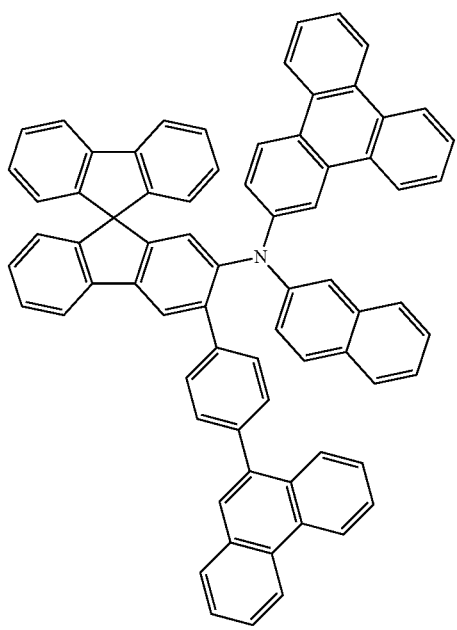
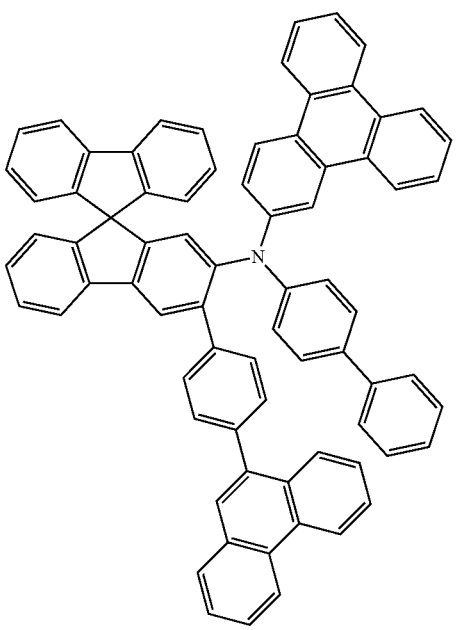
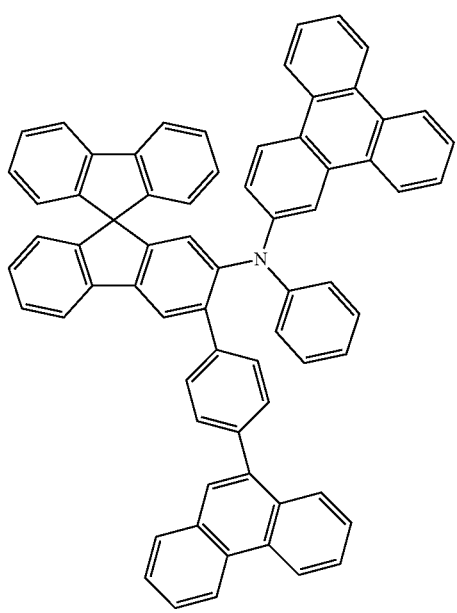
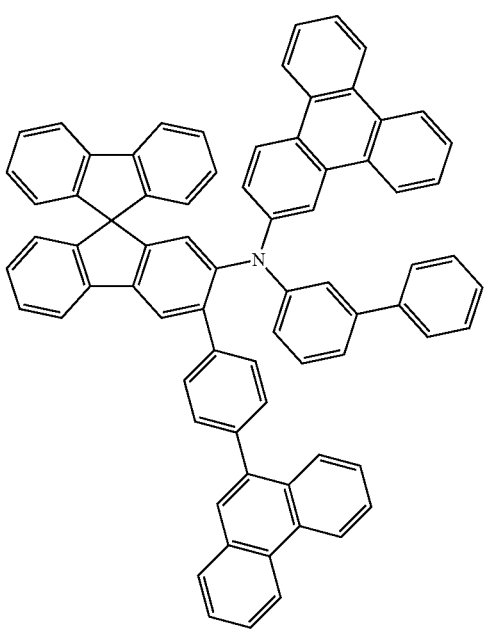

149
-continued
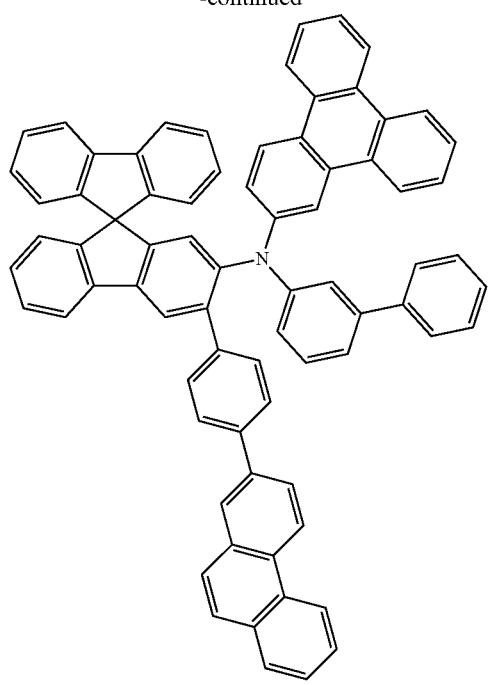
150
-continued
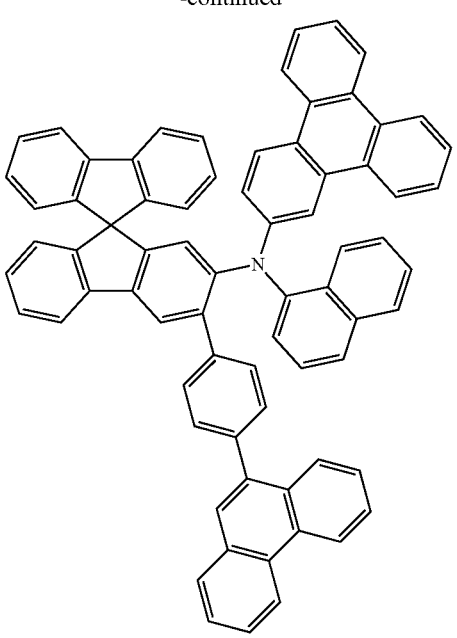
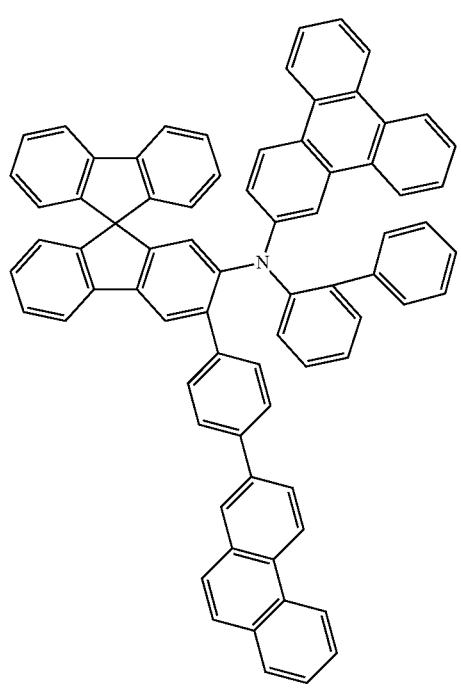

151
-continued
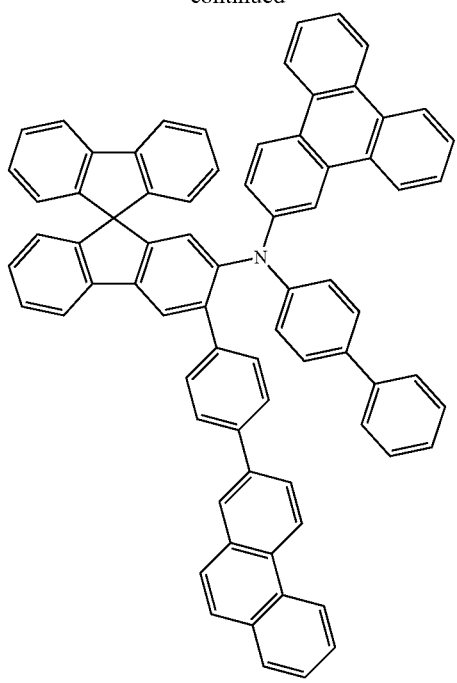
152
-continued
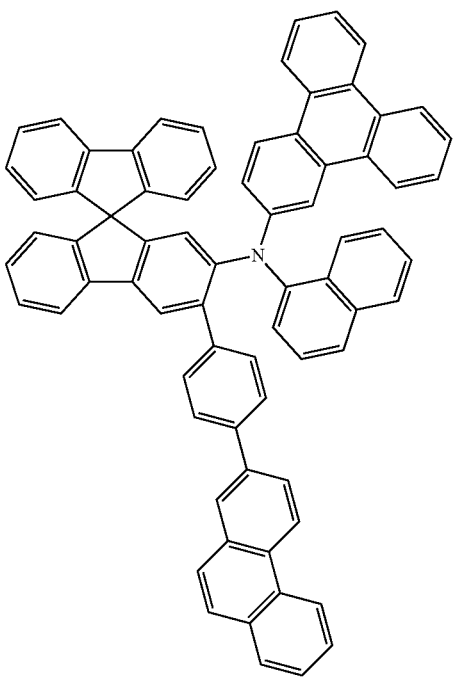 [SMILES: c1ccc2c(c1)-c1ccccc1C21c2ccccc2-c2cc(-c3ccc(-c4ccc5c(ccc6ccccc65)c4)cc3)c(N(c3ccc4c5ccccc5c5ccccc5c4c3)c3cccc4ccccc34)cc21]
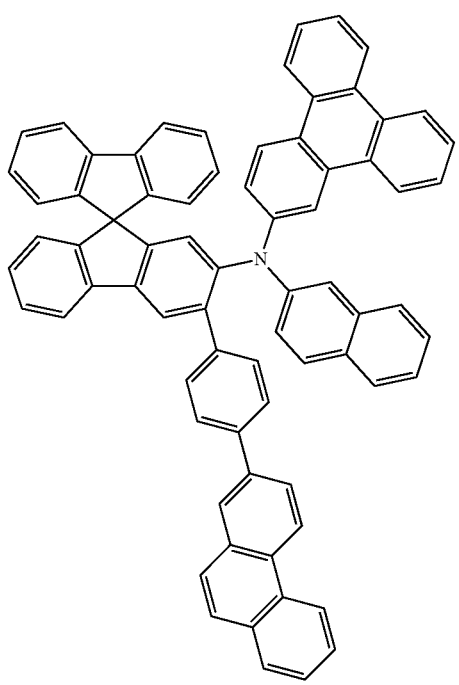
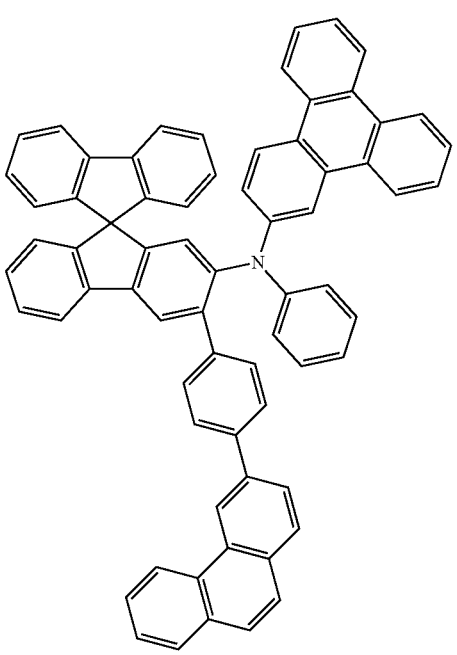

153
-continued
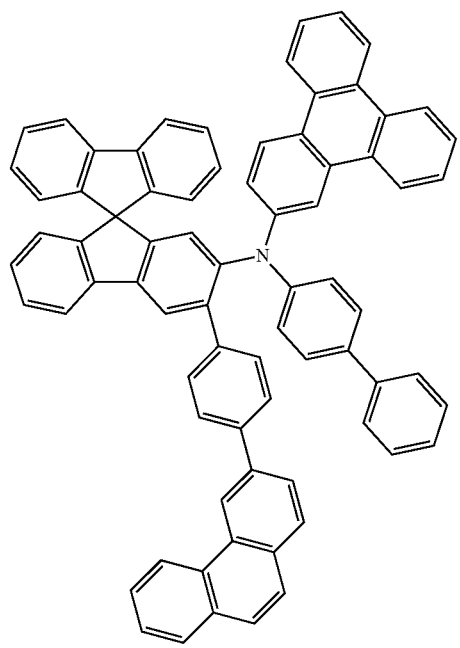
154
-continued
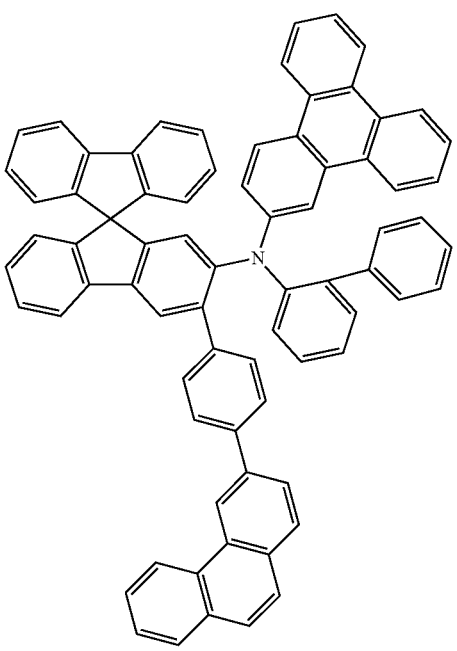
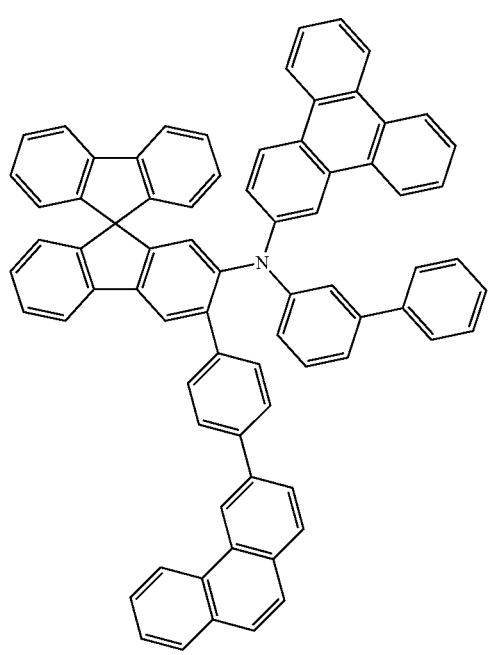
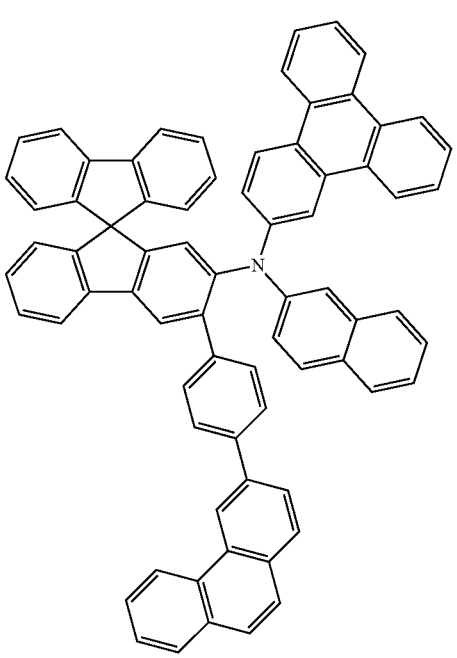

-continued
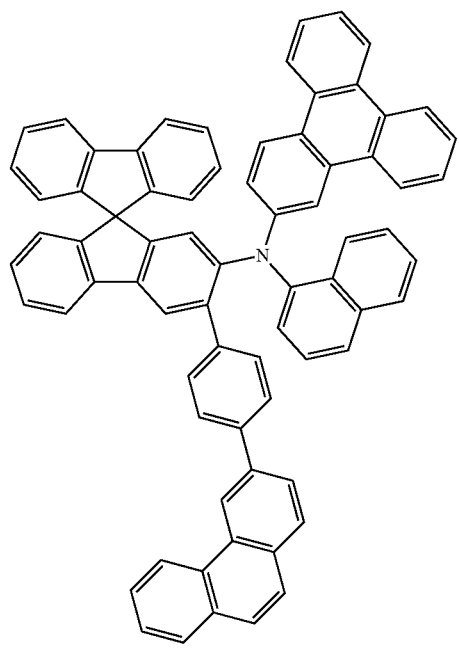
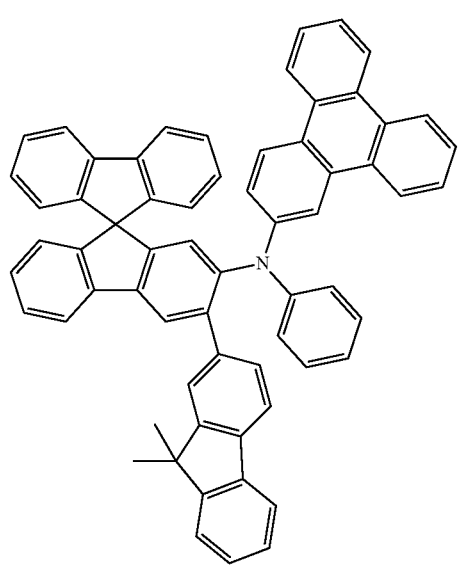
-continued
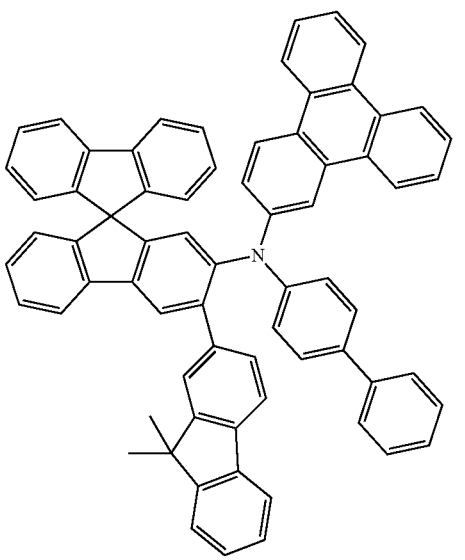
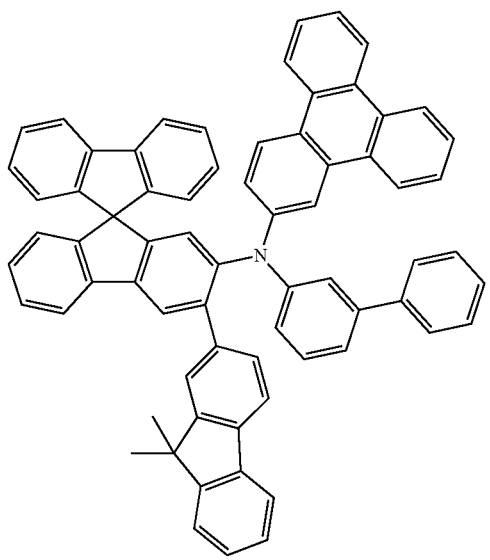

157
-continued
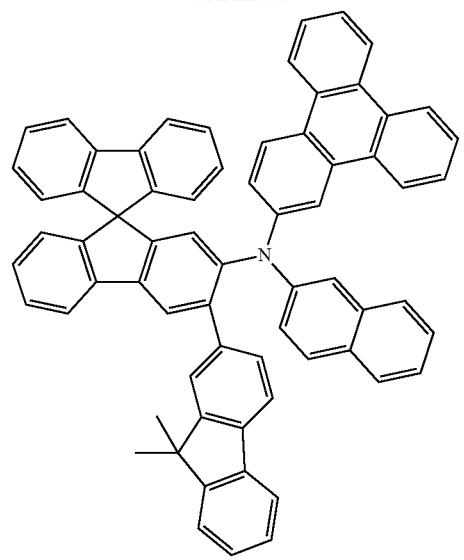
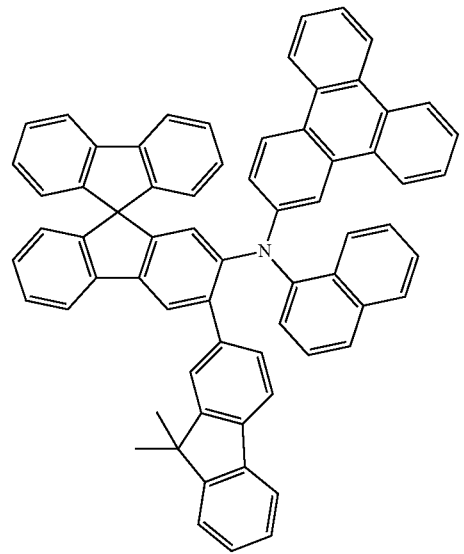
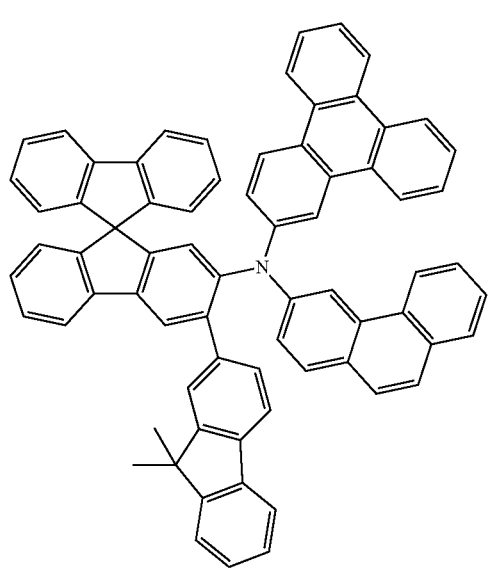
158
-continued
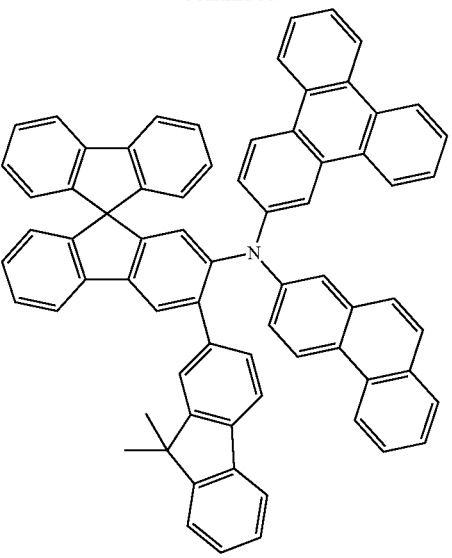
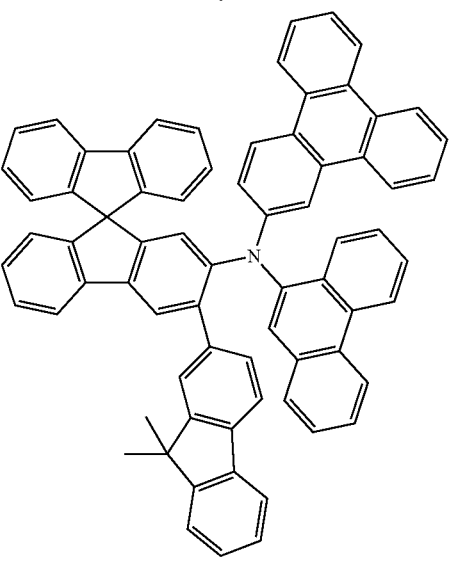
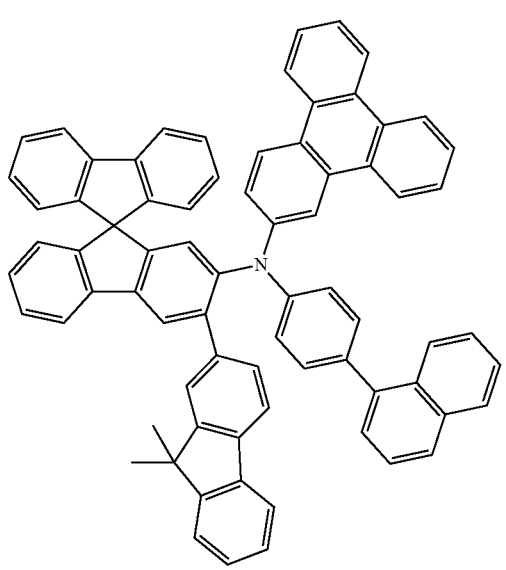

159
-continued
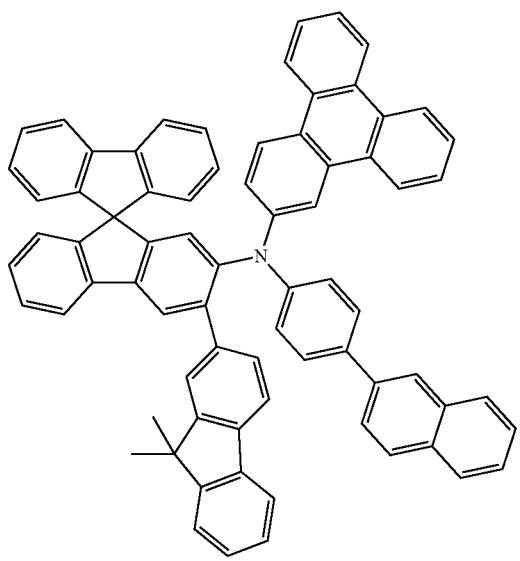
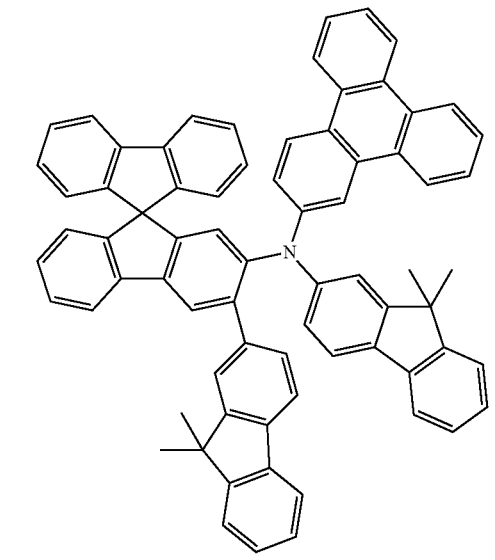
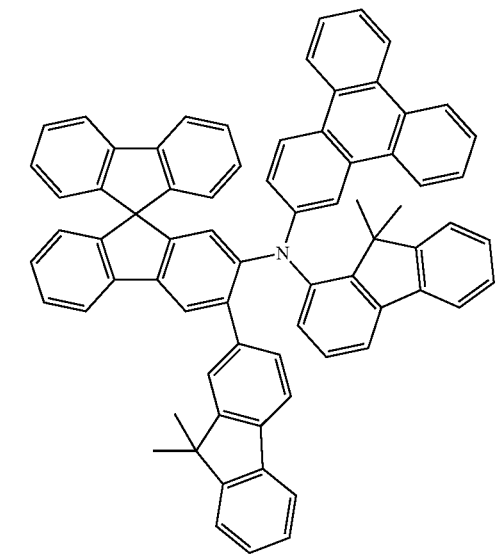
160
-continued
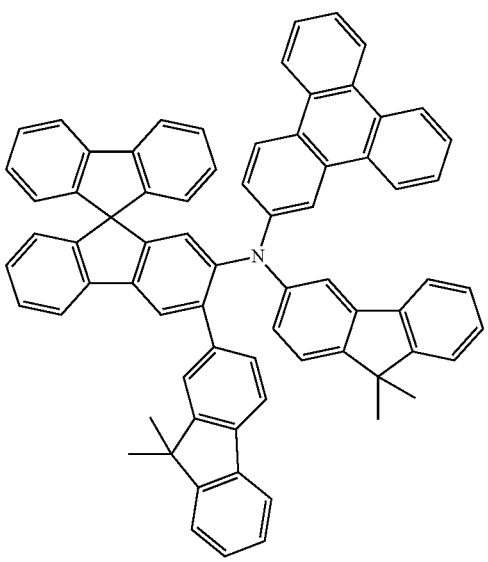
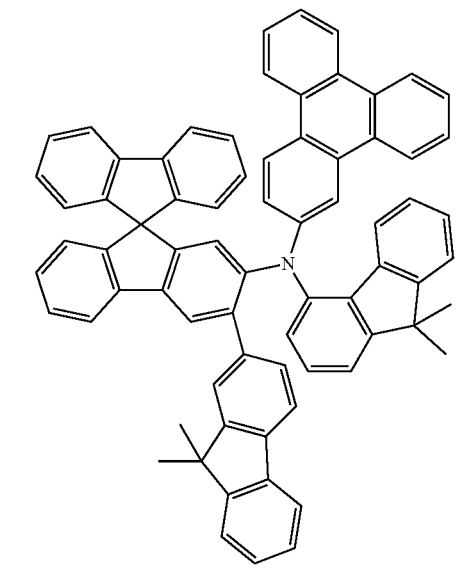
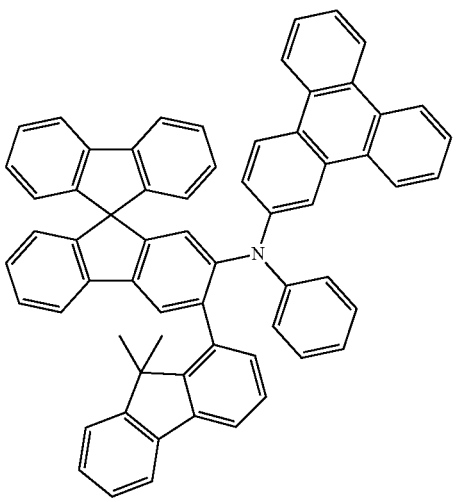

161
-continued
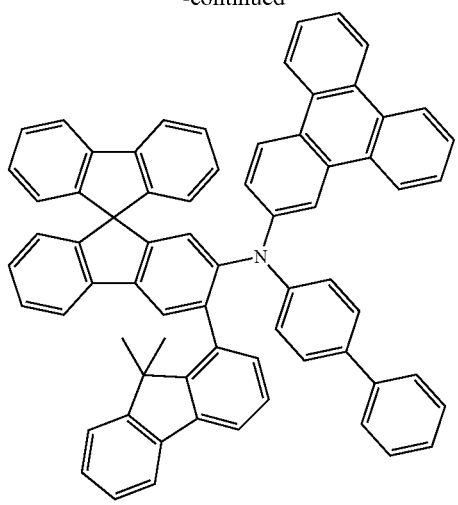
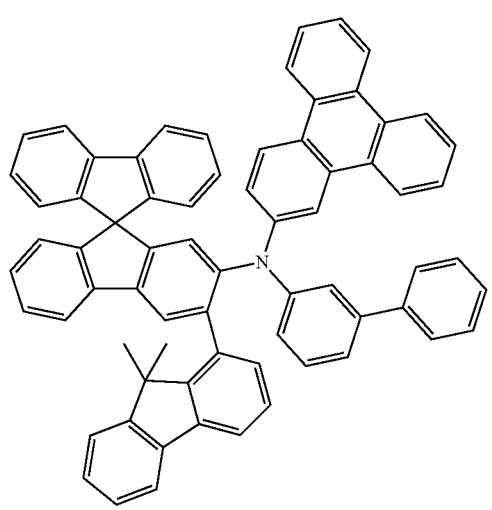
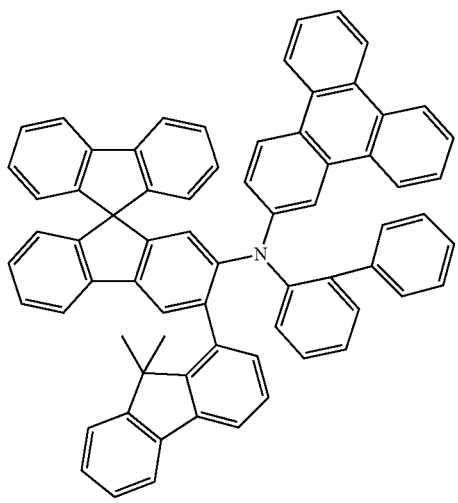
162
-continued
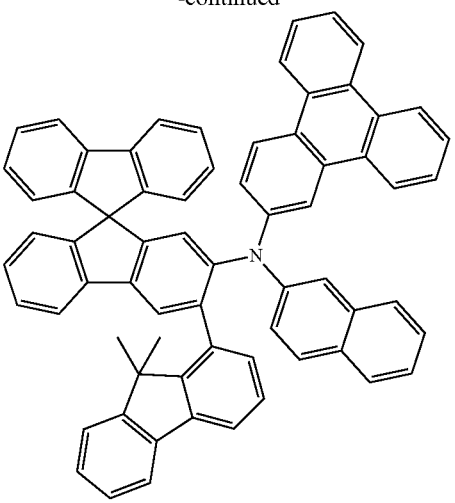
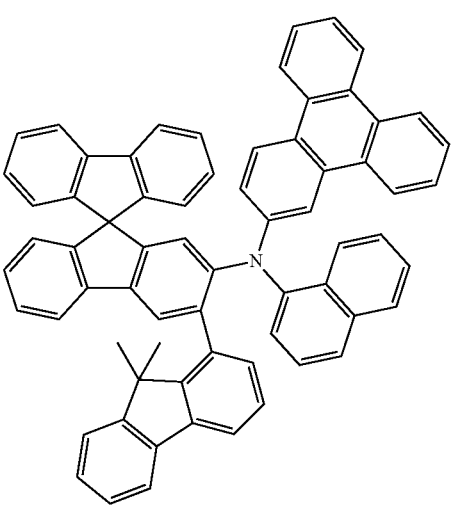
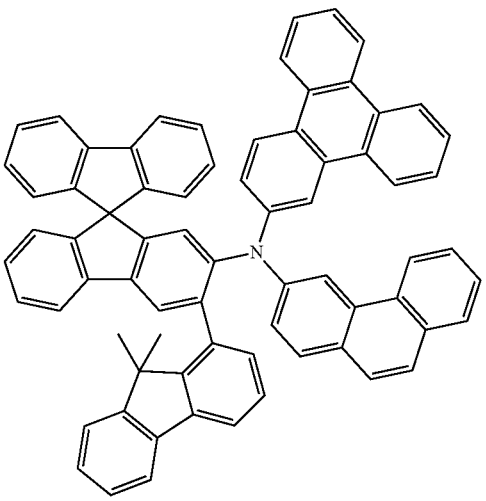

163
-continued
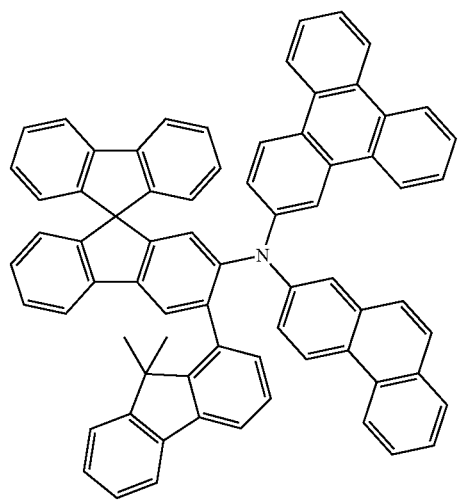
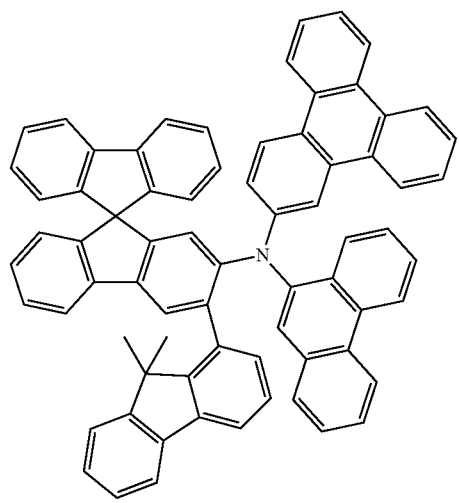
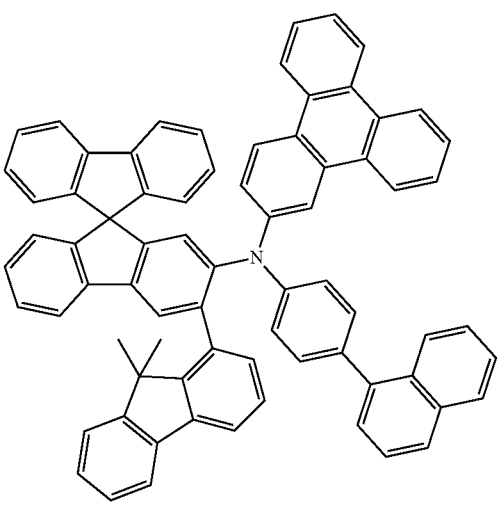
164
-continued
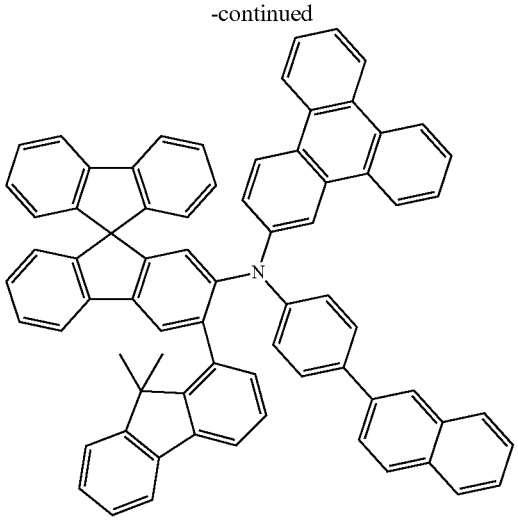
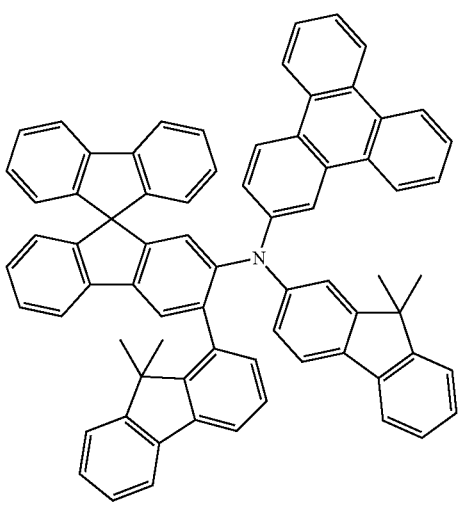
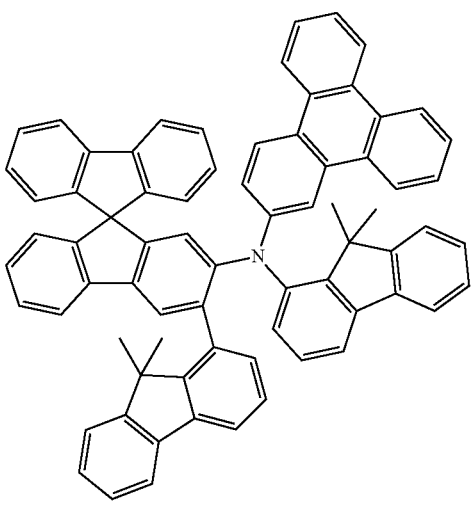

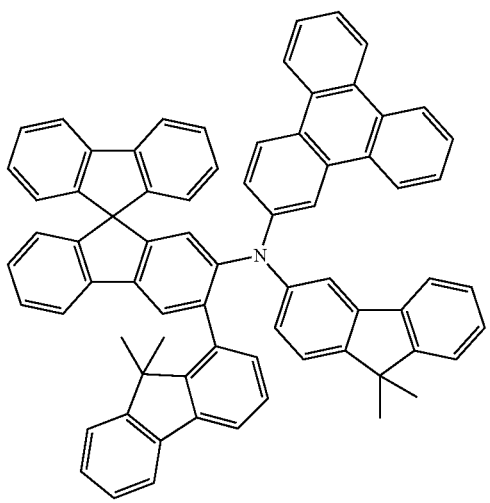
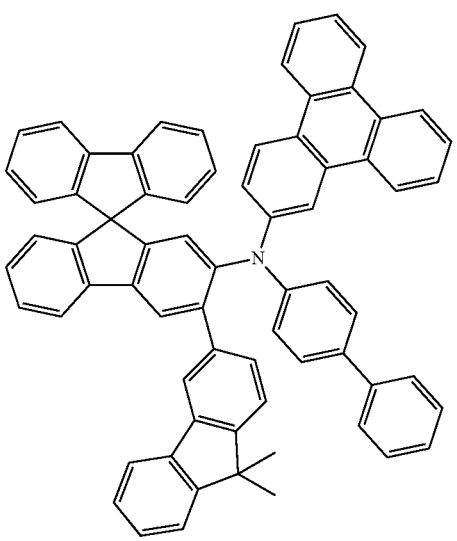
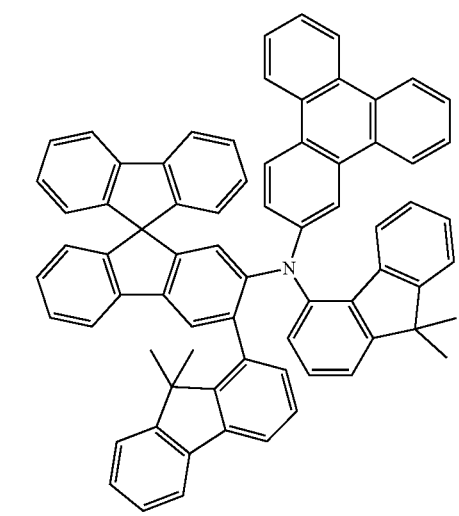
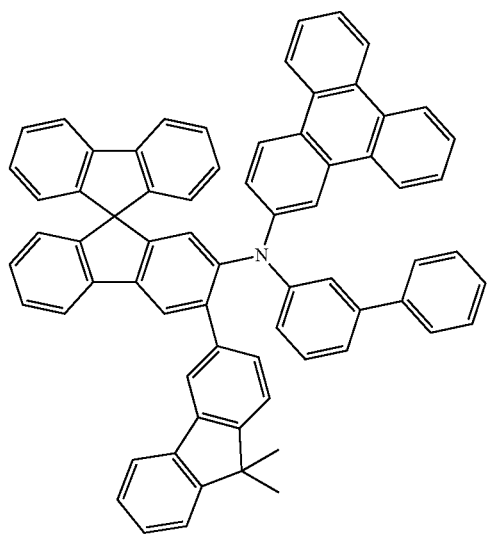
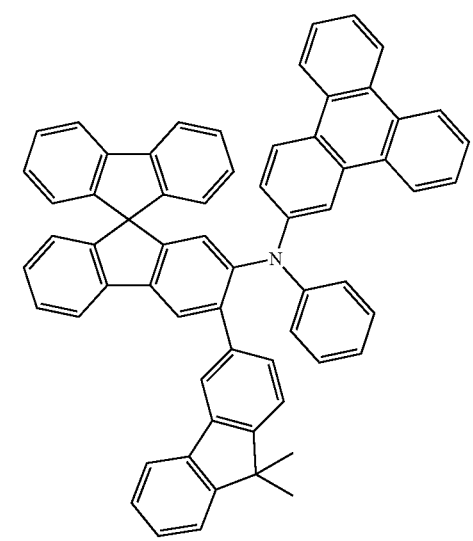
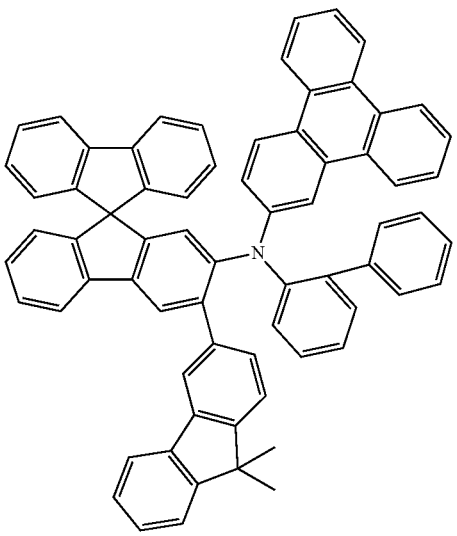

167
-continued
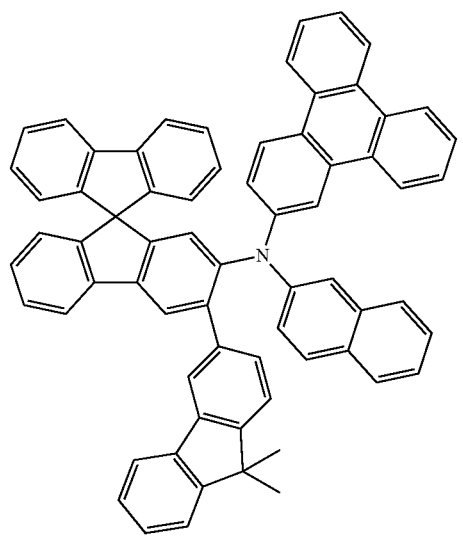
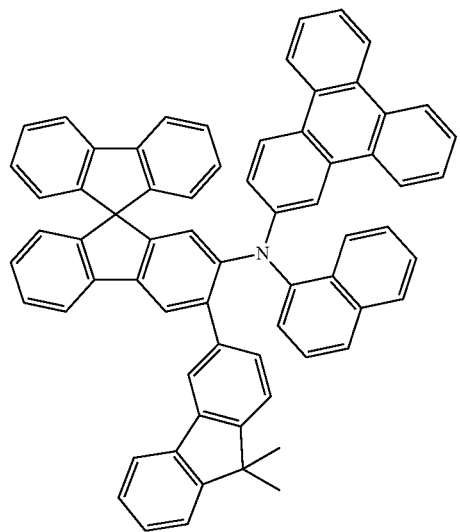
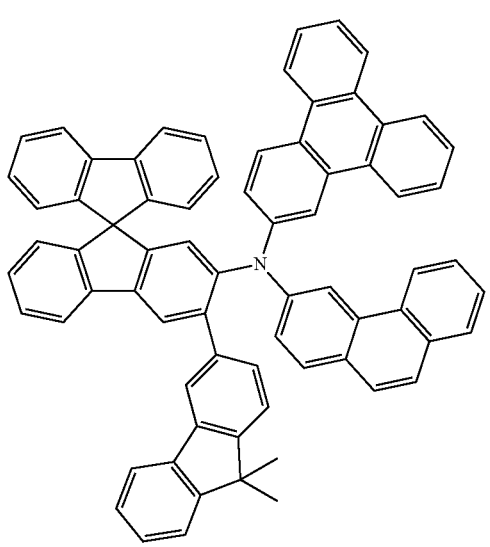
168
-continued
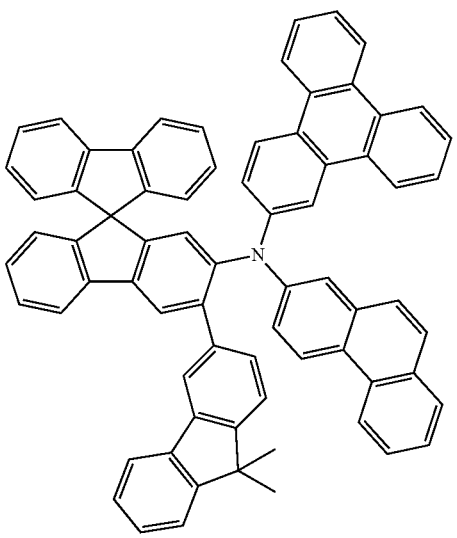
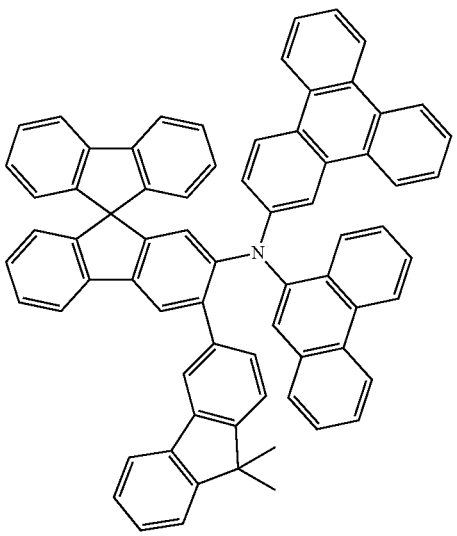
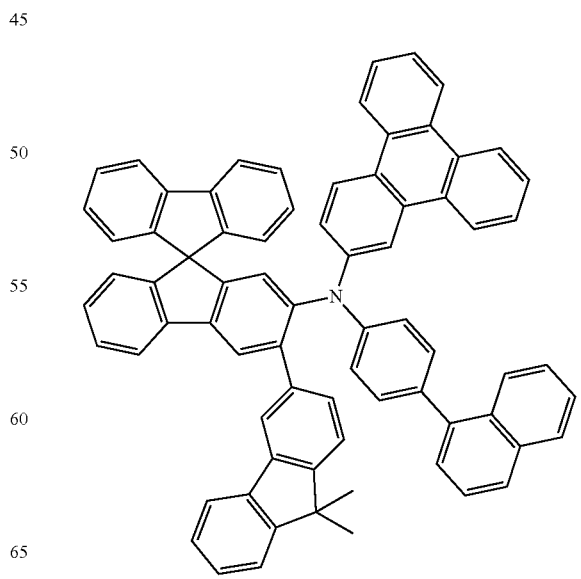

169
-continued
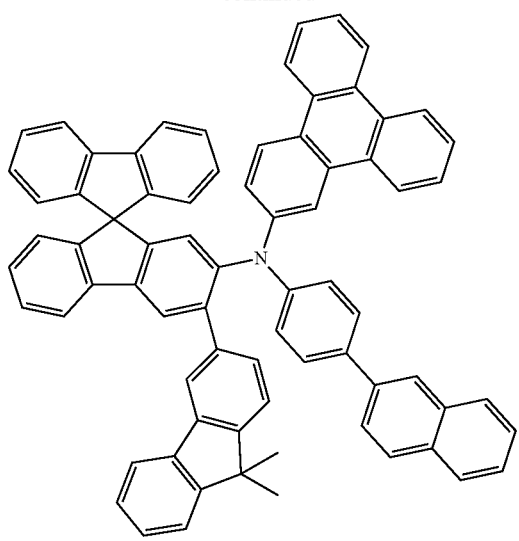
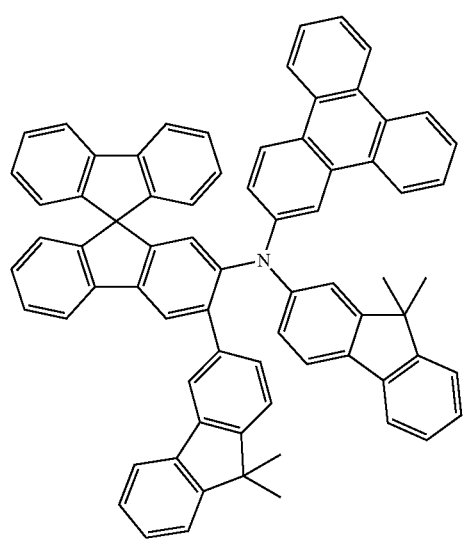
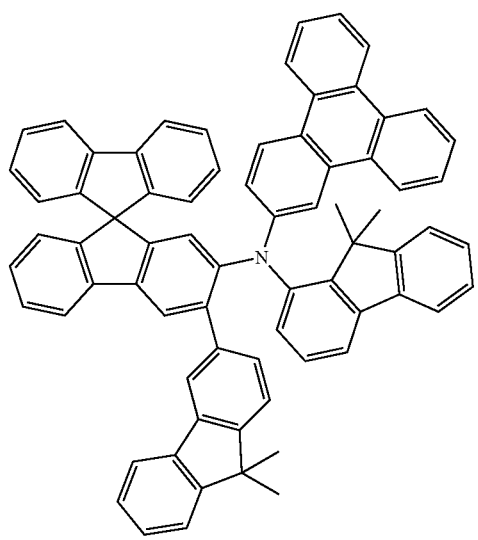
170
-continued
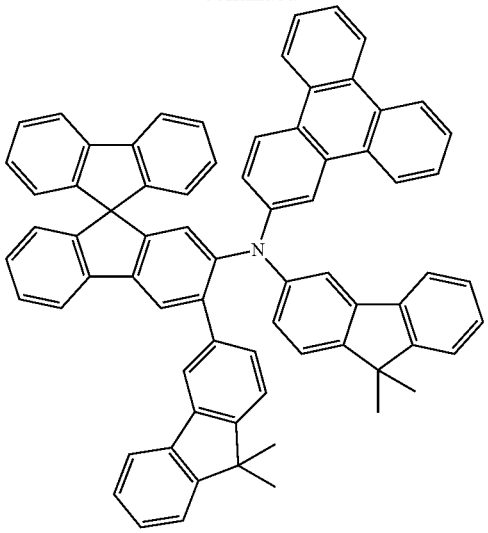
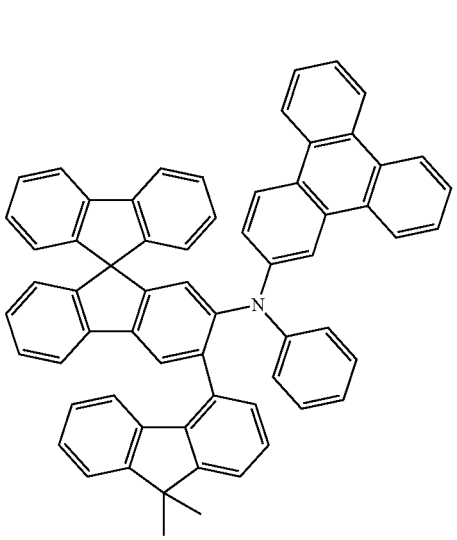

171
-continued
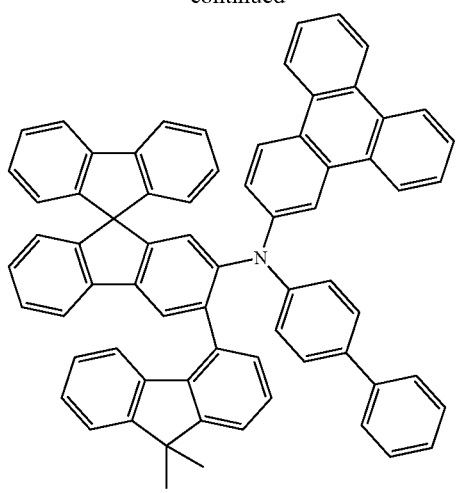
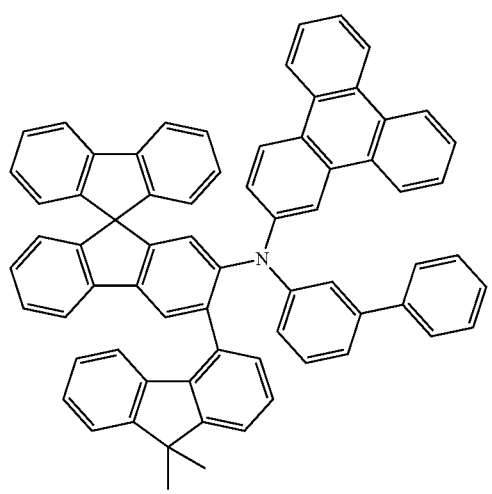
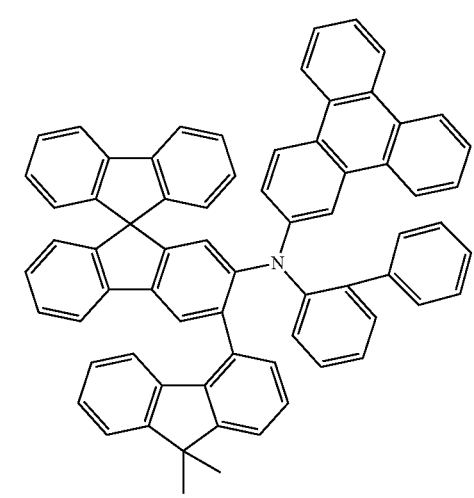 [SMILES: CC1(C)c2ccccc2-c2c(-c3cc4c(cc3N(c3ccc5c6ccccc6c6ccccc6c5c3)c3ccccc3-c3ccccc3)C3(c5ccccc5-c5ccccc53)c3ccccc3-4)cccc21]
172
-continued
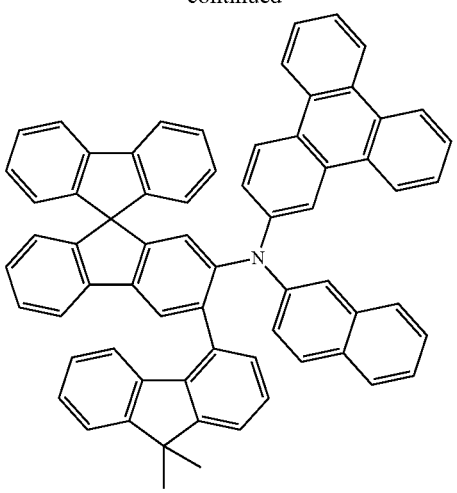
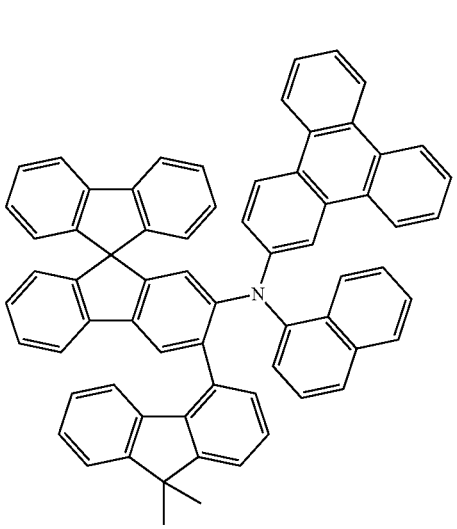
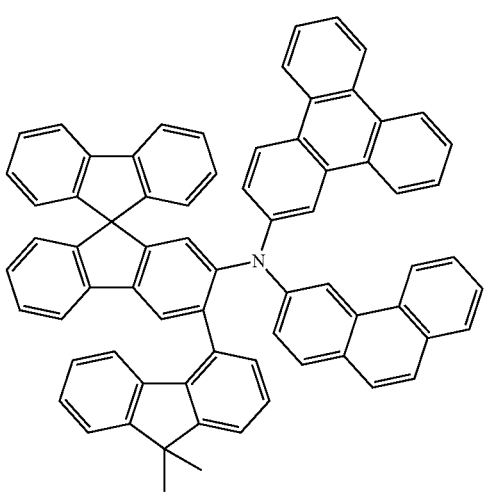

-continued
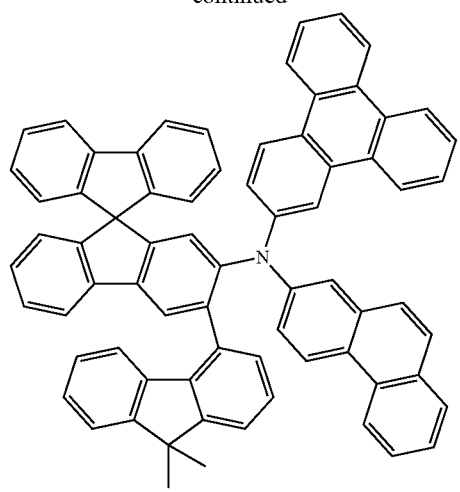
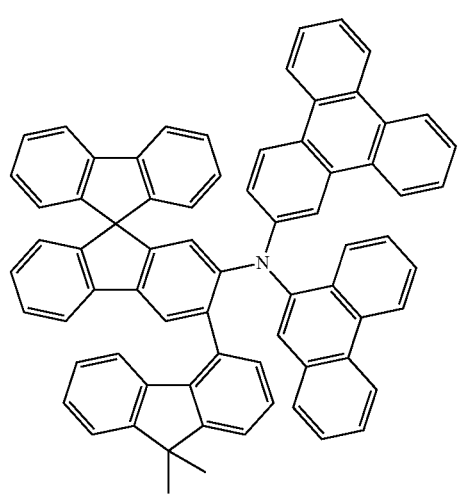
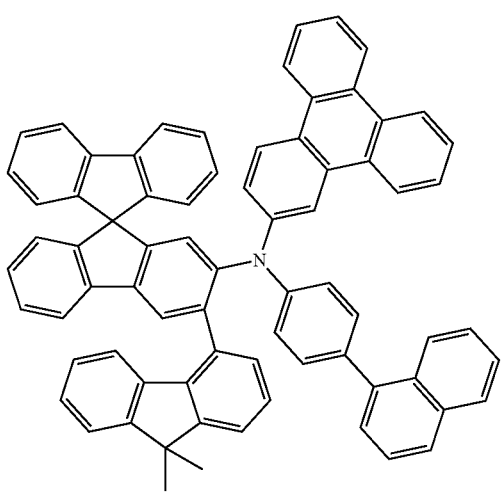
-continued
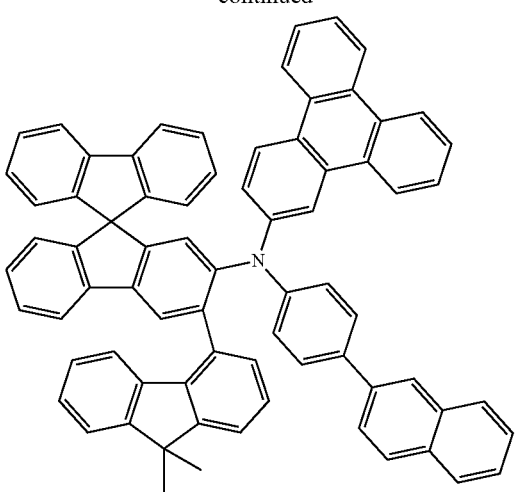
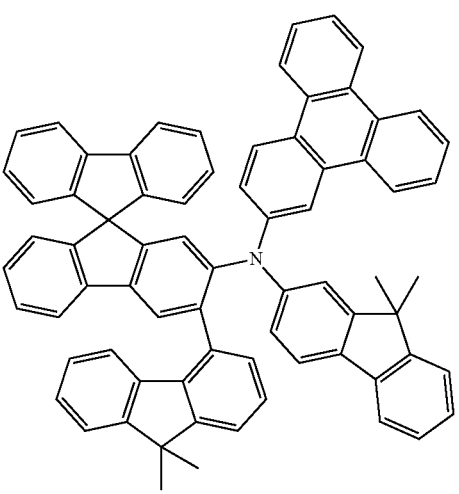
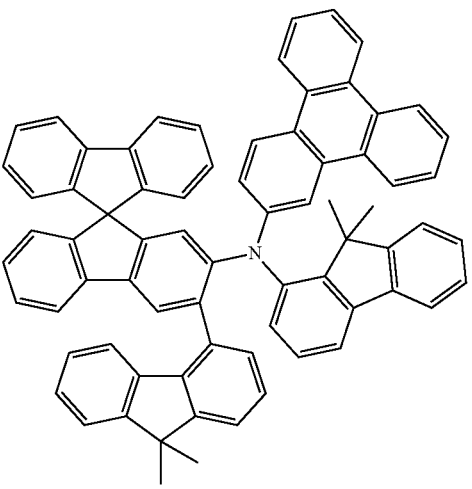

-continued
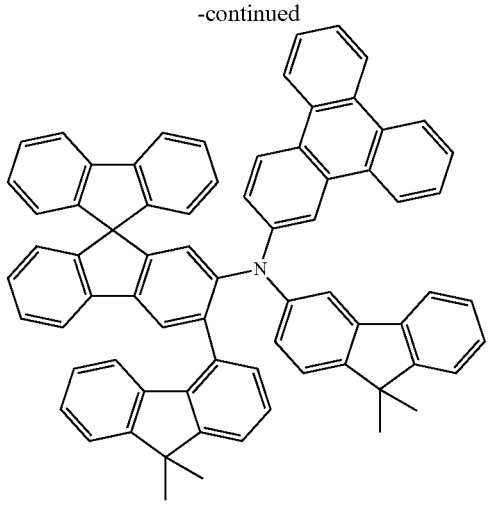
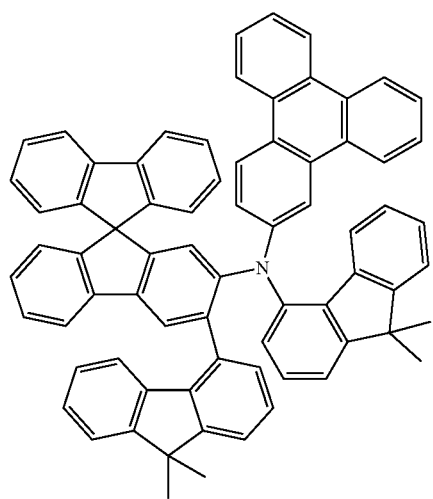
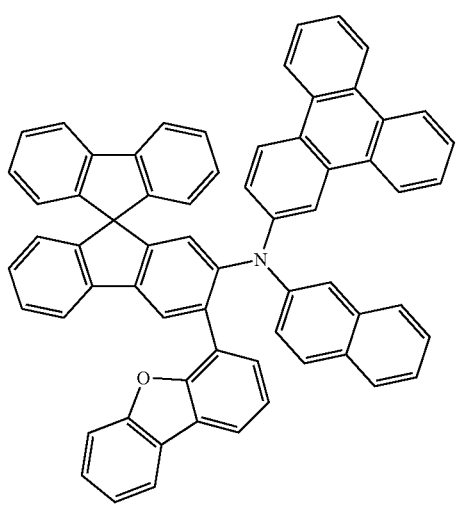
-continued
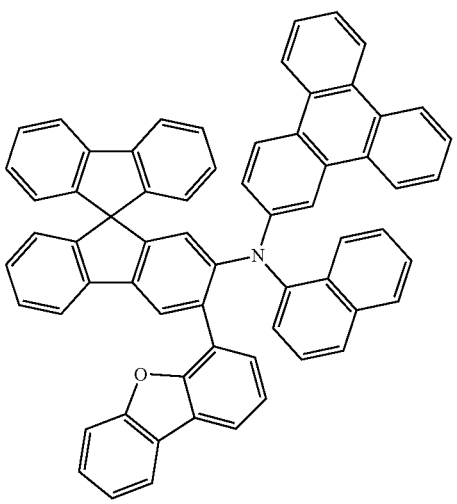
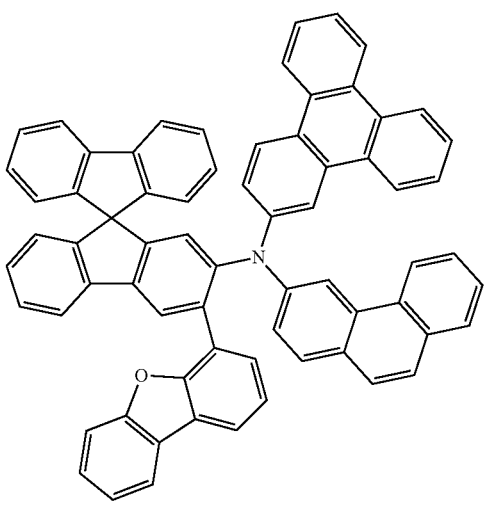
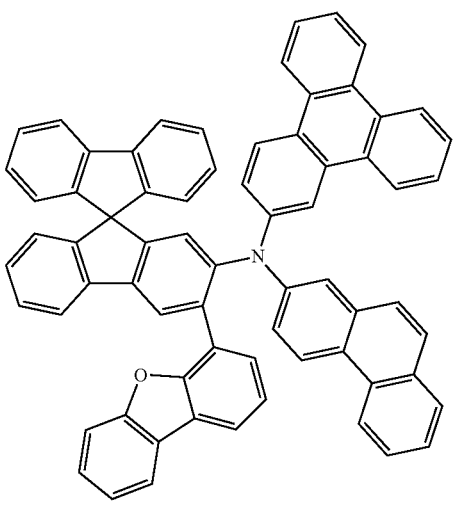

177
-continued
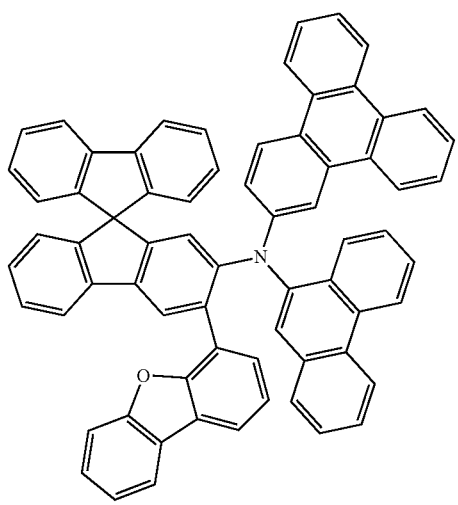
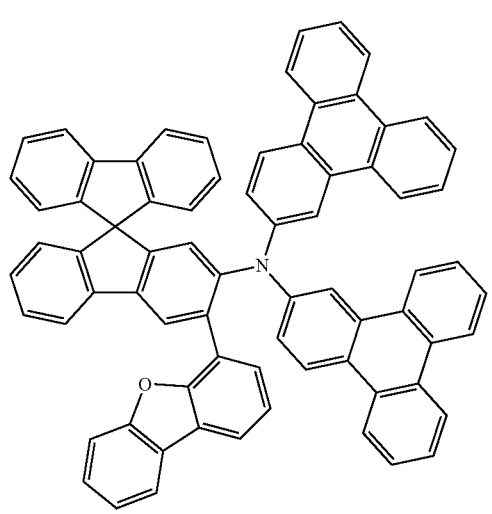
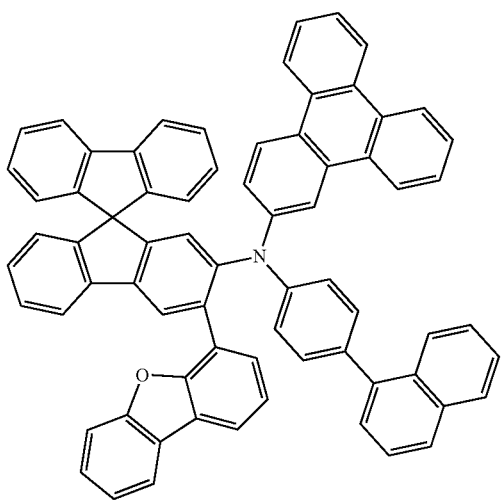
178
-continued
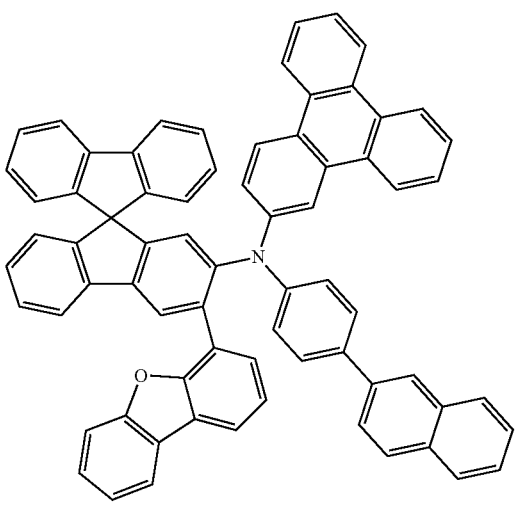
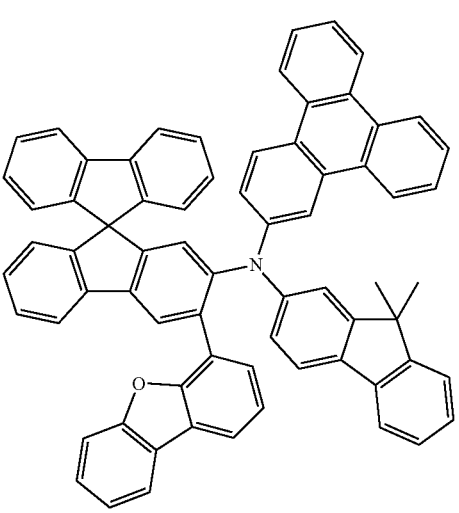
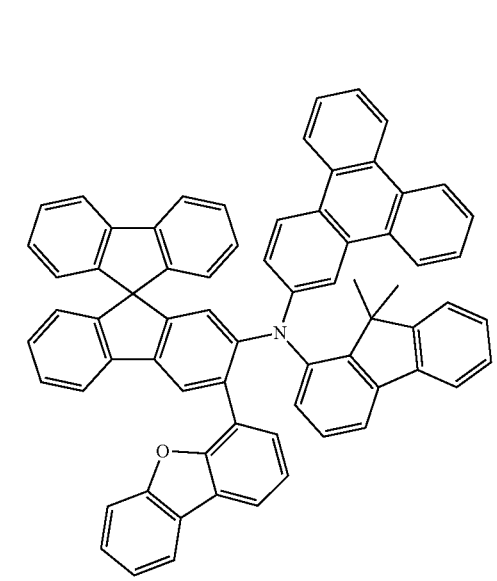

179
-continued
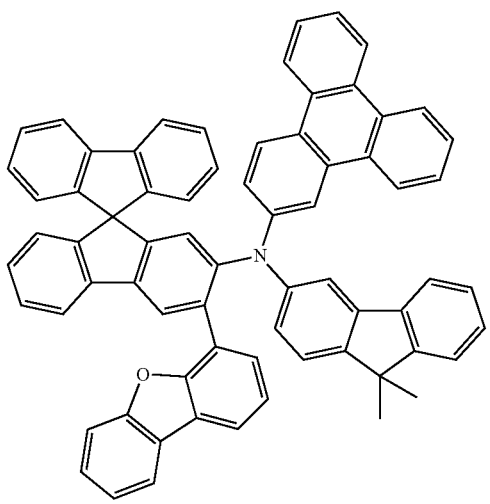
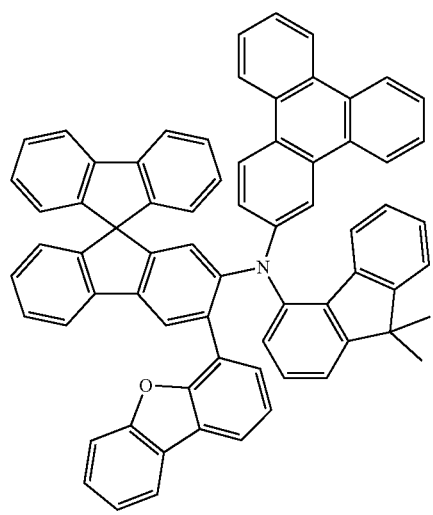
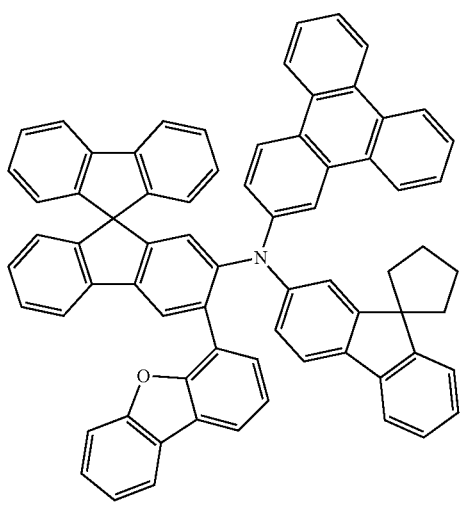
180
-continued
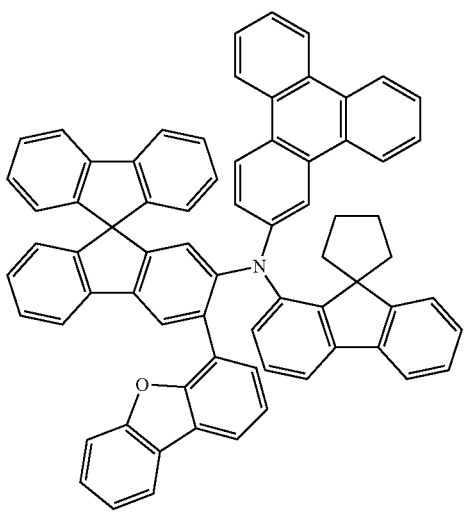
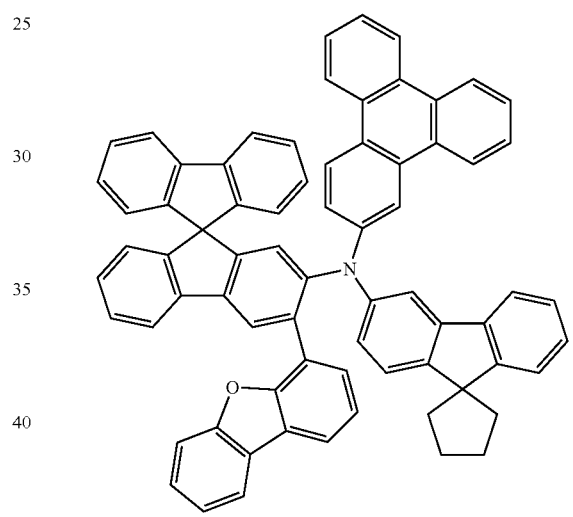
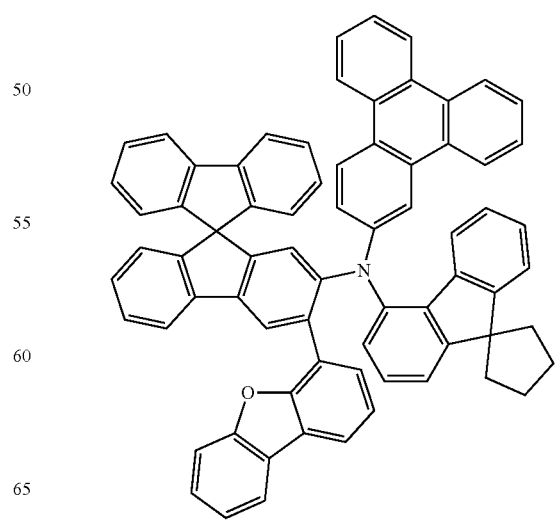

181
-continued
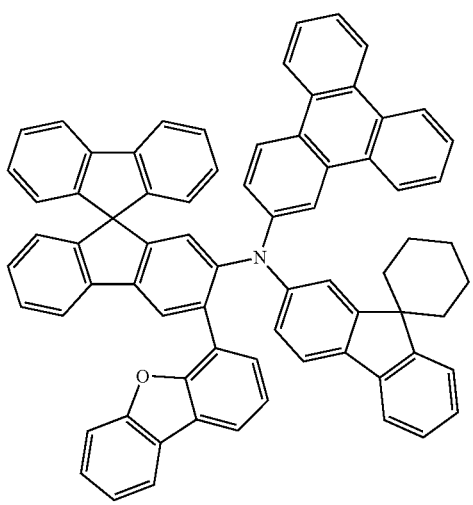
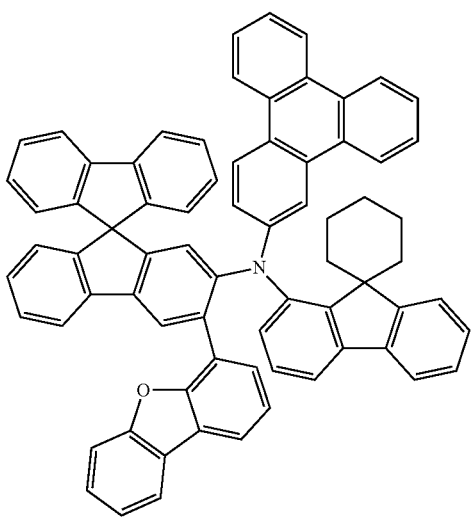
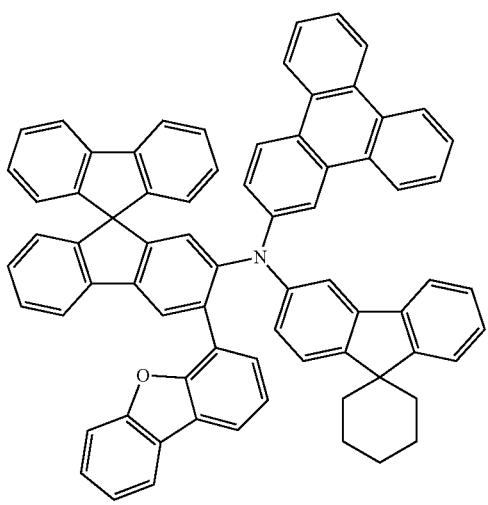
182
-continued
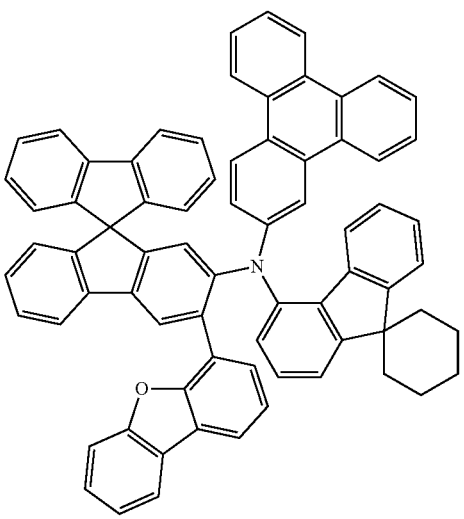
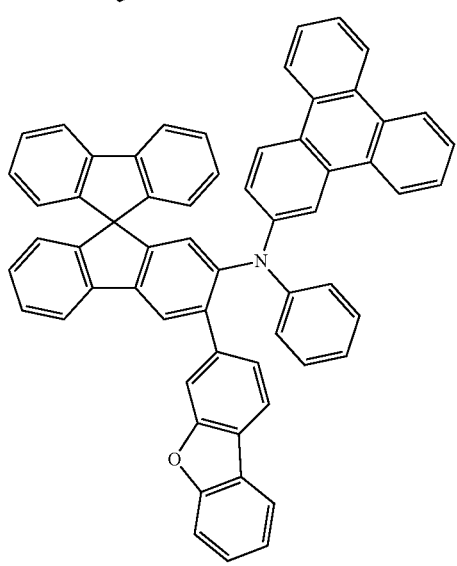
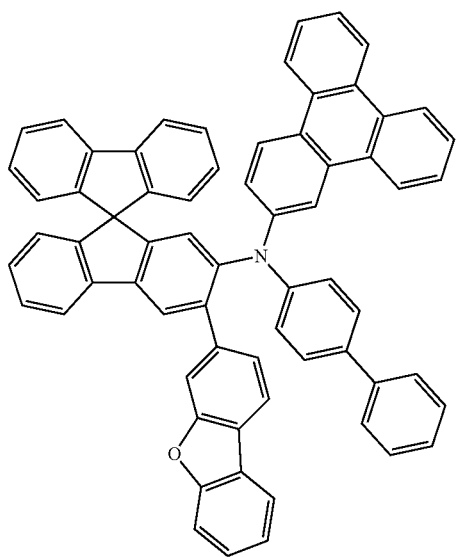

183
-continued
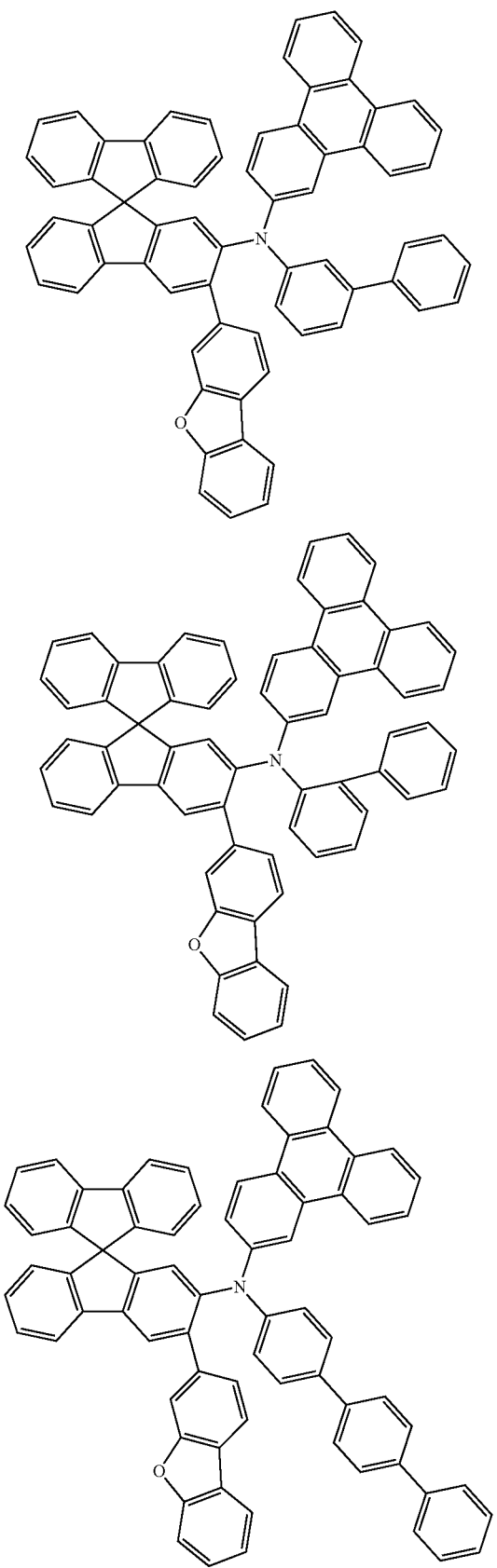
184
-continued
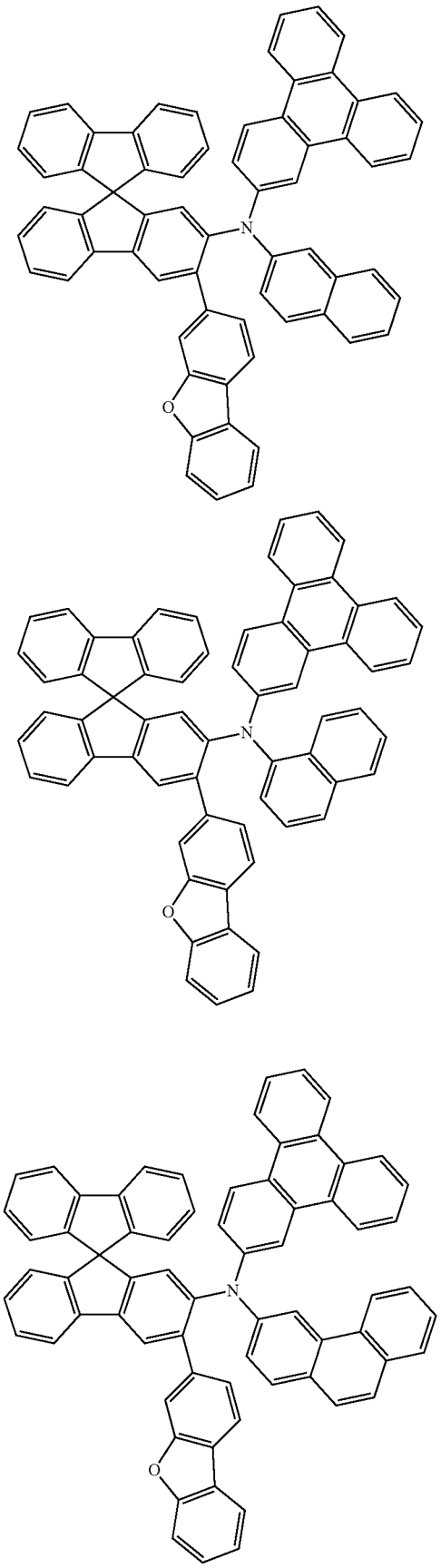

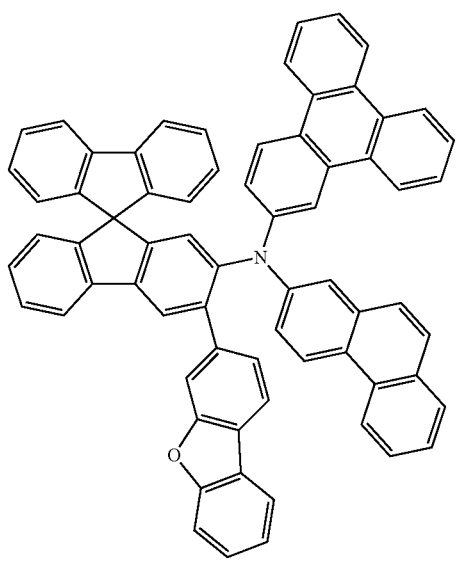
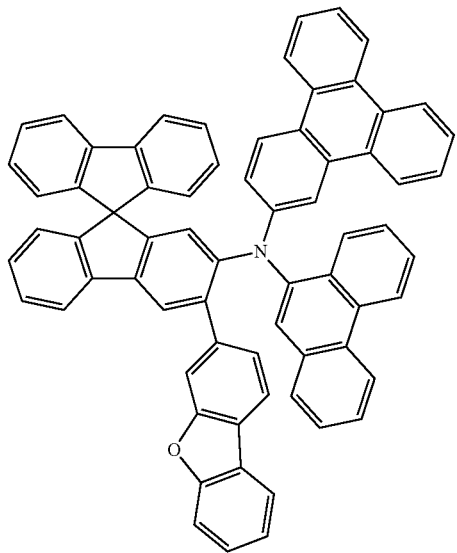
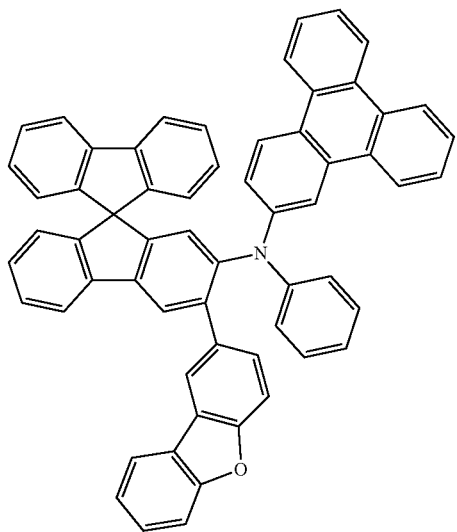
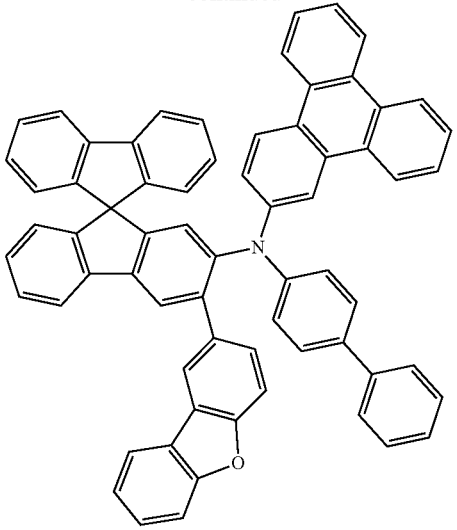
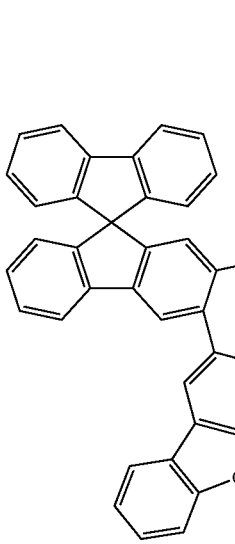

187
-continued
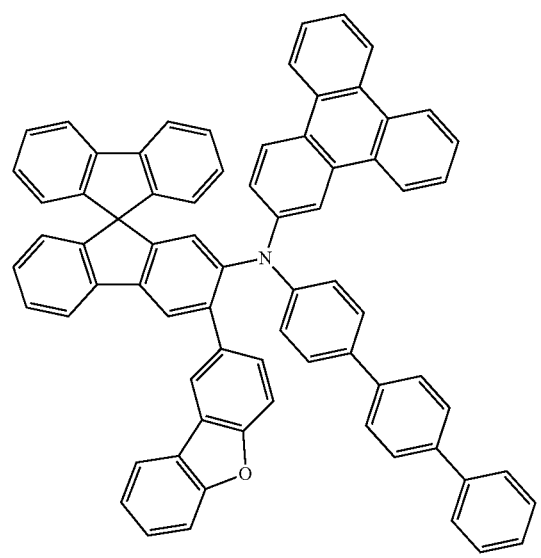
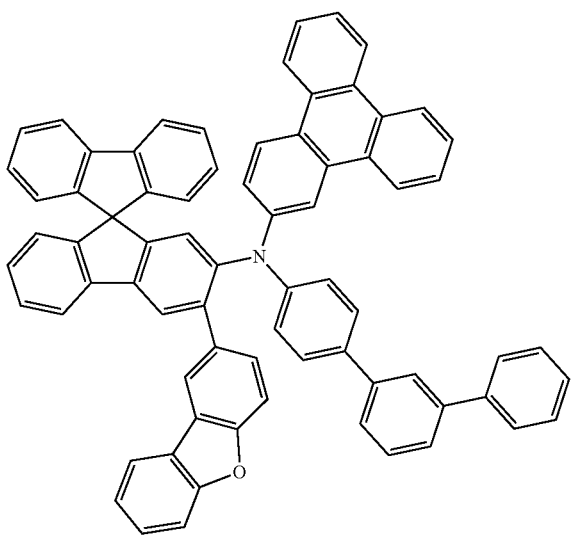
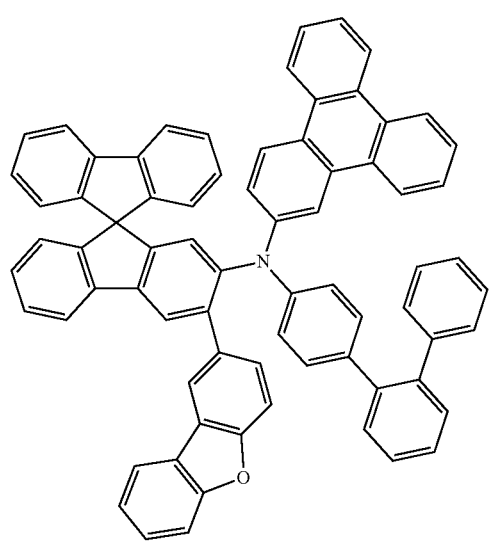
188
-continued
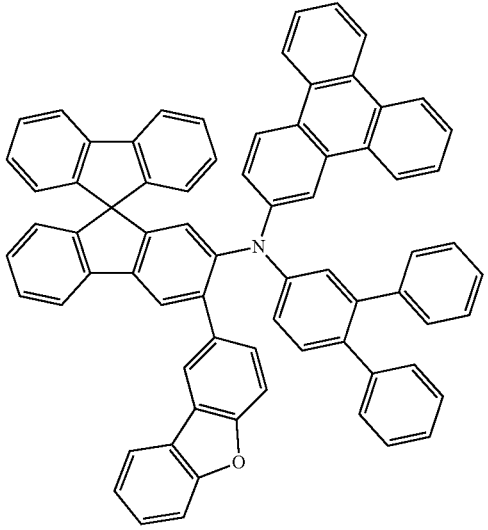
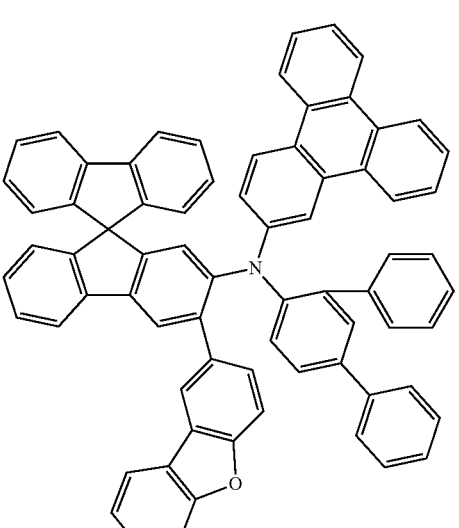
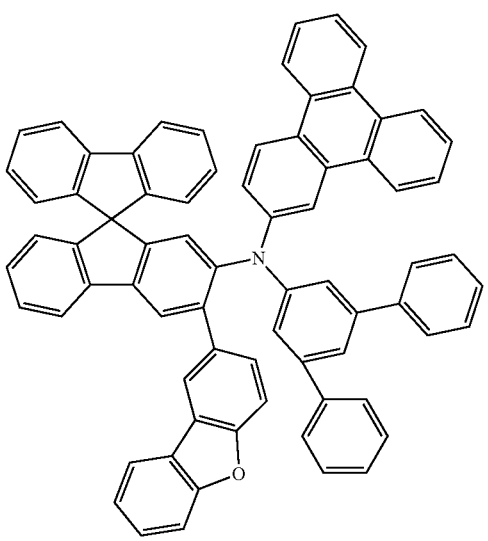

189
-continued
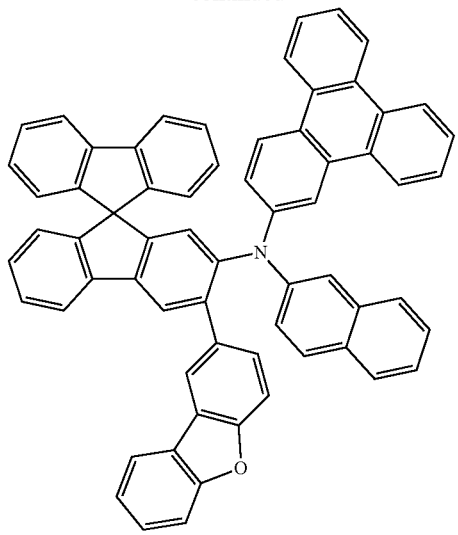
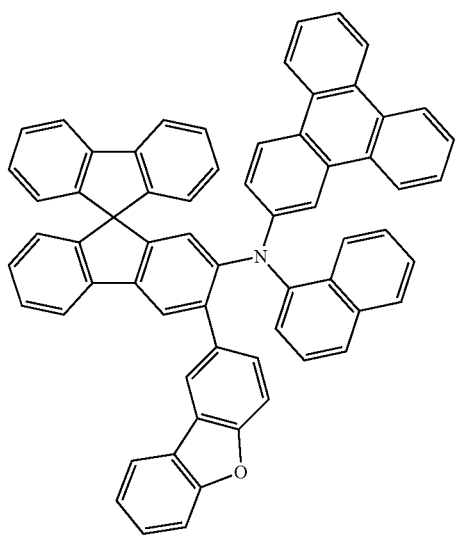
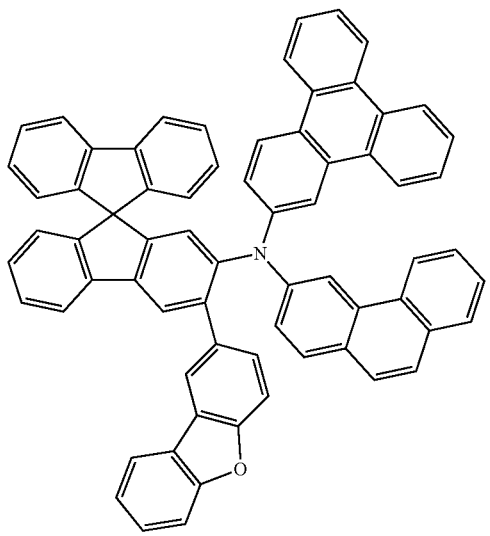
190
-continued
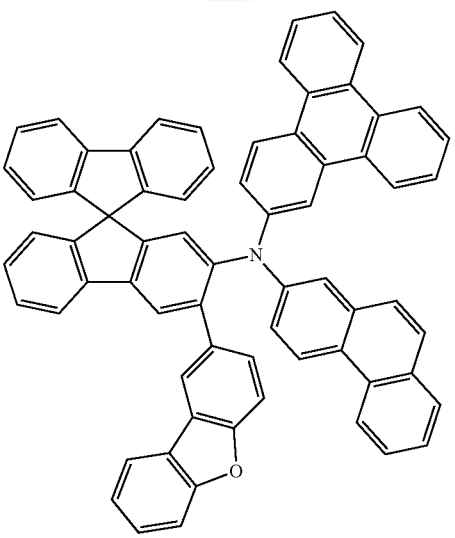
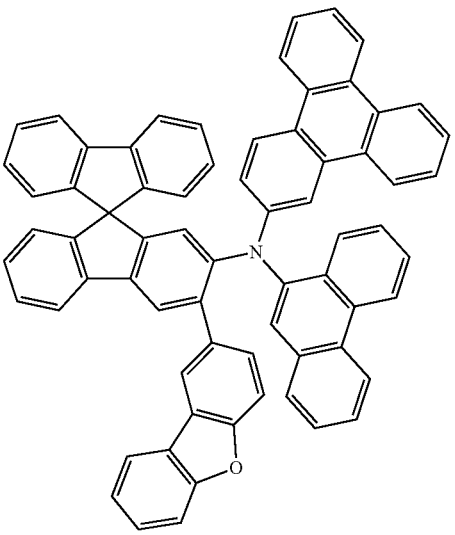
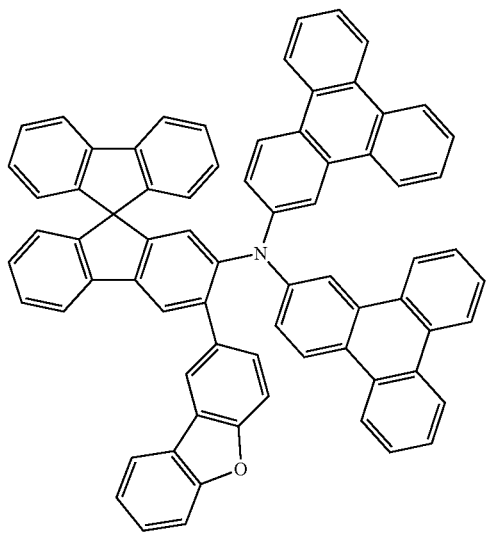

191
-continued
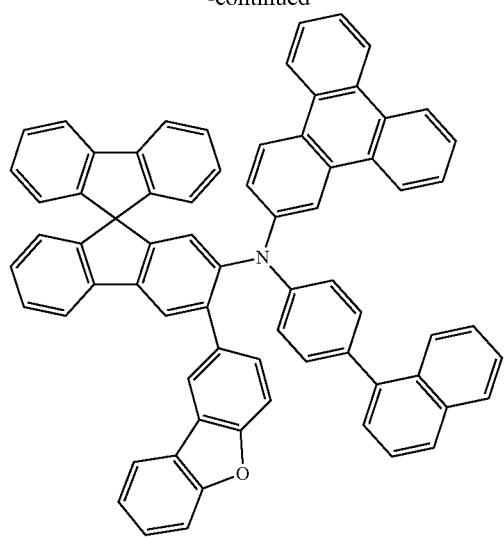
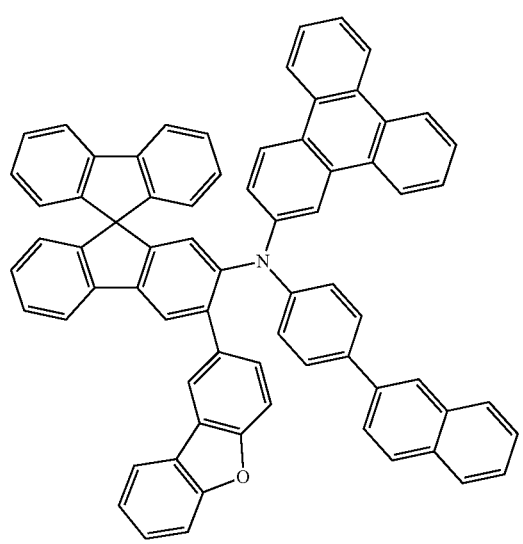
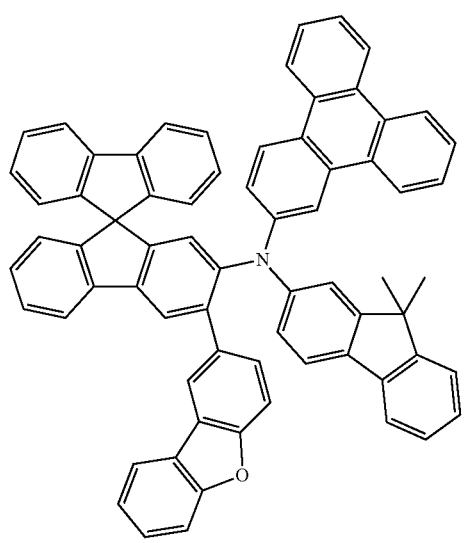
192
-continued
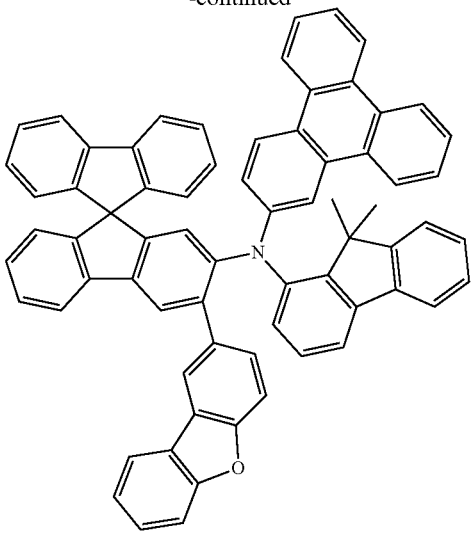
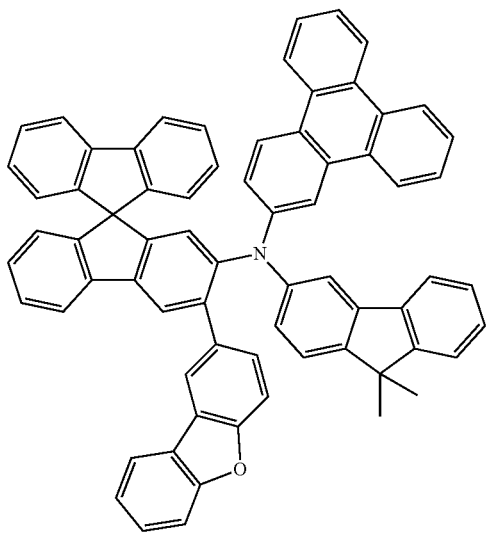
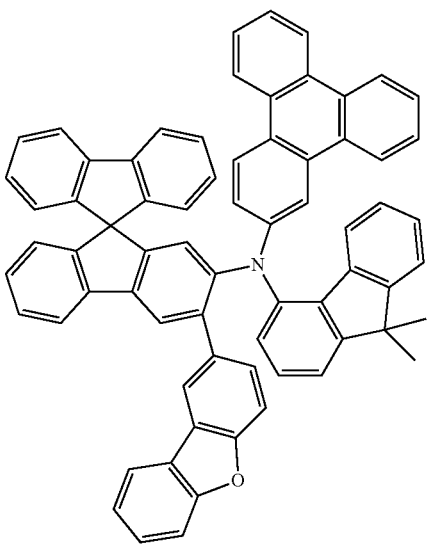

-continued
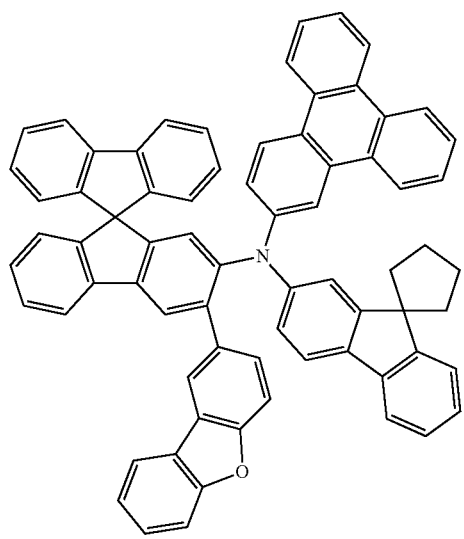
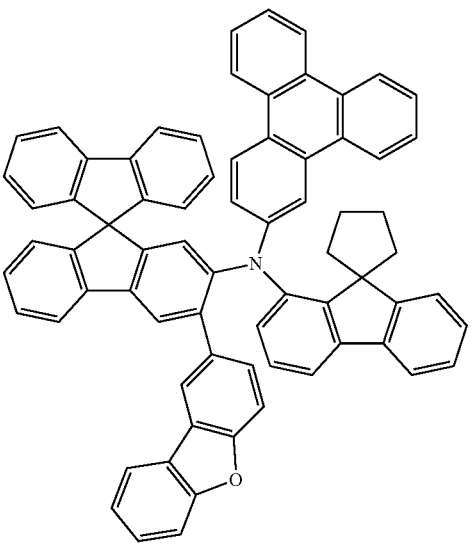
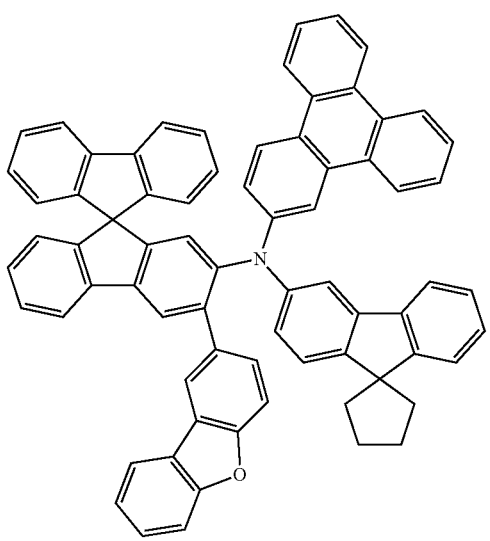
-continued
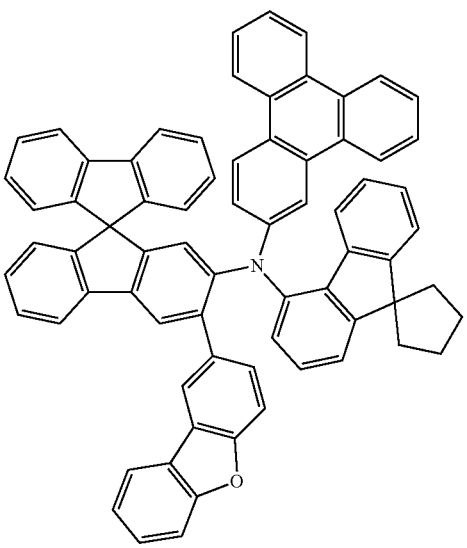
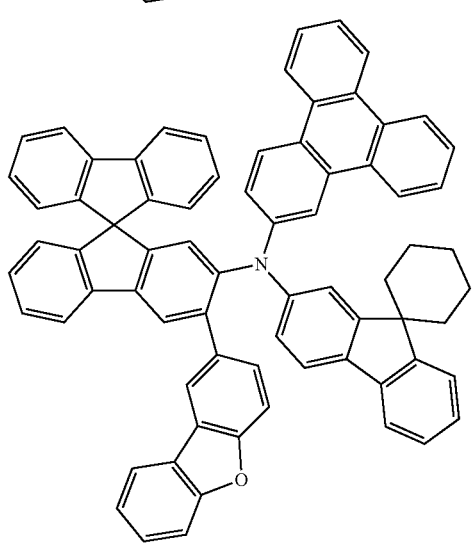
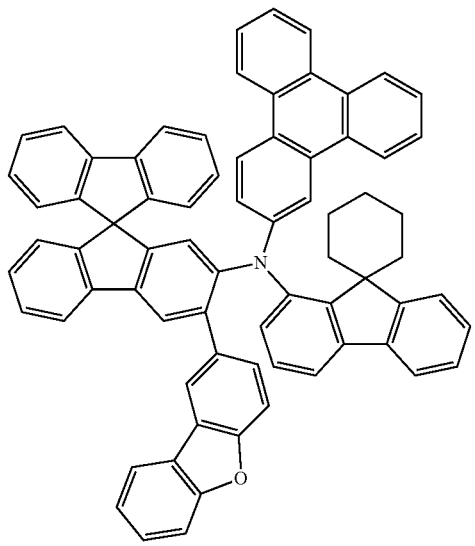

195
-continued
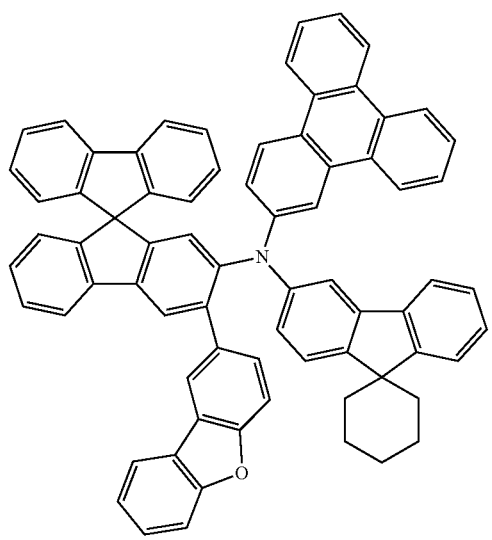
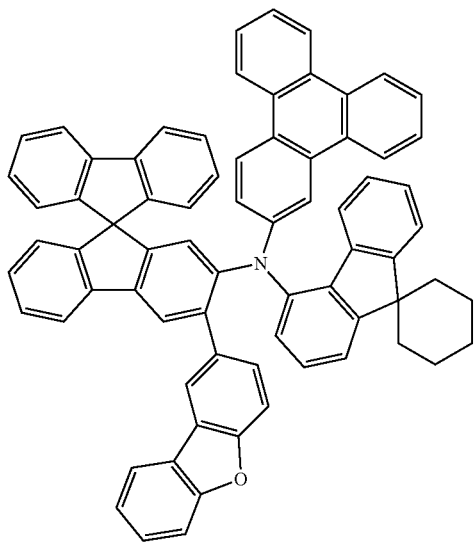
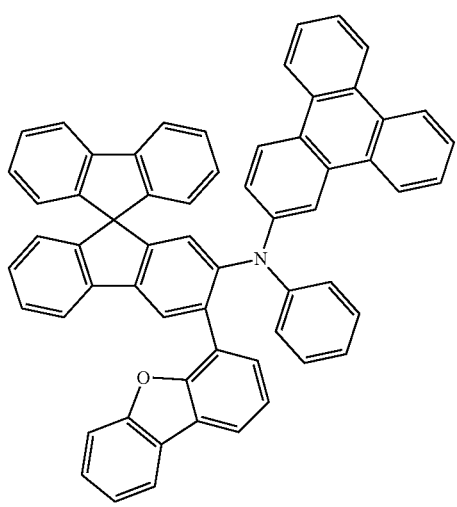
196
-continued
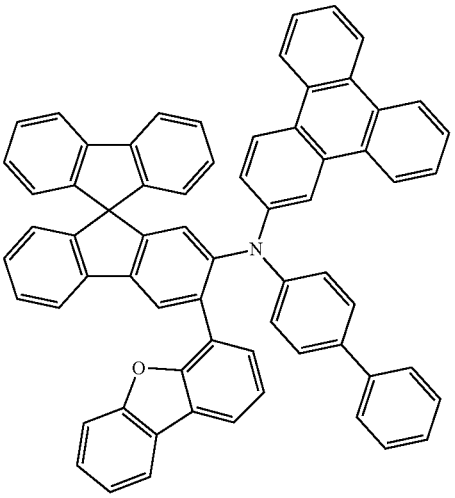
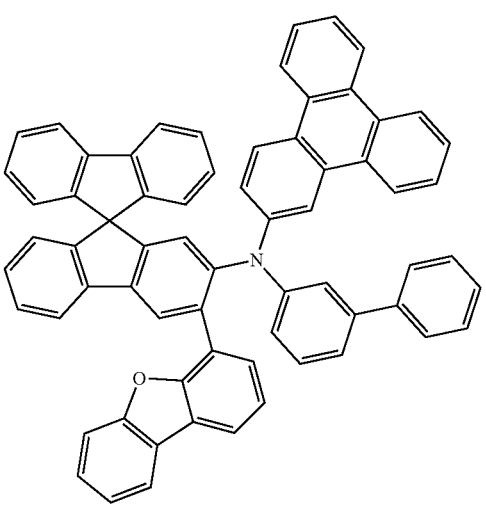
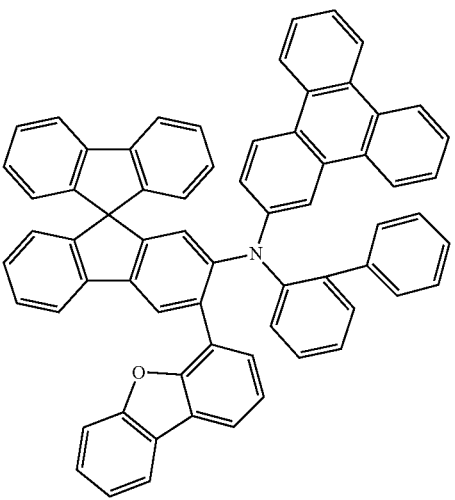

197
-continued
198
-continued
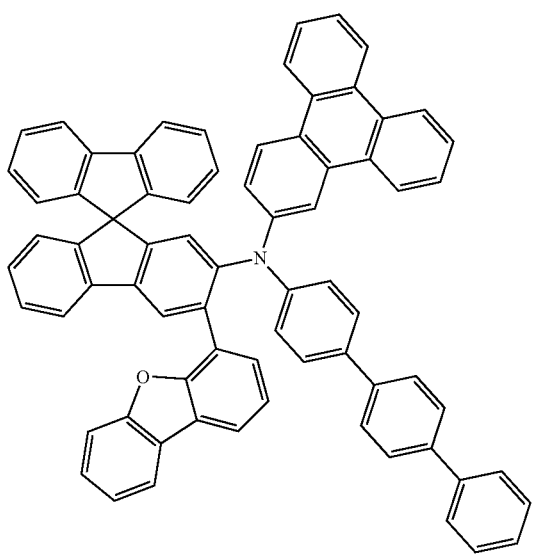
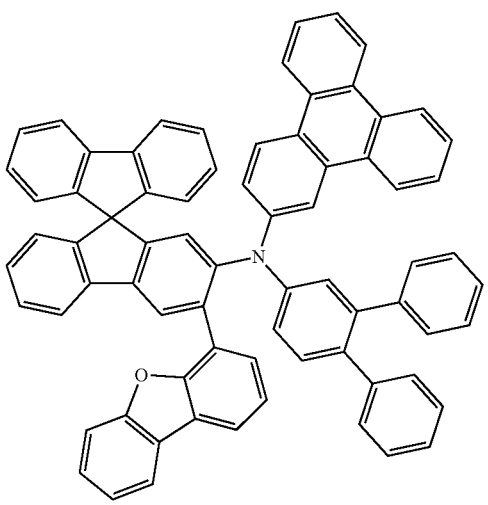
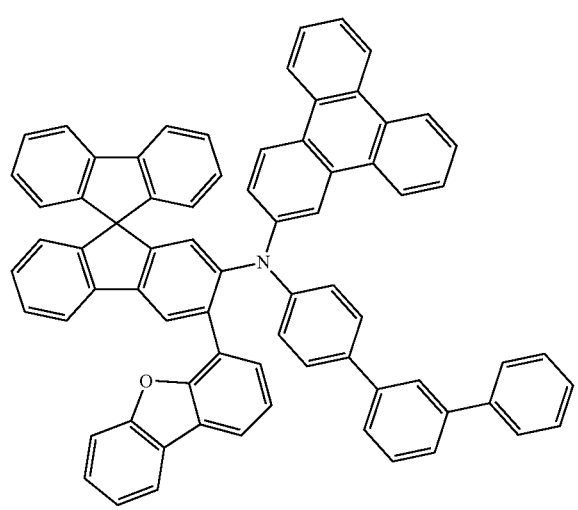
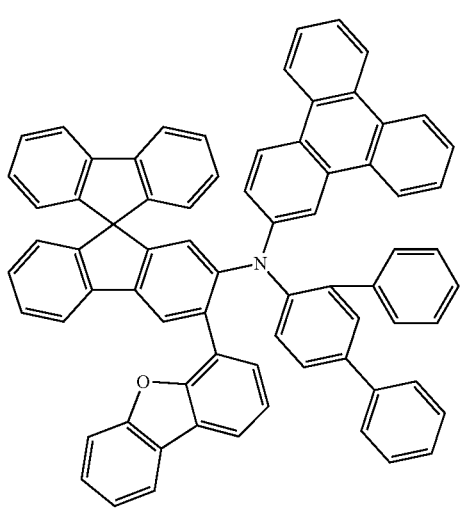
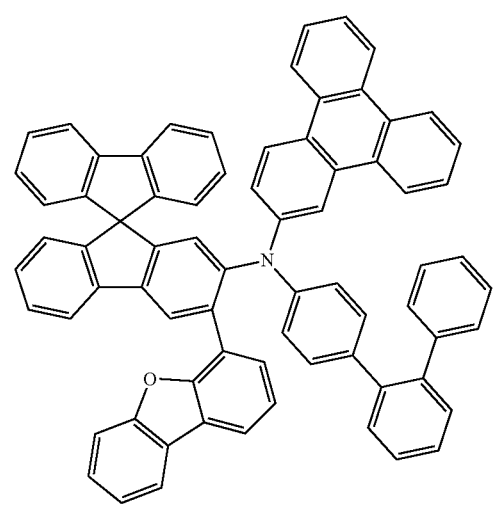
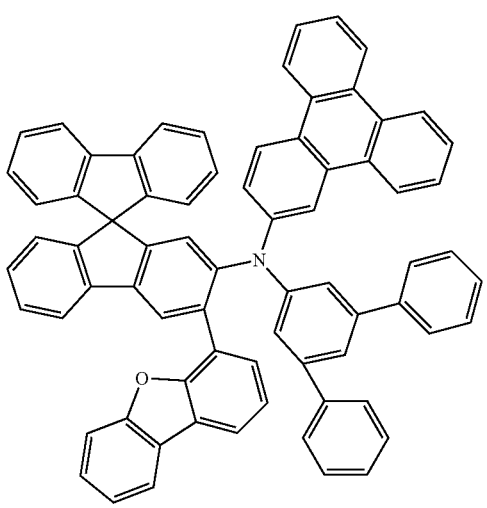

199
-continued
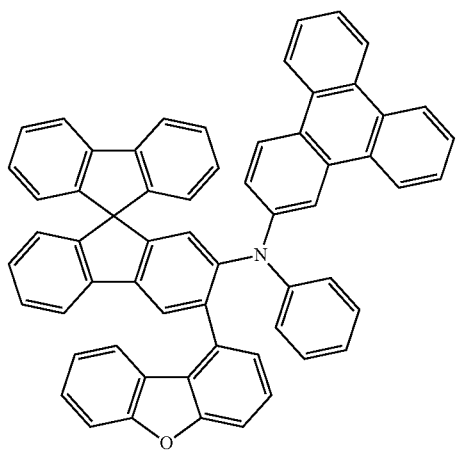
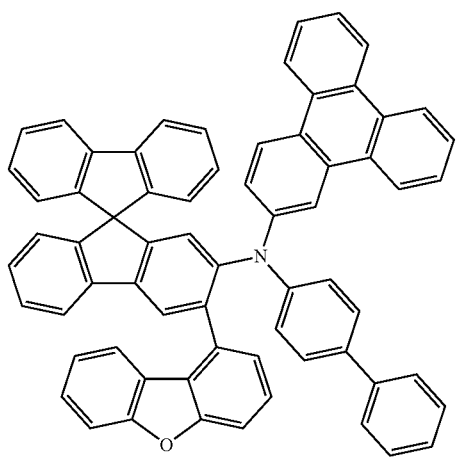
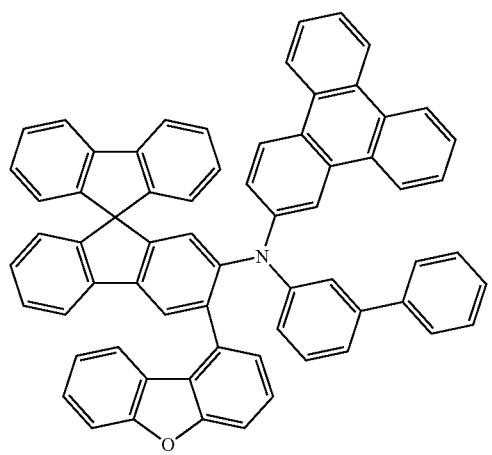
200
-continued
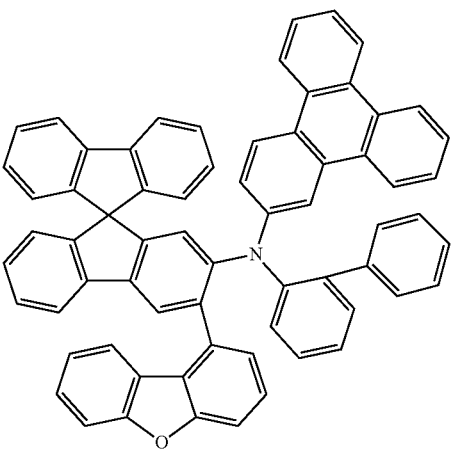
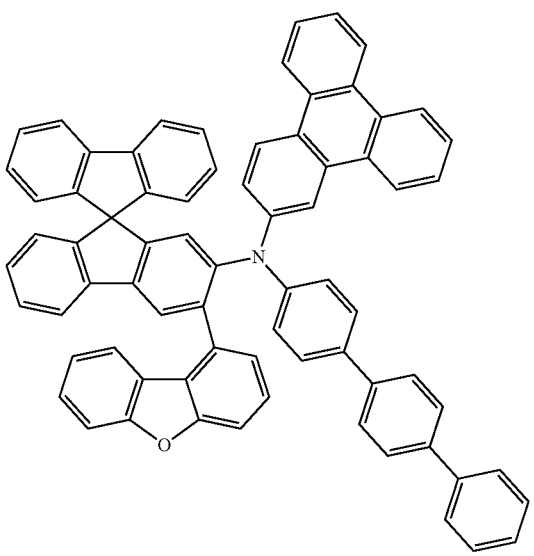
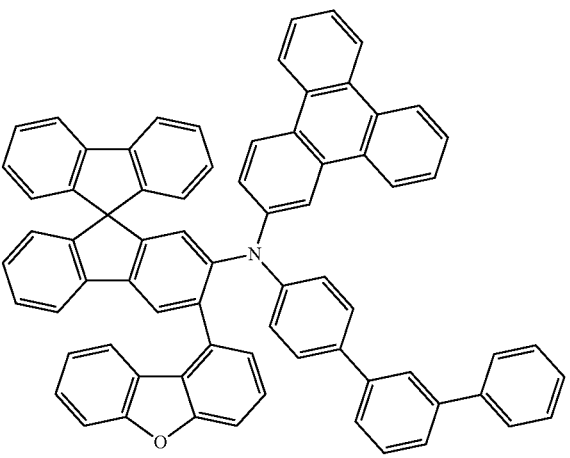

201
-continued
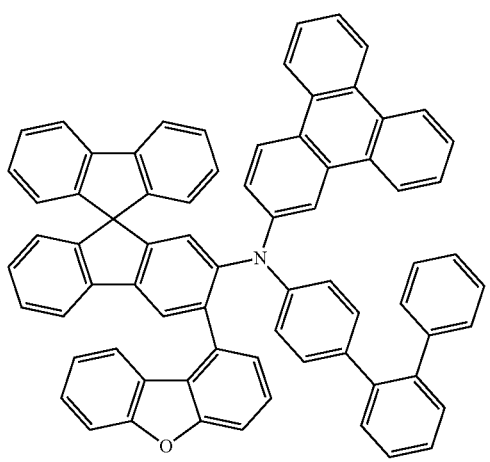
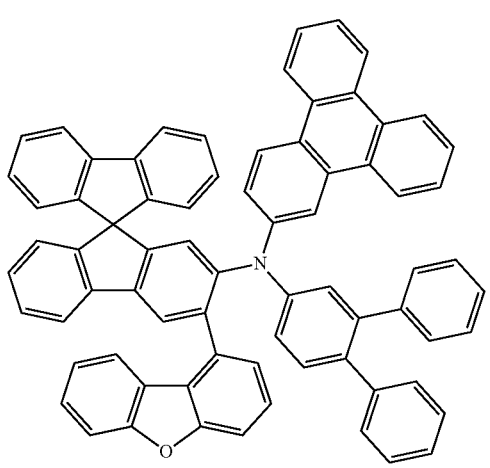
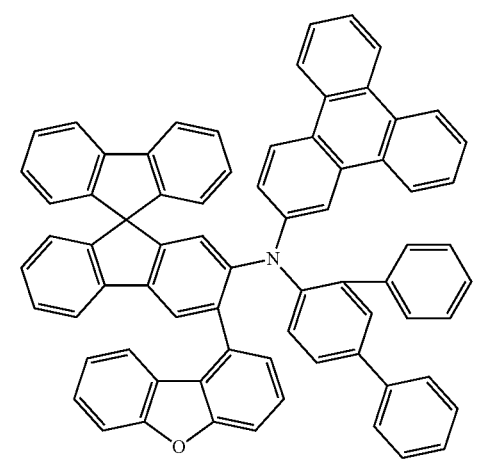
202
-continued
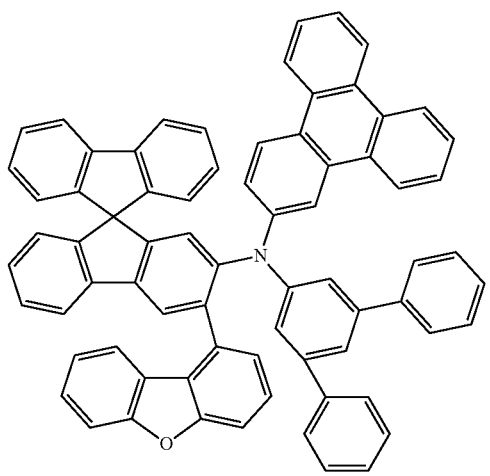
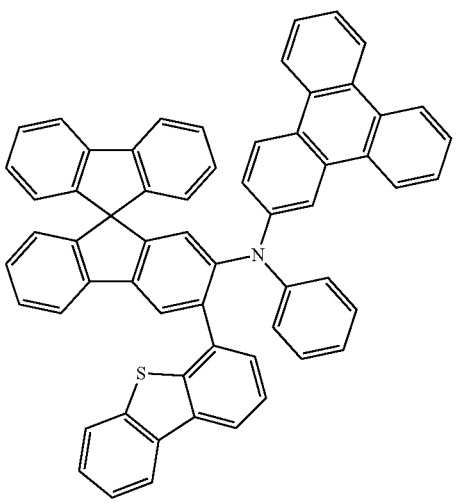
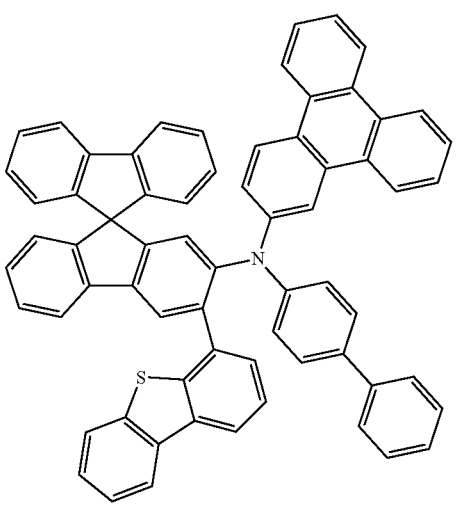

203
-continued
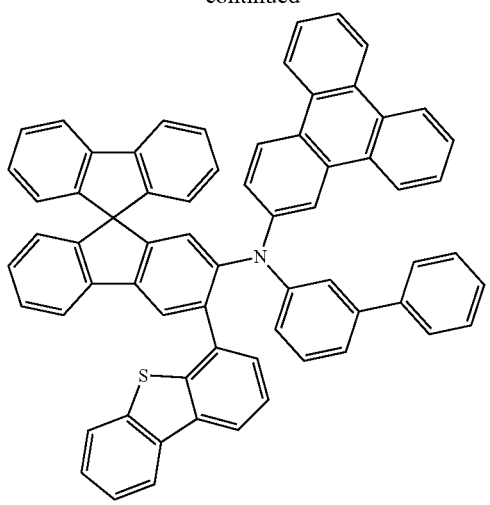
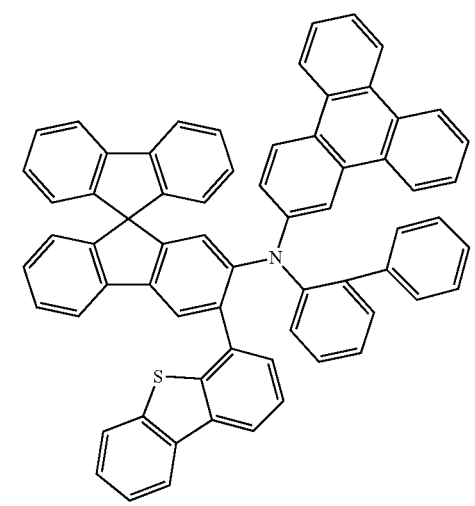
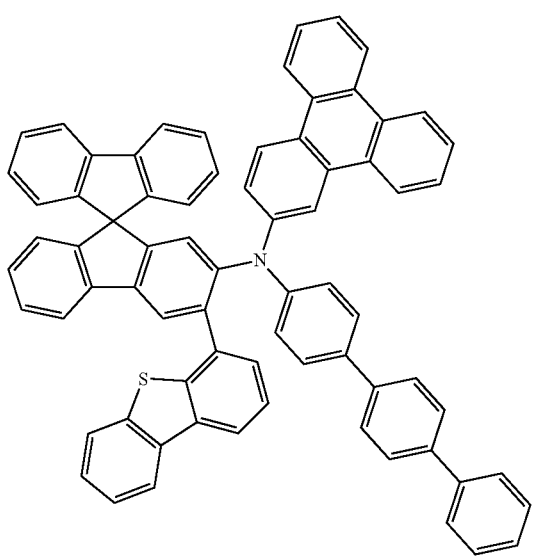
204
-continued
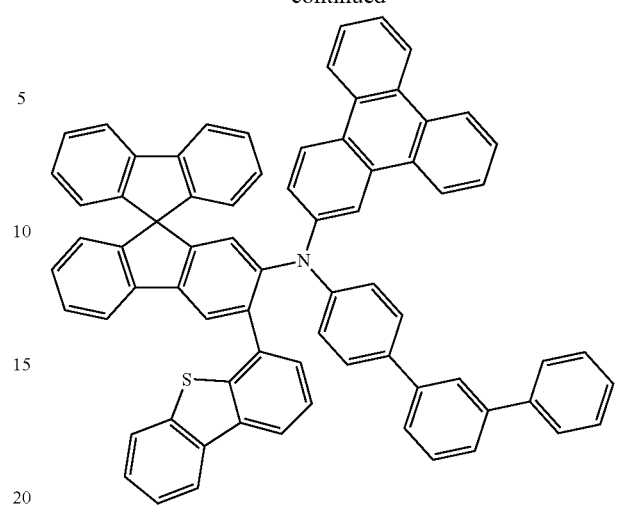
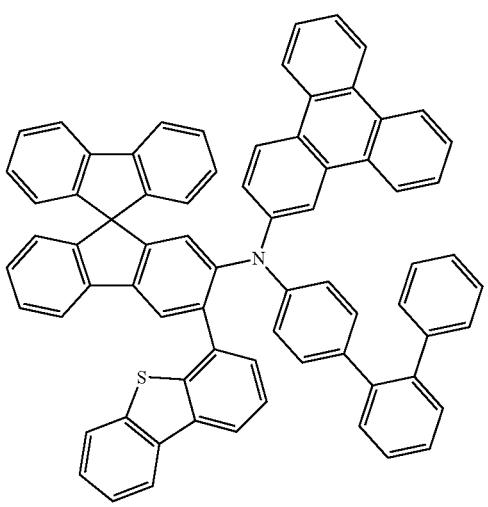
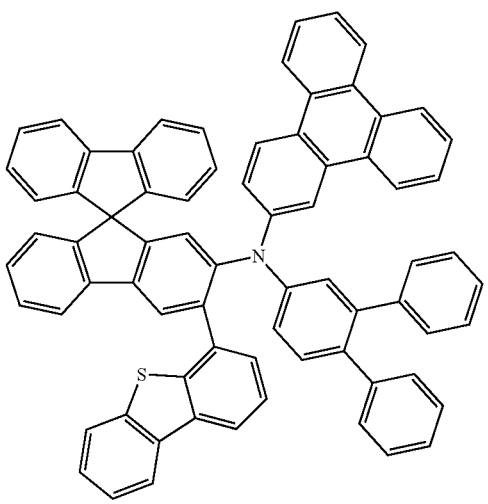

205
-continued
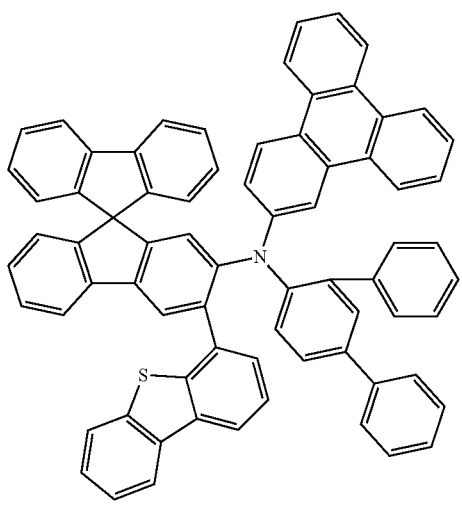
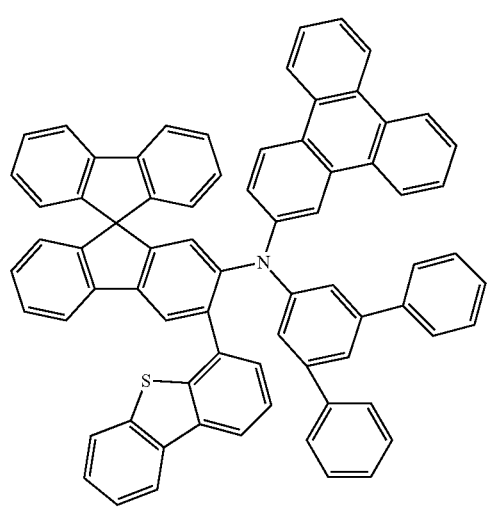
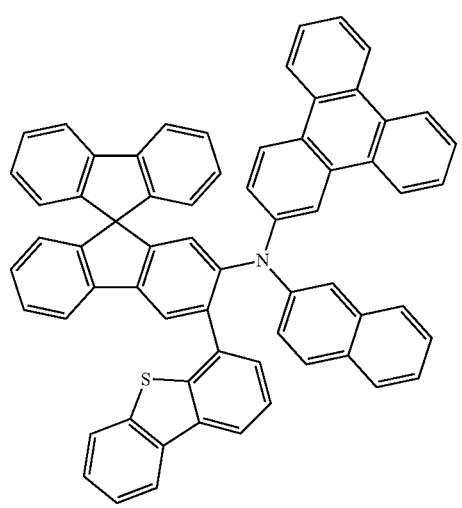
206
-continued
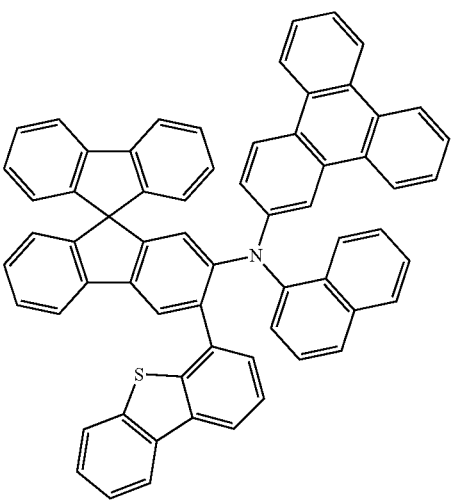
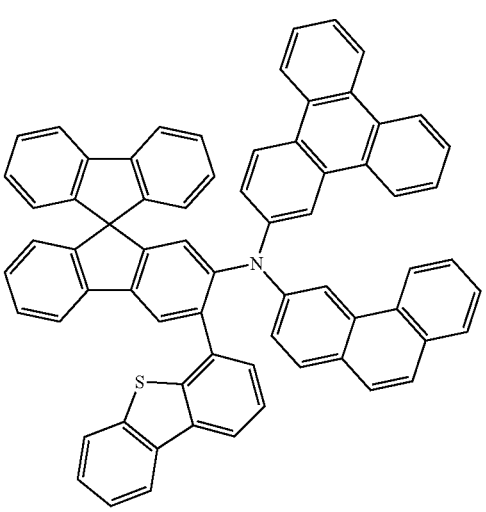
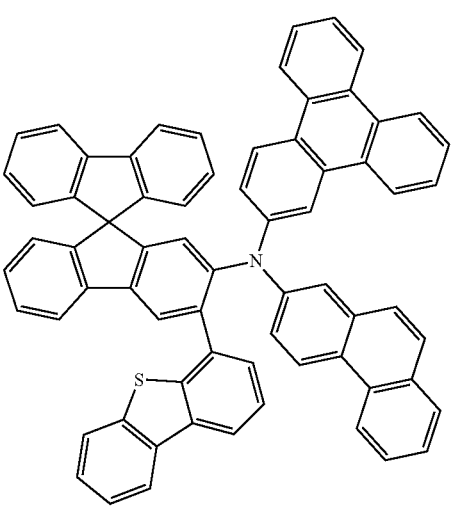

207
-continued
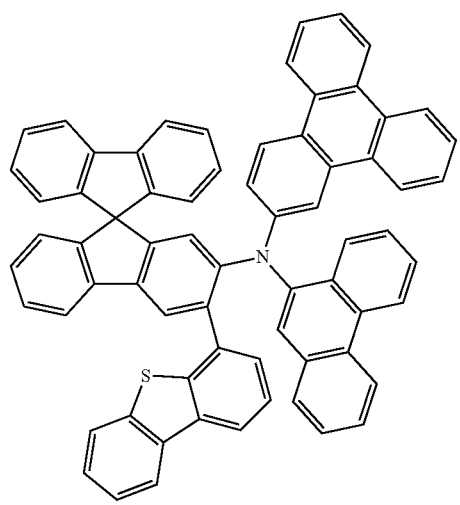
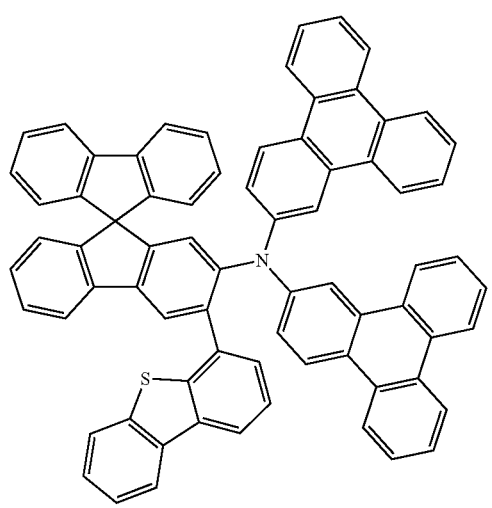
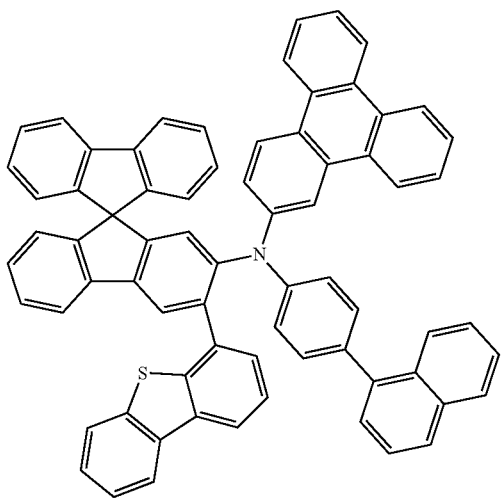
208
-continued
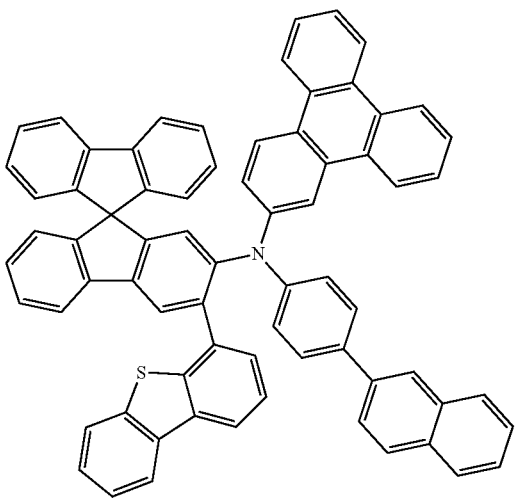
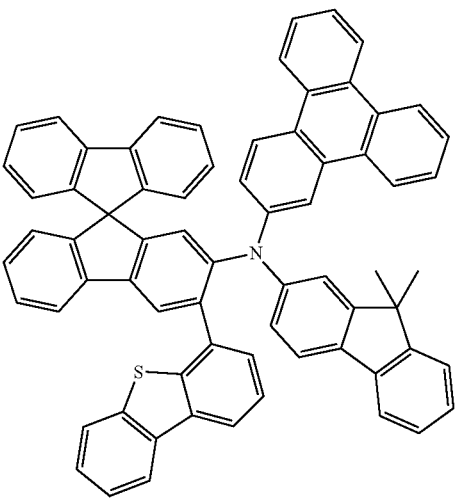
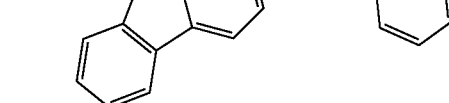
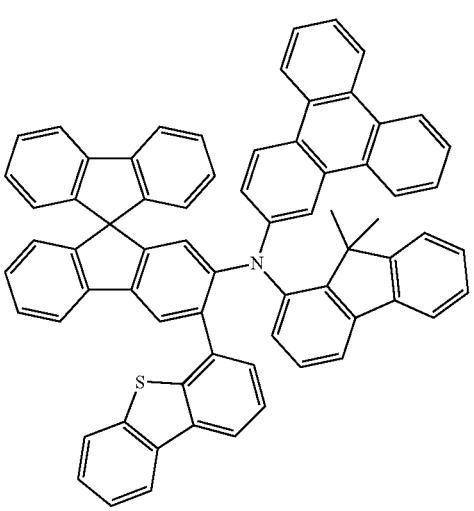

209
-continued
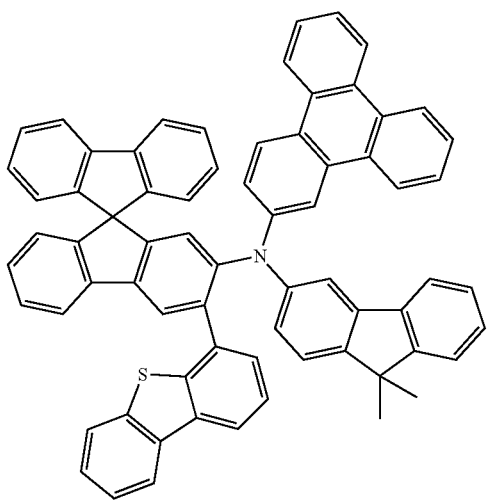
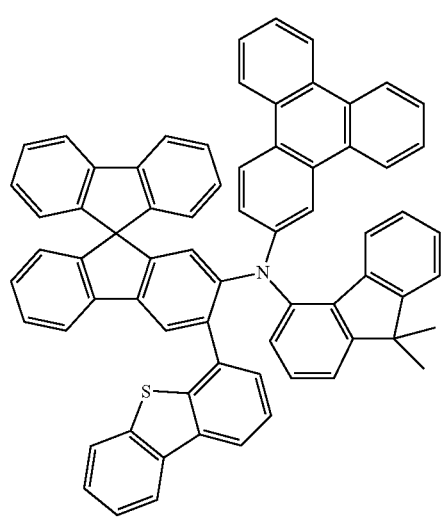
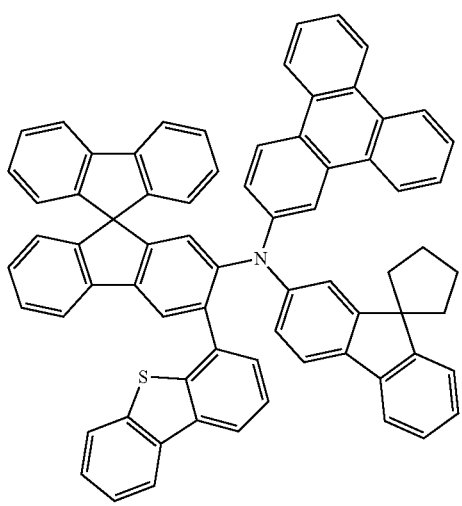
210
-continued
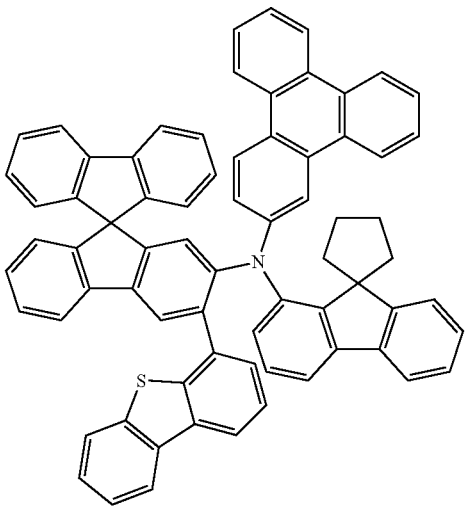
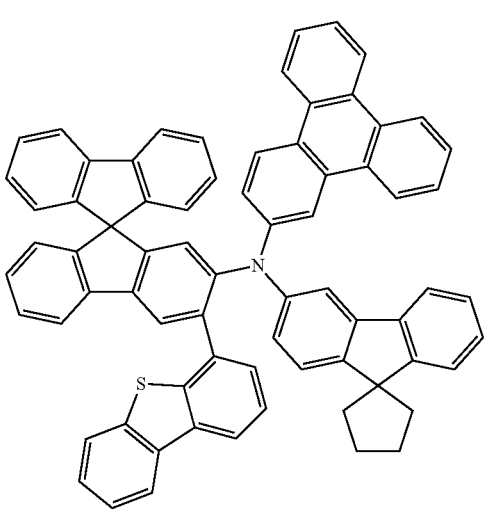
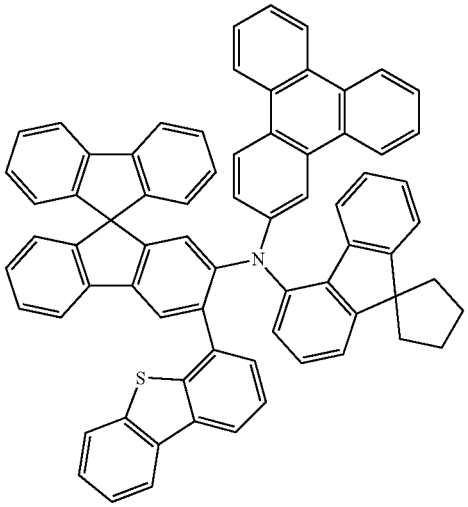

211
-continued
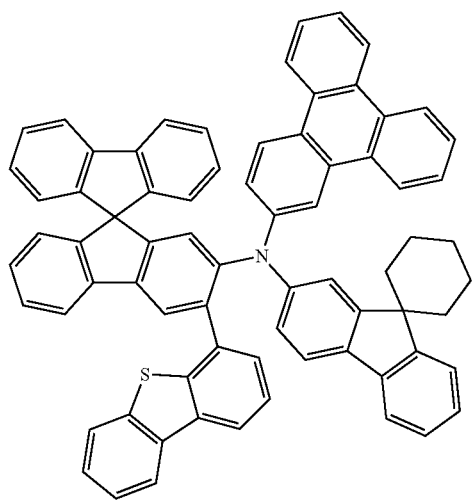
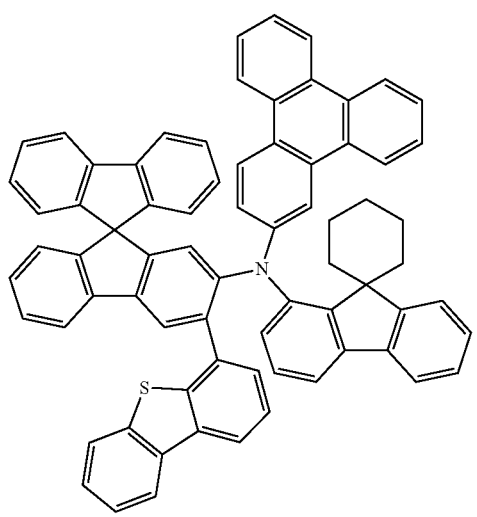
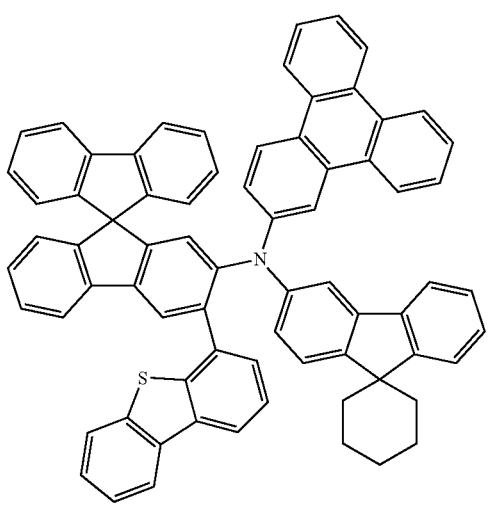
212
-continued
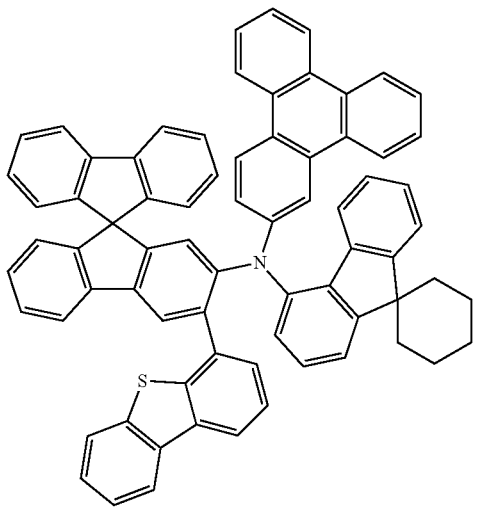
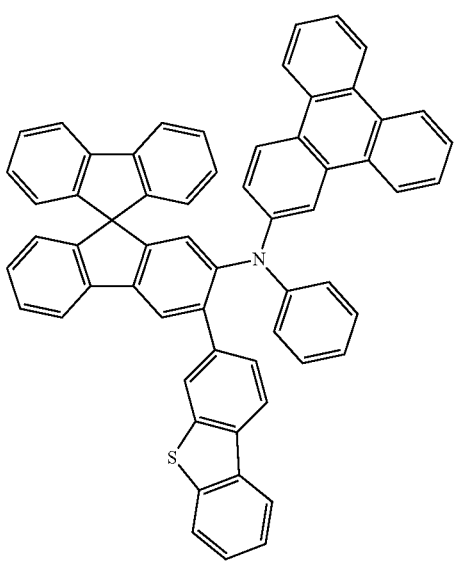
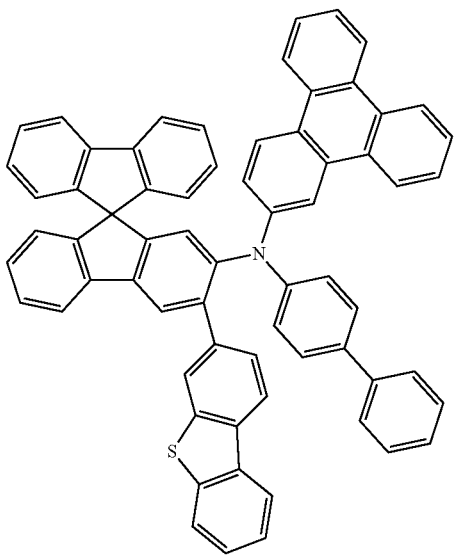

213
-continued
214
-continued
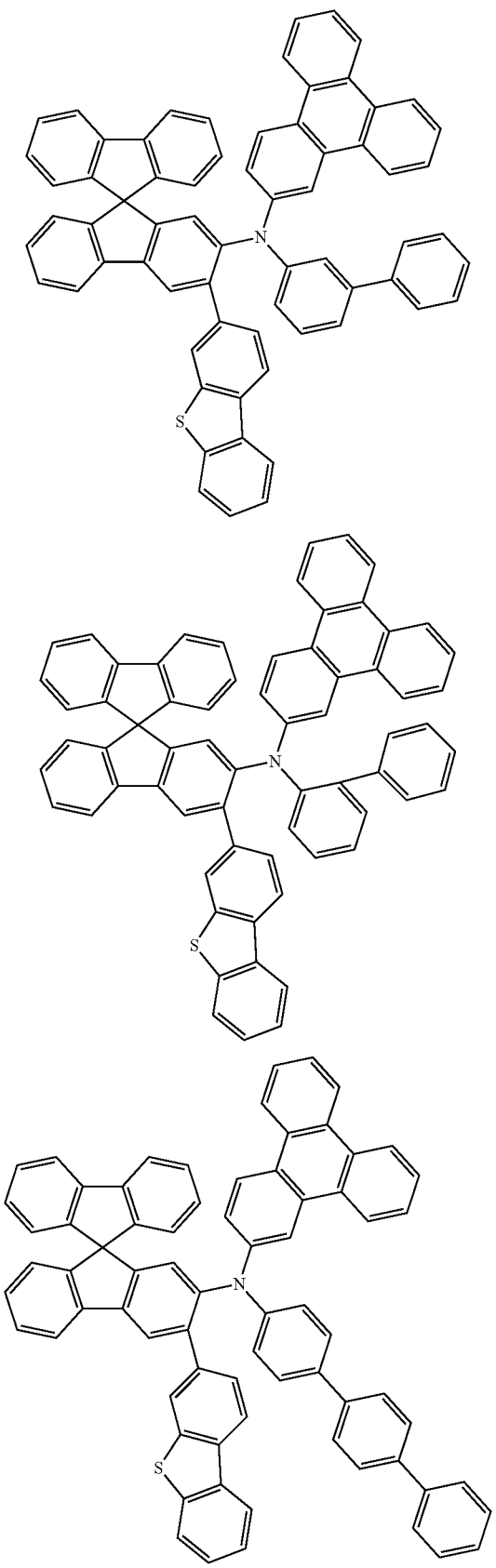
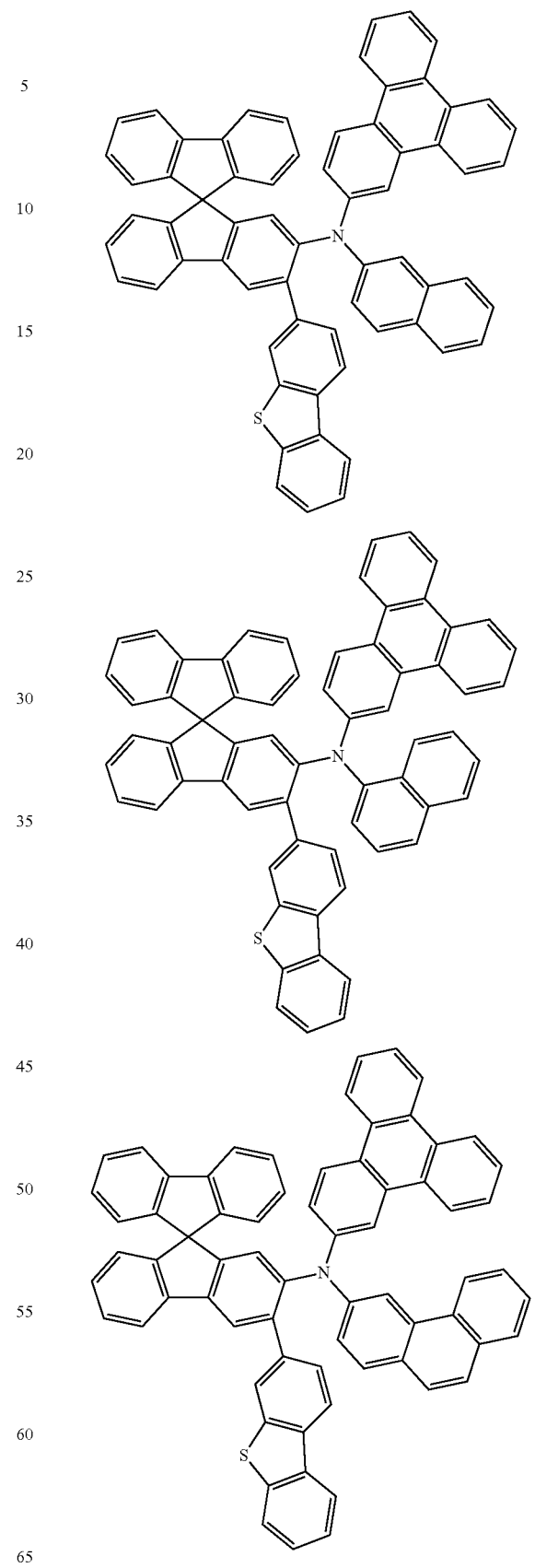

-continued
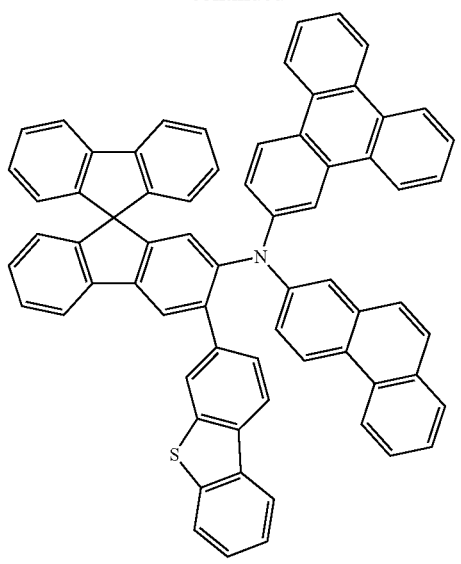
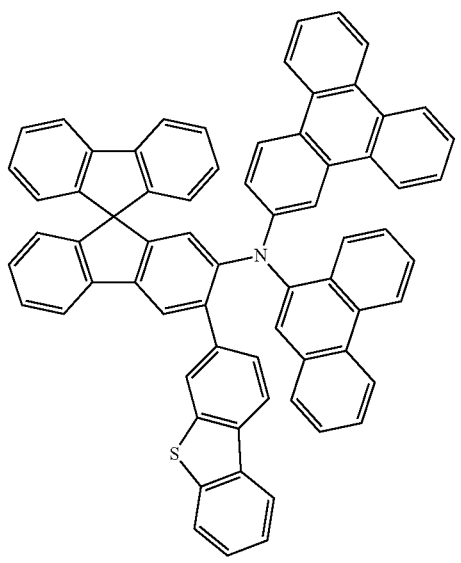
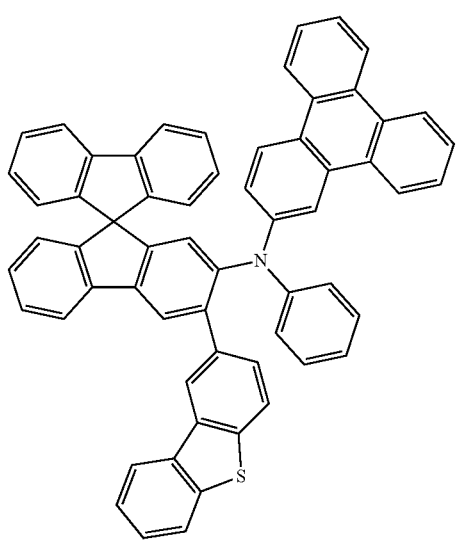
-continued
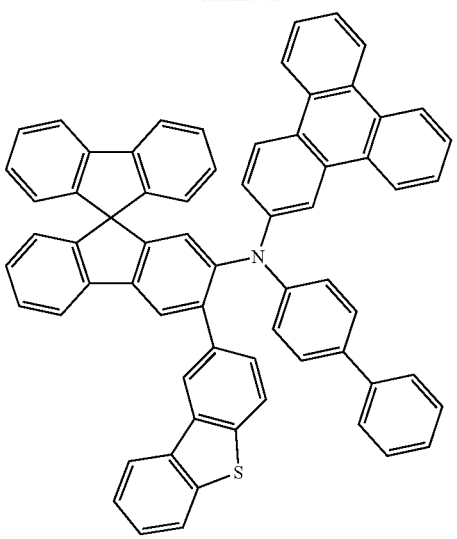
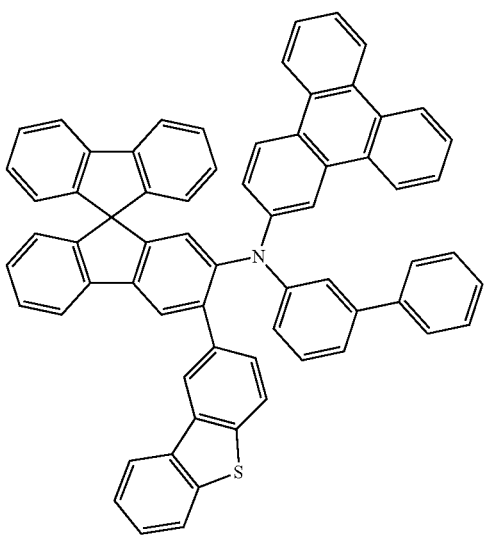
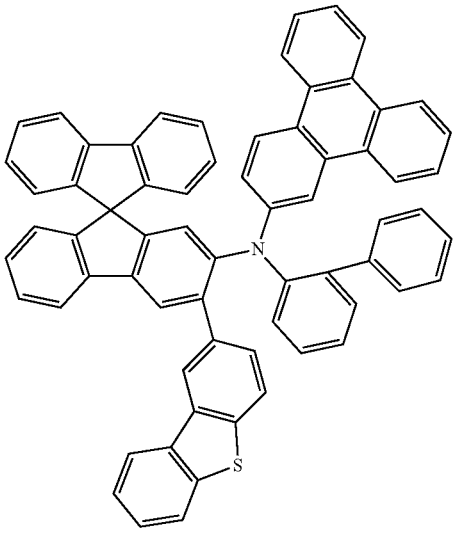

217
-continued
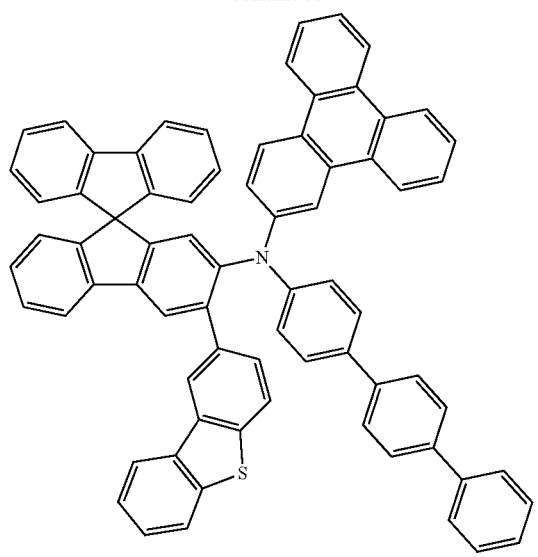
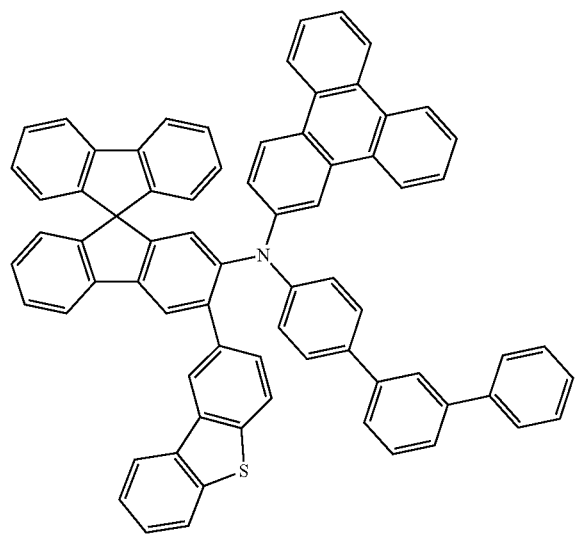
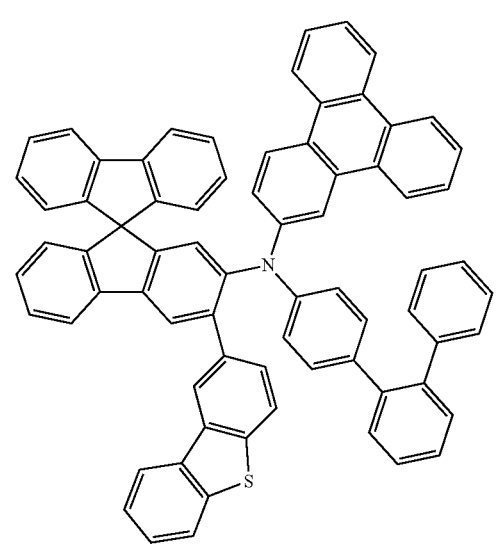
218
-continued
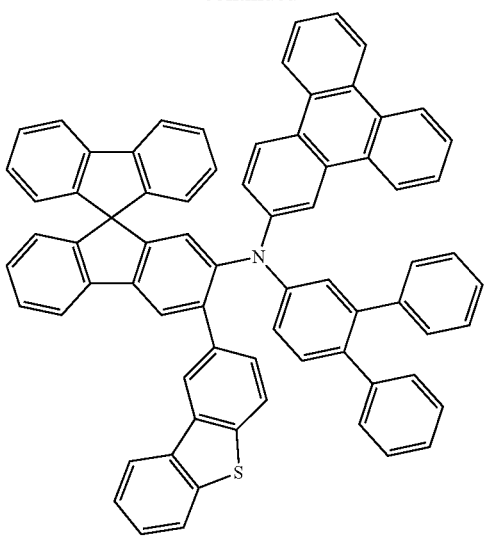

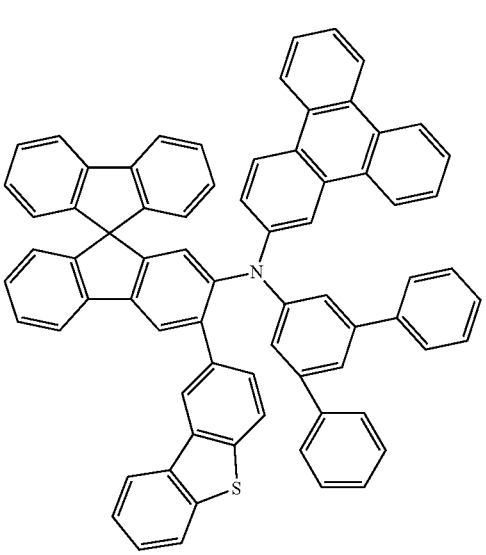

219
-continued
220
-continued
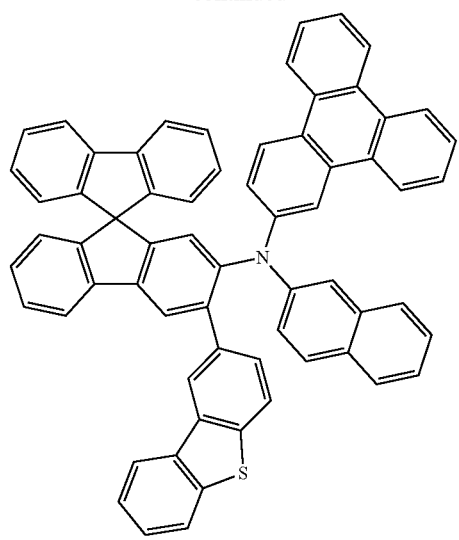
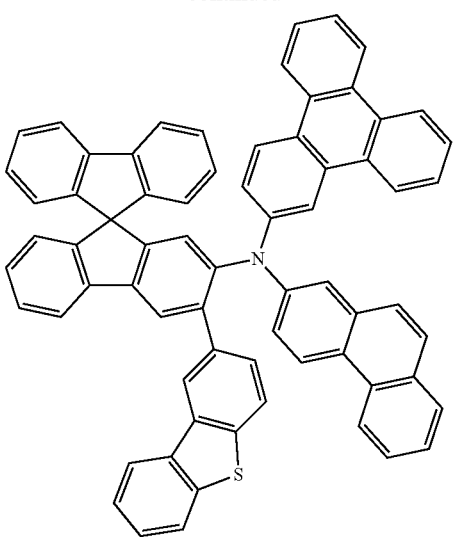

221
-continued
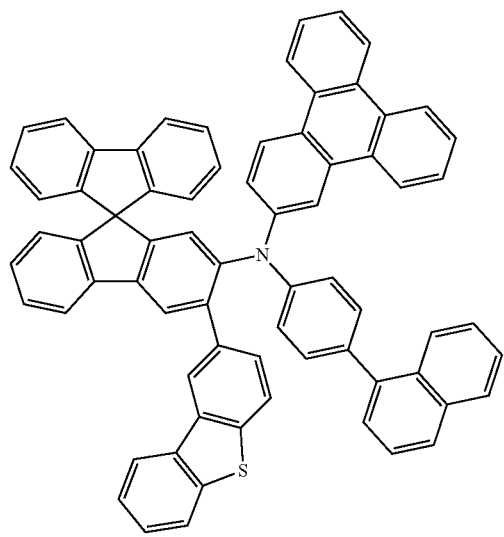
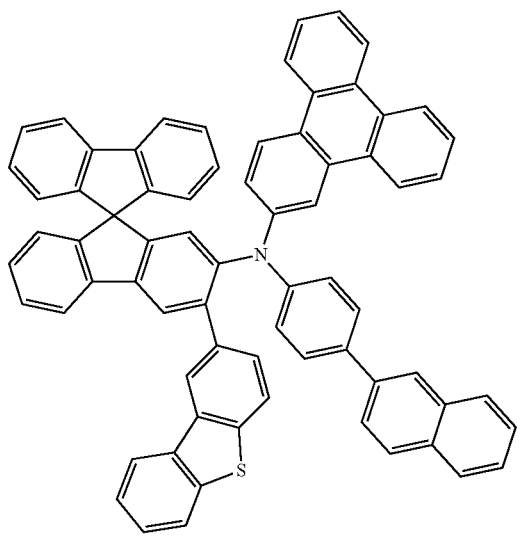
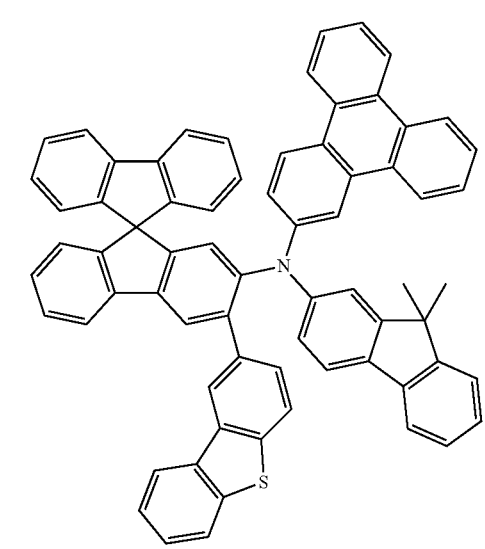
222
-continued
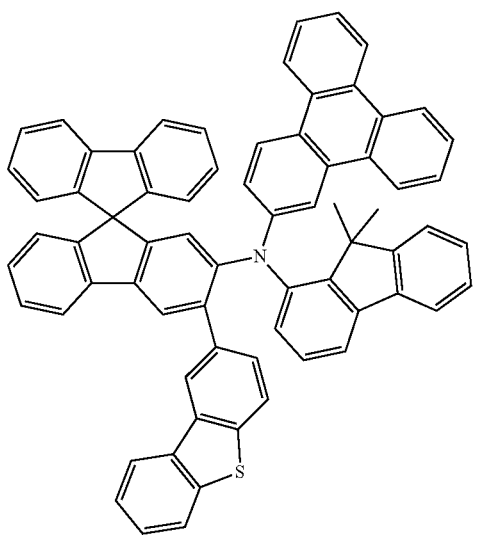
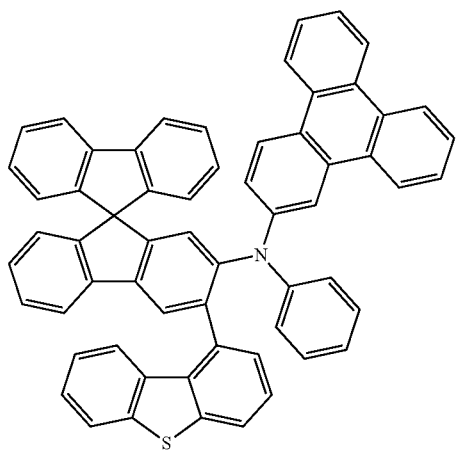
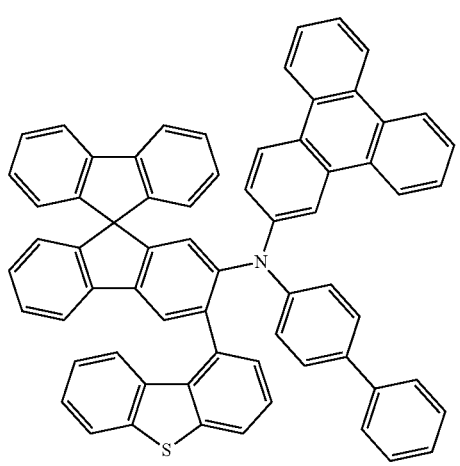

223
-continued
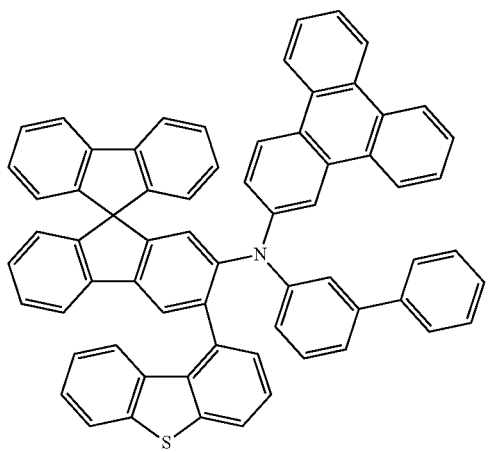
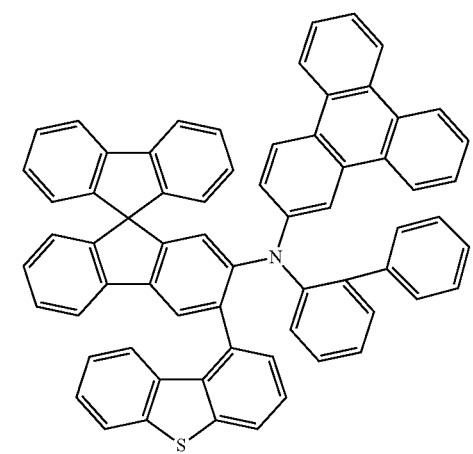
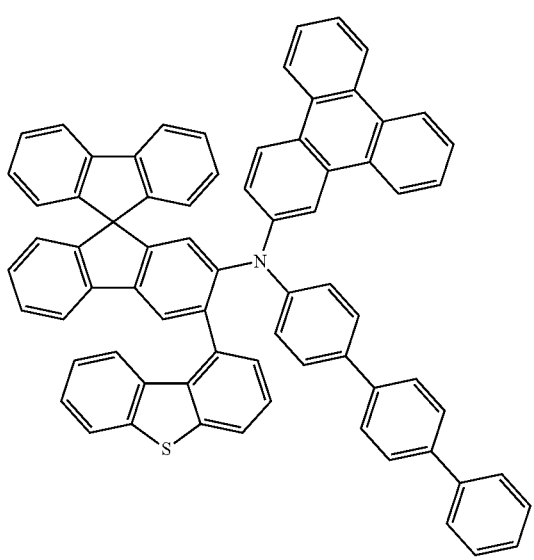
224
-continued
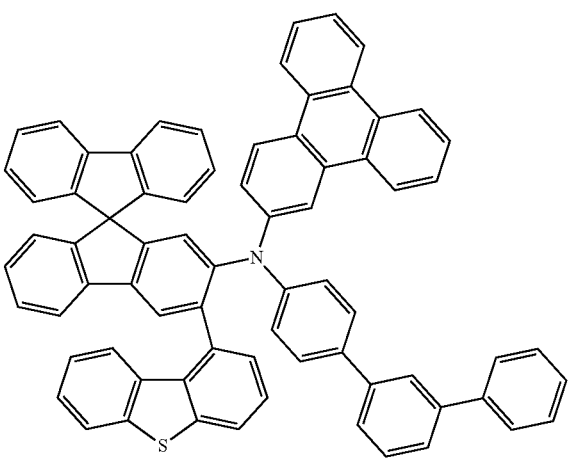
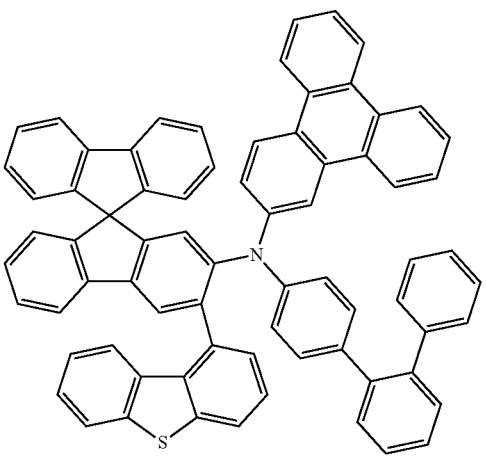
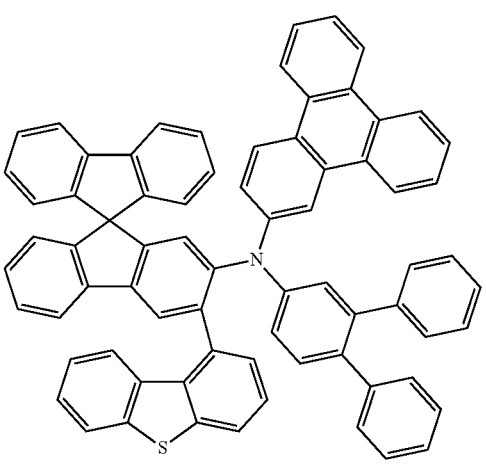

225
-continued
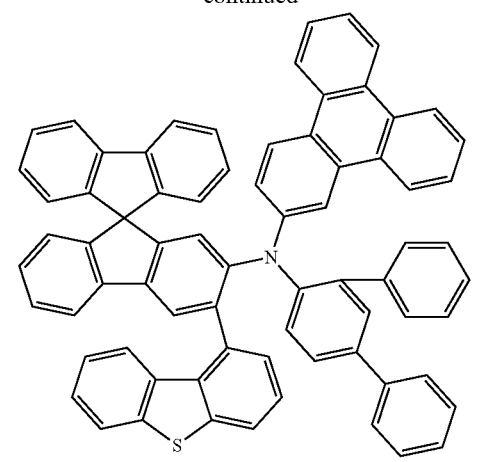
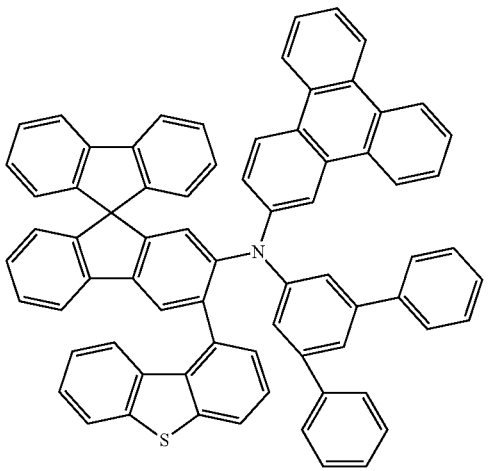
226
-continued
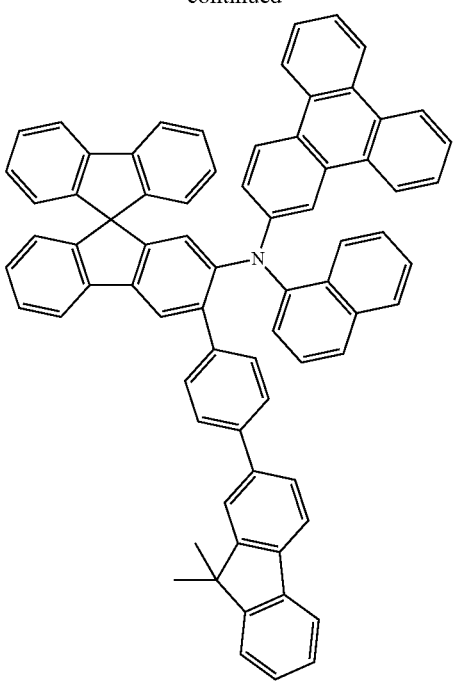
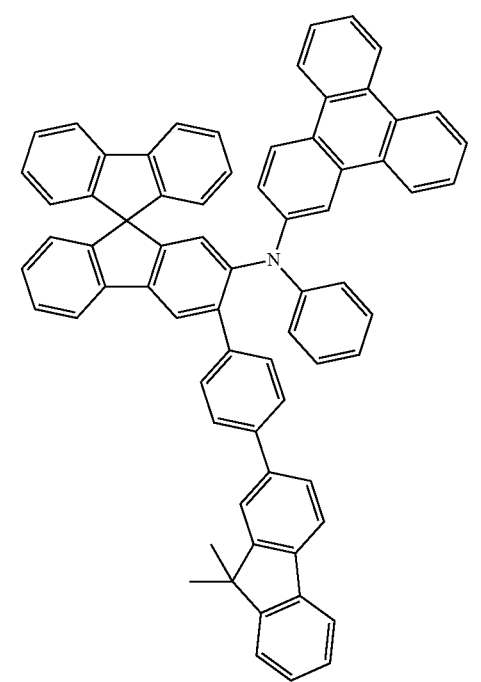
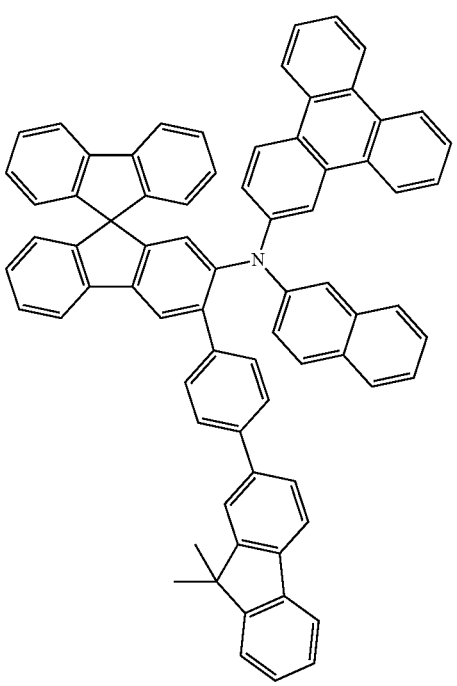

227
-continued
228
-continued
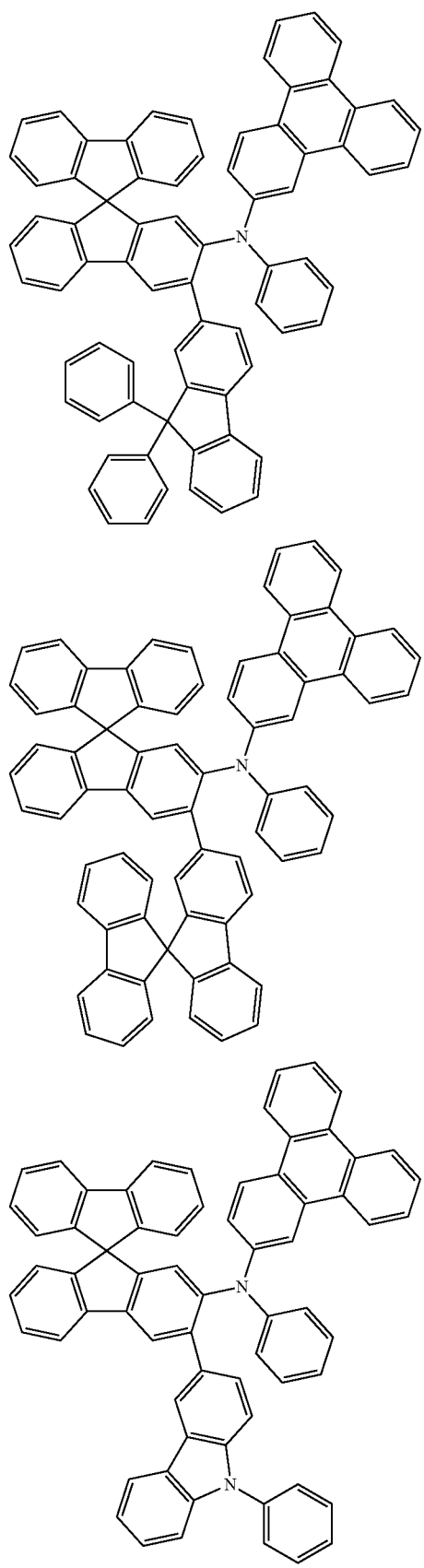
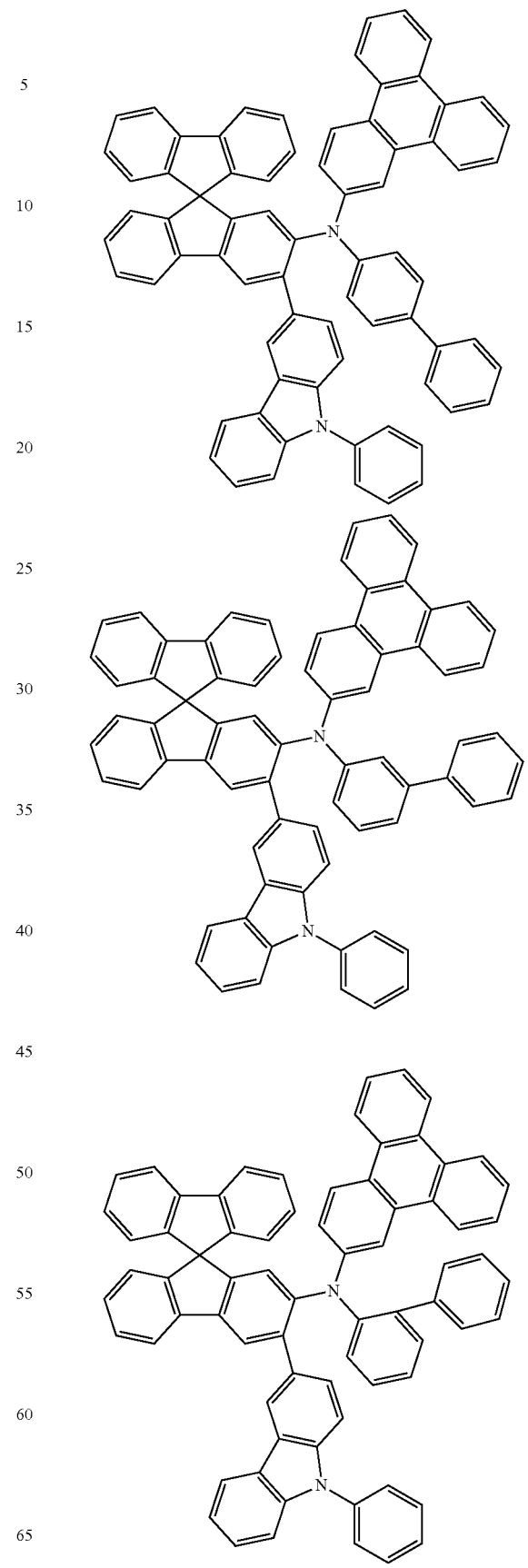

229
-continued
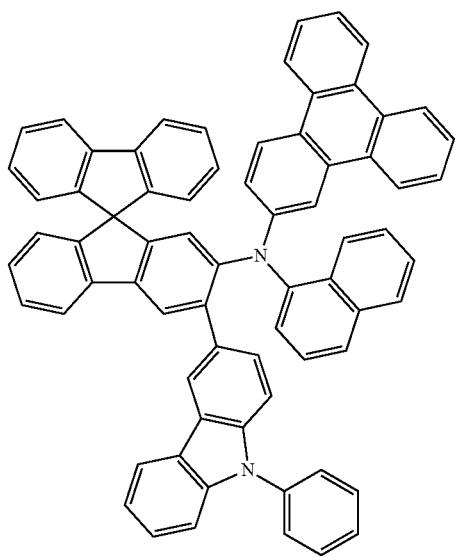
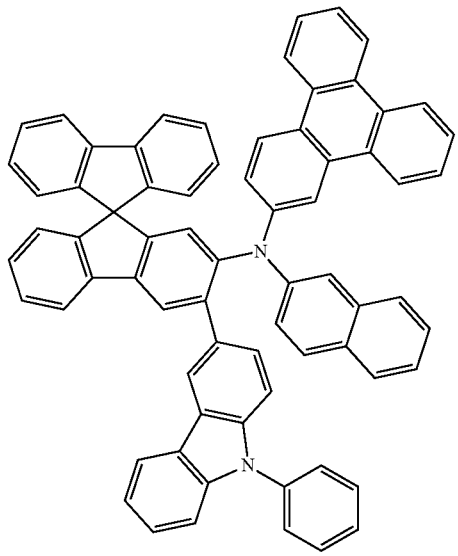
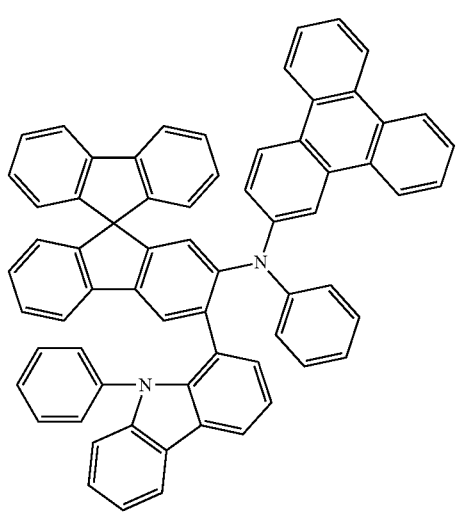
230
-continued
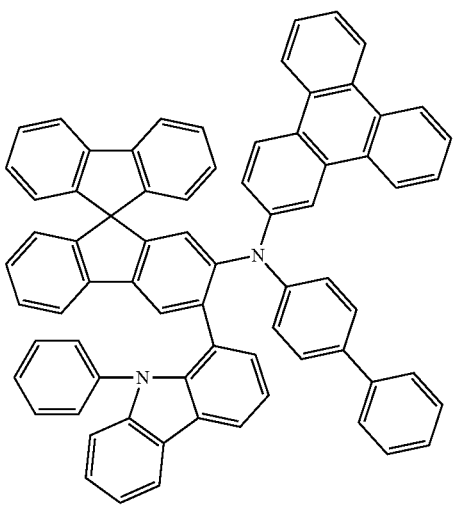
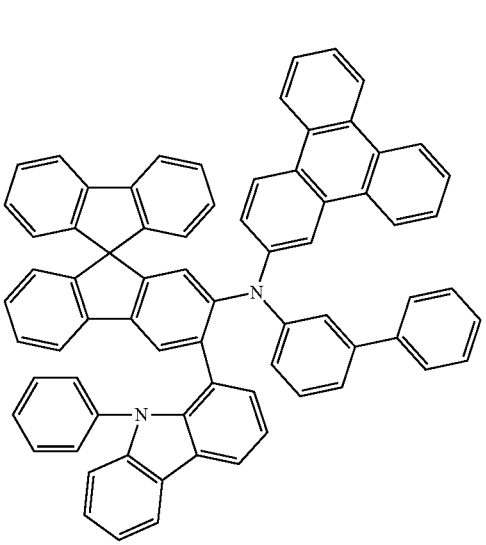
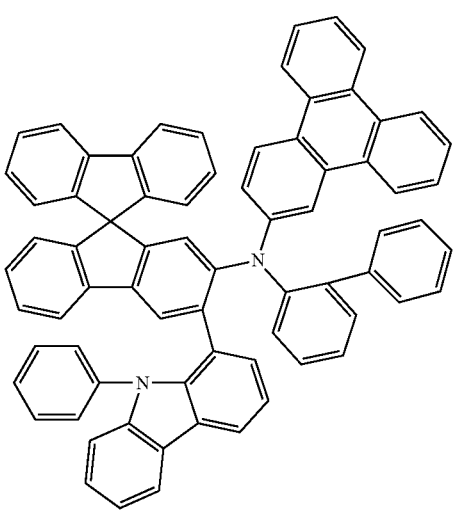

231
-continued
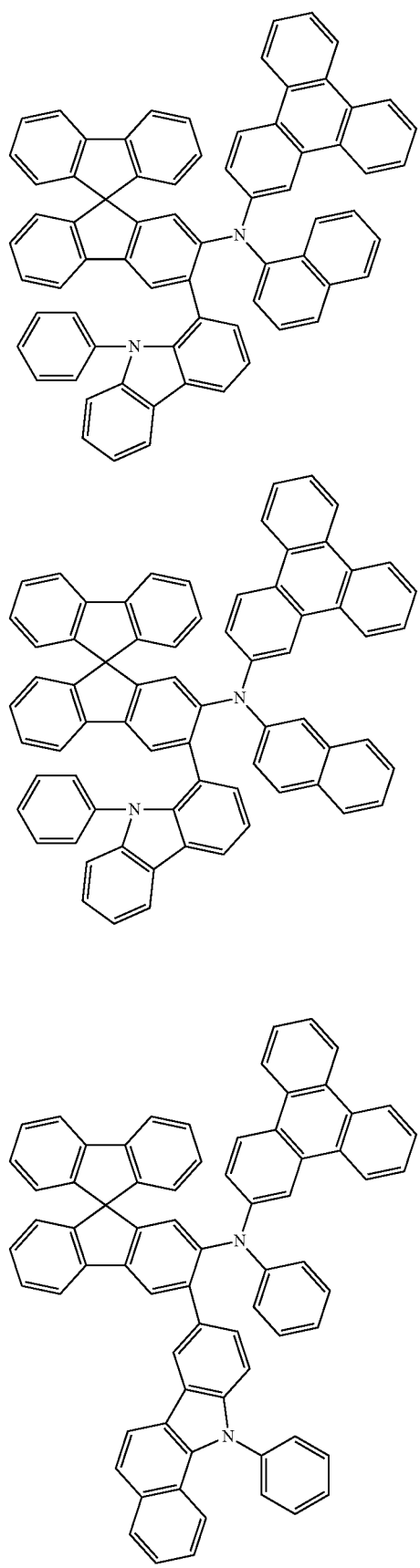
232
-continued
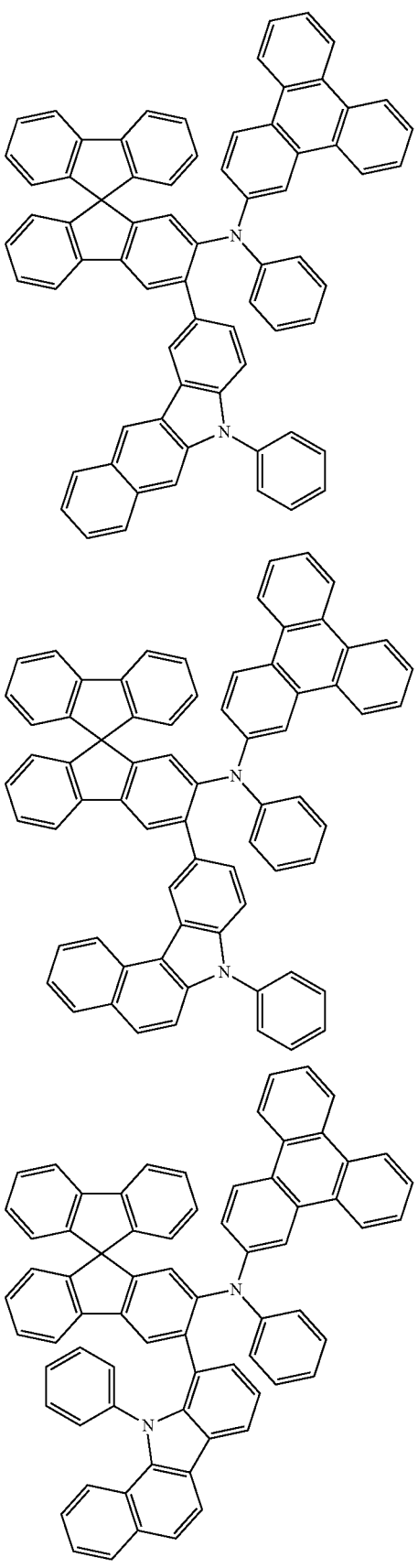

233
-continued
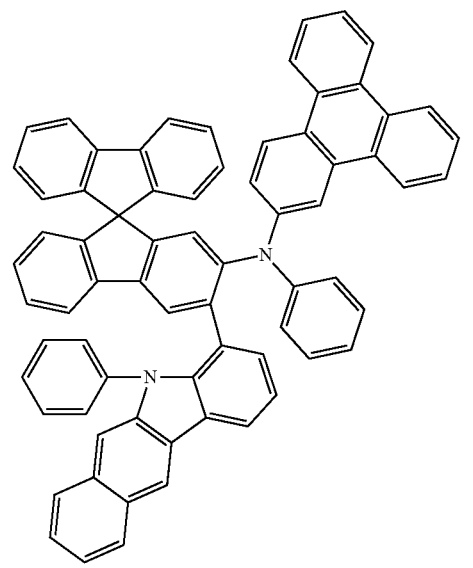
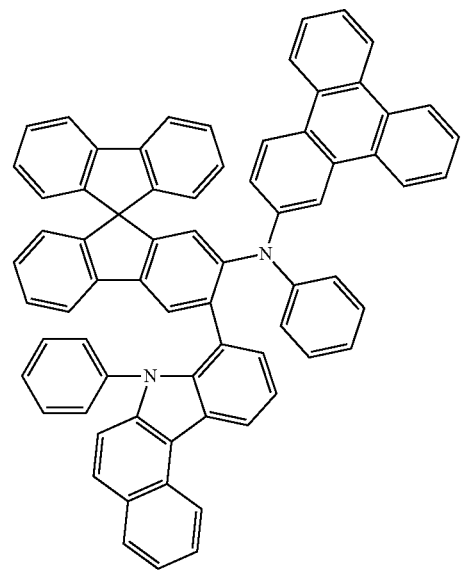
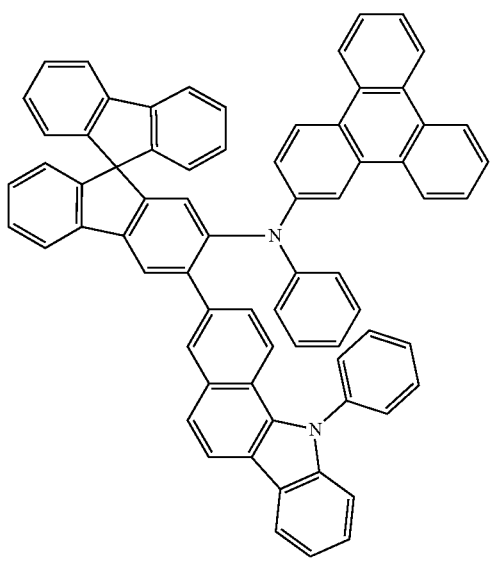
234
-continued
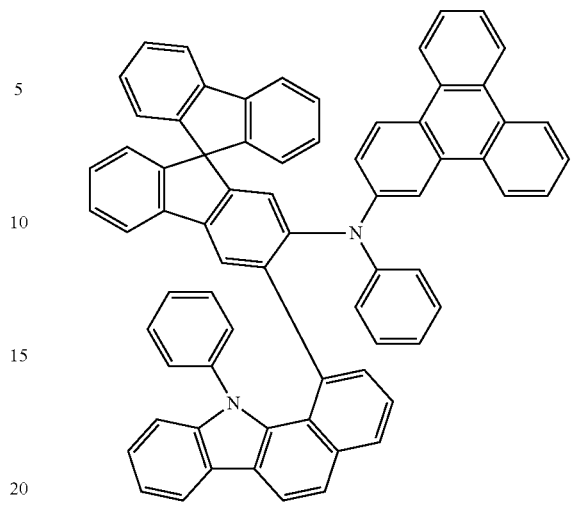
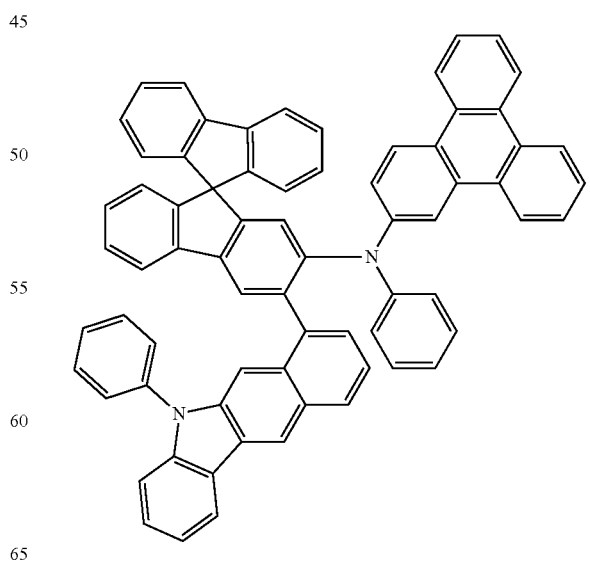

235
-continued
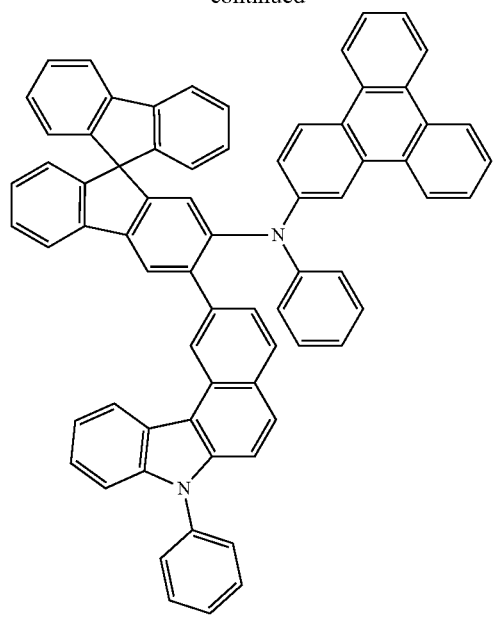
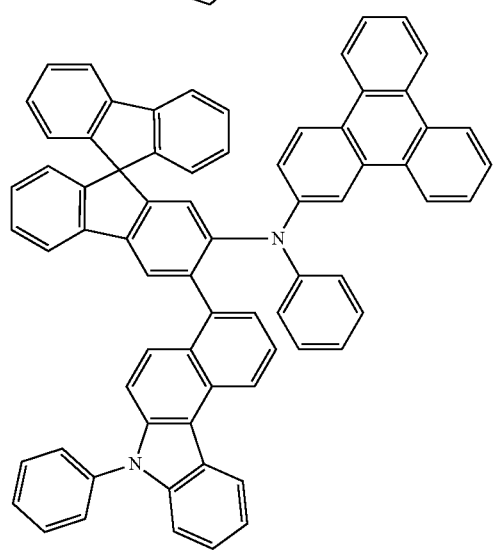
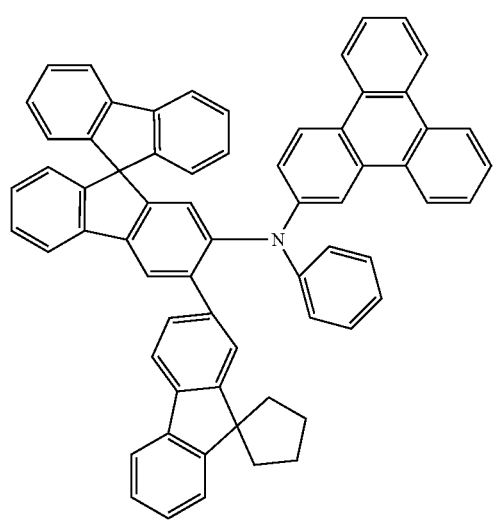
236
-continued
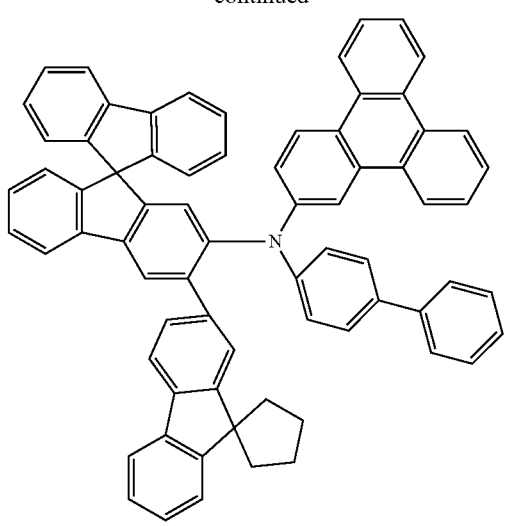
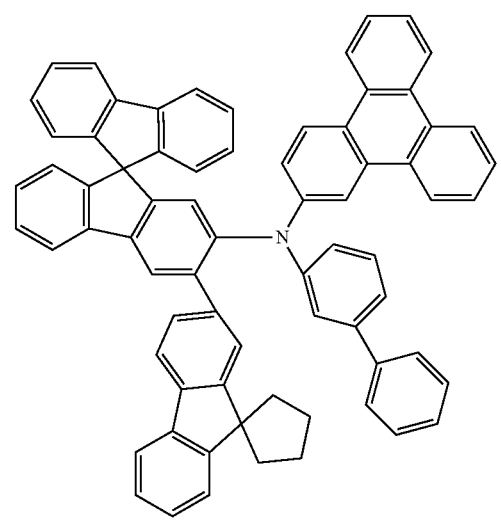
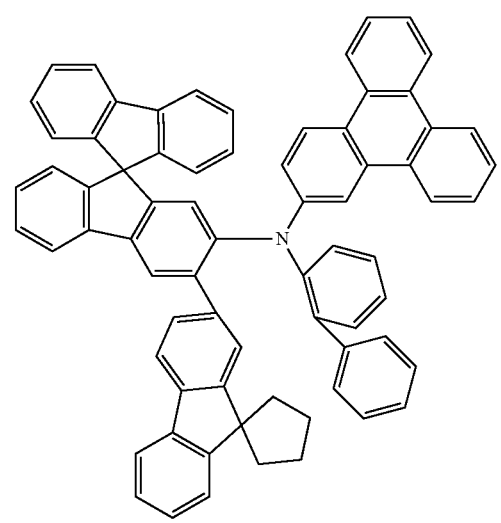

237
-continued
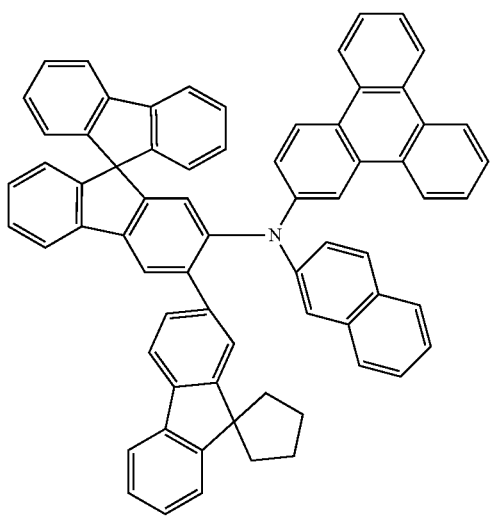 [SMILES: c1ccc2c(c1)-c1ccc(-c3cc4c(cc3N(c3ccc5ccccc5c3)c3ccc5c6ccccc6c6ccccc6c5c3)C3(c5ccccc5-c5ccccc53)c3ccccc3-4)cc1C21CCCC1]
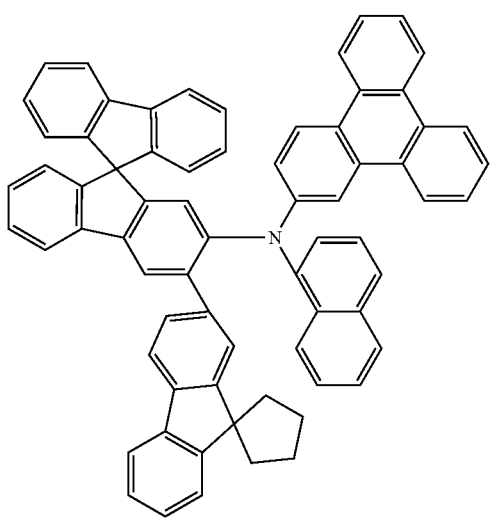
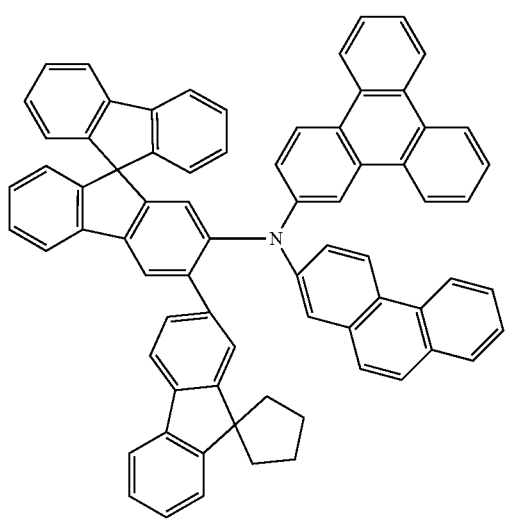
238
-continued
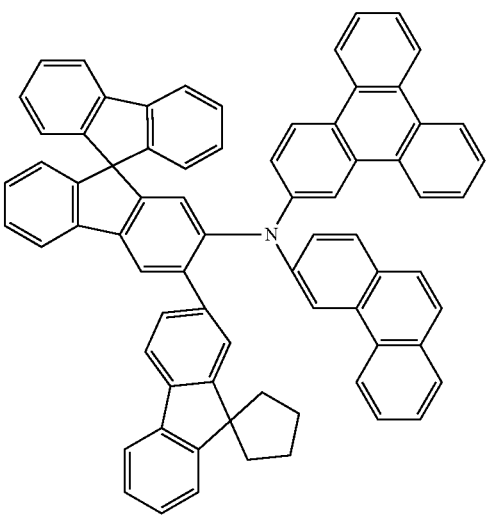
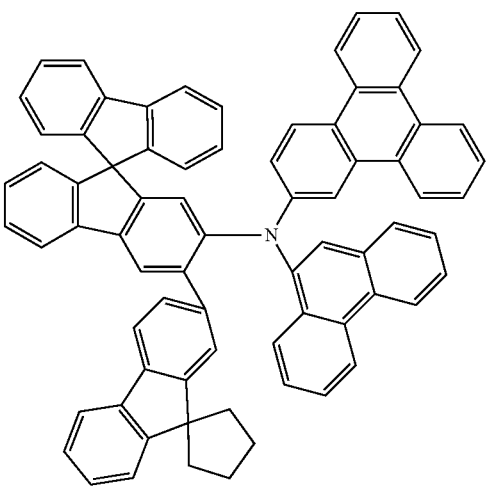
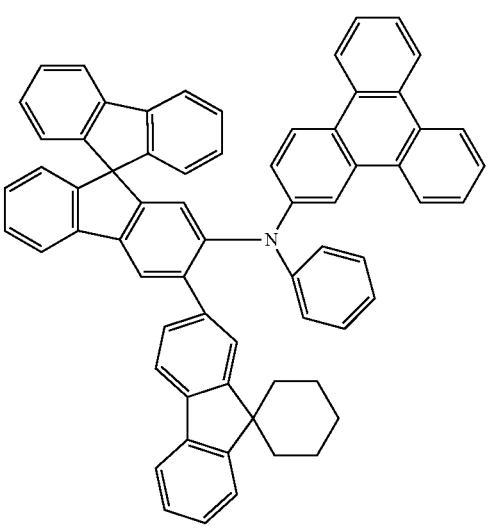

239
-continued
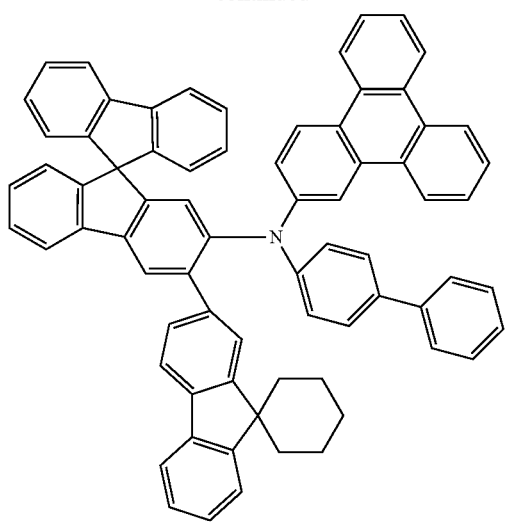
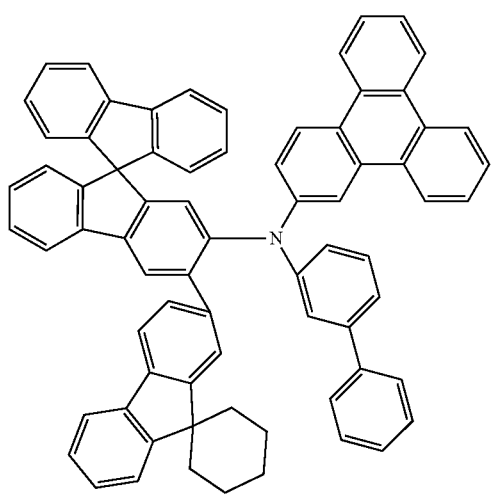
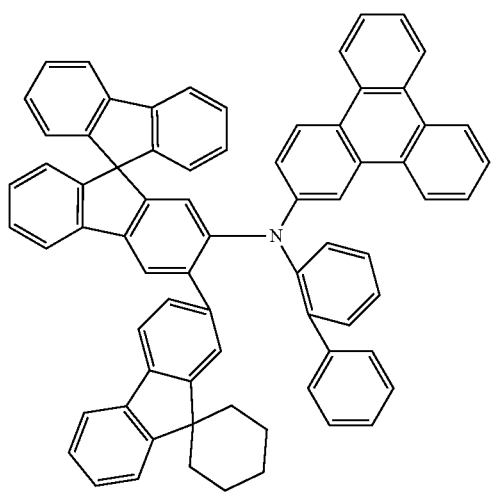
240
-continued
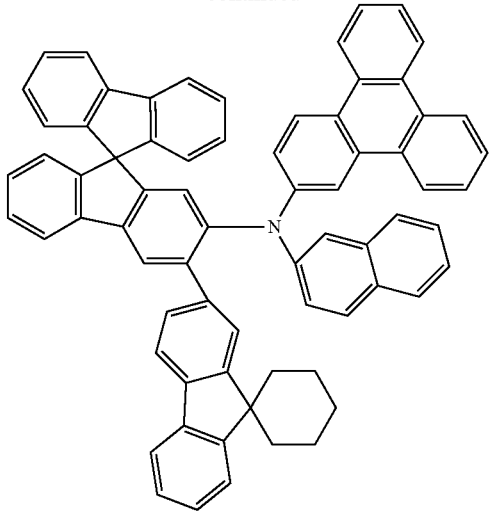
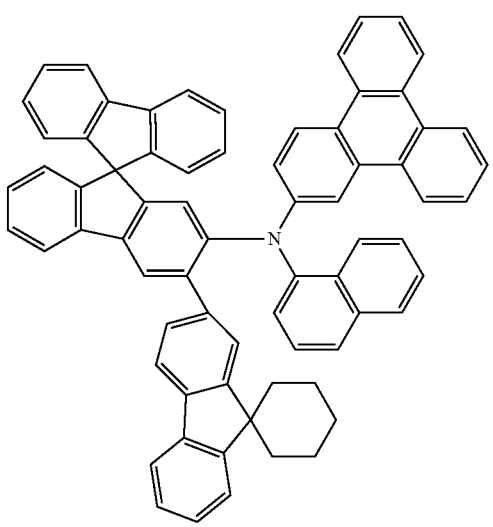
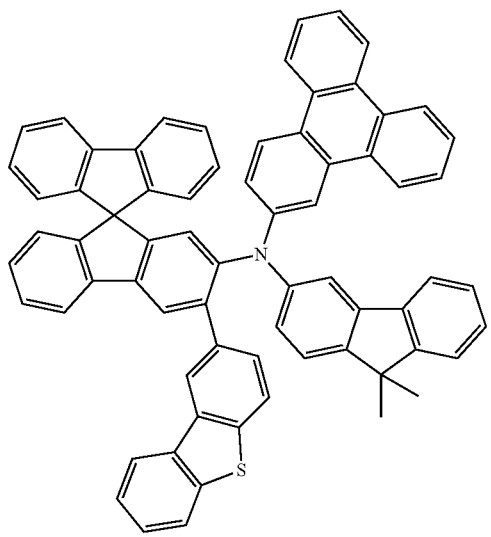

241
-continued
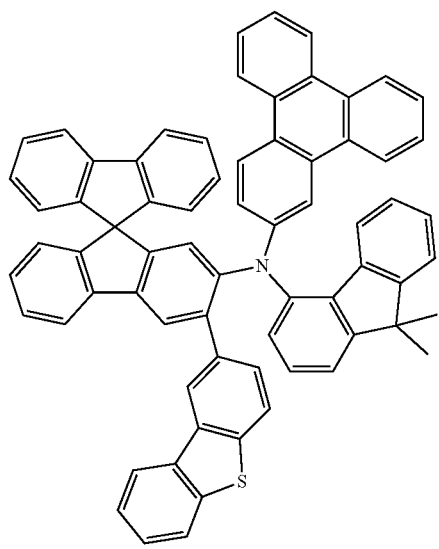
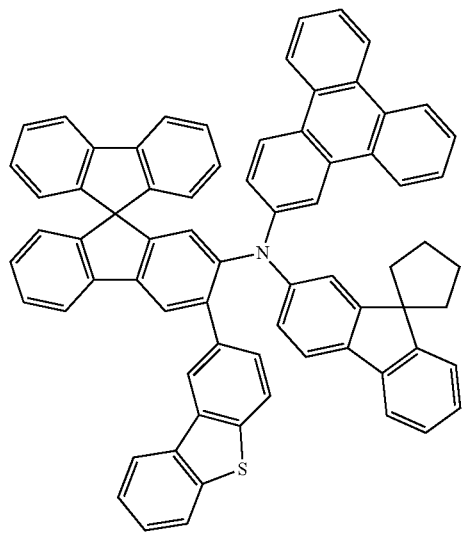
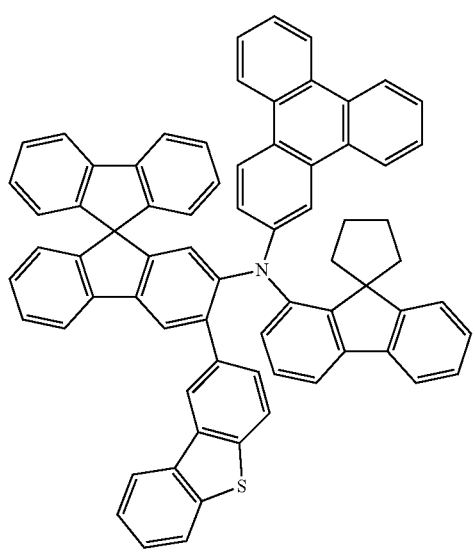
242
-continued
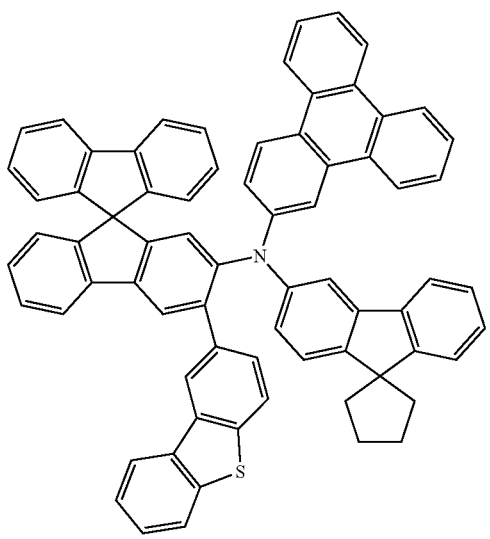
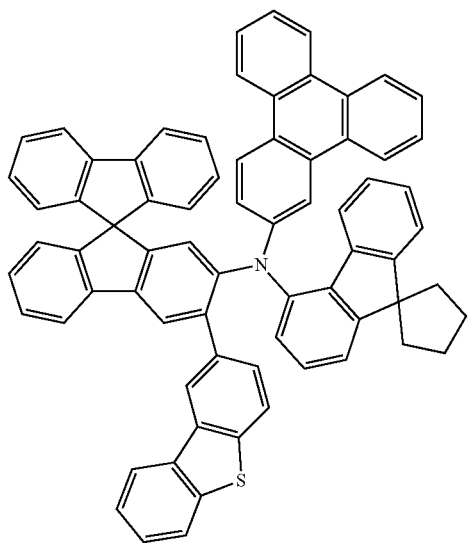
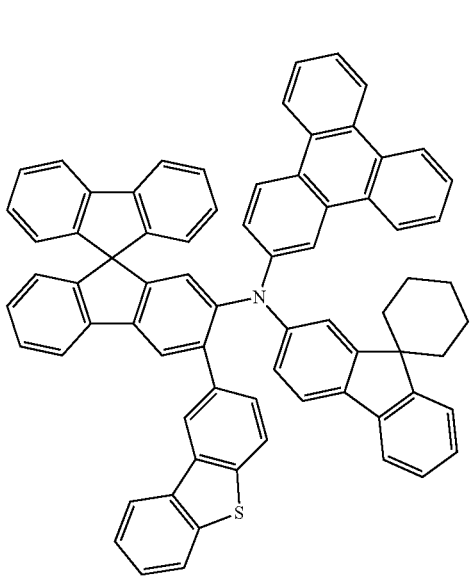

243
-continued
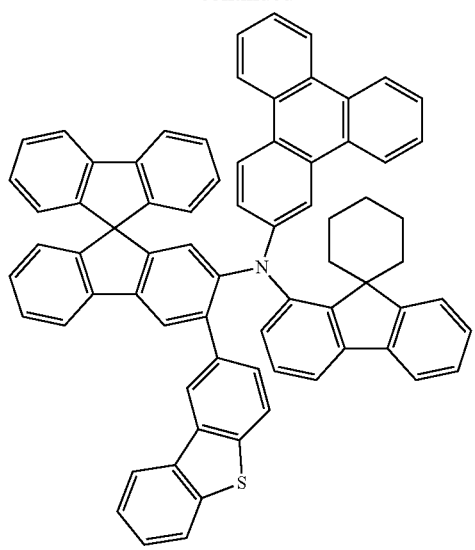
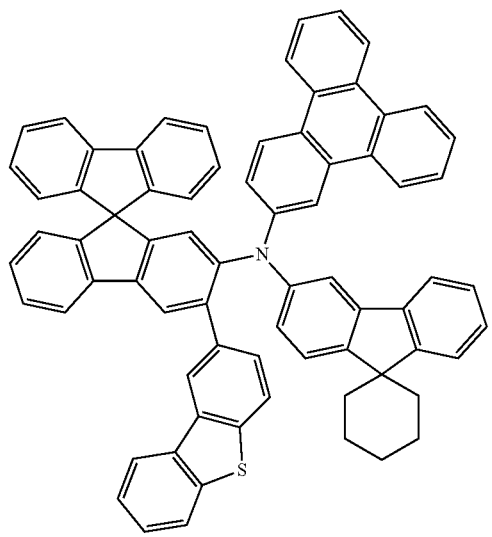
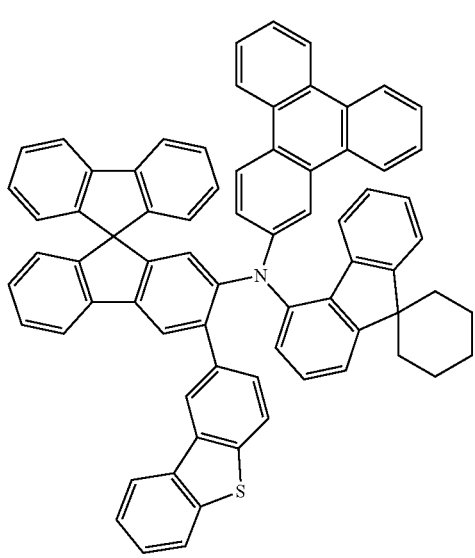
244
-continued
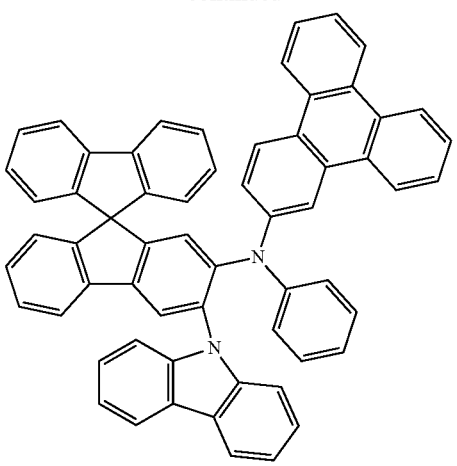
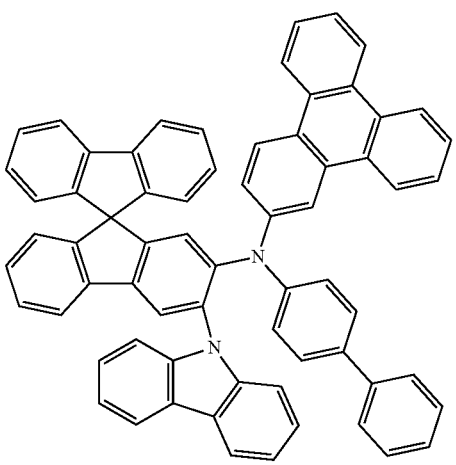
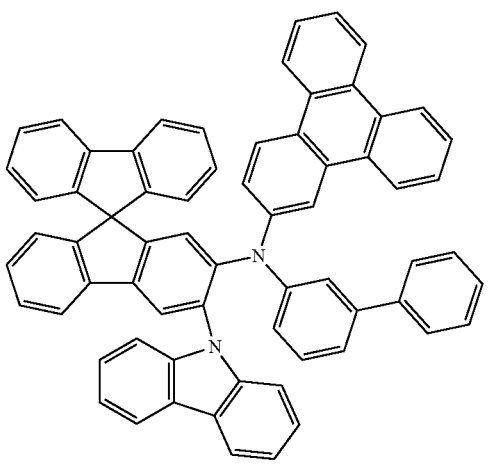

245
-continued
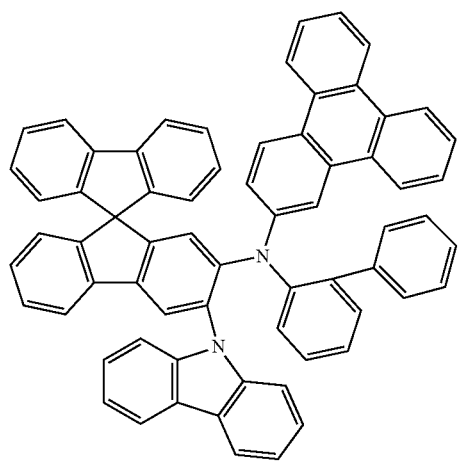
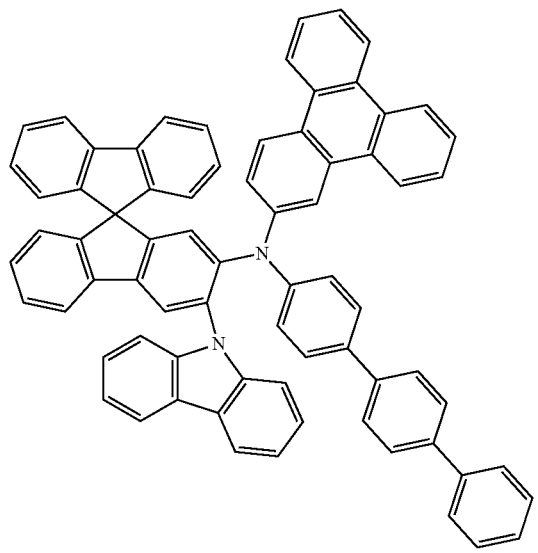
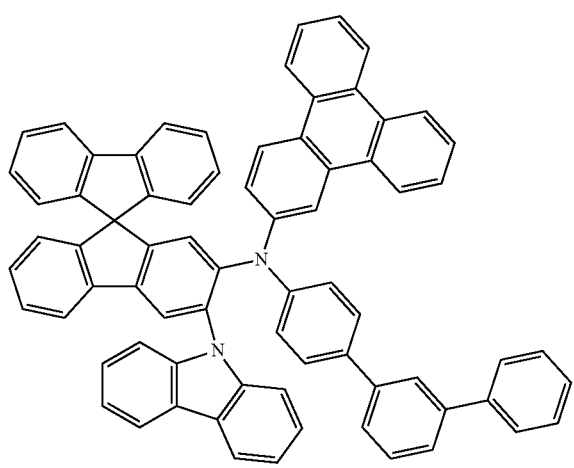
246
-continued
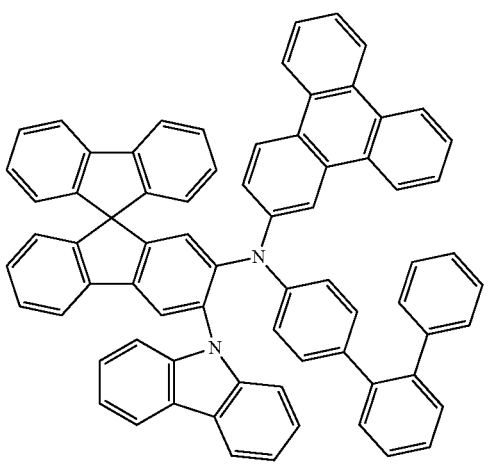
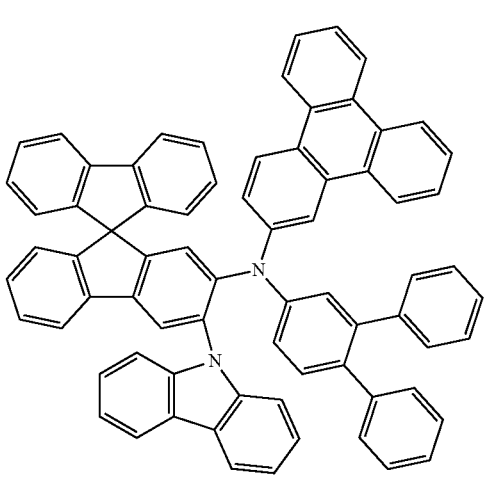
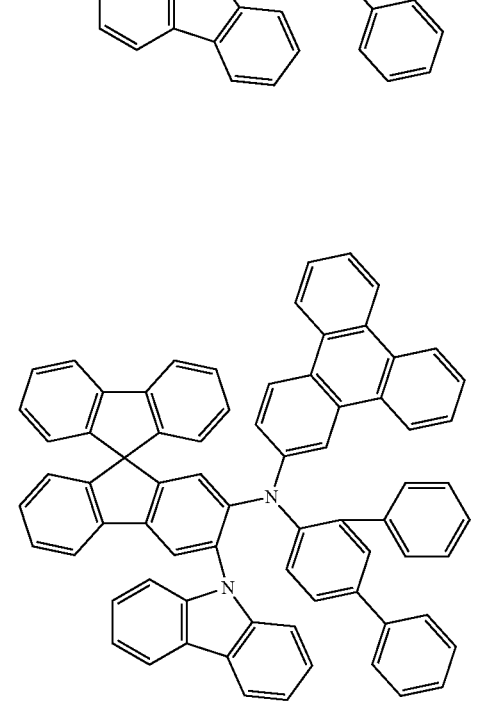

247
-continued
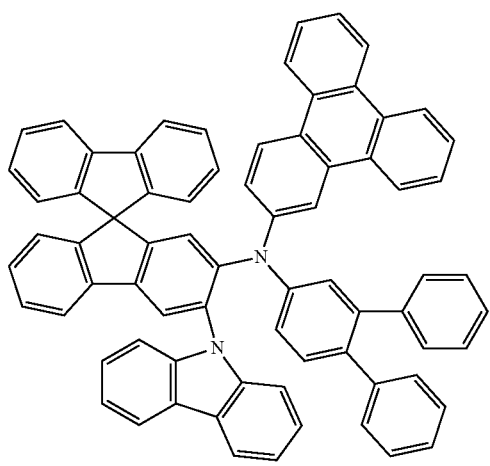
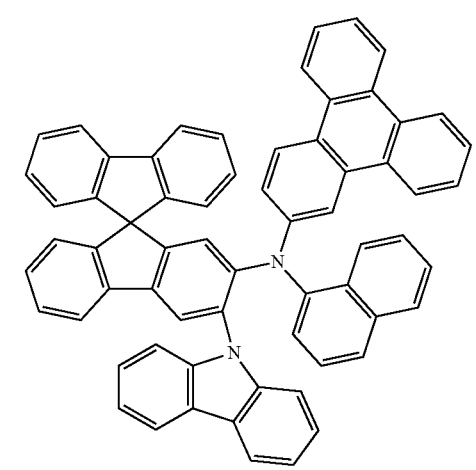
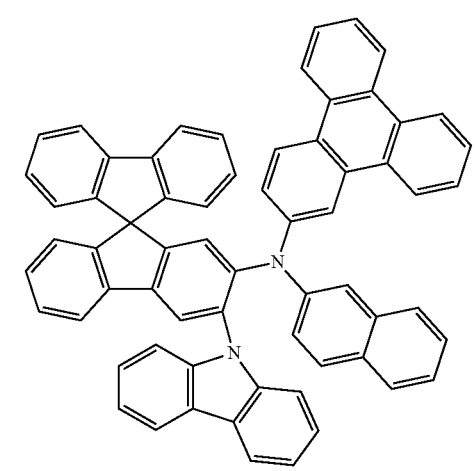
248
-continued
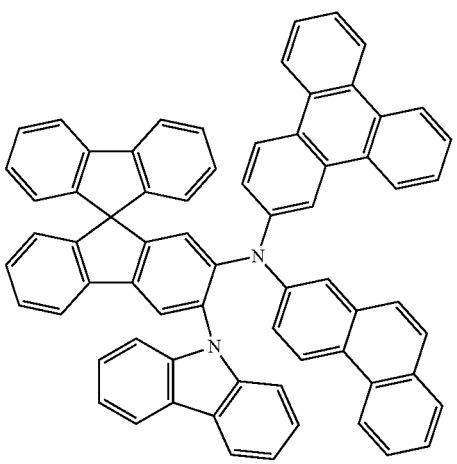
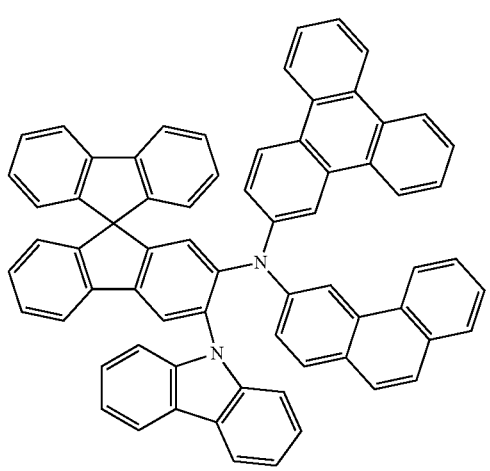
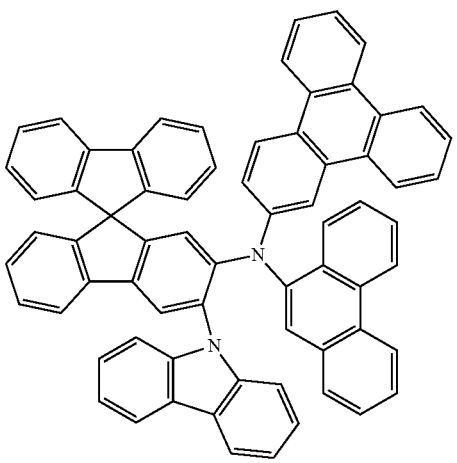

249
-continued

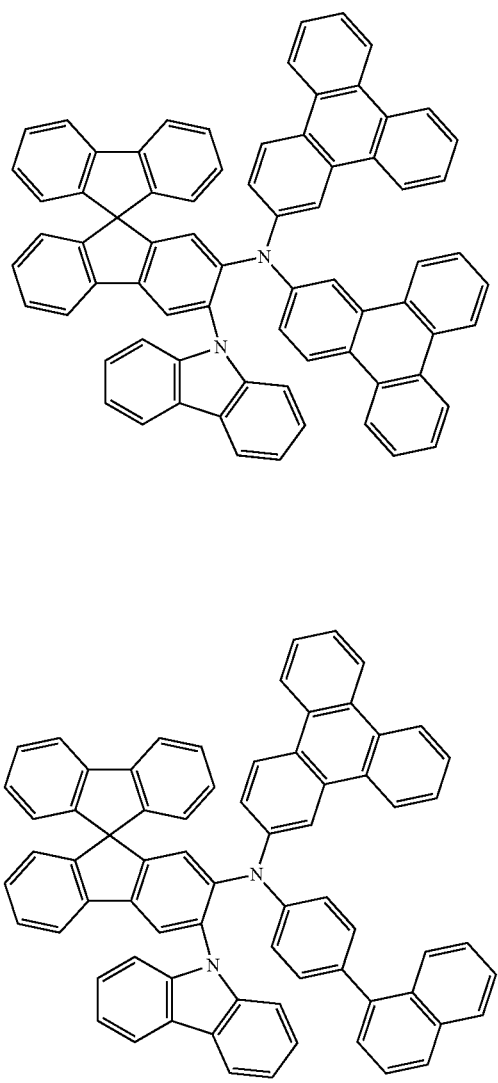

250
-continued

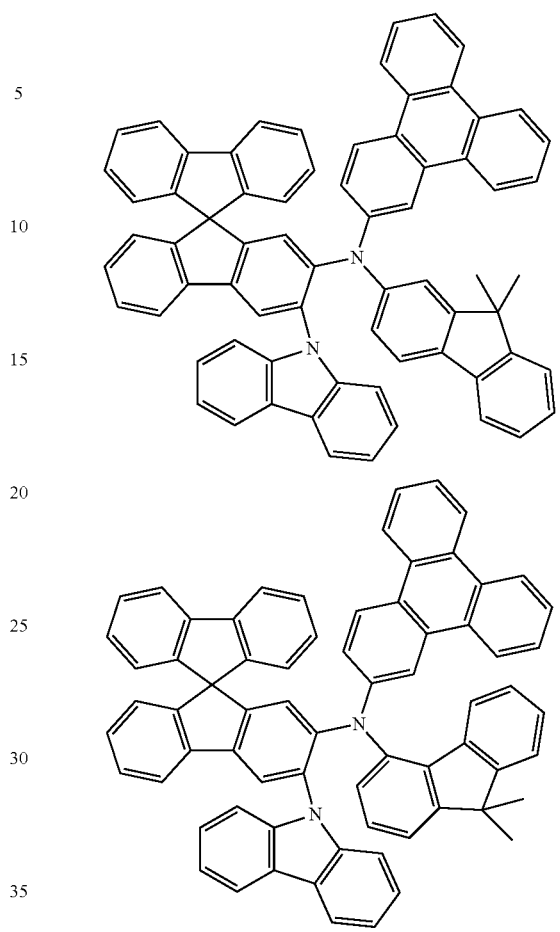

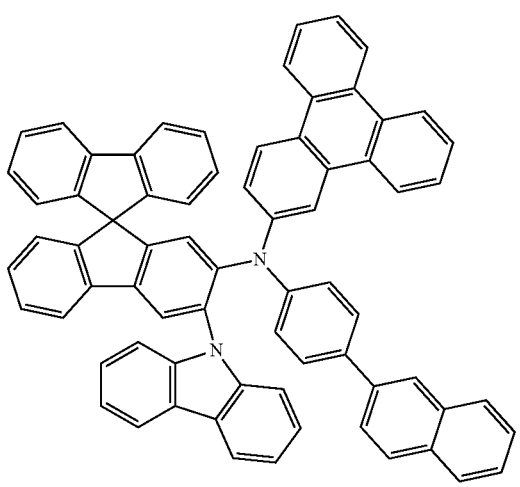

The compound according to one embodiment of the present specification may be prepared using preparation methods to describe later.

For example, the core structure of the compound of Chemical Formula 1 may be prepared as in the following reaction formula. Substituents may bond thereto using methods known in the art, and the types, the positions or the number of the substituents may vary depending on technologies known in the art.

The compound according to the present specification may be synthesized as follows.

Step 1)

Synthesis of bromine-substituted primary amine through a bromination reaction of spirobifluorene amine and N-bromosuccinimide (NBS)

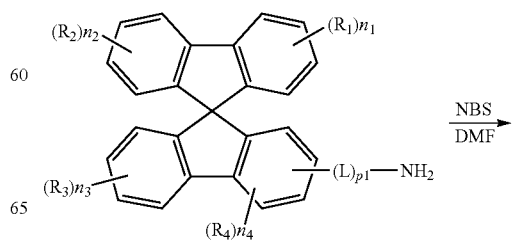

-continued

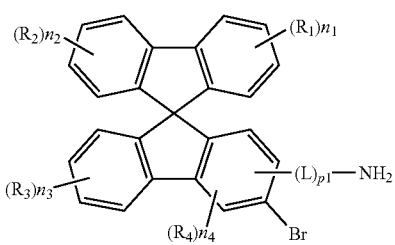

Step 2)

Synthesis of X1-substituted primary amine through a coupling reaction of the bromine-substituted primary amine obtained in Step 1 and X1-boronic acid

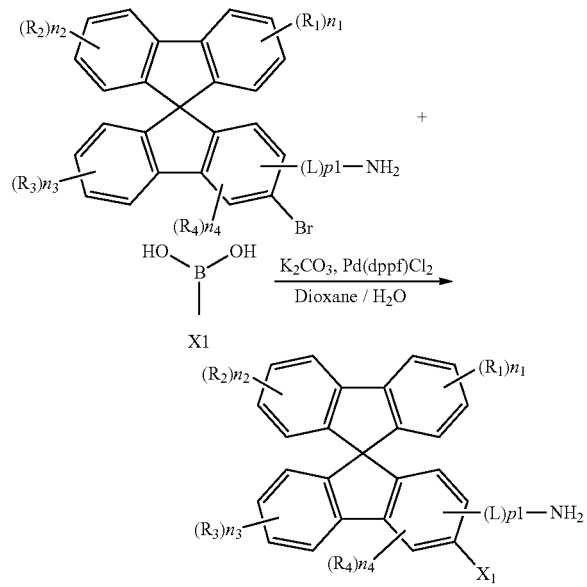

Step 3)

Synthesis of secondary amine through an amination reaction of the X1-substituted primary amine obtained in Step 2 and triphenylene (Xa=halide)

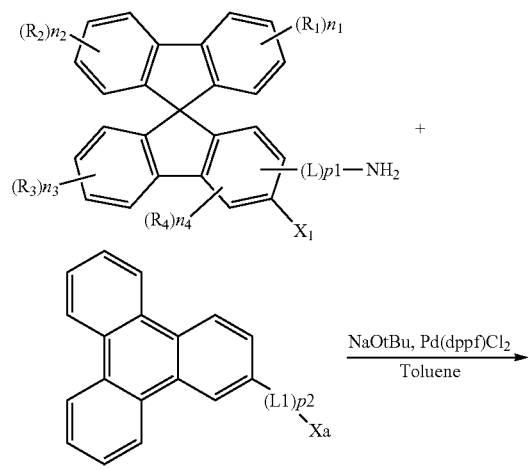

-continued

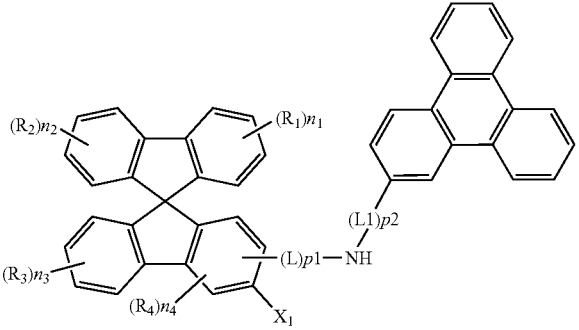

Step 4)

Synthesis of tertiary amine through an amination reaction of the secondary amine obtained in Step 3 and aryl halide (Ar2-(L2)$_{p3}$-Xb, Xb=halide)

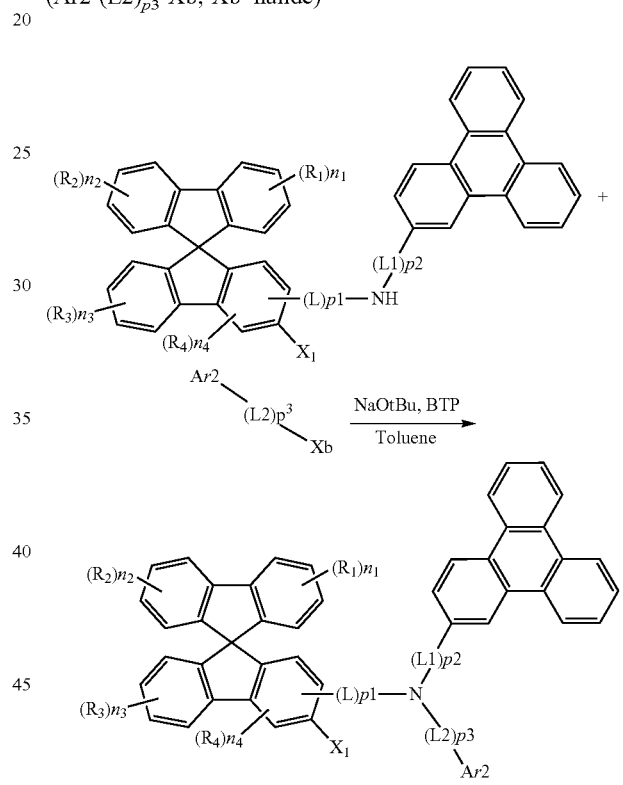

A conjugation length of a compound and an energy band gap thereof are closely related. Specifically, as a conjugation length of a compound increases, an energy band gap thereof decreases.

By introducing various substituents to the core structure as above, compounds having various energy band gaps may be synthesized in the present disclosure. In addition, by introducing various substituents to the core structure having structures as above, HOMO and LUMO energy levels of the compound may also be controlled in the present disclosure.

In addition, by introducing various substituents to the core structure having structures as above, compounds having unique properties of the introduced substituents may be synthesized. For example, by introducing substituents normally used as a hole injection layer material, a material for hole transfer, a light emitting layer material and an electron transfer layer material used for manufacturing an organic light emitting device to the core structure, materials satisfying needs required from each organic material layer may be synthesized.

In addition, an organic light emitting device according to the present disclosure includes a first electrode, a second electrode, and one or more organic material layers disposed between the first electrode and the second electrode, wherein one or more layers of the one or more organic material layers include the compound.

In one embodiment of the present disclosure, the first electrode is an anode, and the second electrode is a cathode.

According to another embodiment, the first electrode is a cathode, and the second electrode is an anode.

The organic light emitting device of the present disclosure may be prepared using common methods and materials for preparing an organic light emitting device except that one or more organic material layers are formed using the compound described above.

The compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, but may be formed in a multilayer structure in which two or more organic material layers are laminated. For example, the organic light emitting device of the present disclosure may have a structure including a hole injection layer, a hole transfer layer, a layer carrying out hole injection and hole transfer at the same time, a light emitting layer, an electron transfer layer, an electron injection layer, a layer carrying out electron injection and electron transfer at the same time, an electron blocking layer and the like as the organic material layer. However, the structure of the organic light emitting device is not limited thereto, and may include less numbers of organic material layers.

In one embodiment of the present disclosure, the organic material layer including the compound of Chemical Formula 1 is a hole injection layer or a light emitting layer in the organic light emitting device.

According to another embodiment, the organic material layer including the compound of Chemical Formula 1 is a hole transfer layer or an electron blocking layer in the organic light emitting device.

In the organic light emitting device of the present disclosure, the organic material layer may include a hole injection layer or a hole transfer layer, and one or more layers of the layers may include the compound represented by Chemical Formula 1.

In another embodiment, the organic material layer includes a light emitting layer, and the light emitting layer includes the compound represented by Chemical Formula 1. As another embodiment, the compound represented by Chemical Formula 1 may be included as a dopant of the light emitting layer.

As another embodiment, the organic material layer including the compound represented by Chemical Formula 1 includes the compound represented by Chemical Formula 1 as a dopant, and may include a fluorescent host or a phosphorescent host.

In another embodiment, the organic material layer including the compound represented by Chemical Formula 1 includes the compound represented by Chemical Formula 1 as a dopant, includes a fluorescent host or a phosphorescent host, and may include other organic compounds, metals or metal compounds as a dopant.

As another embodiment, the organic material layer including the compound represented by Chemical Formula 1 includes the compound represented by Chemical Formula 1 as a dopant, includes a fluorescent host or a phosphorescent host, and may be used together with an iridium (Ir)-based dopant.

In the organic light emitting device of the present disclosure, the organic material layer includes an electron injection layer or an electron transfer layer, and the electron injection layer or the electron transfer layer may include the compound represented by Chemical Formula 1.

In the organic light emitting device according to another embodiment, the organic material layer includes an electron blocking layer, and the electron blocking layer may include the compound represented by Chemical Formula 1.

The structure of the organic light emitting device of the present disclosure may be as illustrated in FIG. 1 and FIG. 2, but is not limited thereto.

FIG. 1 illustrates a structure of the organic light emitting device in which an anode (2), a light emitting layer (3) and a cathode (4) are consecutively laminated on a substrate (1). In such a structure, the compound may be included in the light emitting layer (3).

FIG. 2 illustrates a structure of the organic light emitting device in which an anode (2), a hole injection layer (5), a hole transfer layer (6), an electron blocking layer (8), a light emitting layer (3), a layer carrying out electron transfer and electron injection at the same time (7) and a cathode (4) are consecutively laminated on a substrate (1). In such a structure, the compound may be included in the hole injection layer (5), the hole transfer layer (6), the light emitting layer (3) or the electron blocking layer (8).

For example, the organic light emitting device according to the present disclosure may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer and an anode material on a substrate.

The organic material layer may have a multilayer structure including a hole injection layer, a hole transfer layer, a light emitting layer, an electron transfer layer and the like, however, the structure is not limited thereto, and the organic material layer may have a single layer structure. In addition, the organic material layer may be prepared to have less numbers of layers through a solvent process such as spin coating, dip coating, doctor blading, screen printing, inkjet printing or a thermal transfer method instead of a deposition method using various polymer materials.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3- methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection material is a material favorably receiving holes from an anode at a low voltage, and the highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer material is a material capable of receiving holes from an anode or a hole injection layer and transferring the holes to a light emitting layer, and materials having high mobility for the holes are suited. Specific examples thereof include arylamine-based organic materials, conductive polymers, block copolymers having conjugated parts and non-conjugated parts together, and the like, but are not limited thereto.

The light emitting layer may emit light of red, green or blue, and may be formed with phosphorescent materials or fluorescent materials. The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzo quinoline-metal compounds; benzoxazole-, benzothiazole- and benzimidazole-based compounds; poly (p-phenylenevinylene) (PPV)-based polymers; spiro compounds; polyfluorene, rubrene, and the like, but are not limited thereto.

The host material of the light emitting layer includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, however, the material is not limited thereto.

The iridium-based complex used as a dopant of the light emitting layer is as follows.

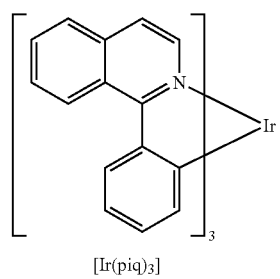

[Ir(piq)$_3$]

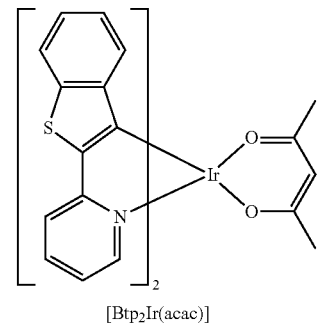

[Btp$_2$Ir(acac)]

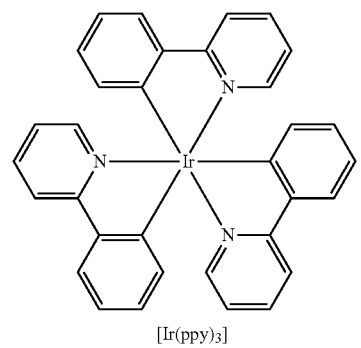

[Ir(ppy)$_3$]

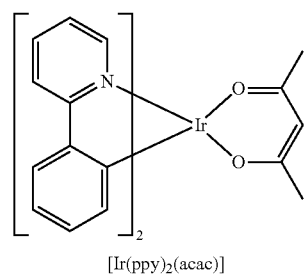

[Ir(ppy)$_2$(acac)]

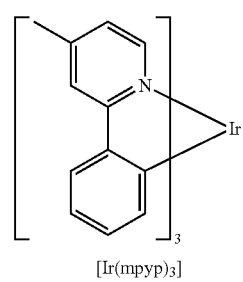

[Ir(mpyp)$_3$]

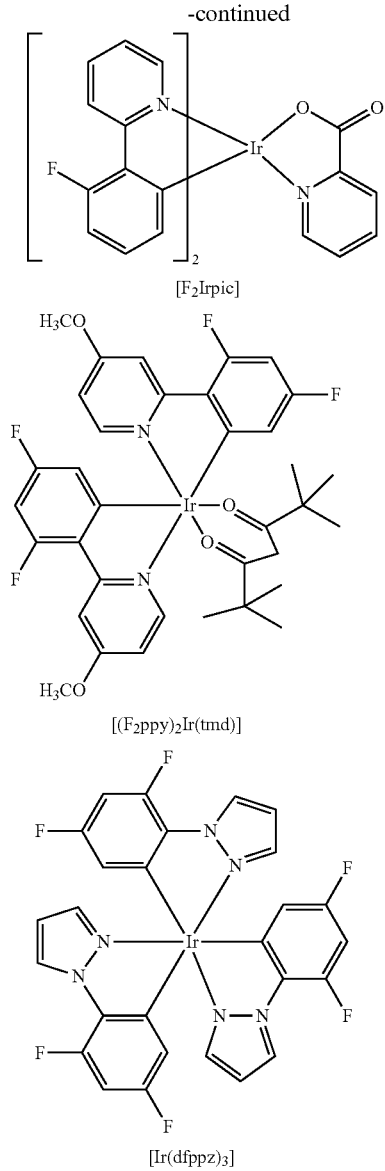

[F₂Irpic]

[(F₂ppy)₂Ir(tmd)]

[Ir(dfppz)₃]

The electron transfer material is a material favorably receiving electrons from a cathode and transferring the electrons to a light emitting layer, materials having high mobility for the electrons are suited. Specific examples thereof include Al complexes of 8-hydroxyquinoline; complexes including Alq₃; organic radical compounds; hydroxyflavon-metal complexes, and the like, but are not limited thereto.

The organic light emitting device according to the present disclosure may be a top-emission type, a bottom-emission type or a dual-emission type depending on the materials used.

The compound according to the present disclosure may also be used in an organic electronic device including an organic solar cell, an organic photo conductor, an organic transistor and the like under a similar principle used in the organic light emitting device.

PREPARATION EXAMPLE

Preparation Example 1

Synthesis of Compound 1

Step 1) Synthesis of Compound 1-A

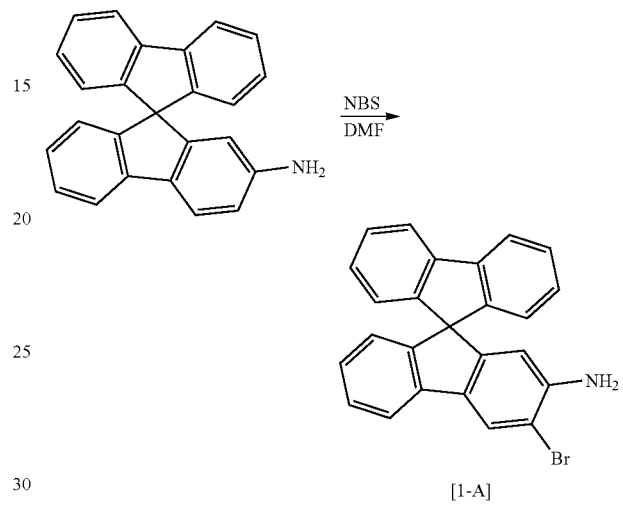

[1-A]

After dissolving 9,9'-spirobi[fluorene]-2-amine (50.00 g, 150.87 mmol) in N,N-dimethylformamide (DMF) (200 ml), the temperature was lowered to 0° C. To the solution, N-bromosuccinimide (NBS) (26.85 g, 150.87 mmol) dissolved in N,N-dimethylformamide (DMF) (100 ml) was slowly introduced, and the result was stirred. After the reaction was completed, the temperature was raised to room temperature, water was added thereto for reverse precipitation, and the result was filtered. The obtained solids were layer separated using chloroform and a sodium thiosulfate solution. After removing the solvent, the result was recrystallized with hexane to obtain Compound 1-A (52.50 g, 84.81% yield).

Step 2) Synthesis of Compound 1-B

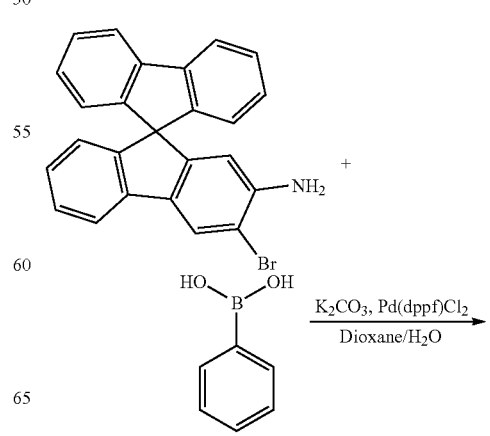

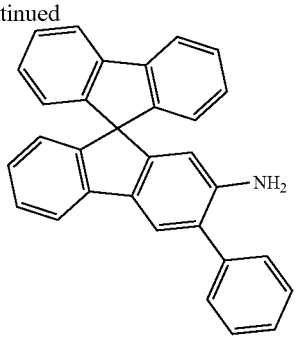

[1-B]

After dissolving Compound 1-A (52.5 g, 127.95 mmol) obtained in Step 1 and phenylboronic acid (15.60 g, 127.95 mmol) in 1,4-dioxane (300 ml), a potassium carbonate (53.05 g, 383.85 mmol:water 150 ml) solution was added thereto, and the result was heated and stirred for 15 minutes. To the solution, 1,1'-bis(diphenylphosphino)ferrocene dichloropalladium(II) (0.47 g, 0.64 mmol) dissolved in 1,4-dioxane (20 ml) was added, and the result was heated and stirred for 1 hour. After the reaction was completed, the result was filtered and then layer separated using chloroform and water. After removing the solvent, the result was recrystallized with hexane to obtain Compound 1-B (44.3 g, 84.96% yield).

Step 3) Synthesis of Compound 1-C

After adding toluene (350 ml) to Compound 1-B (44.3 g, 108.71 mmol) obtained in Step 2, 2-bromotriphenylene (33.40 g, 108.71 mmol) and sodium tert-butoxide (14.63 g, 152.19 mmol), the result was heated and stirred for 15 minutes. To the mixture, 1,1'-bis(diphenylphosphino)ferrocene dichloropalladium(II) (0.40 g, 0.54 mmol) dissolved in toluene (20 ml) was added, and the result was heated and stirred for 1 hour. After the reaction was completed, the result was filtered and then layer separated using chloroform and water. After removing the solvent, the result was recrystallized with ethyl acetate to obtain Compound 1-C (51.6 g, 74.89% yield).

Step 4) Synthesis of Compound 1

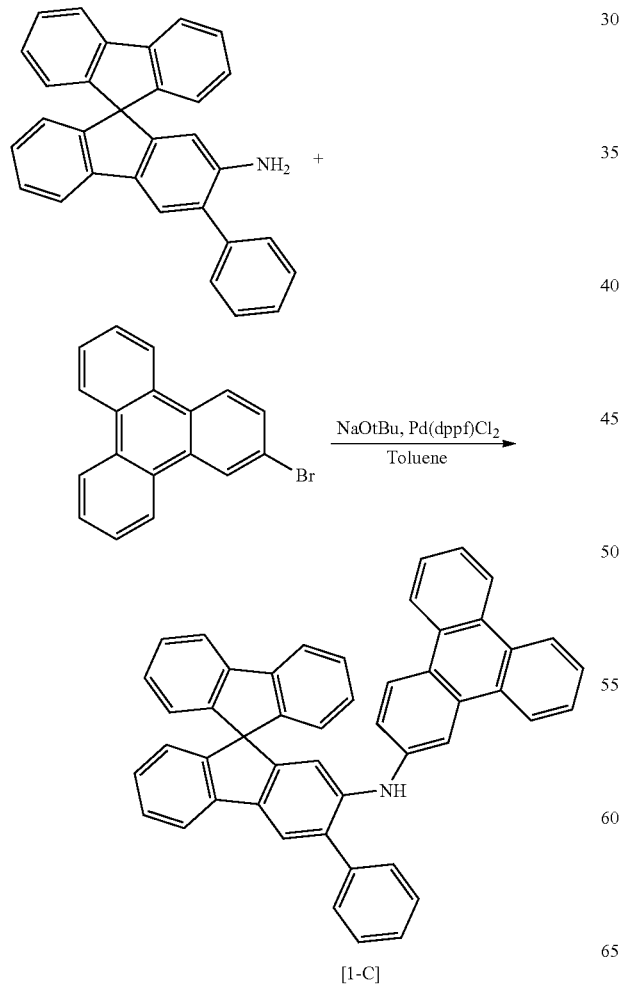

Compound 1

After adding toluene (200 ml) to Compound 1-C (30.0 g, 47.33 mmol) obtained in Step 3, bromobenzene (7.43 g, 47.33 mmol) and sodium tert-butoxide (6.37 g, 66.26 mmol), the result was heated and stirred for 15 minutes. To the mixture, bis(tri-tert-butylphosphine)palladium (0.12 g, 0.24 mmol) dissolved in toluene (20 ml) was added, and the result was heated and stirred for 1 hour. After the reaction was completed, the result was filtered and then layer separated using toluene and water. After removing the solvent, the result was recrystallized with ethyl acetate to obtain Compound 1 (24.6 g, 73.22% yield). (MS[M+H]+=710)

Preparation Example 2

Synthesis of Compound 2

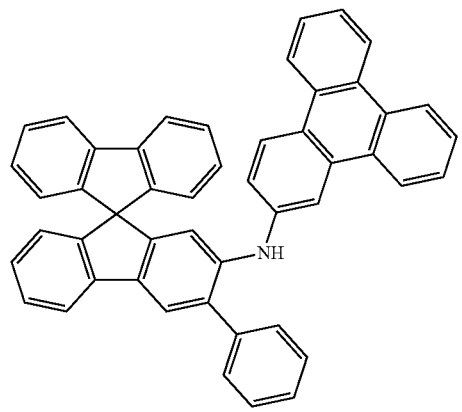

+

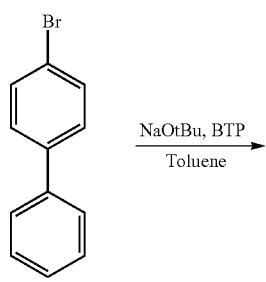

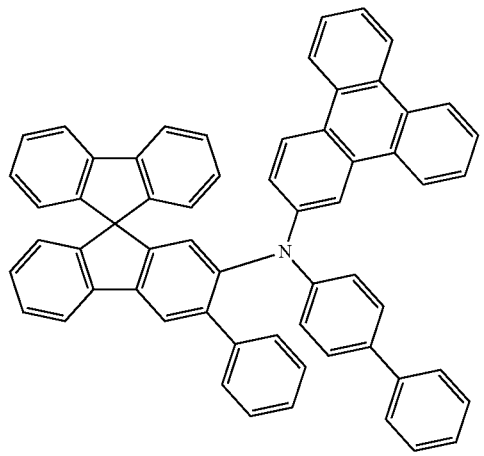

Compound 2

Compound 2 (26.0 g, 69.89% yield) was obtained in the same manner as in Step 4 of Preparation Example 1 using Compound 1-C (30.0 g, 47.33 mmol) obtained in Step 3 of Preparation Example 1 and 4-bromo-1,1'-biphenyl (11.03 g, 47.33 mmol). (MS[M+H]+=786)

Preparation Example 3

Synthesis of Compound 3

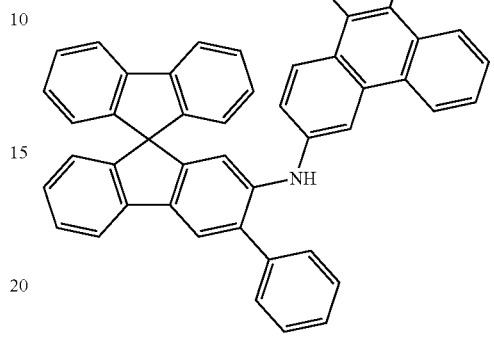

+

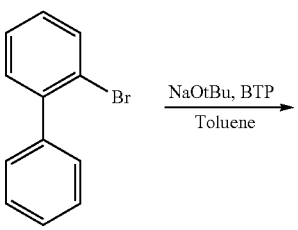

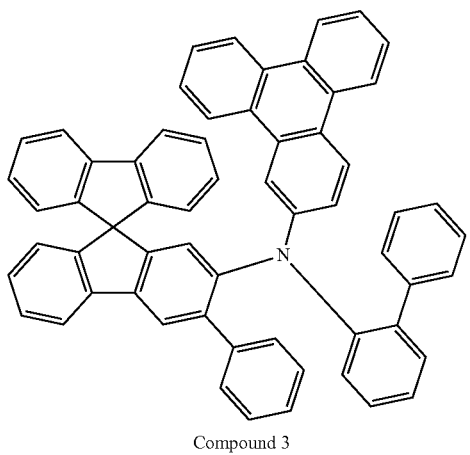

Compound 3

Compound 3 (22.5 g, 60.48% yield) was obtained in the same manner as in Step 4 of Preparation Example 1 using Compound 1-C (30.0 g, 47.33 mmol) obtained in Step 3 of Preparation Example 1 and 2-bromo-1,1'-biphenyl (11.03 g, 47.33 mmol). (MS[M+H]+=786)

Preparation Example 4

Synthesis of Compound 4

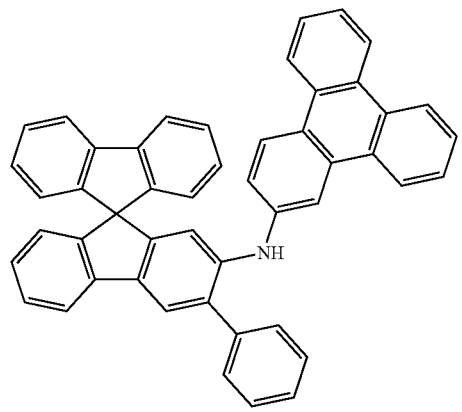

+

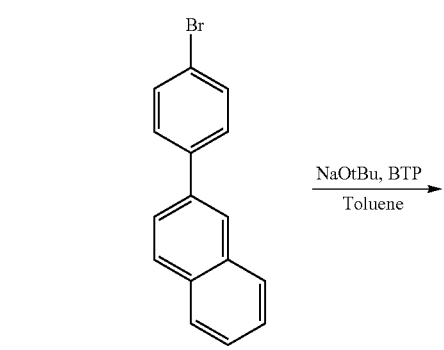

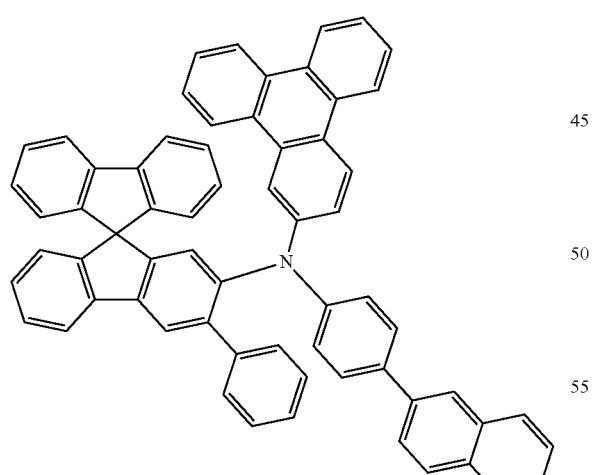

Compound 4

Compound 4 (29.3 g, 74.05% yield) was obtained in the same manner as in Step 4 of Preparation Example 1 using Compound 1-C (30.0 g, 47.33 mmol) obtained in Step 3 of Preparation Example 1 and 2-(4-bromophenyl)naphthalene (13.40 g, 47.33 mmol). (MS[M+H]+=836)

Preparation Example 5

Synthesis of Compound 5

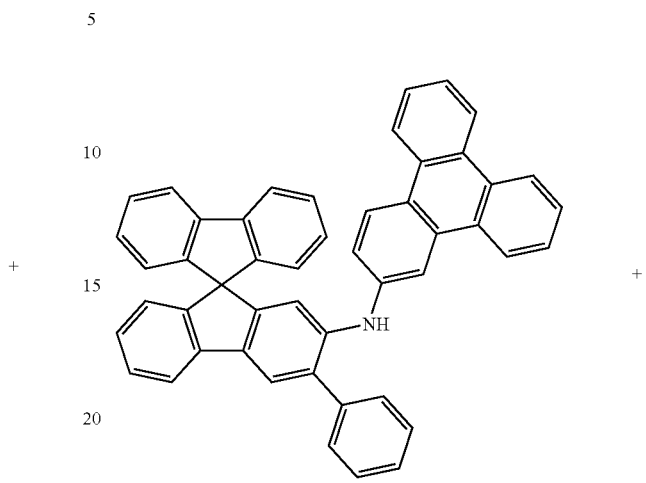

+

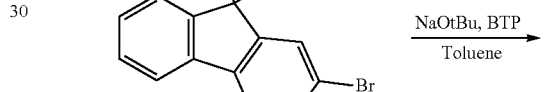

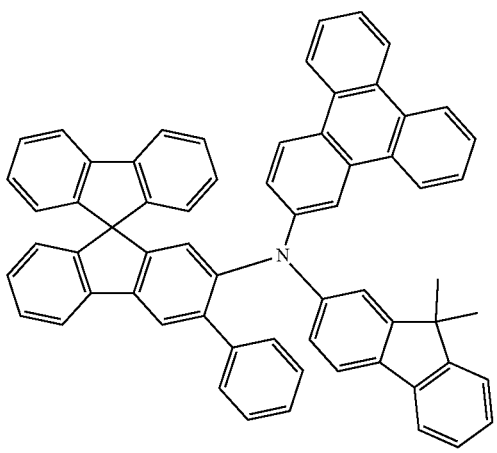

Compound 5

Compound 5 (25.1 g, 64.20% yield) was obtained in the same manner as in Step 4 of Preparation Example 1 using Compound 1-C (30.0 g, 47.33 mmol) obtained in Step 3 of Preparation Example 1 and 2-bromo-9,9-dimethyl-9H-fluorene (12.93 g, 47.33 mmol). (MS[M+H]+=826)

Preparation Example 6

Synthesis of Compound 6

Step 1) Synthesis of Compound 6-A

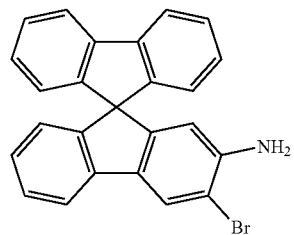

+

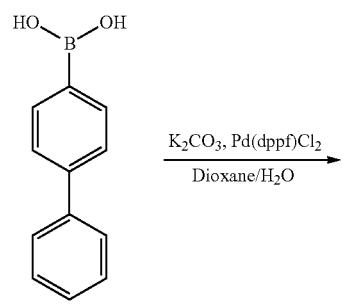

$\xrightarrow{\text{K}_2\text{CO}_3,\ \text{Pd(dppf)Cl}_2}{\text{Dioxane/H}_2\text{O}}$

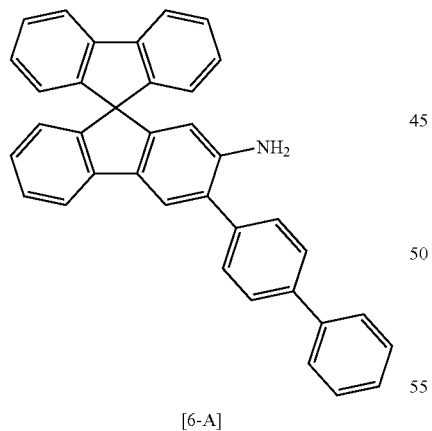

[6-A]

Step 2) Synthesis of Compound 6-B

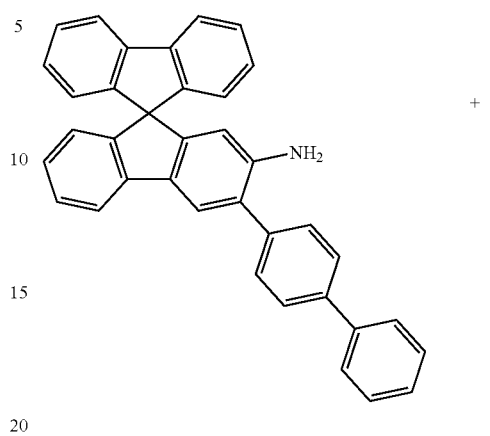

+

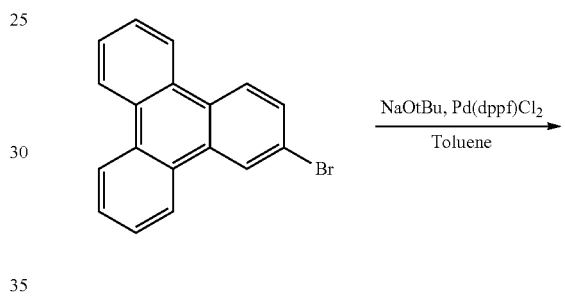

$\xrightarrow{\text{NaOtBu, Pd(dppf)Cl}_2}{\text{Toluene}}$

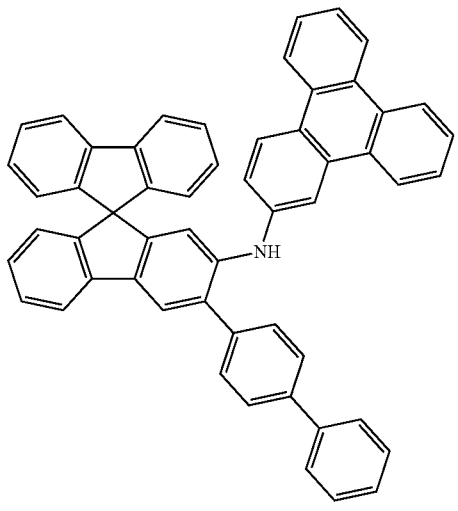

[6-B]

Compound 6-A (51.7 g, 87.73% yield) was obtained in the same manner as in Step 2 of Preparation Example 1 using Compound 1-A (50.0 g, 121.86 mmol) obtained in Step 1 of Preparation Example 1 and [1,1'-biphenyl]-4-ylboronic acid (24.13 g, 121.86 mmol).

Compound 6-B (67.3 g, 88.68% yield) was obtained in the same manner as in Step 3 of Preparation Example 1 using Compound 6-A (51.7 g, 106.90 mmol) obtained in Step 1 and 2-bromotriphenylene (32.84 g, 106.90 mmol).

Step 3) Synthesis of Compound 6

Preparation Example 7

Synthesis of Compound 7

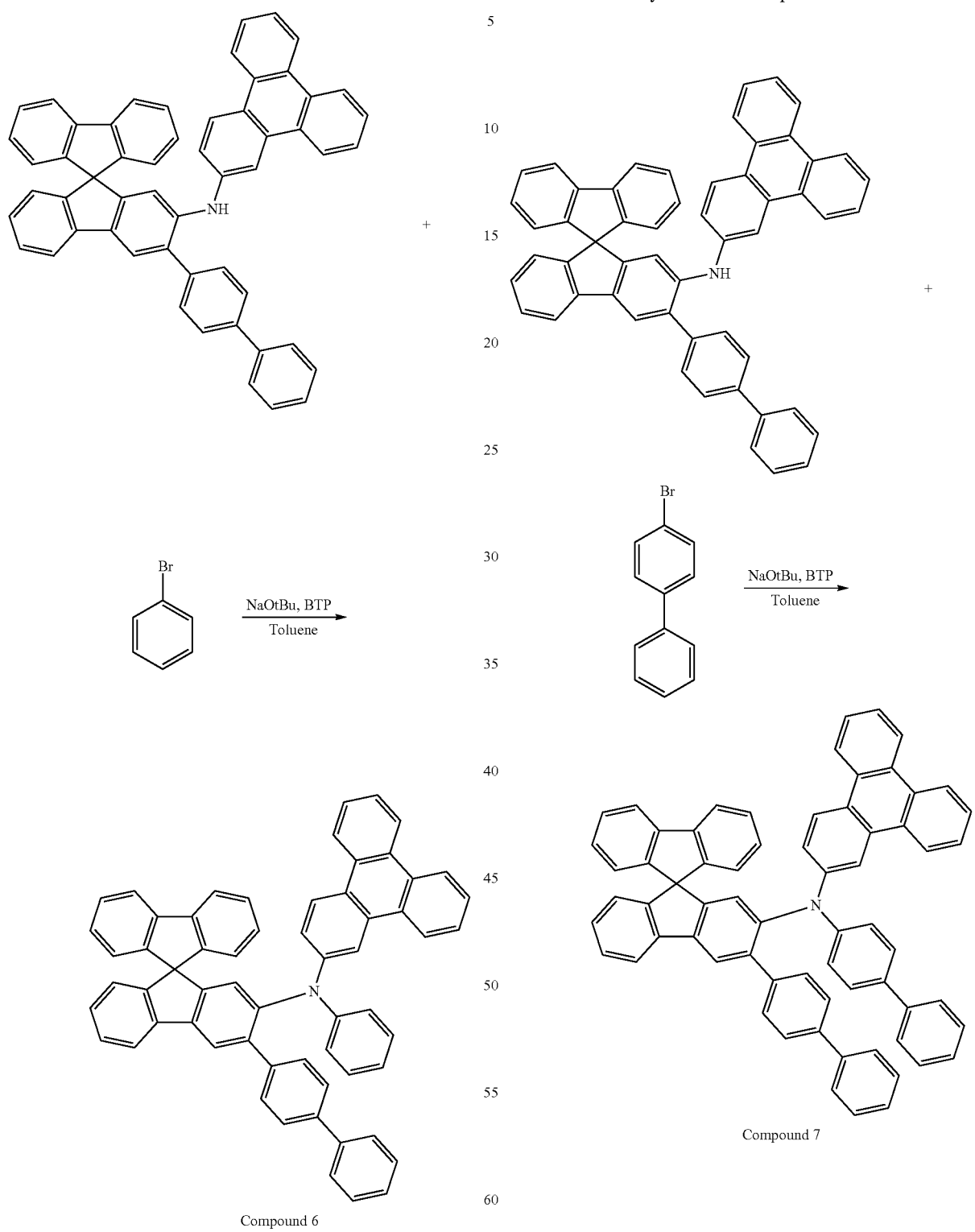

Compound 6 (27.5 g, 82.79% yield) was obtained in the same manner as in Step 4 of Preparation Example 1 using Compound 6-B (30.0 g, 42.26 mmol) obtained in Step 2 and bromobenzene (6.64 g, 42.26 mmol). (MS[M+H]+=786)

Compound 7 (28.3 g, 77.68% yield) was obtained in the same manner as in Step 4 of Preparation Example 1 using Compound 6-B (30.0 g, 42.26 mmol) obtained in Step 2 of Preparation Example 6 and 4-bromo-1,1'-biphenyl (9.85 g, 42.26 mmol). (MS[M+H]+=862)

Preparation Example 8

Synthesis of Compound 8

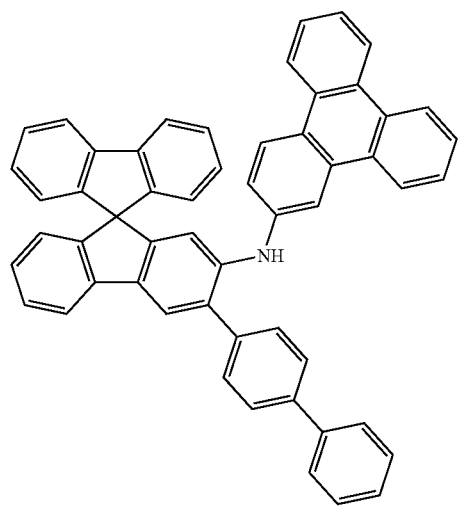

+

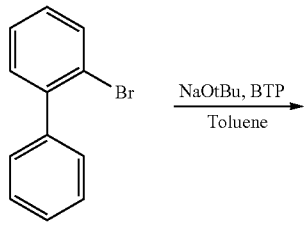

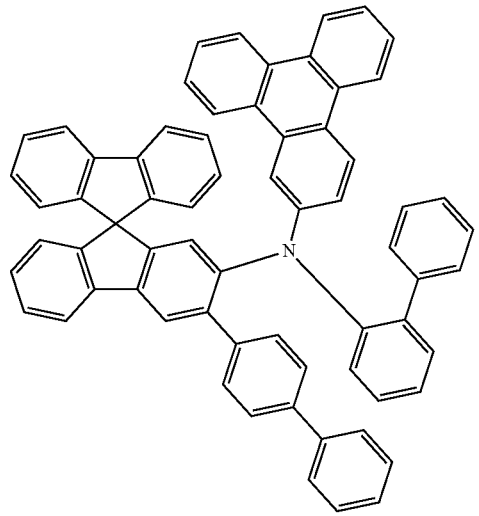

Compound 8

Compound 8 (26.4 g, 72.46% yield) was obtained in the same manner as in Step 4 of Preparation Example 1 using Compound 6-B (30.0 g, 42.26 mmol) obtained in Step 2 of Preparation Example 6 and 2-bromo-1,1'-biphenyl (9.85 g, 42.26 mmol). (MS[M+H]+=862)

Preparation Example 9

Synthesis of Compound 9

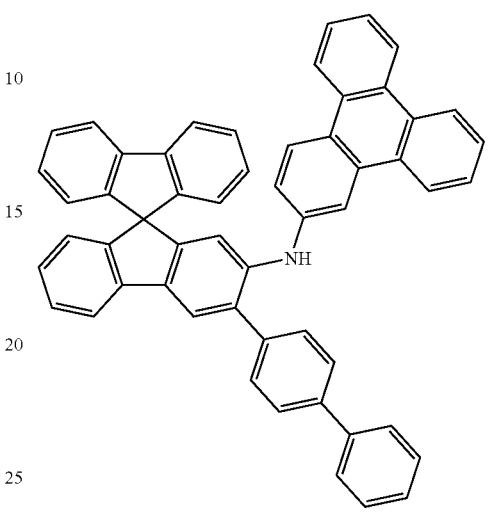

+

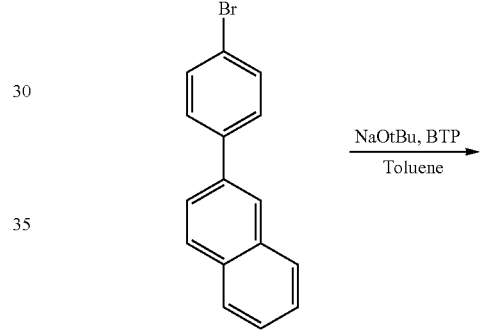

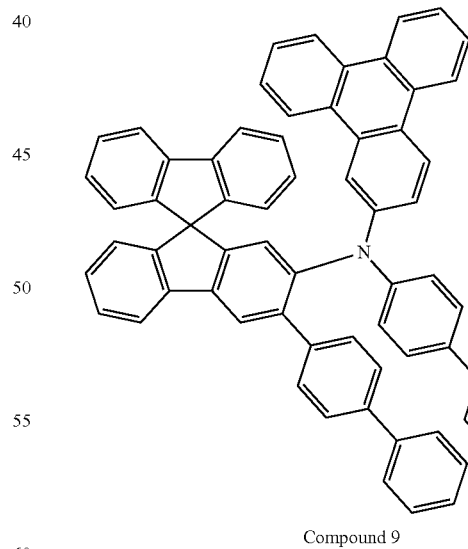

Compound 9

Compound 9 (26.9 g, 69.78% yield) was obtained in the same manner as in Step 4 of Preparation Example 1 using Compound 6-B (30.0 g, 42.26 mmol) obtained in Step 2 of Preparation Example 6 and 2-(4-bromophenyl)naphthalene (11.97 g, 42.26 mmol). (MS[M+H]+=912)

Preparation Example 10

Synthesis of Compound 10

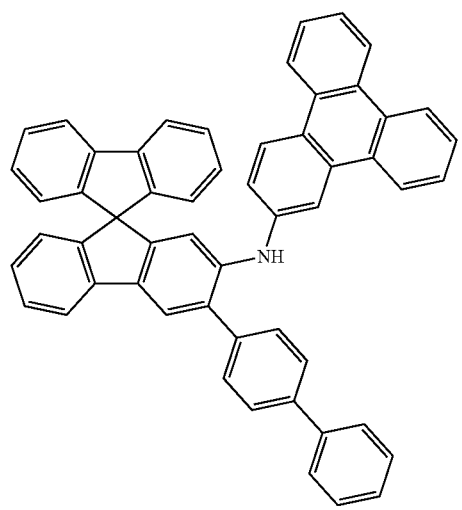

+

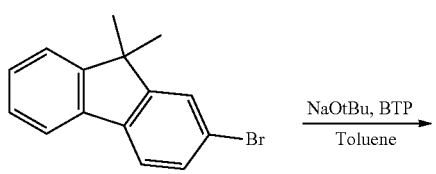

NaOtBu, BTP / Toluene →

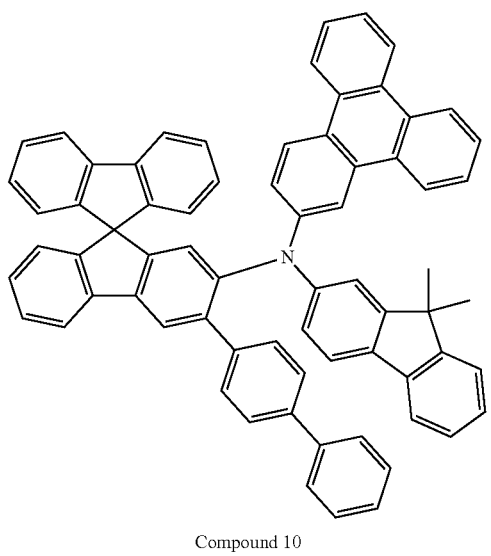

Compound 10

Compound 10 (27.1 g, 71.34% yield) was obtained in the same manner as in Step 4 of Preparation Example 1 using Compound 6-B (30.0 g, 42.26 mmol) obtained in Step 2 of Preparation Example 6 and 2-bromo-9,9-dimethyl-9H-fluorene (11.54 g, 42.26 mmol). (MS[M+H]+=902)

Preparation Example 11

Synthesis of Compound 11

Step 1) Synthesis of Compound 11-A

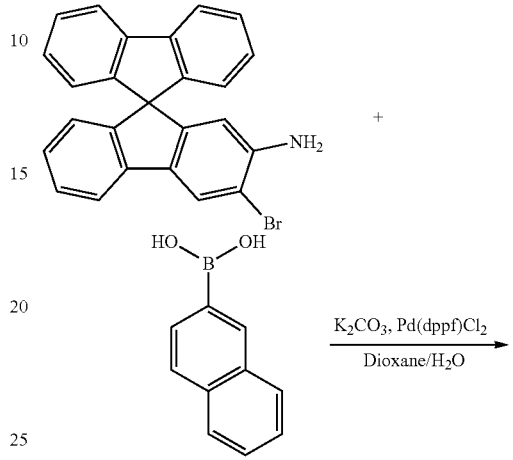

K$_2$CO$_3$, Pd(dppf)Cl$_2$ / Dioxane/H$_2$O →

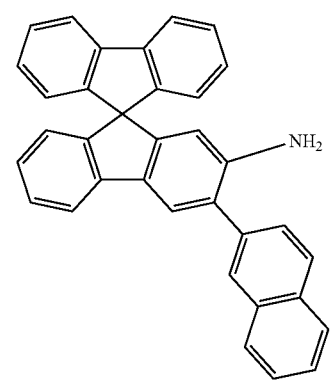

[11-A]

Compound 11-A (49.6 g, 88.95% yield) was obtained in the same manner as in Step 2 of Preparation Example 1 using Compound 1-A (50.0 g, 121.86 mmol) obtained in Step 1 of Preparation Example 1 and naphthalen-2-ylboronic acid (20.96 g, 121.86 mmol).

Step 2) Synthesis of Compound 11-B

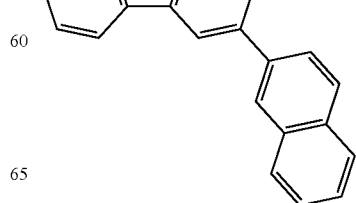

+

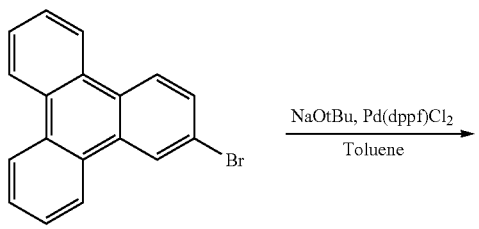

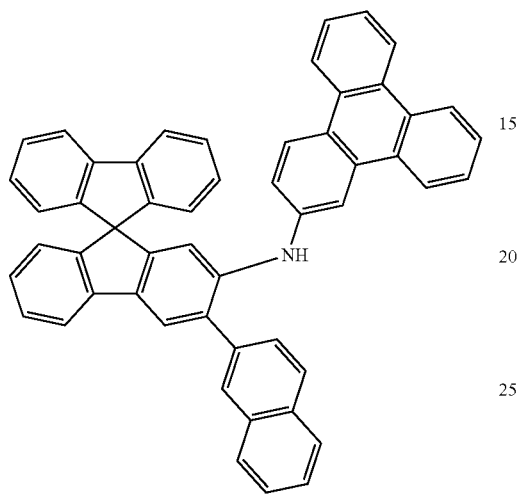

[11-B]

Compound 11-B (62.9 g, 84.85% yield) was obtained in the same manner as in Step 3 of Preparation Example 1 using Compound 11-A (49.6 g, 108.40 mmol) obtained in Step 1 and 2-bromotriphenylene (33.30 g, 108.40 mmol).

Step 3) Synthesis of Compound 11

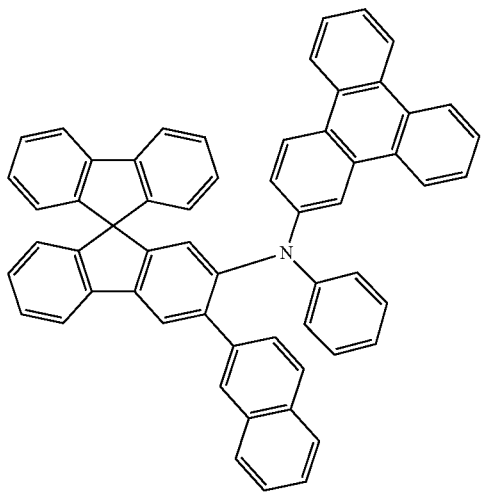

Compound 11

Compound 11 (26.4 g, 79.19% yield) was obtained in the same manner as in Step 4 of Preparation Example 1 using Compound 11-B (30.0 g, 43.87 mmol) obtained in Step 2 and bromobenzene (6.89 g, 43.87 mmol). (MS[M+H]+ =760)

Preparation Example 12

Synthesis of Compound 12

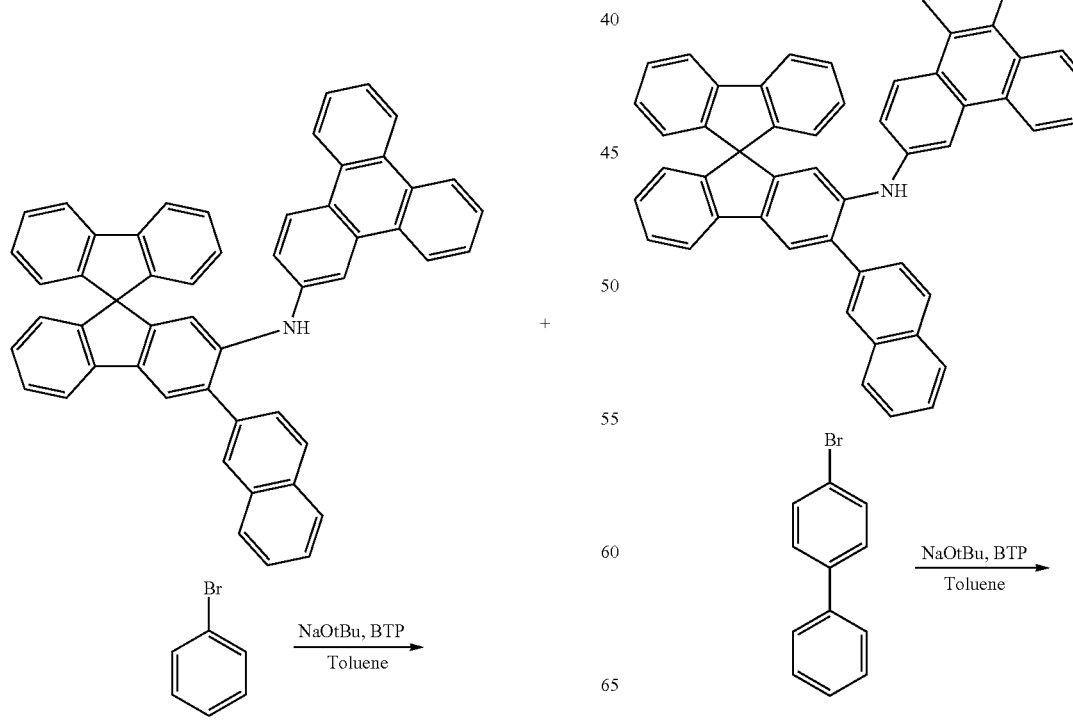

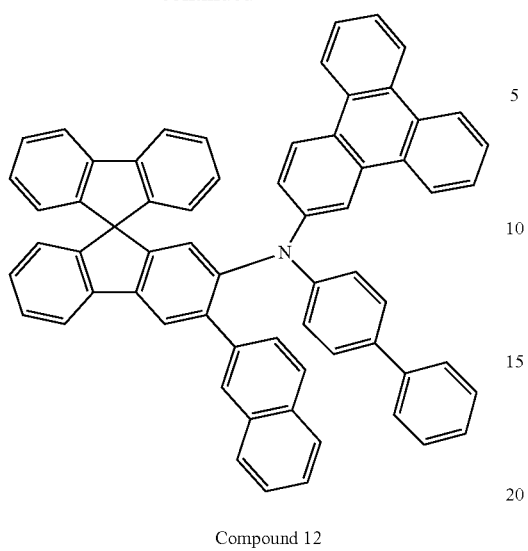

Compound 12

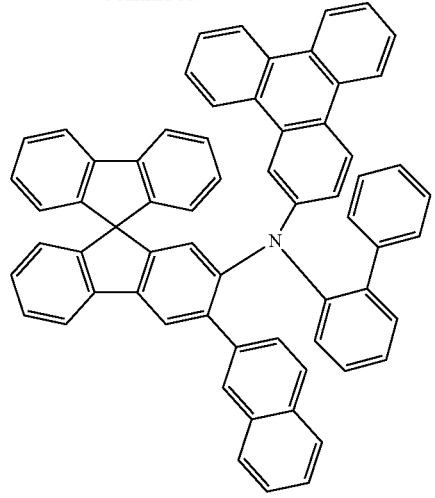

Compound 13

Compound 12 (28.6 g, 77.98% yield) was obtained in the same manner as in Step 4 of Preparation Example 1 using Compound 11-B (30.0 g, 43.87 mmol) obtained in Step 2 of Preparation Example 11 and 4-bromo-1,1'-biphenyl (10.23 g, 43.87 mmol). (MS[M+H]+=836)

Compound 13 (26.9 g, 73.34% yield) was obtained in the same manner as in Step 4 of Preparation Example 1 using Compound 11-B (30.0 g, 43.87 mmol) obtained in Step 2 of Preparation Example 11 and 2-bromo-1,1'-biphenyl (10.23 g, 43.87 mmol). (MS[M+H]+=836)

Preparation Example 13

Synthesis of Compound 13

Preparation Example 14

Synthesis of Compound 14

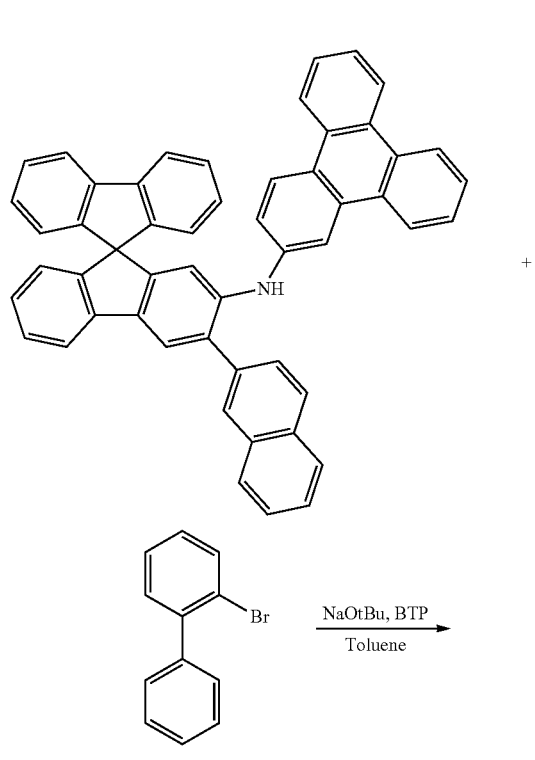

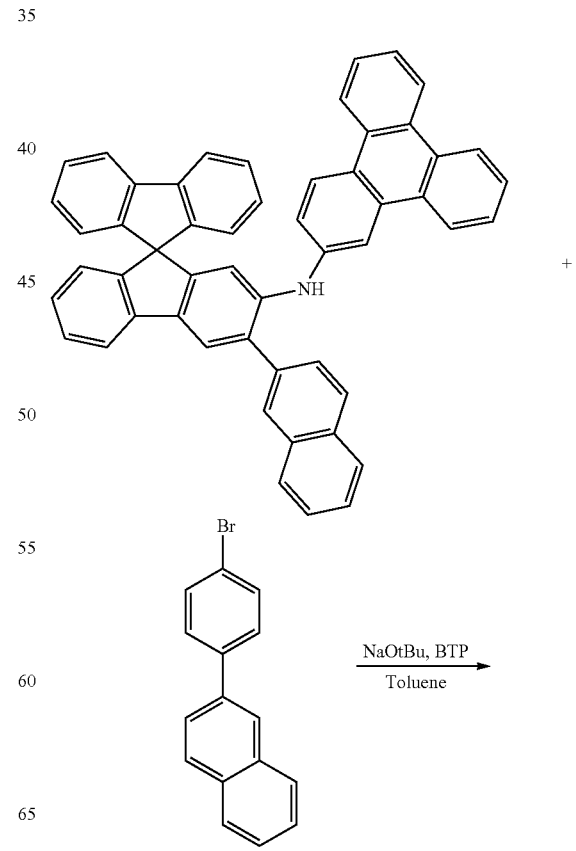

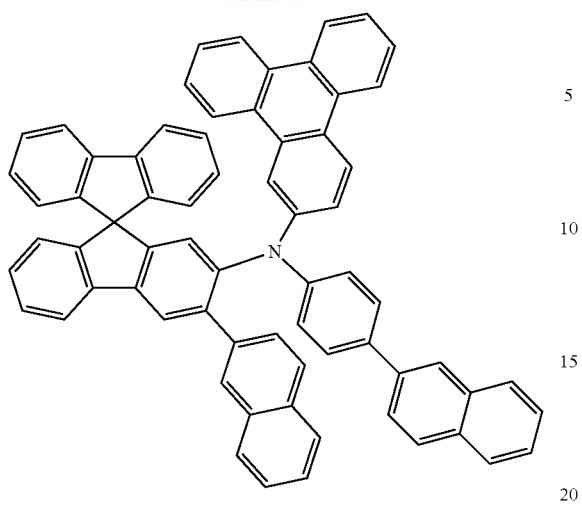

Compound 14

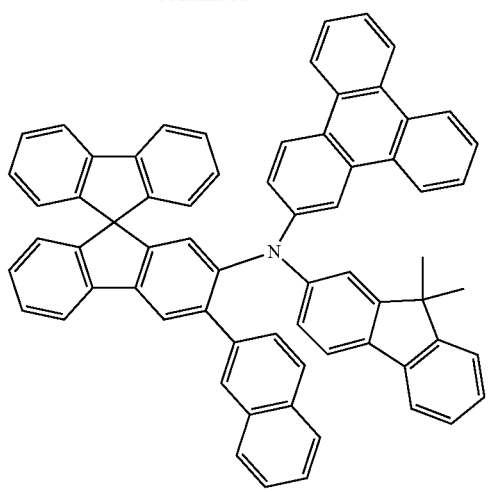

Compound 15

Compound 14 (30.2 g, 77.69% yield) was obtained in the same manner as in Step 4 of Preparation Example 1 using Compound 11-B (30.0 g, 43.87 mmol) obtained in Step 2 of Preparation Example 11 and 2-(4-bromophenyl)naphthalene (12.42 g, 43.87 mmol). (MS[M+H]+=886)

Preparation Example 15

Synthesis of Compound 15

Compound 15 (25.9 g, 67.39% yield) was obtained in the same manner as in Step 4 of Preparation Example 1 using Compound 11-B (30.0 g, 43.87 mmol) obtained in Step 2 of Preparation Example 11 and 2-bromo-9,9-dimethyl-9H-fluorene (11.98 g, 43.87 mmol). (MS[M+H]+=876)

Preparation Example 16

Synthesis of Compound 16

Step 1) Synthesis of Compound 16-A

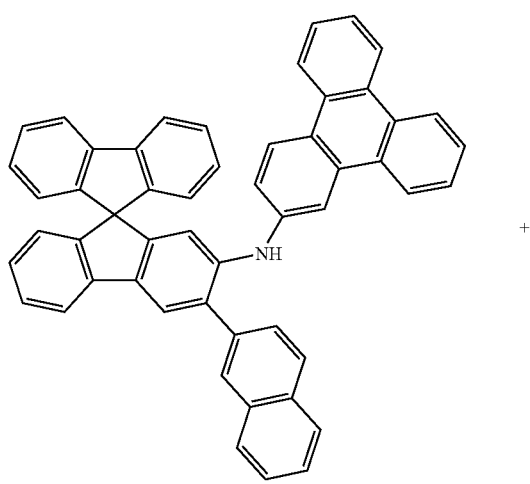

+

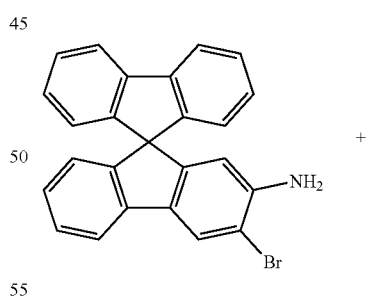

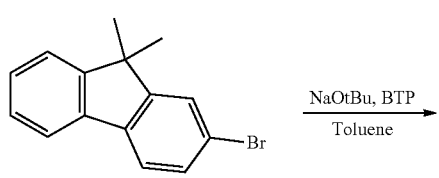

$\xrightarrow{\text{NaOtBu, BTP}}$
Toluene

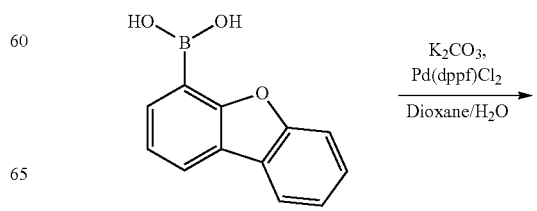

$\xrightarrow{\text{K}_2\text{CO}_3,\ \text{Pd(dppf)Cl}_2}{\text{Dioxane/H}_2\text{O}}$

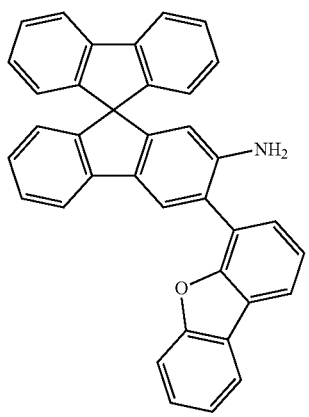

[16-A]

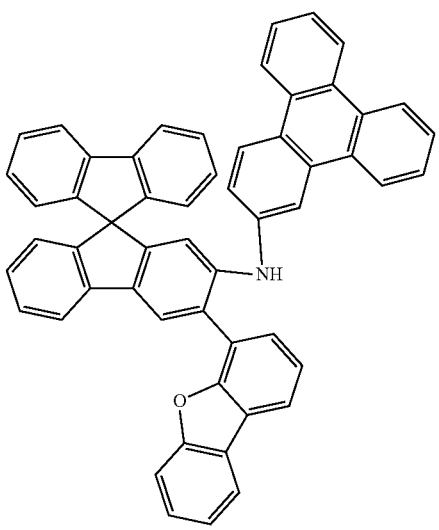

[16-B]

Compound 16-A (52.6 g, 86.75% yield) was obtained in the same manner as in Step 2 of Preparation Example 1 using Compound 1-A (50.0 g, 121.86 mmol) obtained in Step 1 of Preparation Example 1 and dibenzo[b,d]furan-4-ylboronic acid (25.84 g, 121.86 mmol).

Step 2) Synthesis of Compound 16-B

Compound 16-B (65.1 g, 85.07% yield) was obtained in the same manner as in Step 3 of Preparation Example 1 using Compound 16-A (52.6 g, 105.71 mmol) obtained in Step 1 and 2-bromotriphenylene (32.47 g, 105.71 mmol).

Step 3) Synthesis of Compound 16

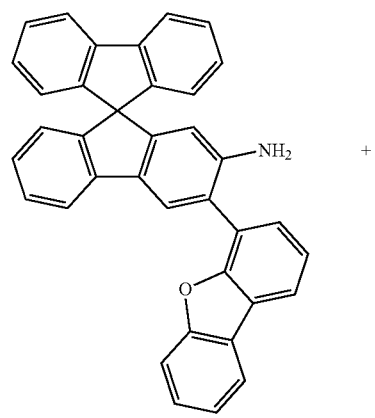

+

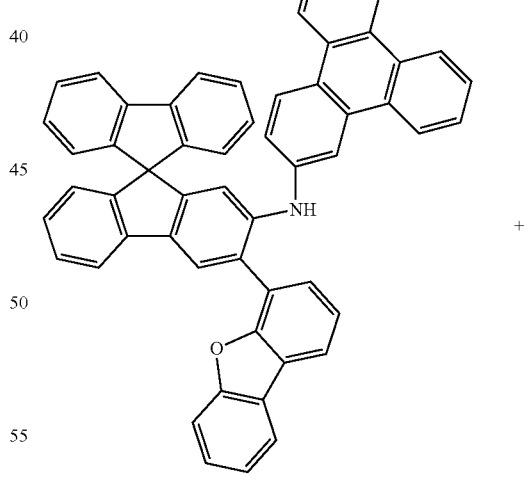

+

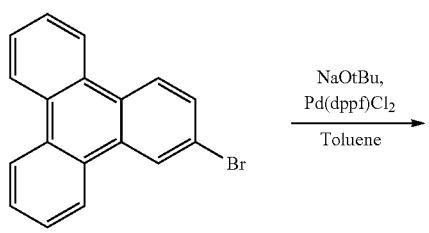

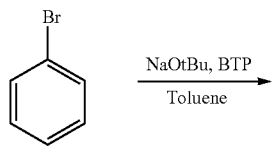

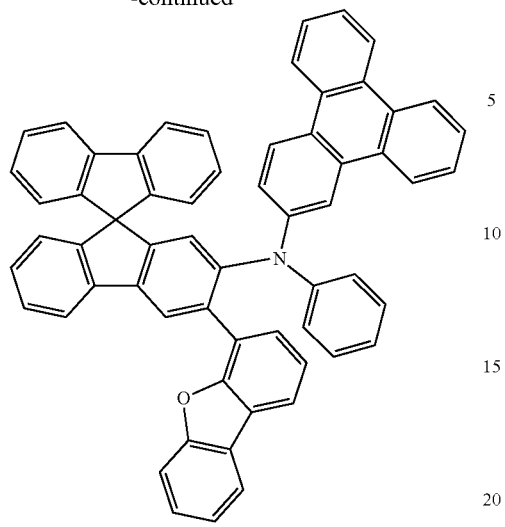

Compound 16

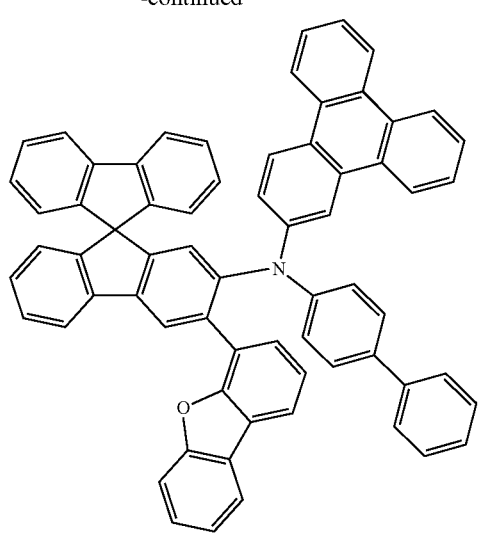

Compound 17

Compound 16 (24.8 g, 74.81% yield) was obtained in the same manner as in Step 4 of Preparation Example 1 using Compound 16-B (30.0 g, 41.44 mmol) obtained in Step 2 and bromobenzene (6.51 g, 41.44 mmol). (MS[M+H]+ =800)

Preparation Example 17

Synthesis of Compound 17

Compound 17 (26.4 g, 72.72% yield) was obtained in the same manner as in Step 4 of Preparation Example 1 using Compound 16-B (30.0 g, 41.44 mmol) obtained in Step 2 of Preparation Example 16 and 4-bromo-1,1'-biphenyl (9.66 g, 41.44 mmol). (MS[M+H]+=876)

Preparation Example 18

Synthesis of Compound 18

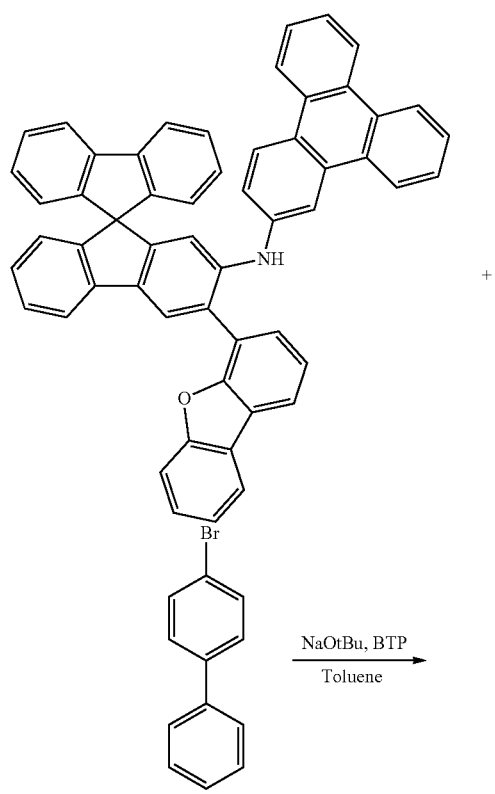

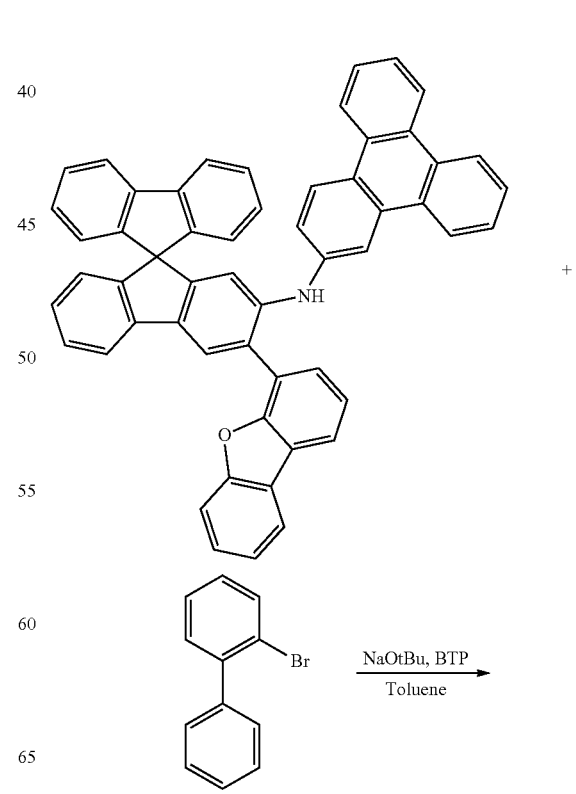

-continued

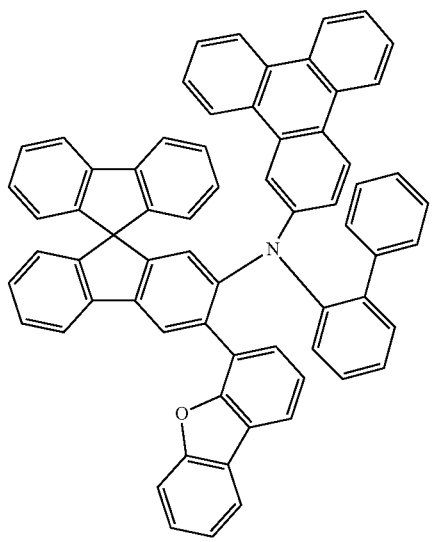

Compound 18

Compound 18 (24.6 g, 67.76% yield) was obtained in the same manner as in Step 4 of Preparation Example 1 using Compound 16-B (30.0 g, 41.44 mmol) obtained in Step 2 of Preparation Example 16 and 2-bromo-1,1'-biphenyl (9.66 g, 41.44 mmol). (MS[M+H]+=876)

Preparation Example 19

Synthesis of Compound 19

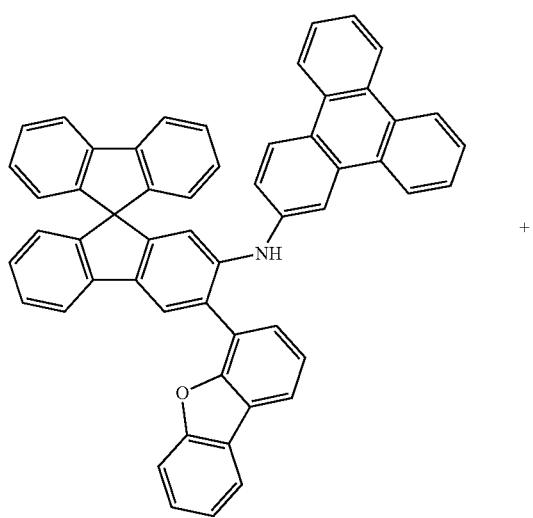

+

-continued

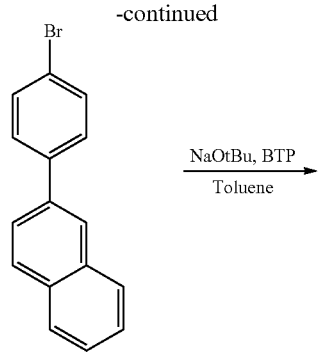

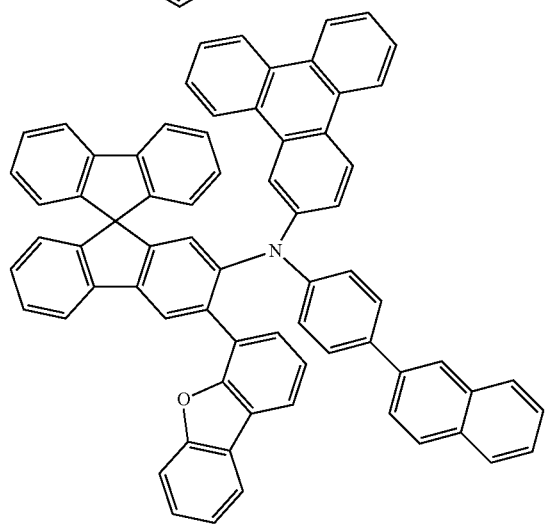

Compound 19

Compound 19 (27.1 g, 70.61% yield) was obtained in the same manner as in Step 4 of Preparation Example 1 using Compound 16-B (30.0 g, 41.44 mmol) obtained in Step 2 of Preparation Example 16 and 2-(4-bromophenyl)naphthalene (11.73 g, 41.44 mmol). (MS[M+H]+=926)

Preparation Example 20

Synthesis of Compound 20

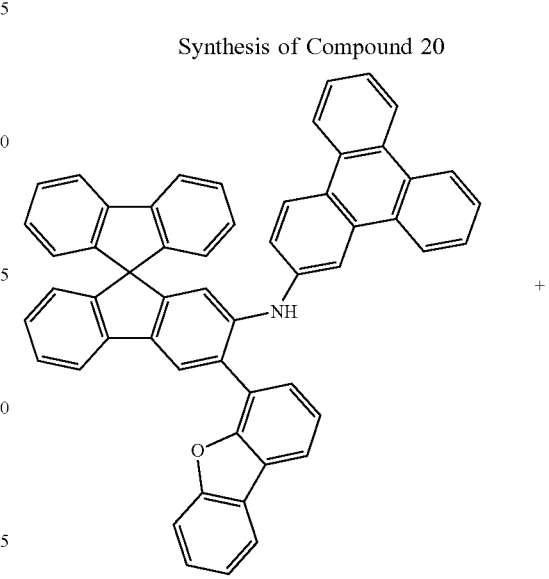

+

-continued

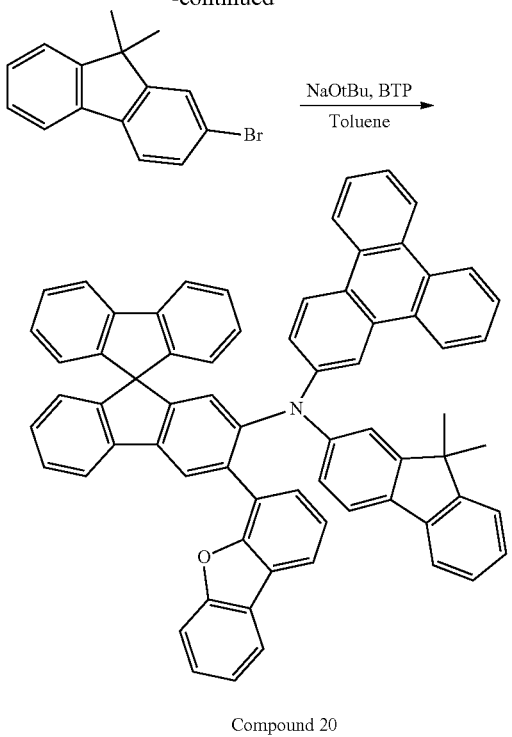

Compound 20

Compound 20 (26.1 g, 68.75% yield) was obtained in the same manner as in Step 4 of Preparation Example 1 using Compound 16-B (30.0 g, 41.44 mmol) obtained in Step 2 of Preparation Example 16 and 2-bromo-9,9-dimethyl-9H-fluorene (11.32 g, 41.44 mmol). (MS[M+H]+=916)

Experimental Example

Comparative Example 1-1

A glass substrate on which indium tin oxide (ITO) was coated as a thin film to a thickness of 1,400 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing a compound represented by the following chemical formula HAT to a thickness of 100 Å. A compound represented by the following chemical formula HT1 was vacuum deposited to a thickness of 1150 Å thereon as a hole transfer layer, and then the following compound EB1 was thermal vacuum deposited to a thickness of 150 Å as an electron blocking layer. Subsequently, as a light emitting layer, a compound represented by the following chemical formula BH and a compound represented by the following chemical formula BD were vacuum deposited in a weight ratio of 25:1 to a thickness of 200 Å. Subsequently, a compound represented by the following chemical formula HB1 was vacuum deposited to a thickness of 50 Å as a hole blocking layer. Subsequently, as an electron transfer layer and an electron injection layer, a compound represented by the following chemical formula ET1 and a compound represented by the following Liq were thermal vacuum deposited in a weight ratio of 1:1 to a thickness of 310 Å. Subsequently, a compound represented by the following Liq was vacuum deposited to a thickness of 5 Å. On the electron transfer and electron injection layer, a cathode was formed by depositing lithium fluoride (LiF) to a thickness of 12 Å and aluminum to a thickness of 1,000 Å in consecutive order, and as a result, an organic light emitting device was manufactured.

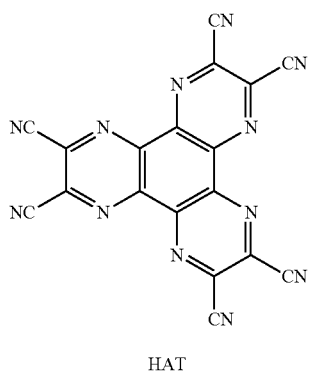

HAT

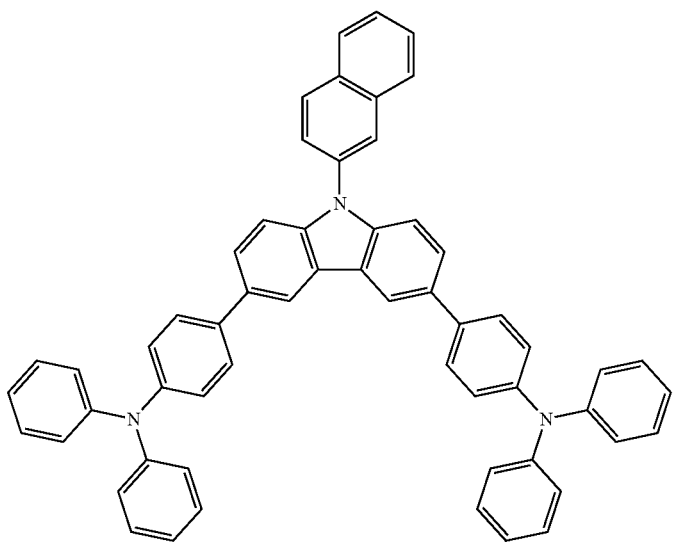

HT1

-continued
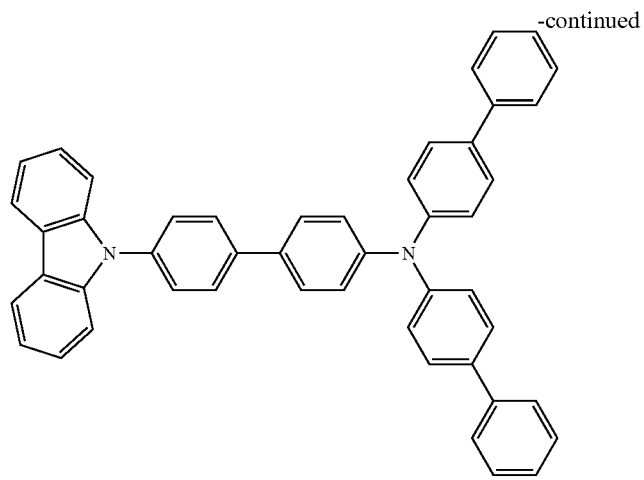
EB1
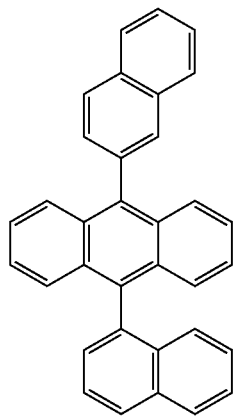
BH
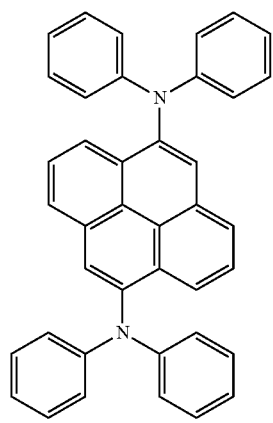
BD
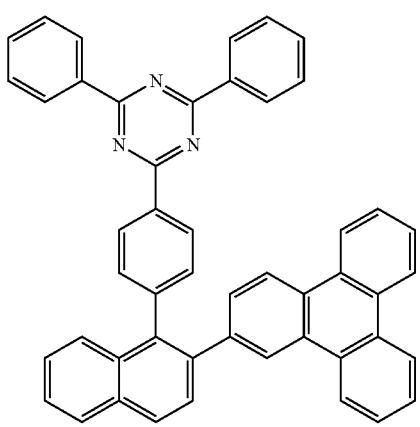
HB1
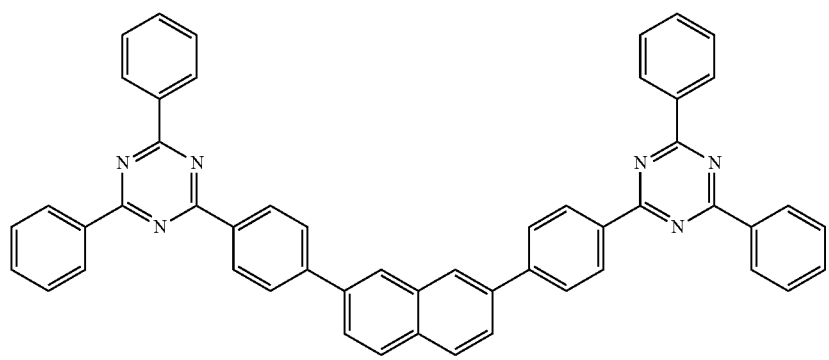
ET1
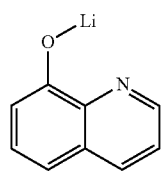
LiQ

Comparative Examples 1-2 to 1-5

Organic light emitting devices of Comparative Examples 1-2 to 1-5 were manufactured in the same manner as in Comparative Example 1-1 except that compounds described in the following Table 1 were used instead of EB1.

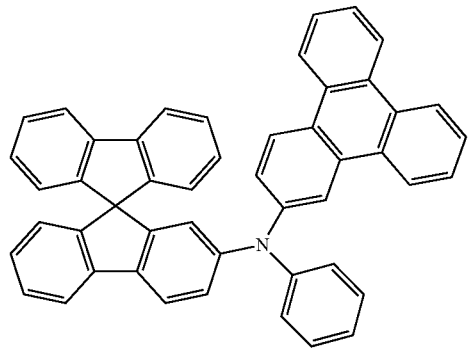

EB2

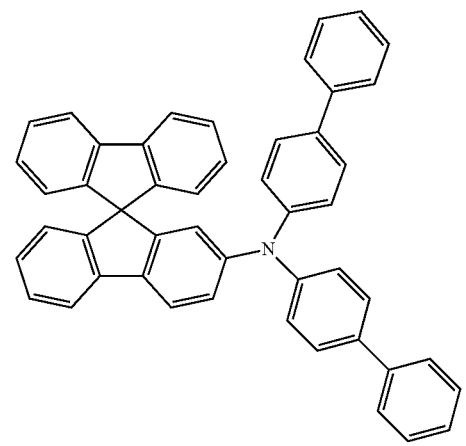

EB3

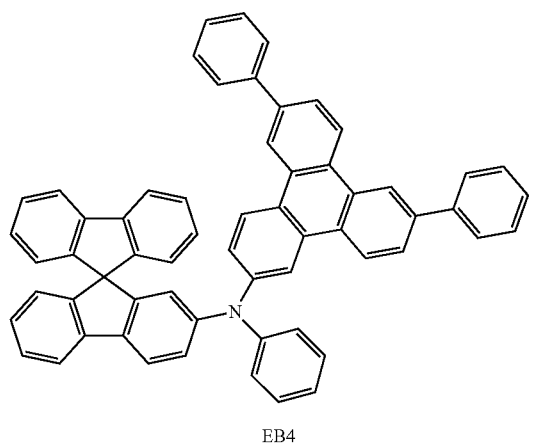

EB4

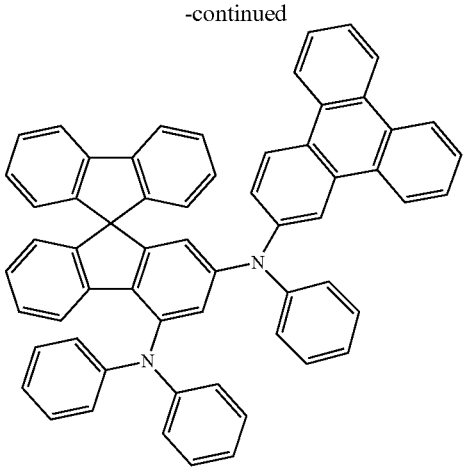

EB5

Examples 1-1 to 1-20

Organic light emitting devices of Examples 1-1 to 1-20 were manufactured in the same manner as in Comparative Example 1-1 except that compounds described in the following Table 1 were used instead of EB1.

Experimental Example 1

When a current was applied to the organic light emitting devices manufactured in Examples 1-1 to 1-20 and Comparative Examples 1-1 to 1-5, a voltage, efficiency, a color coordinate and a lifetime were measured, and the results are shown in the following Table 1. T95 means time taken for the luminance decreasing to 95% from its initial luminance (6000 nit).

TABLE 1

| | Compound (Electron Blocking Layer) | Voltage (V @ 10 mA/cm$^2$) | Efficiency (cd/A @ 10 mA/cm$^2$) | Color Coordinate (x, y) | Lifetime (T95, hr) |
|---|---|---|---|---|---|
| Example 1-1 | Compound 1 | 3.53 | 6.31 | 0.140, 0.044 | 285 |
| Example 1-2 | Compound 2 | 3.51 | 6.21 | 0.141, 0.045 | 270 |
| Example 1-3 | Compound 3 | 3.45 | 6.30 | 0.140, 0.044 | 290 |
| Example 1-4 | Compound 4 | 3.55 | 6.15 | 0.141, 0.044 | 285 |
| Example 1-5 | Compound 5 | 3.48 | 6.28 | 0.142, 0.044 | 290 |
| Example 1-6 | Compound 6 | 3.52 | 6.12 | 0.141, 0.045 | 280 |
| Example 1-7 | Compound 7 | 3.51 | 6.13 | 0.142, 0.043 | 285 |
| Example 1-8 | Compound 8 | 3.48 | 6.17 | 0.139, 0.044 | 270 |
| Example 1-9 | Compound 9 | 3.53 | 6.11 | 0.140, 0.043 | 270 |
| Example 1-10 | Compound 10 | 3.48 | 6.23 | 0.139, 0.043 | 295 |
| Example 1-11 | Compound 11 | 3.55 | 6.21 | 0.143, 0.043 | 280 |
| Example 1-12 | Compound 12 | 3.53 | 6.17 | 0.141, 0.044 | 280 |
| Example 1-13 | Compound 13 | 3.50 | 6.11 | 0.140, 0.044 | 275 |

TABLE 1-continued

| | Compound (Electron Blocking Layer) | Voltage (V @ 10 mA/cm²) | Efficiency (cd/A @ 10 mA/cm²) | Color Coordinate (x, y) | Lifetime (T95, hr) |
|---|---|---|---|---|---|
| Example 1-14 | Compound 14 | 3.56 | 6.08 | 0.139, 0.045 | 280 |
| Example 1-15 | Compound 15 | 3.51 | 6.18 | 0.140, 0.044 | 270 |
| Example 1-16 | Compound 16 | 3.51 | 6.11 | 0.141, 0.043 | 285 |
| Example 1-17 | Compound 17 | 3.51 | 6.16 | 0.141, 0.044 | 285 |
| Example 1-18 | Compound 18 | 3.49 | 6.09 | 0.140, 0.044 | 290 |
| Example 1-19 | Compound 19 | 3.56 | 6.17 | 0.142, 0.043 | 270 |
| Example 1-20 | Compound 20 | 3.52 | 6.23 | 0.142, 0.045 | 265 |
| Comparative Example 1-1 | EB1 | 3.89 | 5.74 | 0.143, 0.045 | 230 |
| Comparative Example 1-2 | EB2 | 4.01 | 5.55 | 0.143, 0.047 | 210 |
| Comparative Example 1-3 | EB3 | 4.05 | 5.49 | 0.144, 0.048 | 215 |
| Comparative Example 1-4 | EB4 | 4.15 | 5.25 | 0.143, 0.048 | 180 |
| Comparative Example 1-5 | EB5 | 4.10 | 5.33 | 0.144, 0.048 | 160 |

As shown in Table 1, it was identified that the organic light emitting device using the compound of the present disclosure as an electron blocking layer exhibited significant effects in terms of a driving voltage, efficiency and a lifetime.

From the results of Table 1, it was identified that the compound according to the present disclosure had an excellent electron blocking ability and thereby was capable of being used in an organic light emitting device.

Comparative Examples 2-1 to 2-4

Organic light emitting devices of Comparative Examples 2-1 to 2-4 were manufactured in the same manner as in Comparative Example 1-1 except that compounds described in the following Table 1 were used instead of the compound represented by HT1.

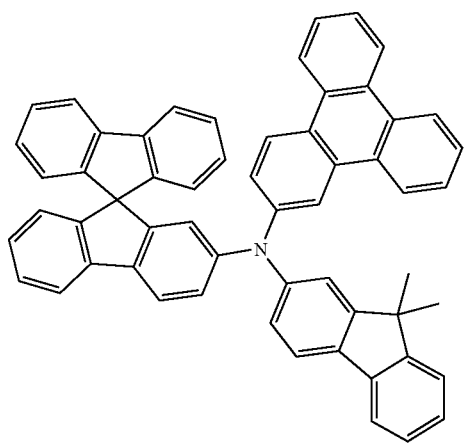

HT2

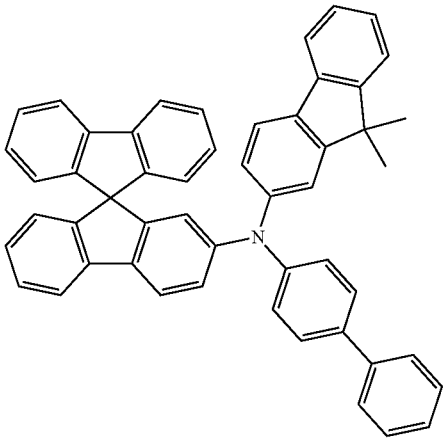

HT3

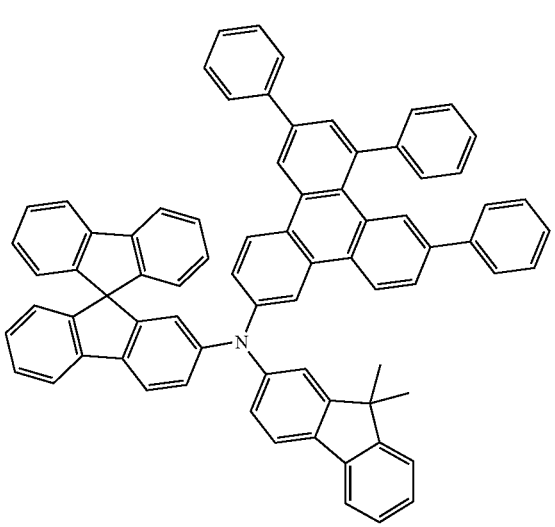

HT4

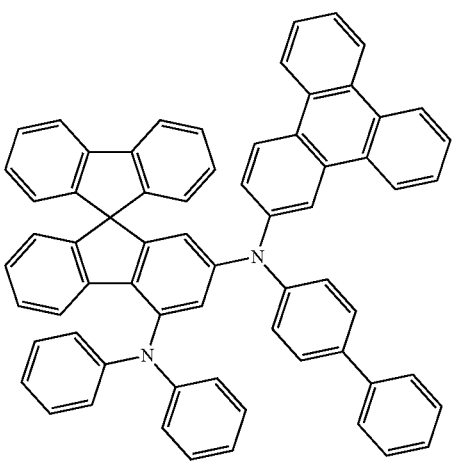

HT5

Examples 2-1 to 2-15

Organic light emitting devices of Examples 2-1 to 2-15 were manufactured in the same manner as in Comparative Example 1-1 except that compounds described in the following Table 1 were used instead of the compound represented by HT1.

Experimental Example 2

When a current was applied to the organic light emitting devices manufactured in Examples 2-1 to 2-15 and Comparative Examples 1-1, 2-1 to 2-4, a voltage, efficiency, a color coordinate and a lifetime were measured, and the results are shown in the following Table 2. T95 means time taken for the luminance decreasing to 95% from its initial luminance (6000 nit).

TABLE 2

| | Compound (Hole Transfer Layer) | Voltage (V @ 10 mA/cm$^2$) | Efficiency (cd/A @ 10 mA/cm$^2$) | Color Coordinate (x, y) | Lifetime (T95, hr) |
|---|---|---|---|---|---|
| Example 2-1 | Compound 1 | 3.56 | 6.20 | 0.141, 0.043 | 290 |
| Example 2-2 | Compound 2 | 3.50 | 6.18 | 0.141, 0.045 | 275 |
| Example 2-3 | Compound 3 | 3.55 | 6.24 | 0.141, 0.045 | 285 |
| Example 2-4 | Compound 4 | 3.53 | 6.21 | 0.142, 0.043 | 270 |
| Example 2-5 | Compound 5 | 3.55 | 6.17 | 0.141, 0.044 | 285 |
| Example 2-6 | Compound 6 | 3.54 | 6.15 | 0.141, 0.044 | 275 |
| Example 2-7 | Compound 7 | 3.57 | 6.11 | 0.142, 0.043 | 285 |
| Example 2-8 | Compound 8 | 3.59 | 6.09 | 0.139, 0.045 | 270 |
| Example 2-9 | Compound 9 | 3.51 | 6.11 | 0.141, 0.043 | 285 |
| Example 2-10 | Compound 10 | 3.54 | 6.21 | 0.139, 0.045 | 290 |
| Example 2-11 | Compound 11 | 3.54 | 6.14 | 0.143, 0.044 | 280 |
| Example 2-12 | Compound 12 | 3.51 | 6.18 | 0.142, 0.043 | 275 |
| Example 2-13 | Compound 13 | 3.60 | 6.21 | 0.143, 0.043 | 275 |
| Example 2-14 | Compound 14 | 3.61 | 6.19 | 0.139, 0.044 | 280 |
| Example 2-15 | Compound 15 | 3.59 | 6.19 | 0.140, 0.044 | 275 |
| Comparative Example 1-1 | HT1 | 3.89 | 5.74 | 0.143, 0.045 | 230 |
| Comparative Example 2-1 | HT2 | 4.05 | 5.49 | 0.144, 0.048 | 210 |
| Comparative Example 2-2 | HT3 | 4.08 | 5.42 | 0.143, 0.047 | 210 |
| Comparative Example 2-3 | HT4 | 4.16 | 5.25 | 0.143, 0.047 | 175 |
| Comparative Example 2-4 | HT5 | 4.16 | 5.34 | 0.144, 0.048 | 150 |

As shown in Table 2, it was identified that the organic light emitting device using the compound of the present disclosure as a hole transfer layer exhibited significant effects in terms of a driving voltage, efficiency and a lifetime.

From the results of Table 2, it was identified that the compound according to the present disclosure had an excellent electron transfer ability and thereby was capable of being used in an organic light emitting device.

The invention claimed is:

1. A compound represented by the following Chemical Formula 1:

[Chemical Formula 1]

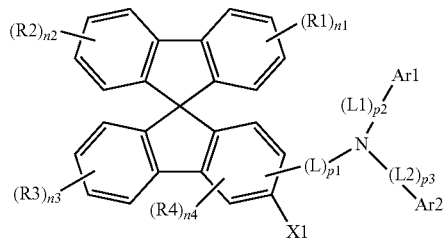

wherein, in Chemical Formula 1,

R1 to R4 are the same as or different from each other, and each independently hydrogen; deuterium; a halogen group; a cyano group; a silyl group; a substituted or unsubstituted alkyl group; a substituted or unsubstituted alkoxy group; a substituted or unsubstituted thioalkyl group; a substituted or unsubstituted cycloalkyl group; a substituted or unsubstituted aryl group; or a substituted or unsubstituted heterocyclic group;

n1 to n3 are each an integer of 0 to 4;

when n1 to n3 are each 2 or greater, substituents in the parentheses are the same as or different from each other;

n4 is an integer of 0 to 2;

when n4 is 2, substituents in the parentheses are the same as or different from each other;

p1 to p3 are each an integer of 0 to 3;

when p1 to p3 are each 2 or greater, substituents in the parentheses are the same as or different from each other;

L, L1 and L2 are the same as or different from each other, and each independently a direct bond; a substituted or unsubstituted arylene group; or a substituted or unsubstituted divalent heterocyclic group;

Ar1 is triphenylene;

Ar2 is hydrogen; deuterium; a substituted or unsubstituted aryl group; a substituted or unsubstituted arylalkyl group; a substituted or unsubstituted arylalkenyl group; or a substituted or unsubstituted heterocyclic group; and X1 is a substituted or unsubstituted aryl group; a substituted or unsubstituted arylalkyl group; a substituted or unsubstituted arylalkenyl group; or a substituted or unsubstituted heterocyclic group.

2. The compound of claim 1, wherein the compound represented by Chemical Formula 1 is represented by one of the following Chemical Formulae 2 to 4:

[Chemical Formula 2]

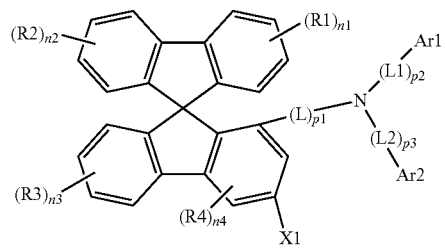

-continued

[Chemical Formula 3]

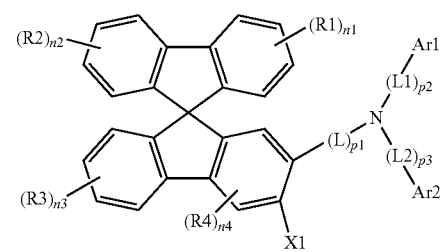

[Chemical Formula 4]

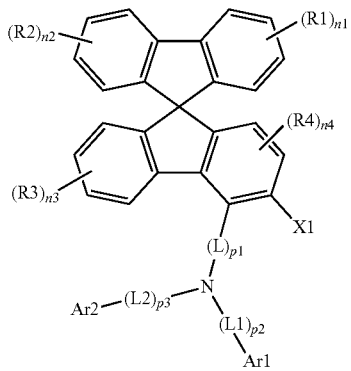

wherein, in Chemical Formulae 2 to 4,

R1 to R4, X1, L, L1, L2, n1 to n4, p1 to p3, Ar1 and Ar2 have the same definitions as in Chemical Formula 1.

3. The compound of claim 1, wherein $-(L)_{p1}-N[(L1)_{p2}Ar1][(L2)_{p3}Ar2]$ is represented by the following Chemical Formula 5:

[Chemical Formula 5]

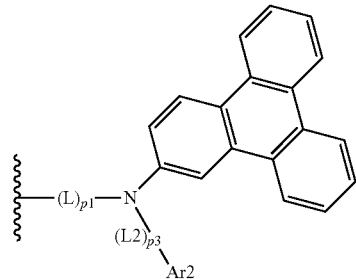

wherein, in Chemical Formula 5,

L, L2, p1, p3 and Ar2 have the same definitions as in Chemical Formula 1.

4. The compound of claim 1, wherein L is a direct bond or any one selected from the following structures:

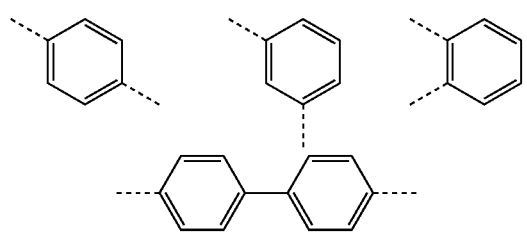

-continued

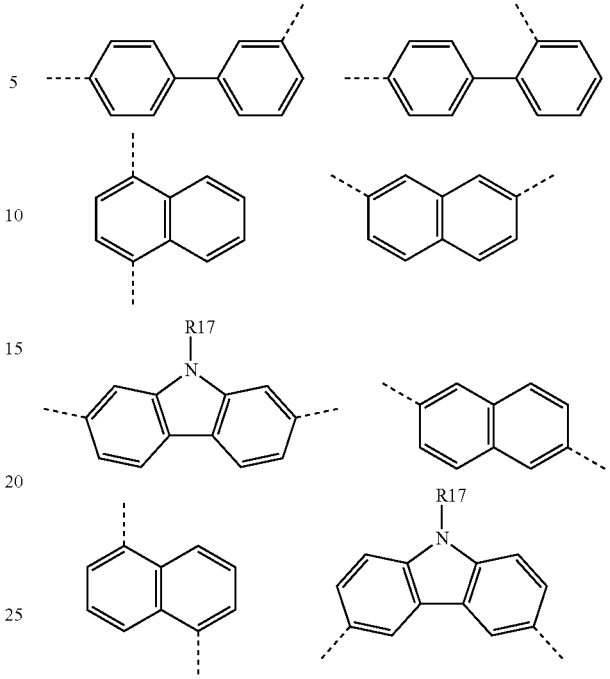

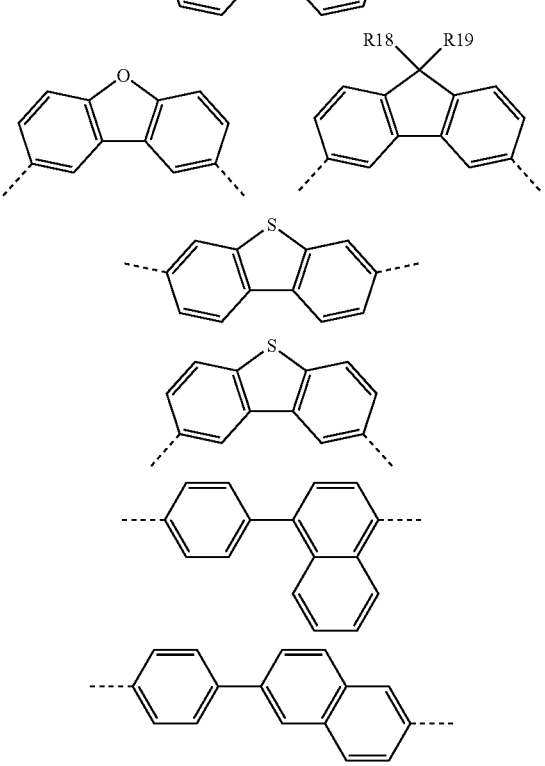

297
-continued

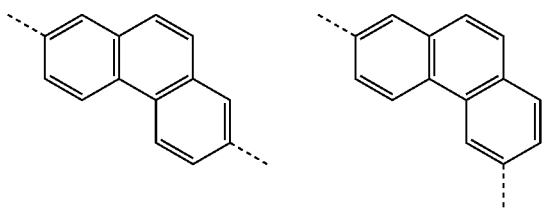

298
-continued

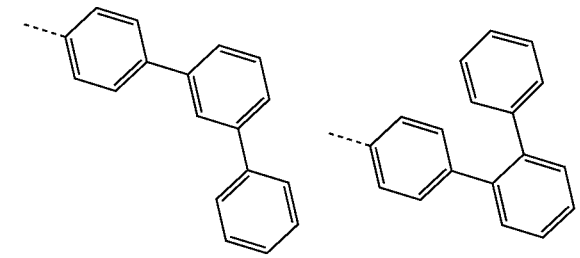

wherein, in the structures,

R17 to R19 are the same as or different from each other, and each independently hydrogen; deuterium; a halogen group; a cyano group; a silyl group; a substituted or unsubstituted alkyl group; a substituted or unsubstituted cycloalkyl group; a substituted or unsubstituted alkoxy group; a substituted or unsubstituted alkenyl group; a substituted or unsubstituted boron group; a substituted or unsubstituted amine group; a substituted or unsubstituted aryl group; or a substituted or unsubstituted heterocyclic group.

5. The compound of claim 1, wherein X1 is a substituted or unsubstituted aryl group; or a substituted or unsubstituted heterocyclic group.

6. The compound of claim 1, wherein X1 is any one selected from the following structures:

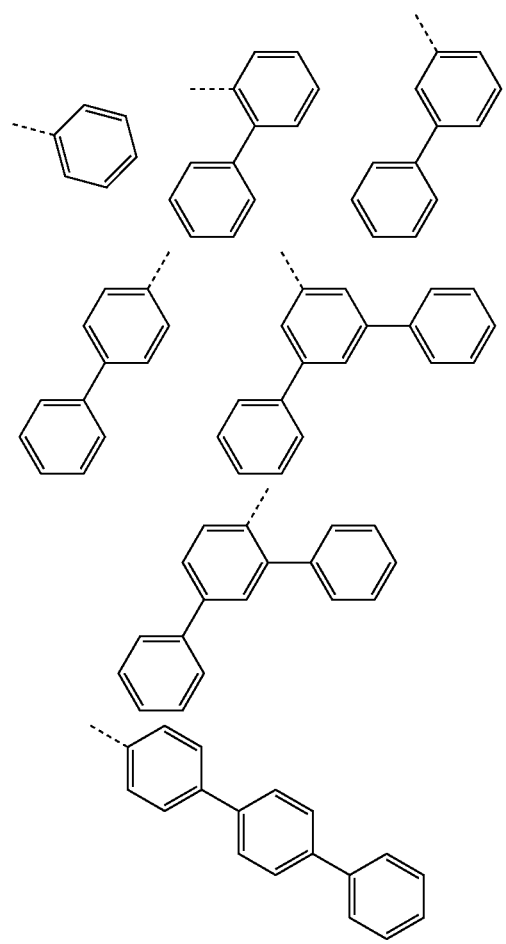

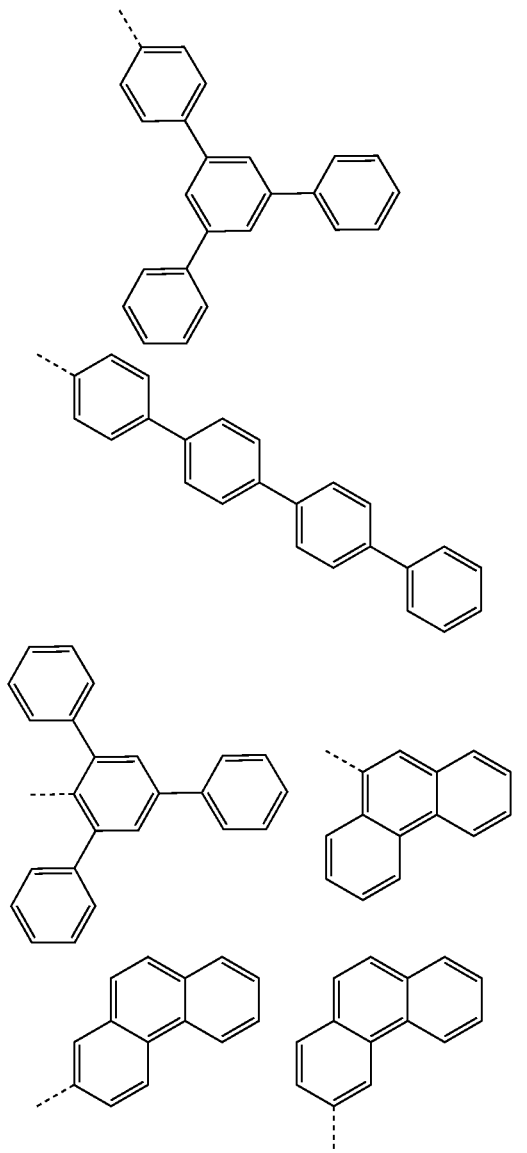

299
-continued
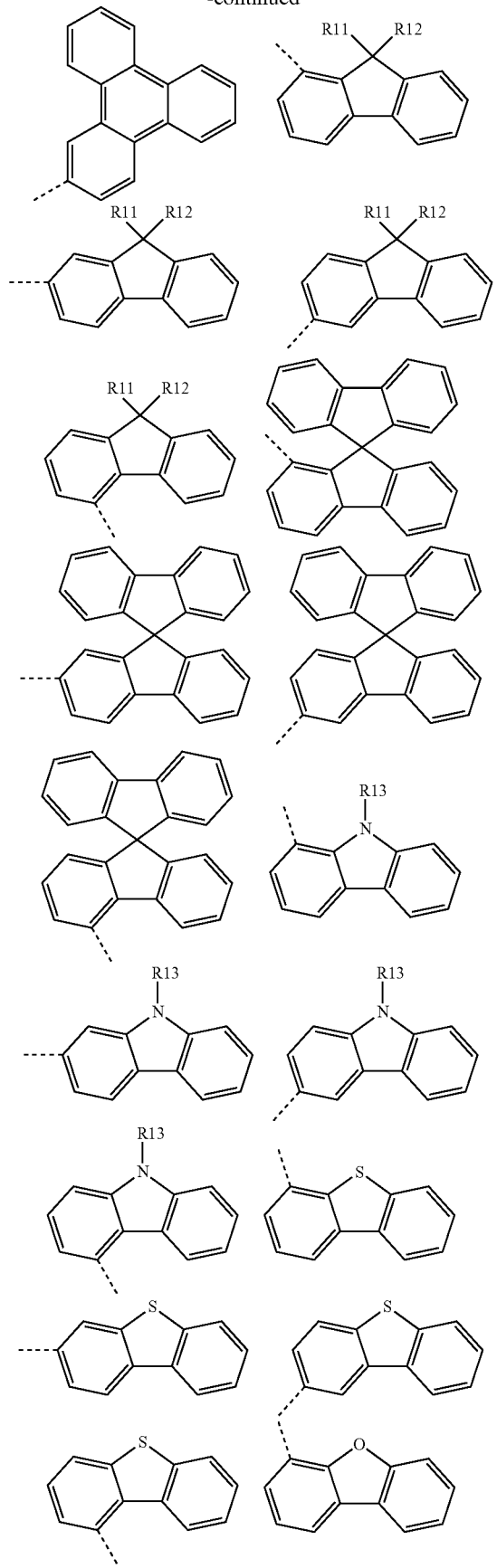
300
-continued
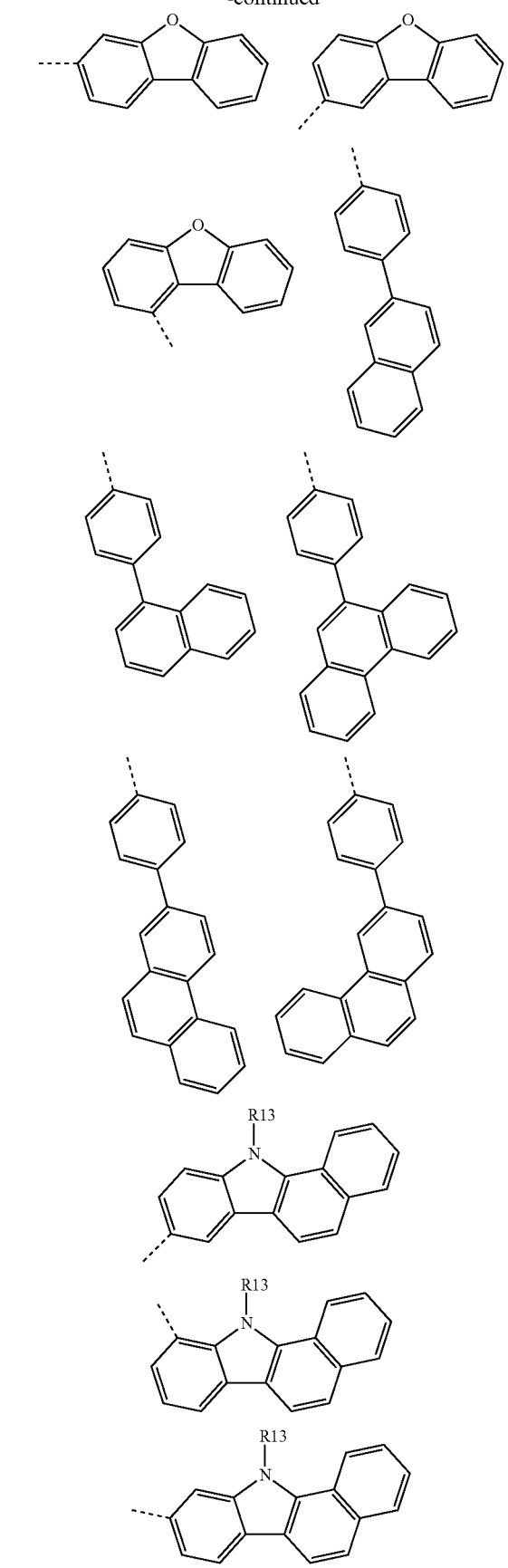

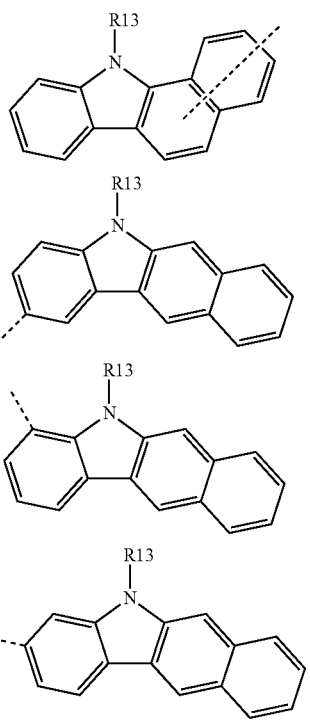

wherein, in the structures,

R11 to R13 are the same as or different from each other, and each independently hydrogen; deuterium; a halogen group; a cyano group; a silyl group; a substituted or unsubstituted alkyl group; a substituted or unsubstituted cycloalkyl group; a substituted or unsubstituted alkoxy group; a substituted or unsubstituted alkenyl group; a substituted or unsubstituted boron group; a substituted or unsubstituted amine group; a substituted or unsubstituted aryl group; or a substituted or unsubstituted heterocyclic group, or adjacent substituents bond to each other to form a substituted or unsubstituted ring.

7. The compound of claim 1, wherein Ar2 is any one selected from the following structures:

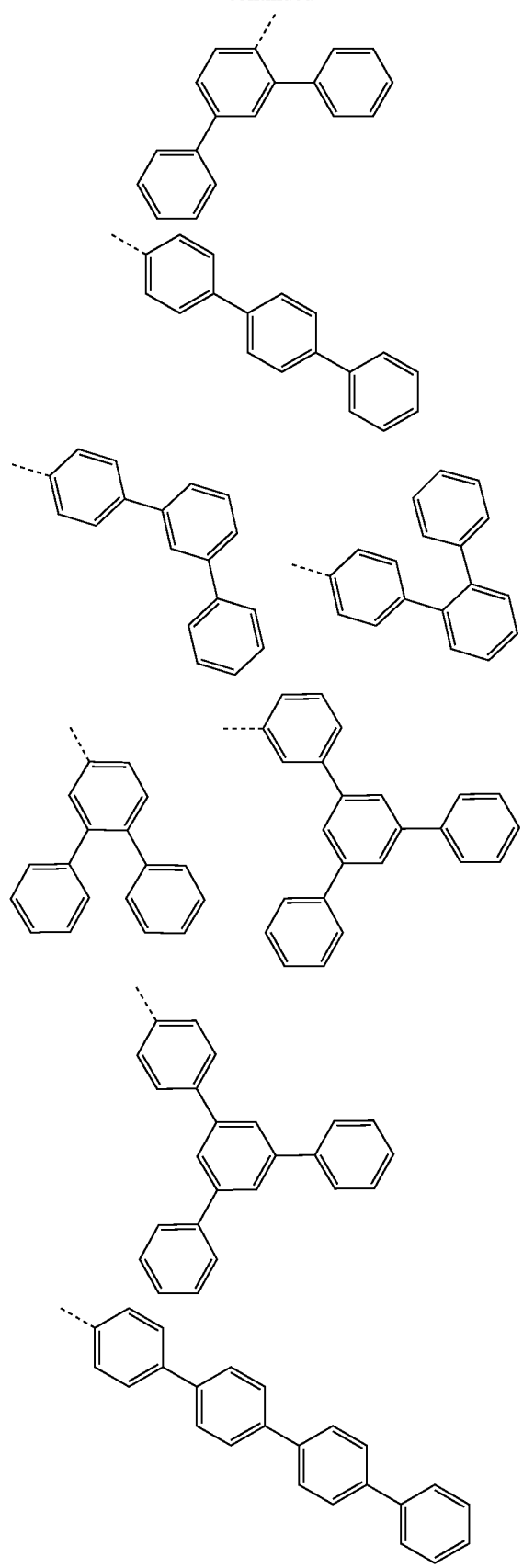
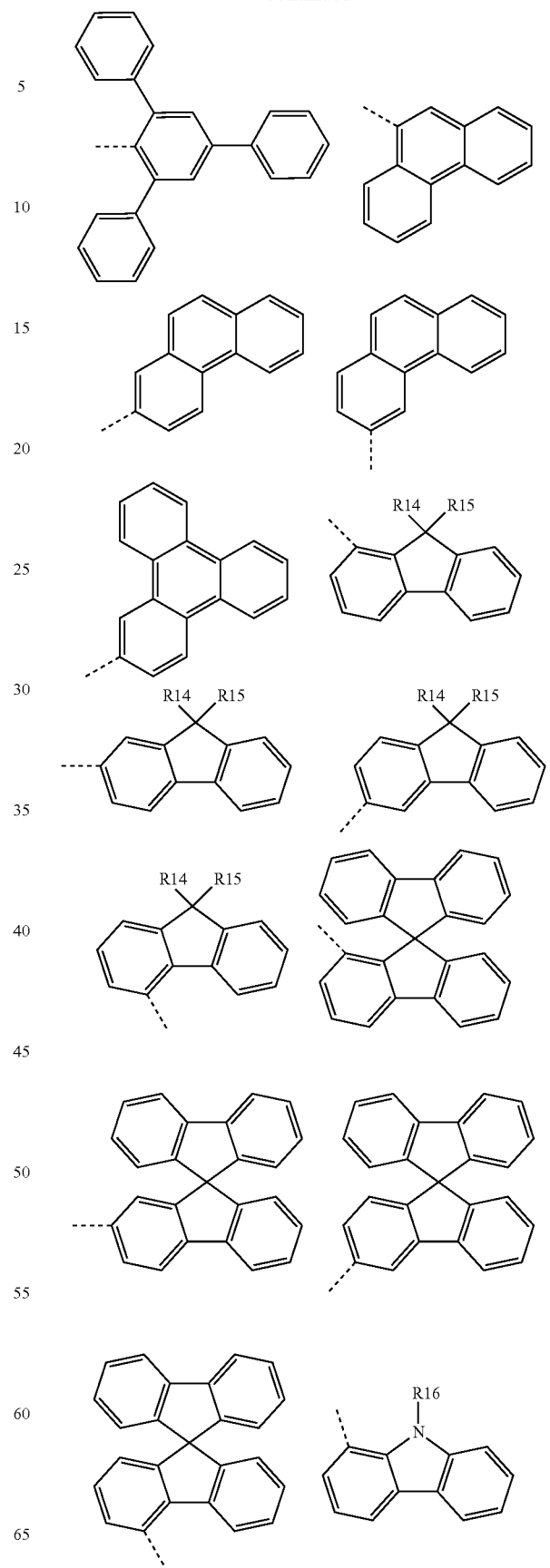

305

-continued

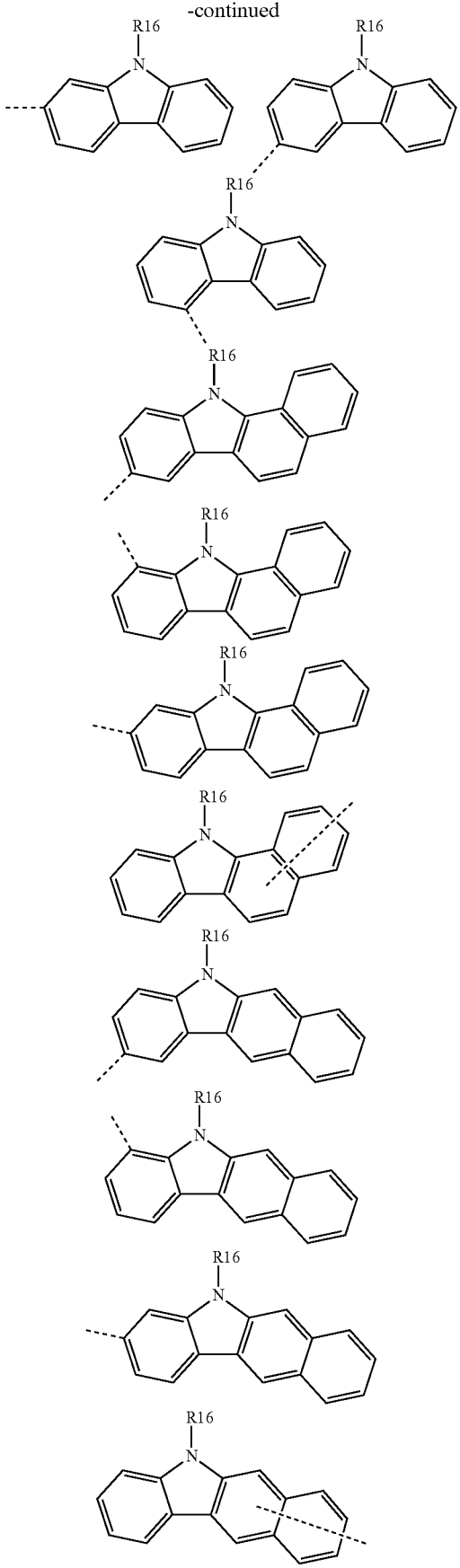

306

-continued

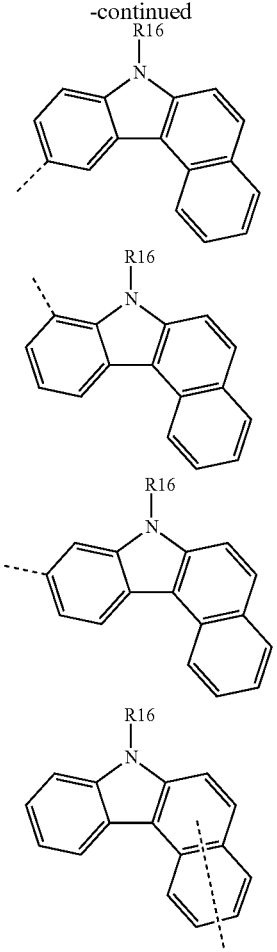

wherein, in the structures,

R14 to R16 are the same as or different from each other, and each independently hydrogen; deuterium; a halogen group; a cyano group; a silyl group; a substituted or unsubstituted alkyl group; a substituted or unsubstituted cycloalkyl group; a substituted or unsubstituted alkoxy group; a substituted or unsubstituted alkenyl group; a substituted or unsubstituted boron group; a substituted or unsubstituted amine group; a substituted or unsubstituted aryl group; or a substituted or unsubstituted heterocyclic group, or adjacent substituents bond to each other to form a substituted or unsubstituted ring.

8. The compound of claim 1, wherein L1 and L2 are the same as or different from each other, and each independently a direct bond; or any one selected from the following structures:

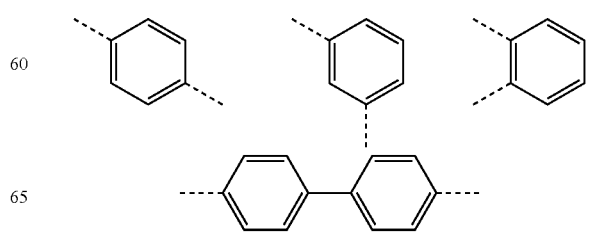

307

-continued

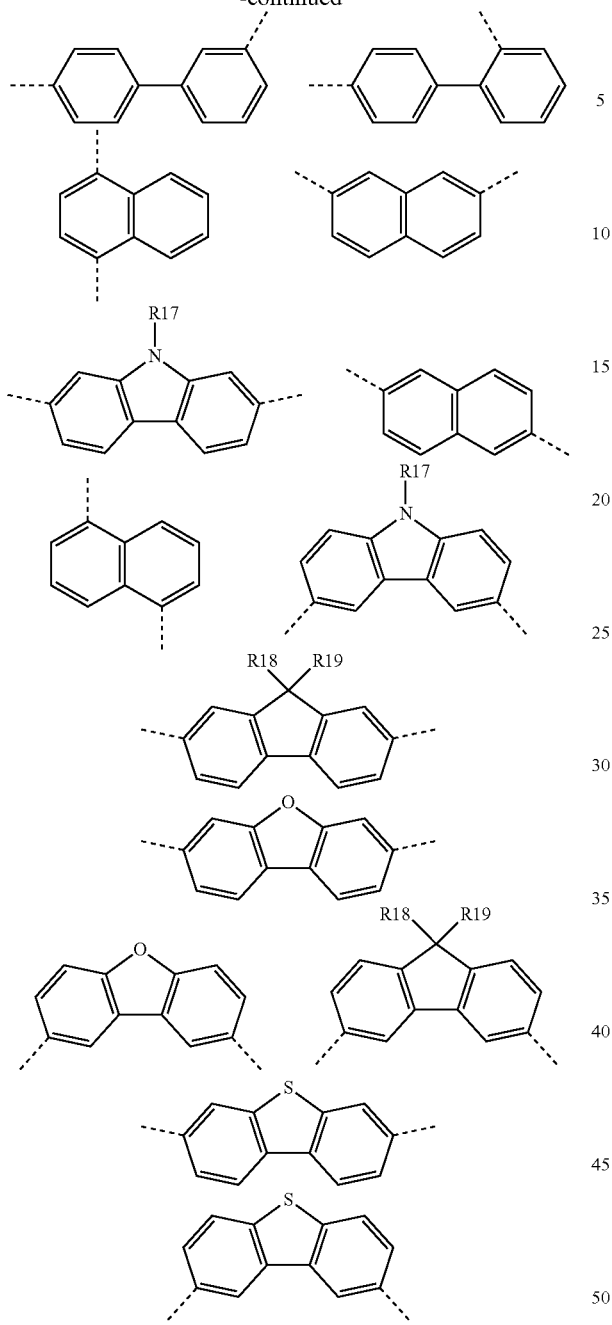

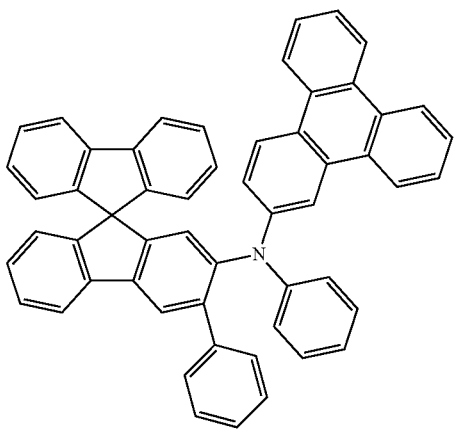

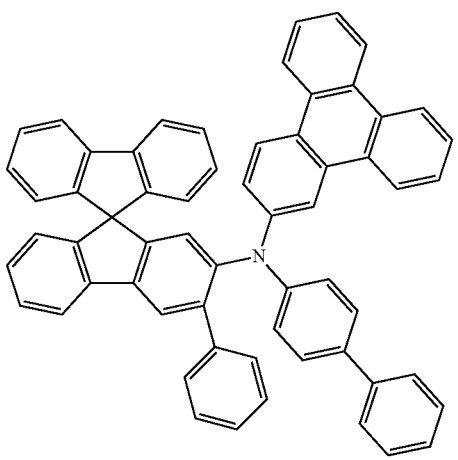

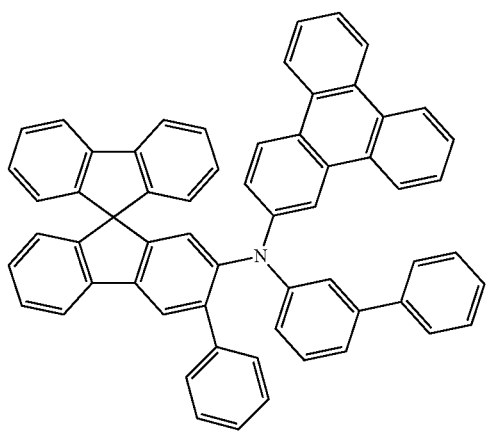

wherein, in the structures,

R17 to R19 are the same as or different from each other, and each independently hydrogen; deuterium; a halogen group; a cyano group; a silyl group; a substituted or unsubstituted alkyl group; a substituted or unsubstituted cycloalkyl group; a substituted or unsubstituted alkoxy group; a substituted or unsubstituted alkenyl group; a substituted or unsubstituted boron group; a substituted or unsubstituted amine group; a substituted or unsubstituted aryl group; or a substituted or unsubstituted heterocyclic group.

9. The compound of claim 1, wherein the compound represented by Chemical Formula 1 is any one selected from the following structures:

309
-continued
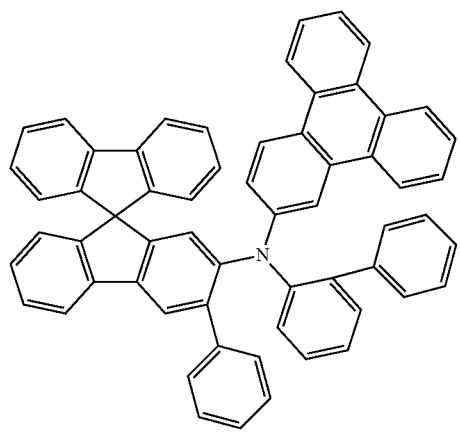
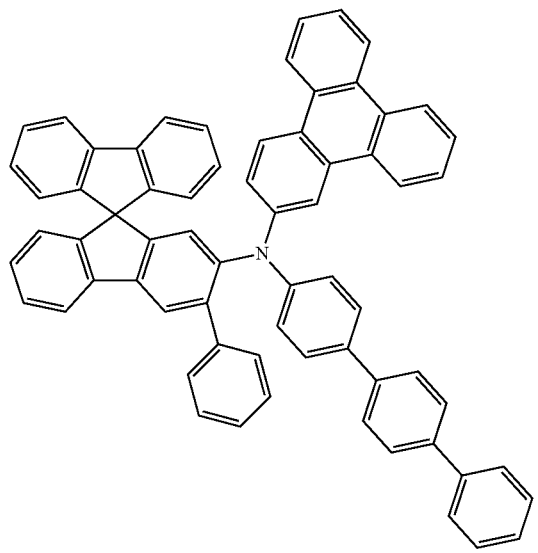
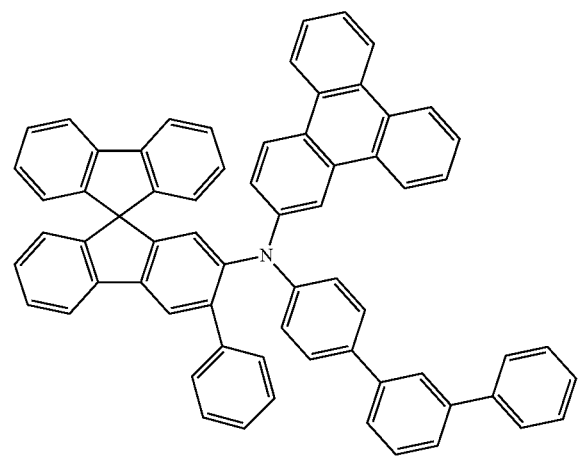
310
-continued
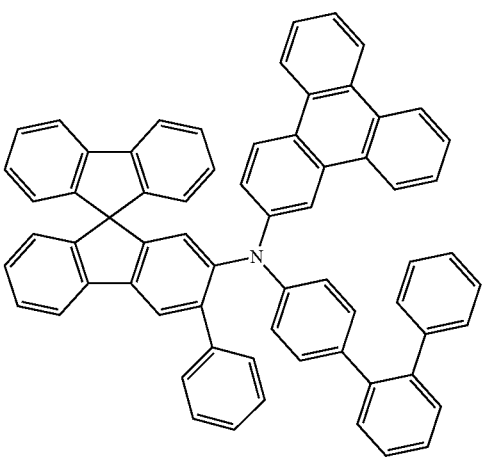
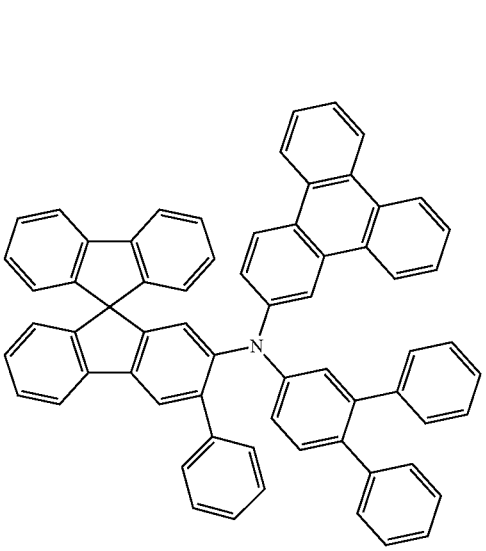
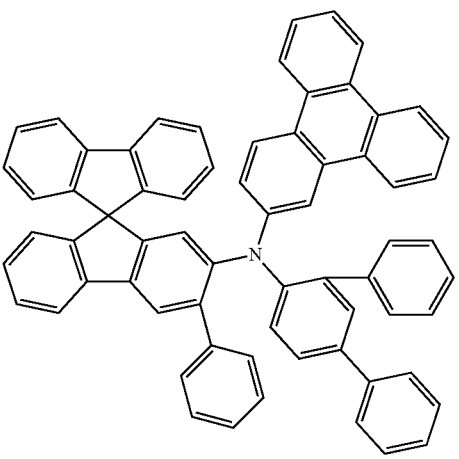

311
-continued
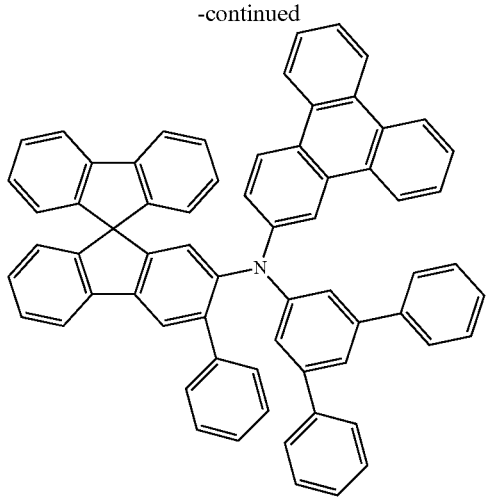
312
-continued
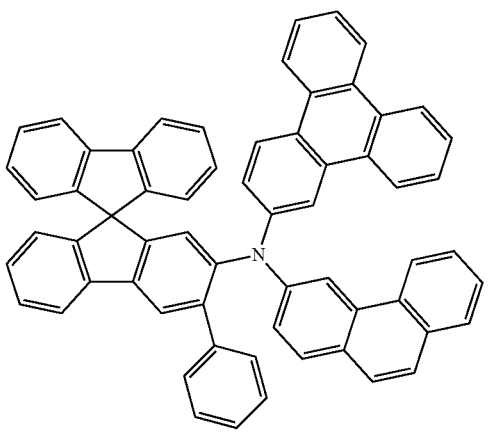
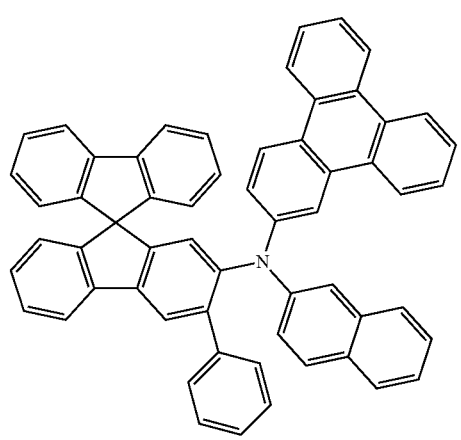
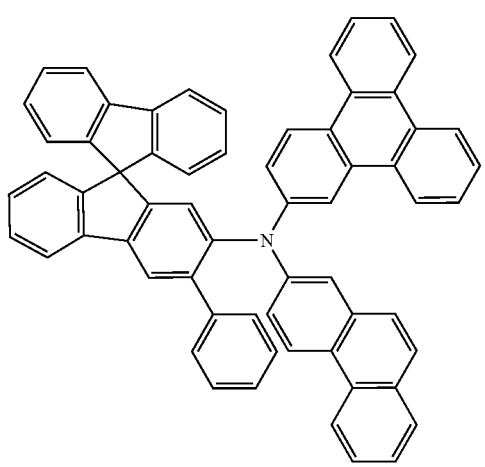
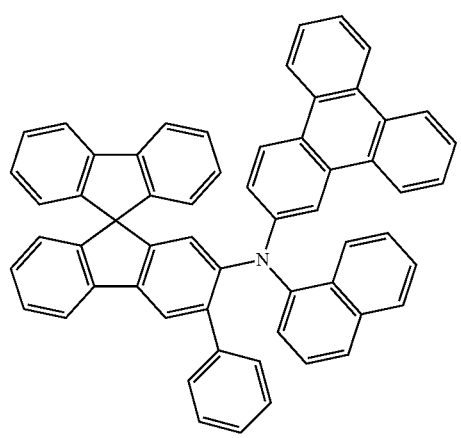
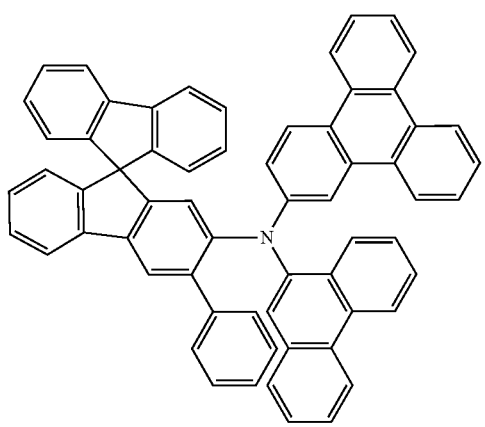

313
-continued
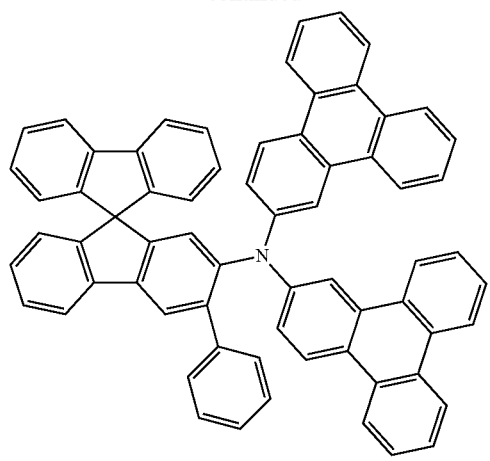
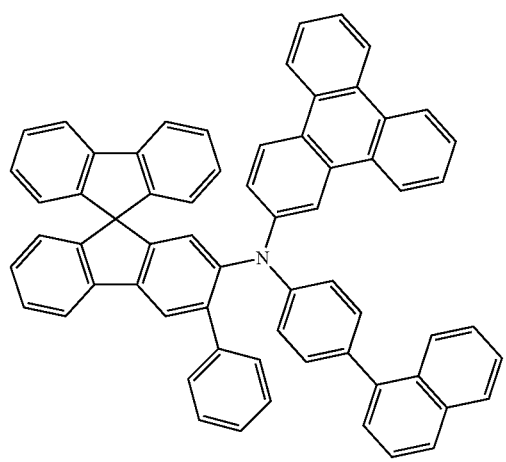
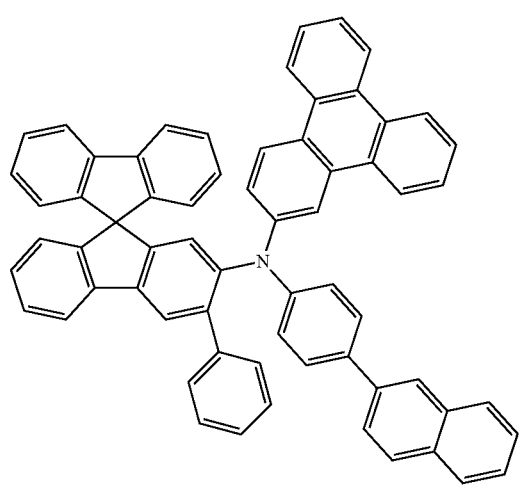
314
-continued
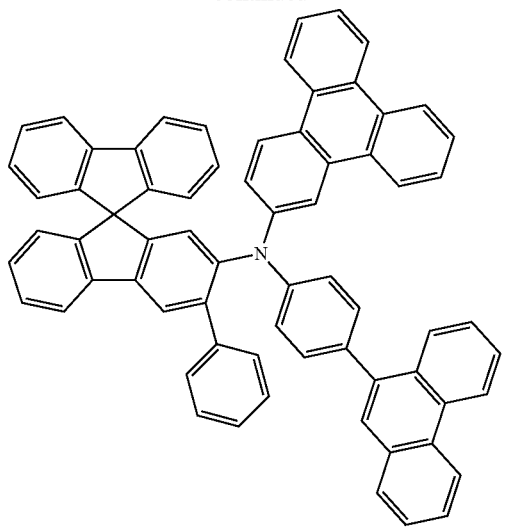
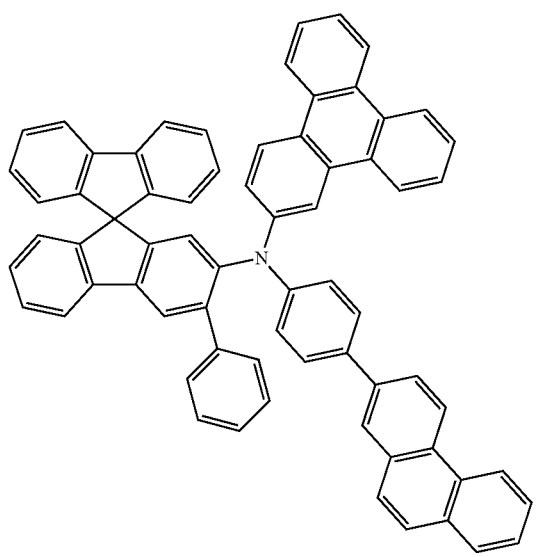
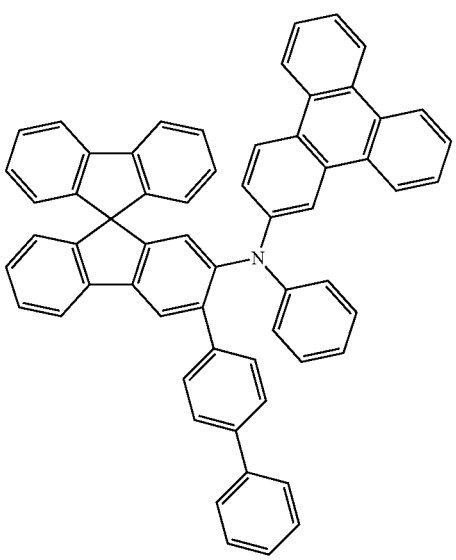

315
-continued
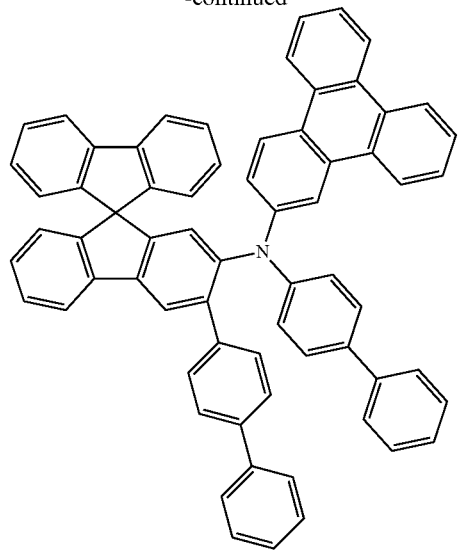
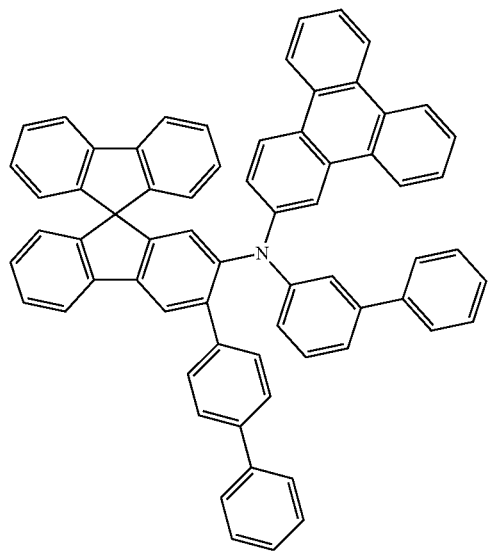
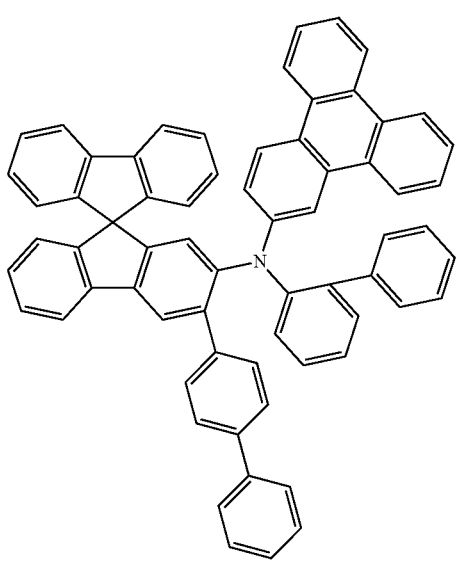
316
-continued
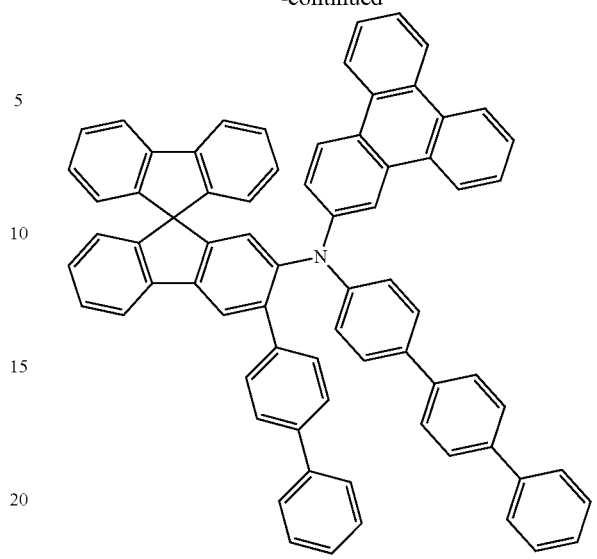
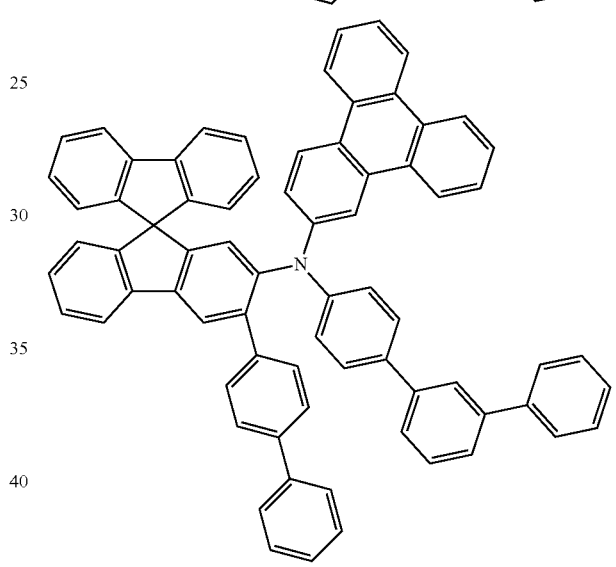
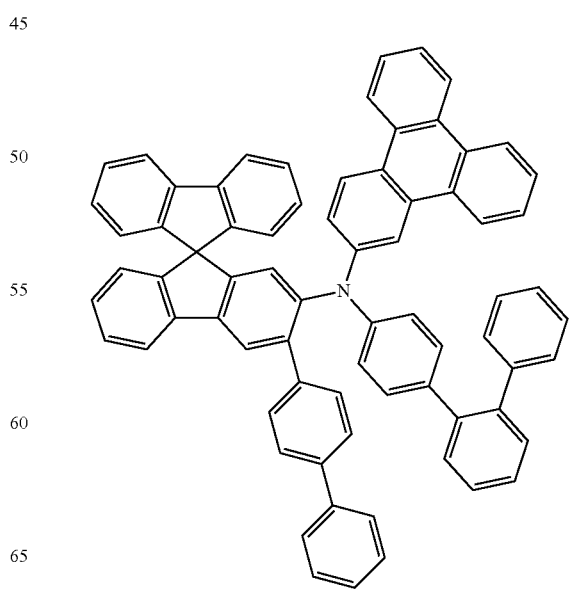

317
-continued
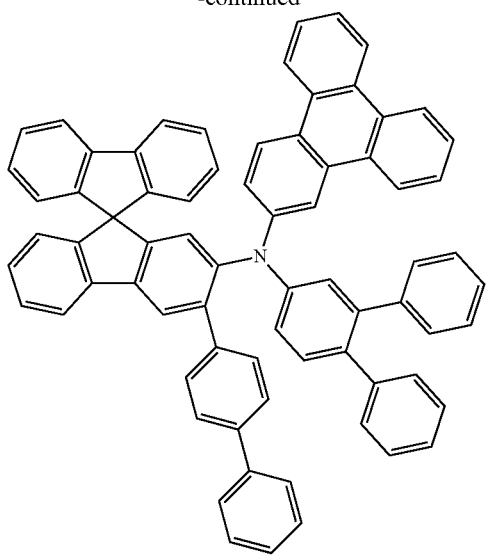
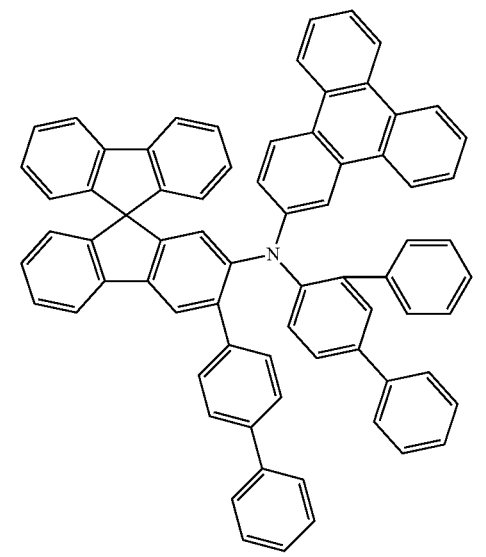
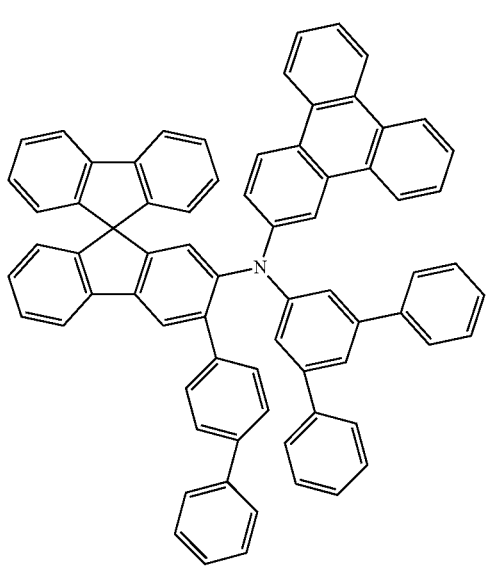
318
-continued
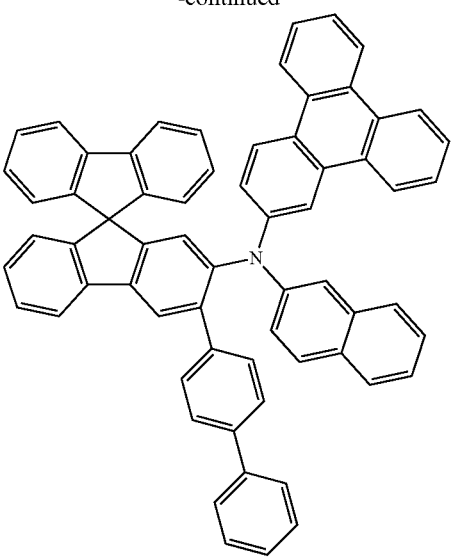
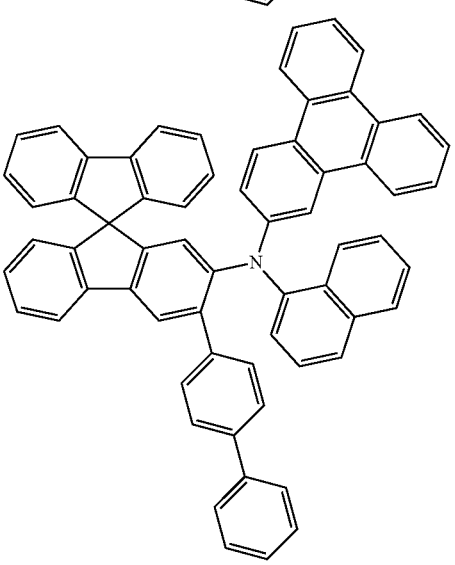
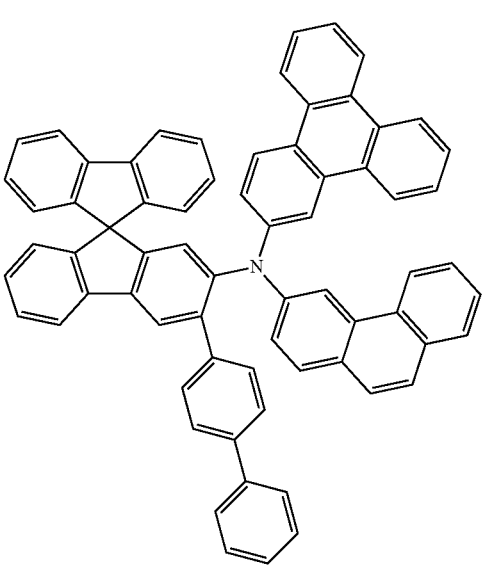

319
-continued
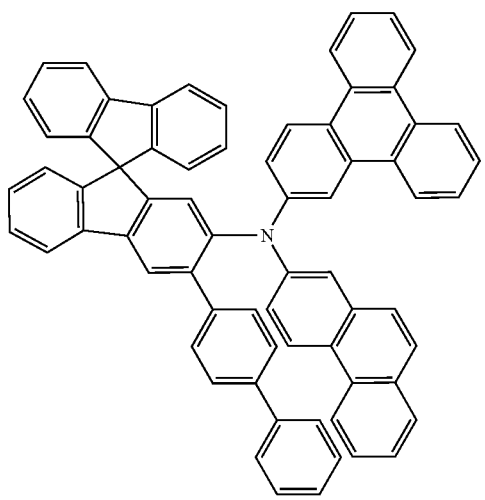
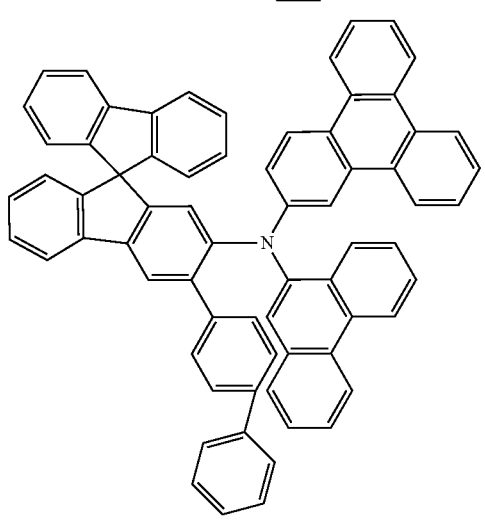
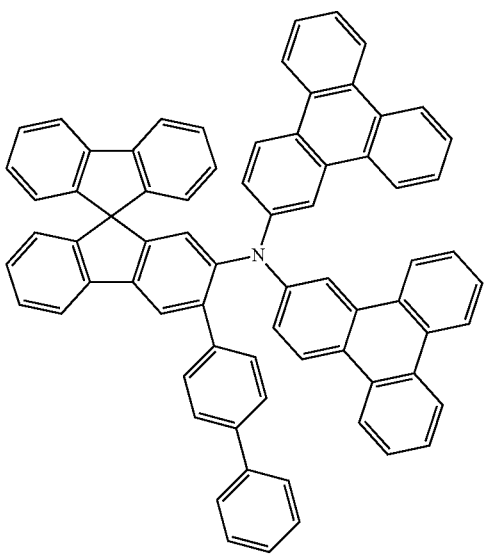
320
-continued
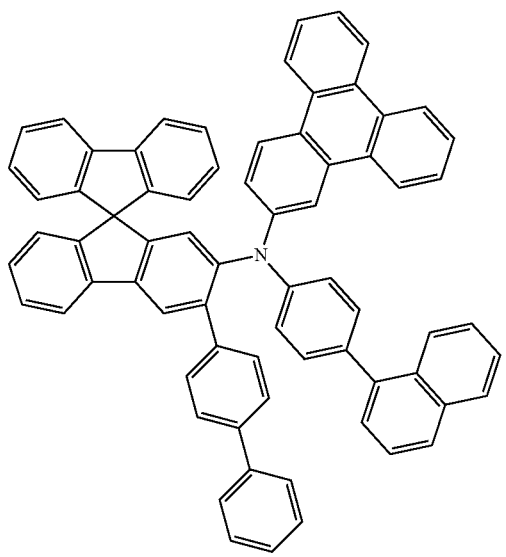
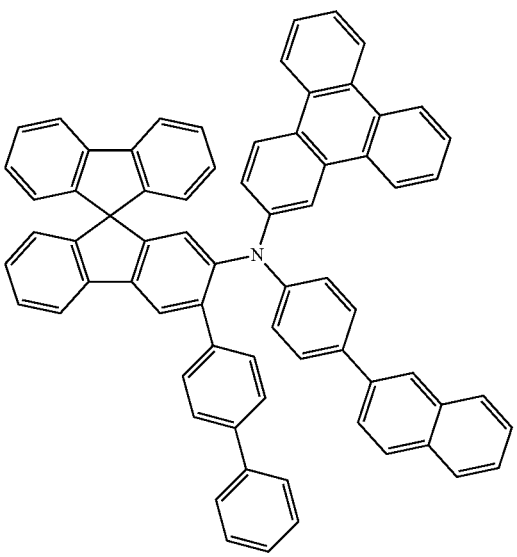
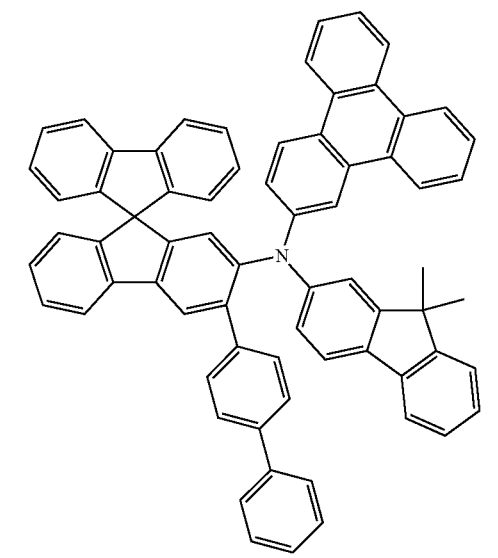

321
-continued
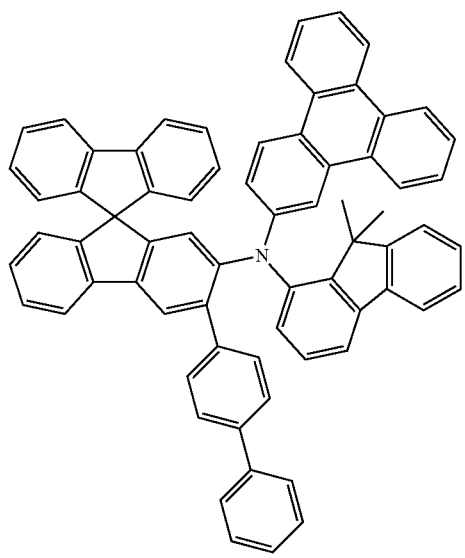
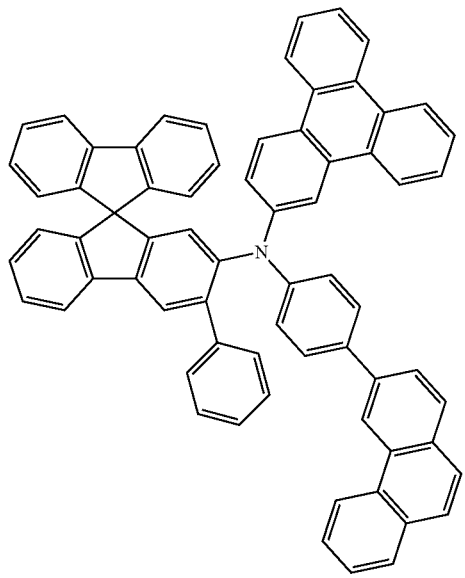
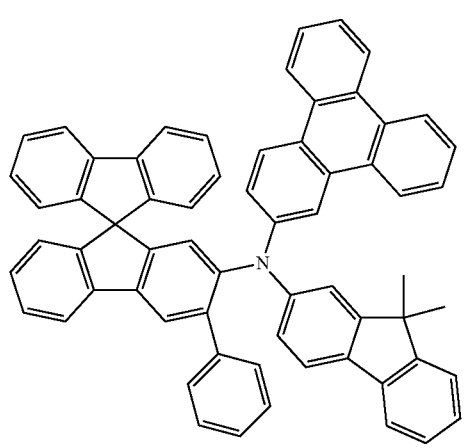
322
-continued
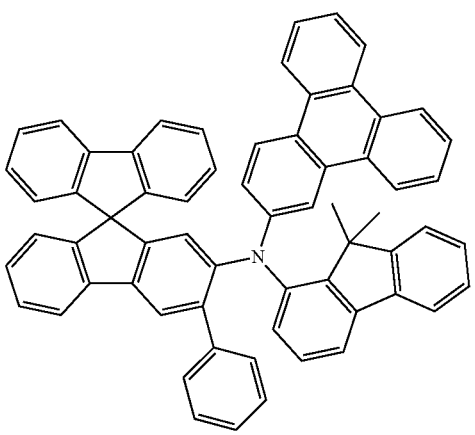
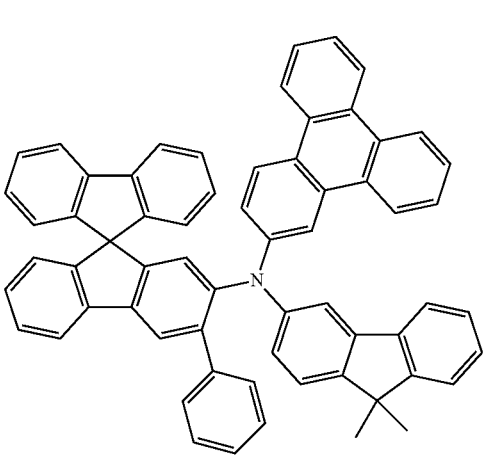
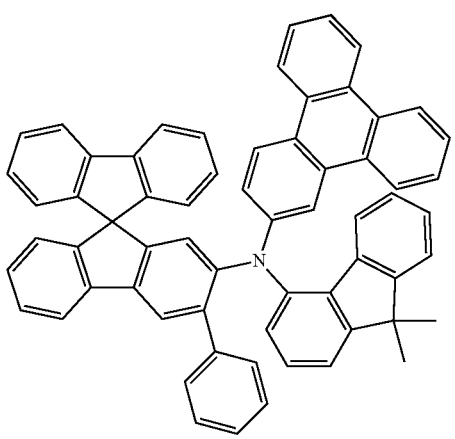

323
-continued
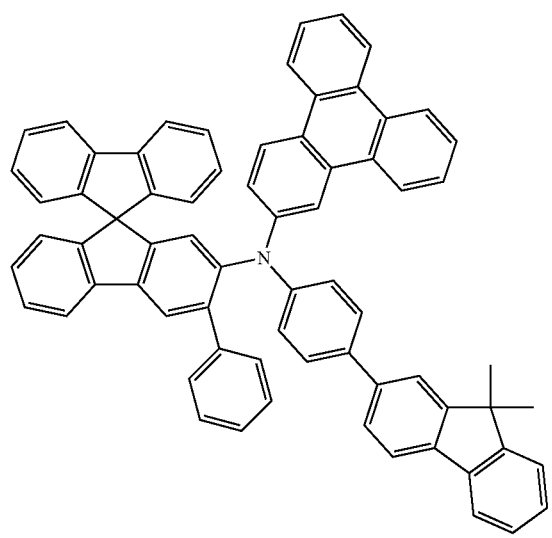
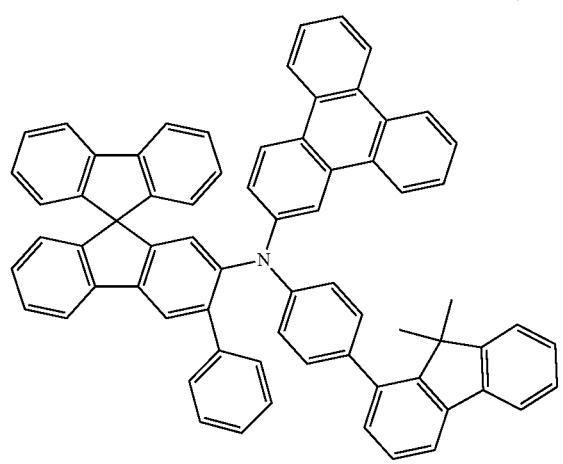
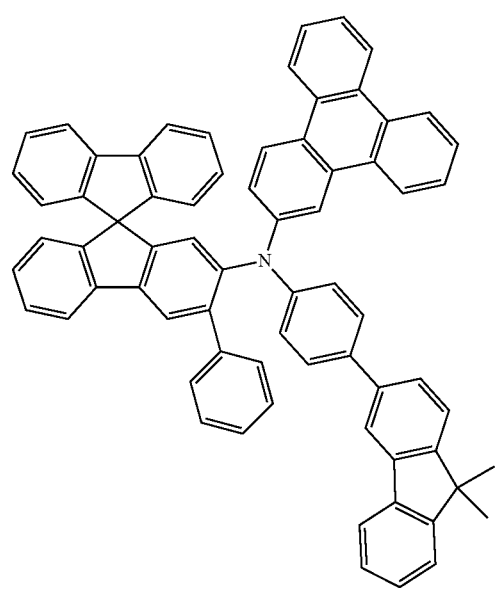
324
-continued
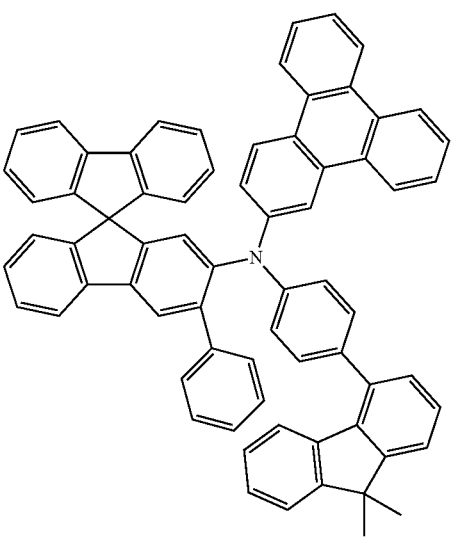
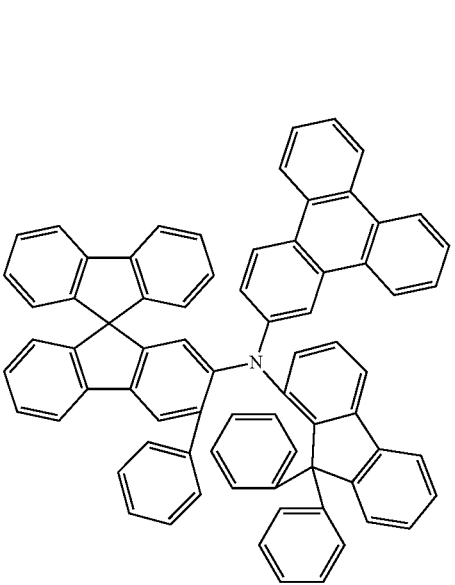

325
-continued
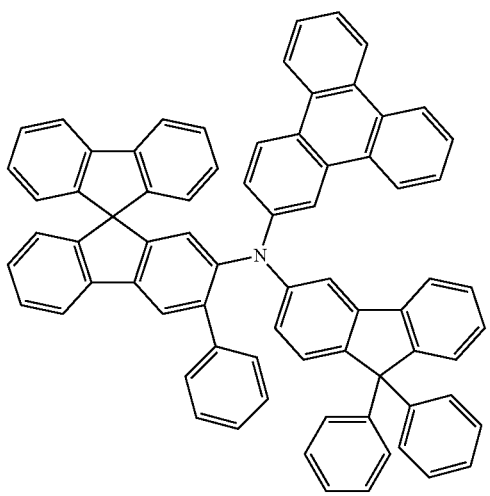
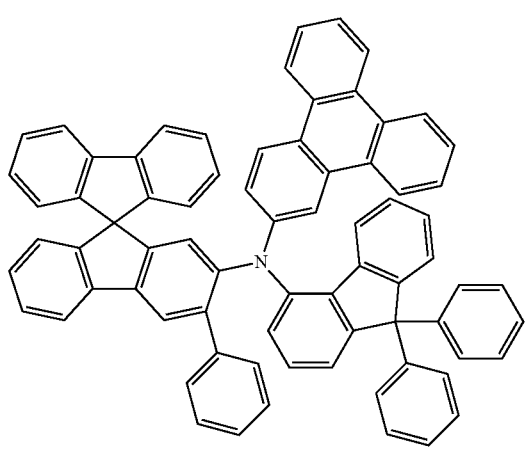
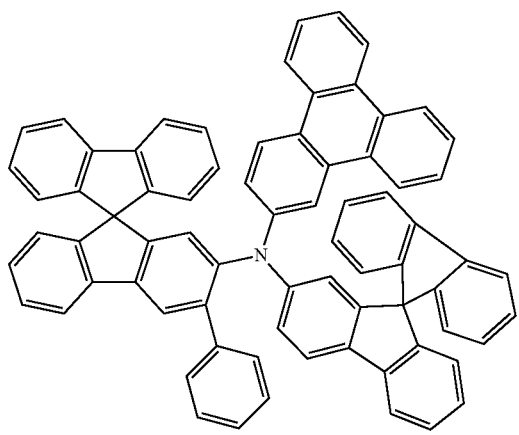
326
-continued
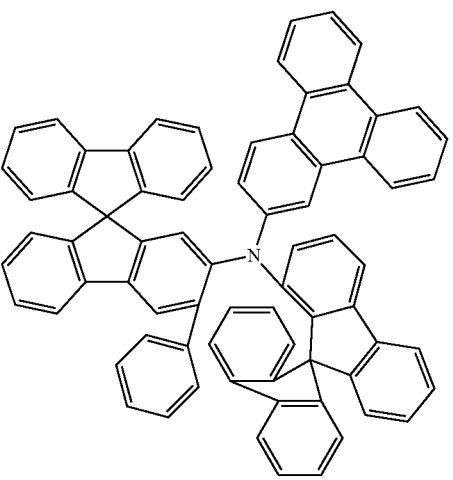
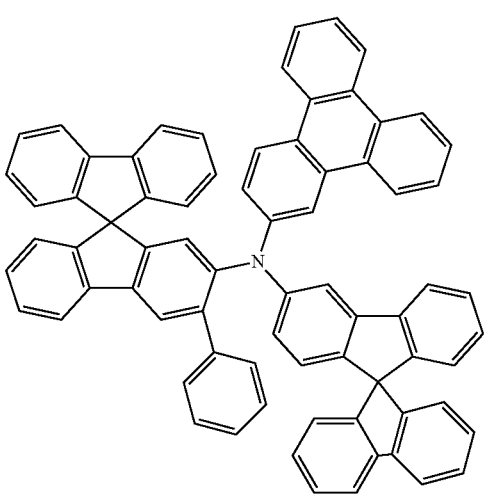
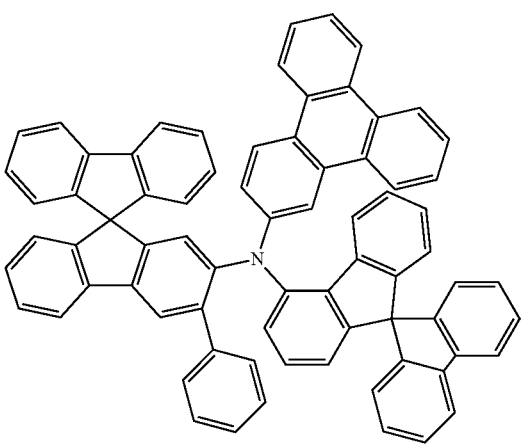

327
-continued
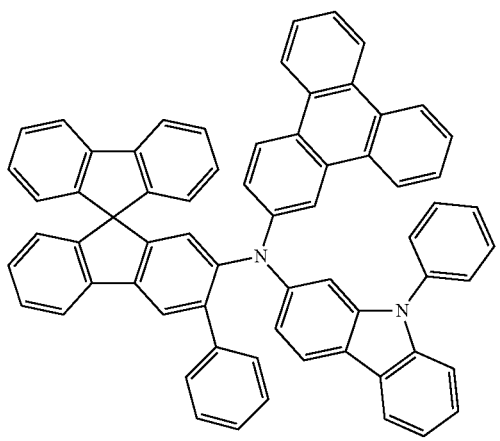
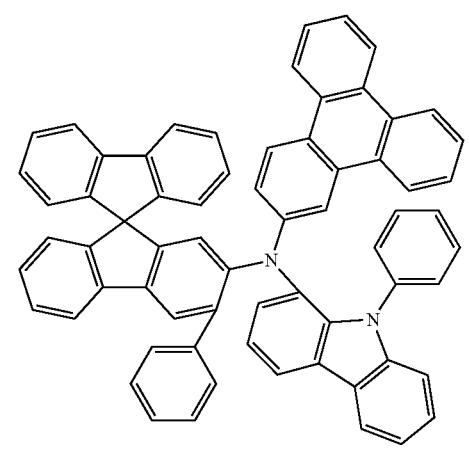
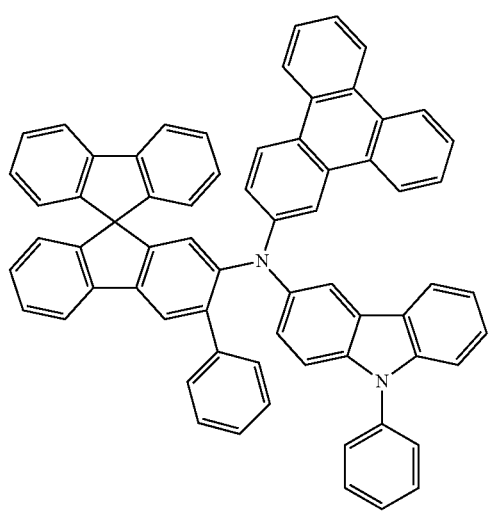
328
-continued
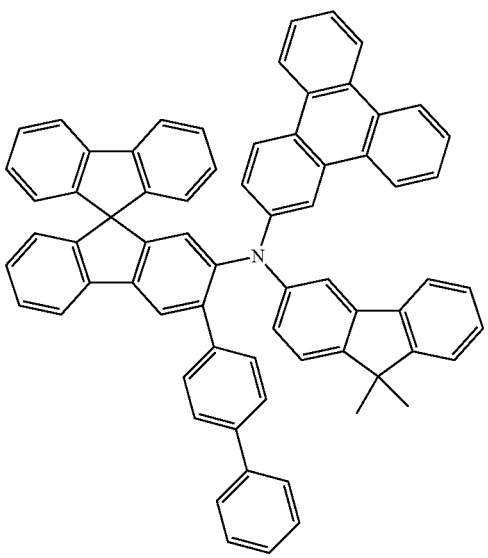
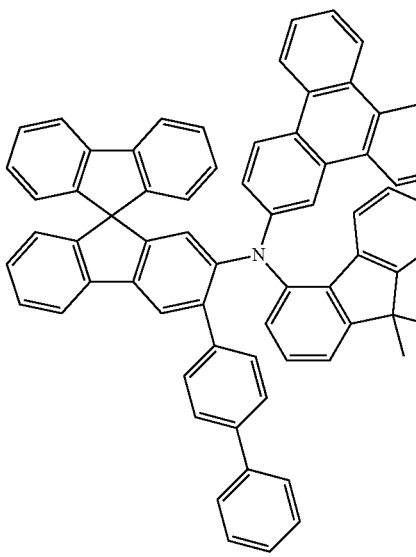
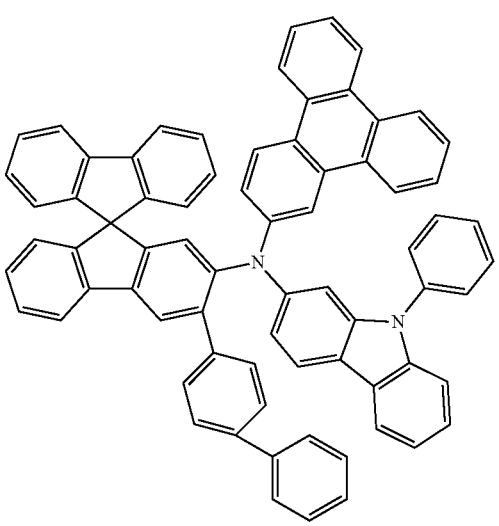

329
-continued
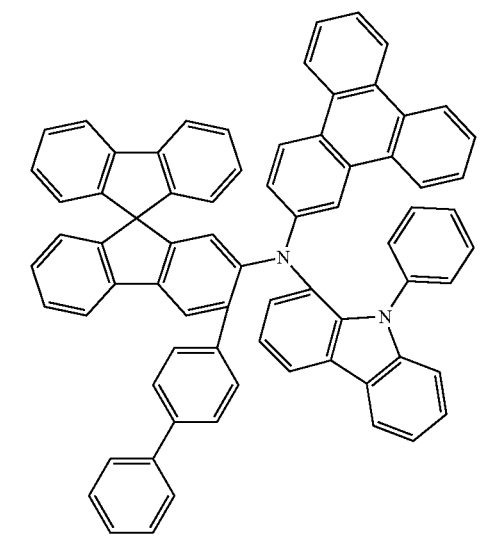
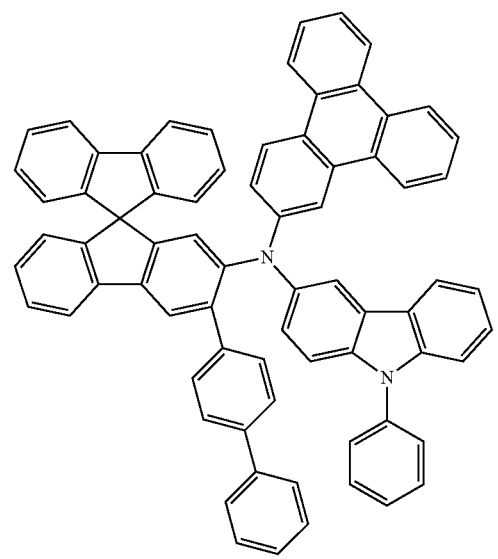
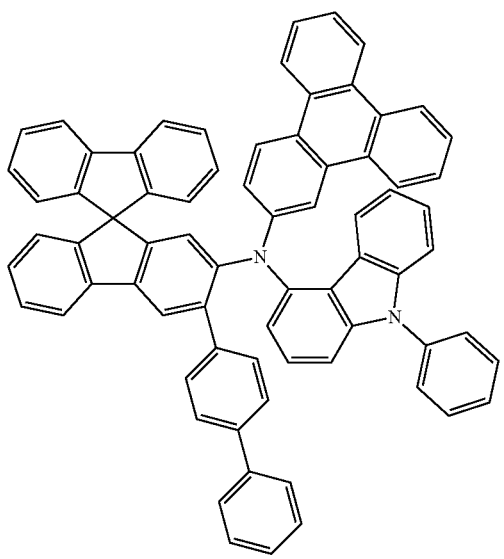
330
-continued
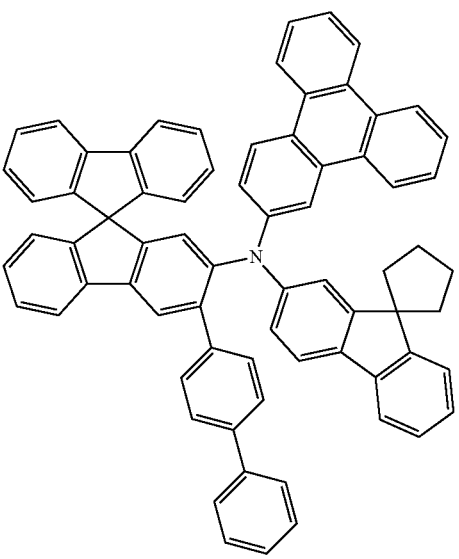
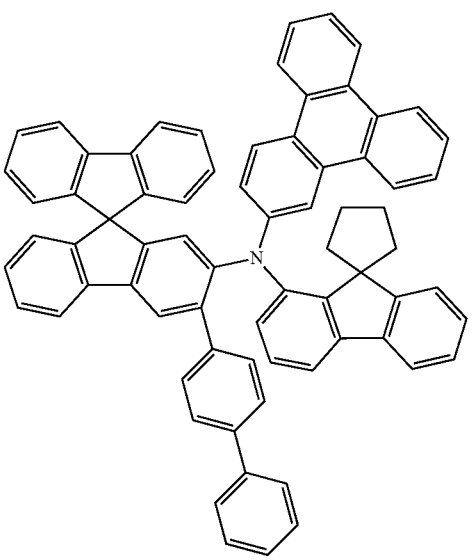
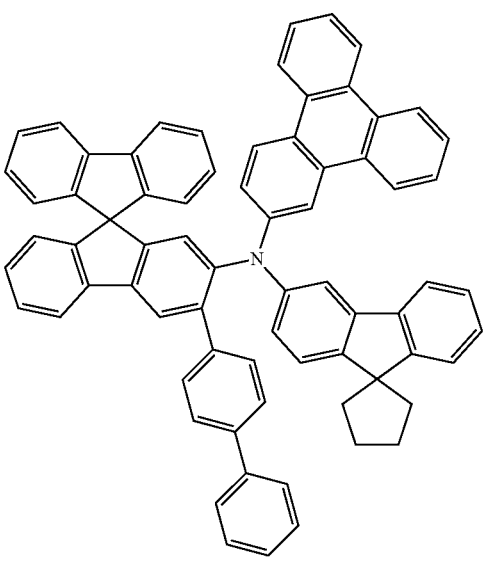

331
-continued
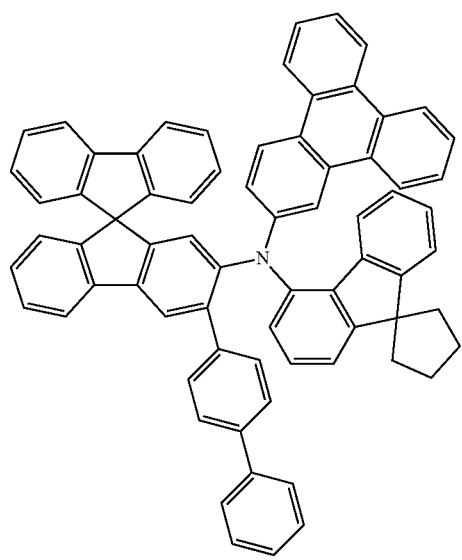
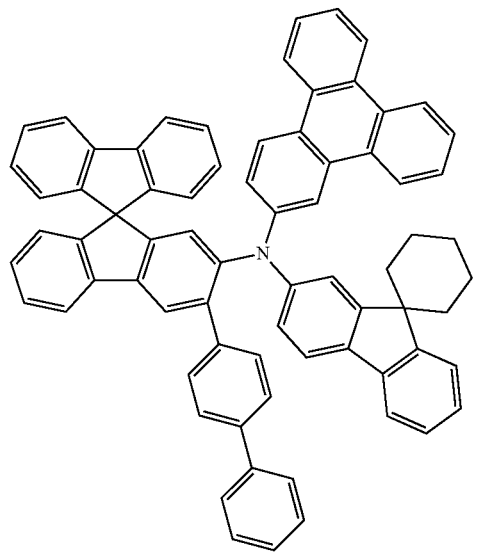
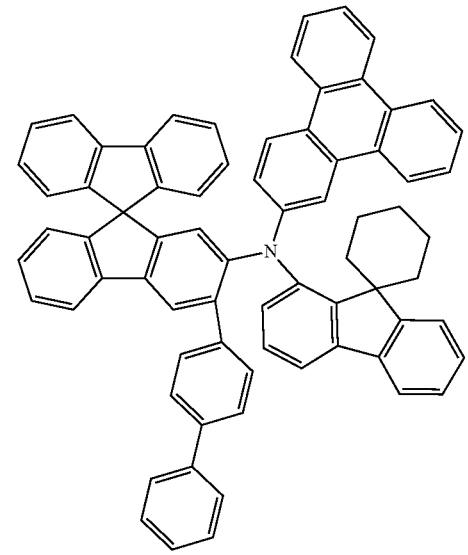
332
-continued
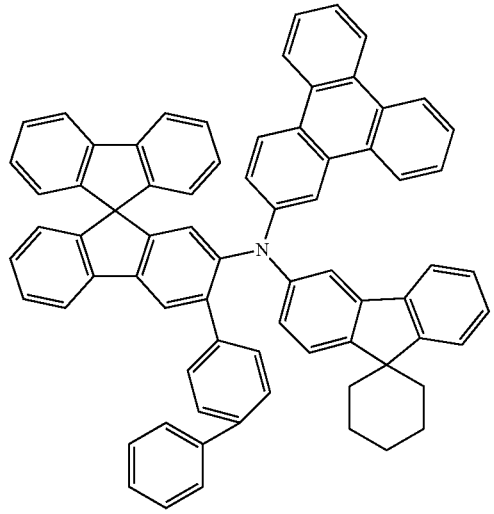
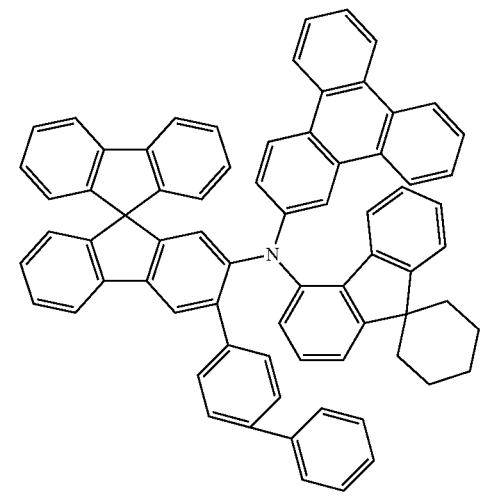
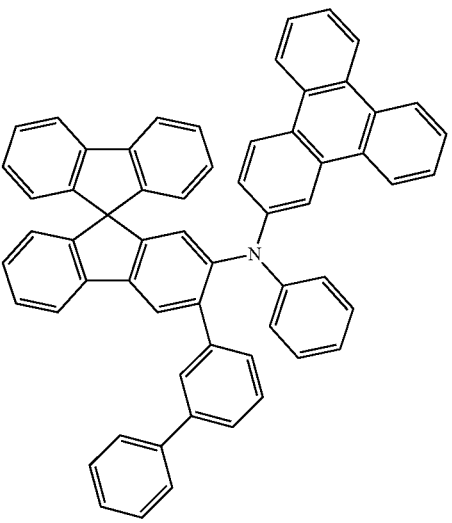

333
-continued
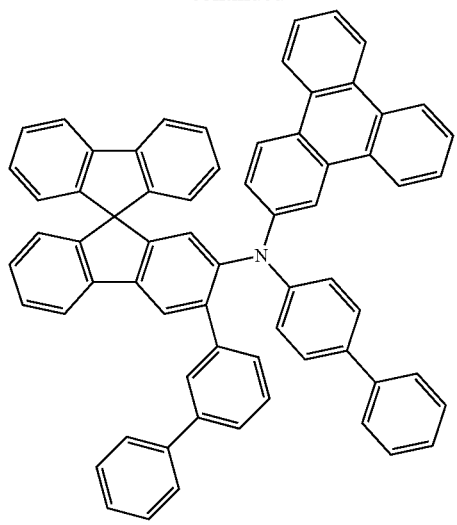
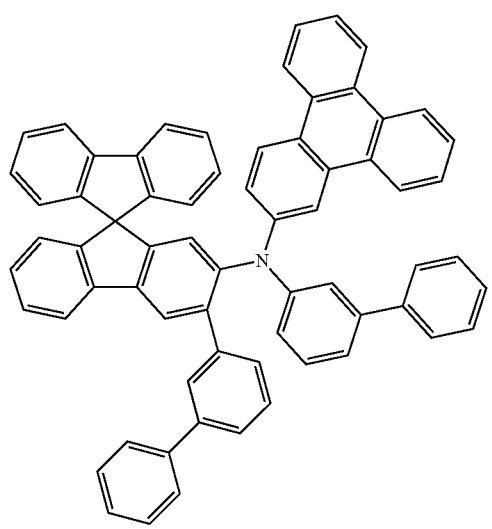
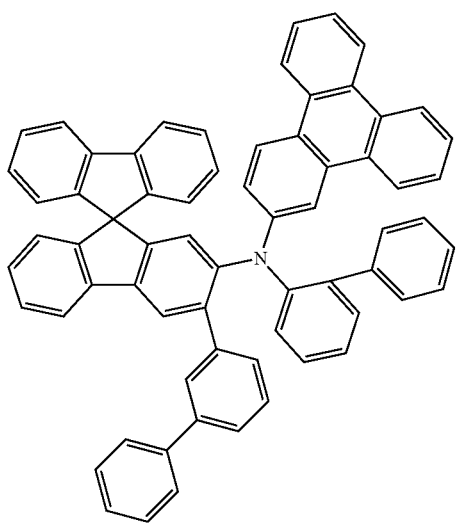
334
-continued
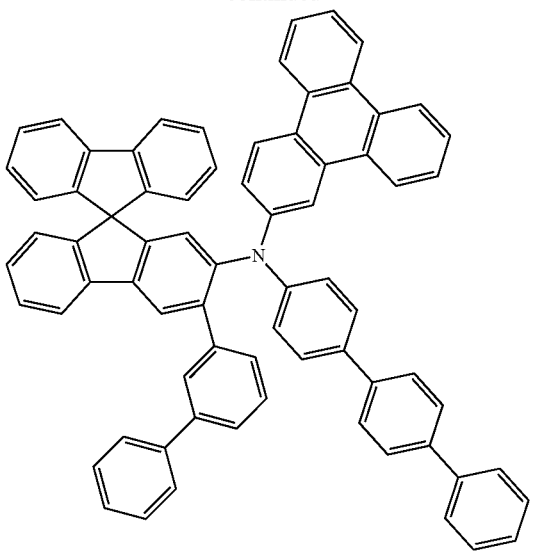
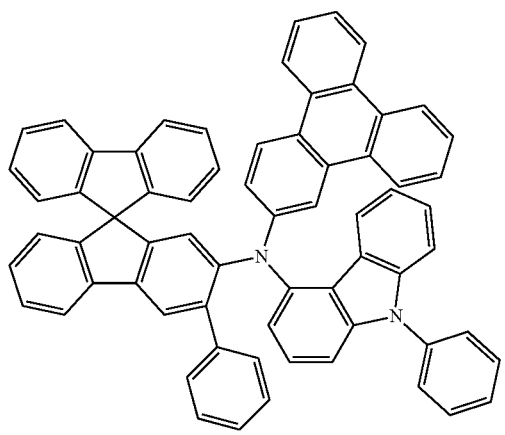
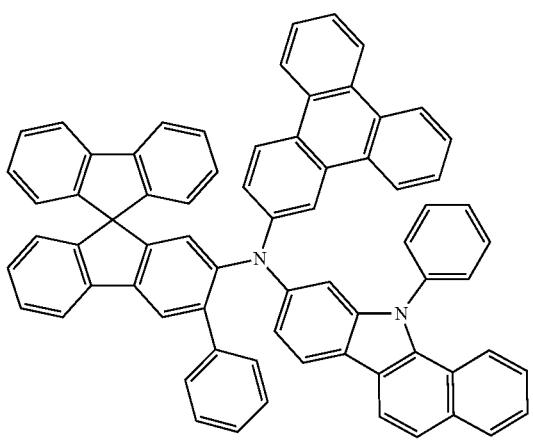

335
-continued
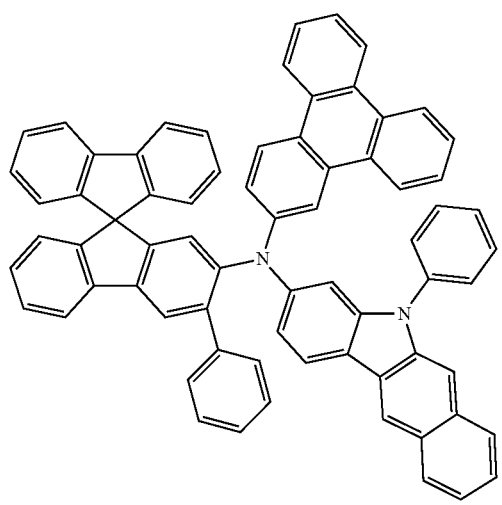
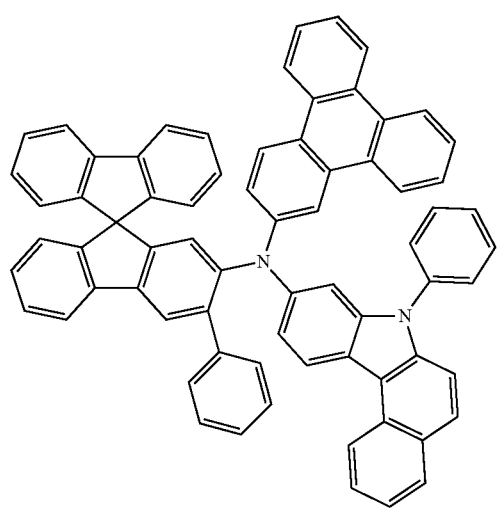
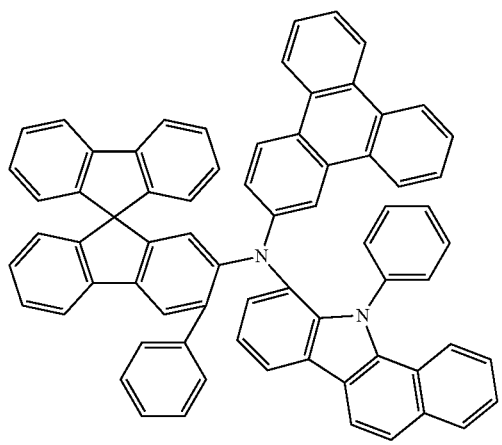
336
-continued
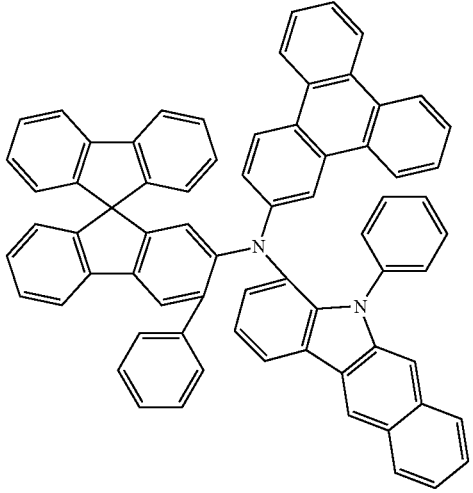
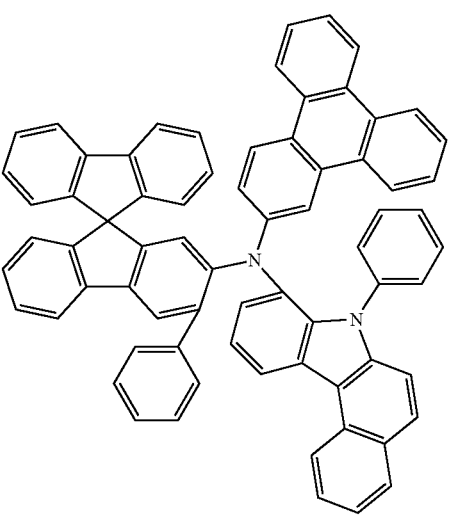
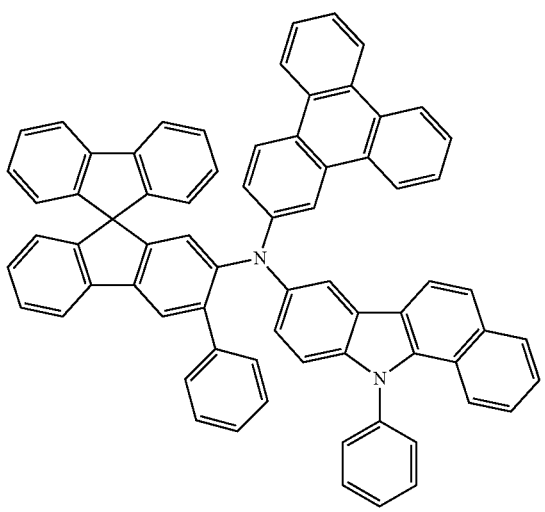

337
-continued
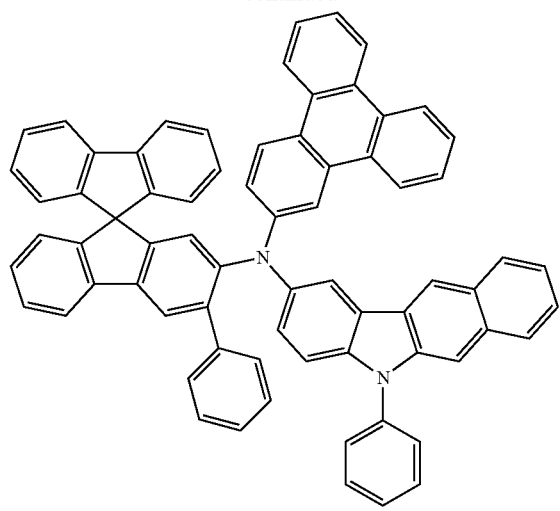
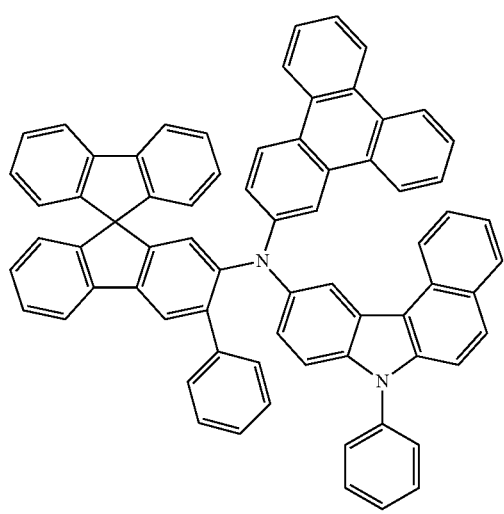
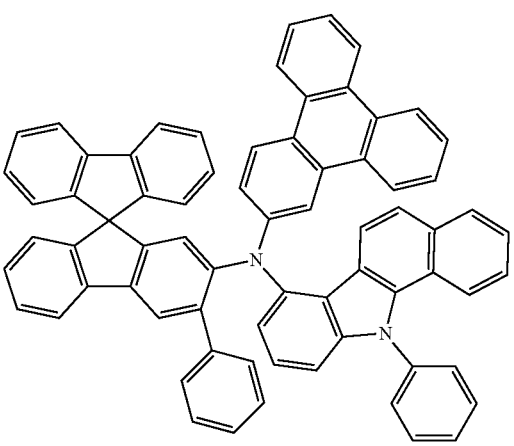
338
-continued
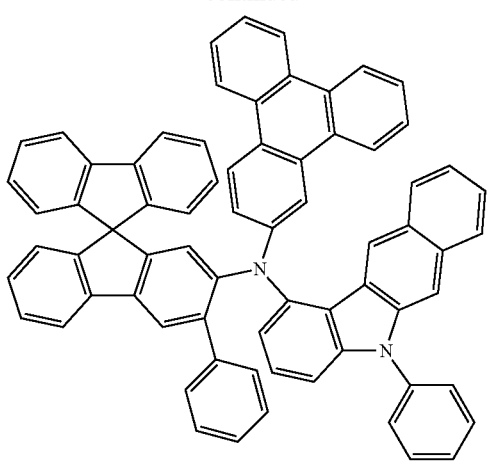
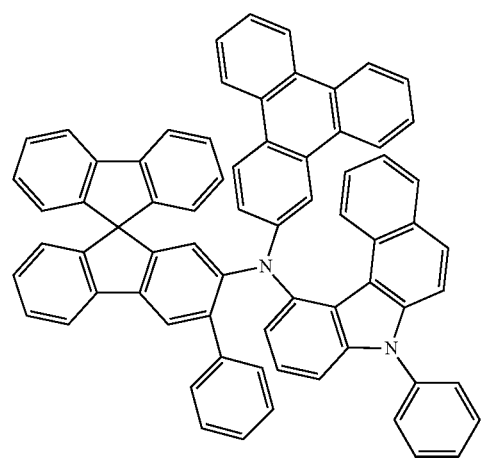
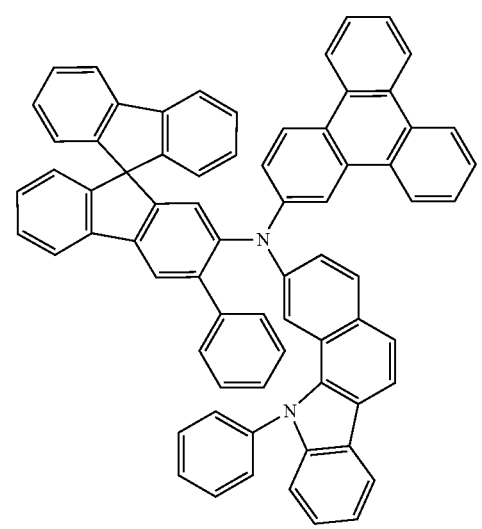

339
-continued
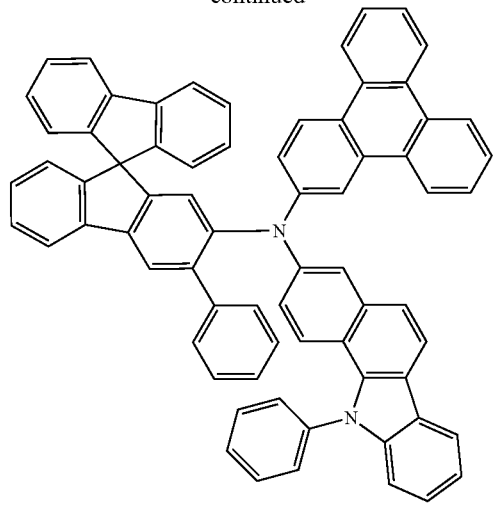
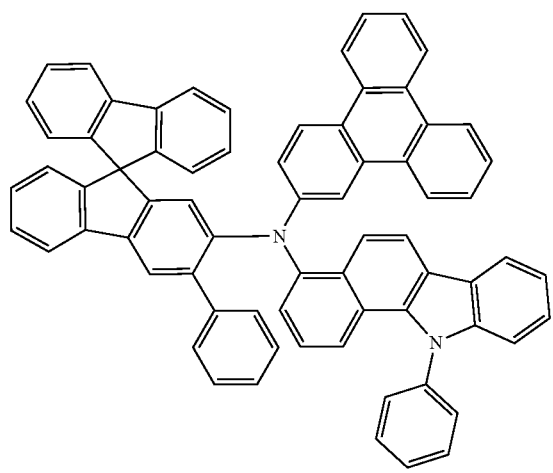
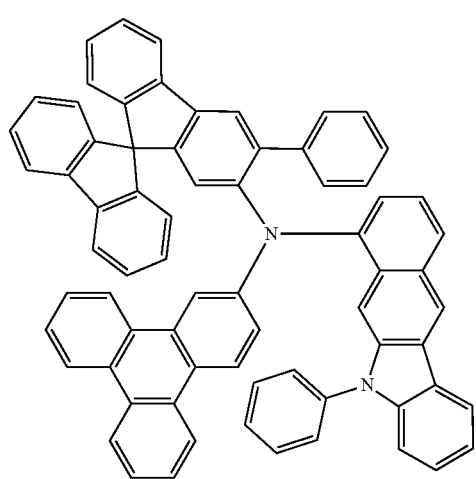
340
-continued
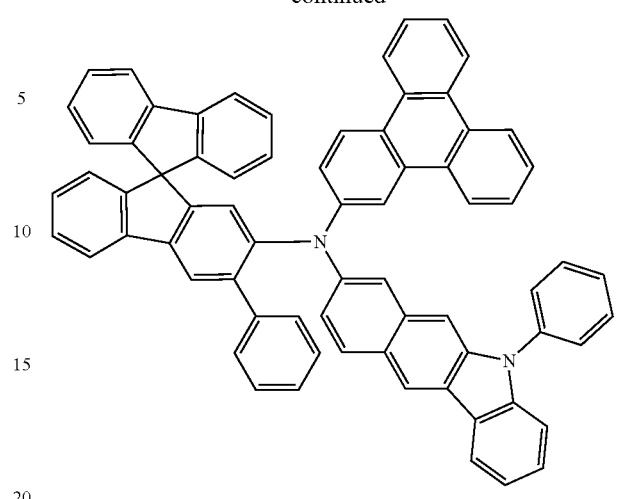
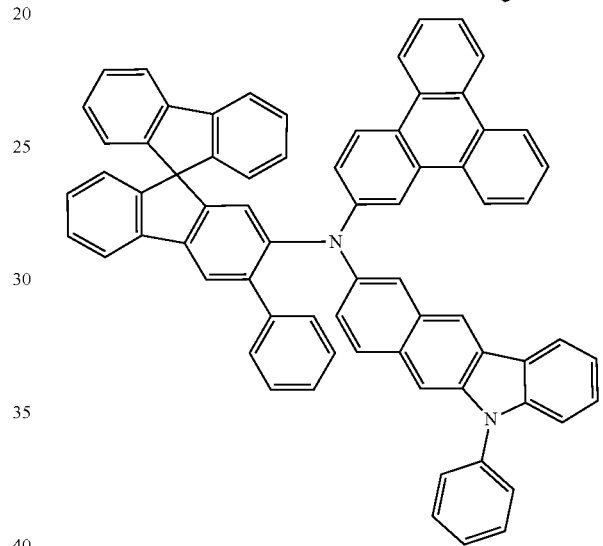
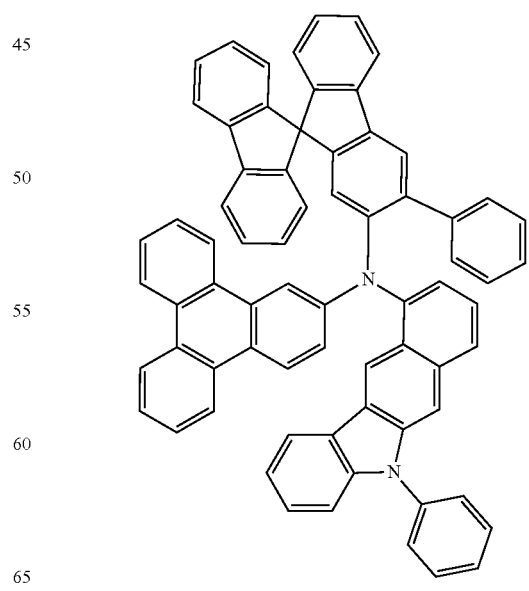

341
-continued
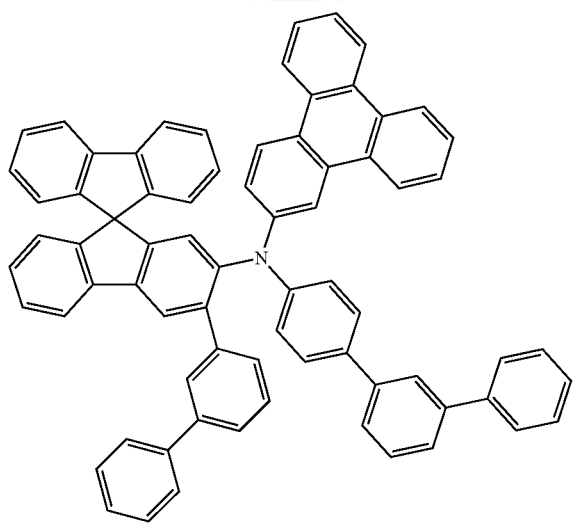
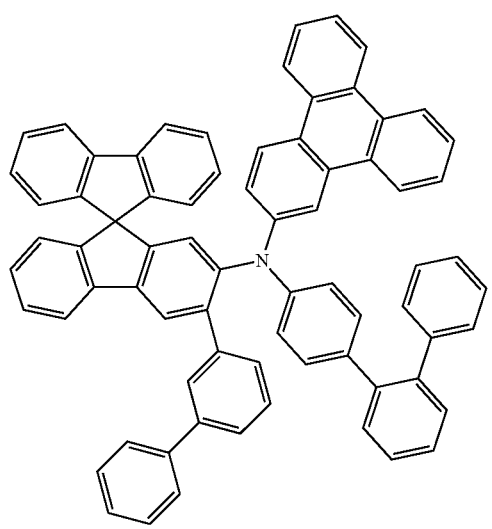
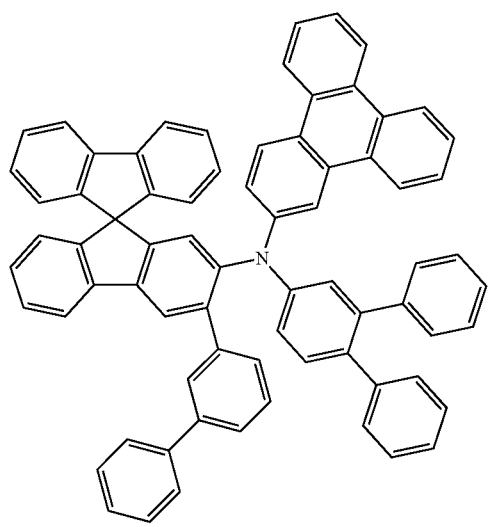
342
-continued
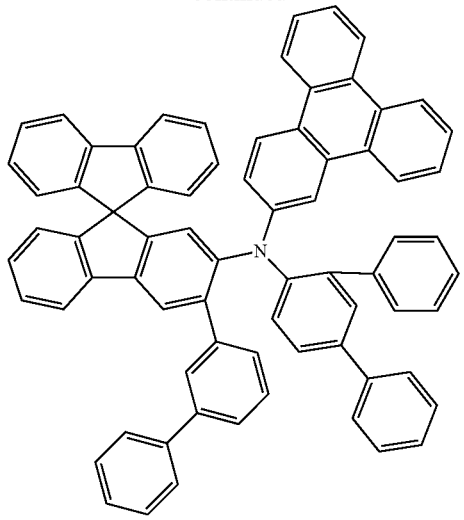
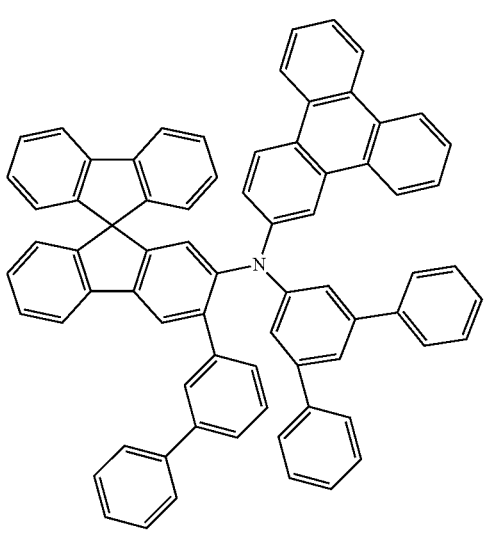
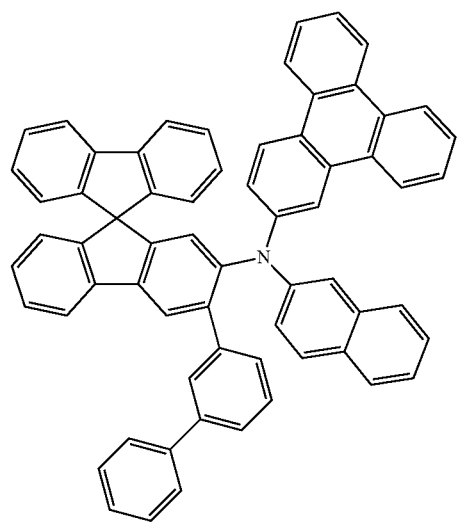

343
-continued
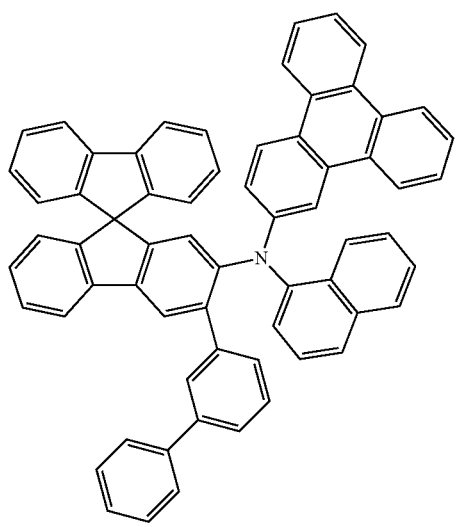
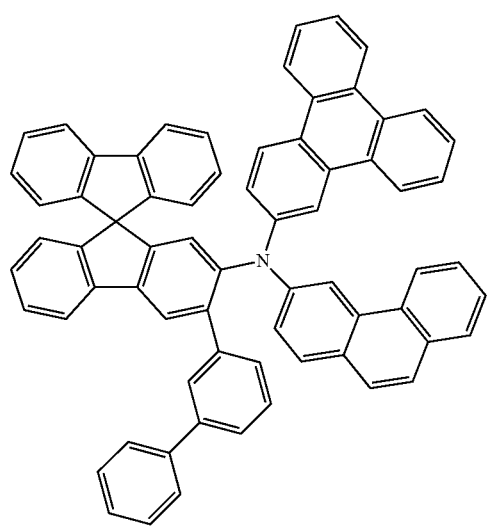
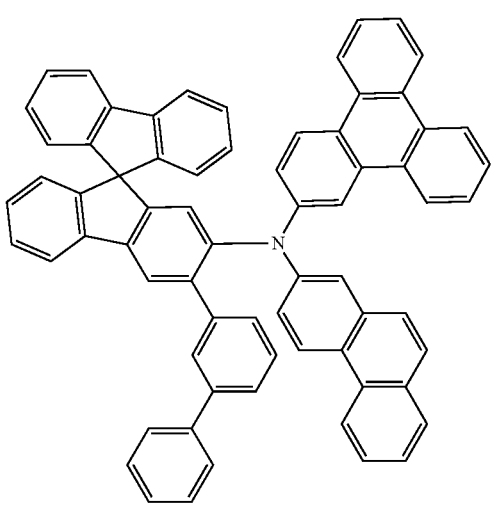
344
-continued
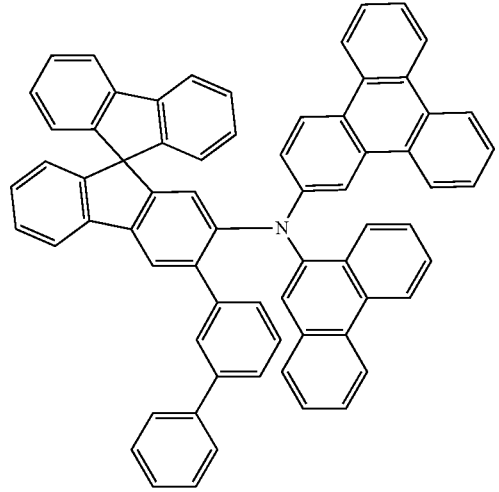
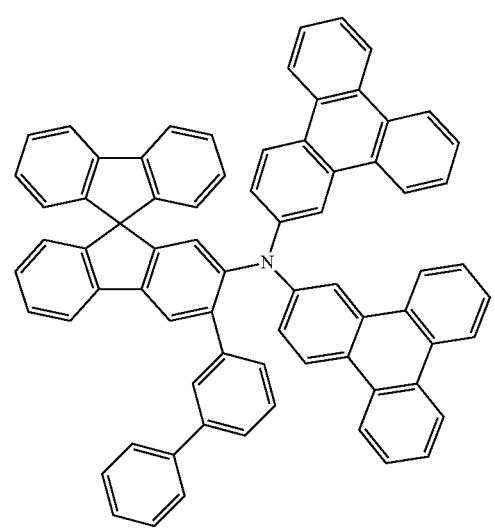
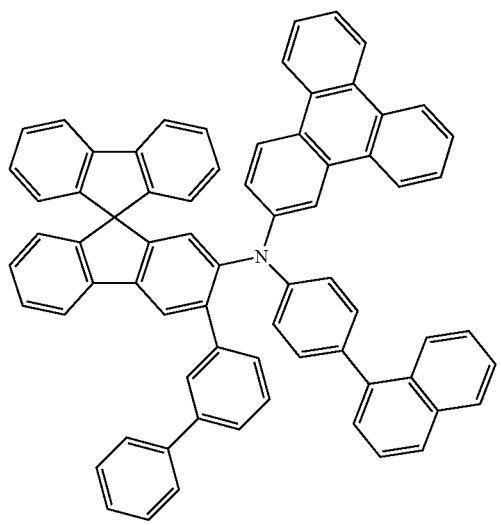

345
-continued
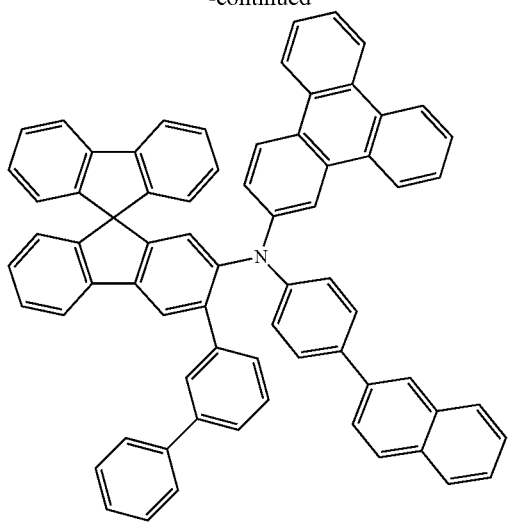
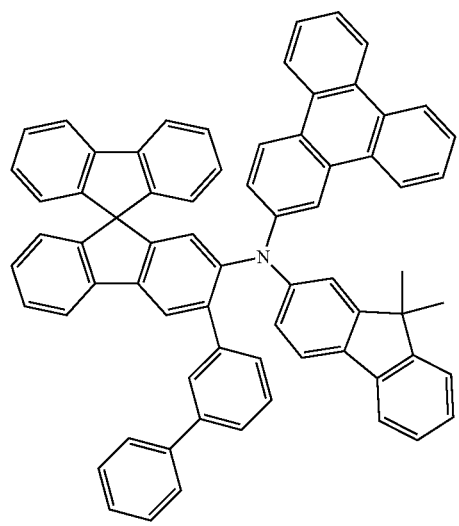
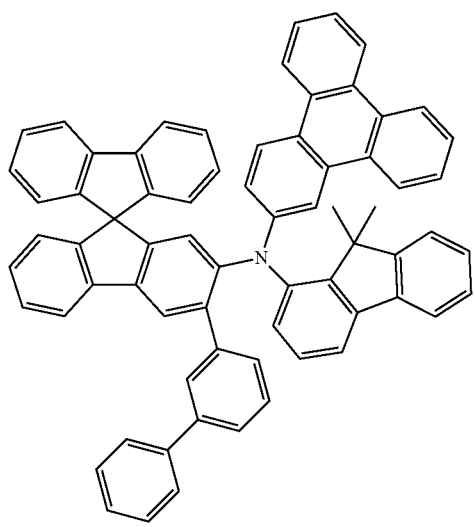
346
-continued
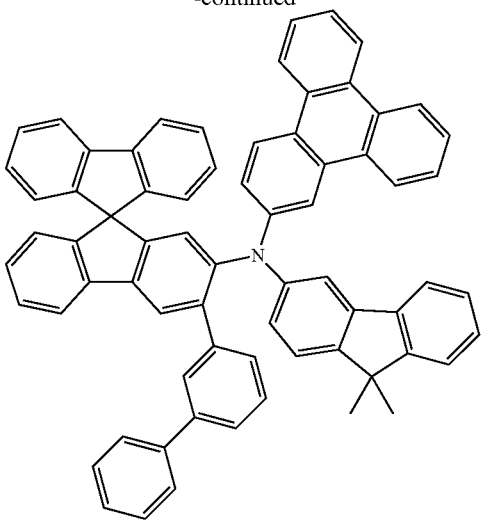
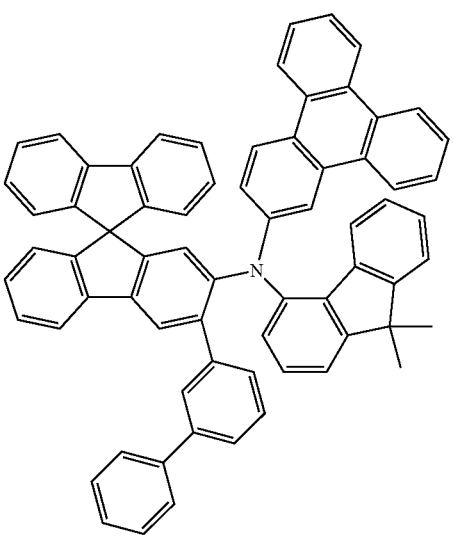
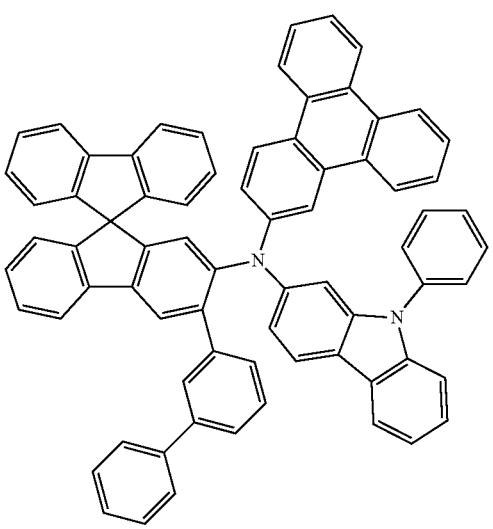

347
-continued
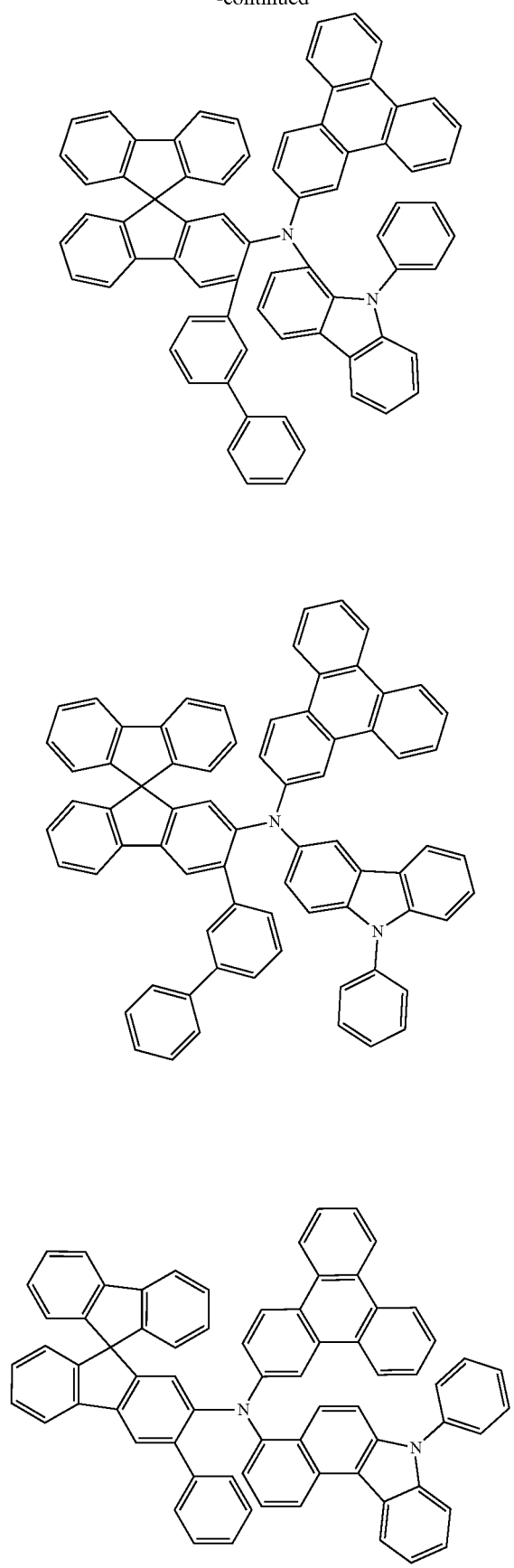
348
-continued
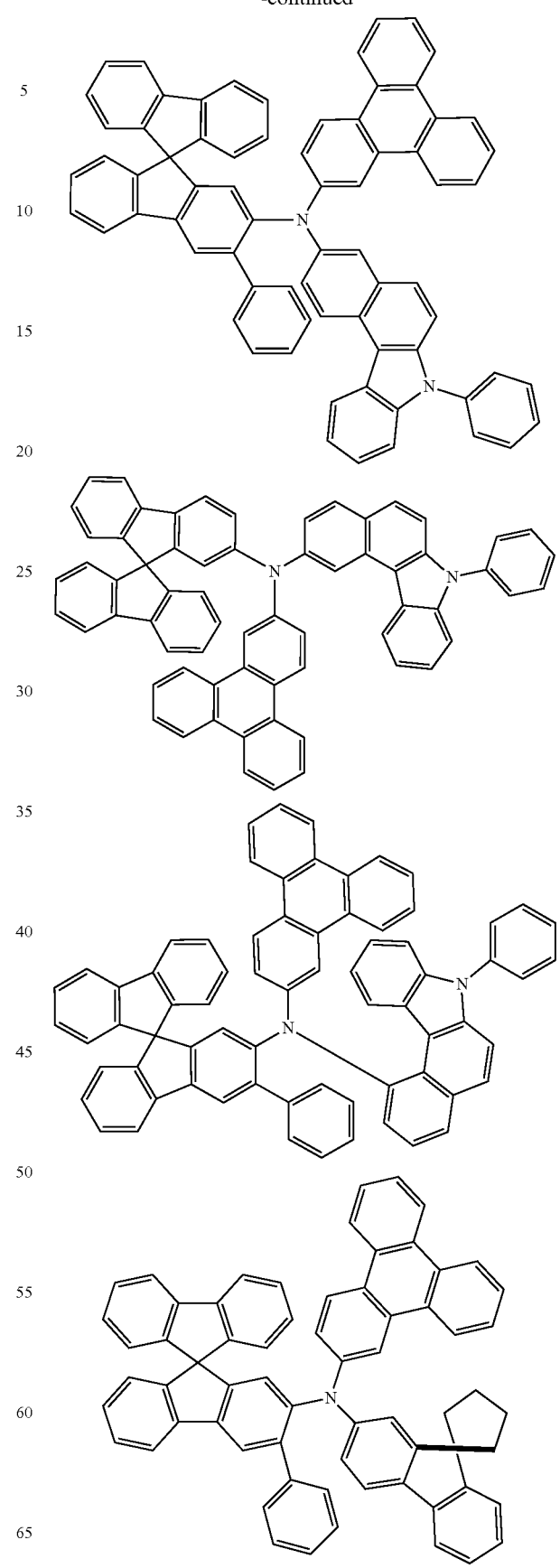

349
-continued
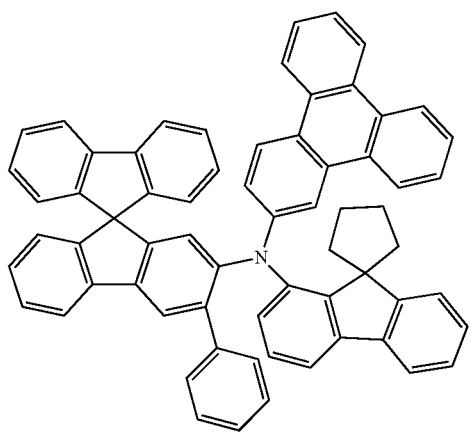
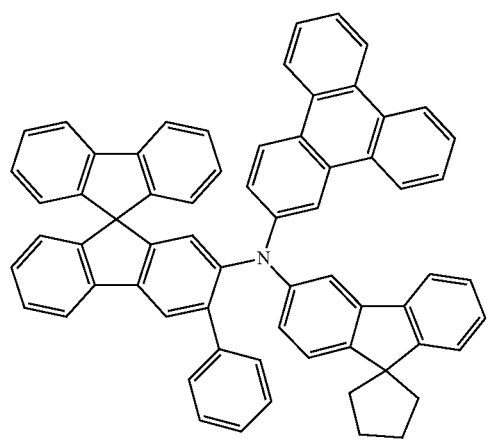
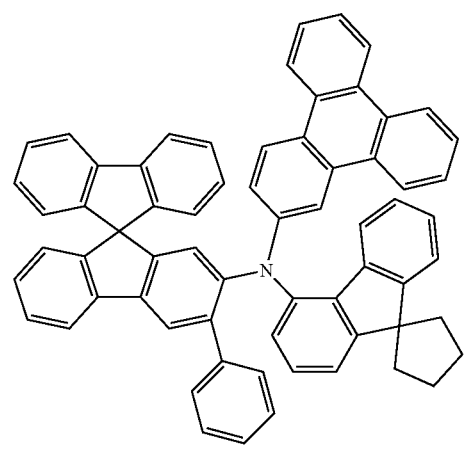
350
-continued
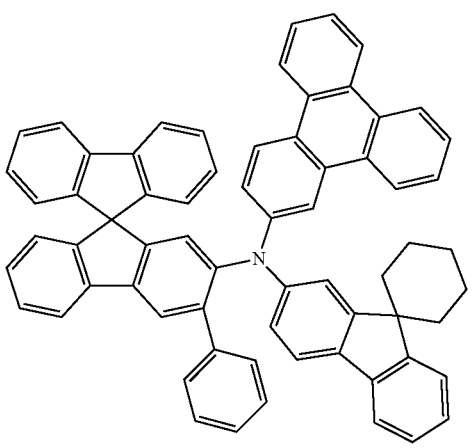
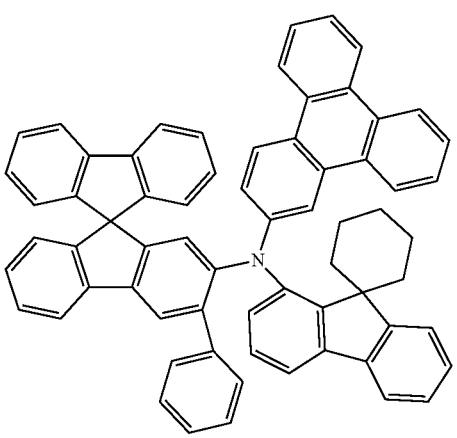
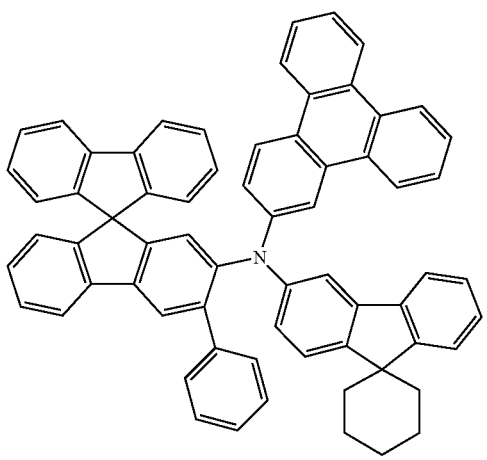

351
-continued
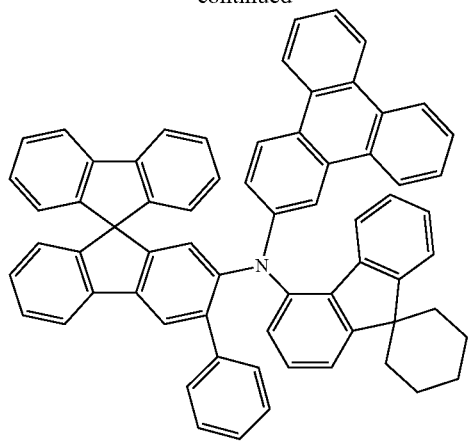
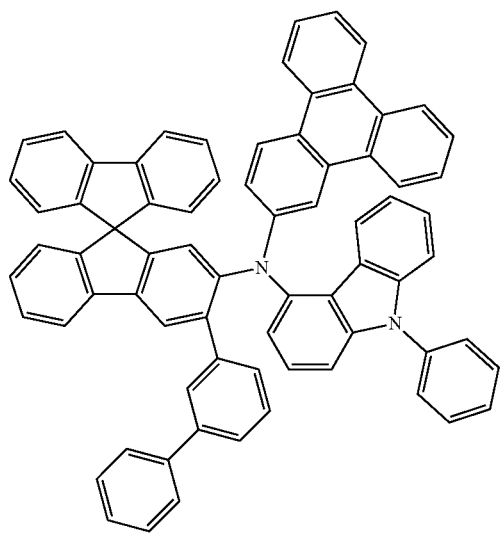
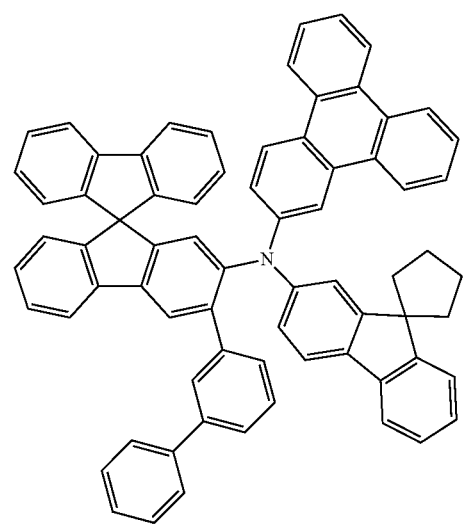
352
-continued
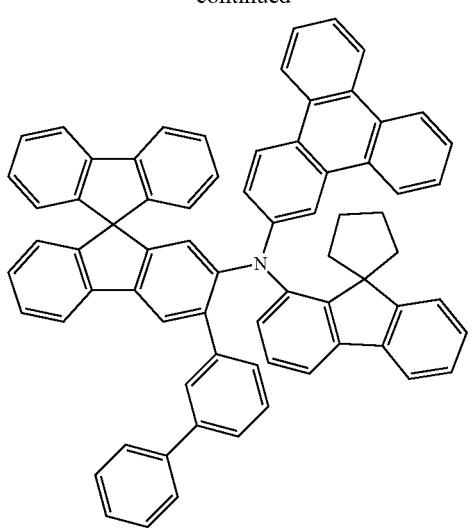
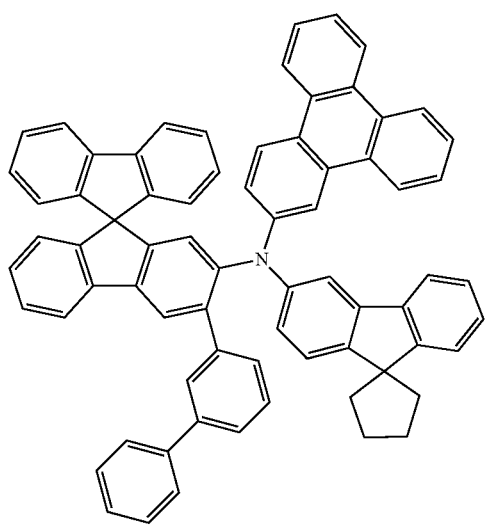
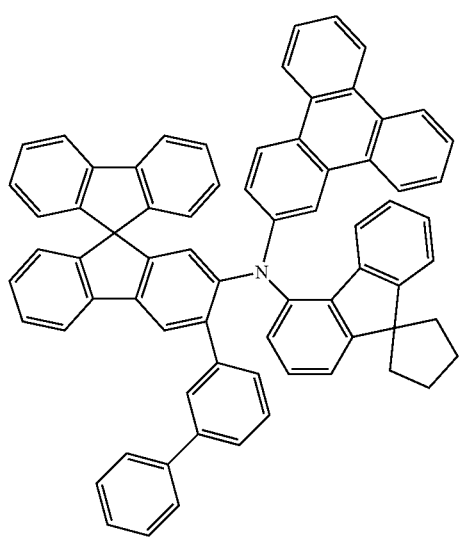

353
-continued
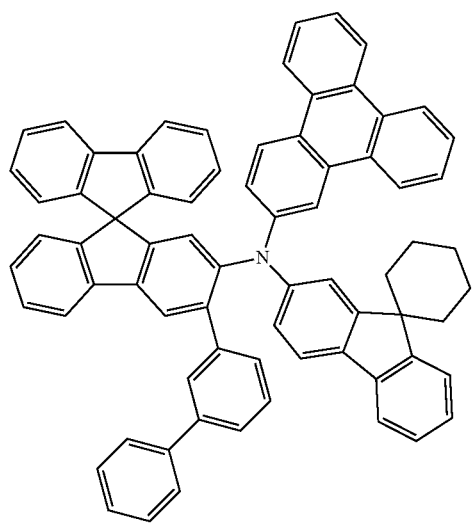
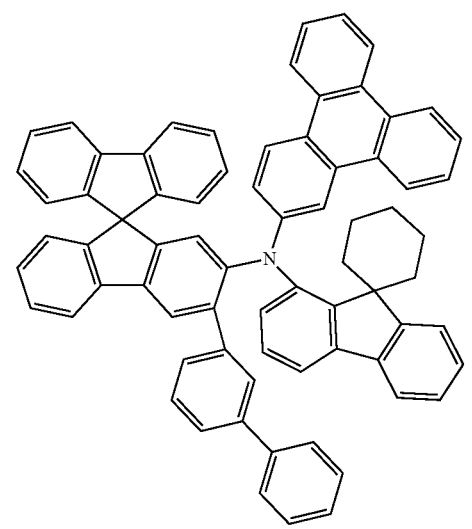
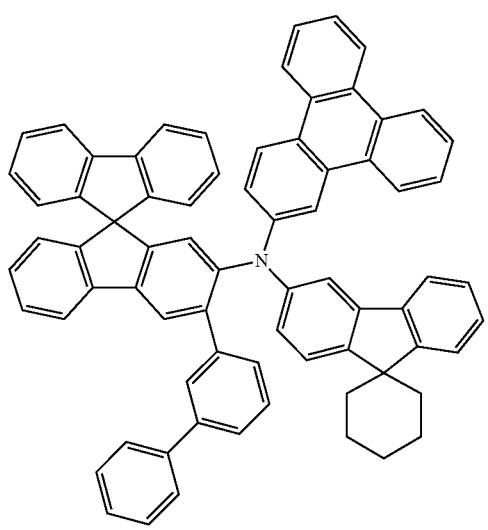
354
-continued
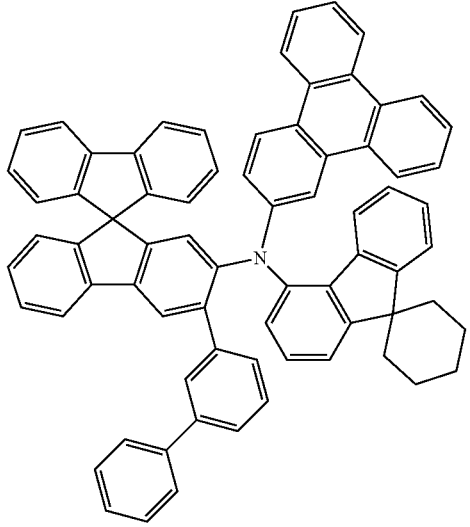
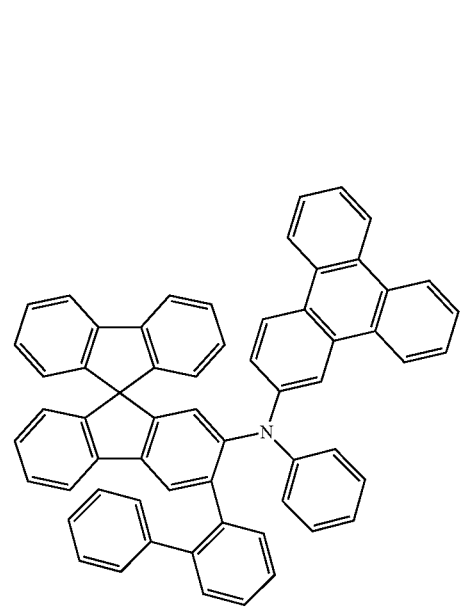
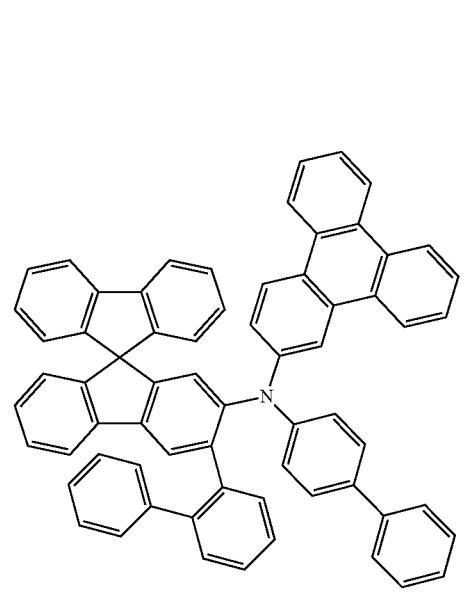

355
-continued
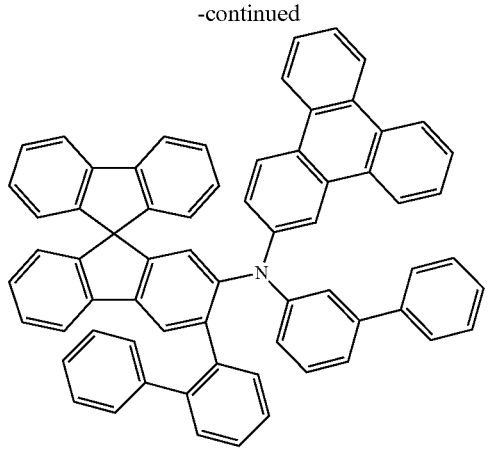
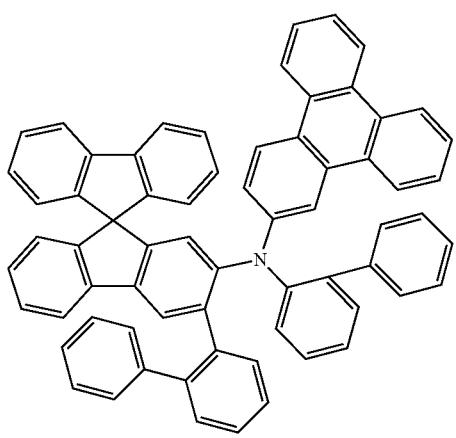
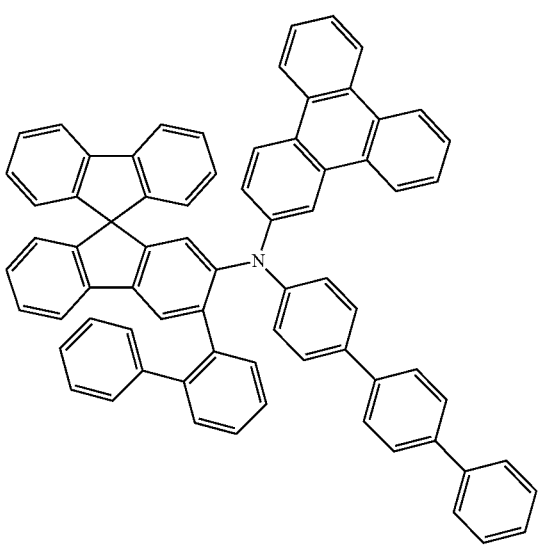
356
-continued
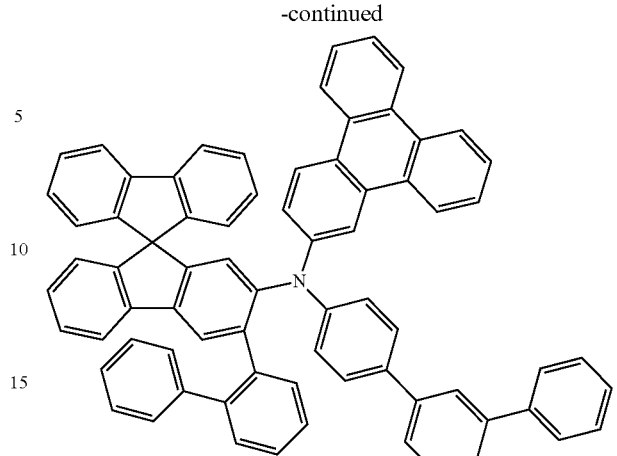
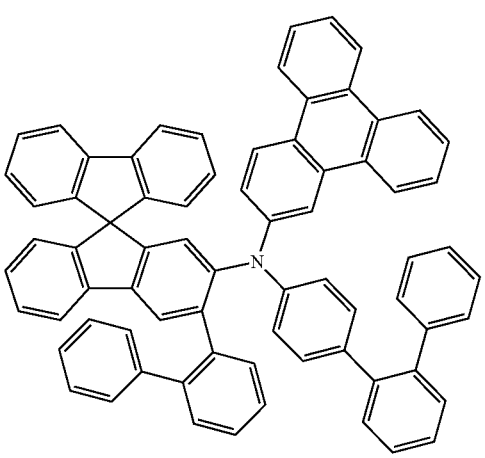
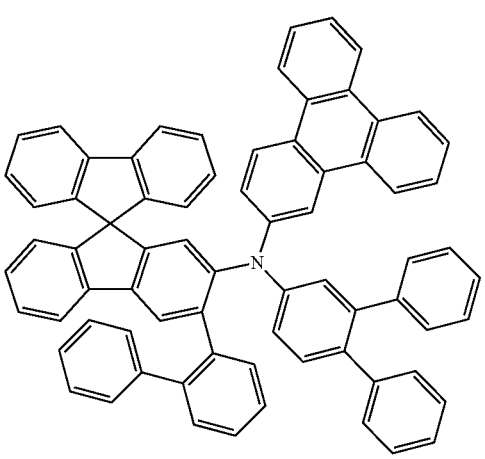

357
-continued
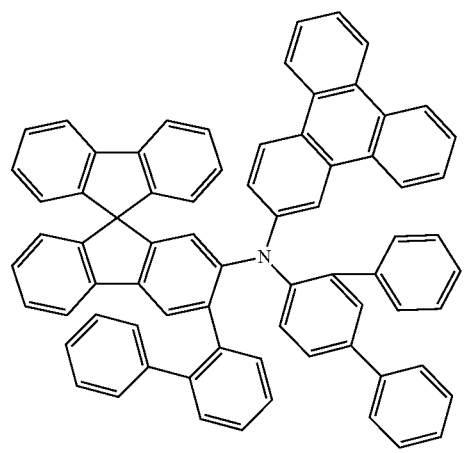
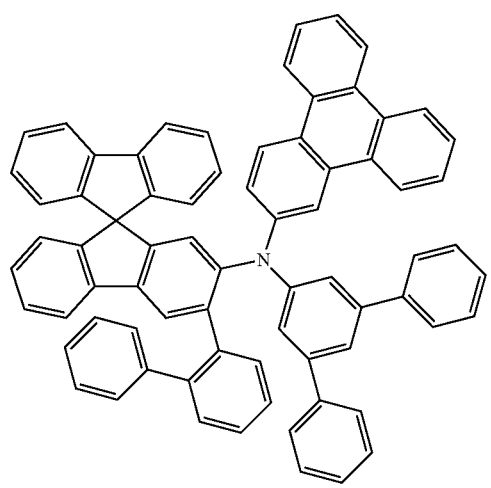
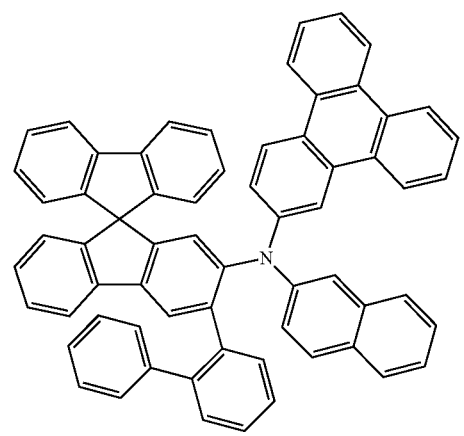
358
-continued
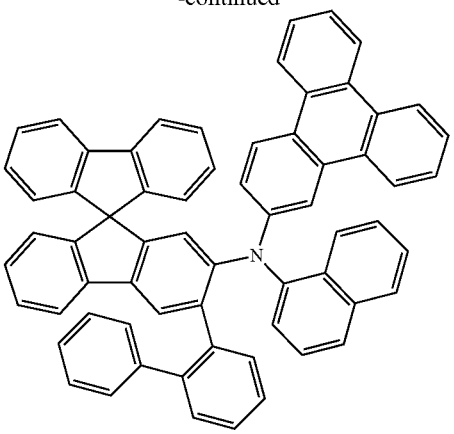
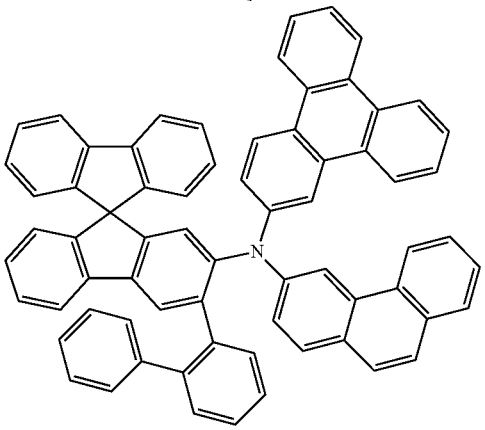
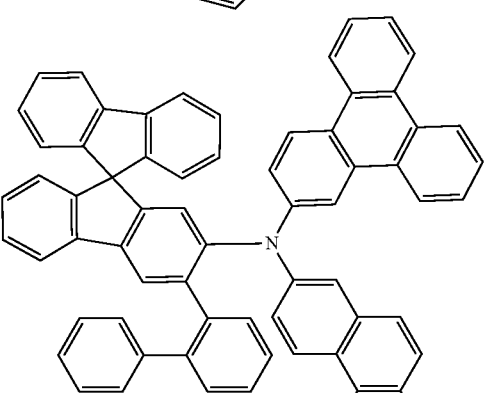
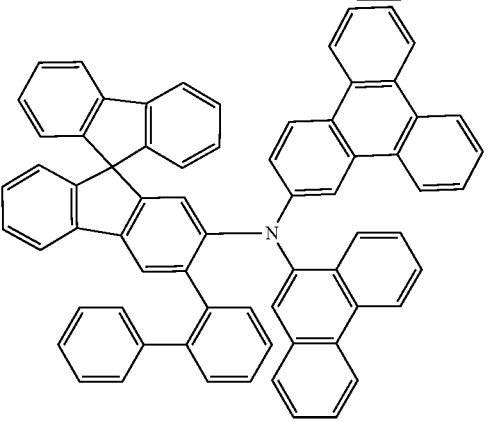

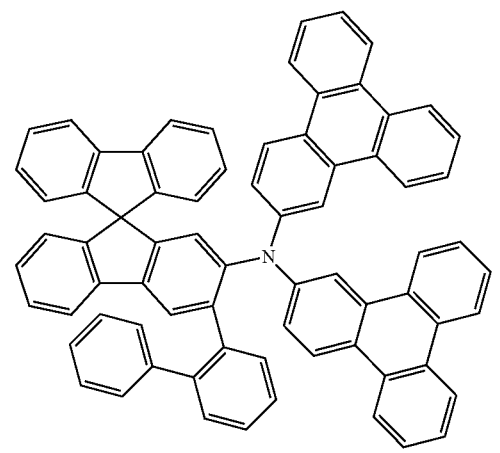
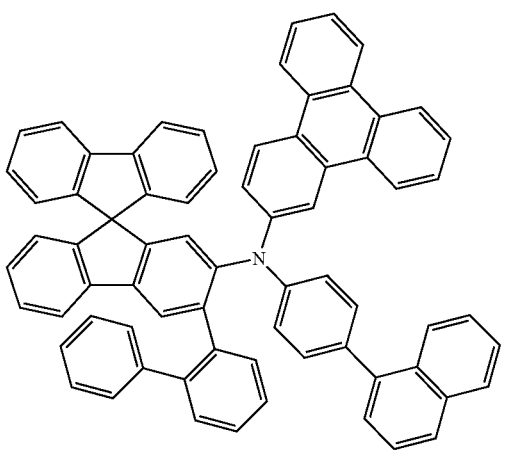
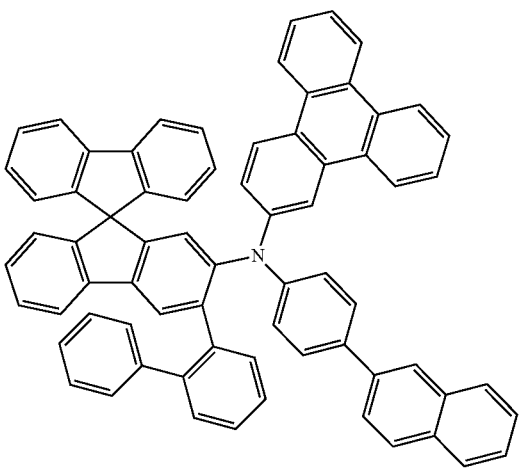
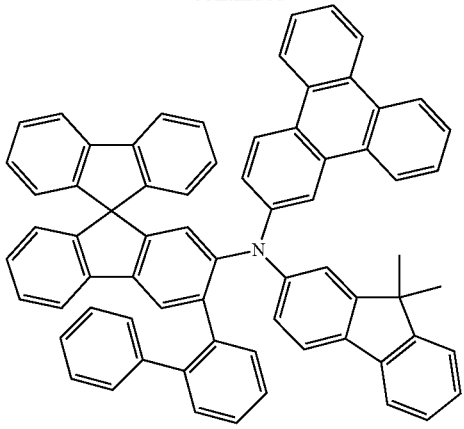
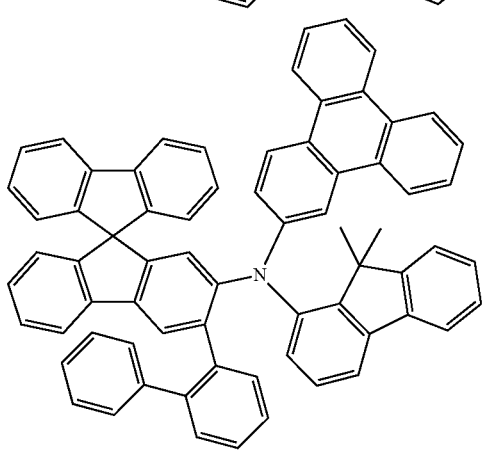
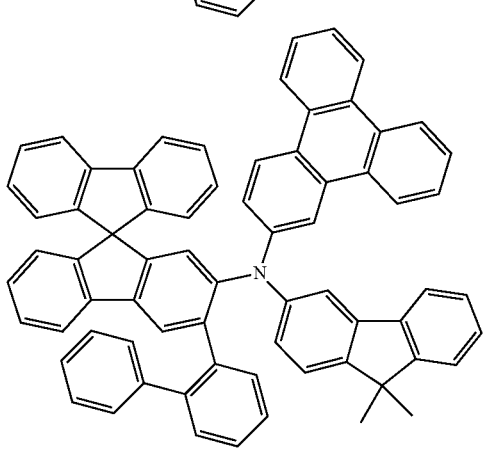
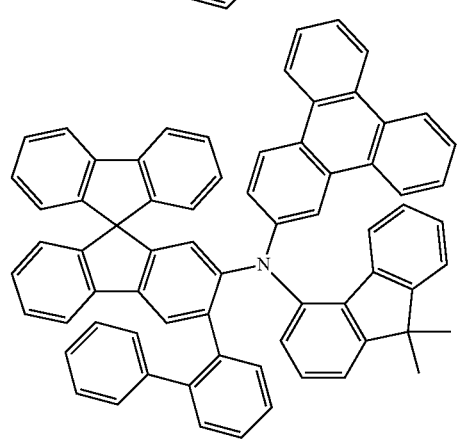

-continued
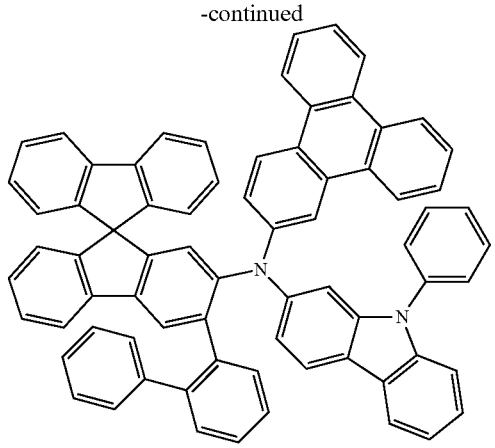
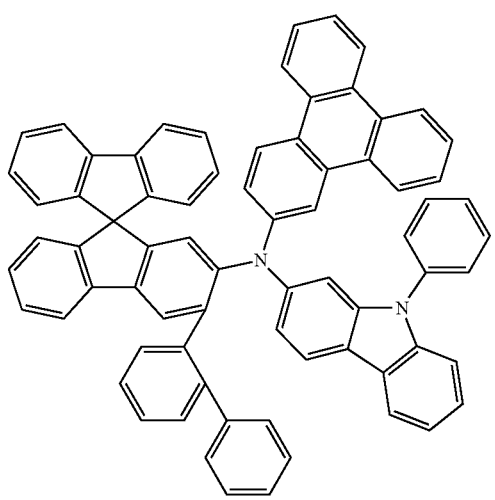
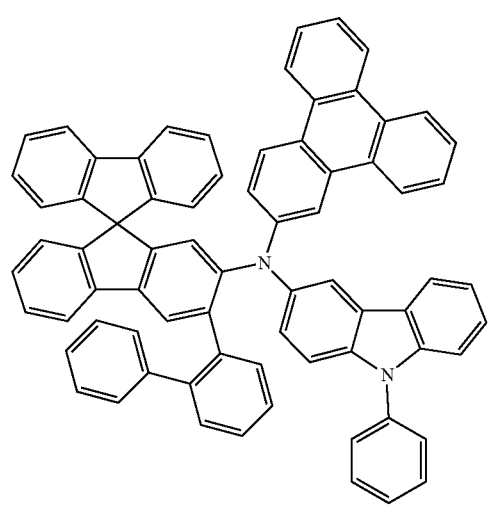
-continued
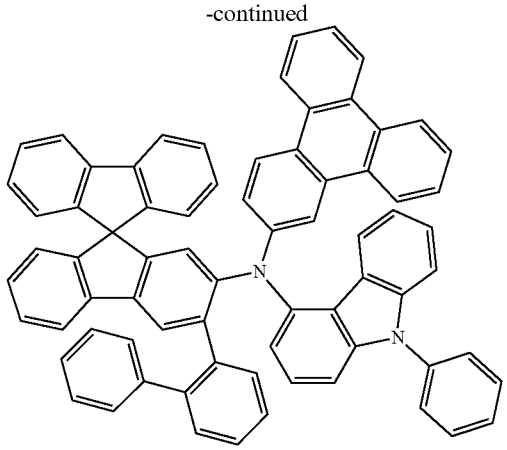
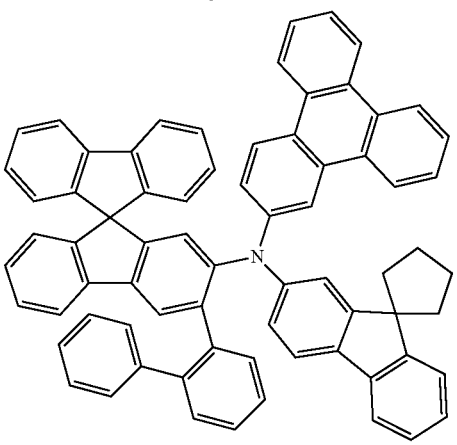
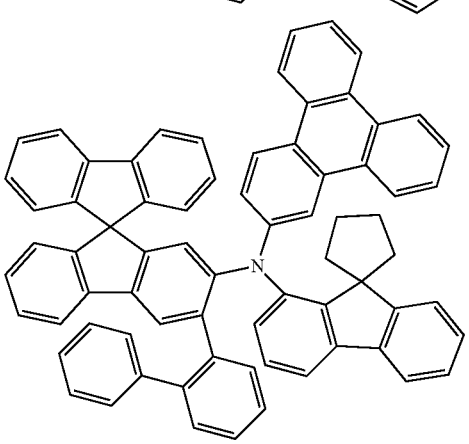
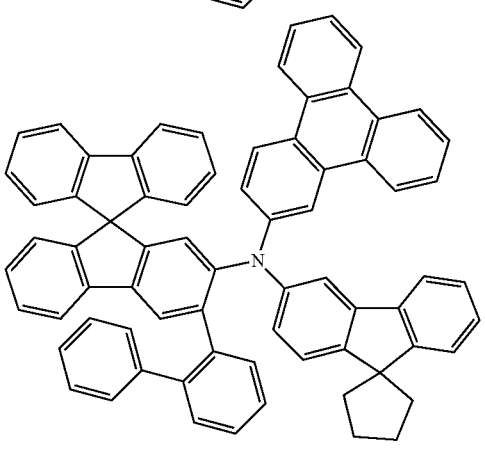

363
-continued
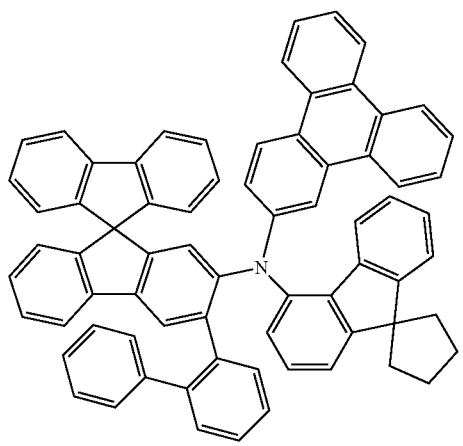
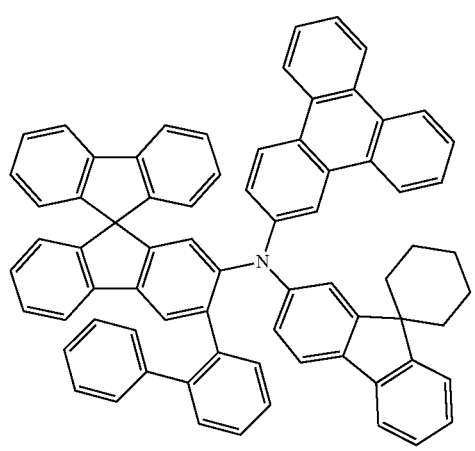
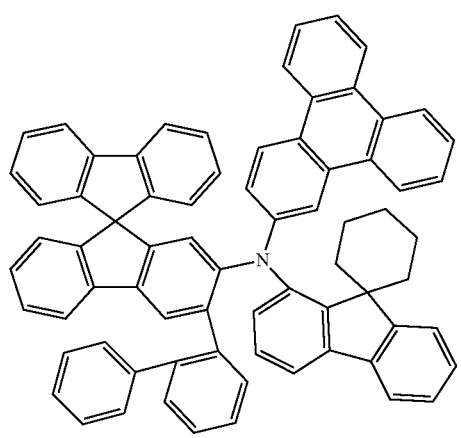
364
-continued
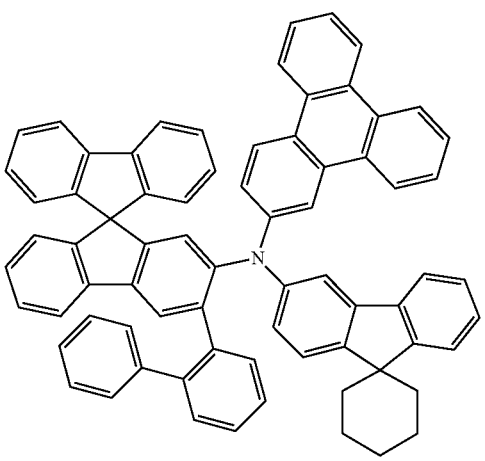
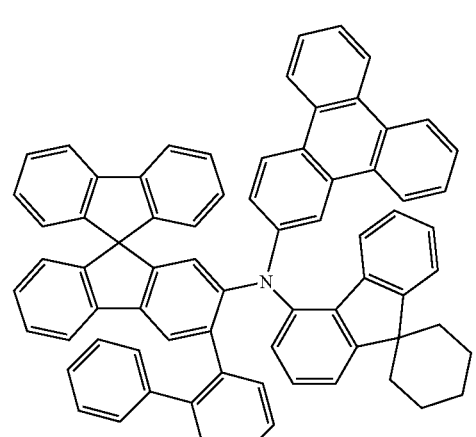
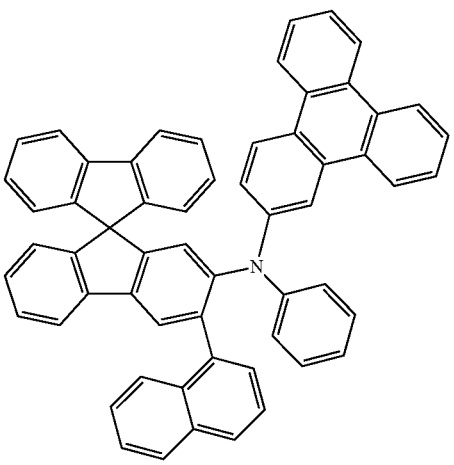

365
-continued
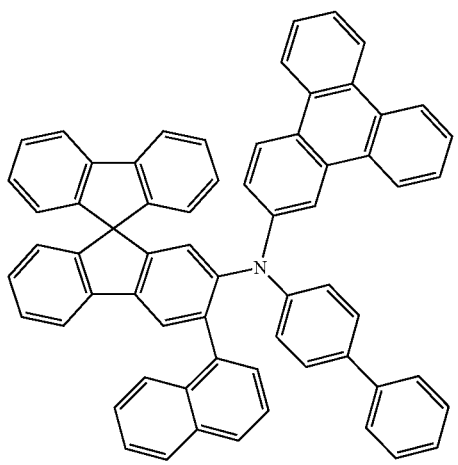
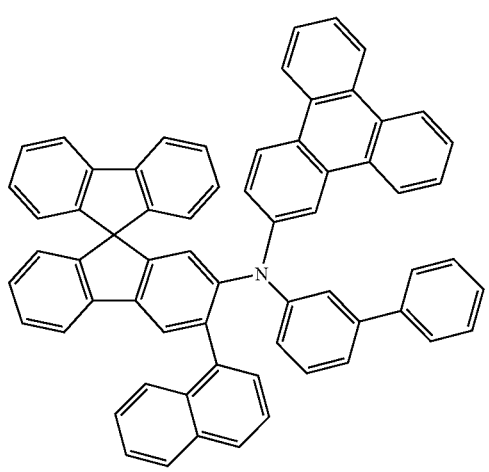
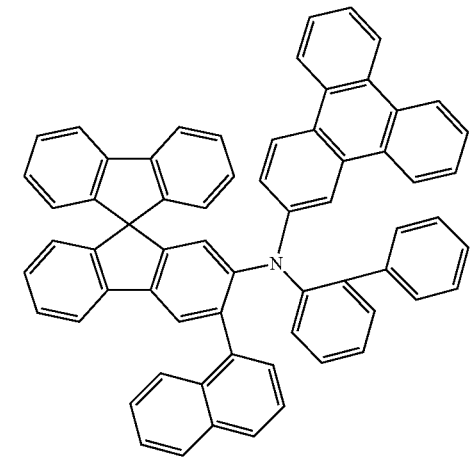
366
-continued
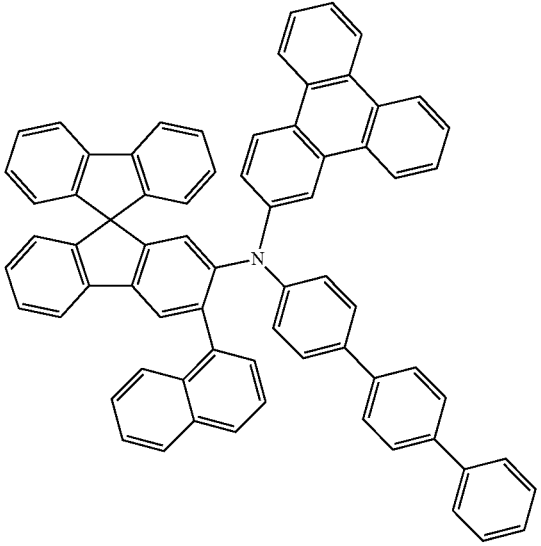
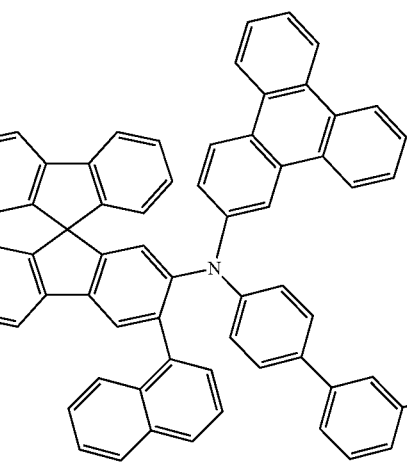
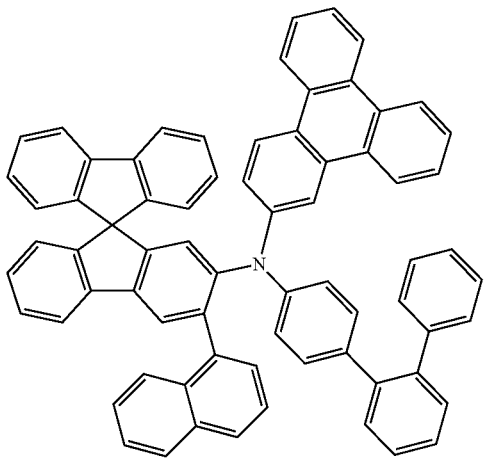

367
-continued
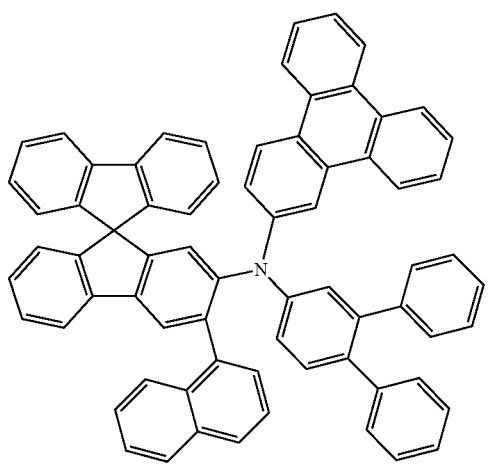
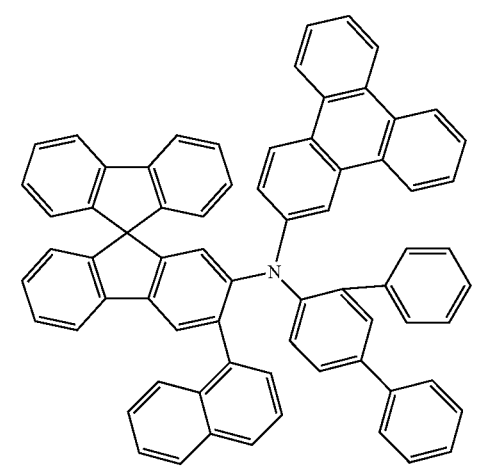
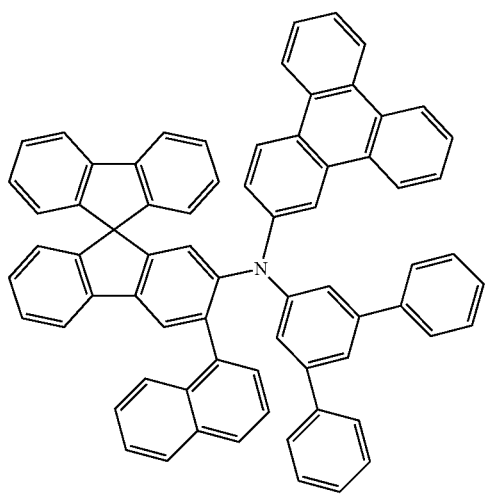
368
-continued
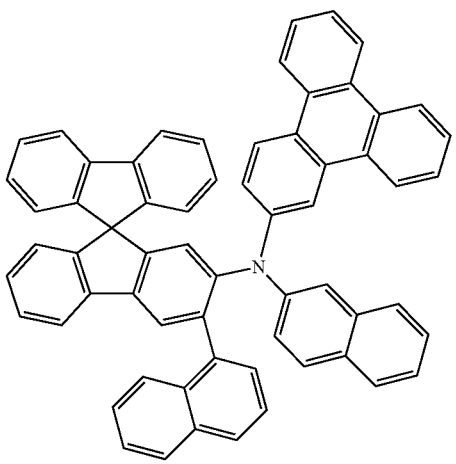
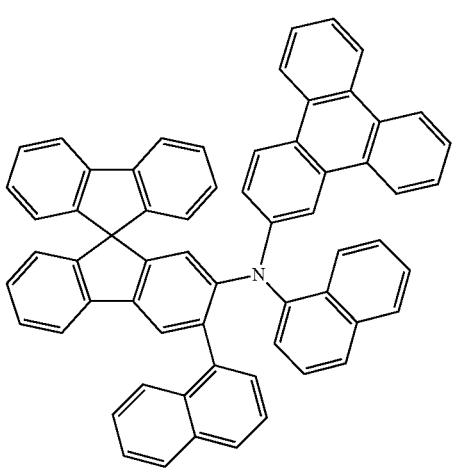
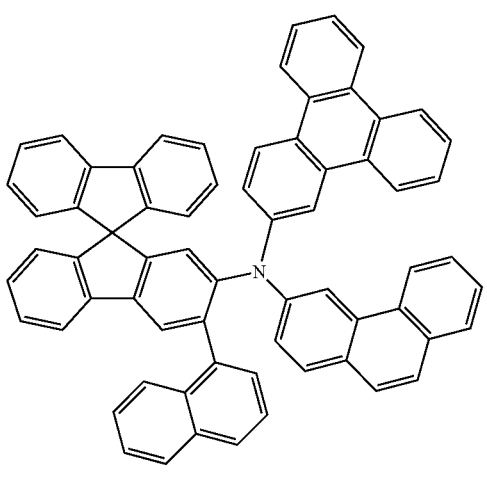

369
-continued
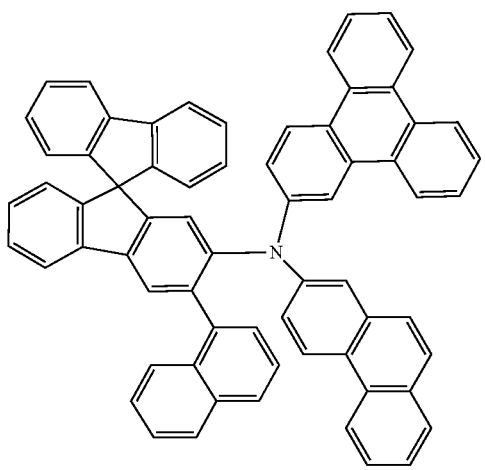
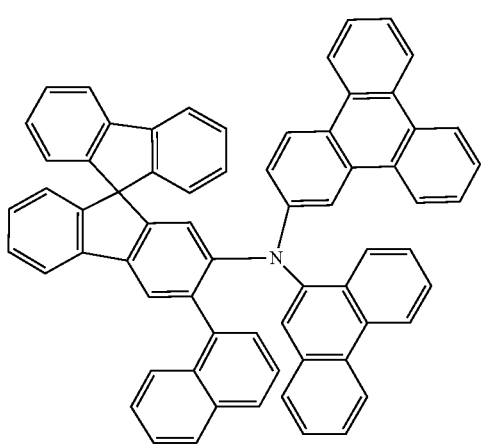
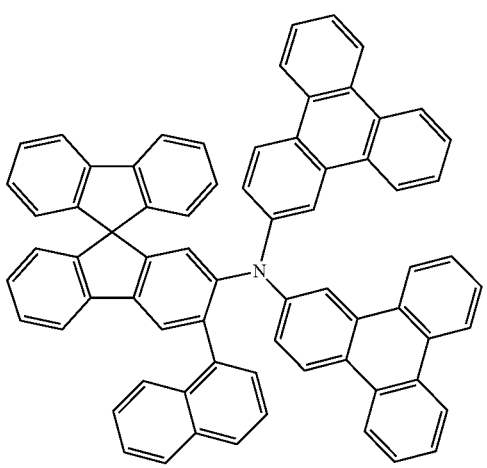
370
-continued
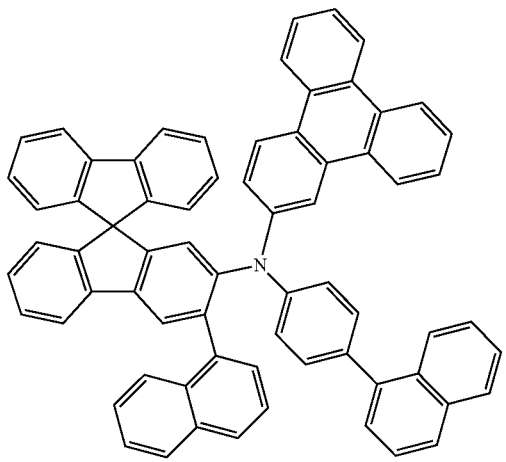
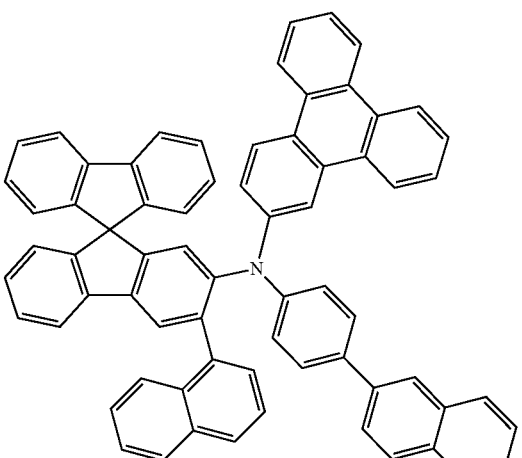
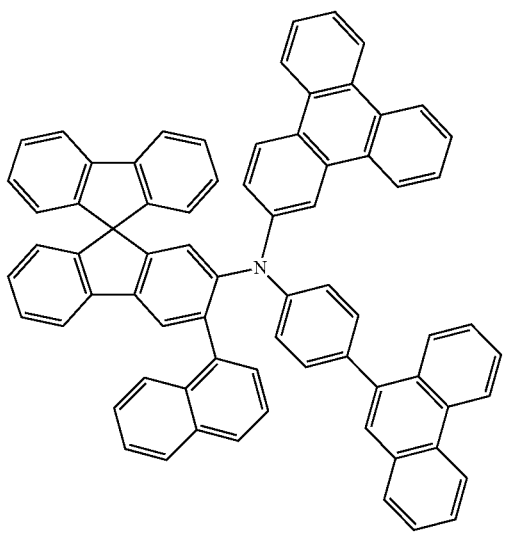

371
-continued
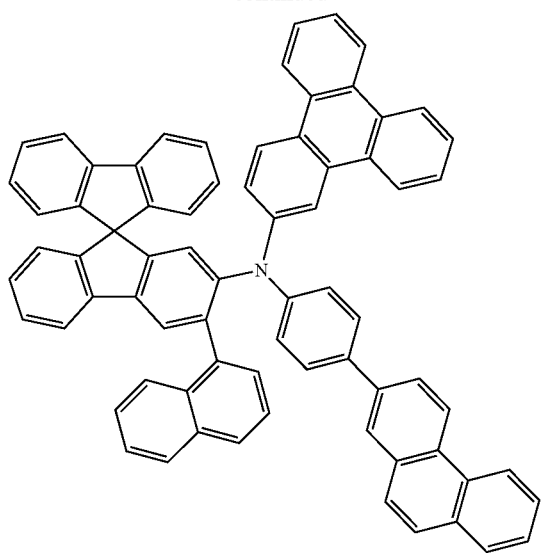
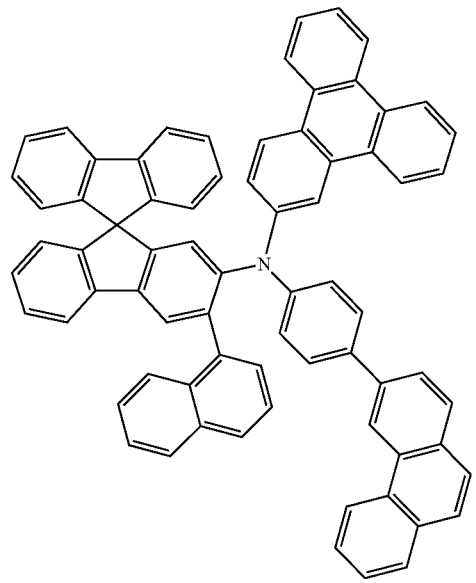
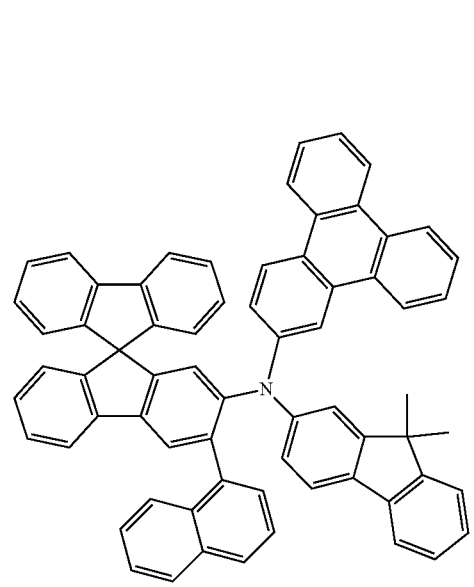
372
-continued
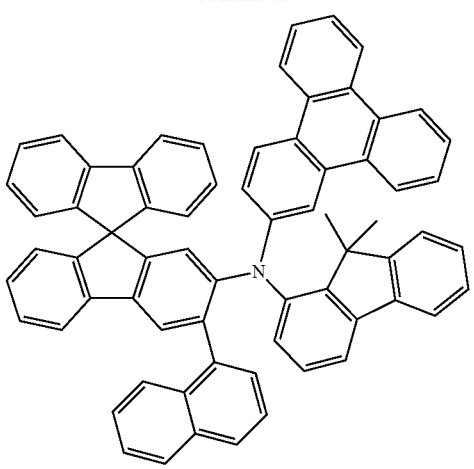
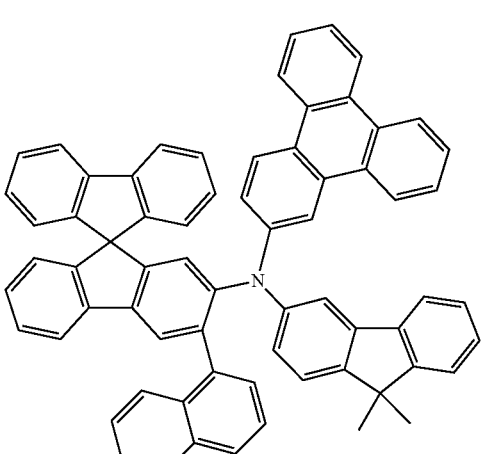
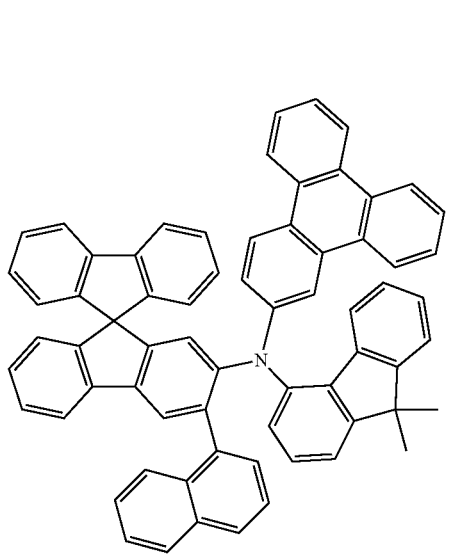

373
-continued
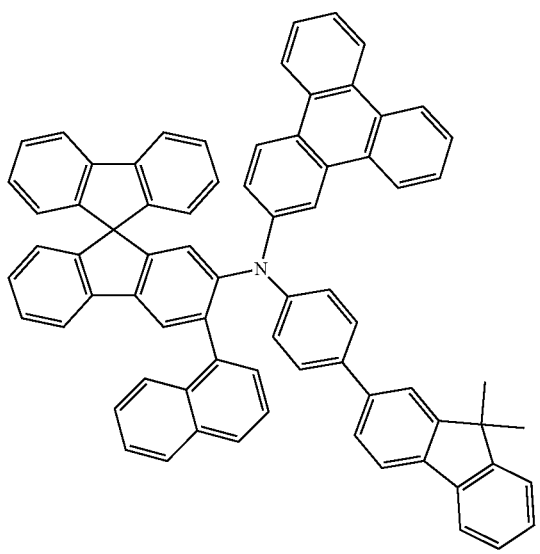
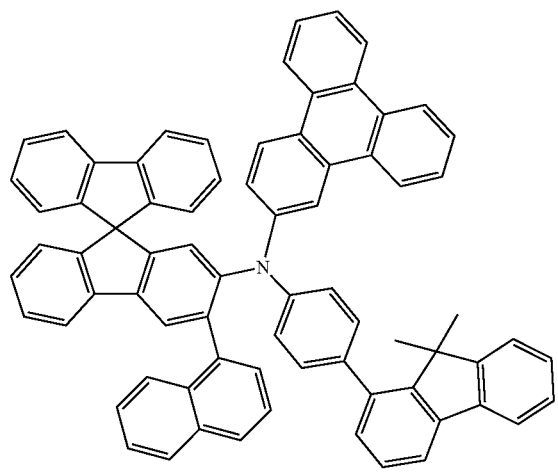
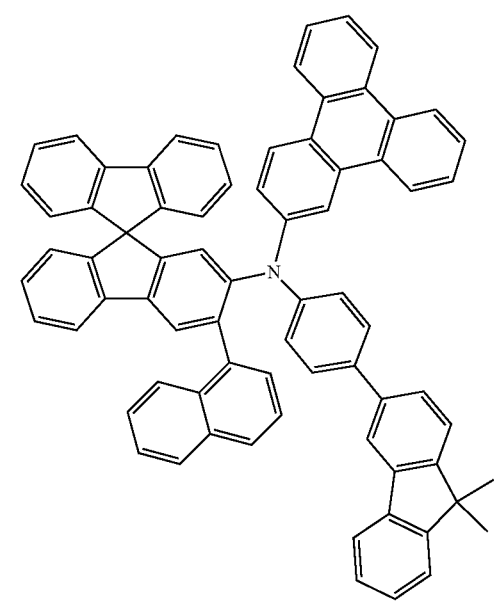
374
-continued
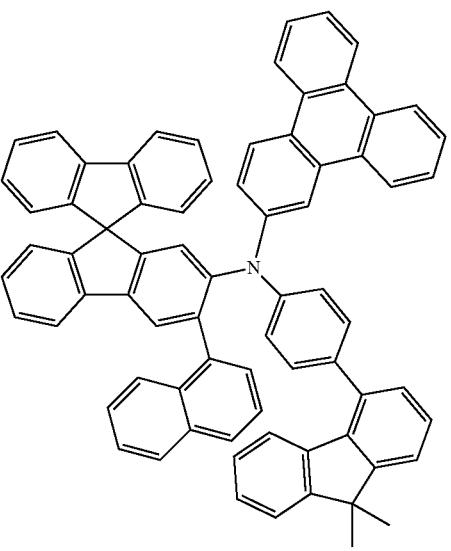
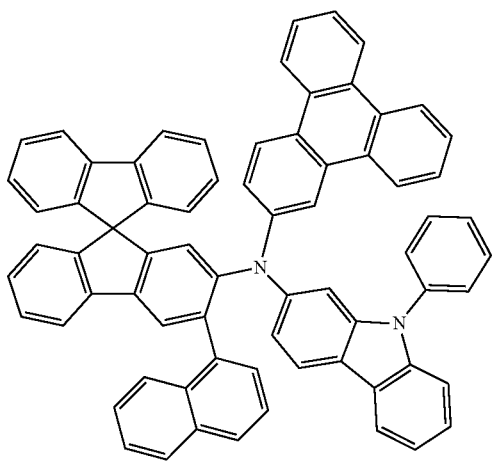
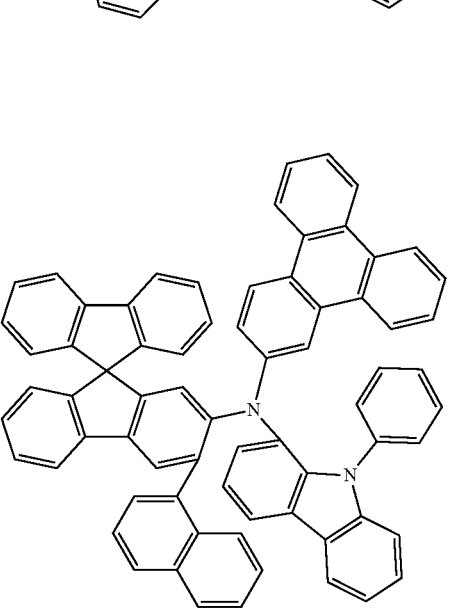

375
-continued
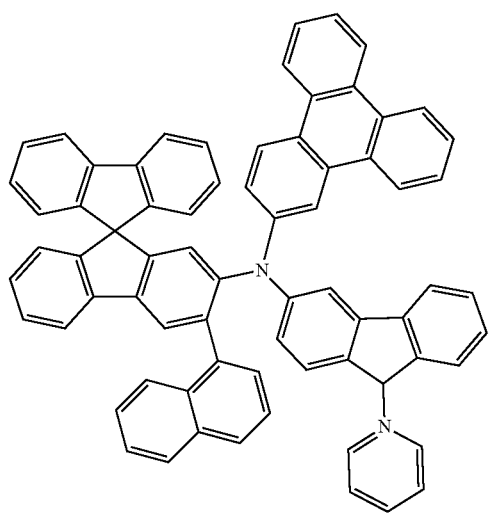
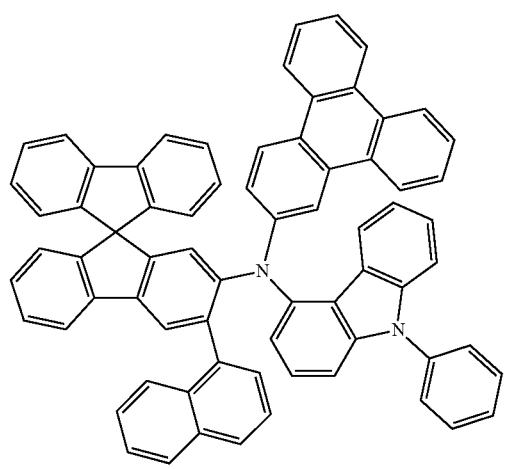
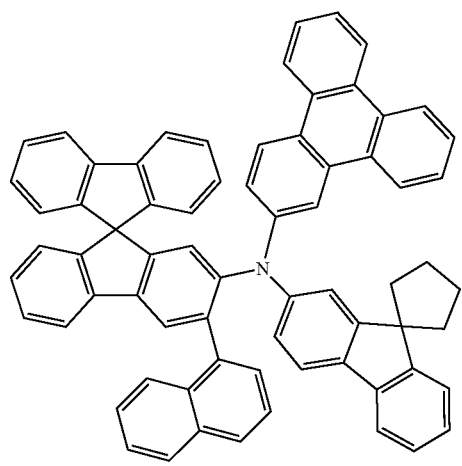
376
-continued
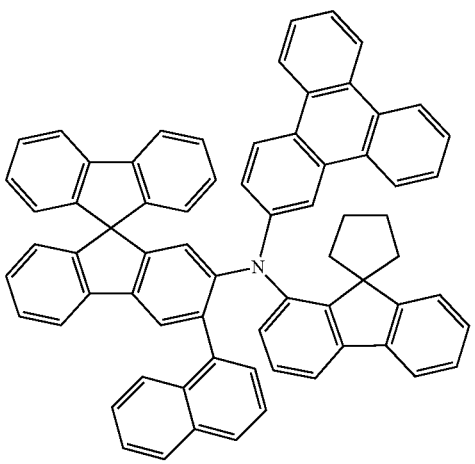
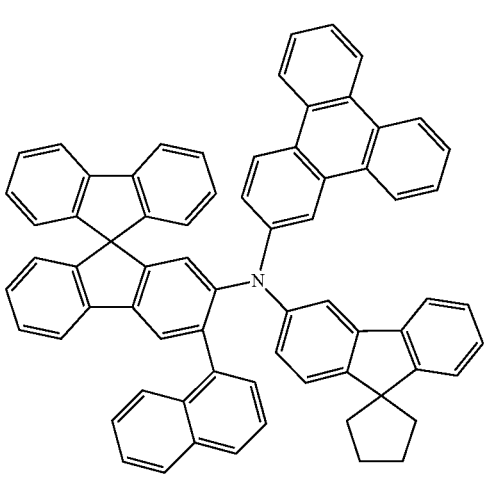
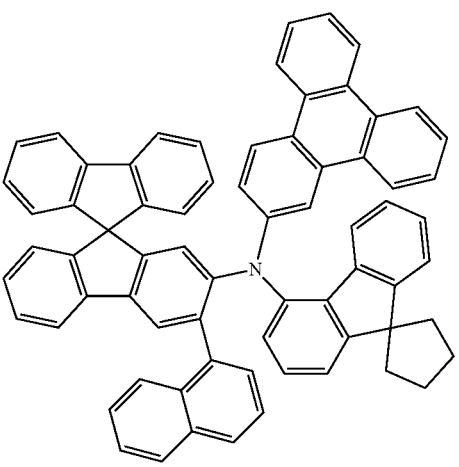

377
-continued
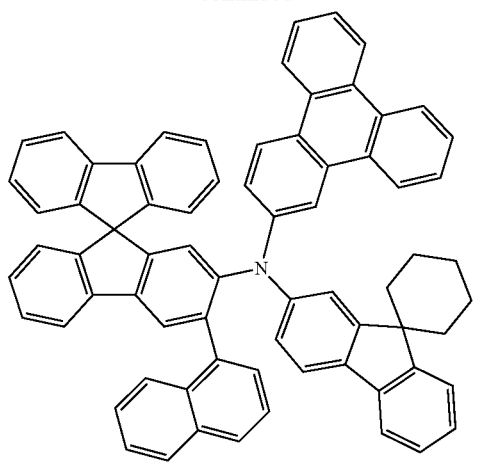
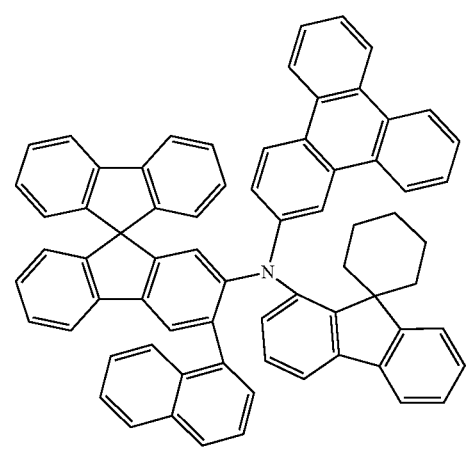
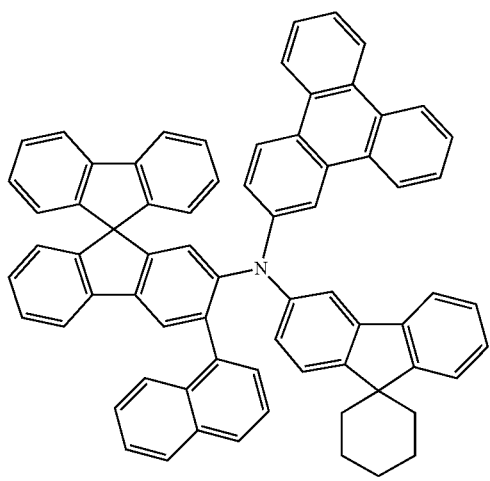
378
-continued
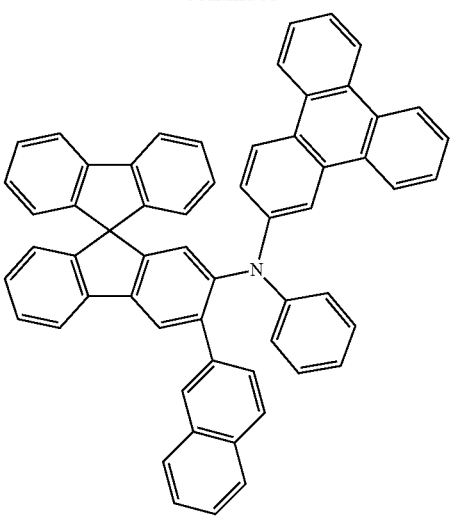
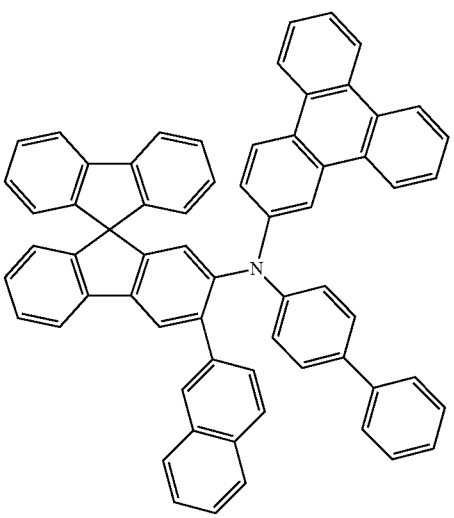
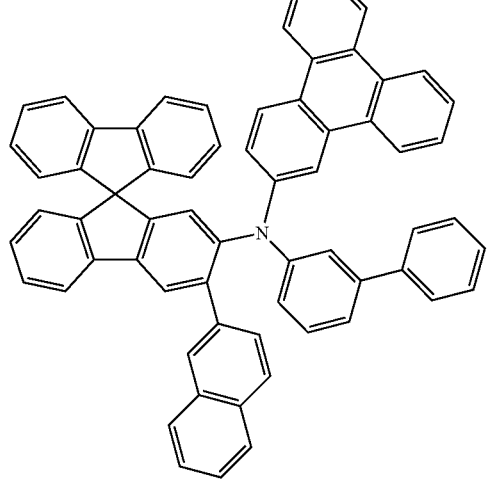

379
-continued
380
-continued
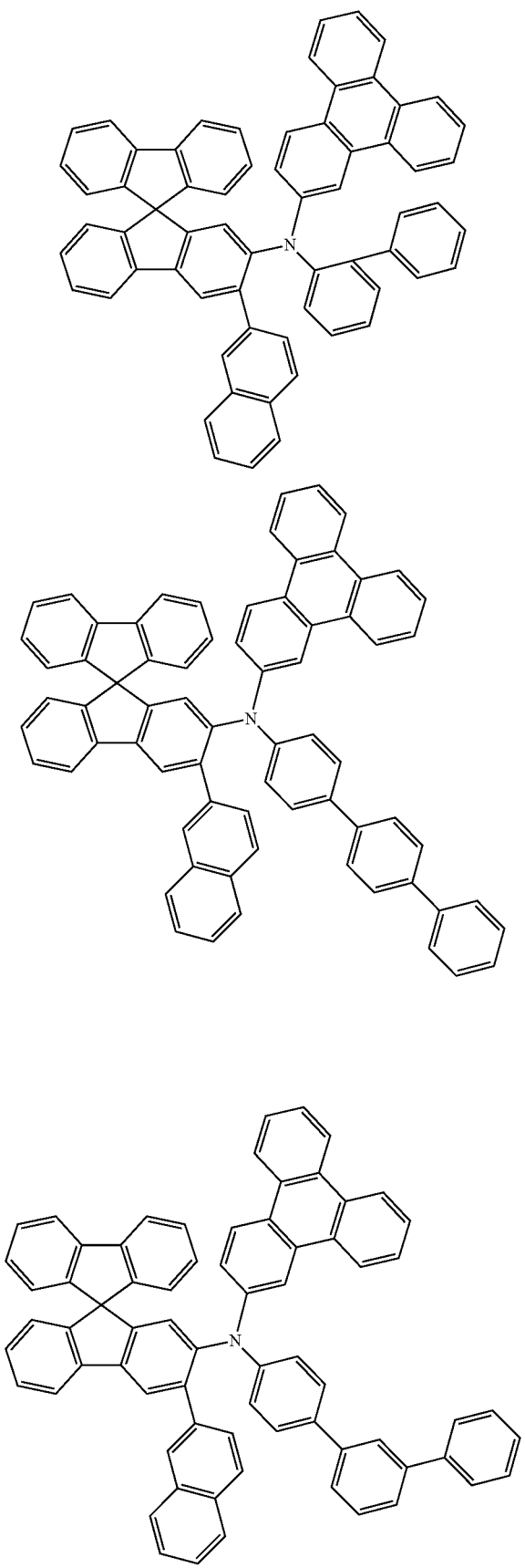
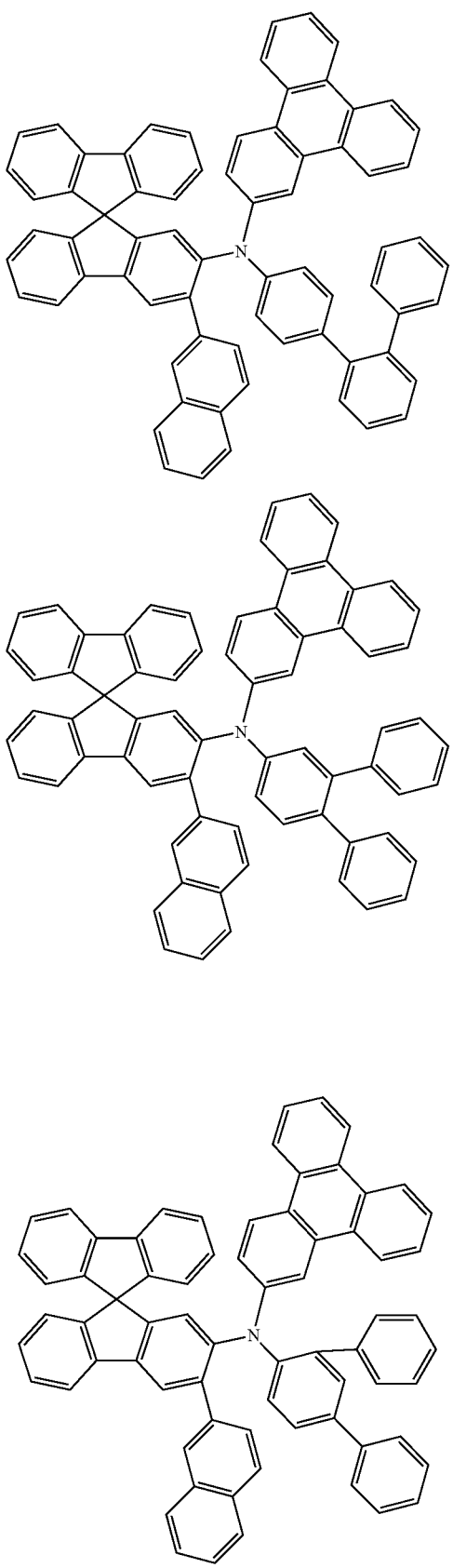

381
-continued
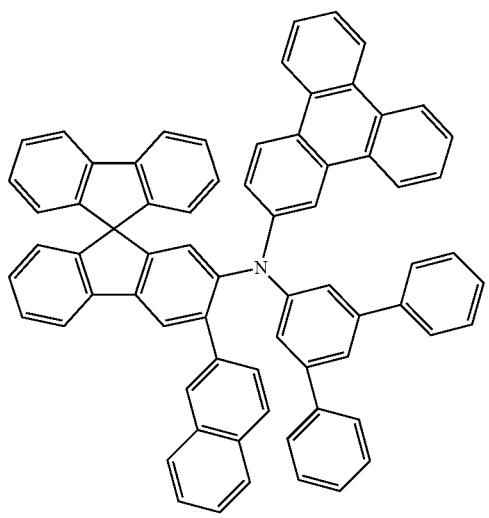
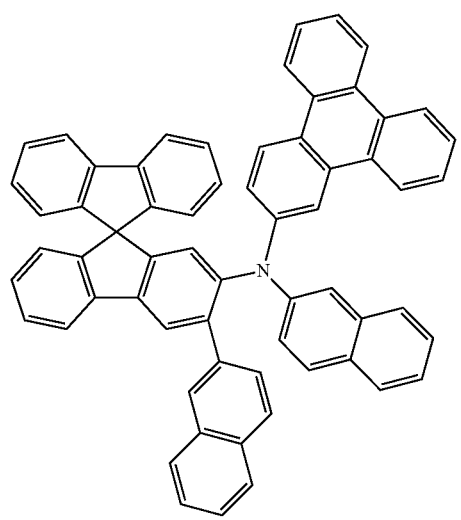
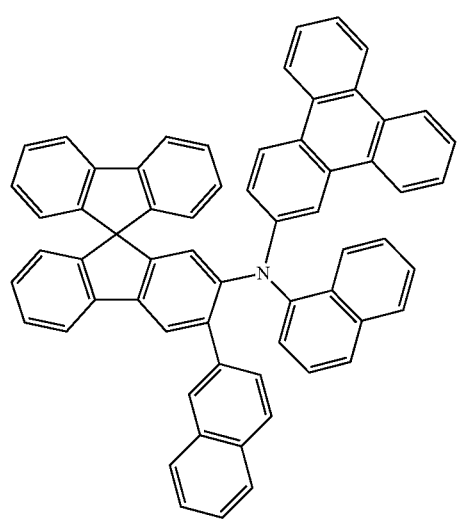
382
-continued
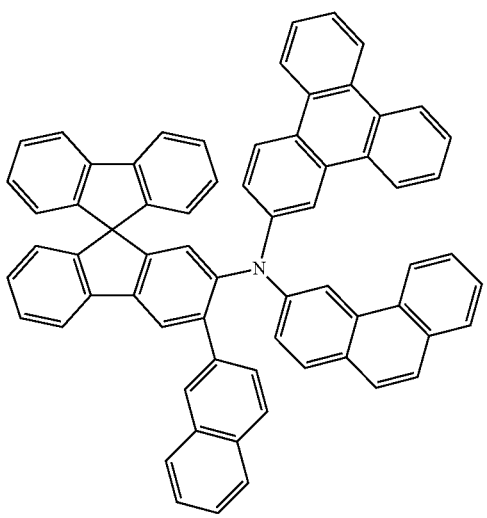
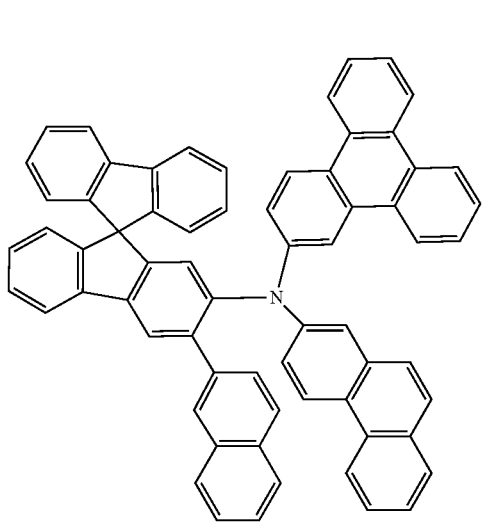
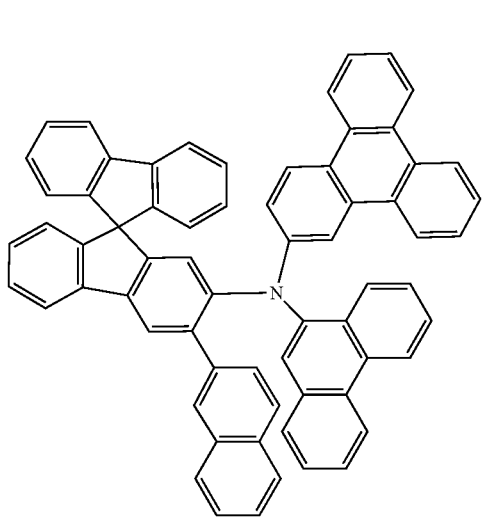

383
-continued
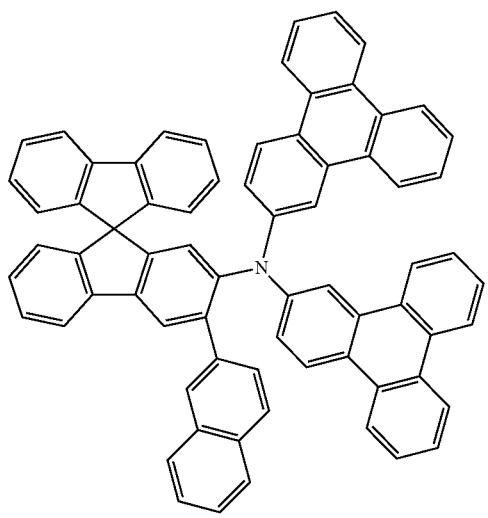
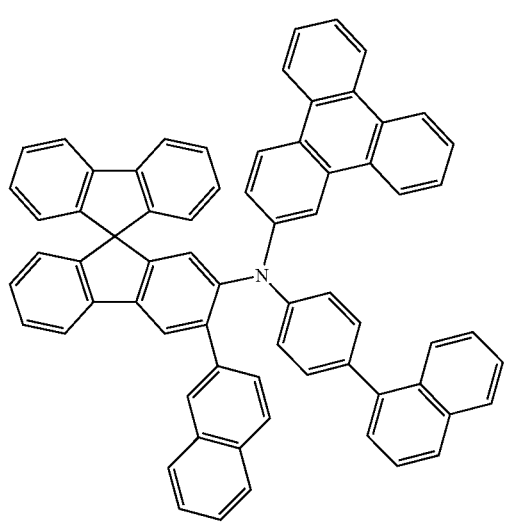
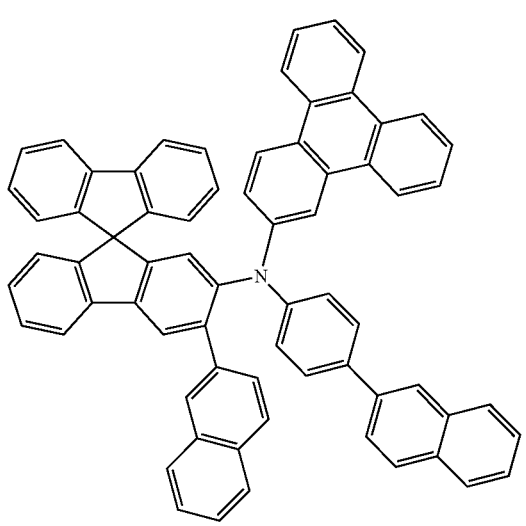
384
-continued
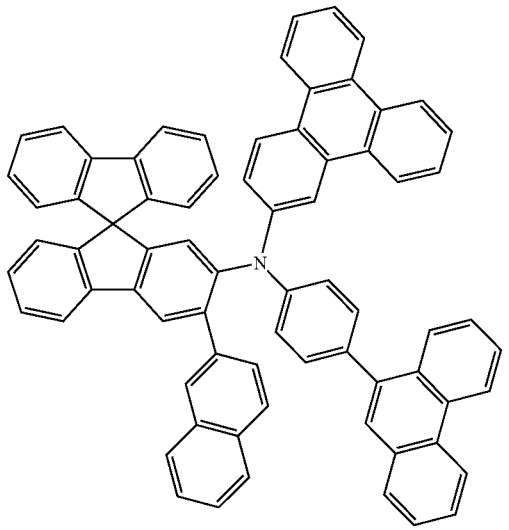
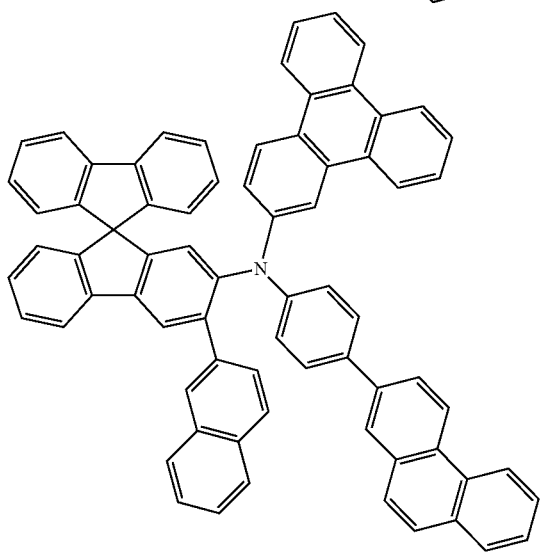
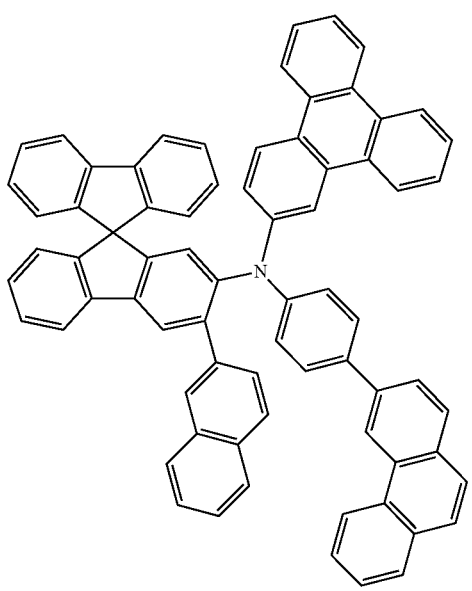

385
-continued
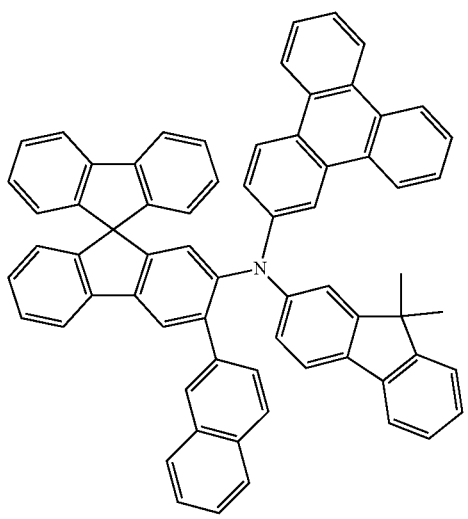
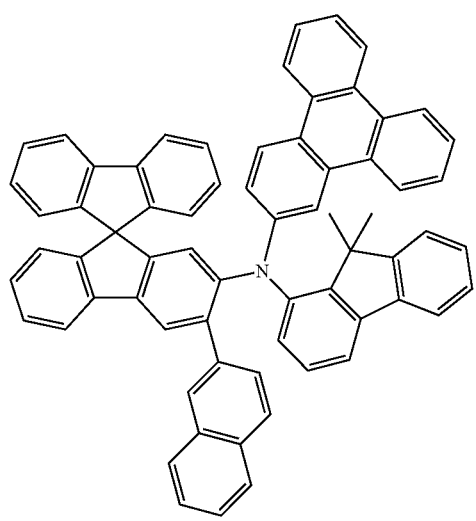
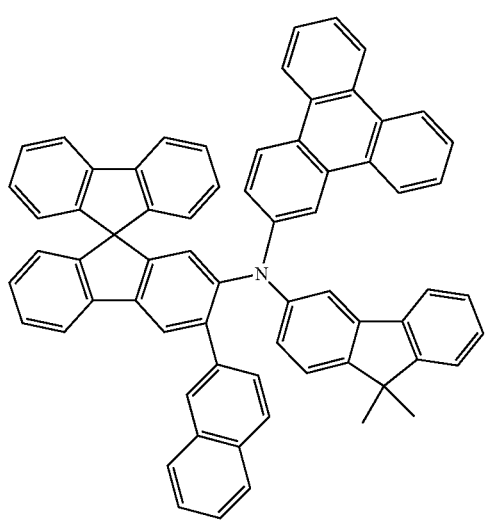
386
-continued
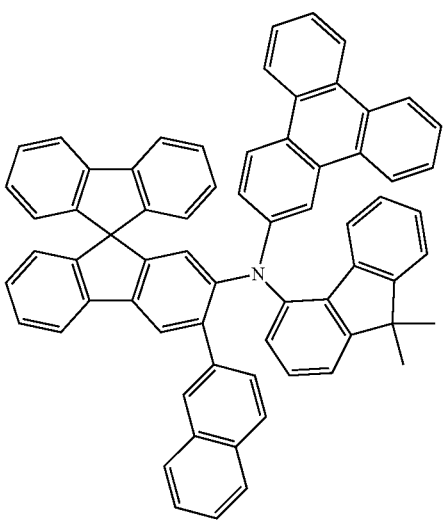
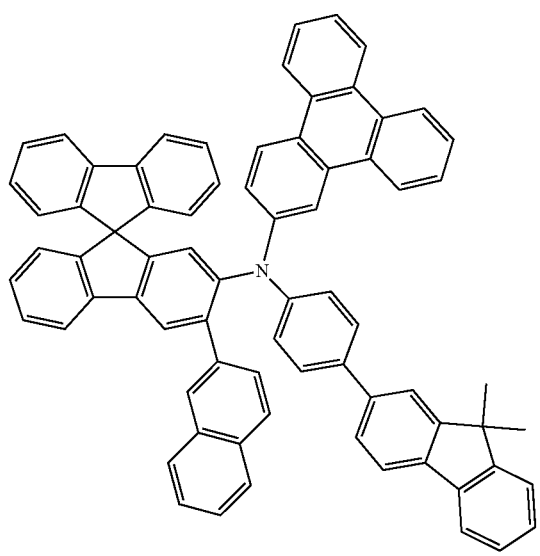
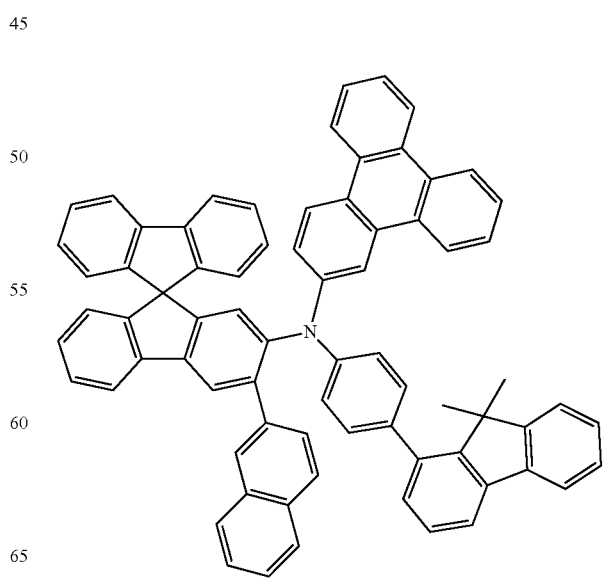

387
-continued
388
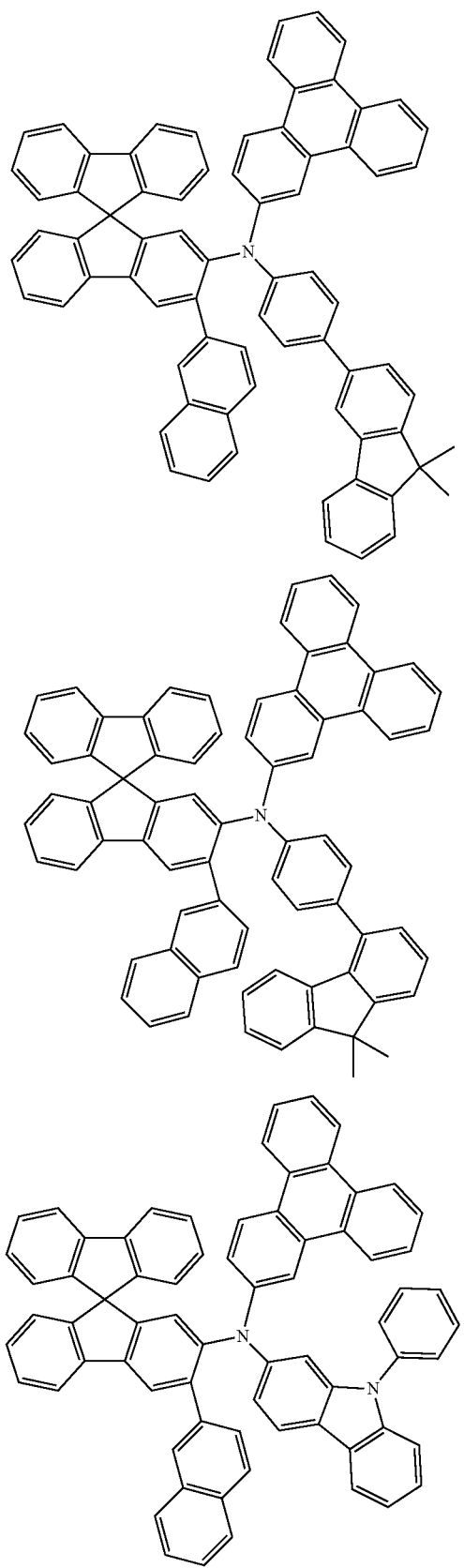
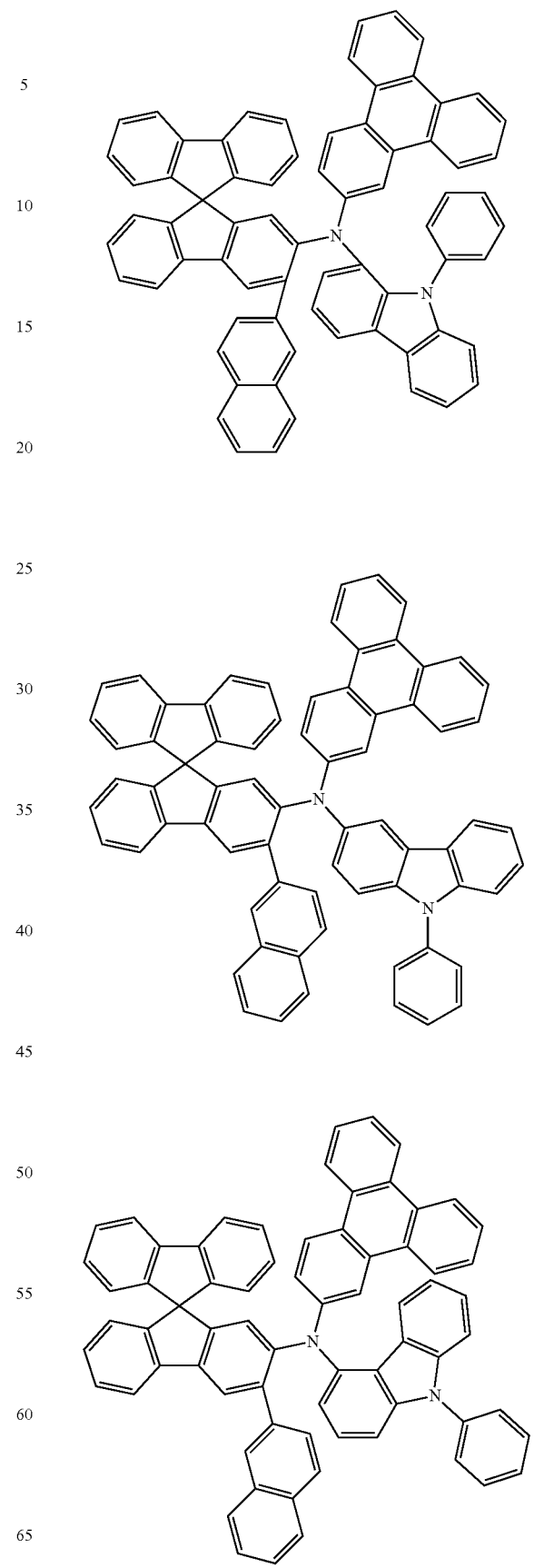

389
-continued
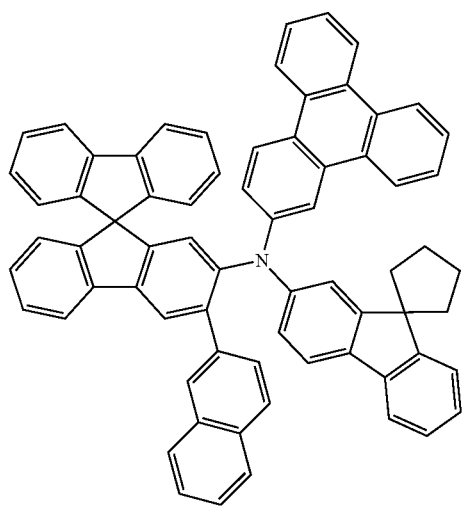
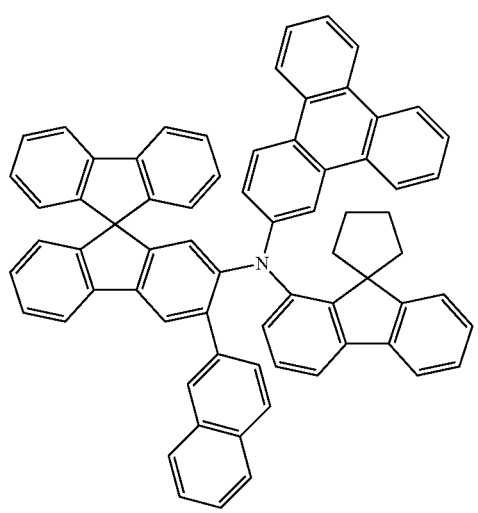
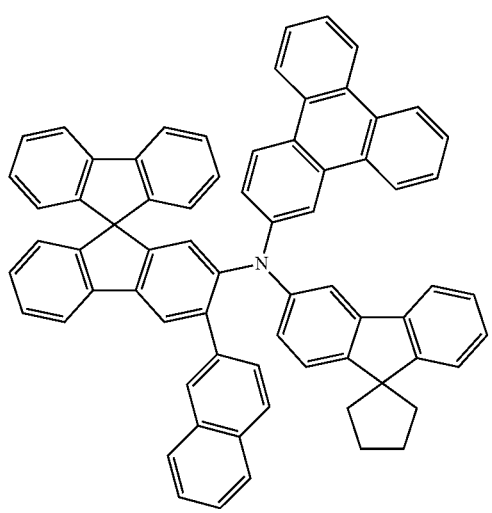
390
-continued
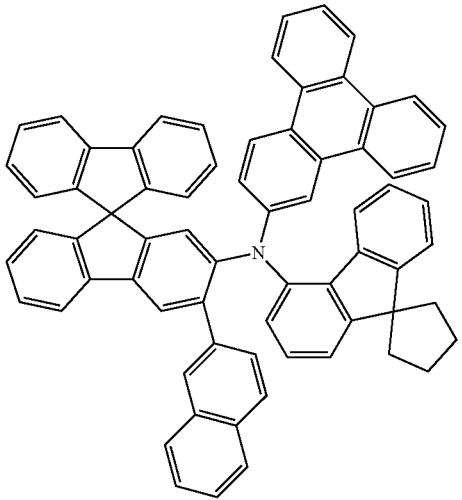
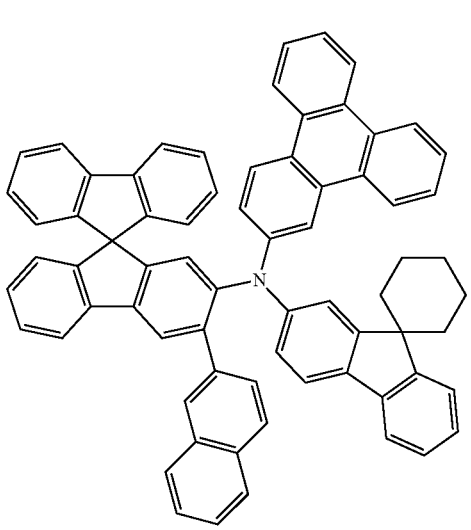
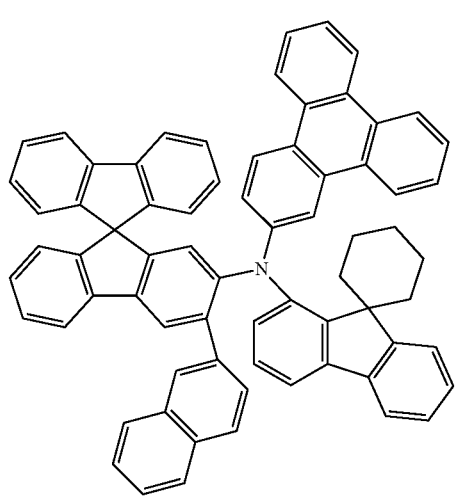

391
-continued
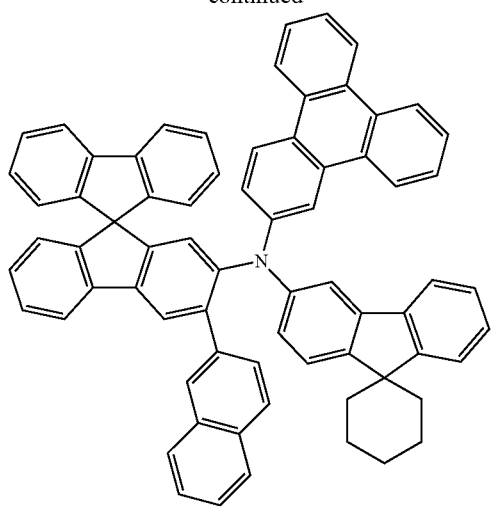
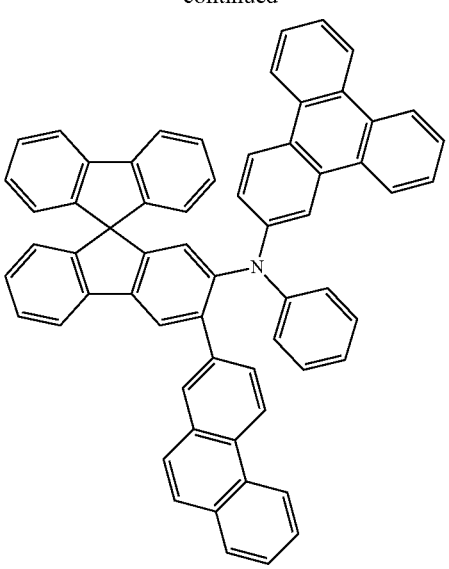
392
-continued
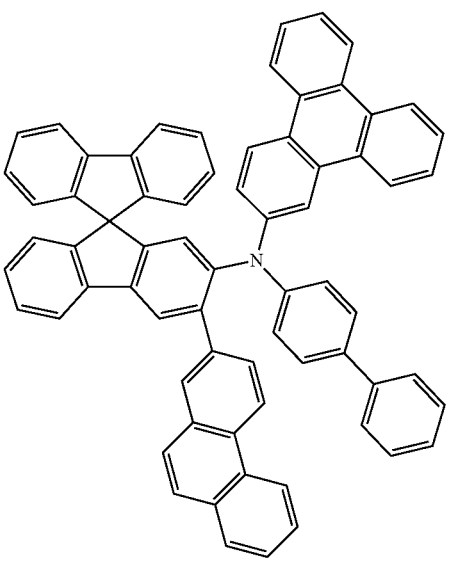
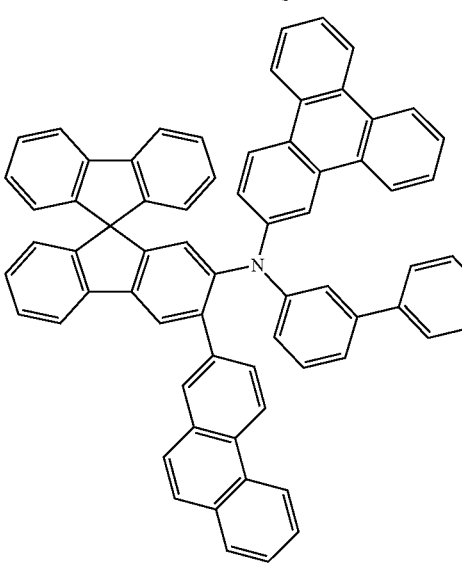

393
-continued
394
-continued
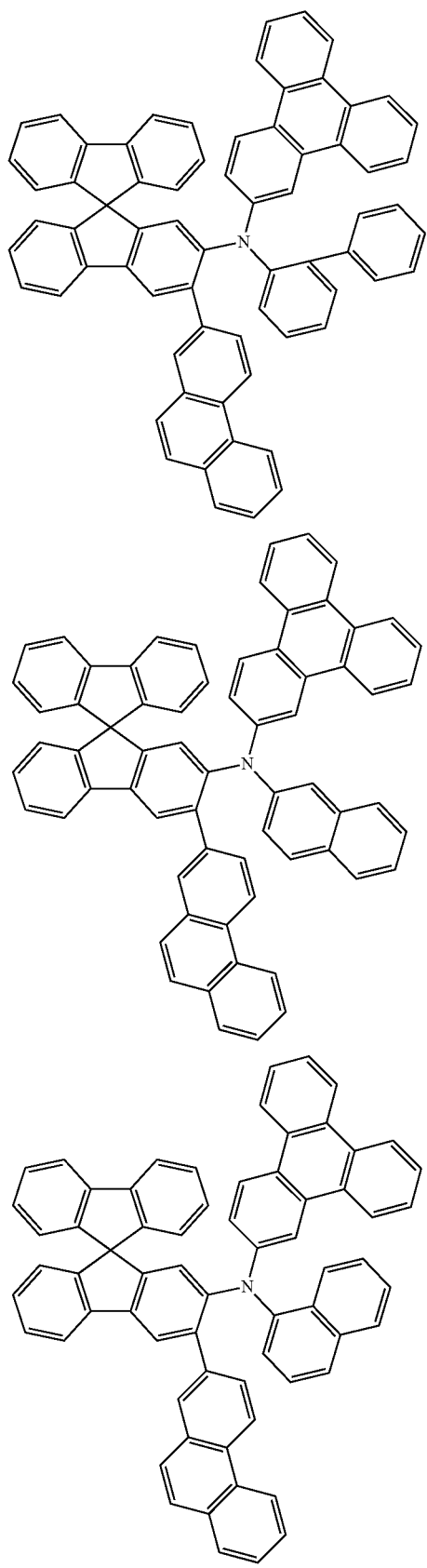
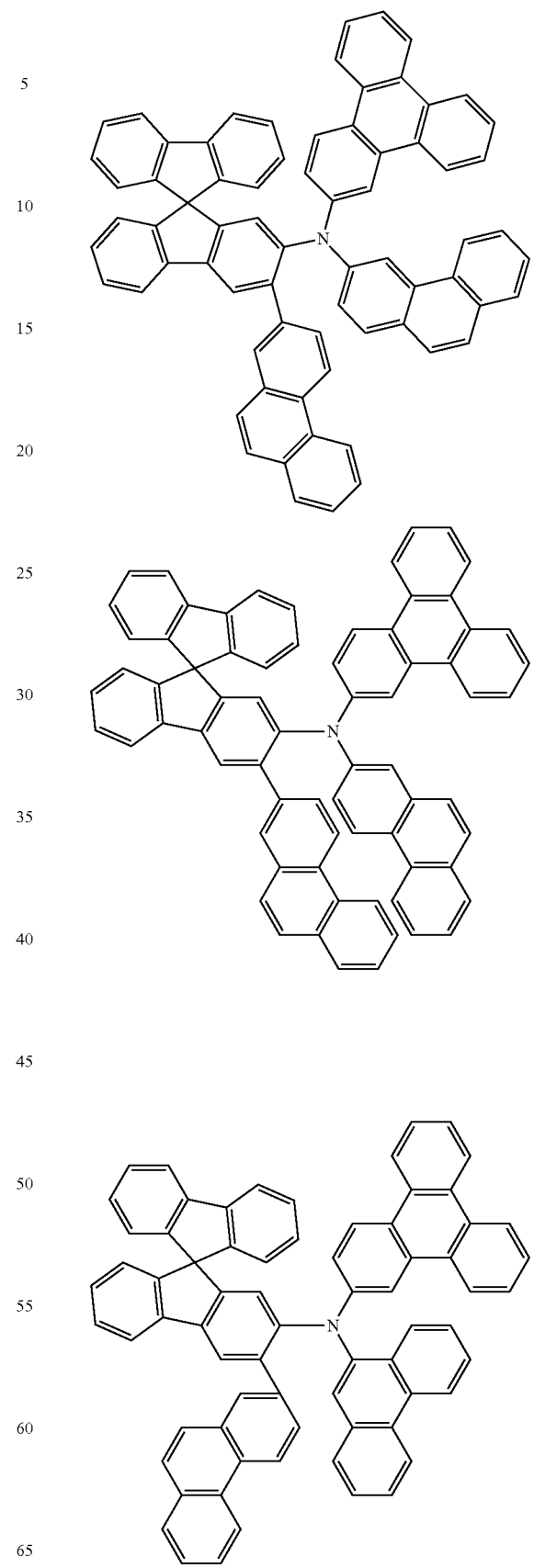

395
-continued
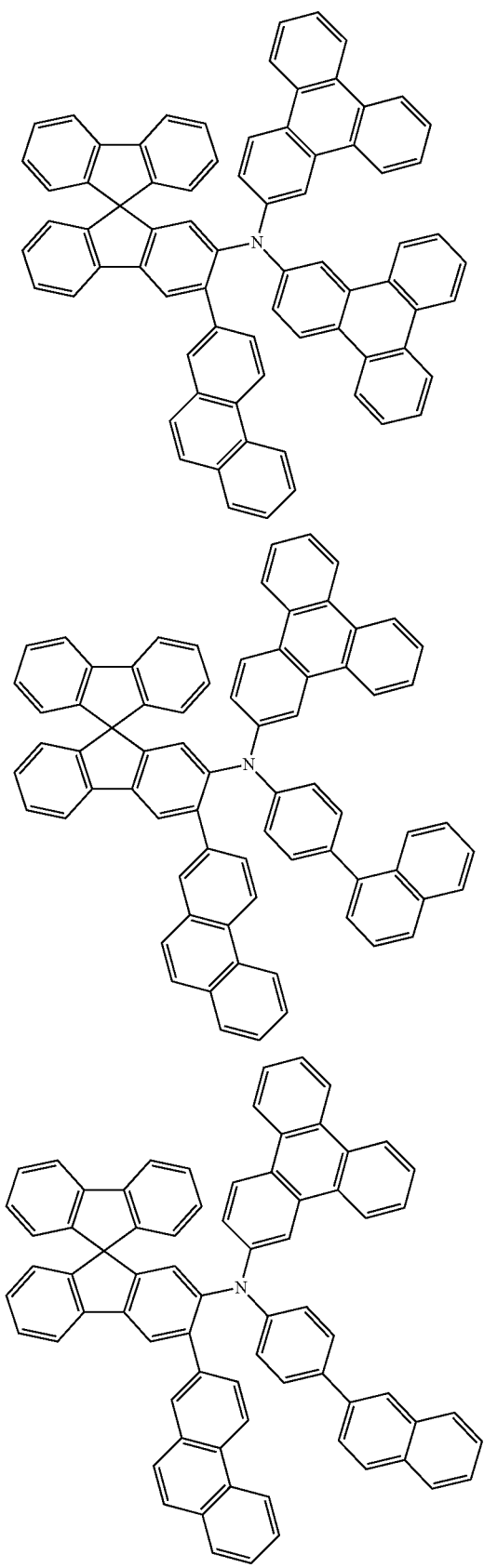
396
-continued
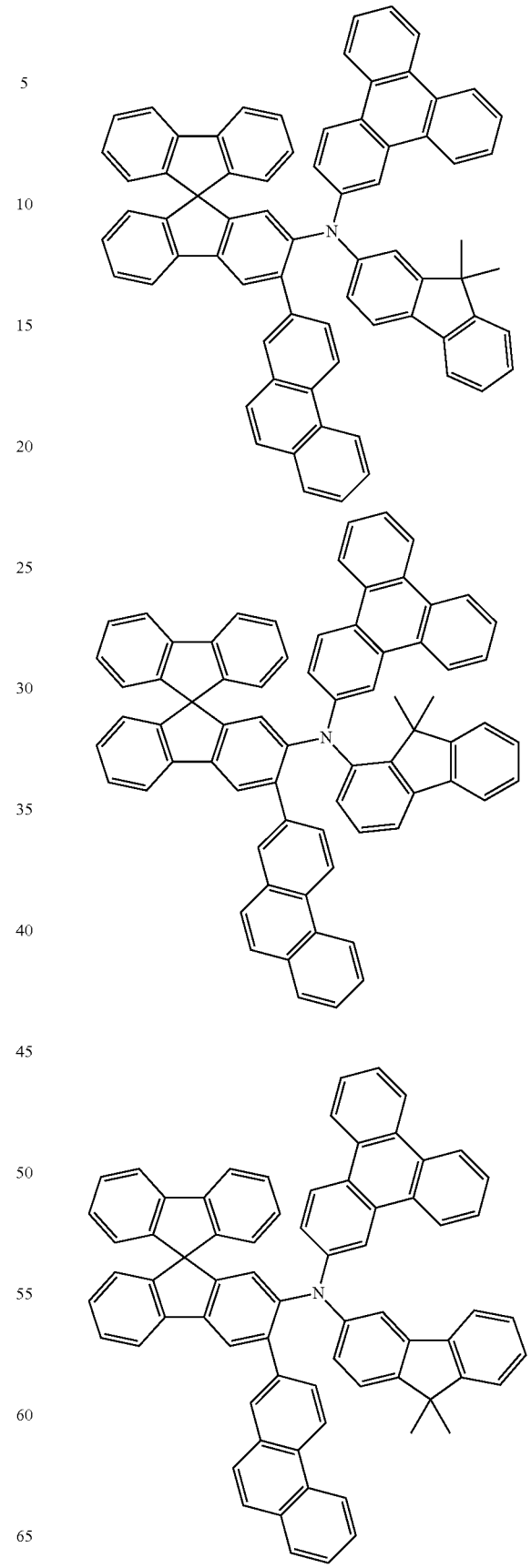

397
-continued
398
-continued
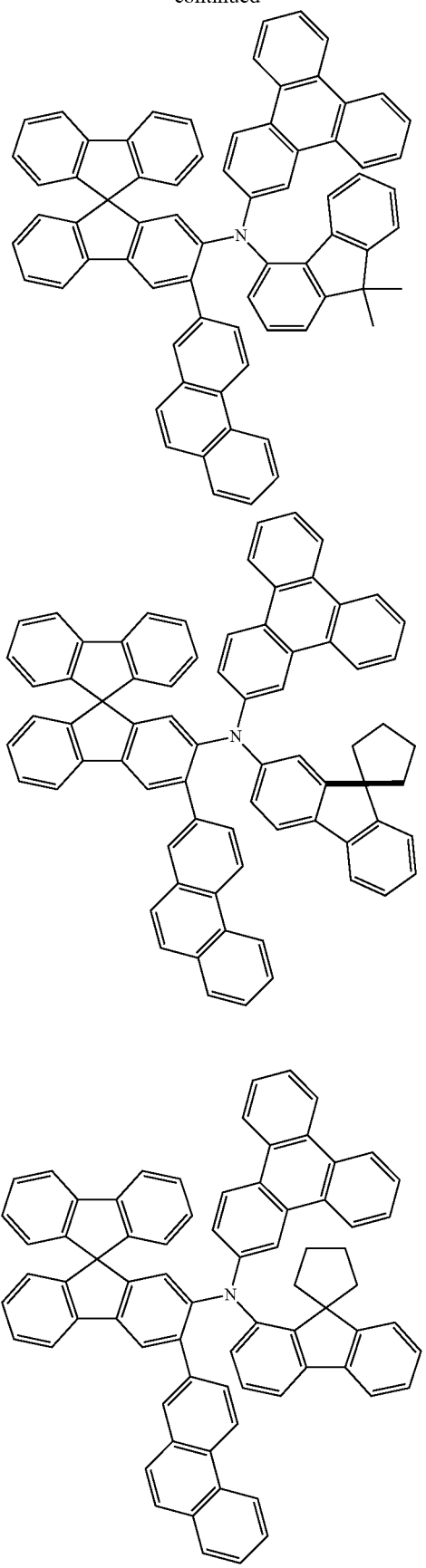
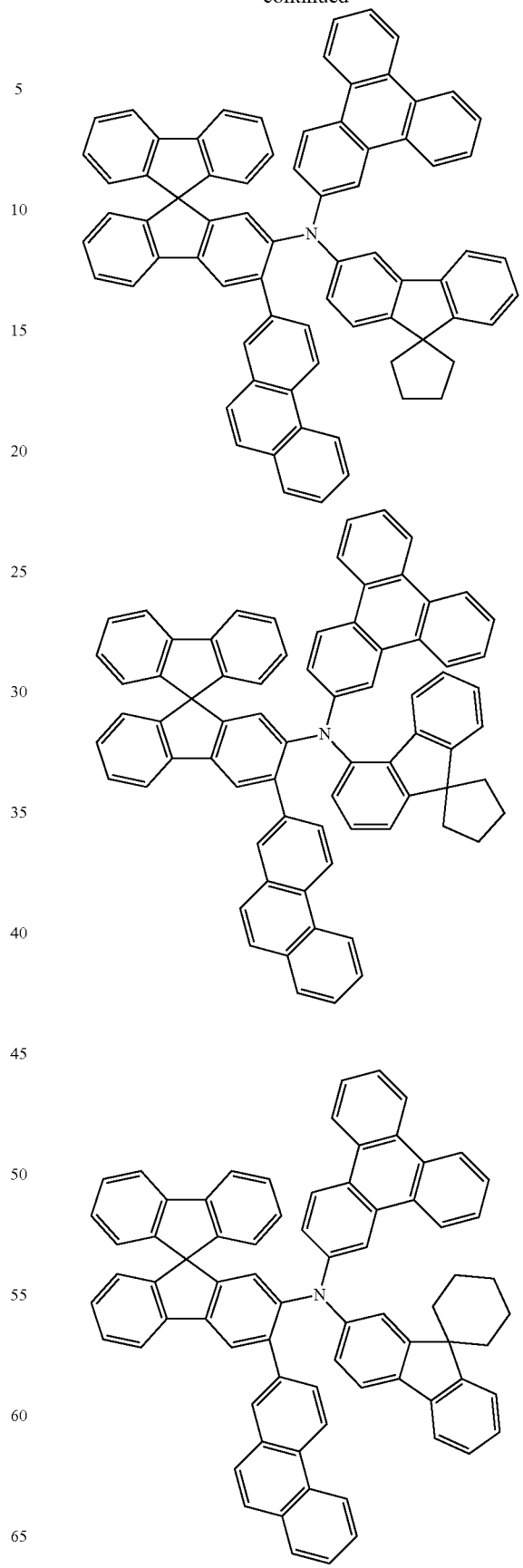

399
-continued
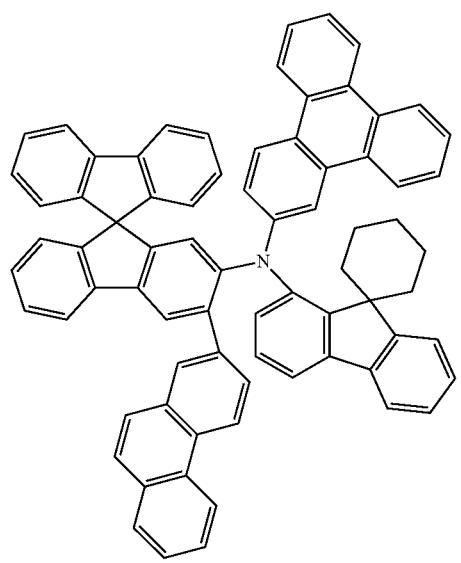
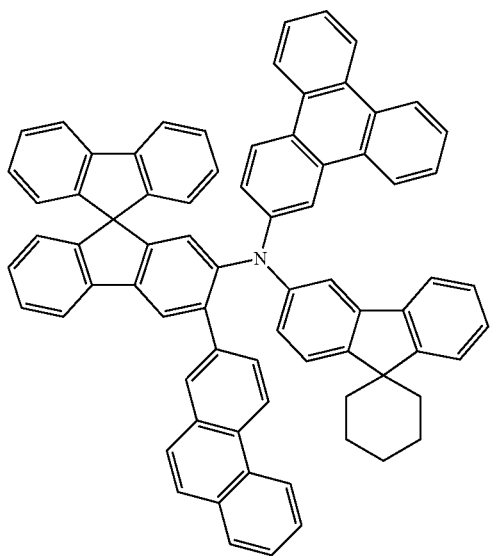
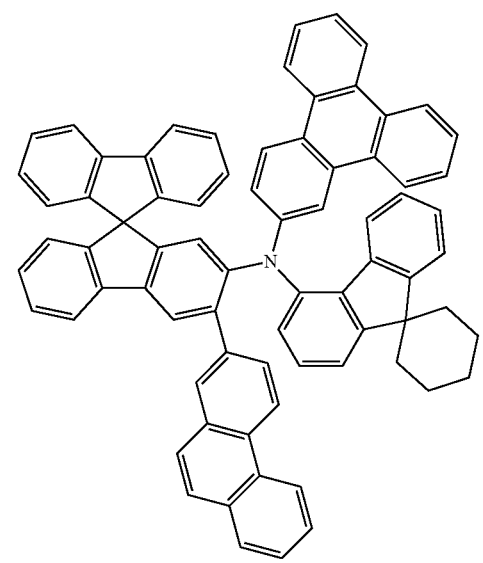
400
-continued
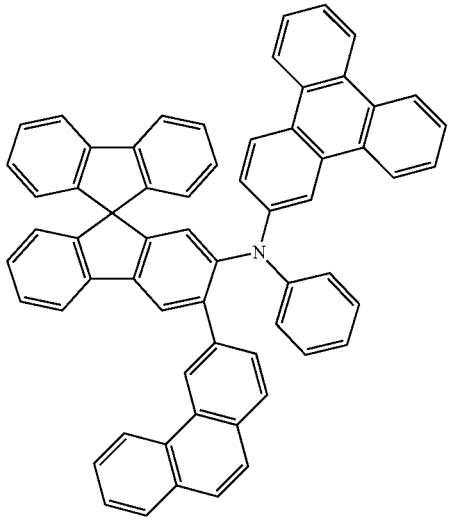
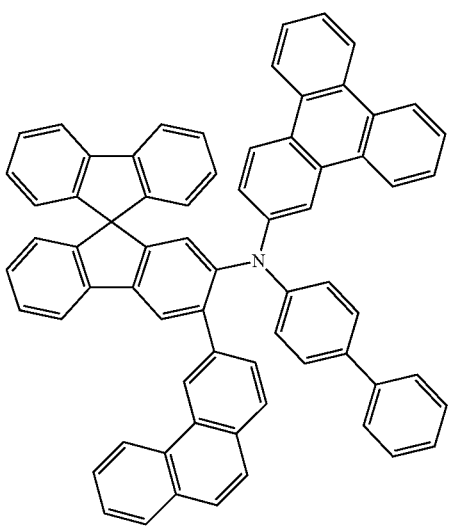
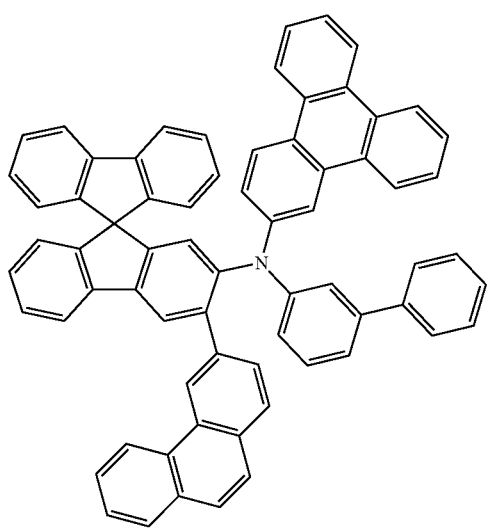

401
-continued
402
-continued
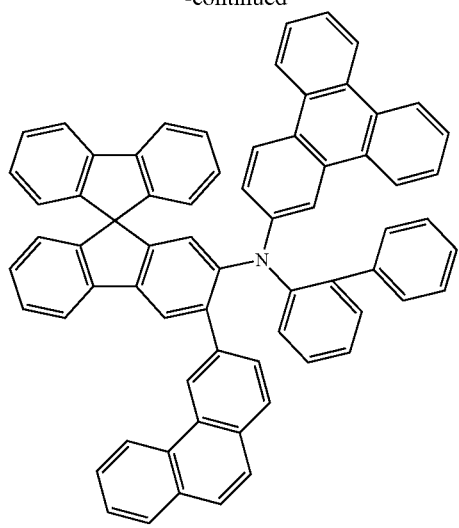
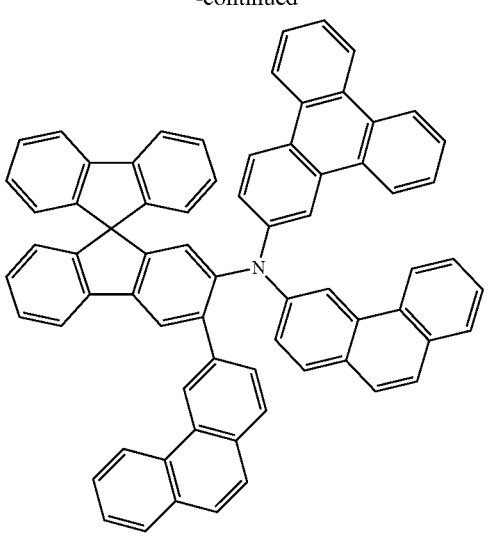
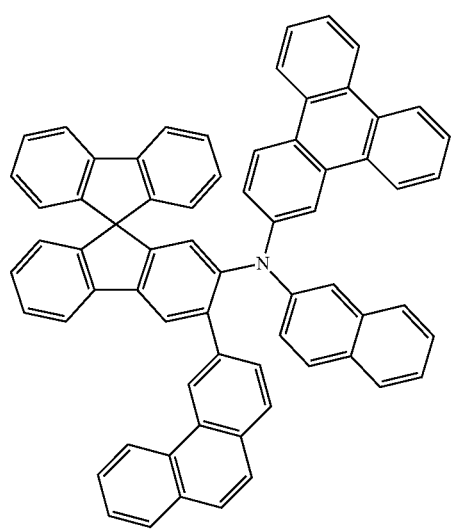
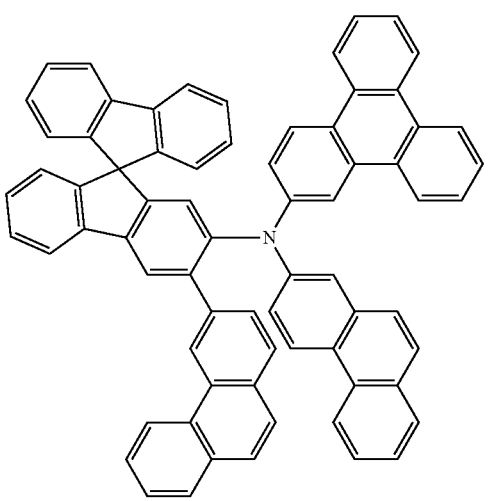
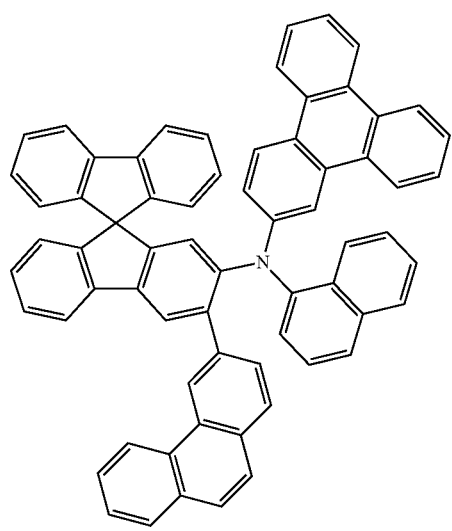
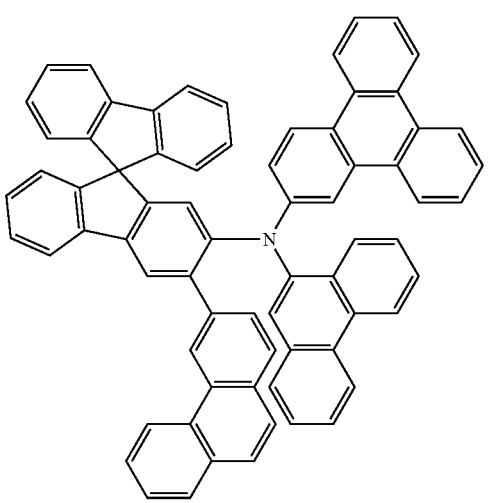

403
-continued
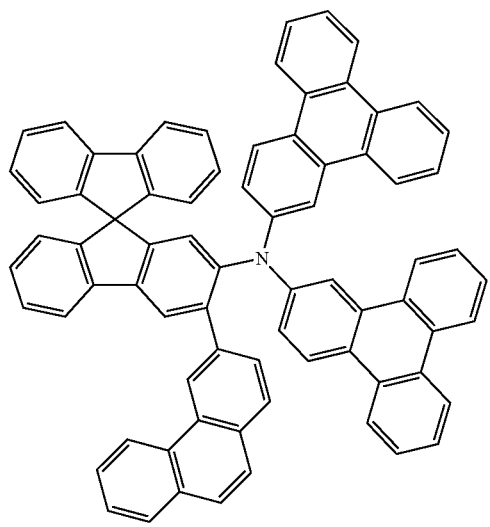
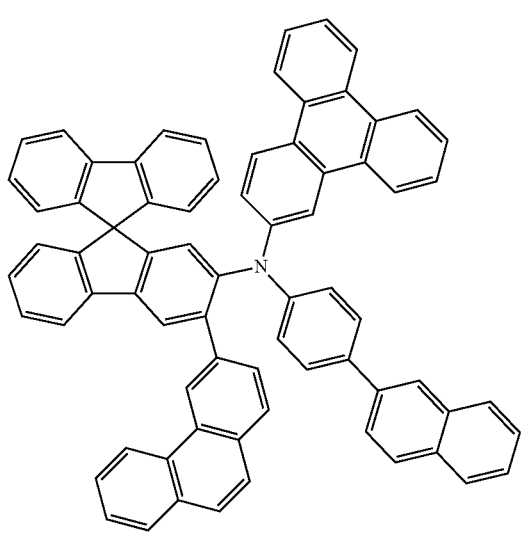
404
-continued
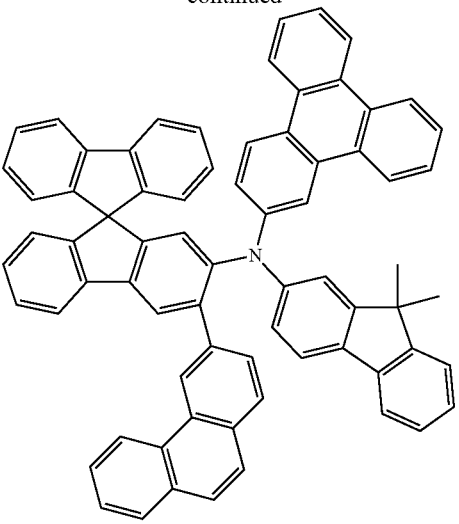
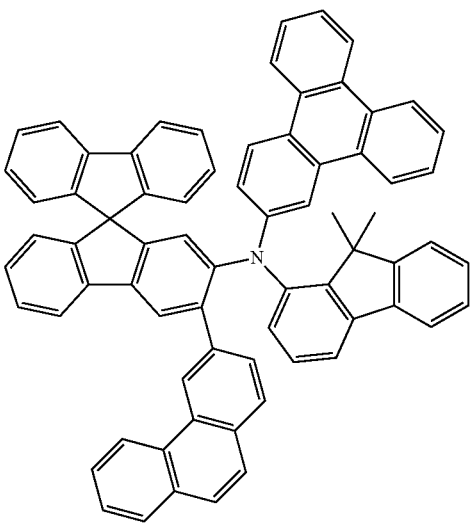
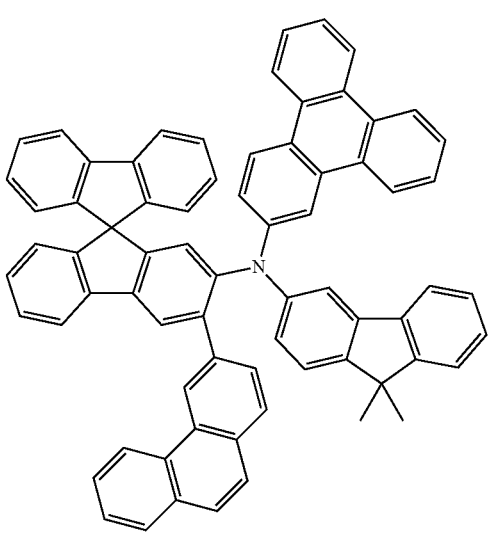

| 405 -continued | 406 -continued |
|---|---|
| 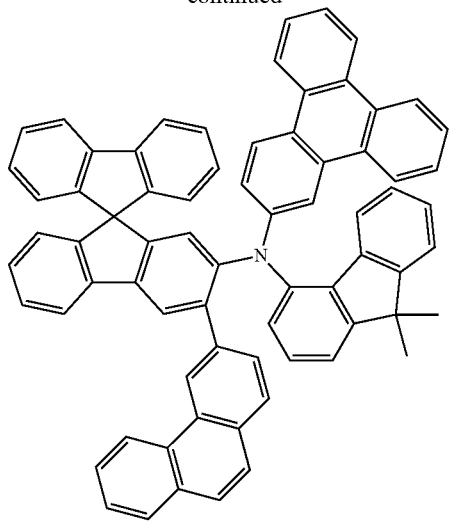 | 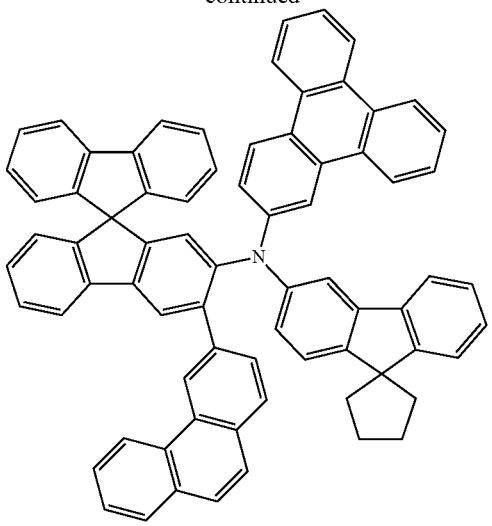 |
| 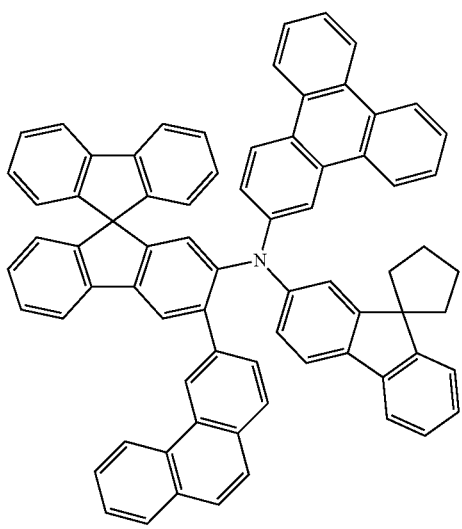 | 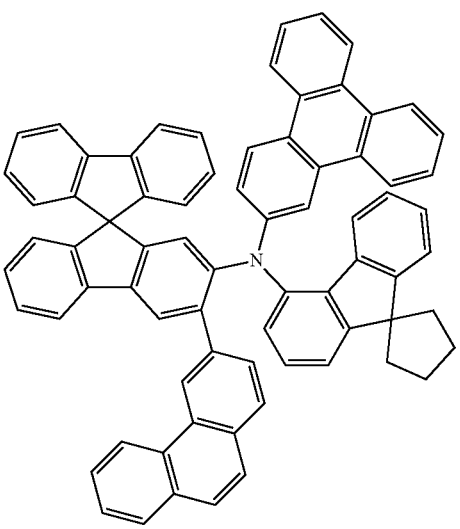 |
| 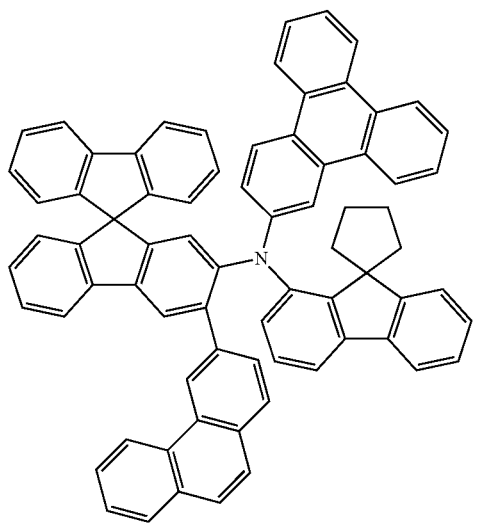 | 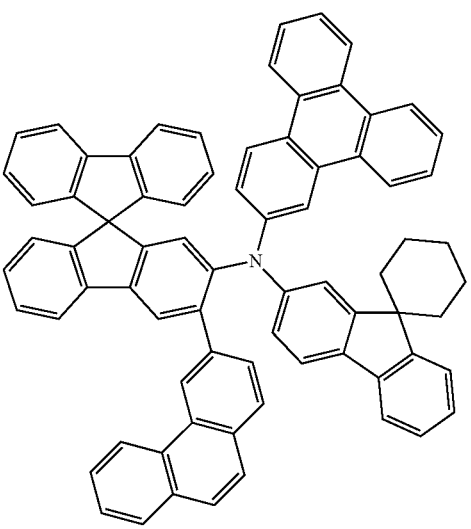 |

| 407 -continued | 408 -continued |
|---|---|
| 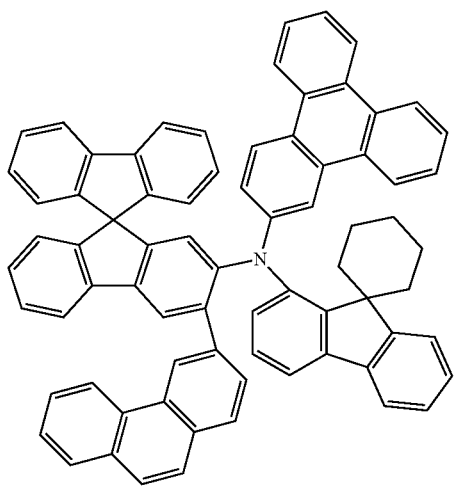 | 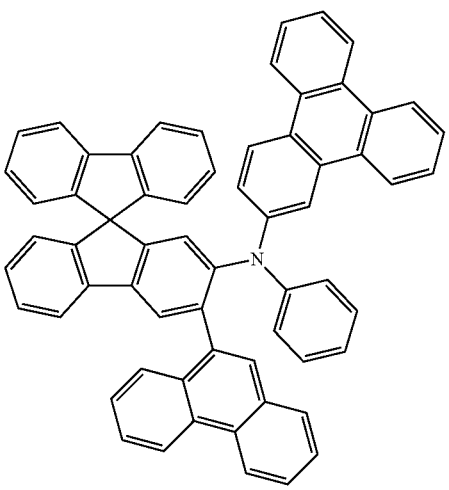 |
| 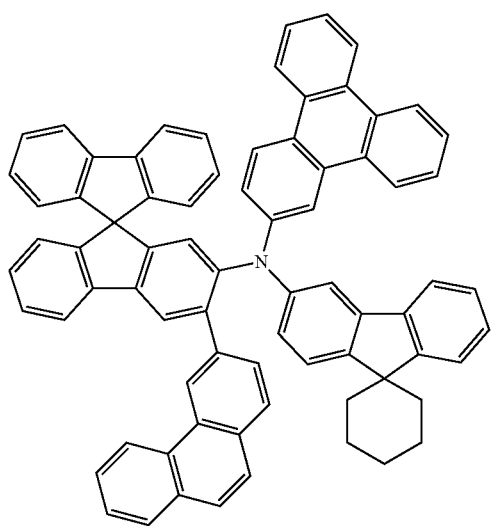 | 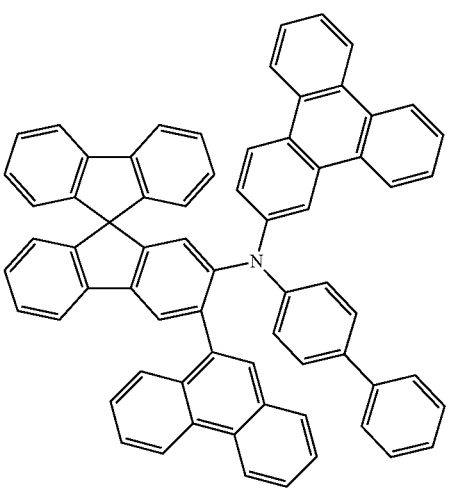 |
| 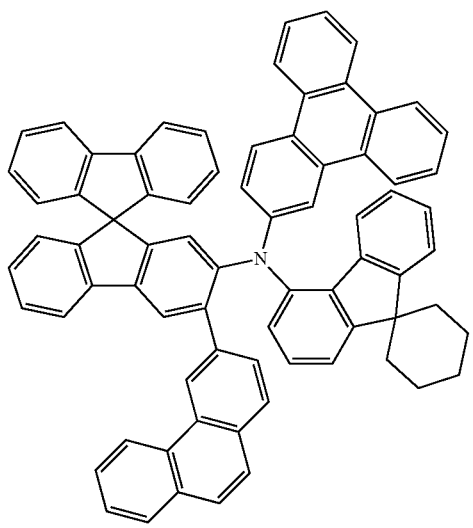 | 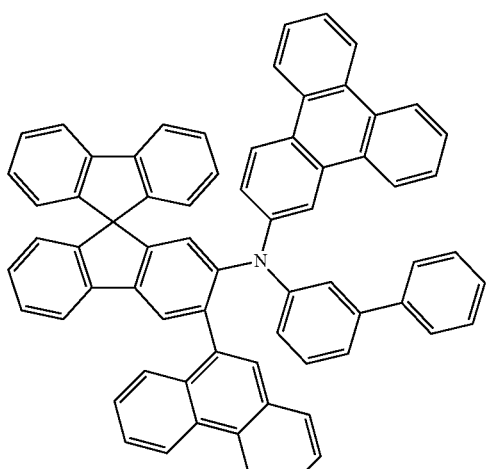 |

409
-continued
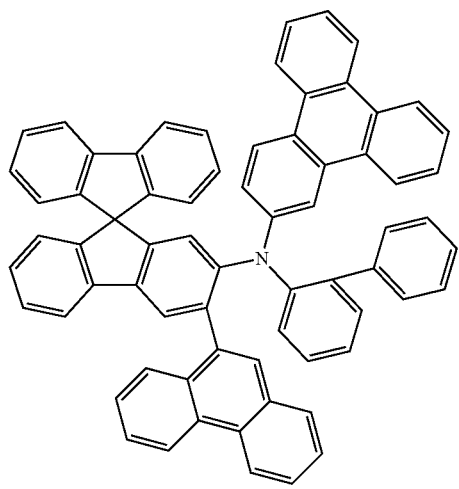
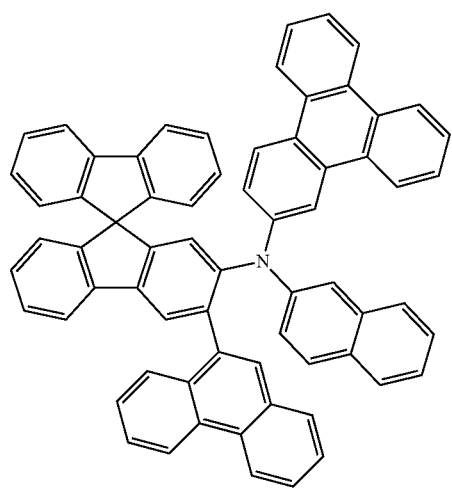
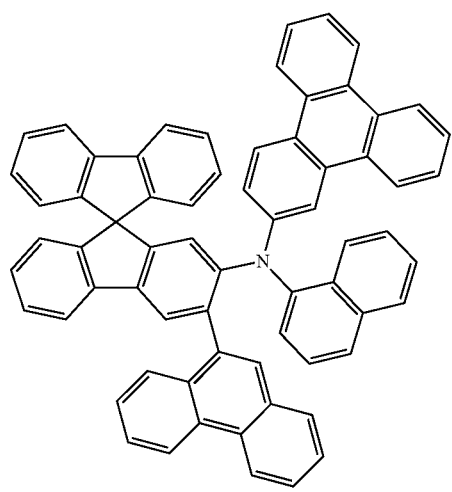
410
-continued
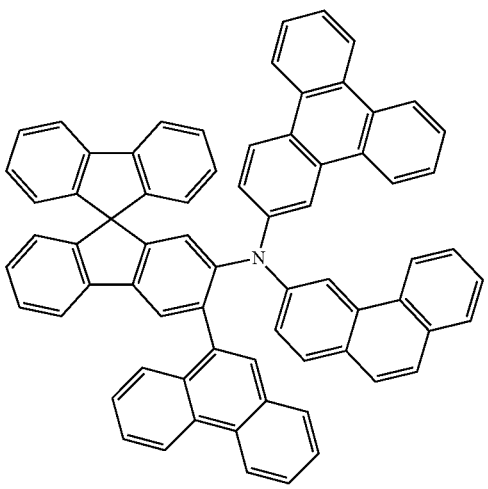
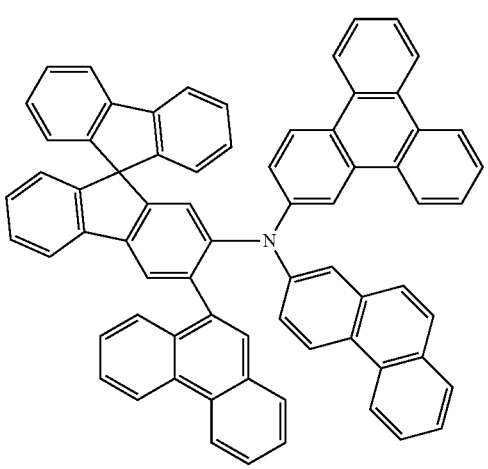
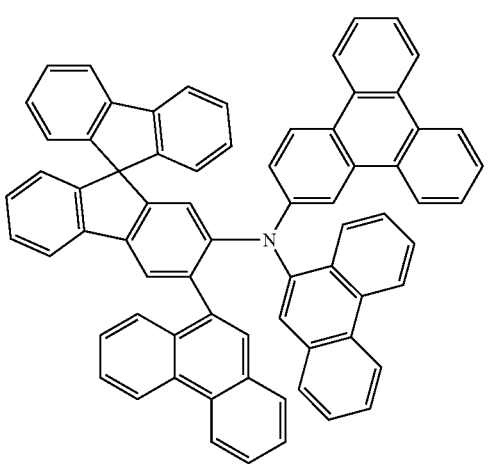

411
-continued
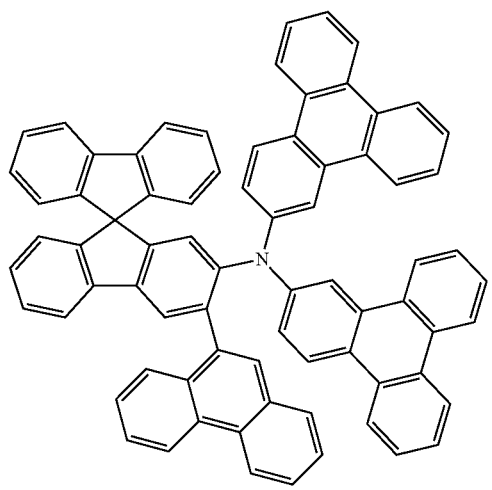
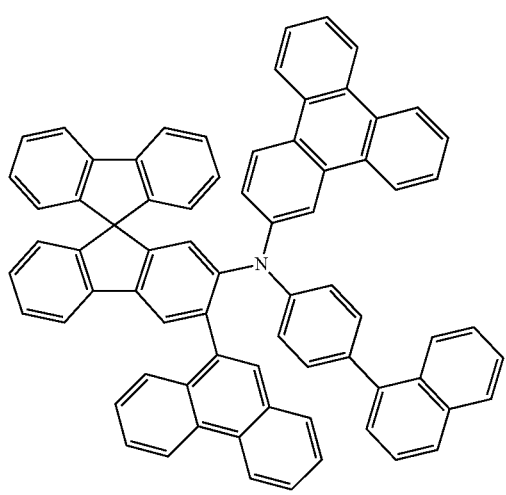
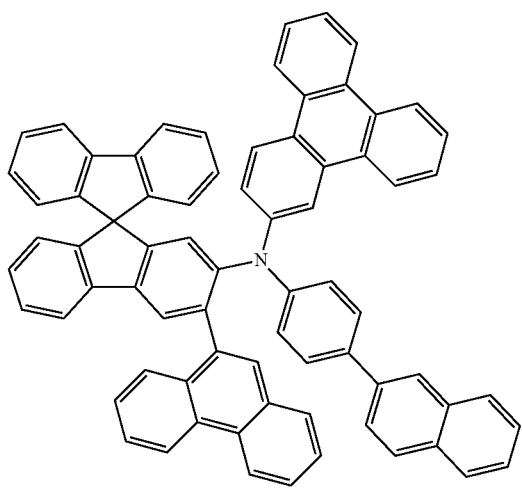
412
-continued
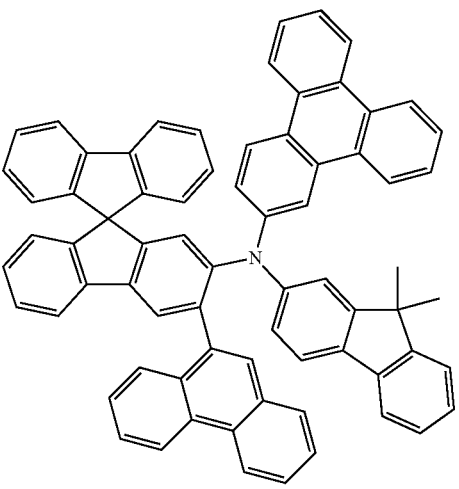
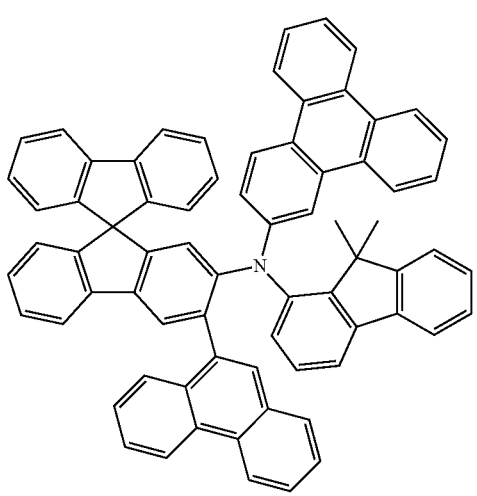
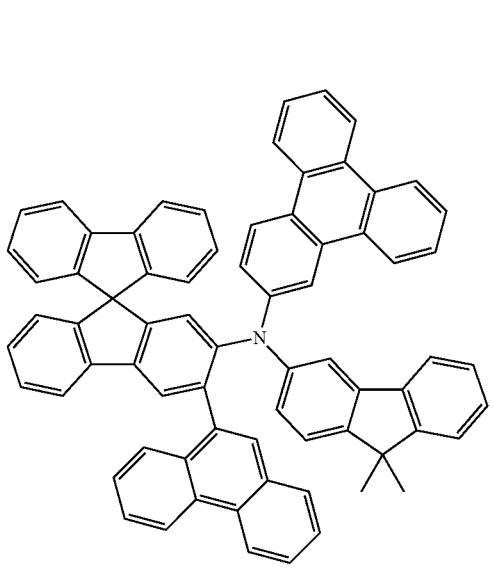

413
-continued
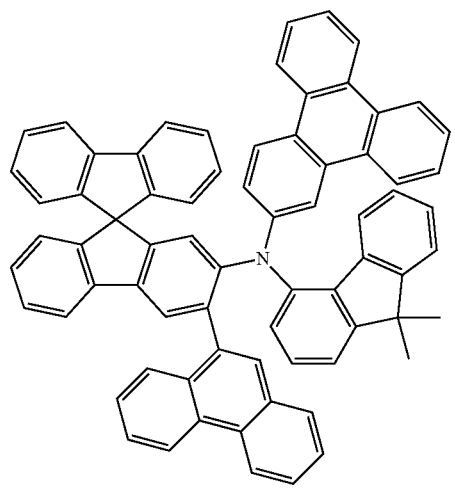
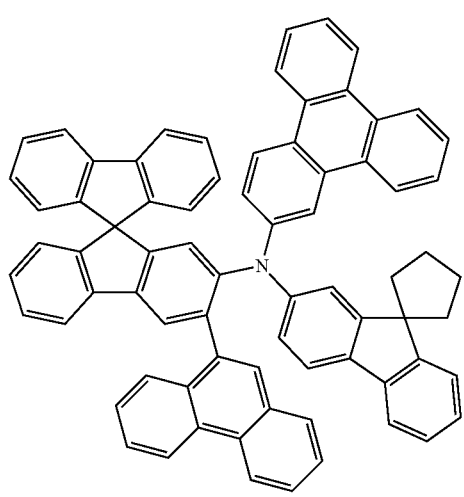
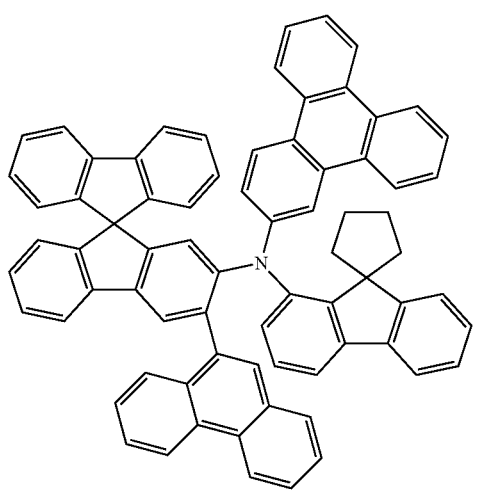
414
-continued
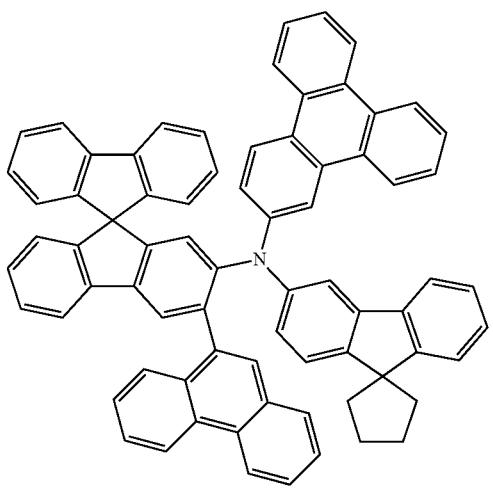
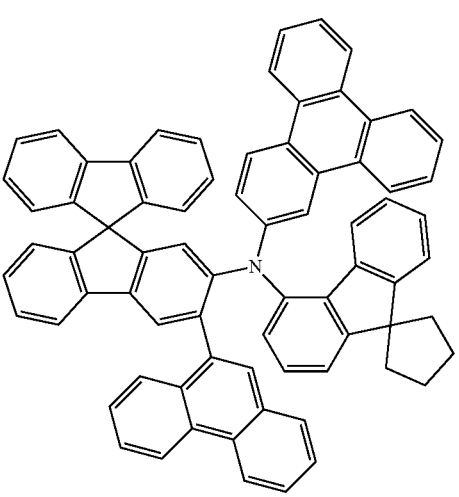
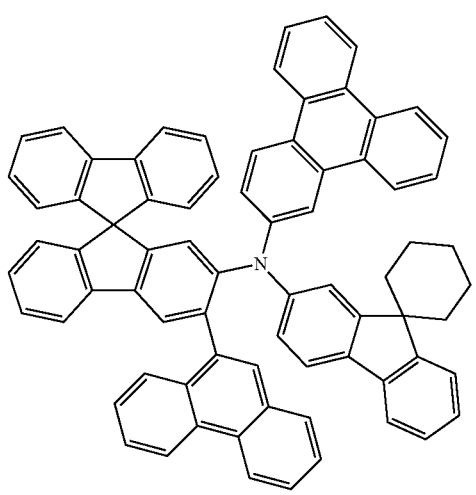

415
-continued
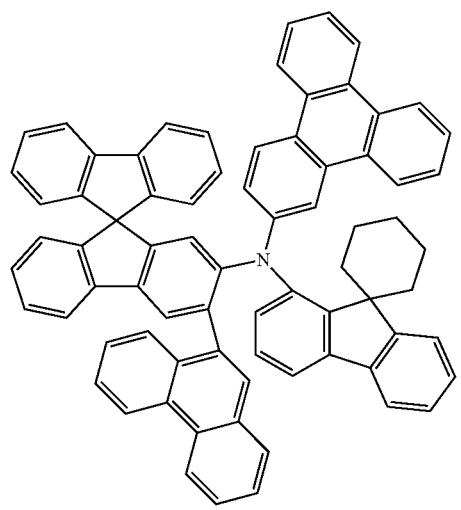
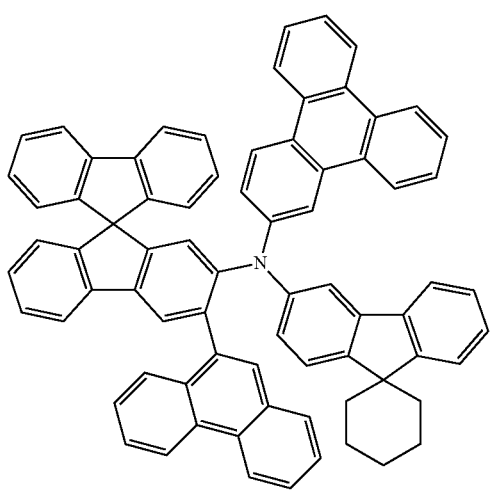
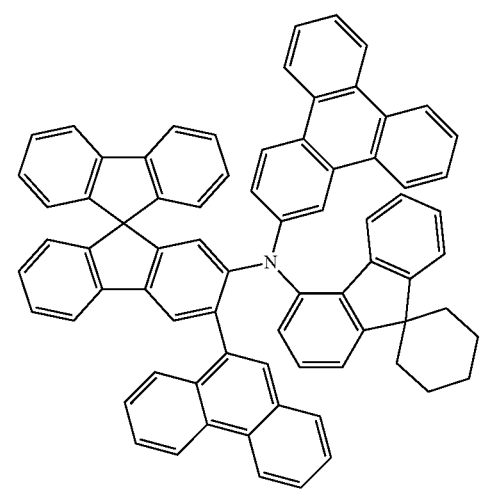
416
-continued
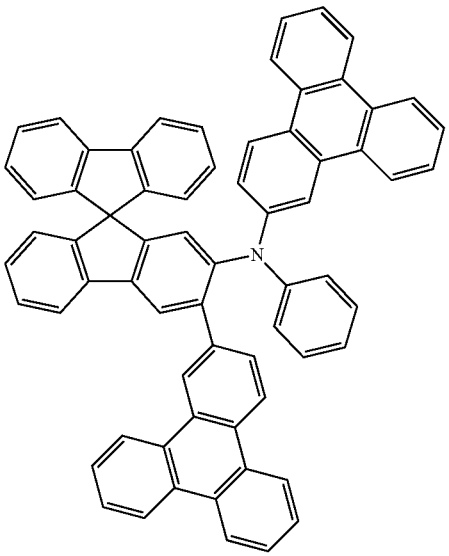
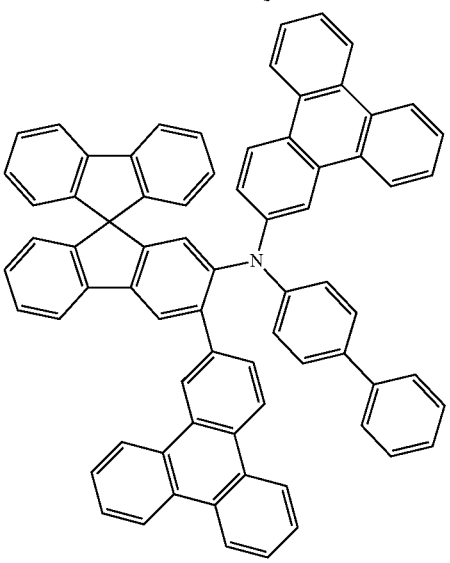
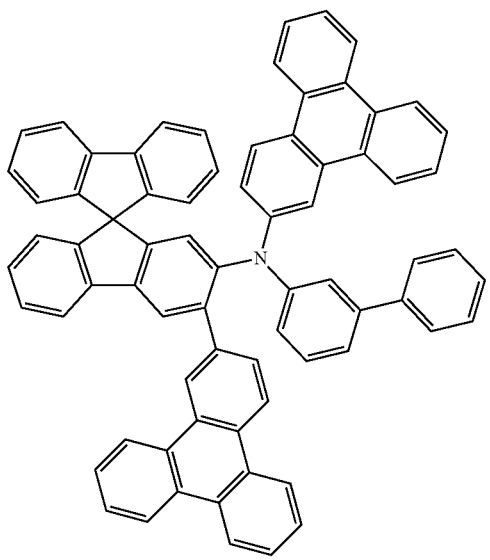

417
-continued
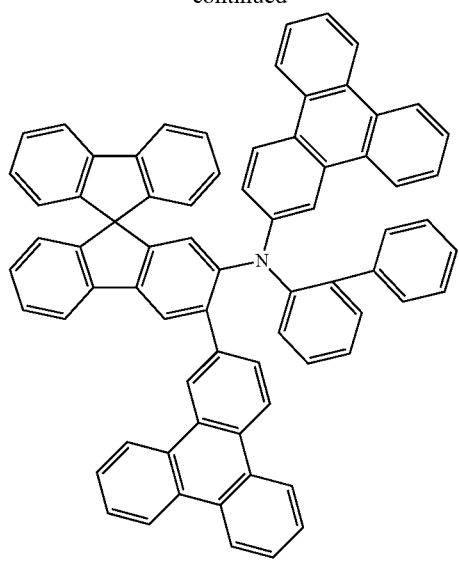
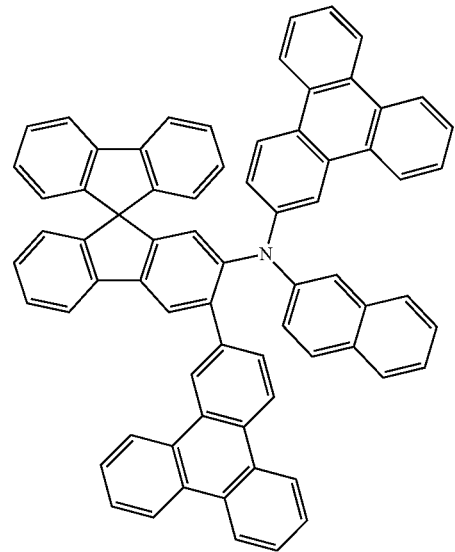
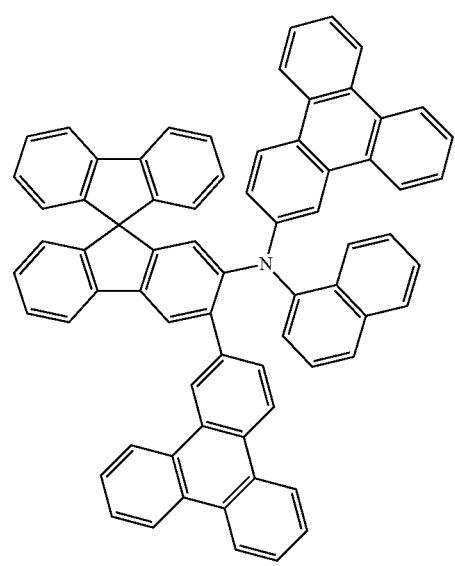
418
-continued
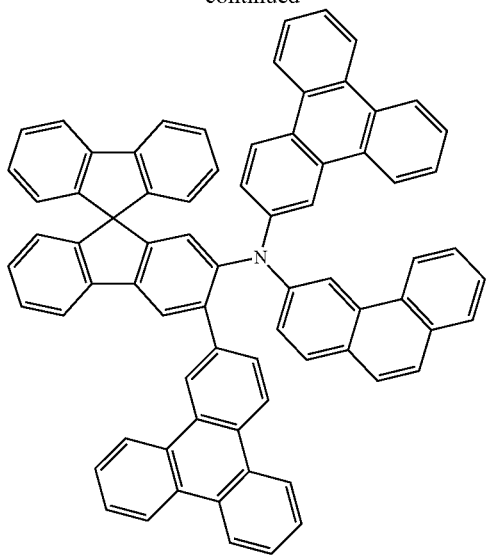
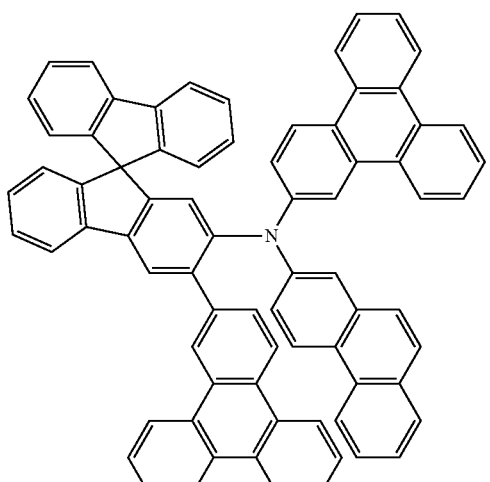
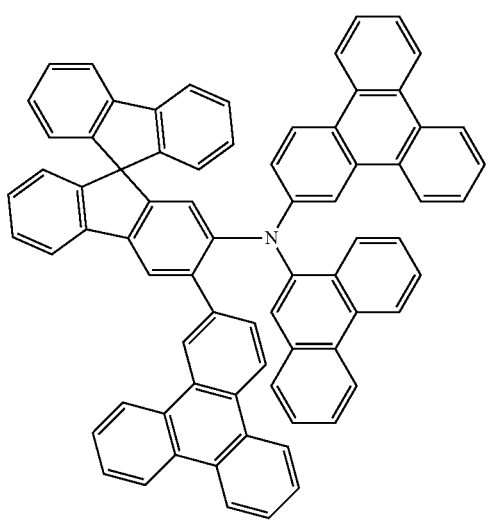

419
-continued
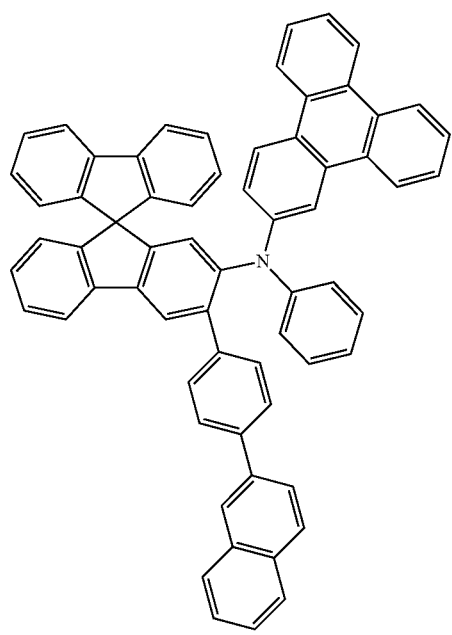
420
-continued
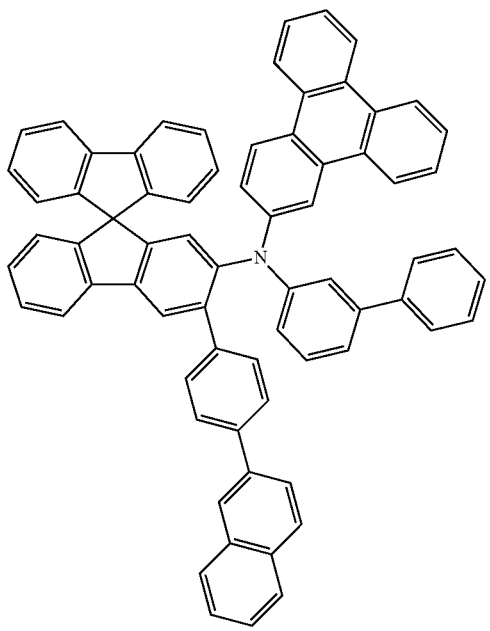
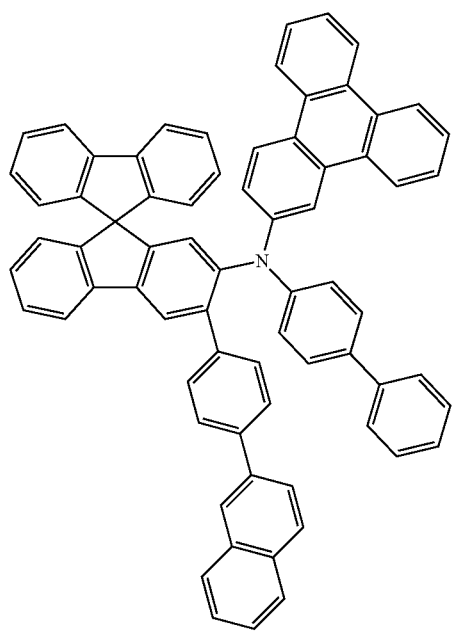
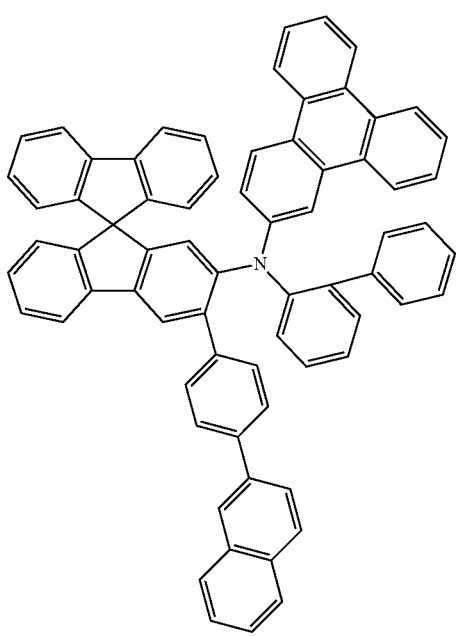

421
-continued
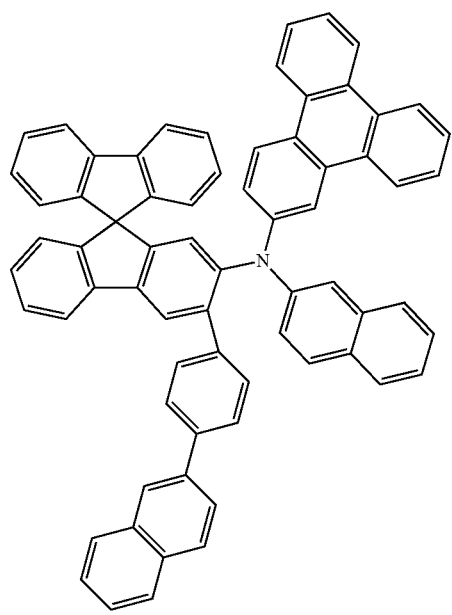
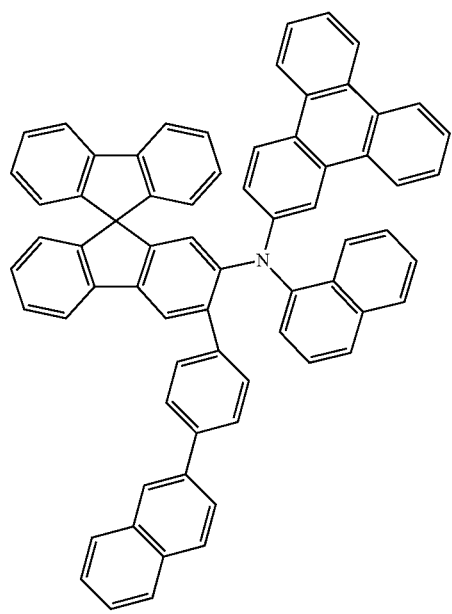
422
-continued
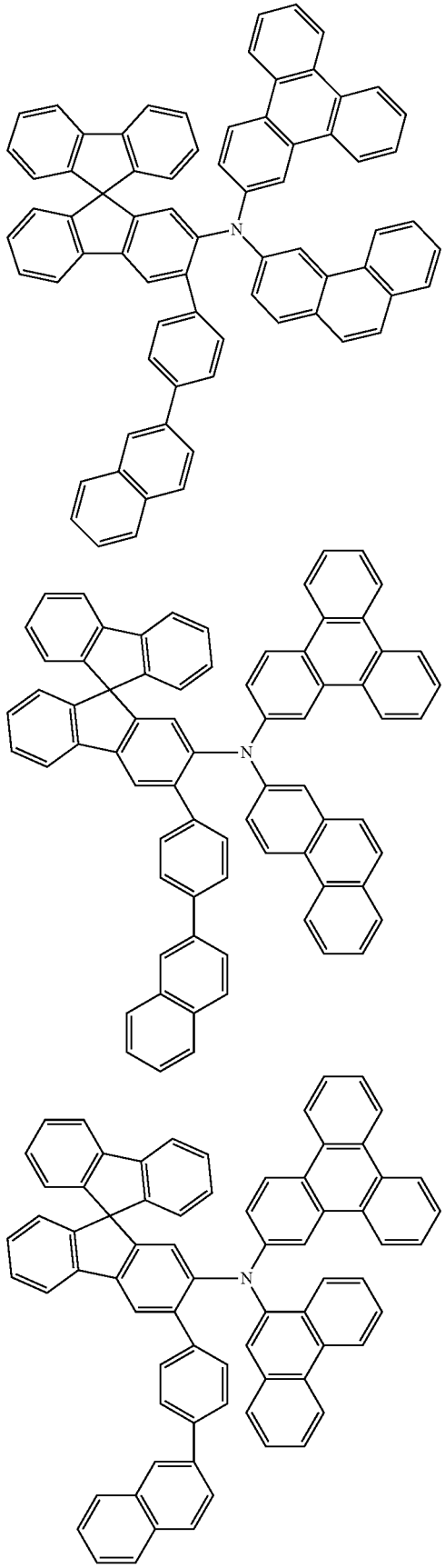 [SMILES: c1ccc2c(c1)-c1ccccc1C21c2ccccc2-c2cc(-c3ccc(-c4ccc5ccccc5c4)cc3)c(N(c3ccc4ccc5ccccc5c4c3)c3ccc4c5ccccc5c5ccccc5c4c3)cc21 ; c1ccc2c(c1)-c1ccccc1C21c2ccccc2-c2cc(-c3ccc(-c4ccc5ccccc5c4)cc3)c(N(c3ccc4c(ccc5ccccc54)c3)c3ccc4c5ccccc5c5ccccc5c4c3)cc21 ; c1ccc2c(c1)-c1ccccc1C21c2ccccc2-c2cc(-c3ccc(-c4ccc5ccccc5c4)cc3)c(N(c3ccc4c5ccccc5c5ccccc5c4c3)c3cc4ccccc4c4ccccc34)cc21]

423
-continued
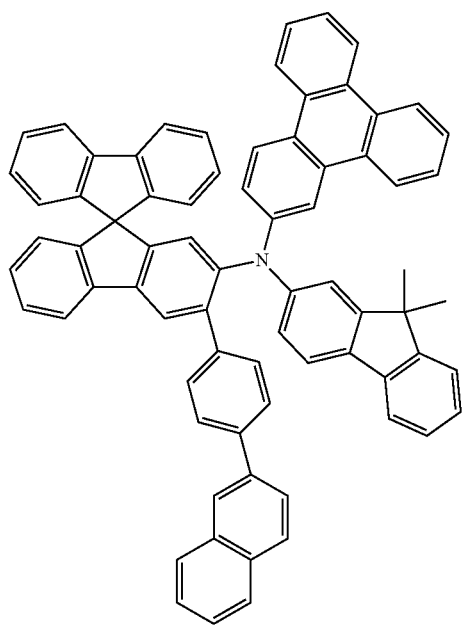
424
-continued
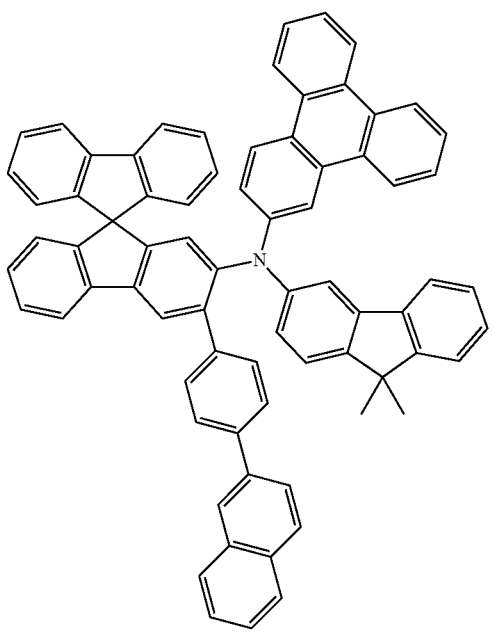
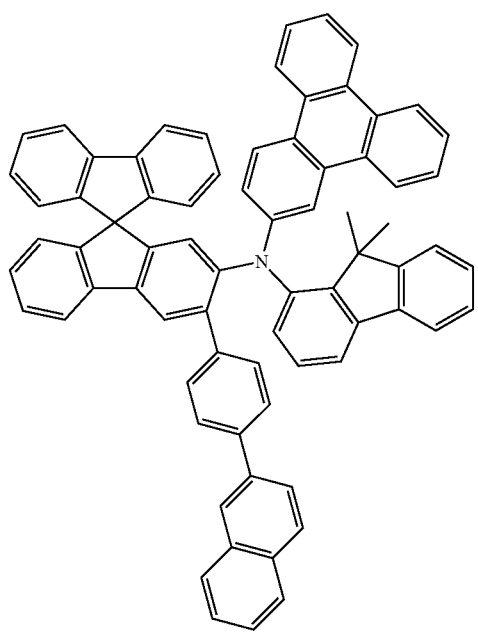
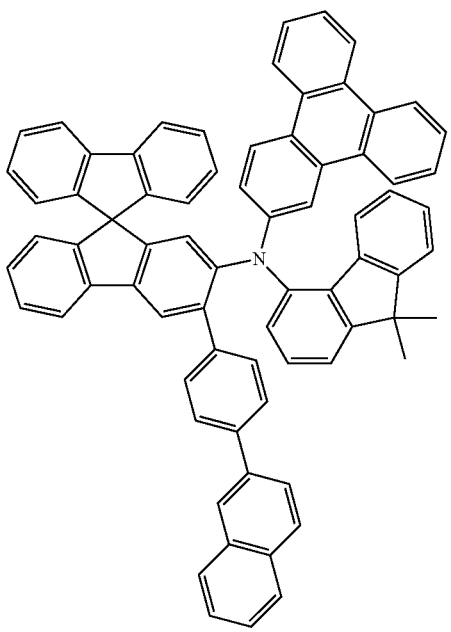

425
-continued
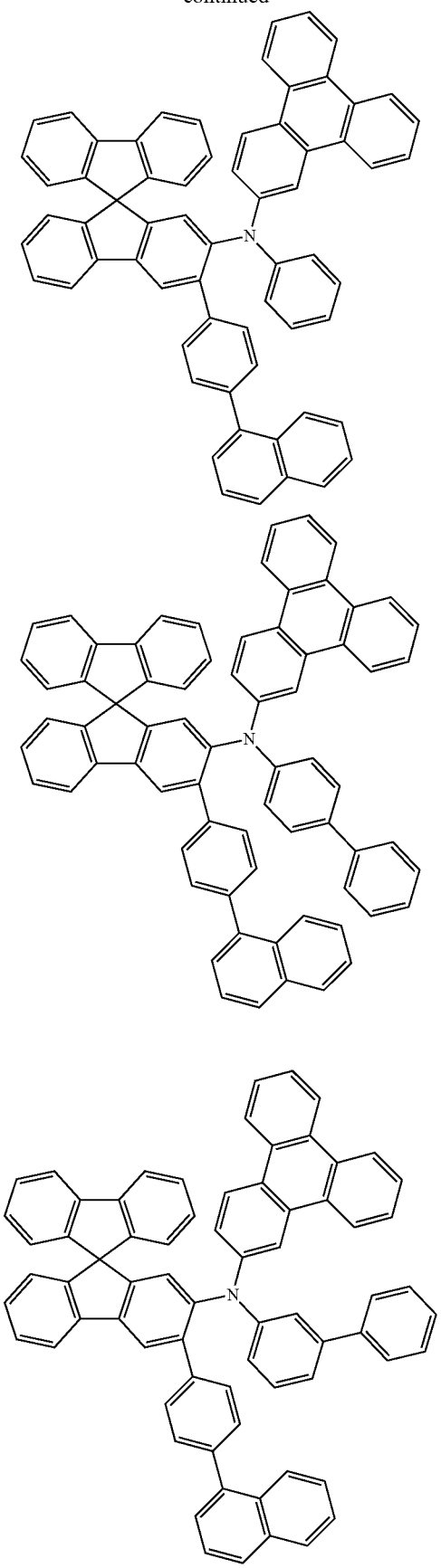
426
-continued
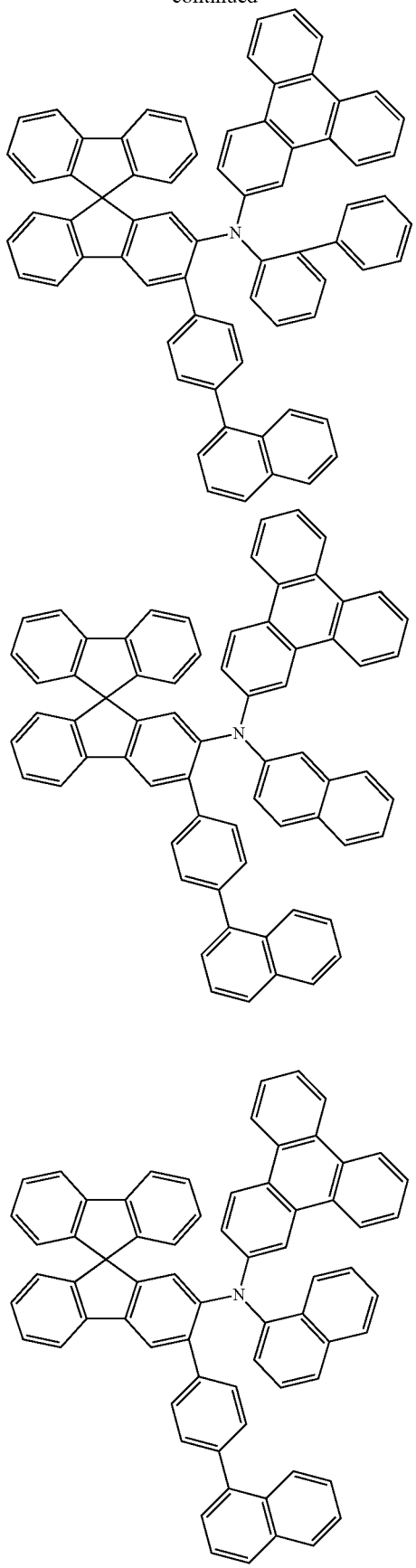

427
-continued
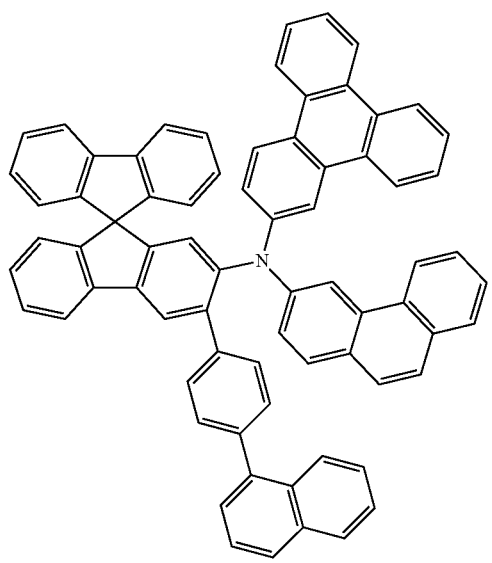
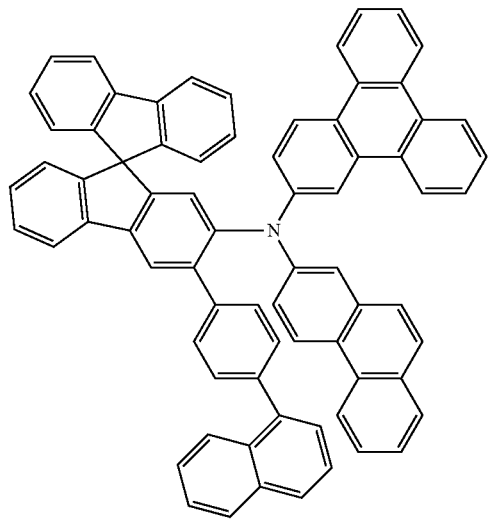
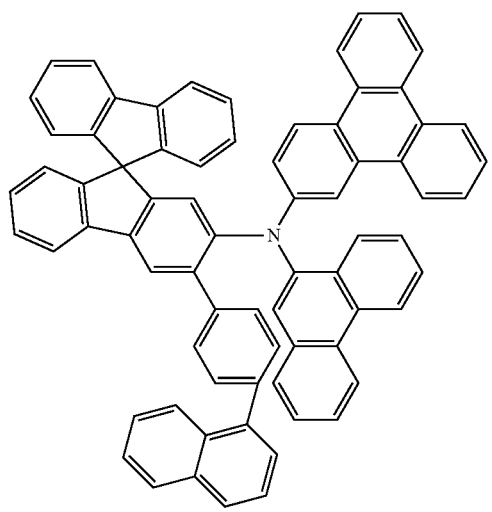
428
-continued
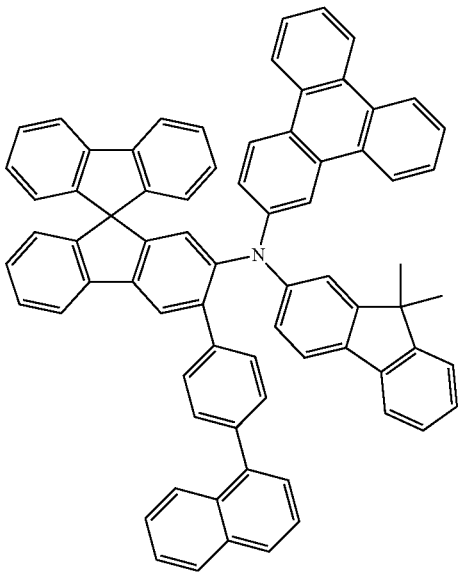
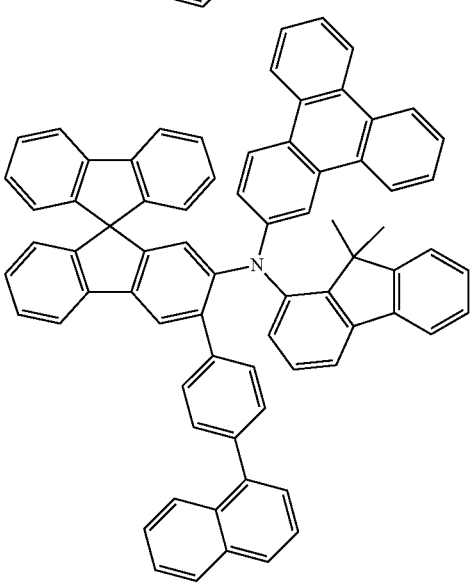
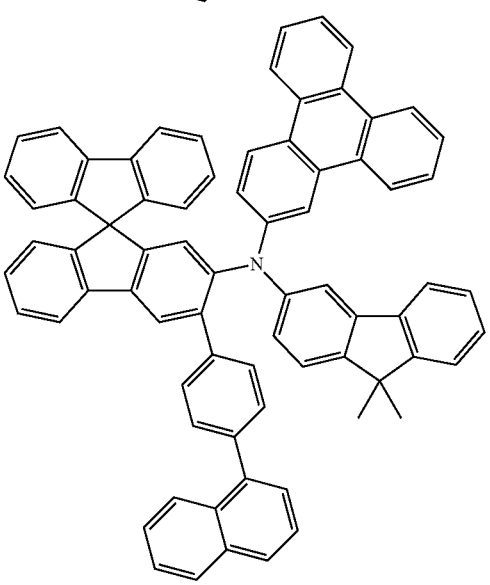

429
-continued
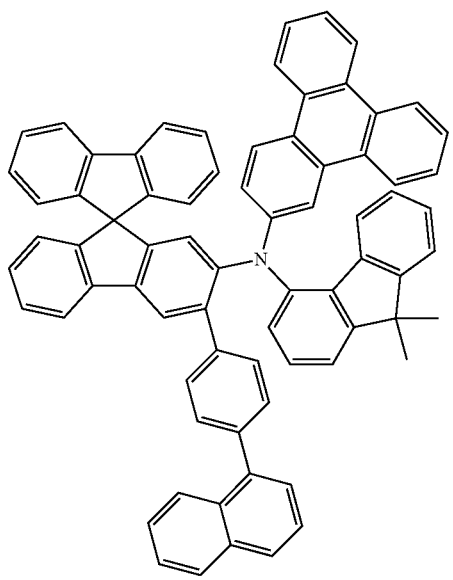
430
-continued
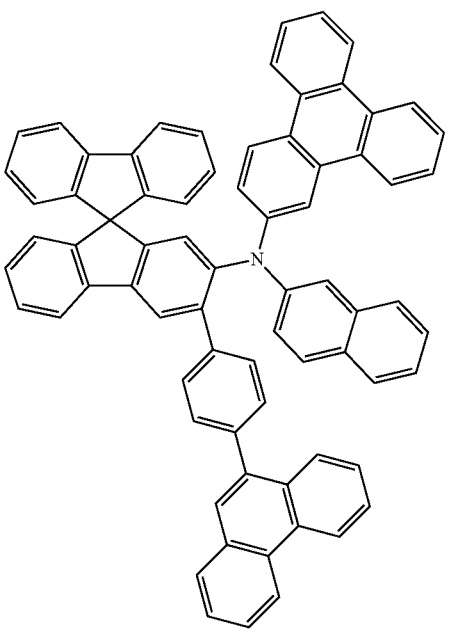
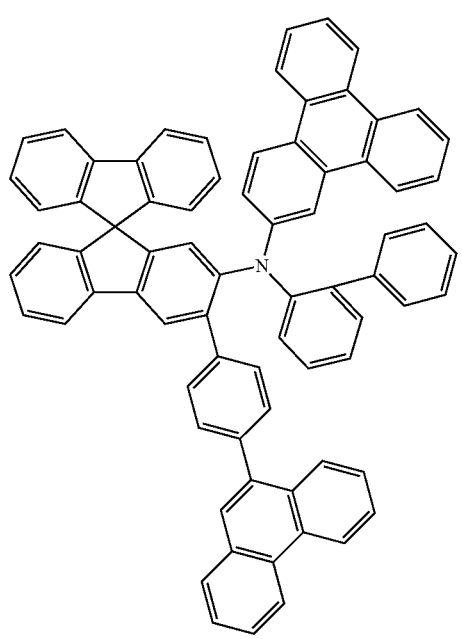
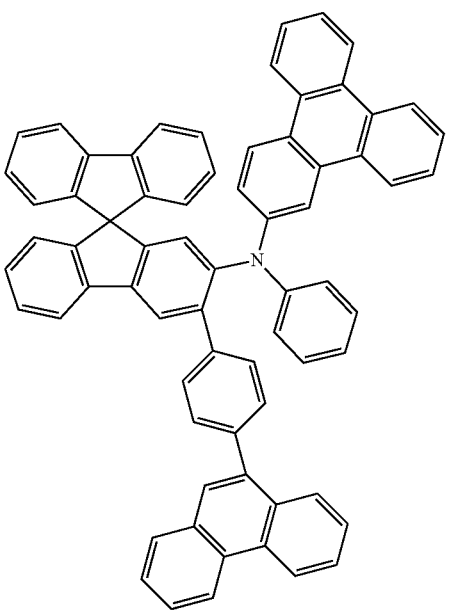

431
-continued
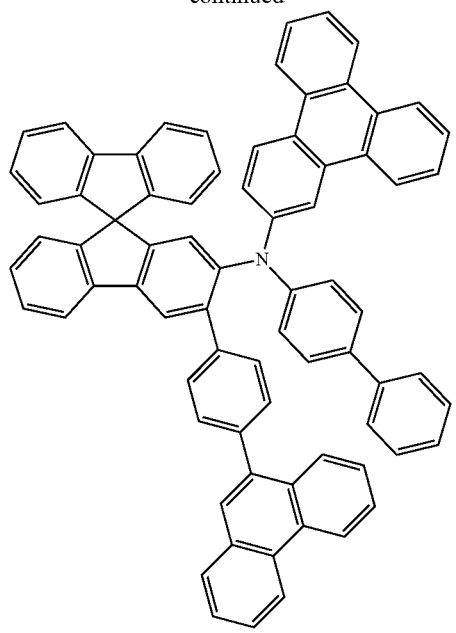
432
-continued
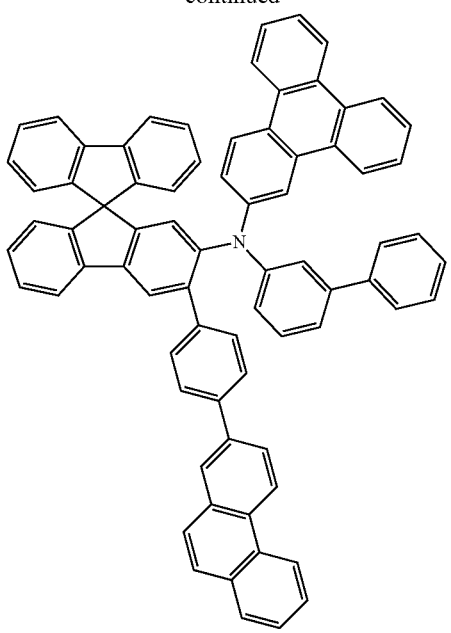
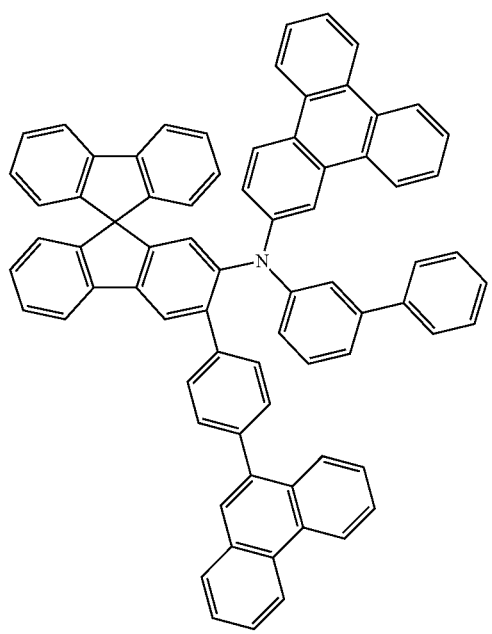
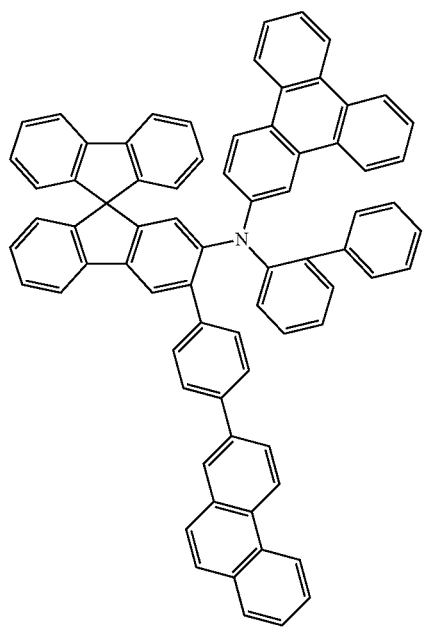

433
-continued
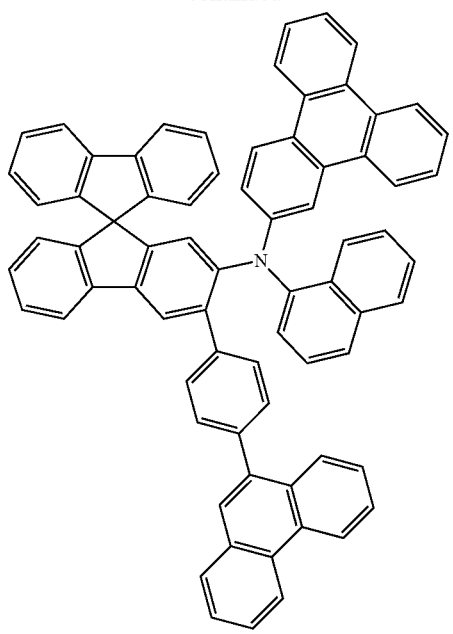
434
-continued
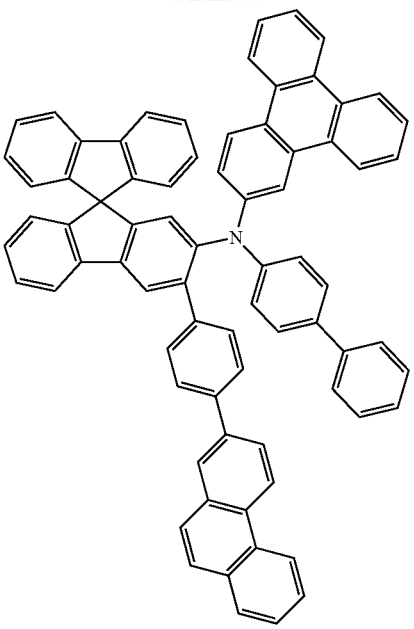
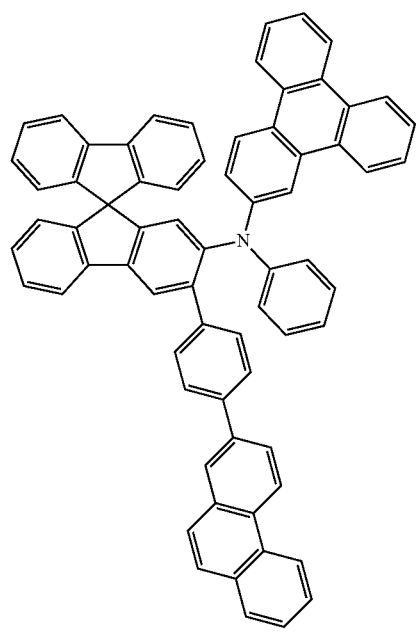
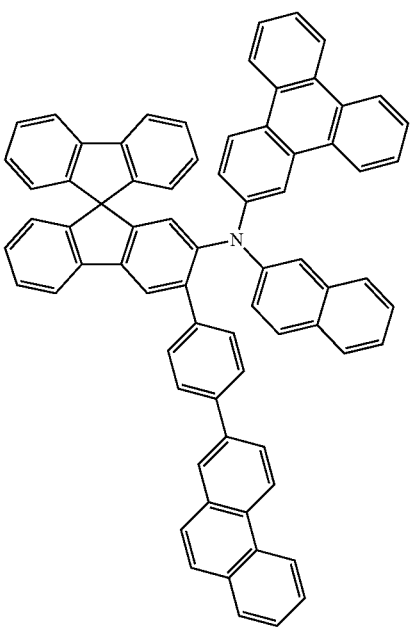

435
-continued
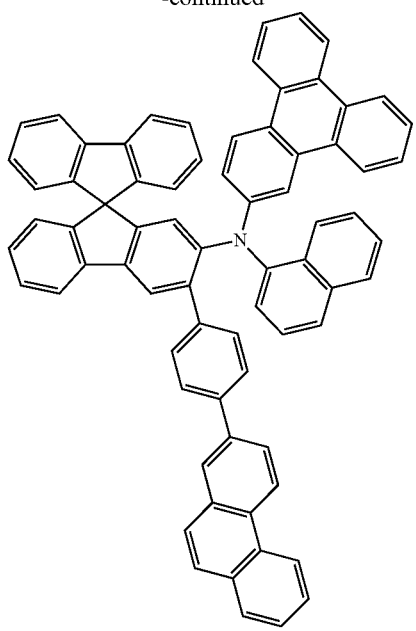
436
-continued
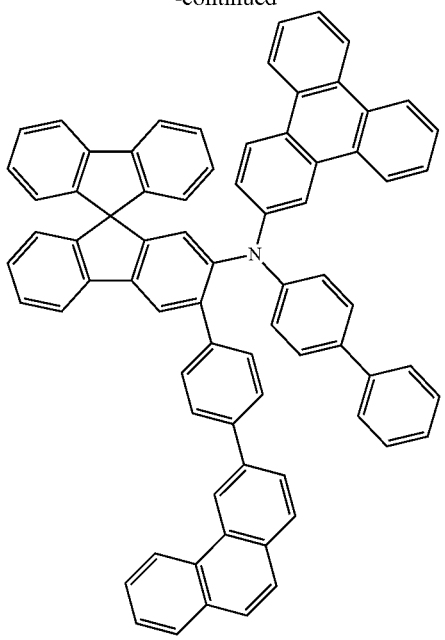
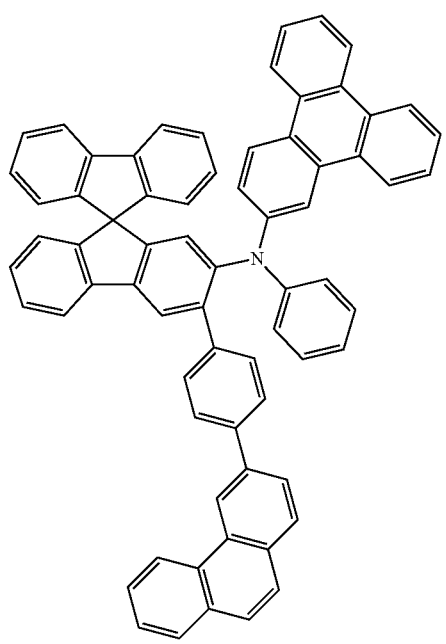
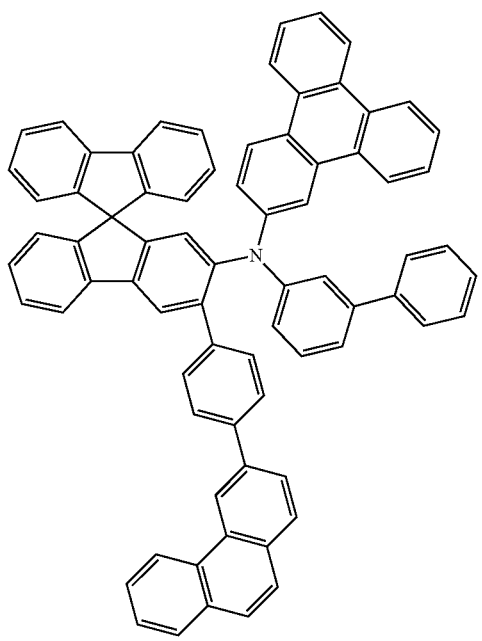

437
-continued
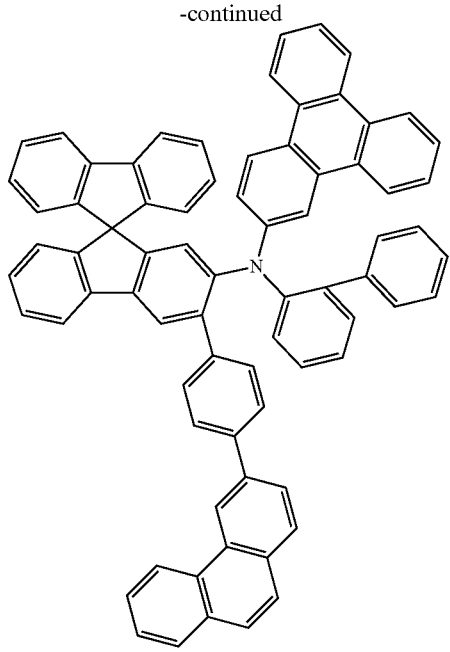
438
-continued
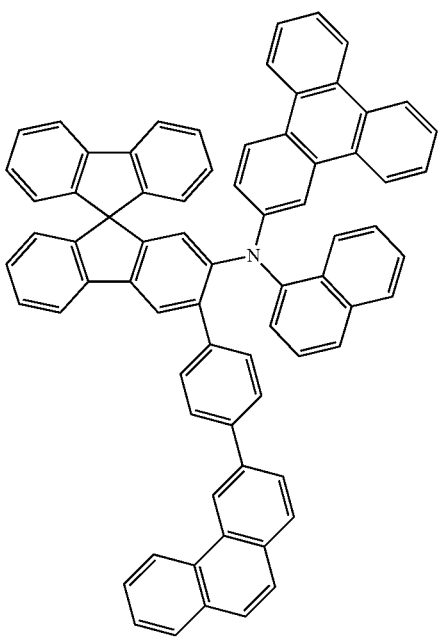
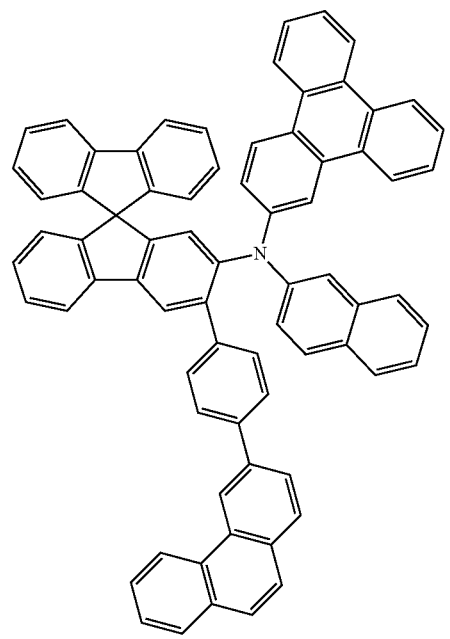
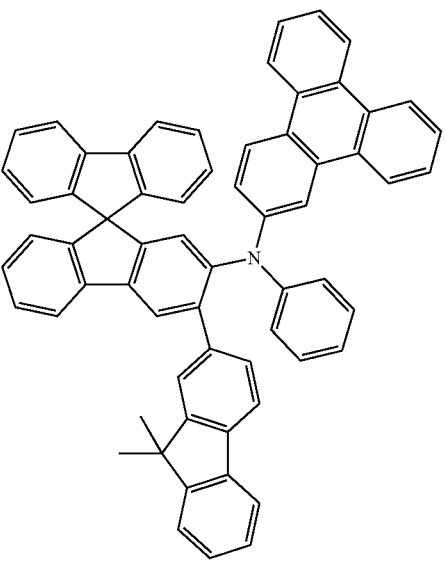

439
-continued
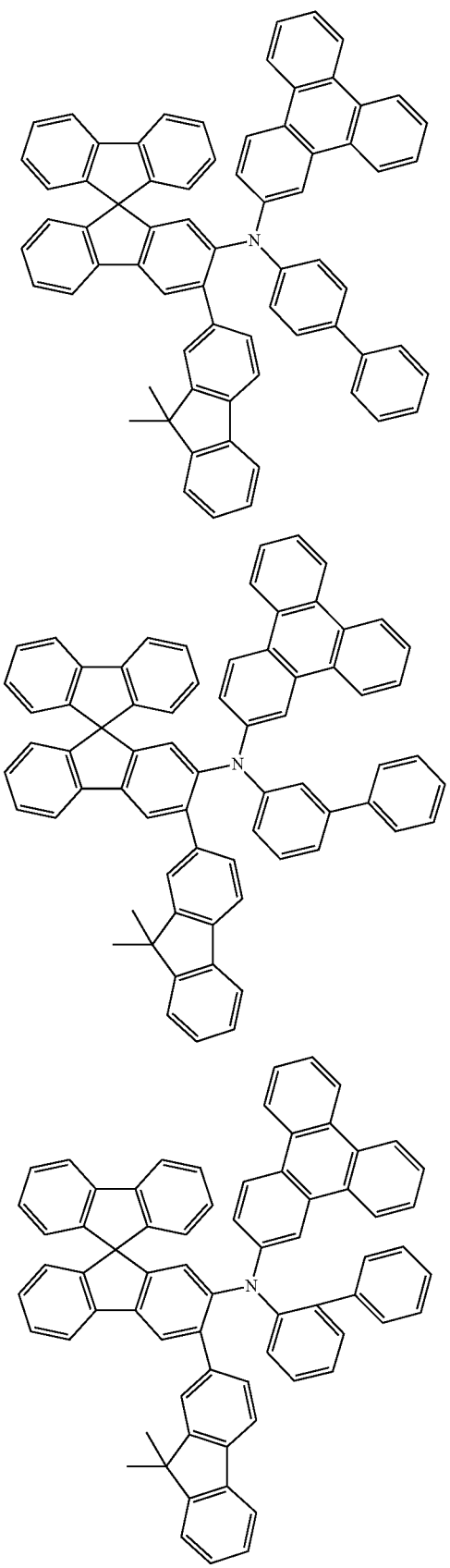 [SMILES: CC1(C)c2ccccc2-c2ccc(-c3cc4c(cc3N(c3ccc(-c5ccccc5)cc3)c3ccc5c6ccccc6c6ccccc6c5c3)C3(c5ccccc5-c5ccccc53)c3ccccc3-4)cc21 ; CC1(C)c2ccccc2-c2ccc(-c3cc4c(cc3N(c3cccc(-c5ccccc5)c3)c3ccc5c6ccccc6c6ccccc6c5c3)C3(c5ccccc5-c5ccccc53)c3ccccc3-4)cc21 ; CC1(C)c2ccccc2-c2ccc(-c3cc4c(cc3N(c3ccc5c6ccccc6c6ccccc6c5c3)c3ccccc3-c3ccccc3)C3(c5ccccc5-c5ccccc53)c3ccccc3-4)cc21]
440
-continued
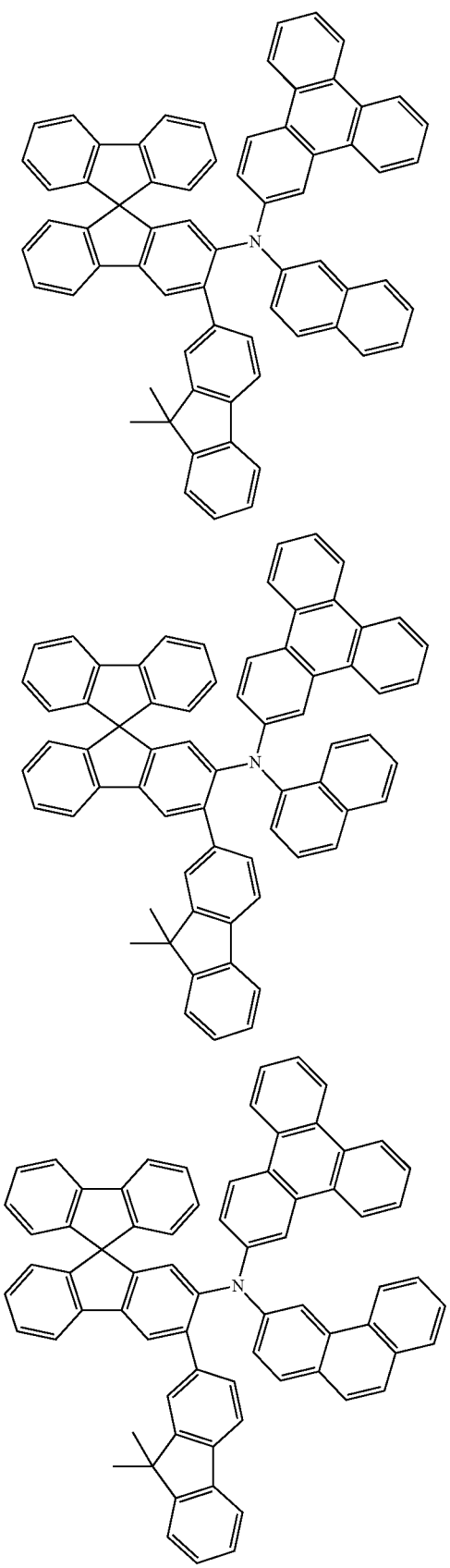

441
-continued
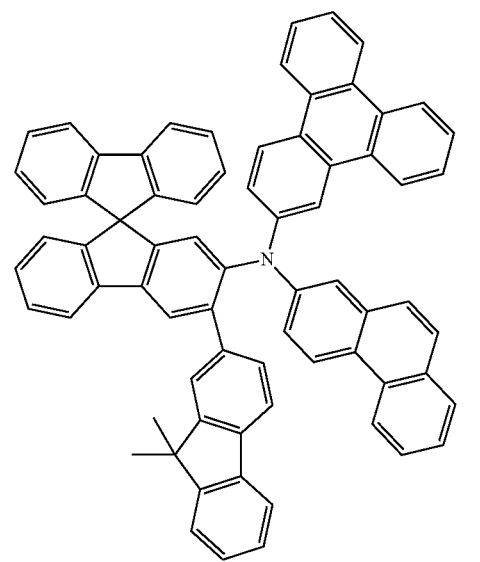
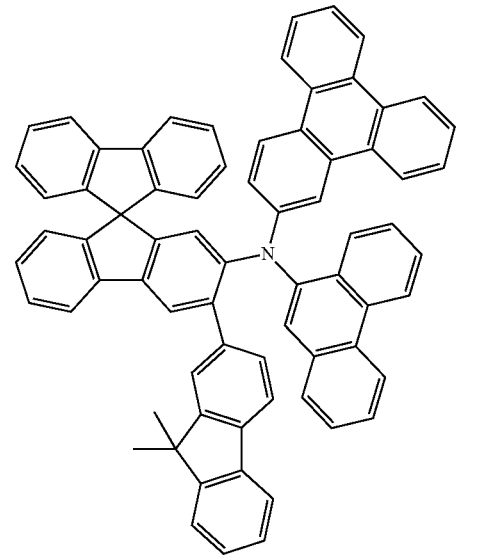
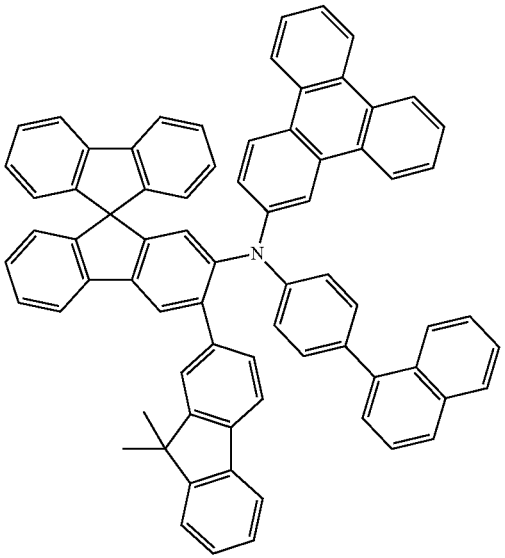
442
-continued
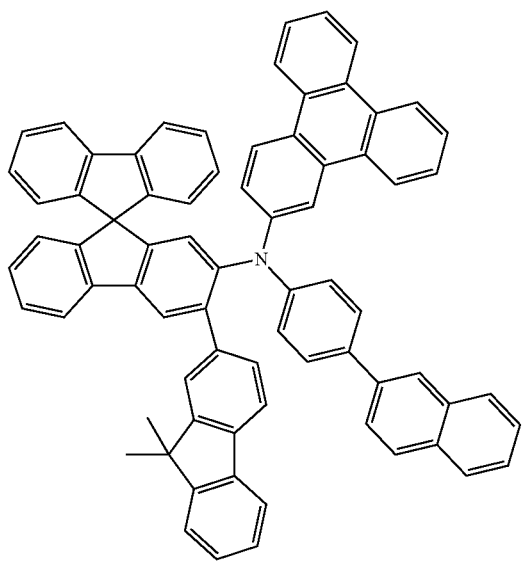
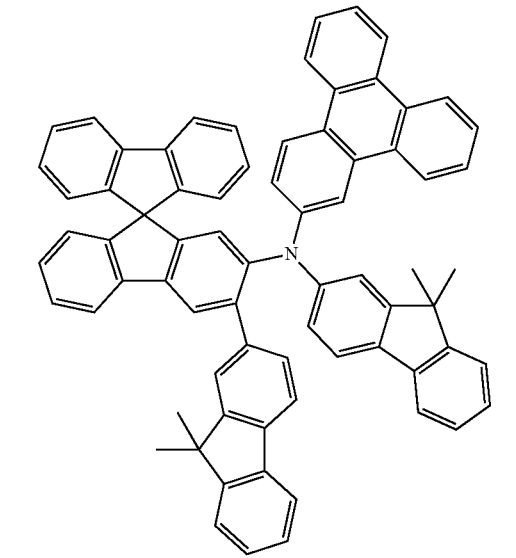
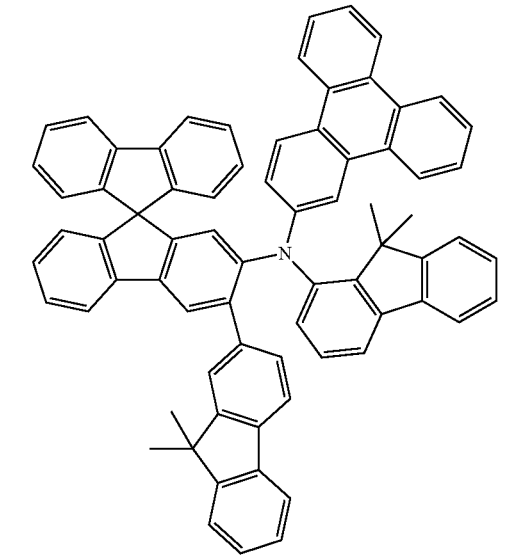

443
-continued
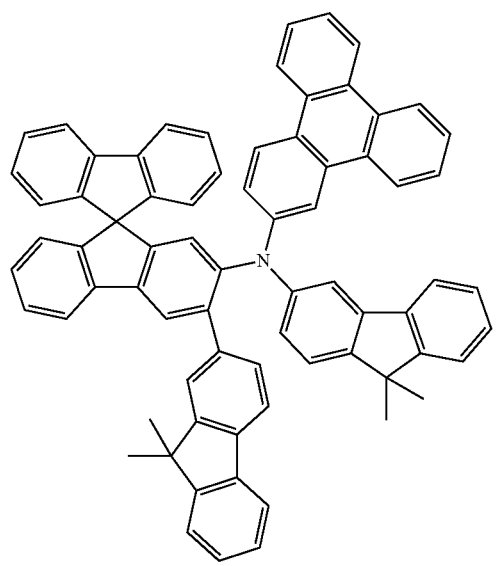
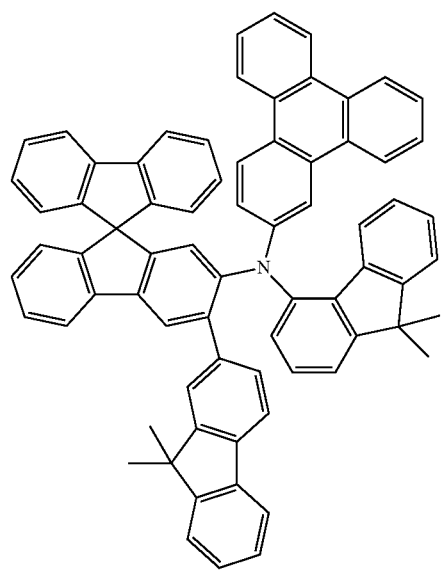
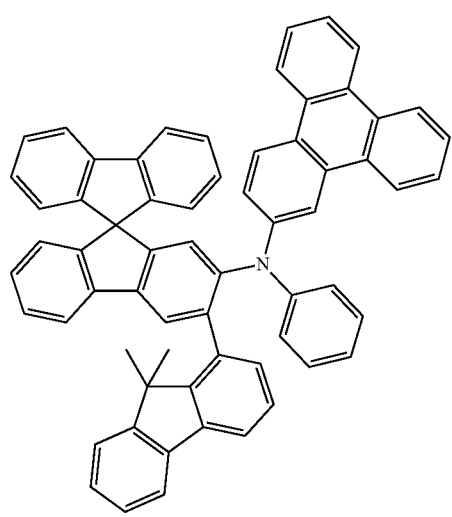
444
-continued
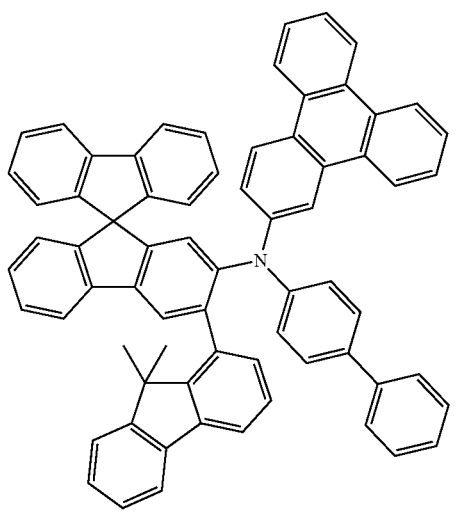
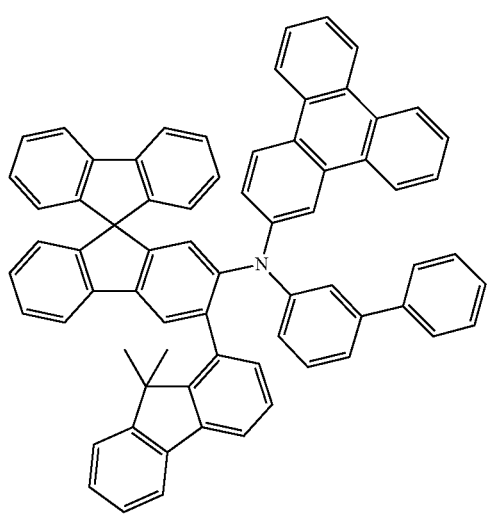
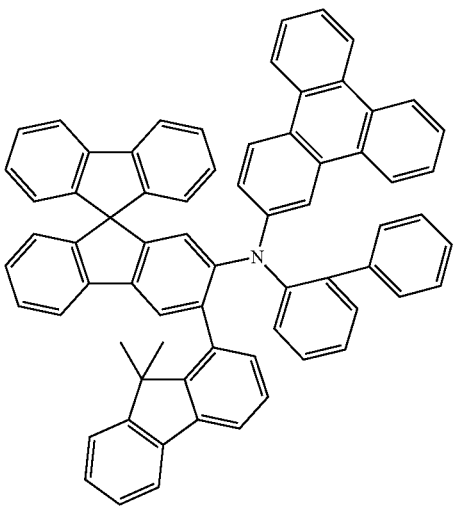

445
-continued
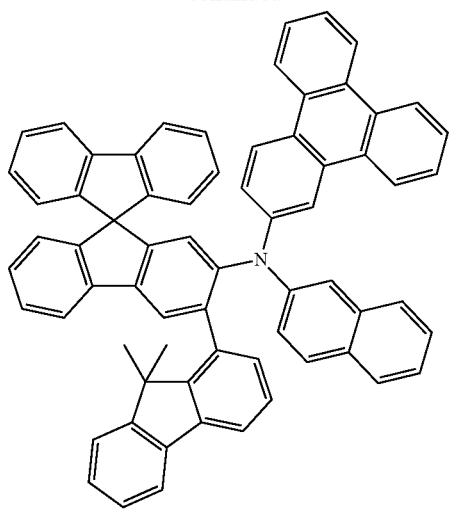
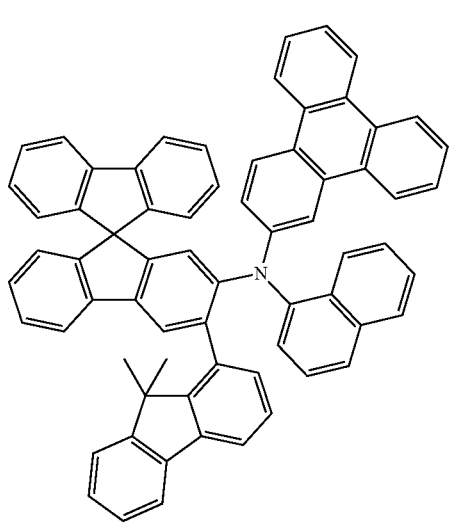
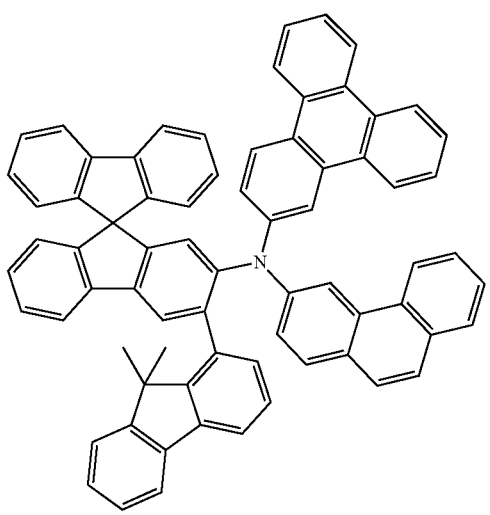
446
-continued
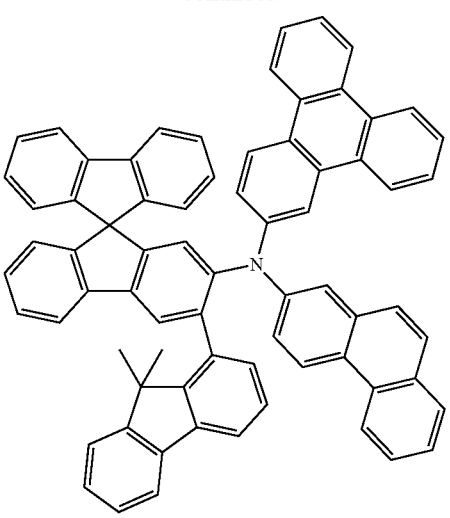
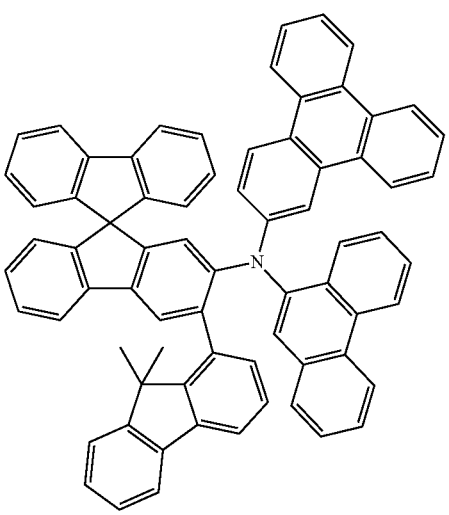
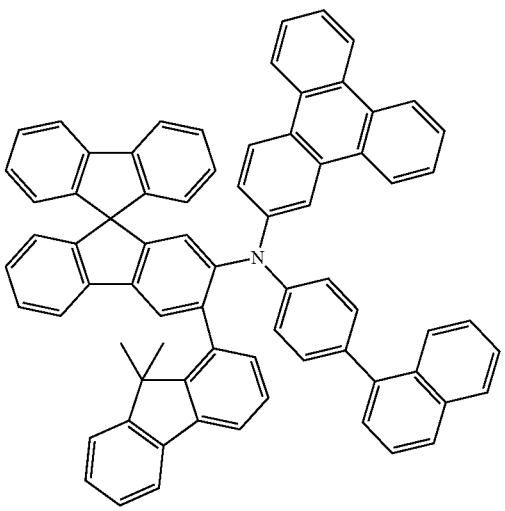

447
-continued
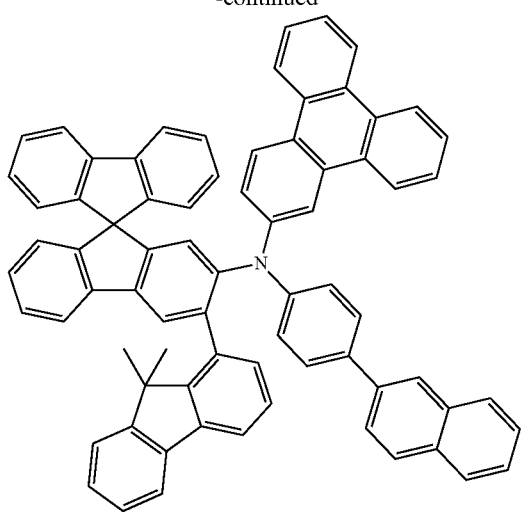
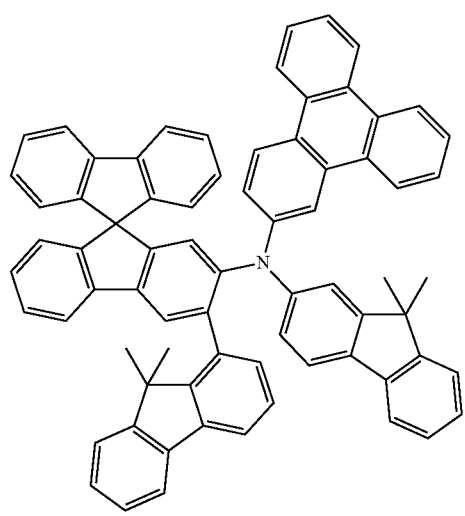
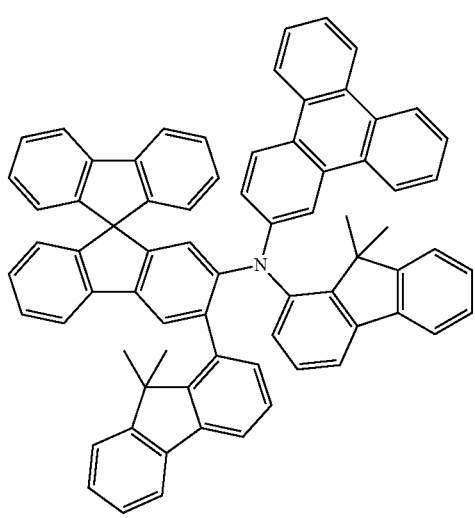
448
-continued
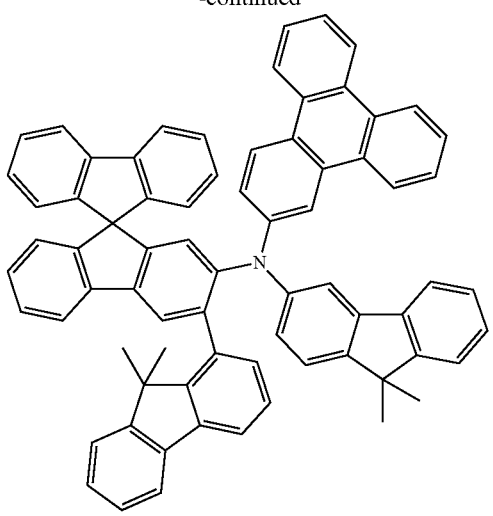
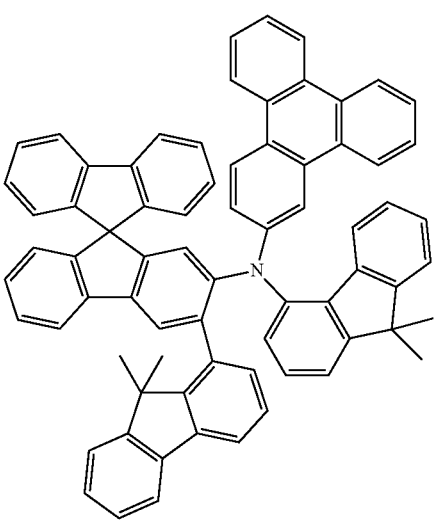
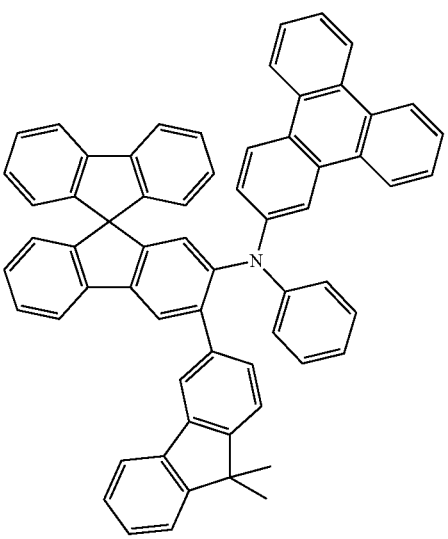

449
-continued
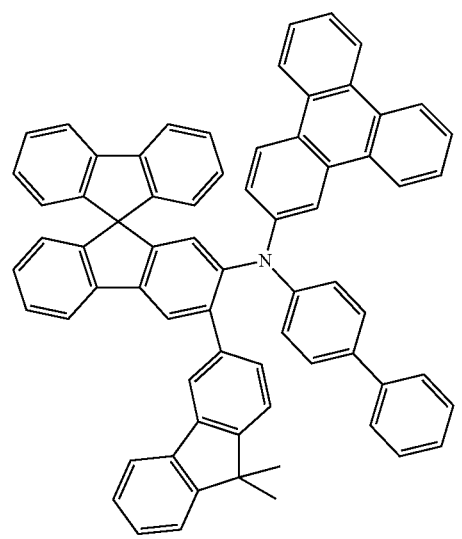
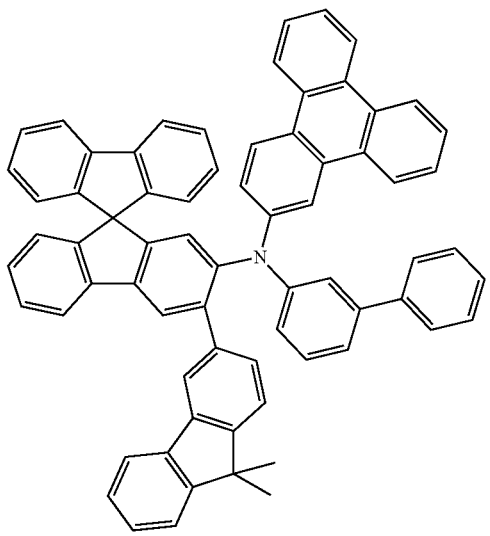
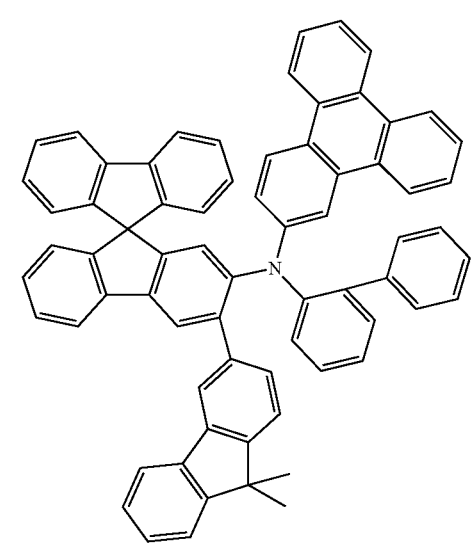
450
-continued
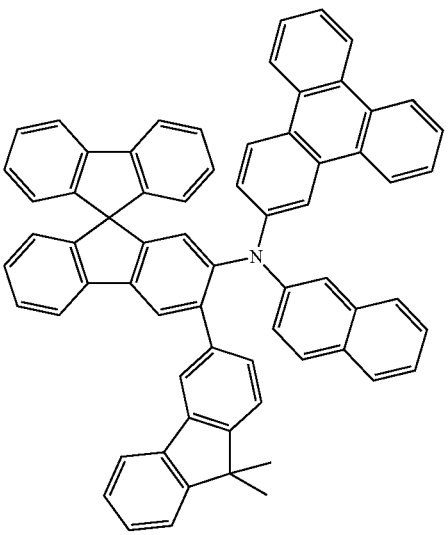
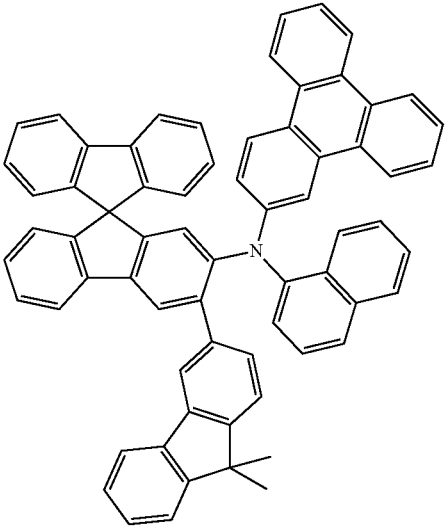
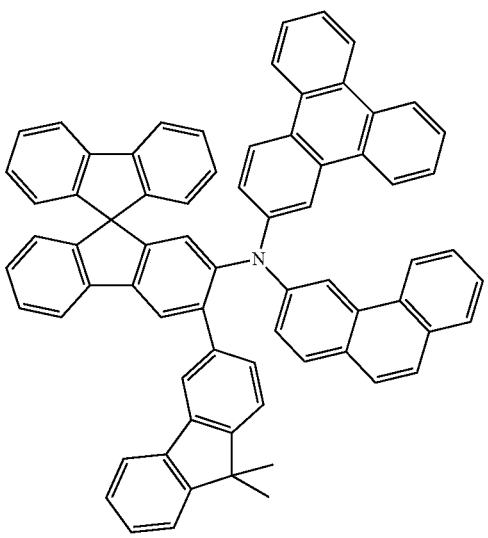

451
-continued
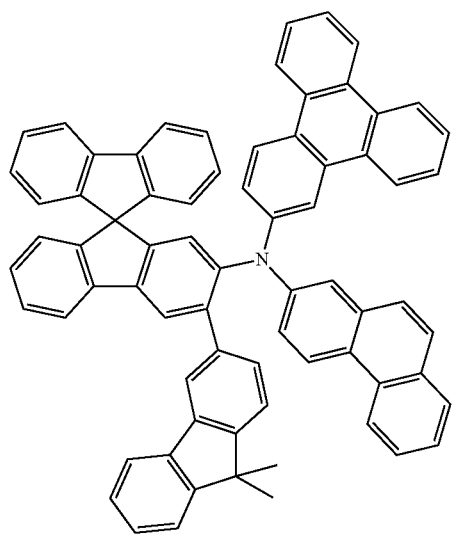
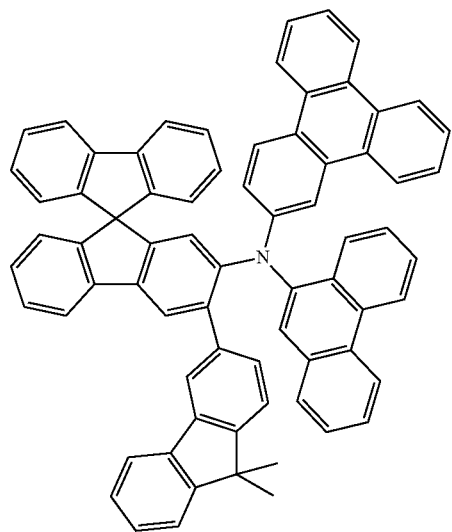
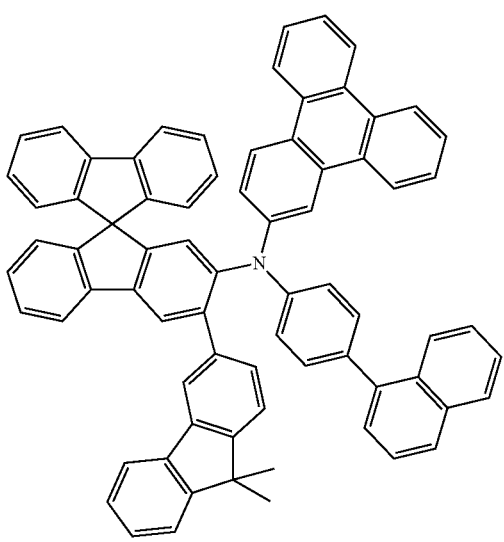
452
-continued
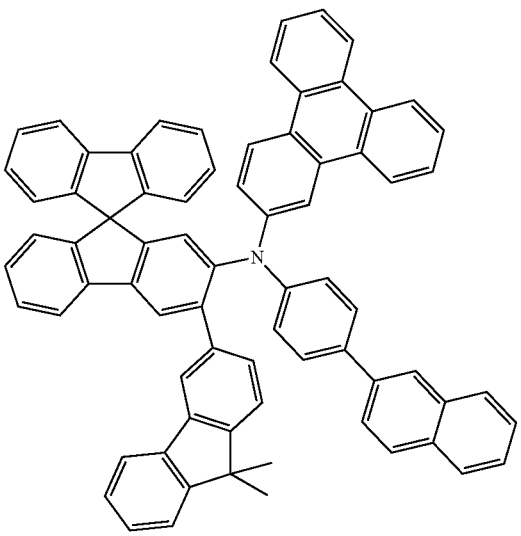
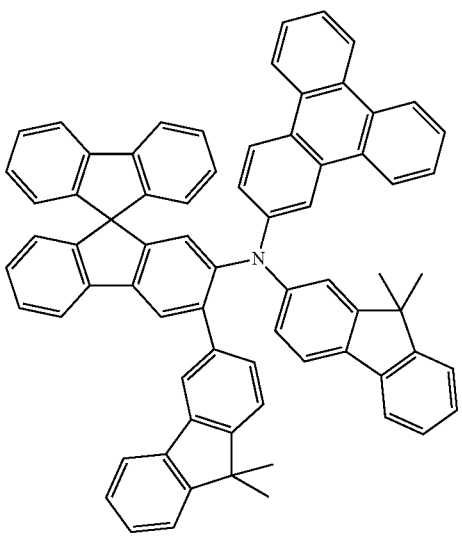
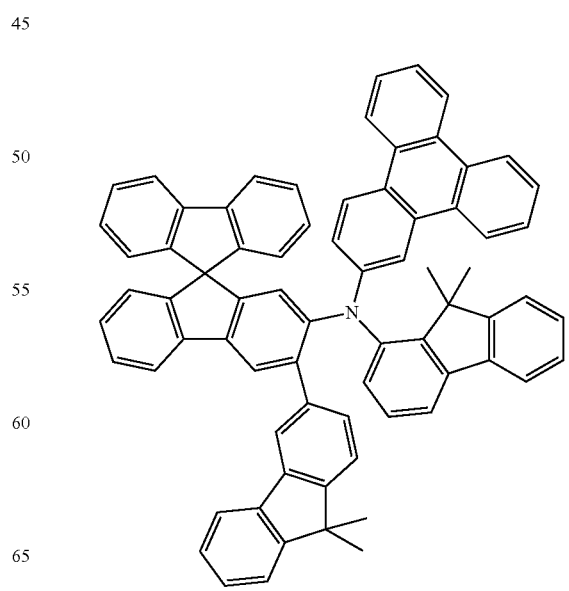

453
-continued
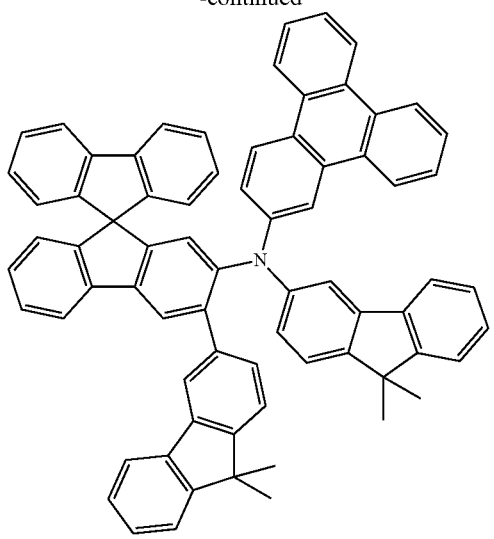
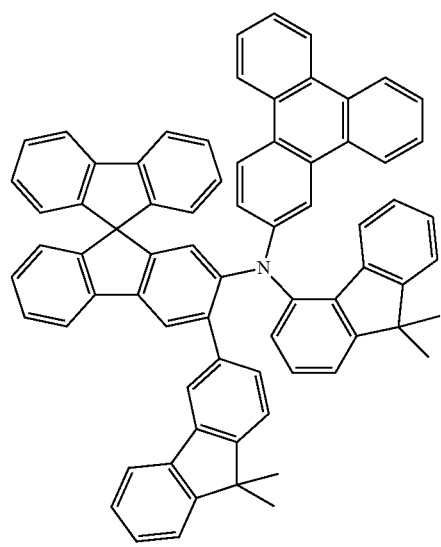
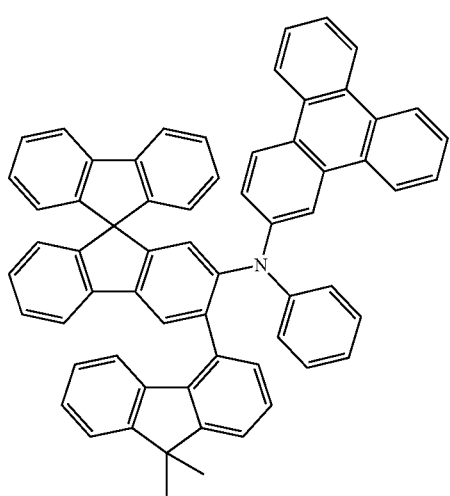
454
-continued
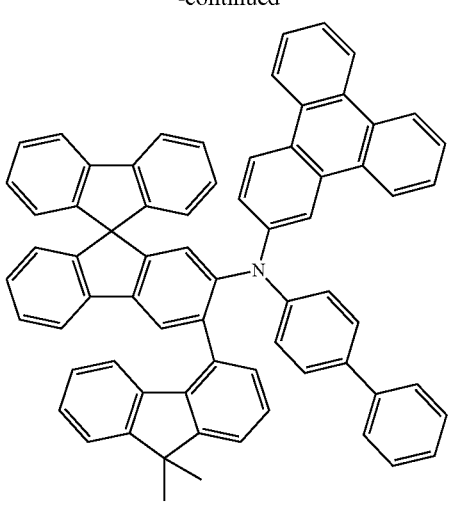
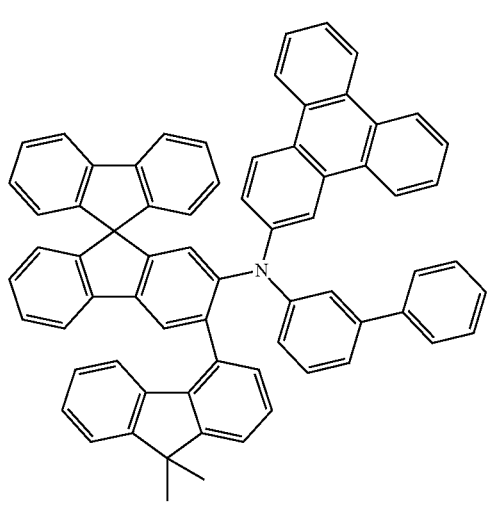
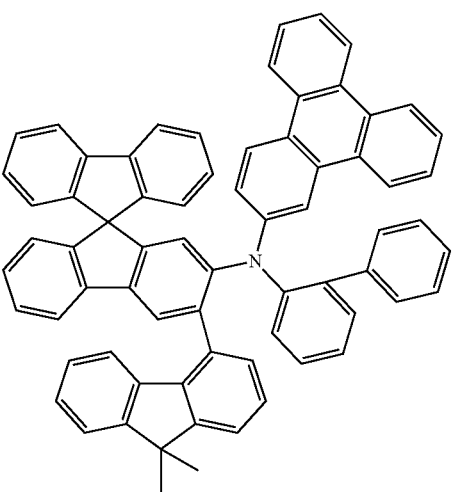

455
-continued
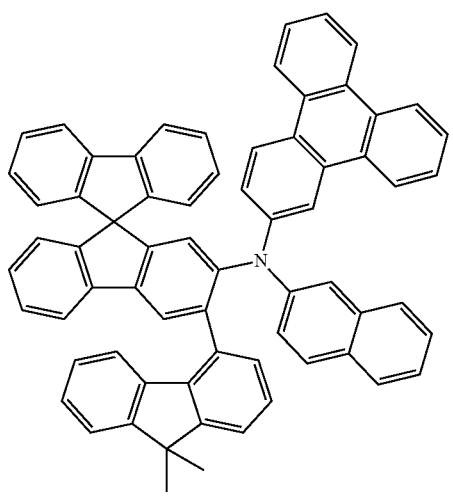
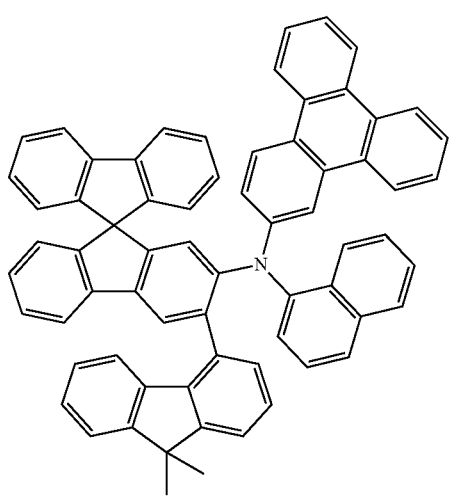
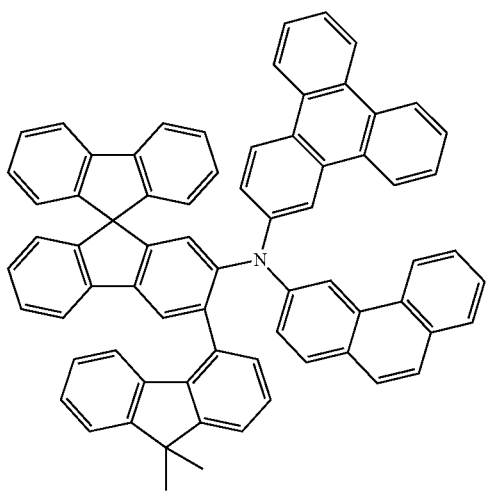
456
-continued
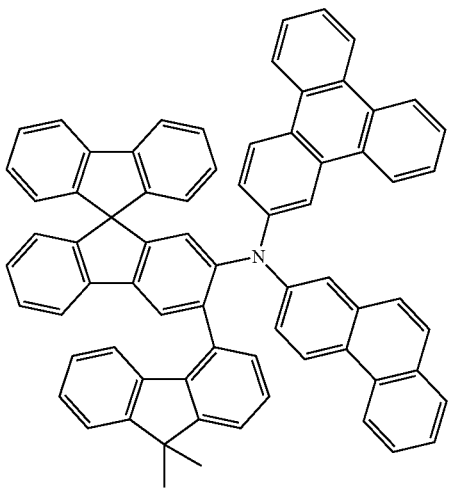
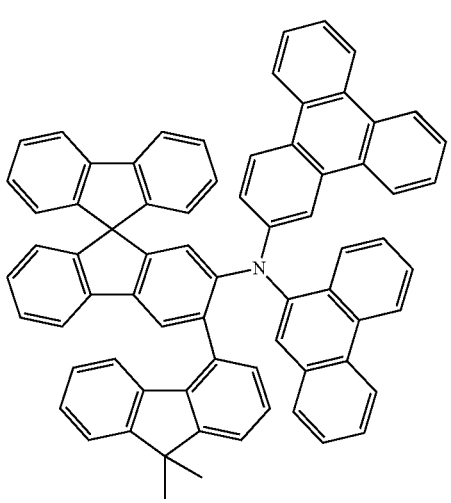
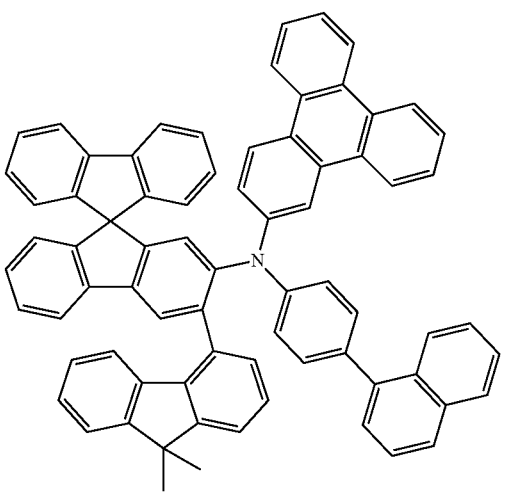

457
-continued
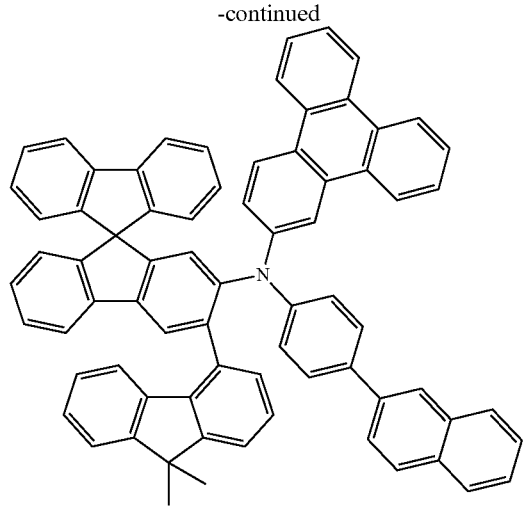
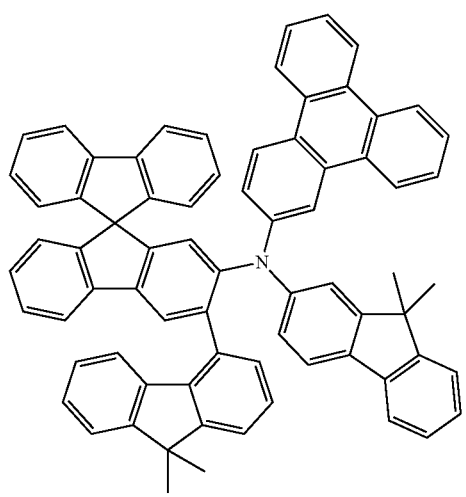
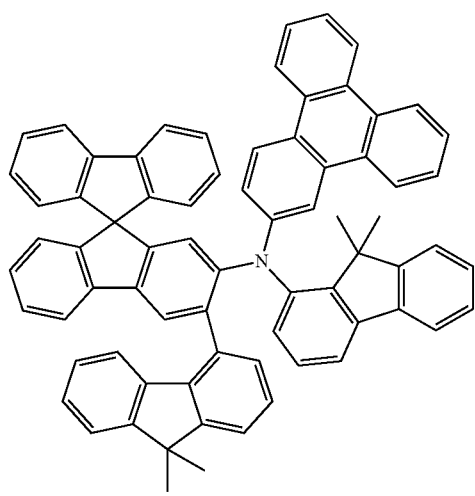
458
-continued
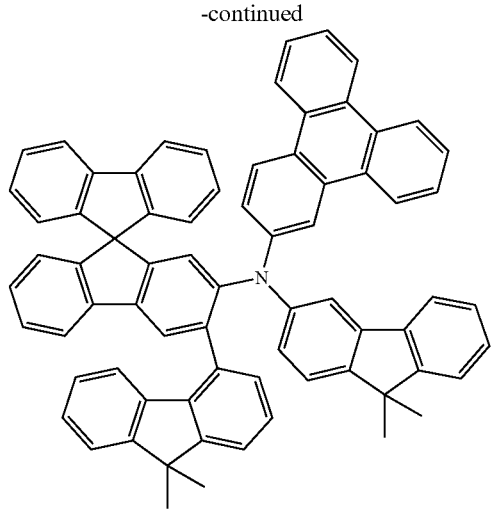
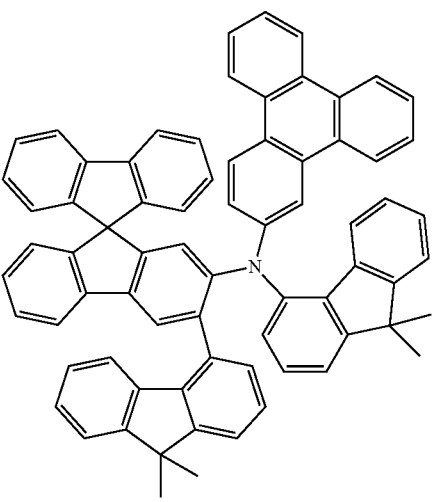
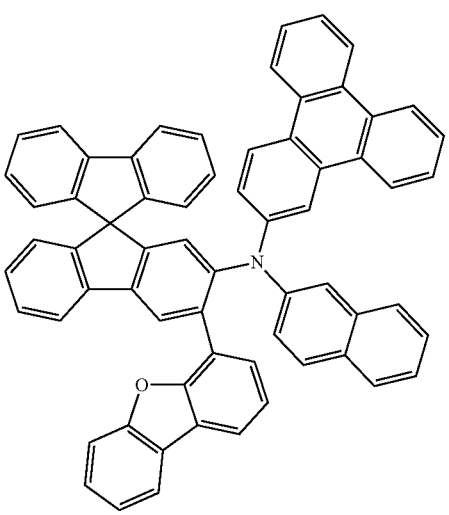

459
-continued
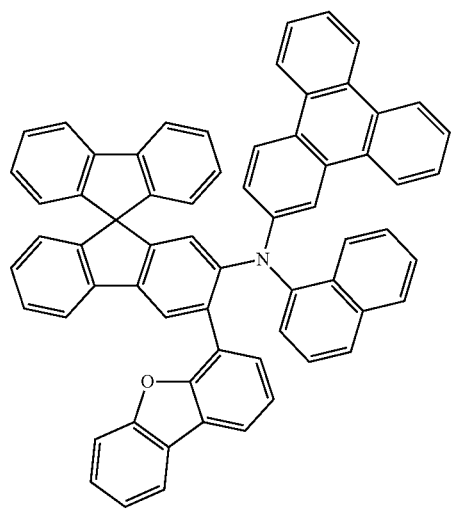
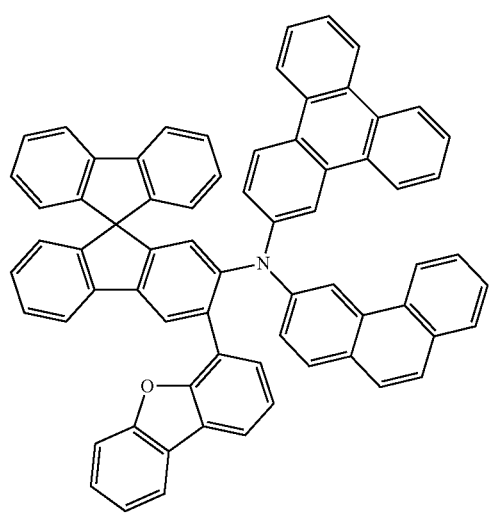
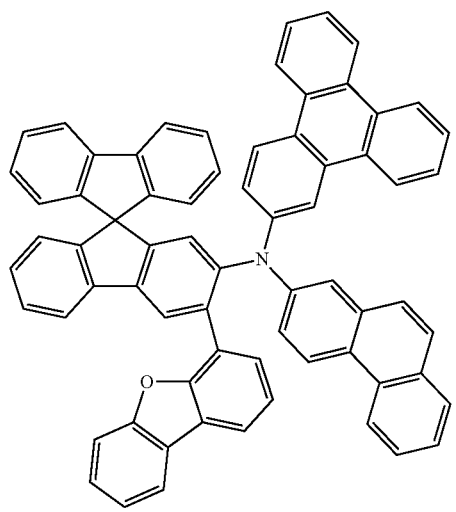
460
-continued
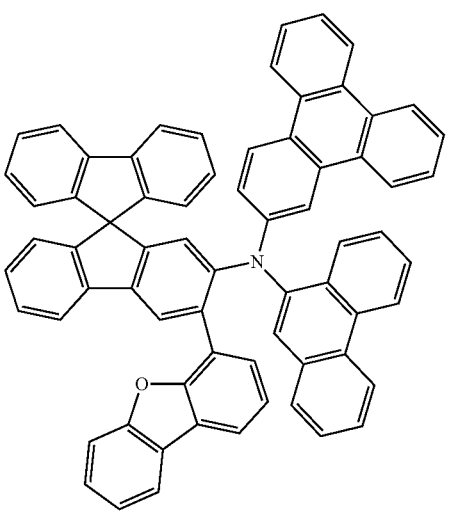
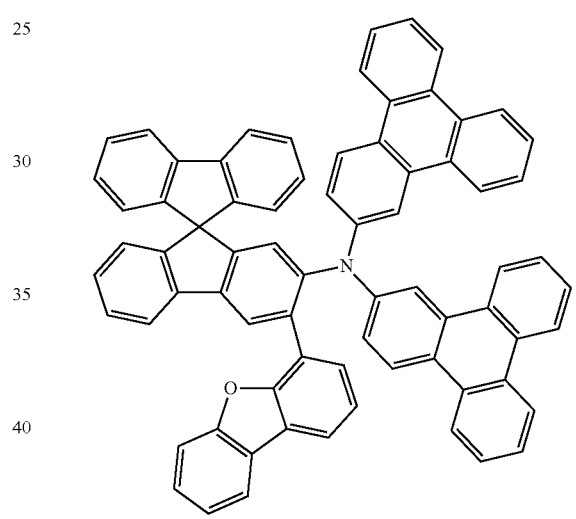
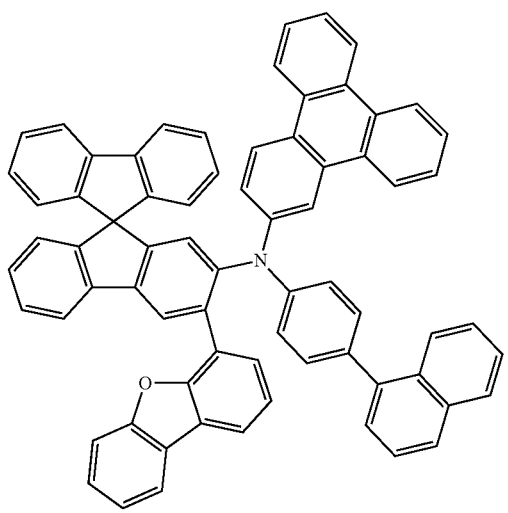

461
-continued
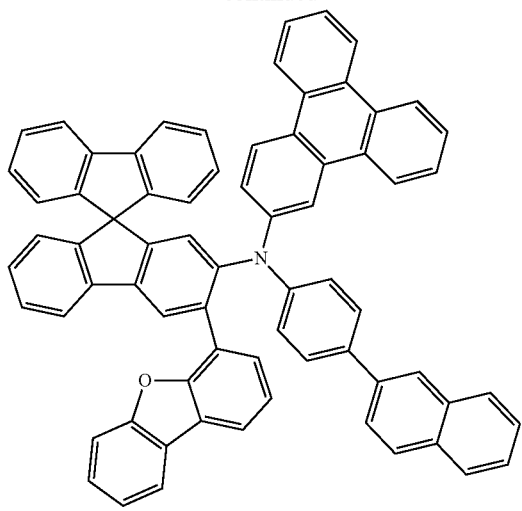
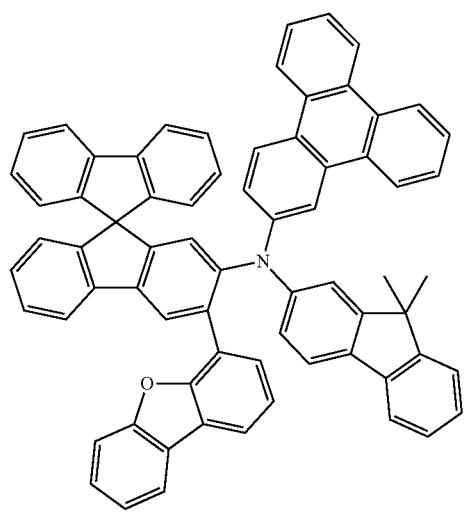
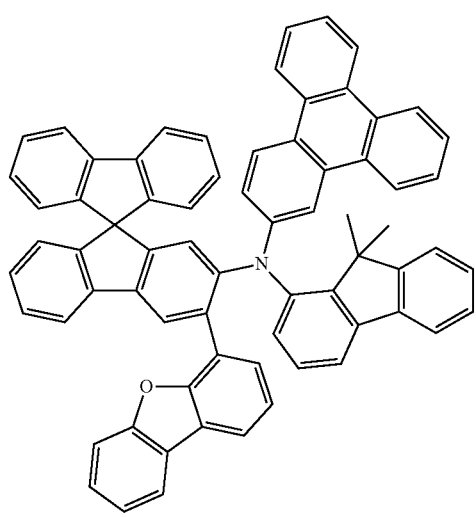
462
-continued
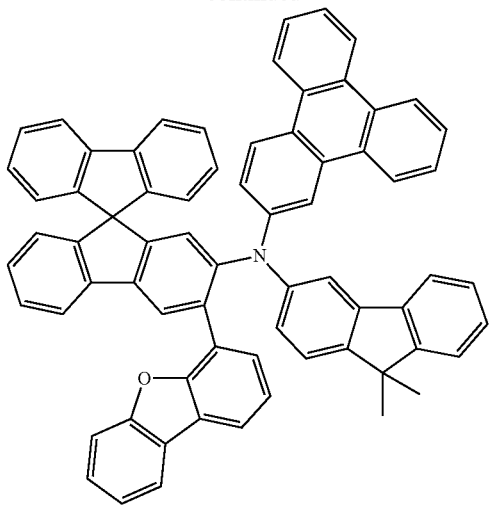
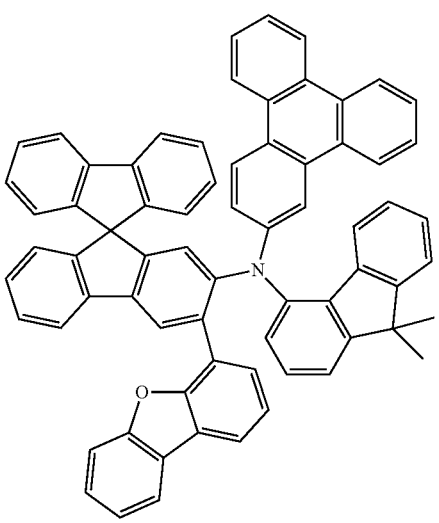
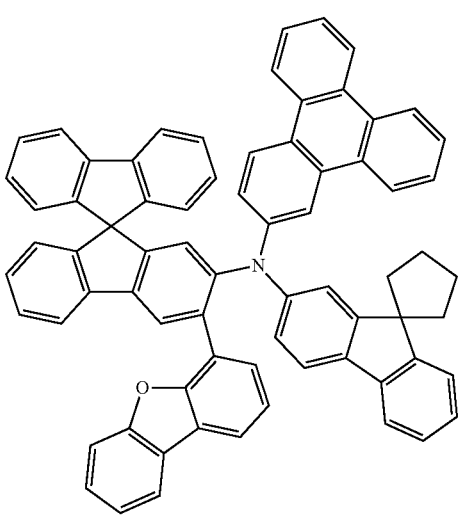

463
-continued
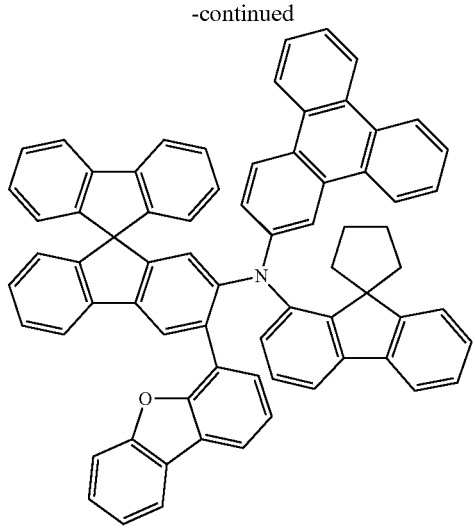
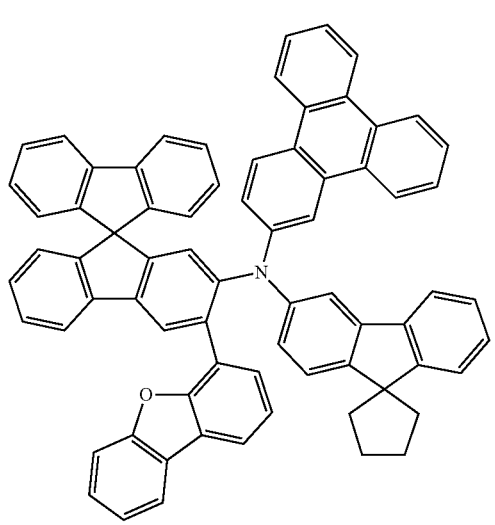
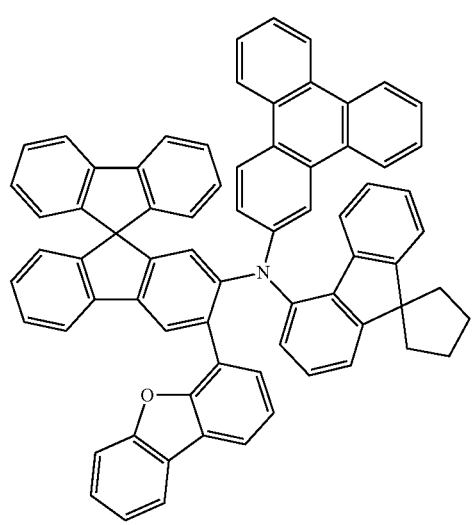
464
-continued
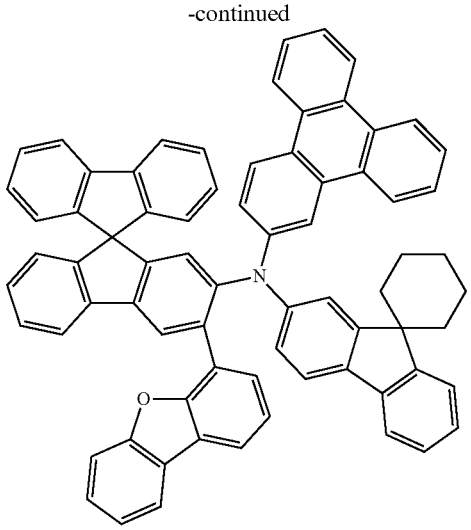
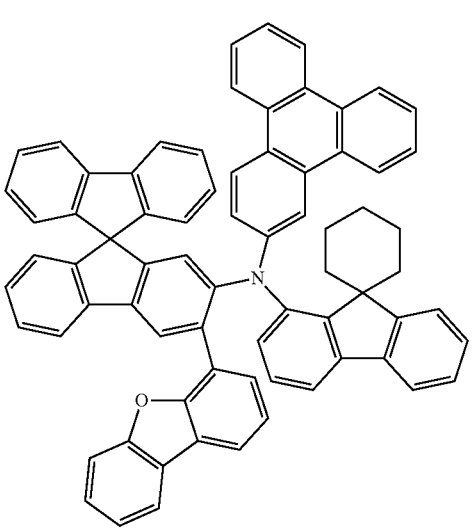

465
-continued
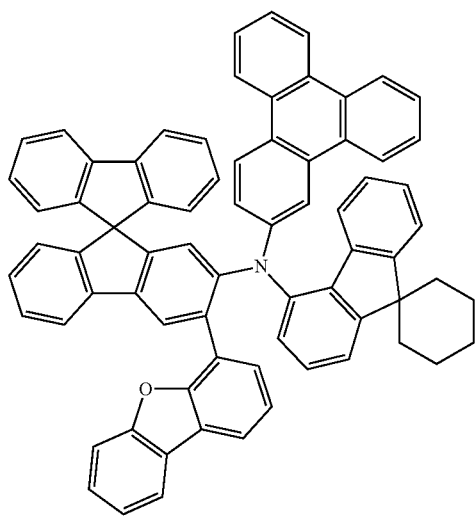
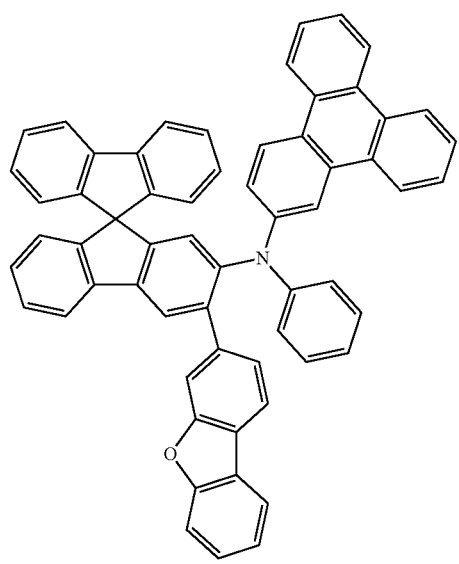
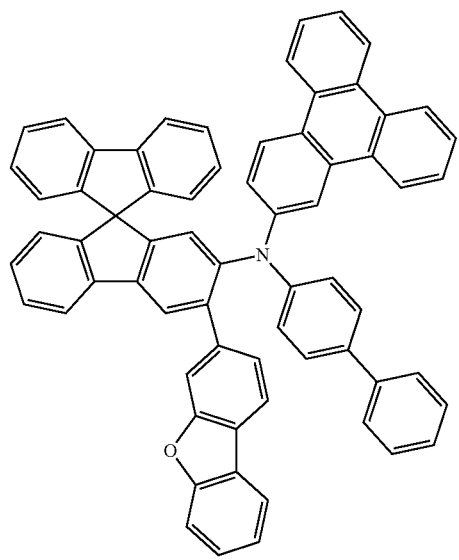
466
-continued
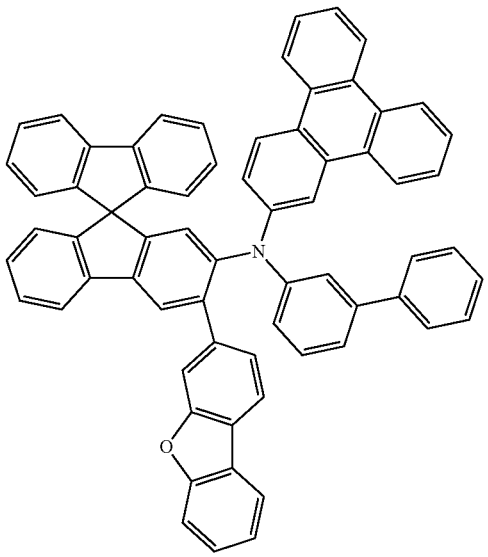
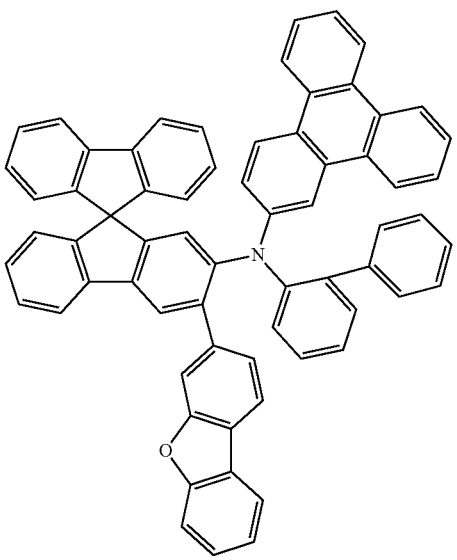

467
-continued
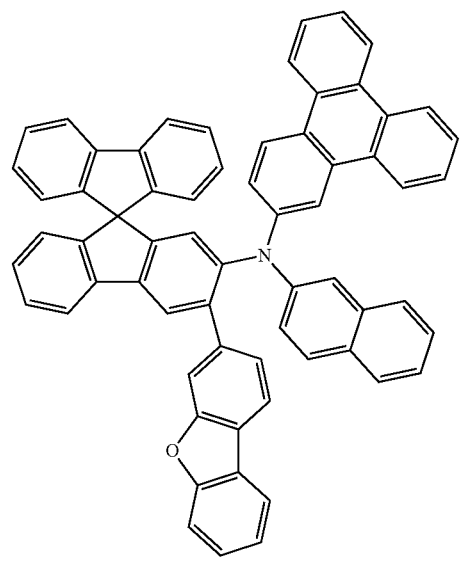
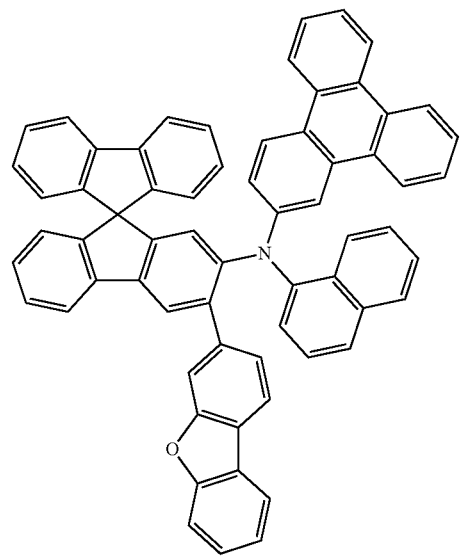
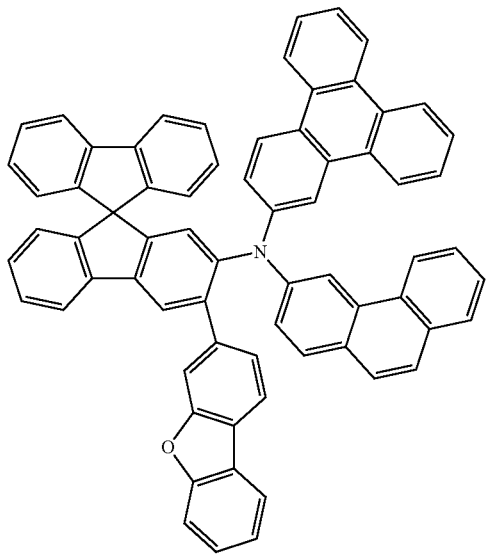
468
-continued
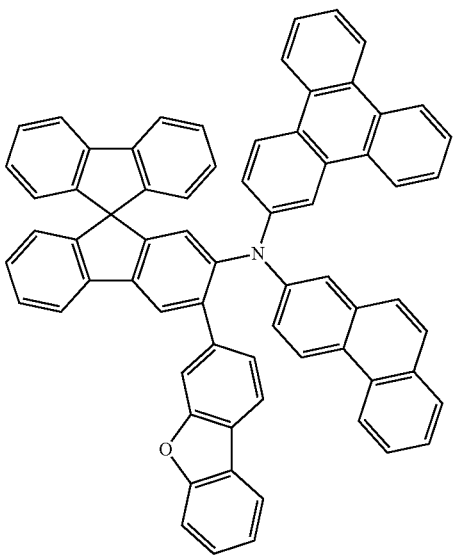
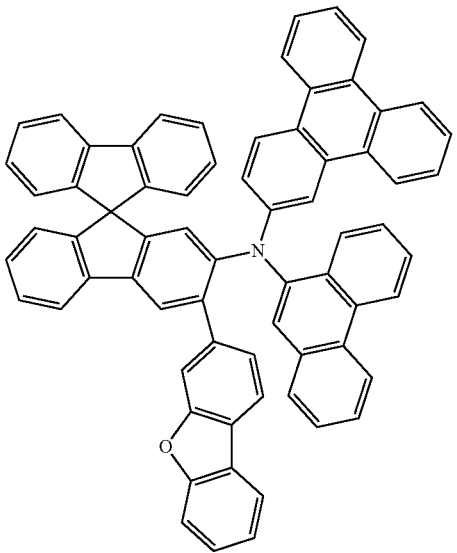
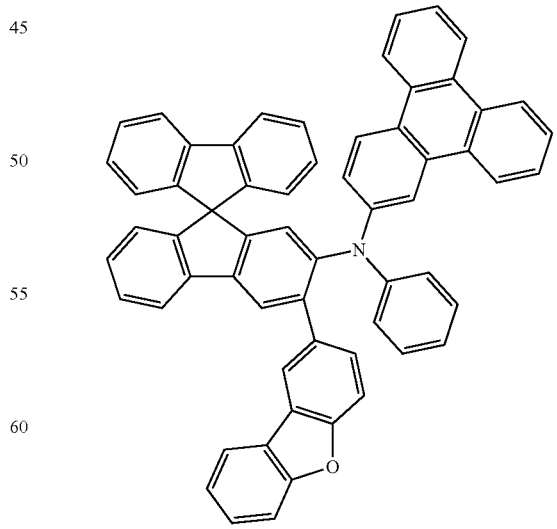

469
-continued
470
-continued
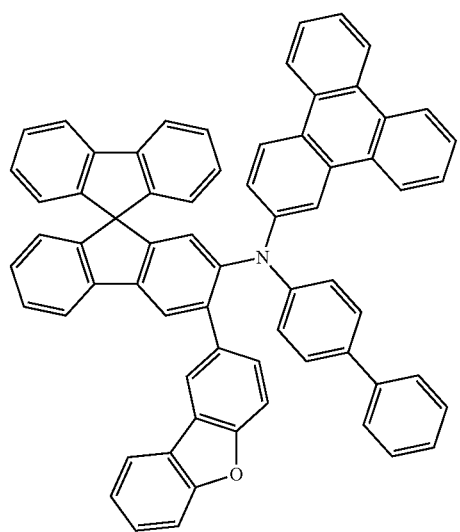
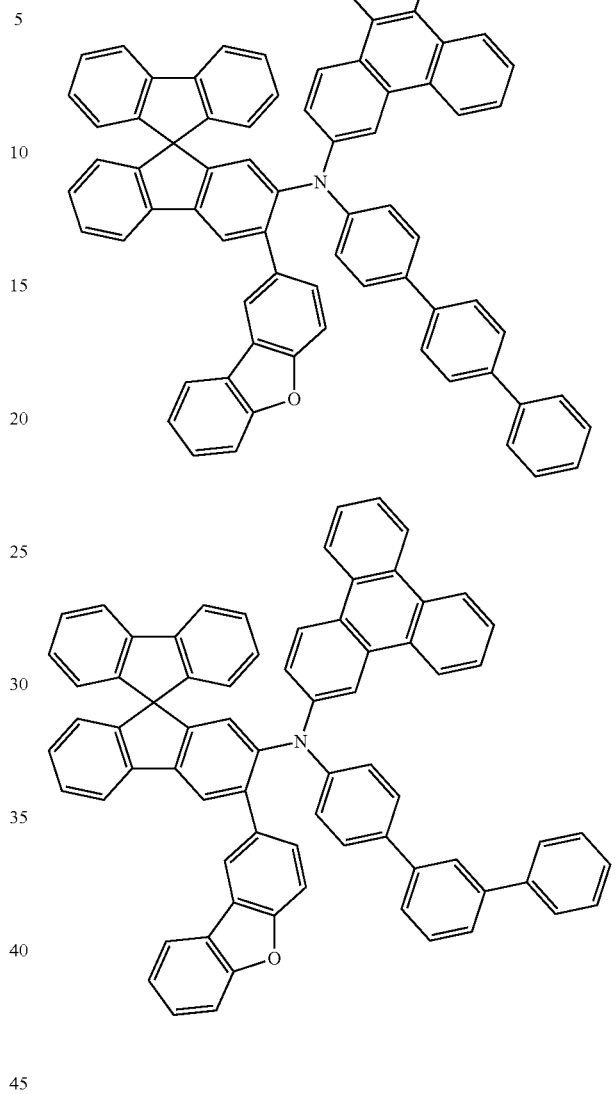
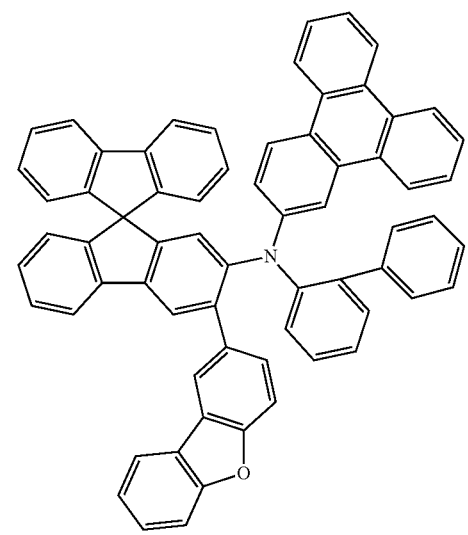

471
-continued
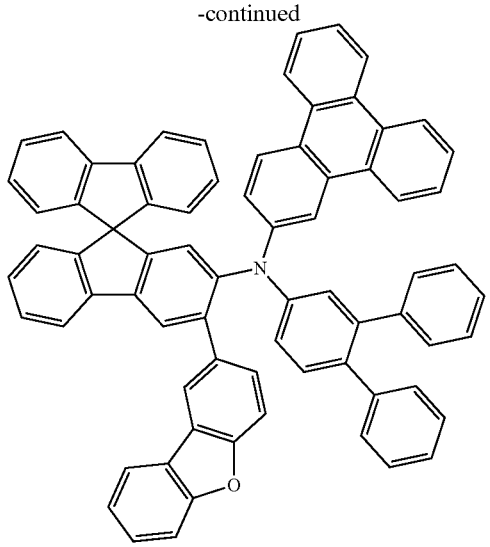
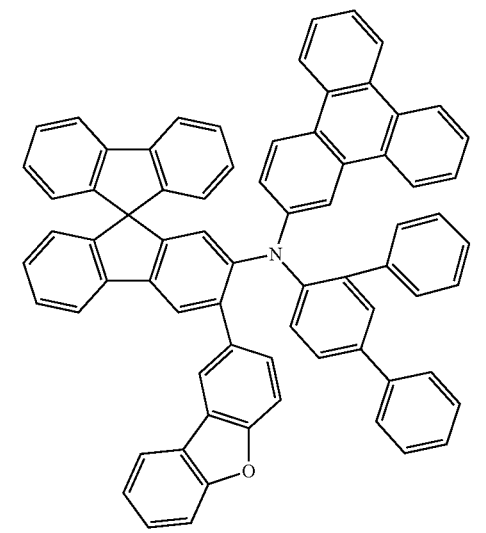
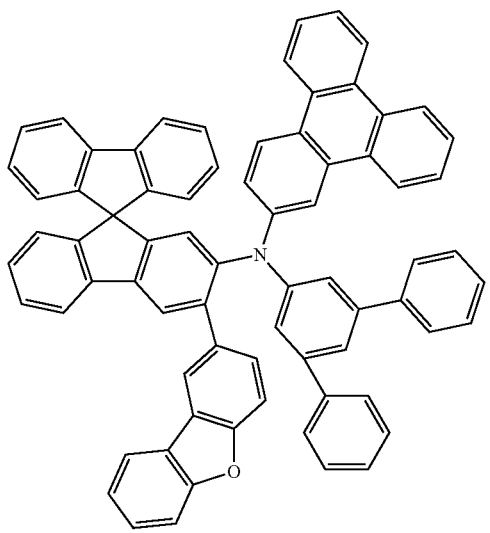
472
-continued
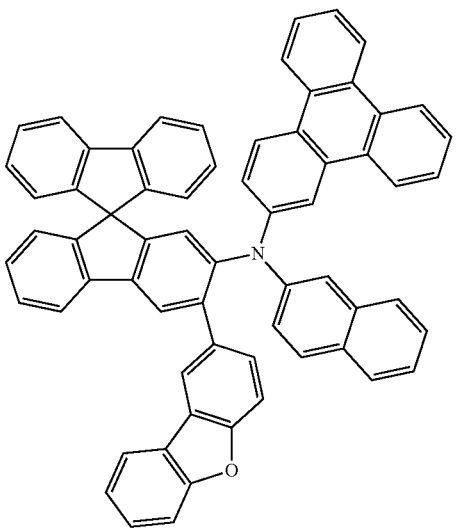
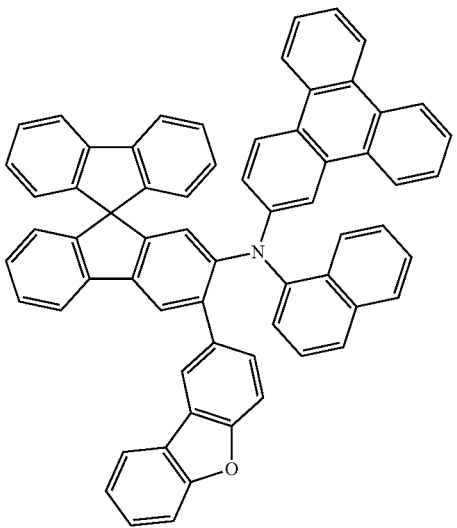
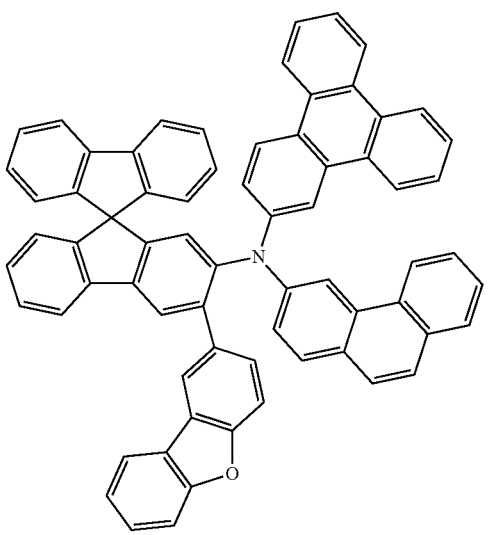

473
-continued
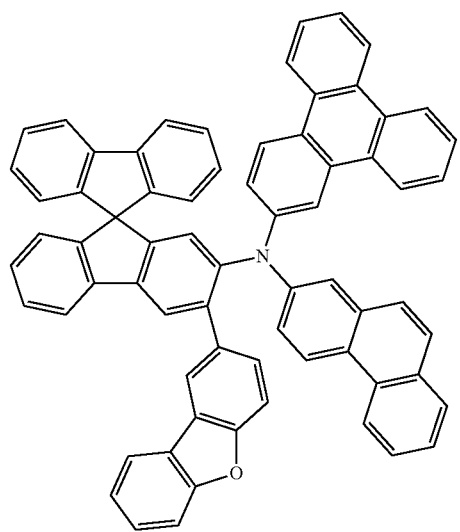
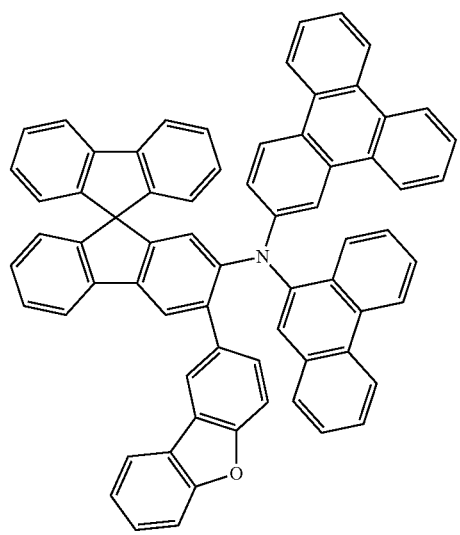
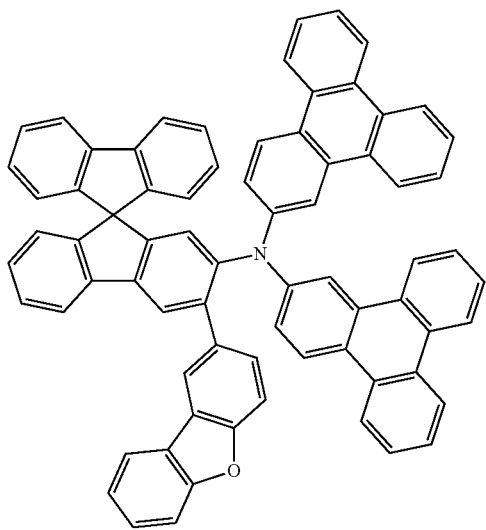
474
-continued
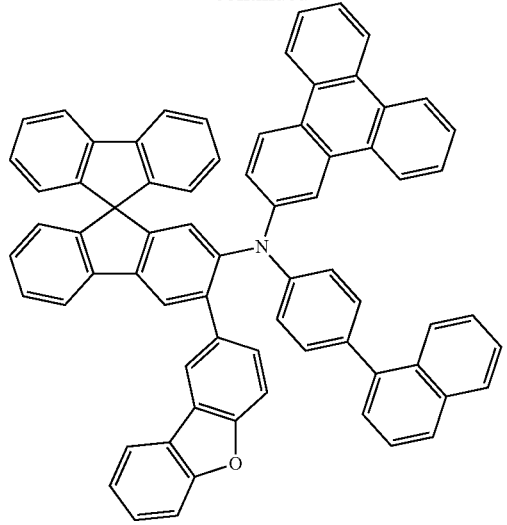
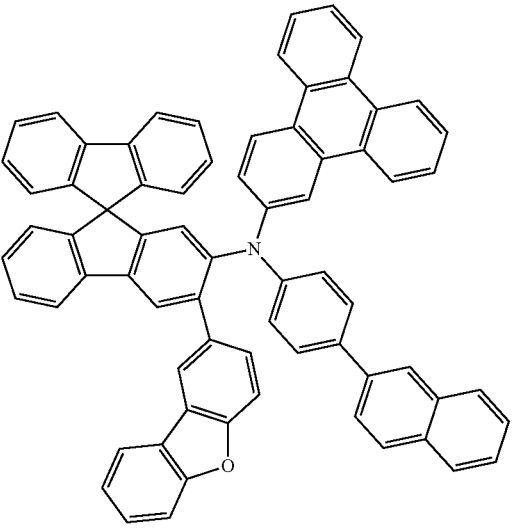
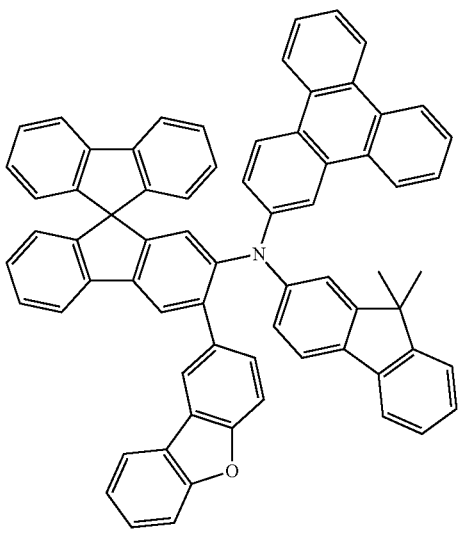

475
-continued
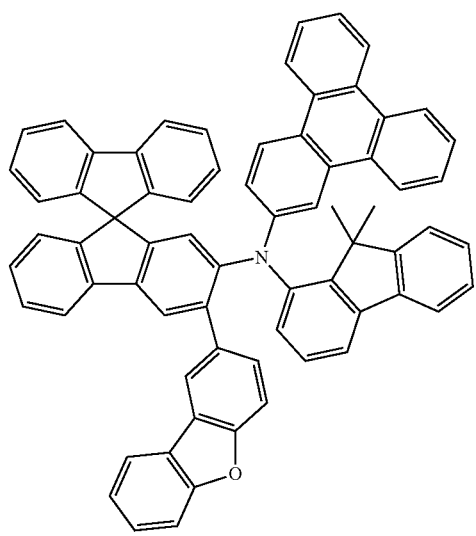
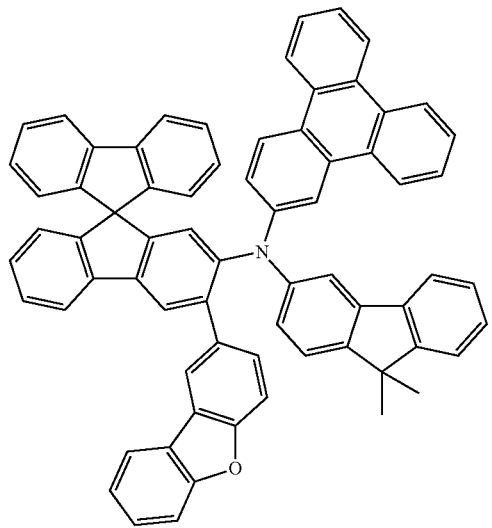
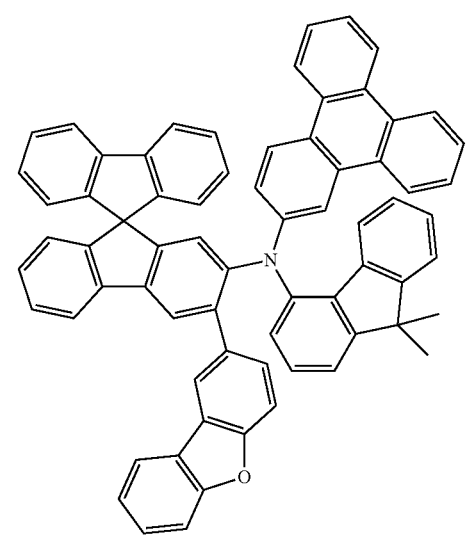
476
-continued
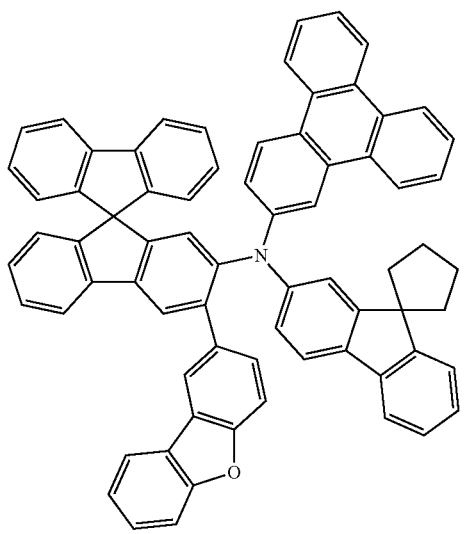
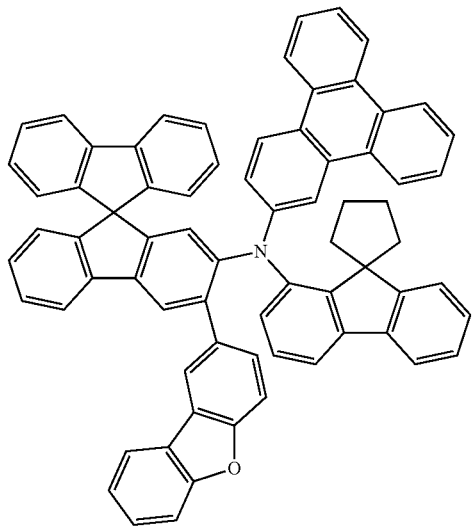
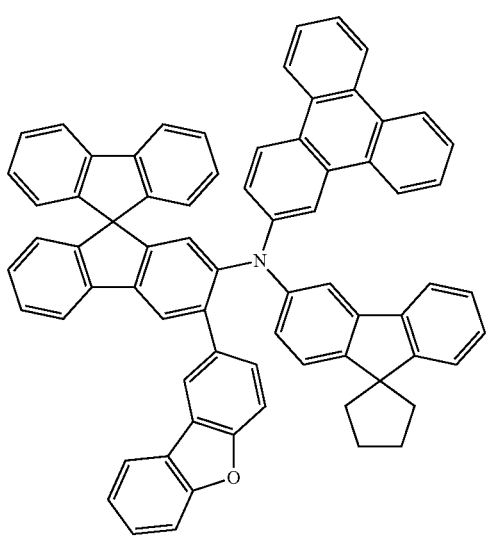

477
-continued
478
-continued
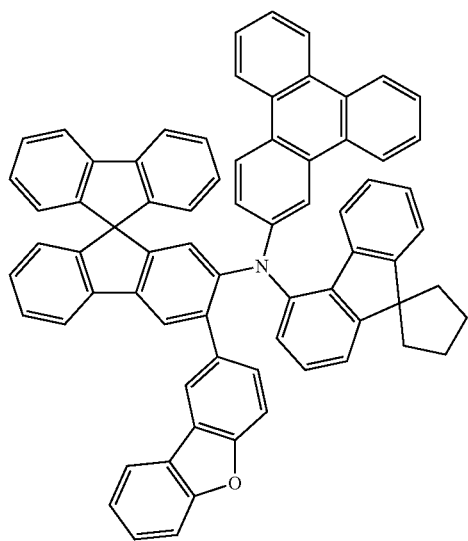
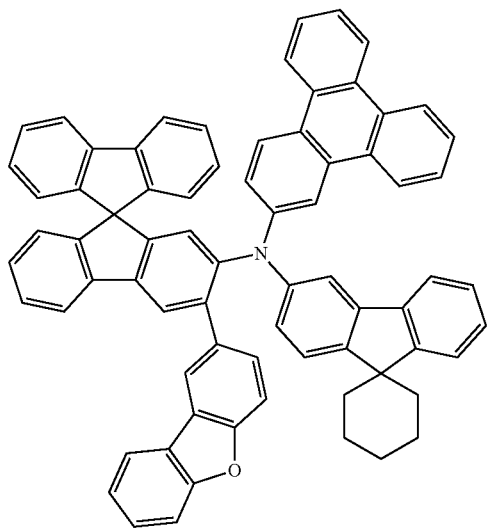

479
-continued
480
-continued
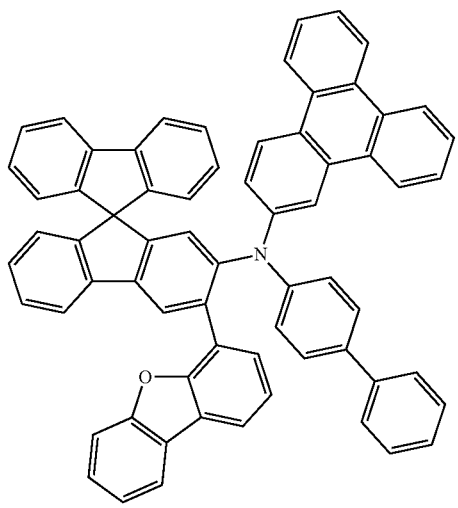
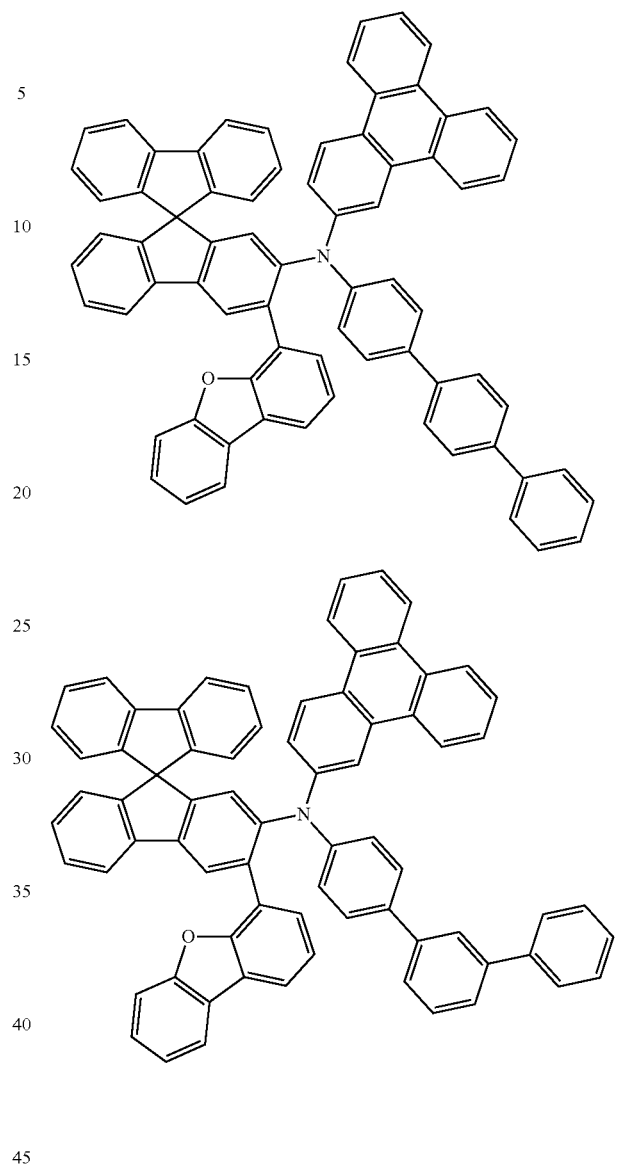
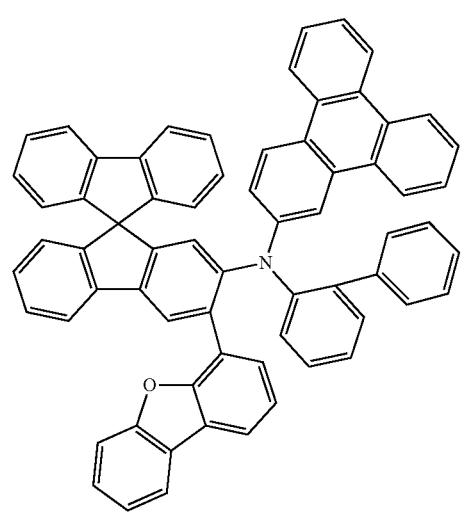

481
-continued
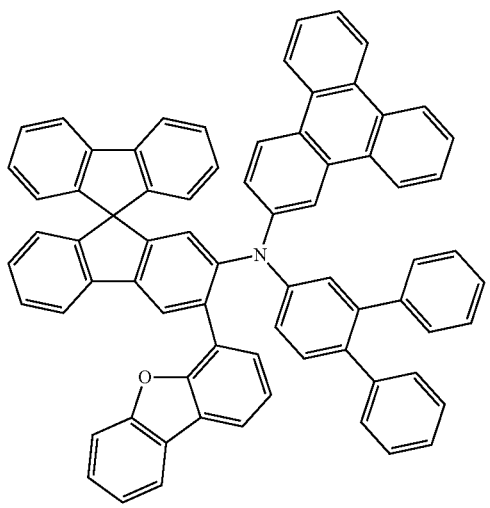
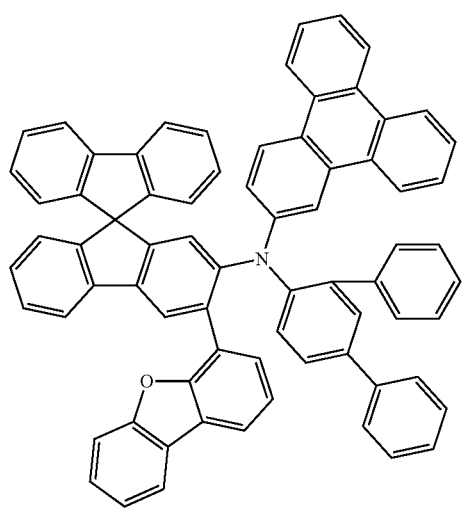
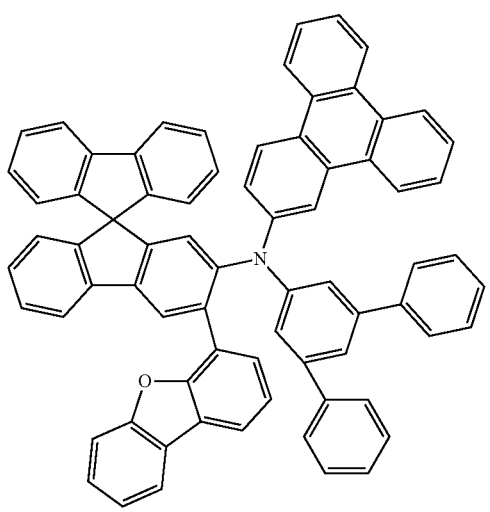
482
-continued
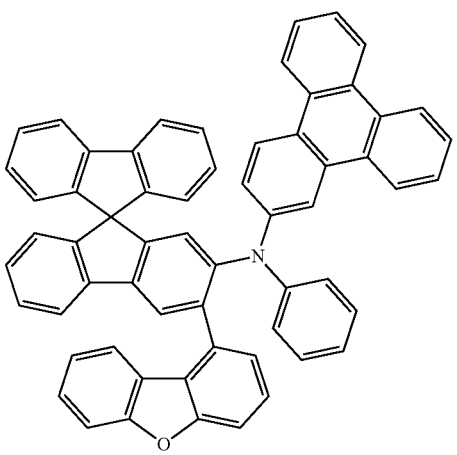
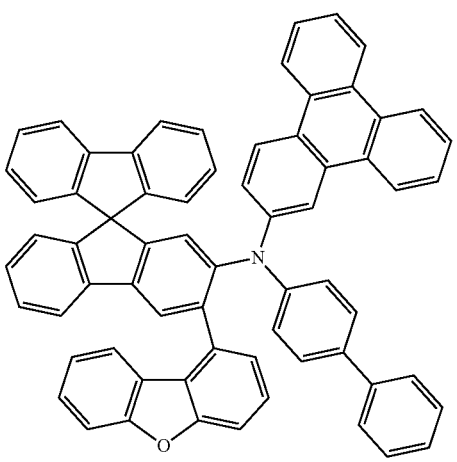
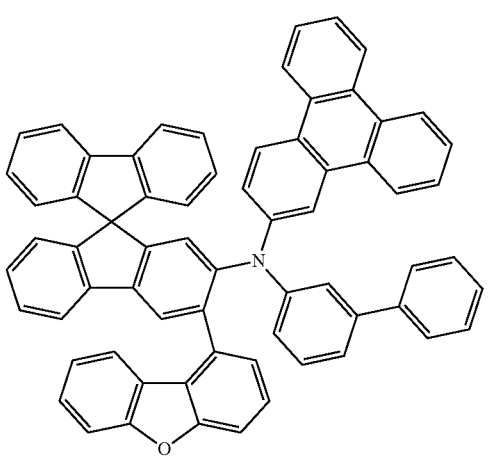

483
-continued
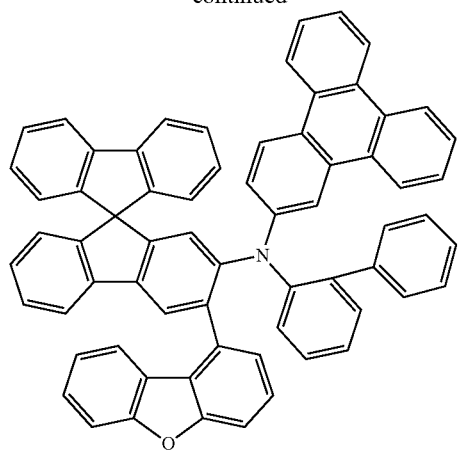
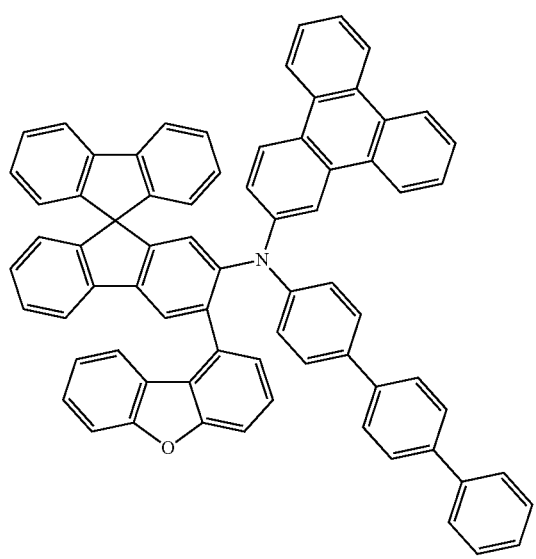
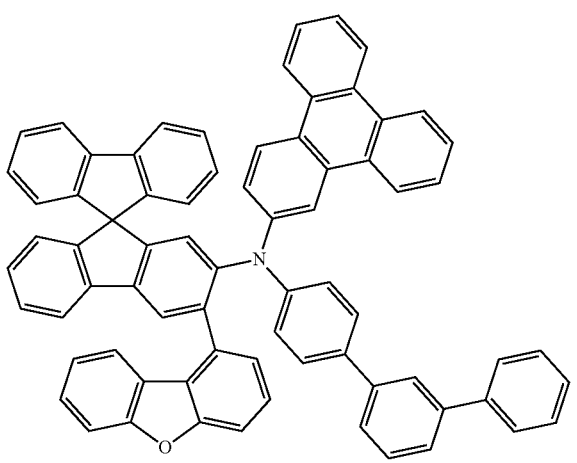
484
-continued
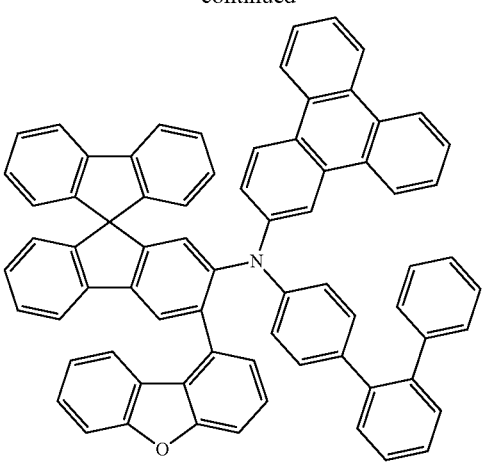
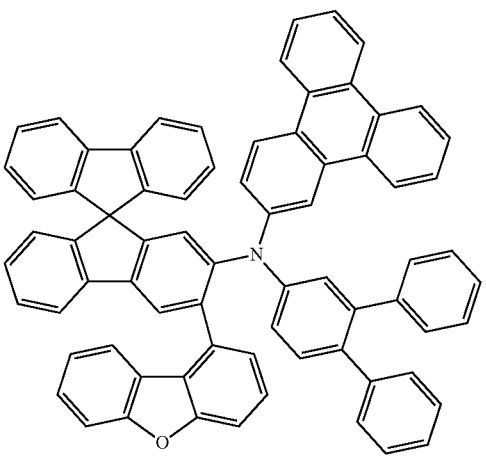
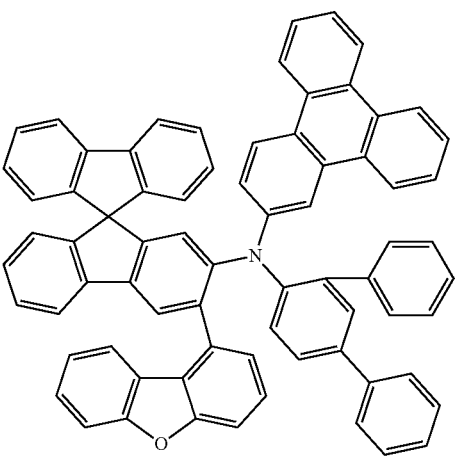

485
-continued
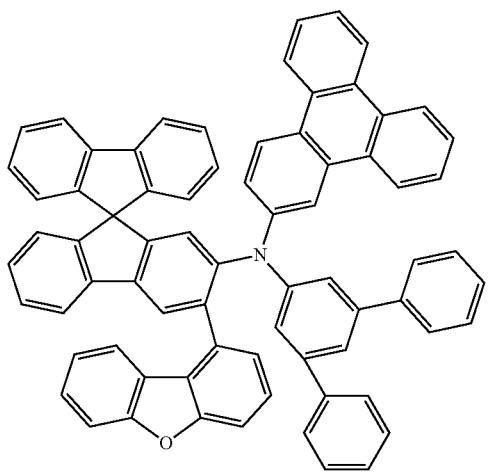
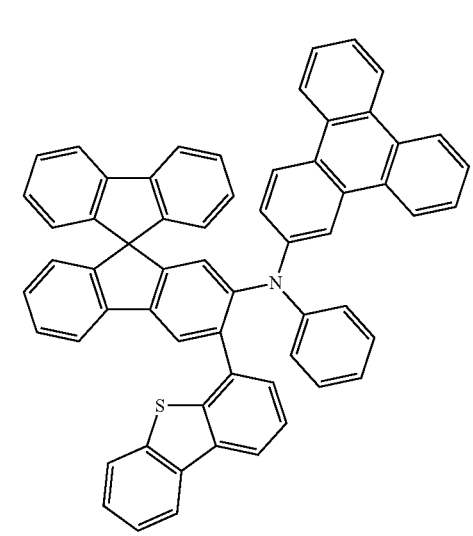
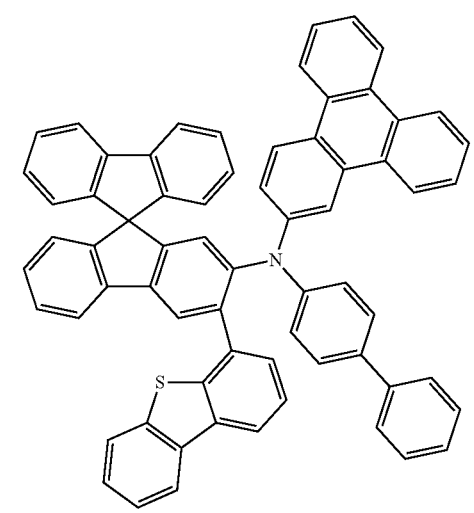
486
-continued
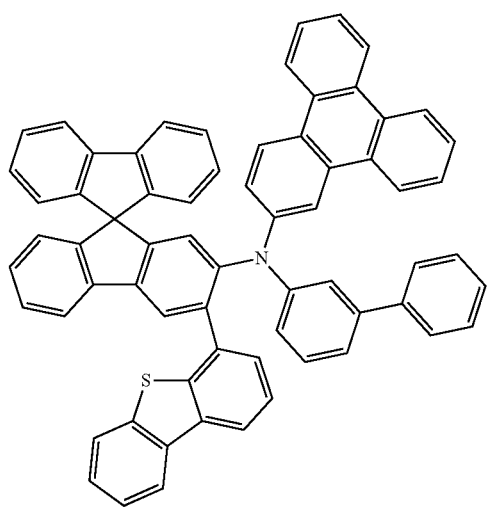
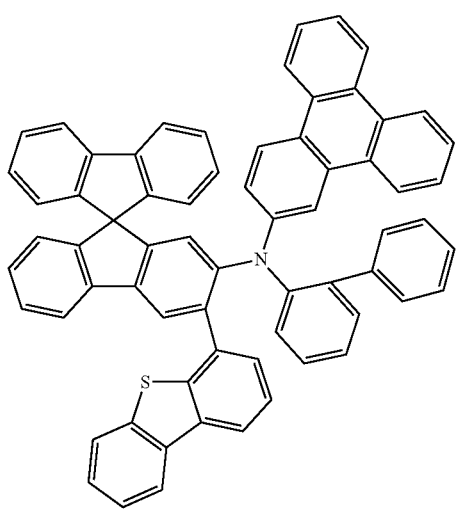
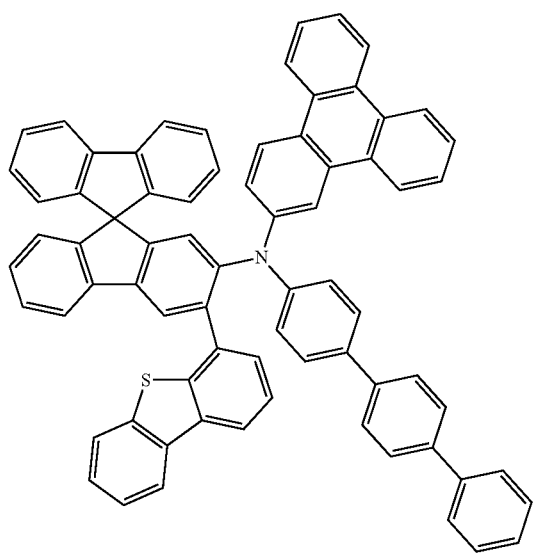

487
-continued
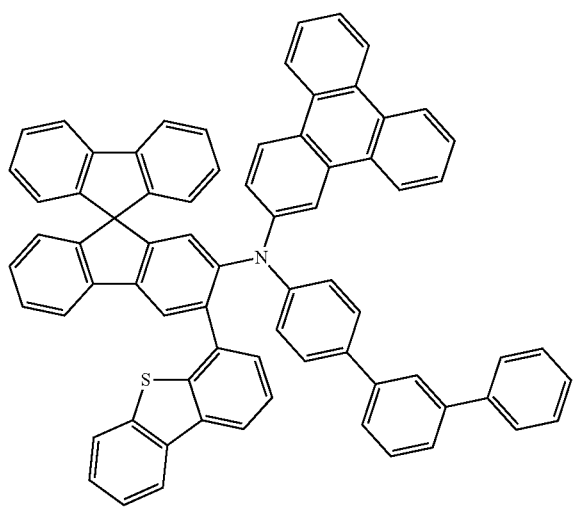
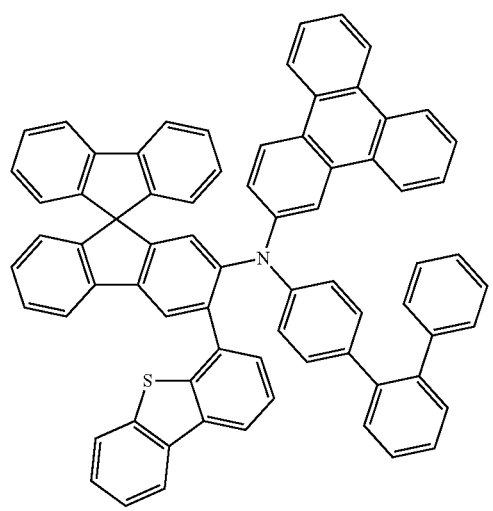
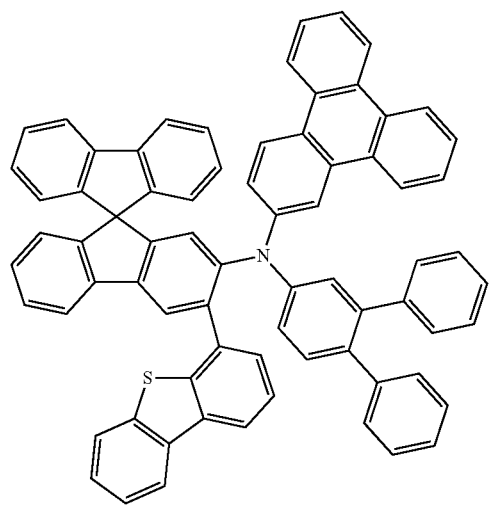
488
-continued
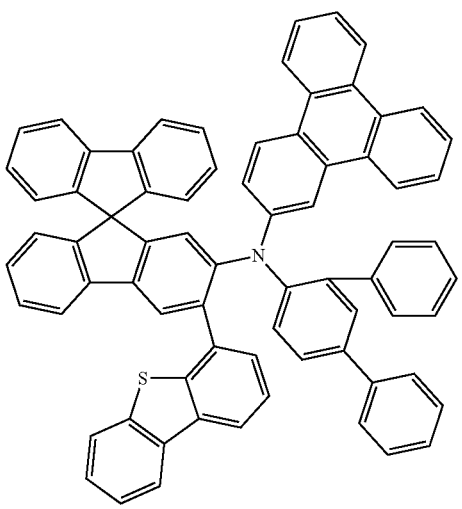
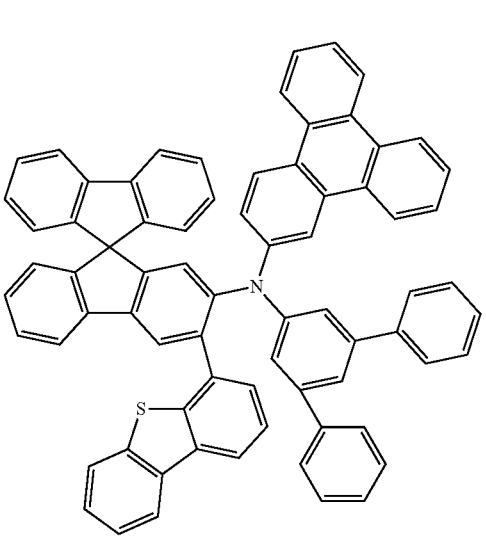
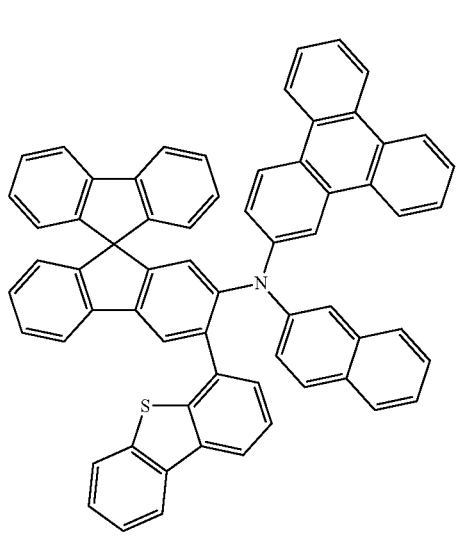

489
-continued
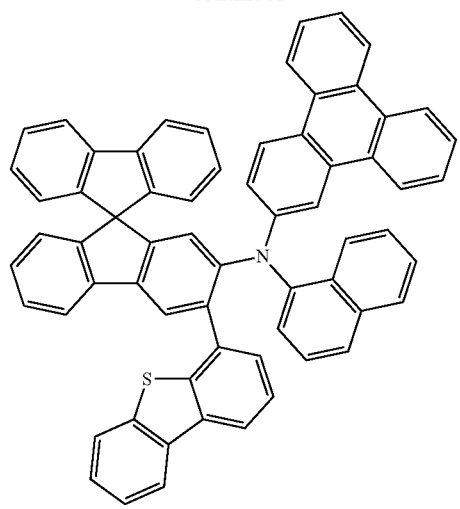
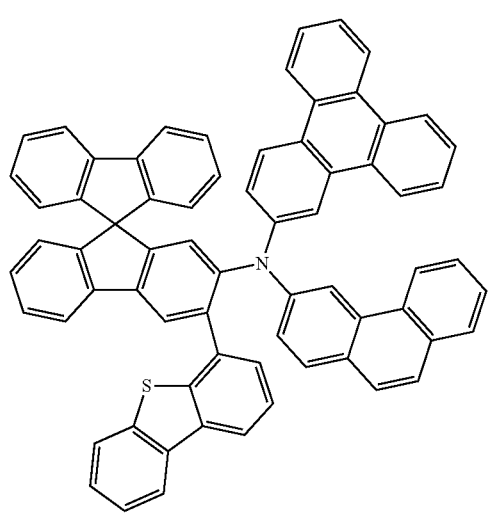
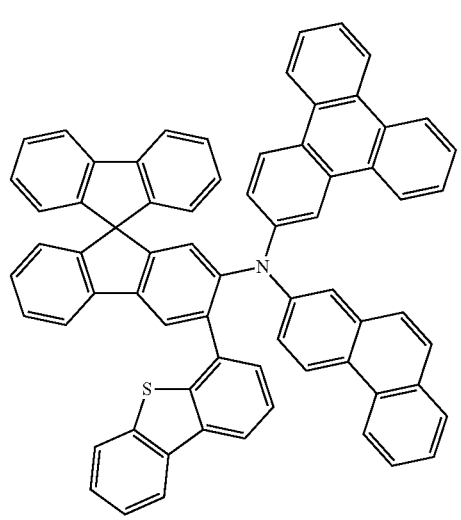
490
-continued
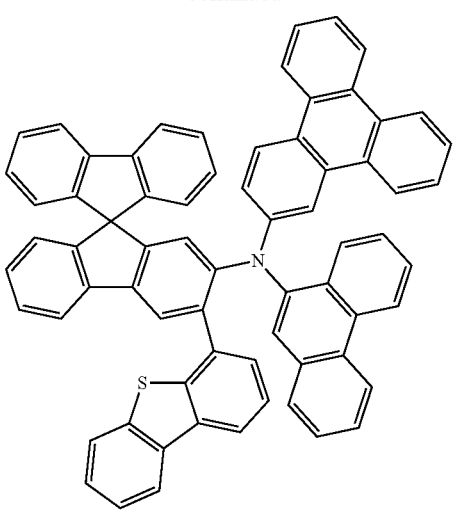
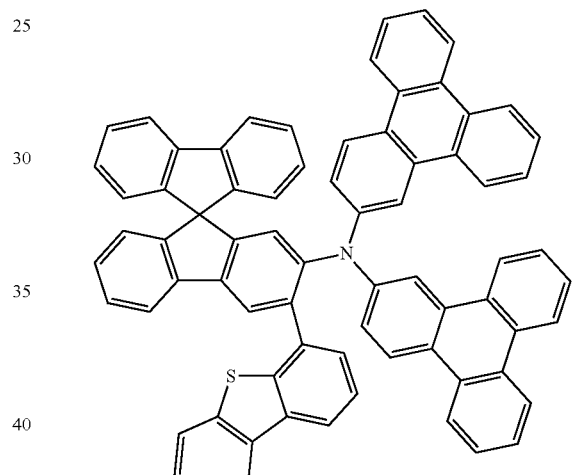
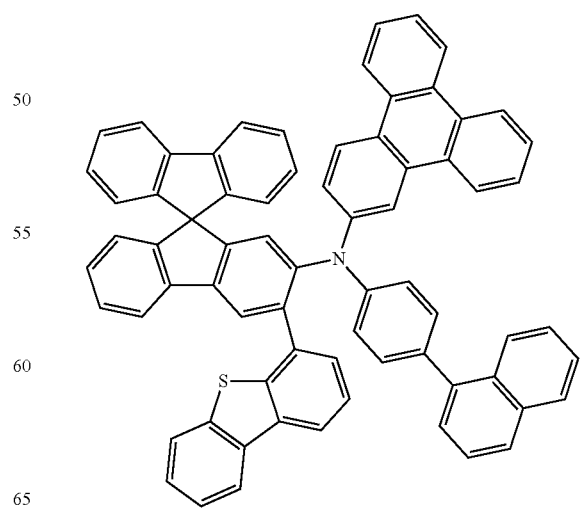

491
-continued
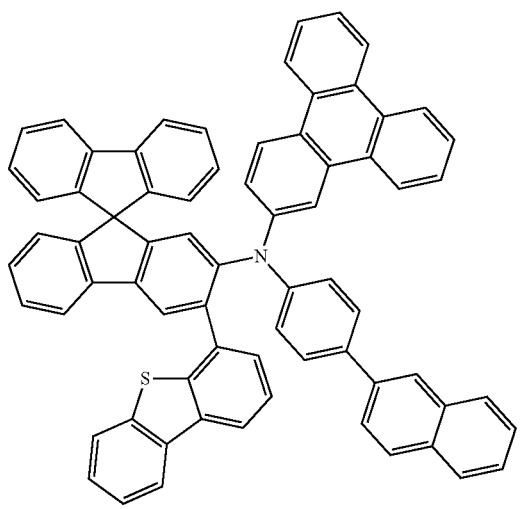
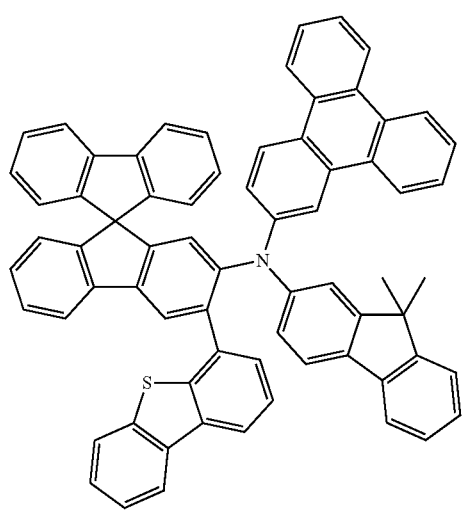
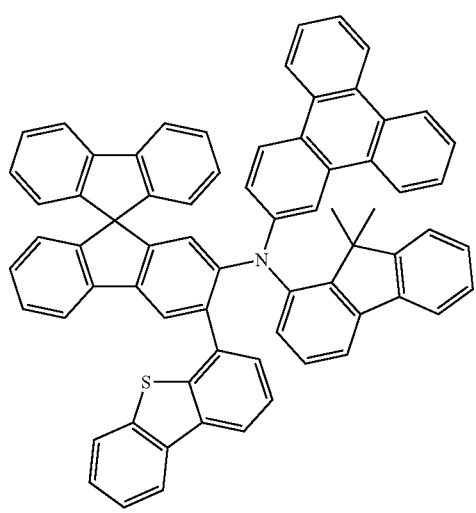
492
-continued
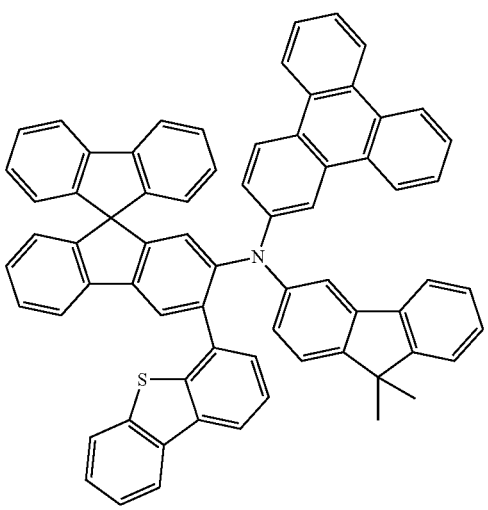
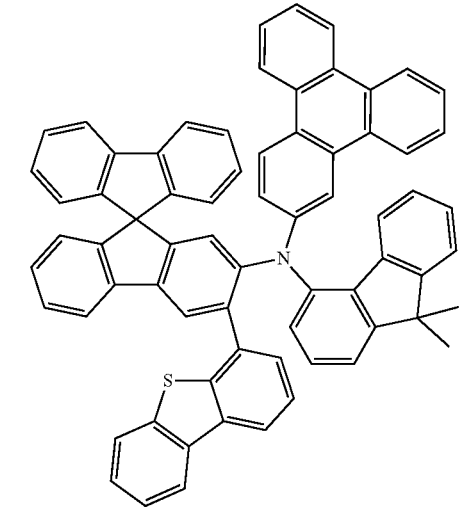
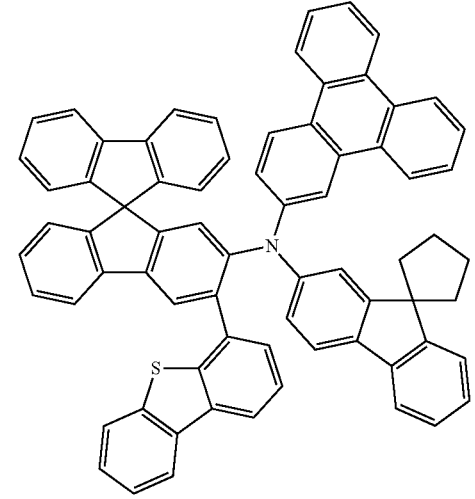

493
-continued
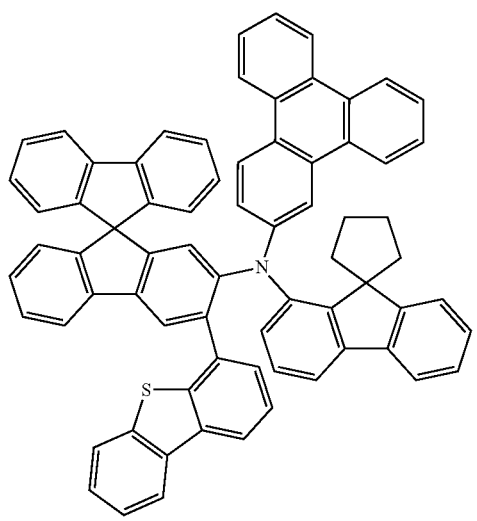
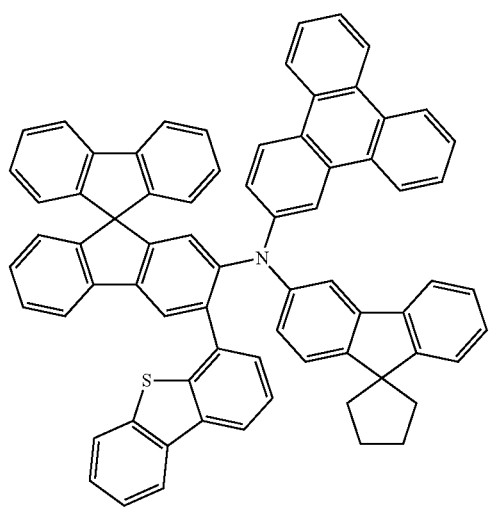
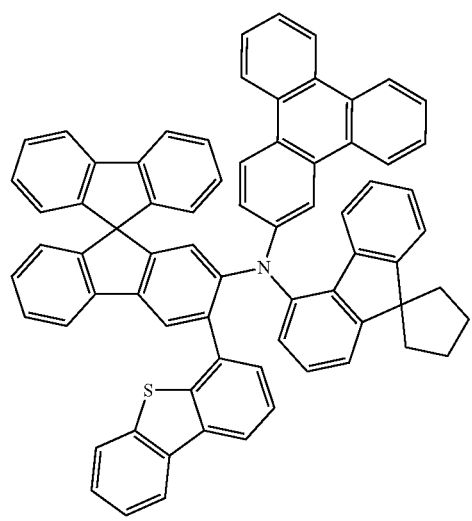
494
-continued
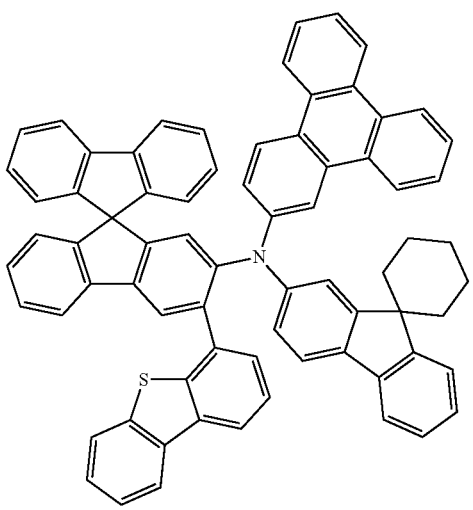
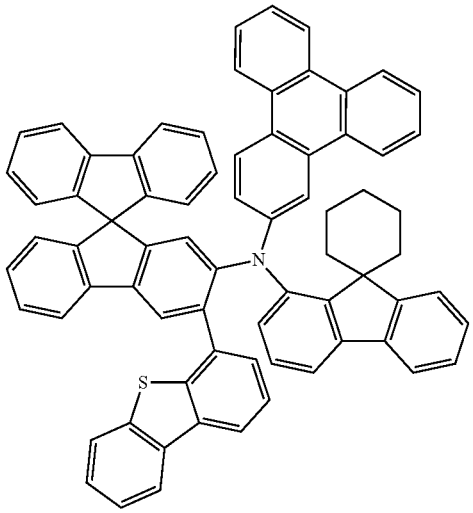
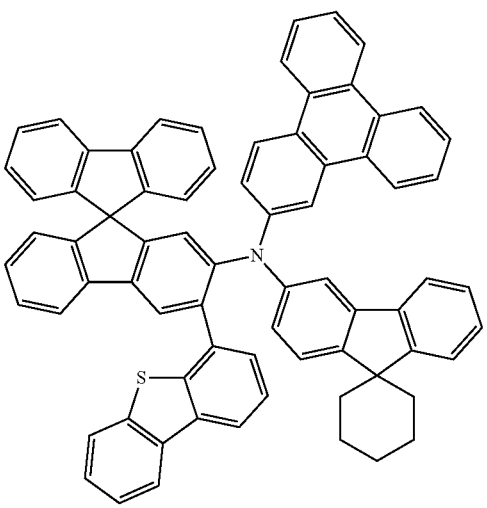

-continued
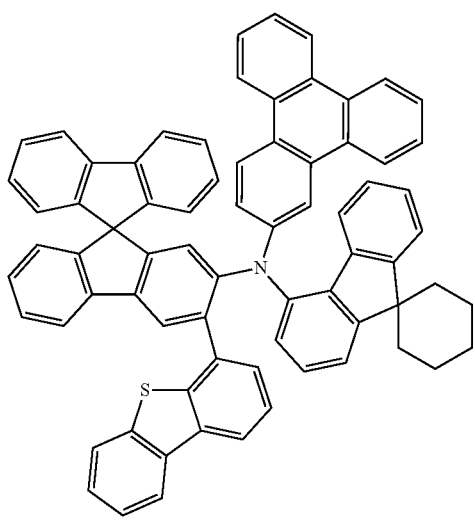
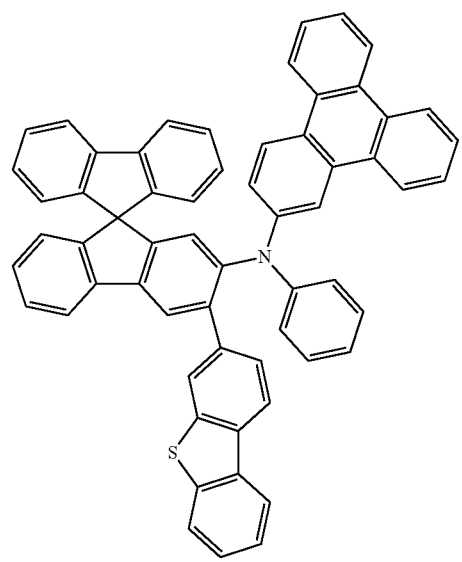
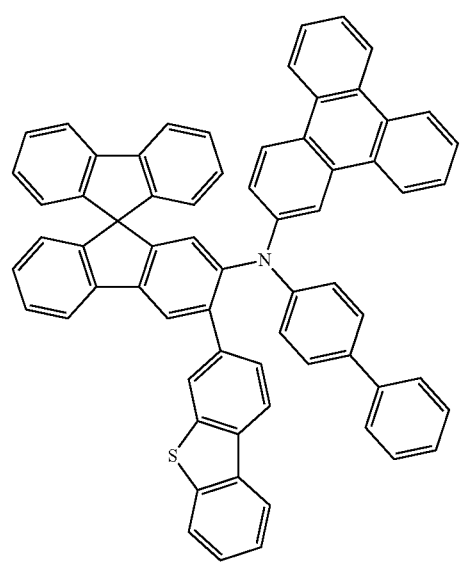
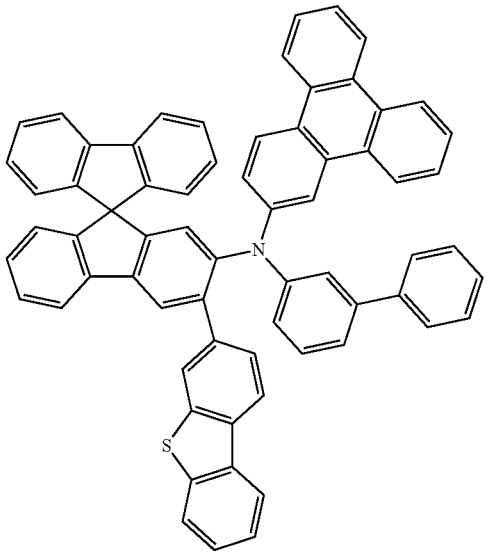
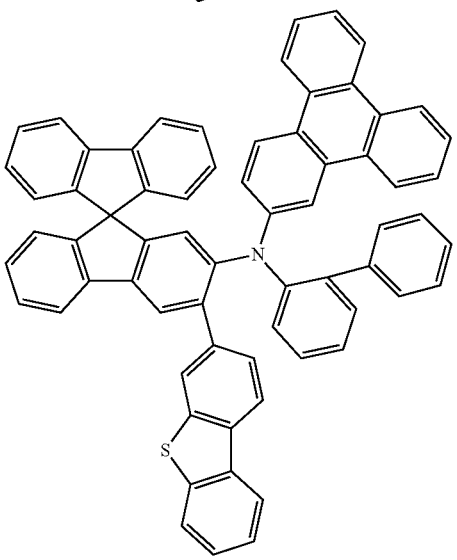
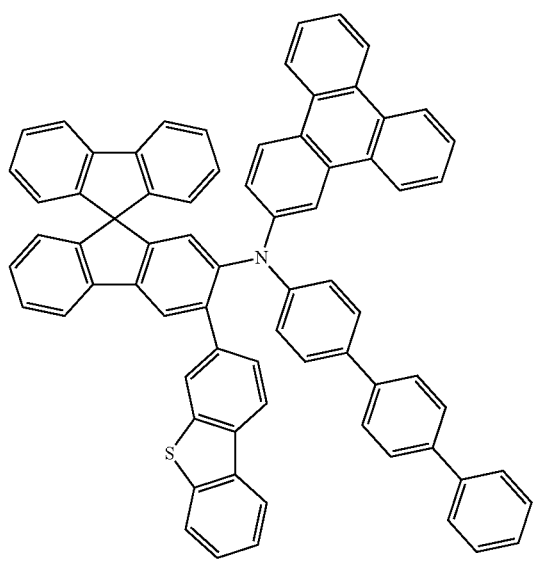

497
-continued

498
-continued

499
-continued
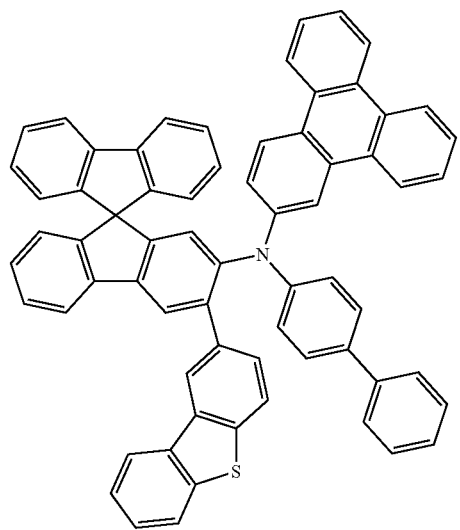
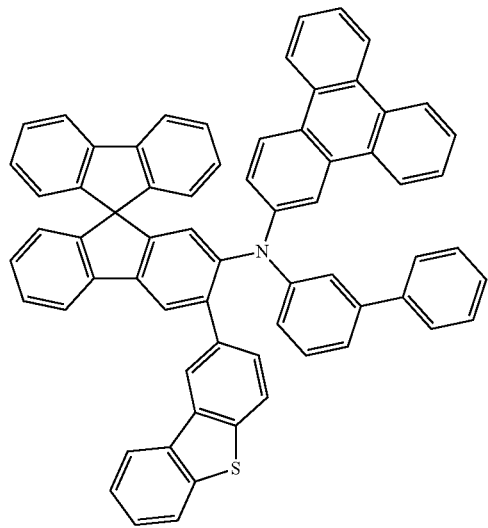
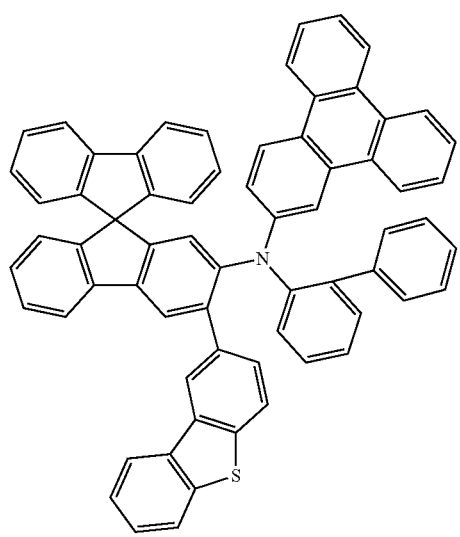
500
-continued
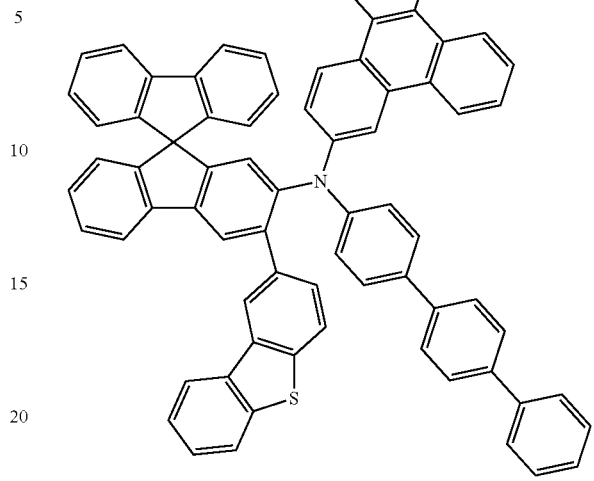
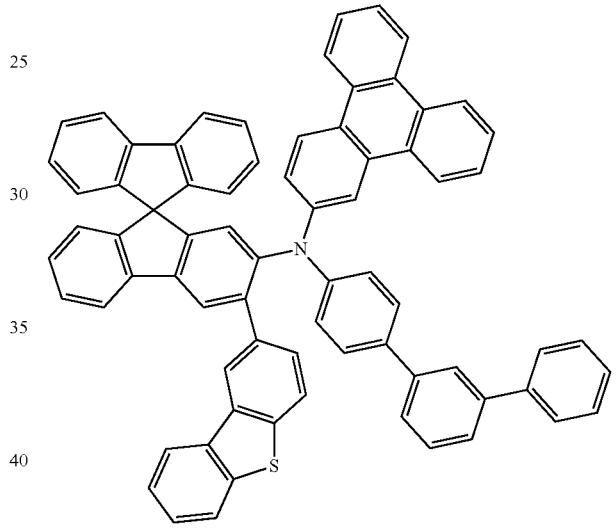
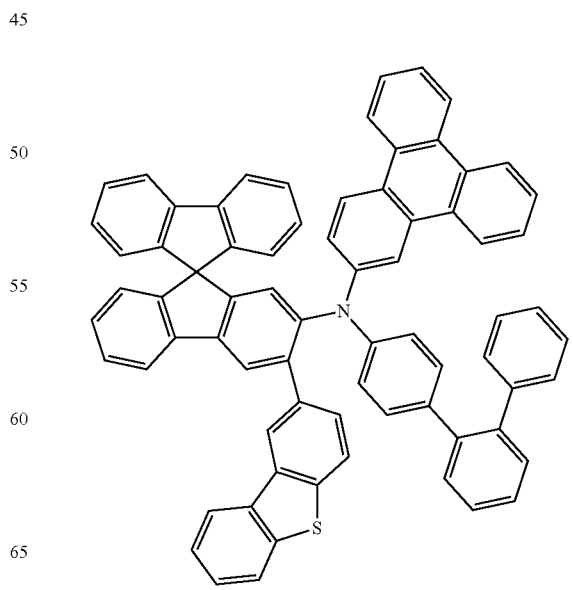

501
-continued
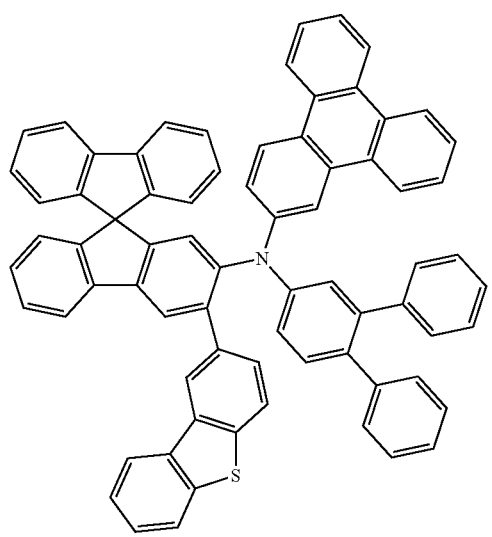
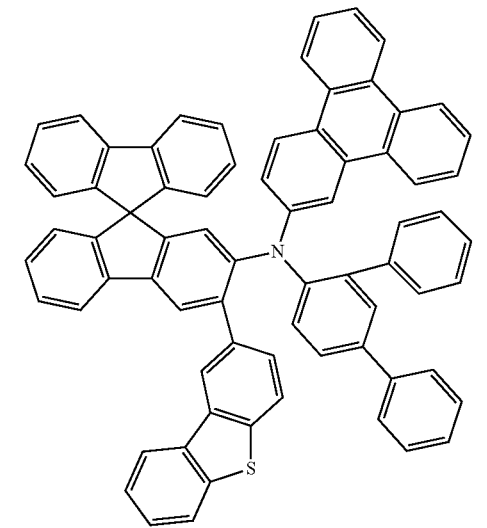
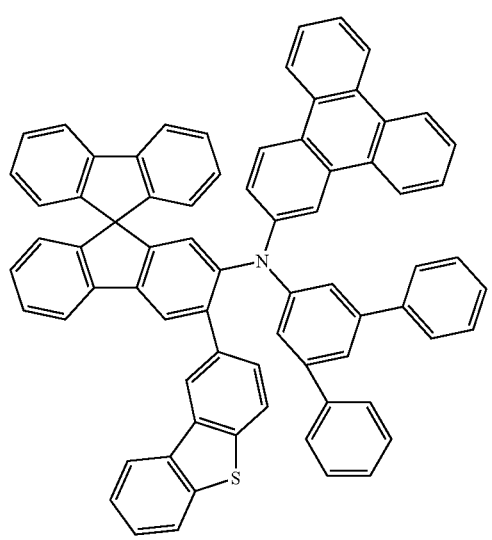
502
-continued
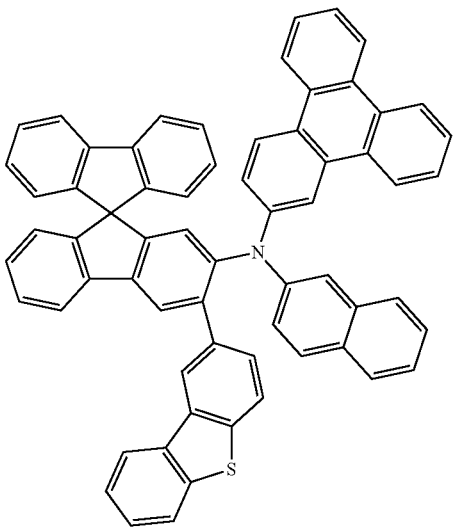
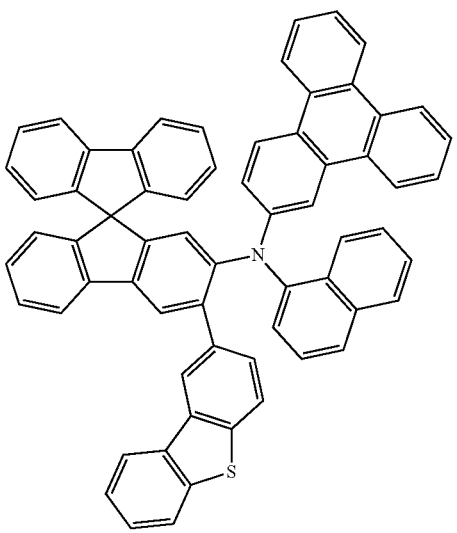
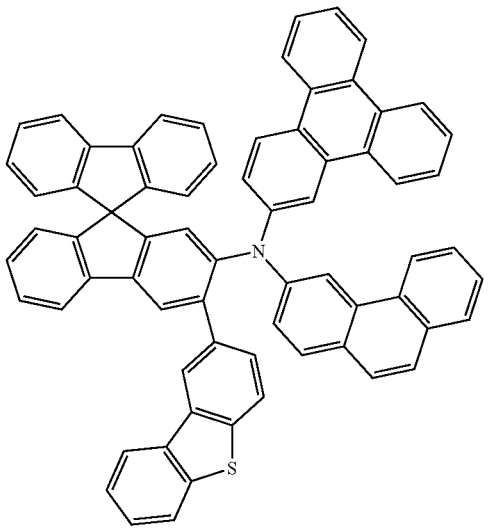

503
-continued
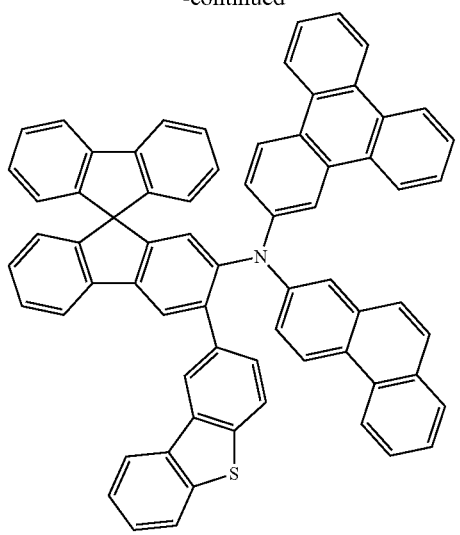
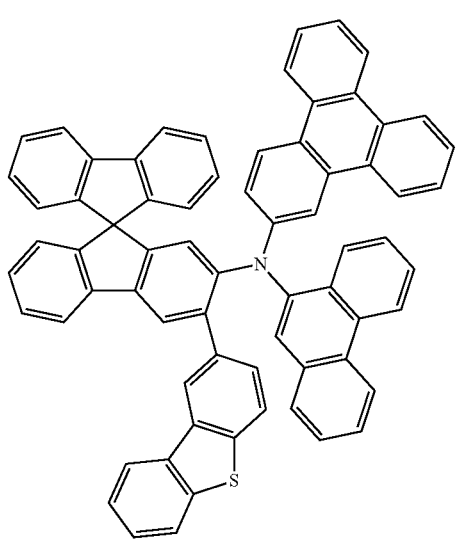
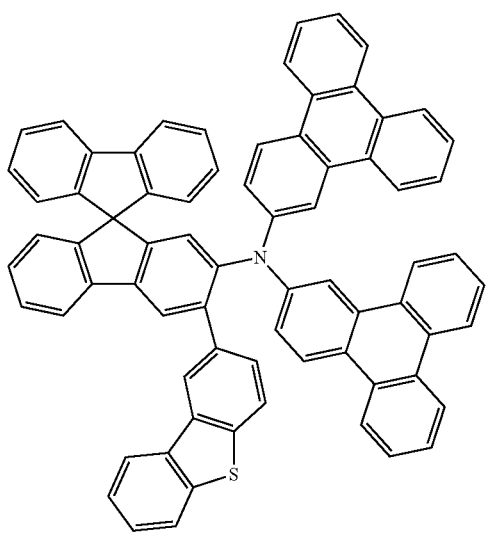
504
-continued
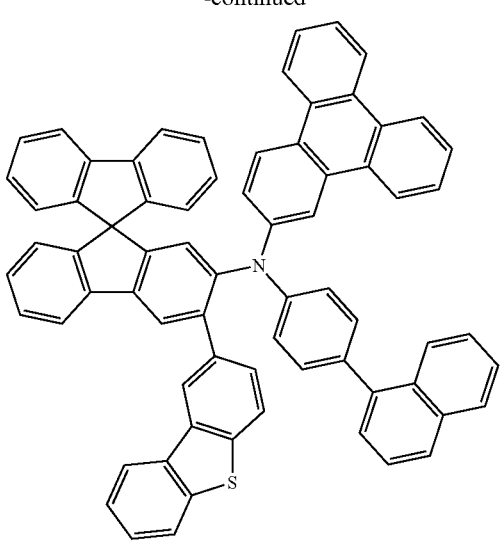
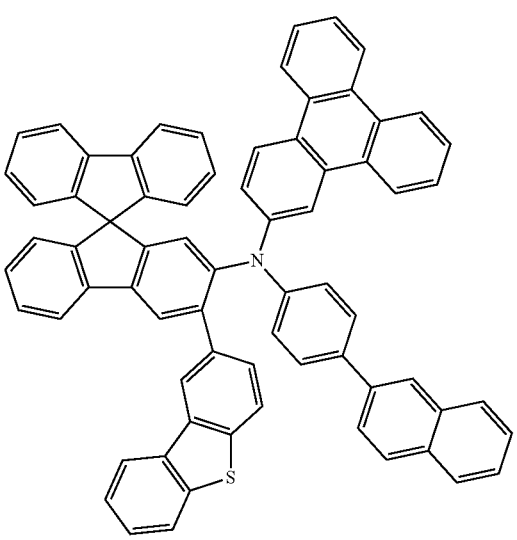
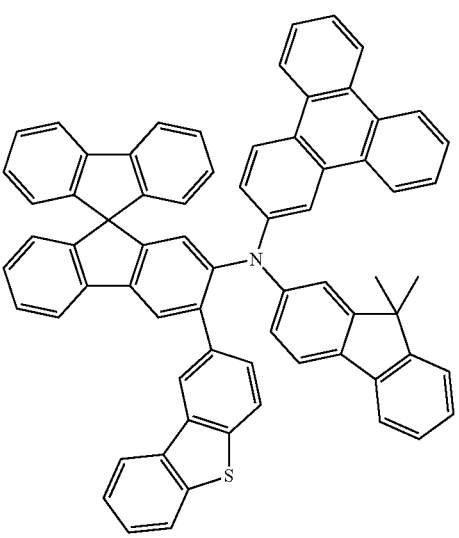

505
-continued
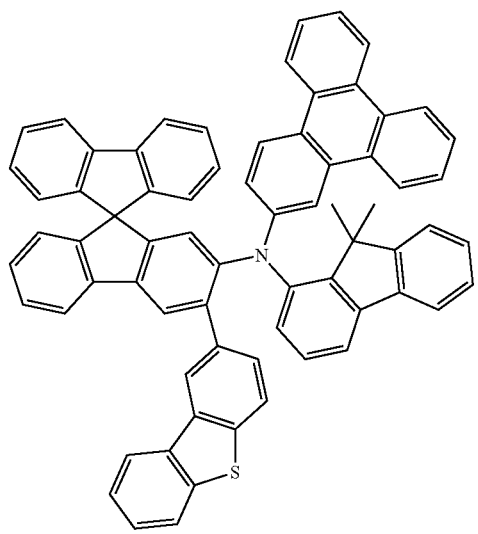
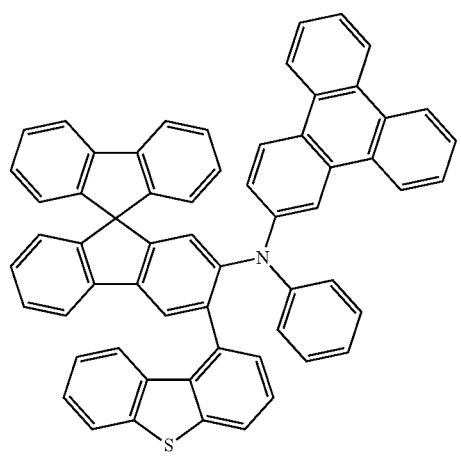
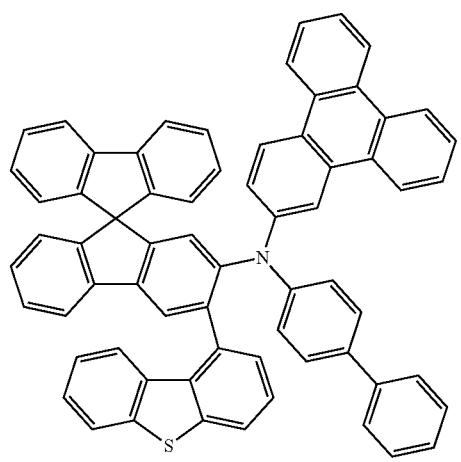
506
-continued
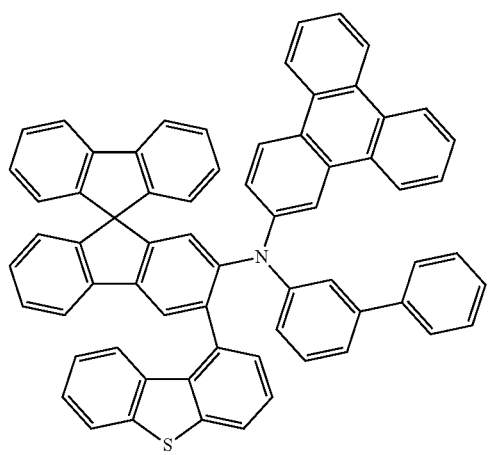
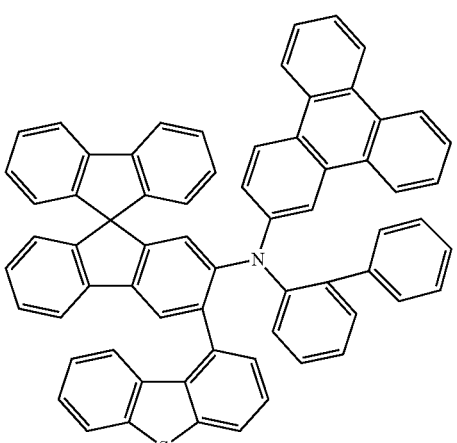
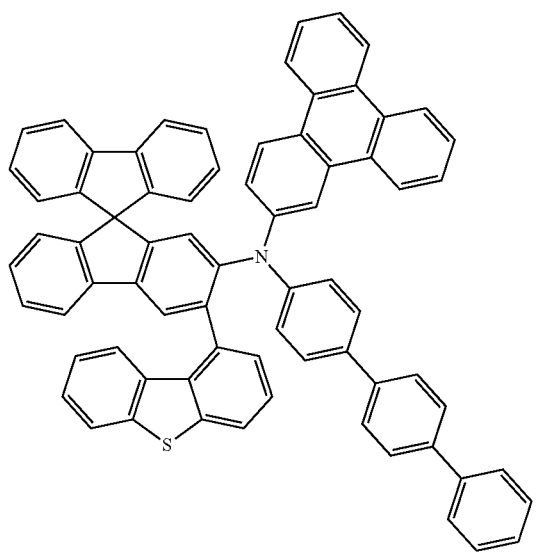

507
-continued
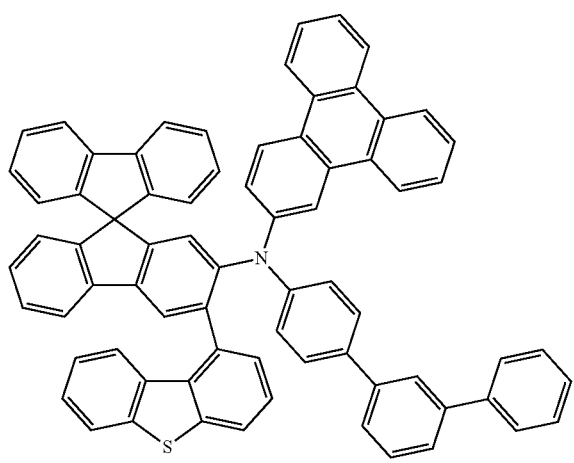
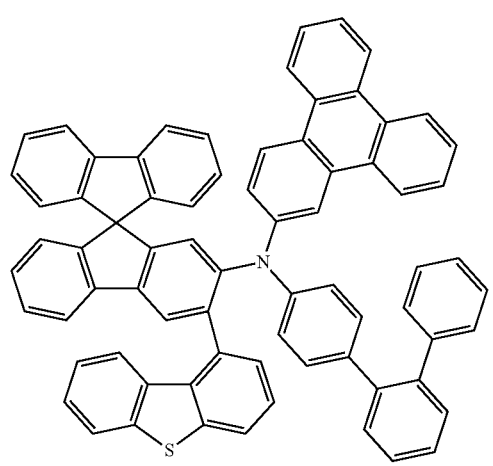
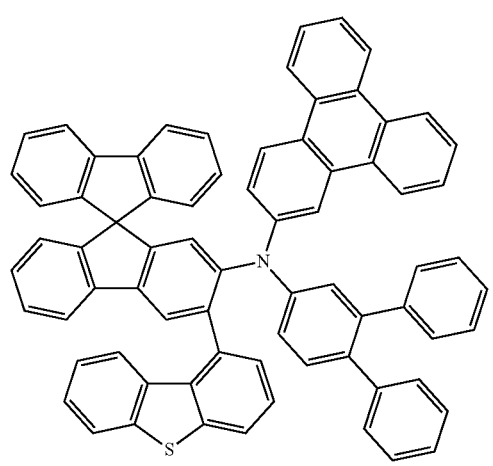
508
-continued
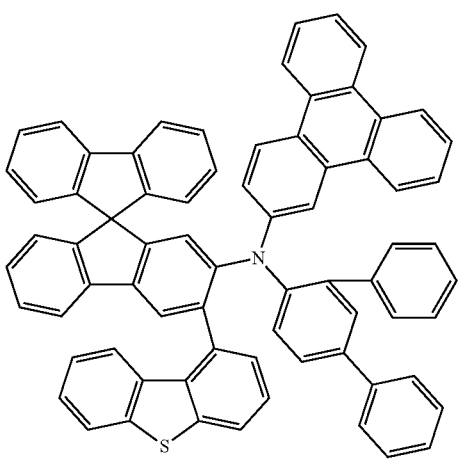
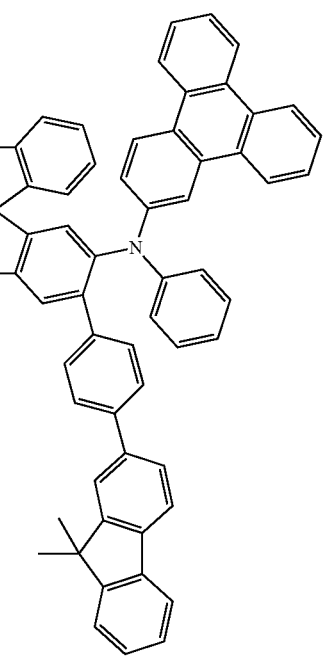

509
-continued
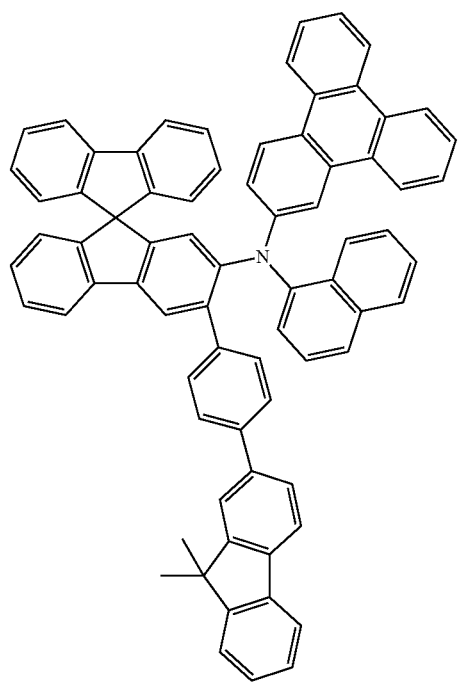
510
-continued
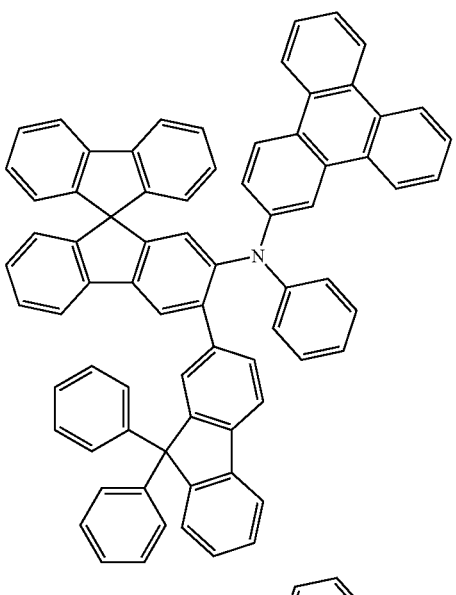
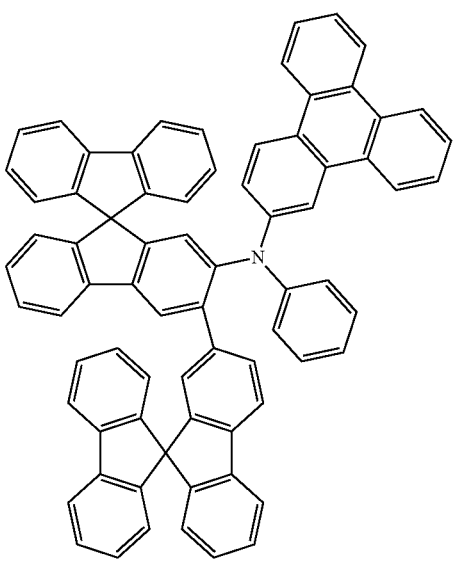
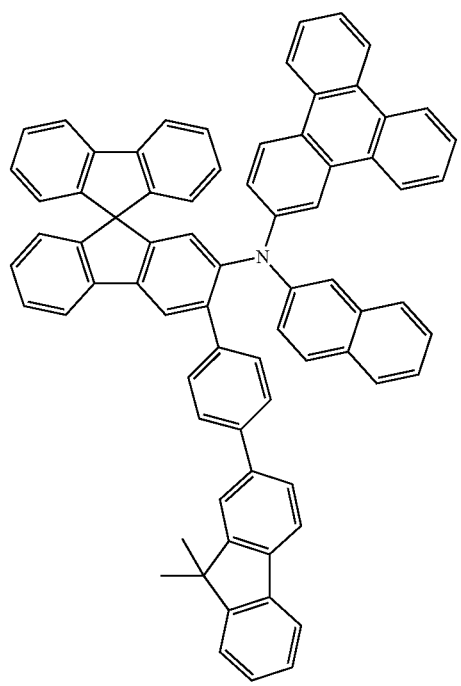
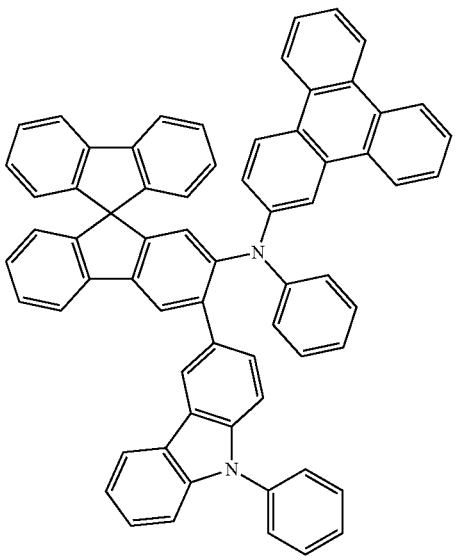

511
-continued
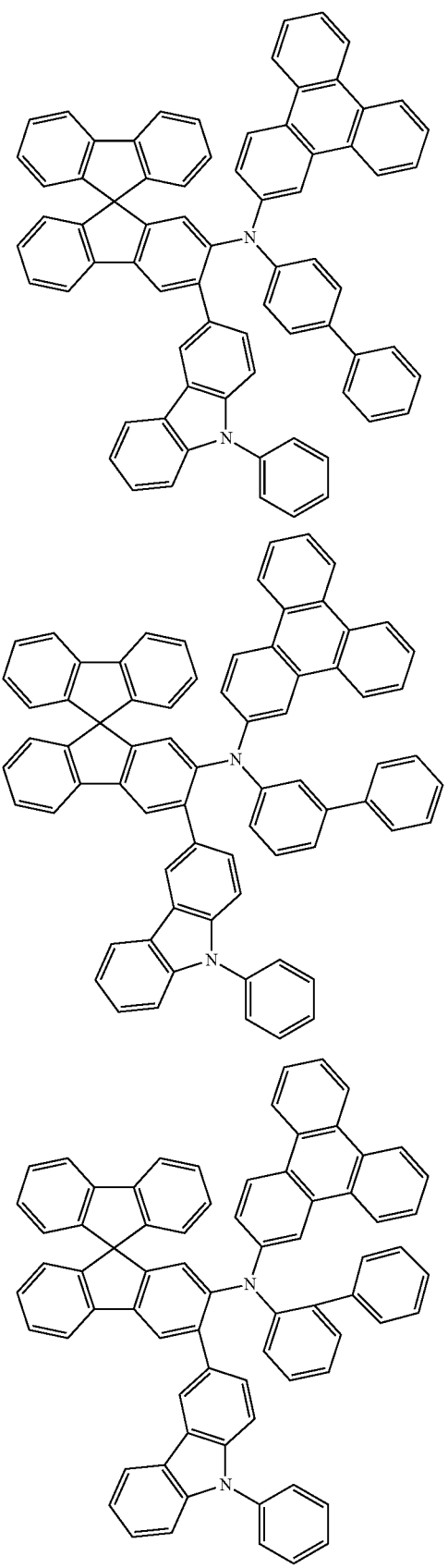
512
-continued
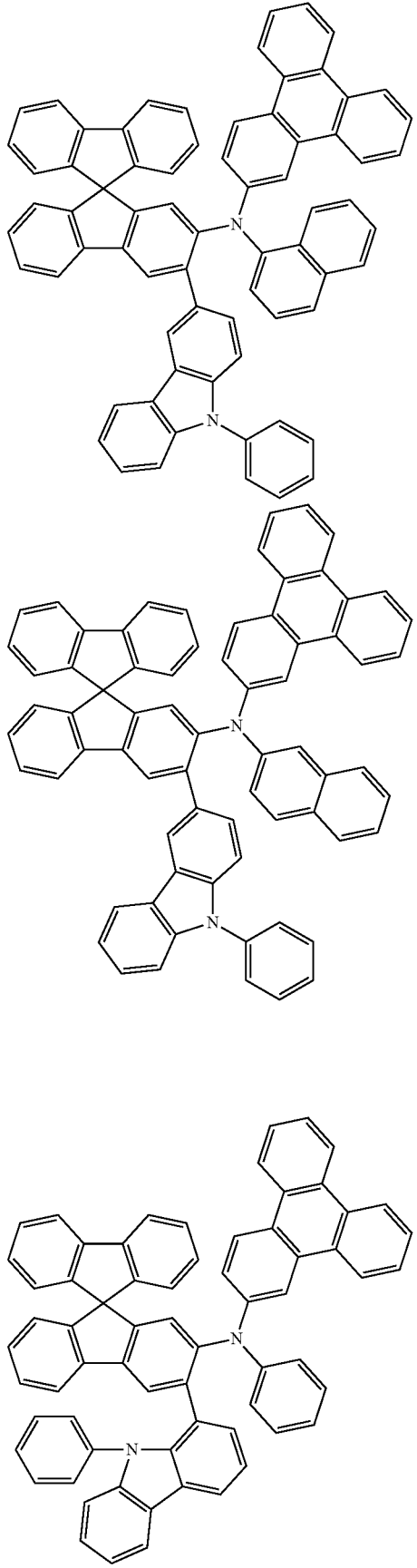

513
-continued
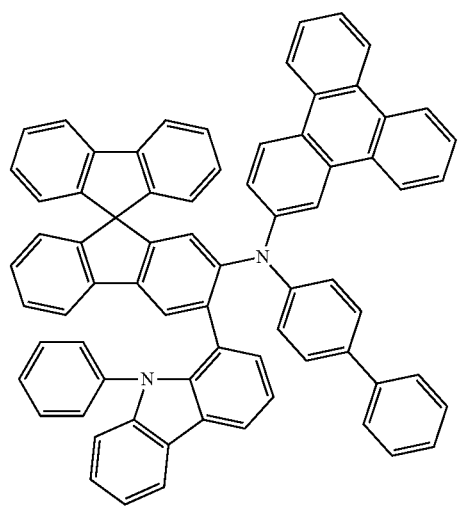
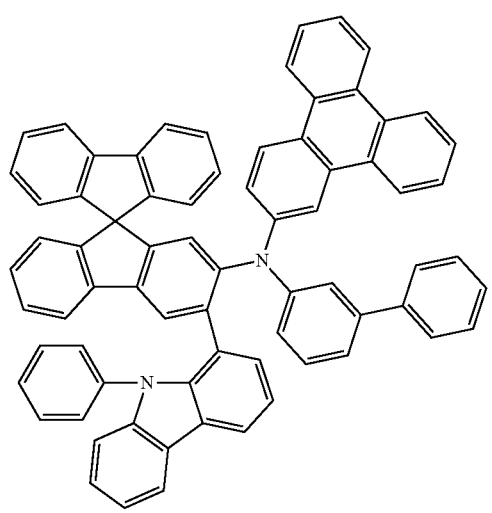
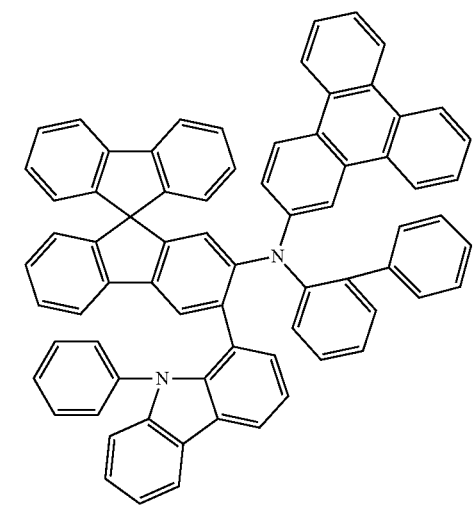
514
-continued
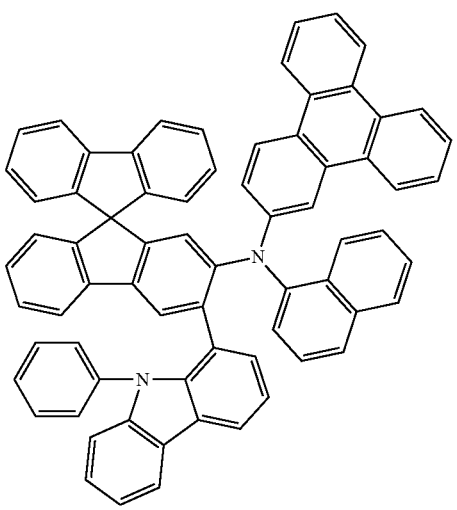
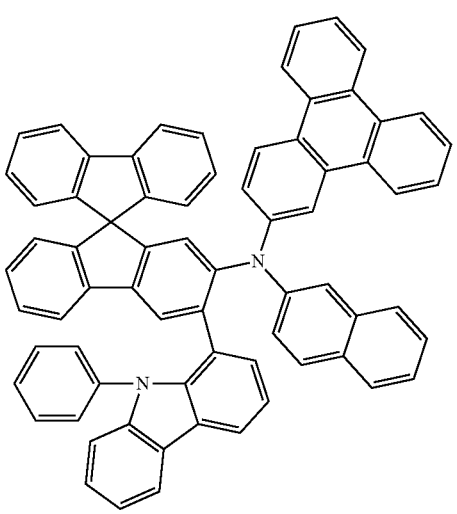
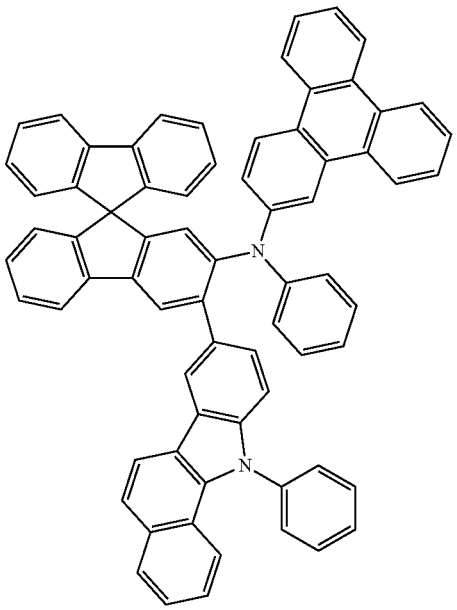

515
-continued
516
-continued
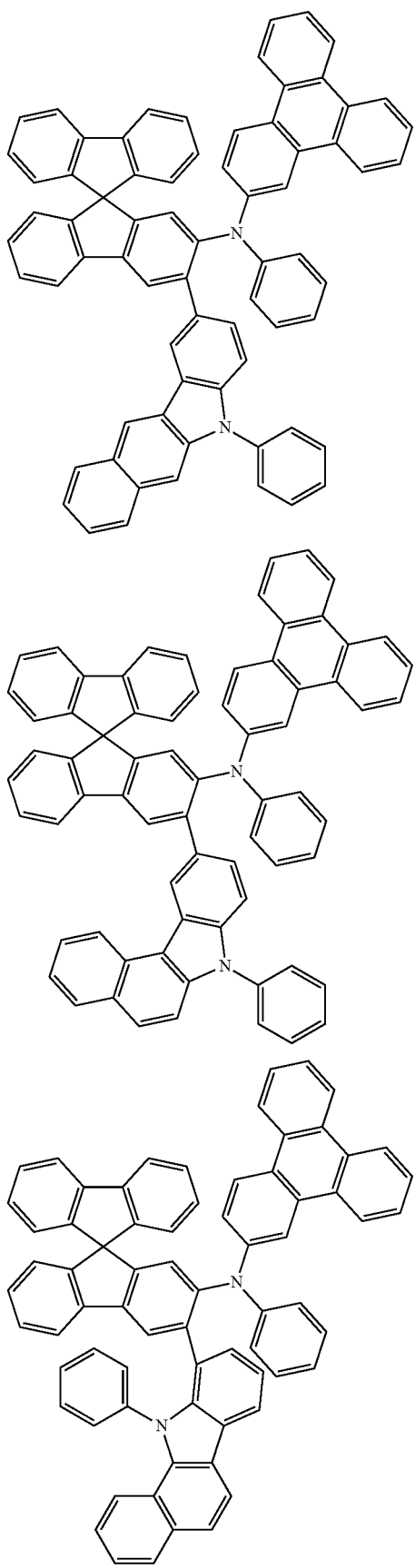
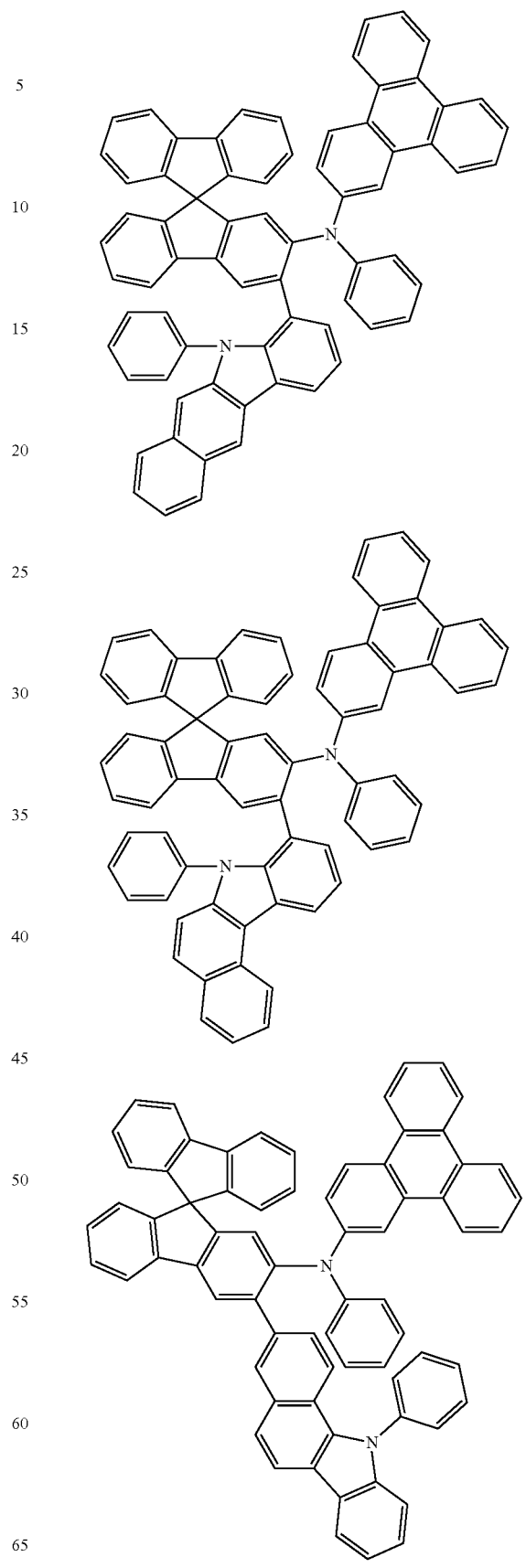

517
-continued
518
-continued
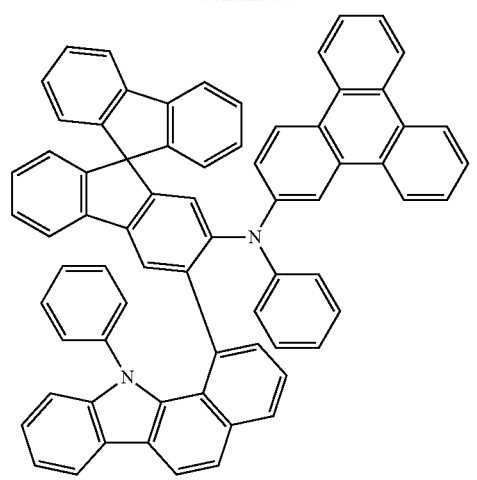
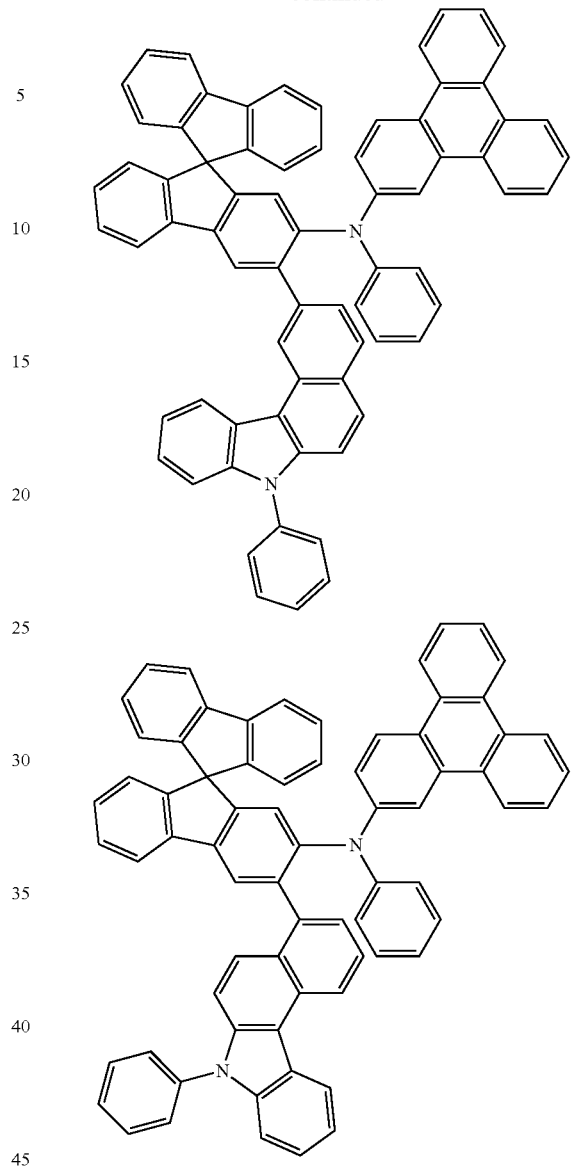
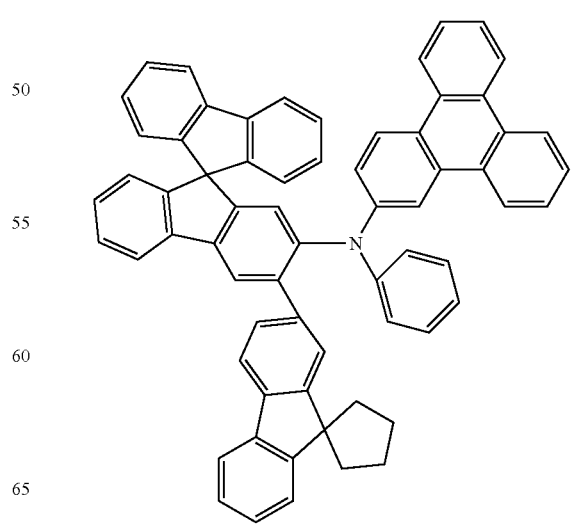

519
-continued
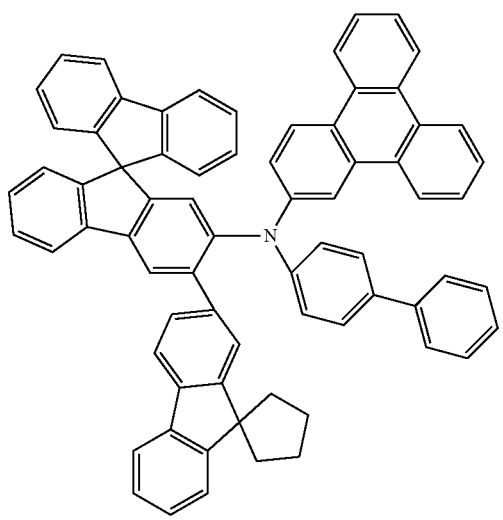
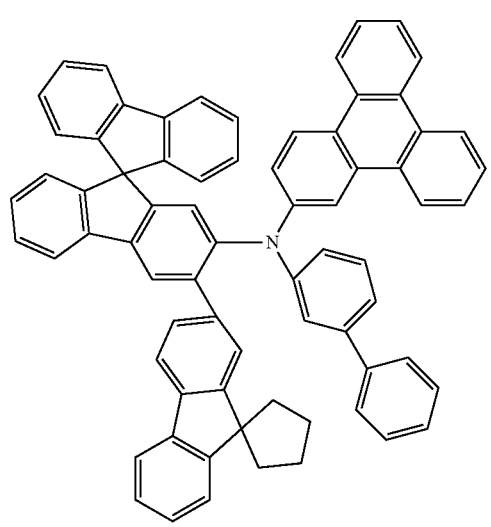
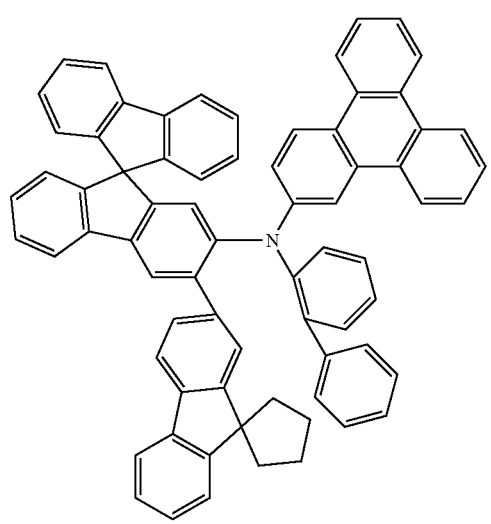
520
-continued
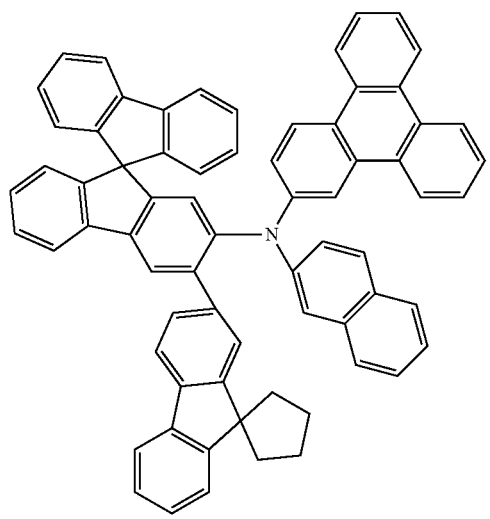
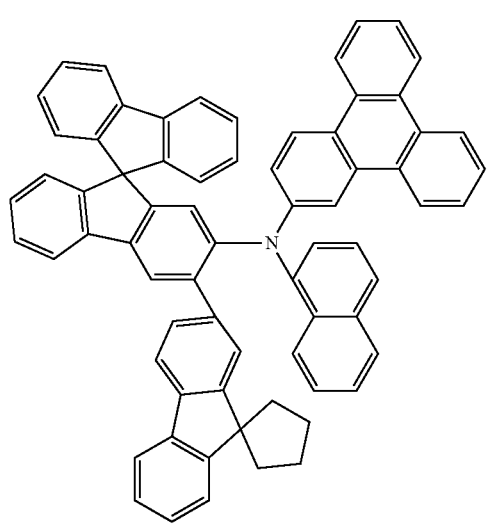
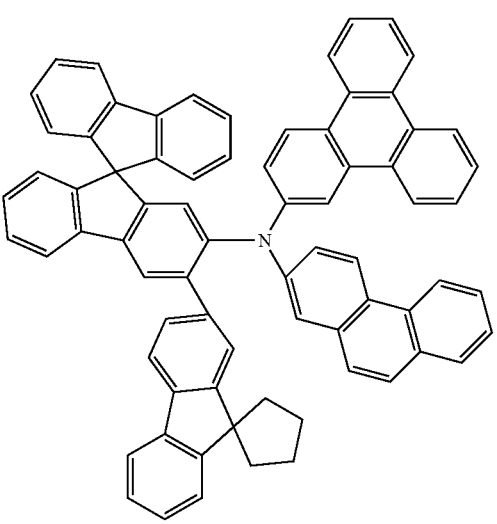

521
-continued
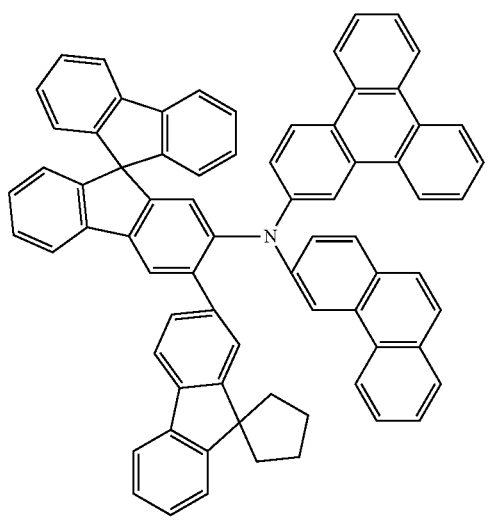
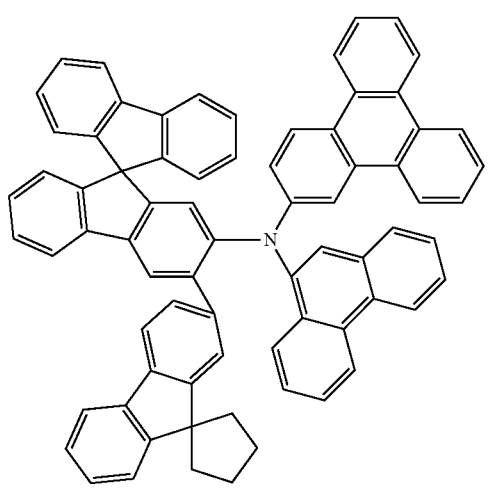
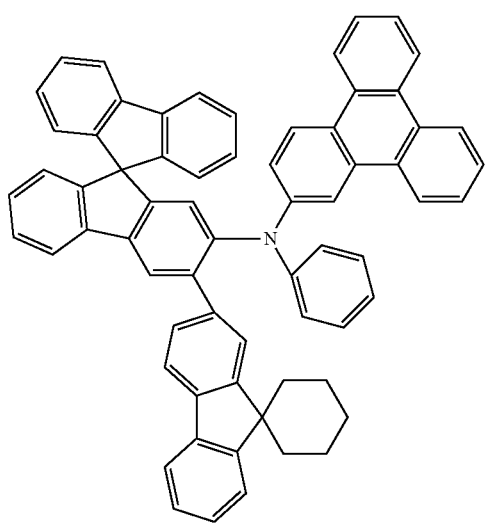
522
-continued
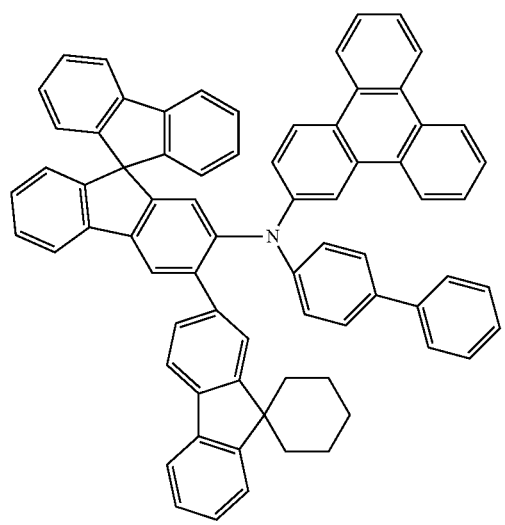
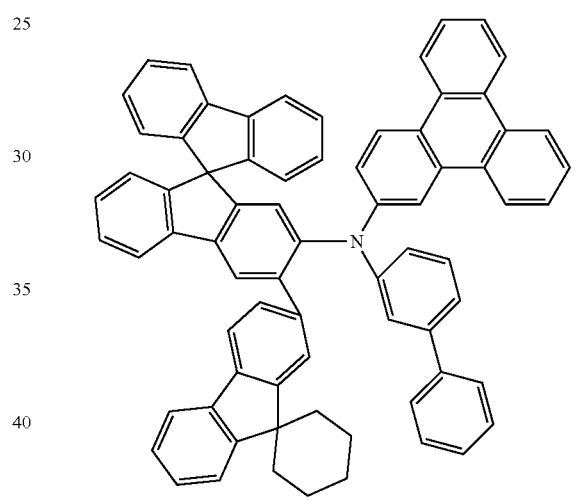
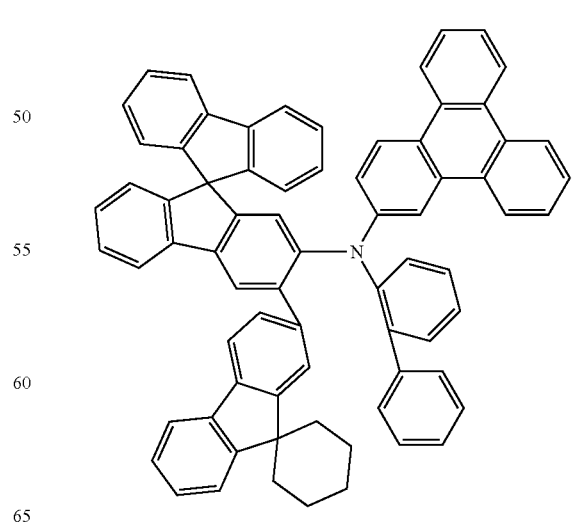

523
-continued
524
-continued
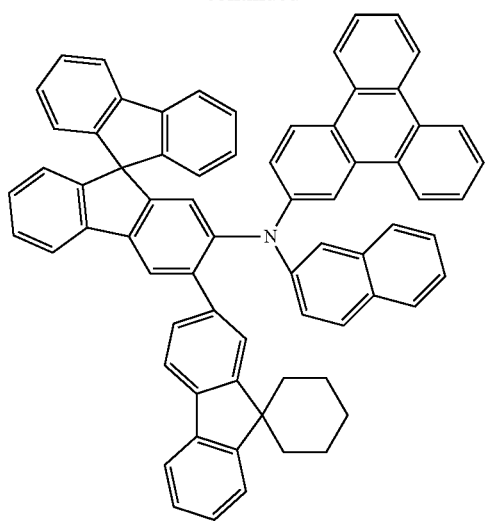
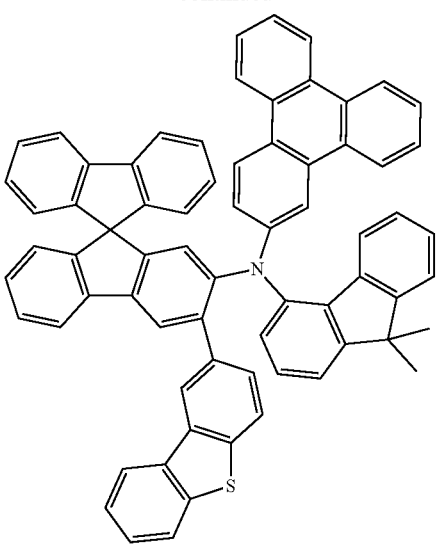

525
-continued
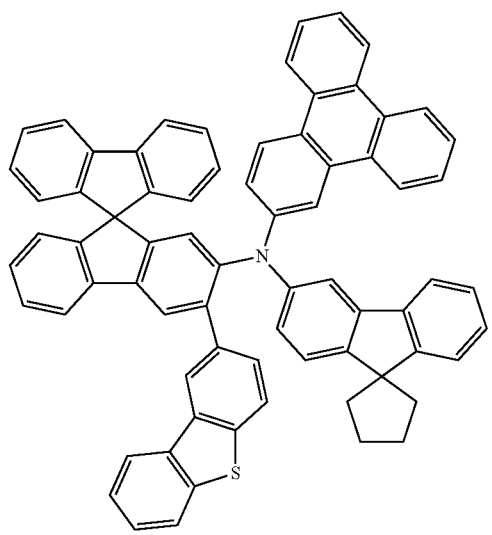
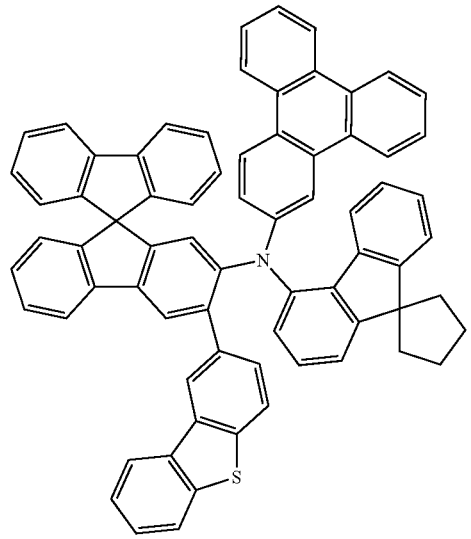
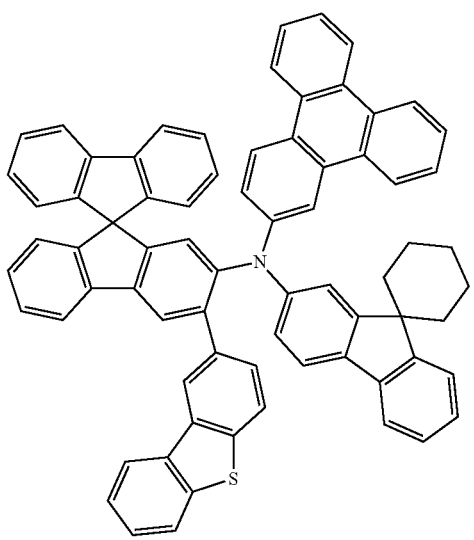
526
-continued
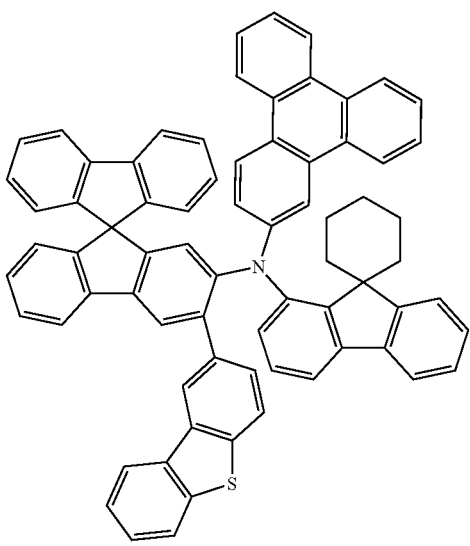
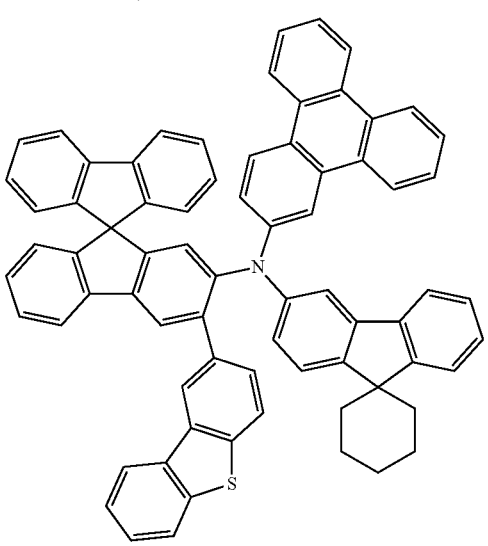
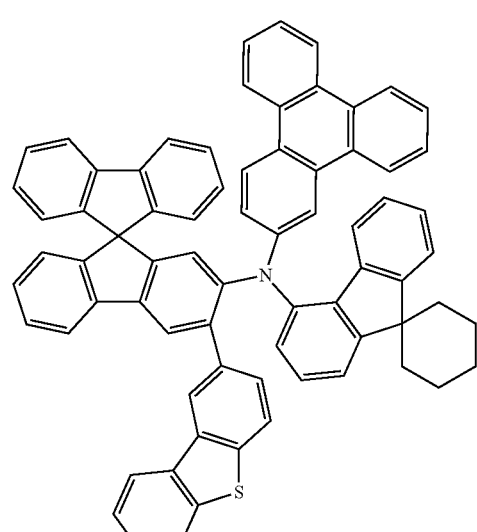

527
-continued
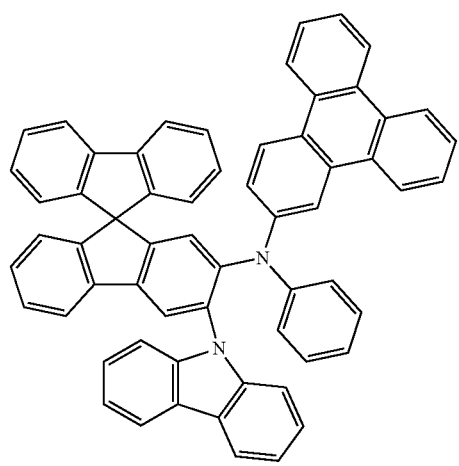
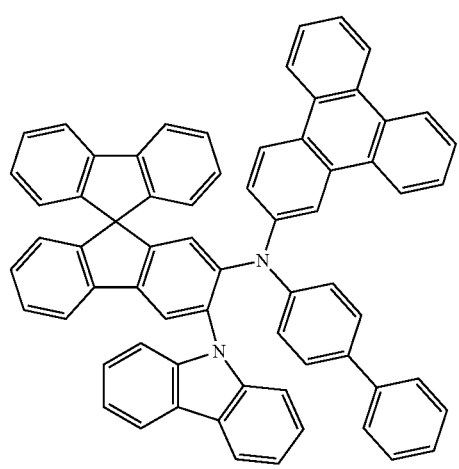
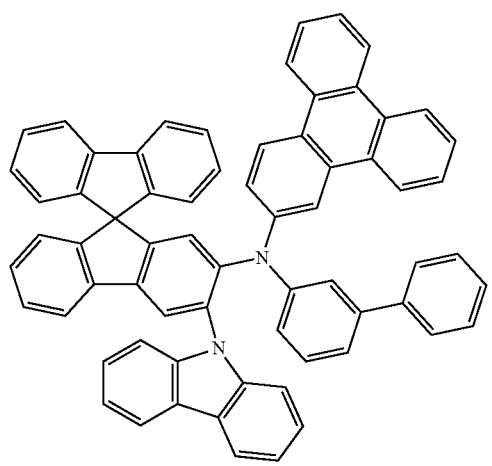
528
-continued
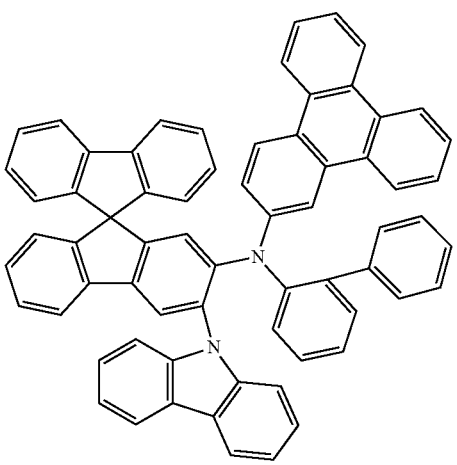
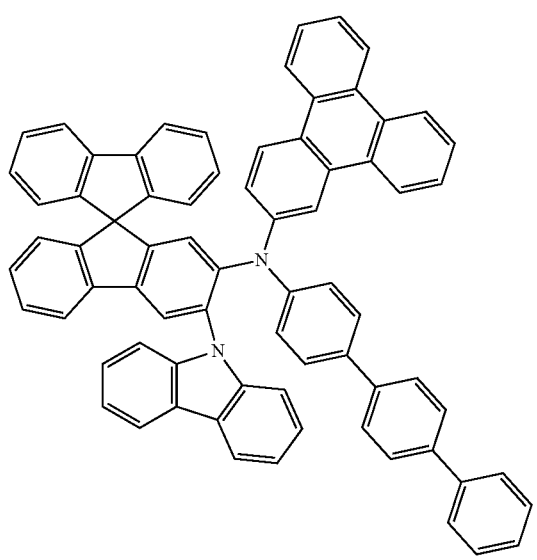
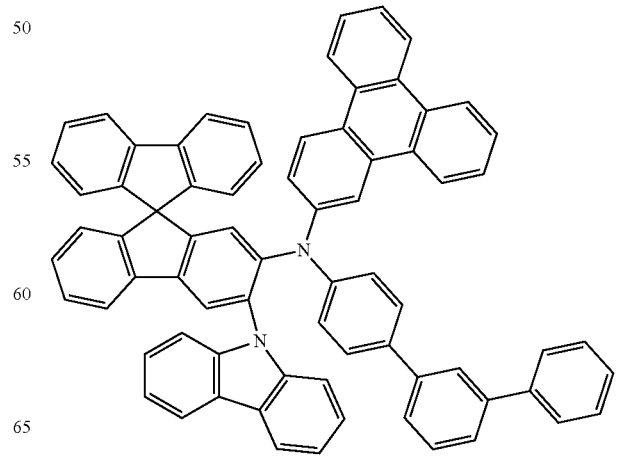

529
-continued
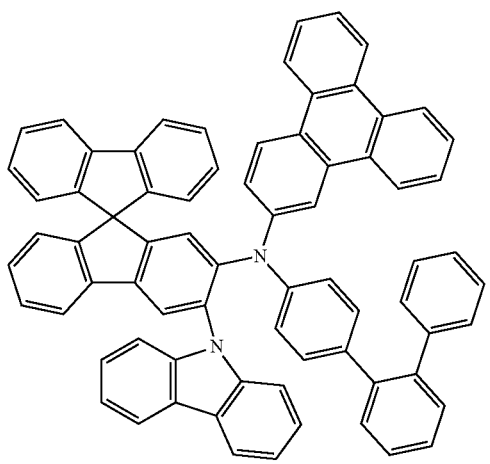
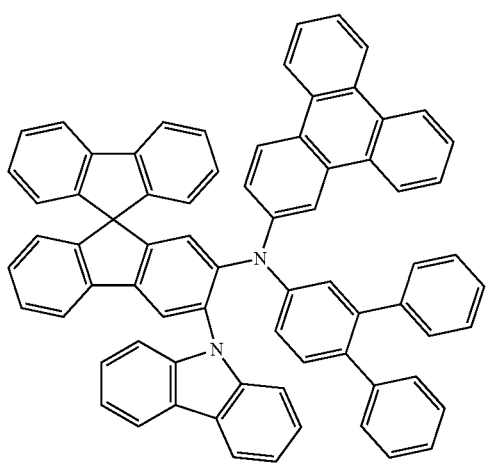
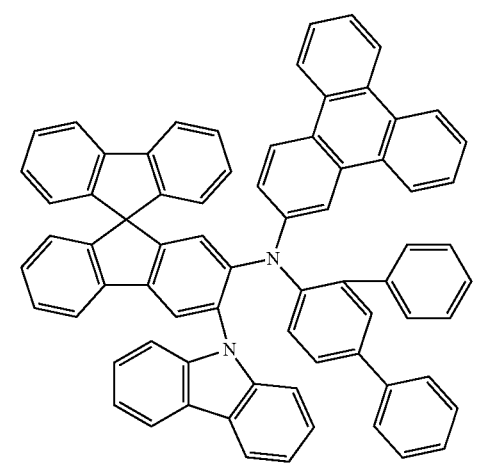
530
-continued
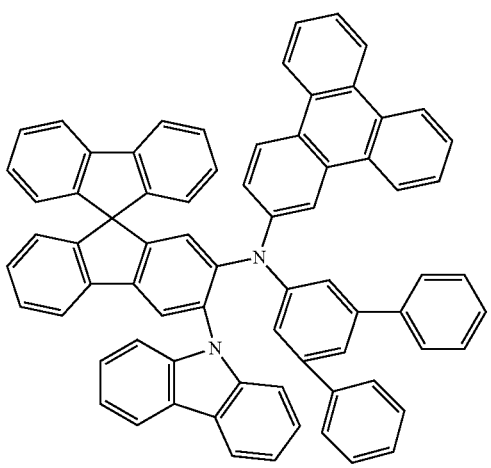
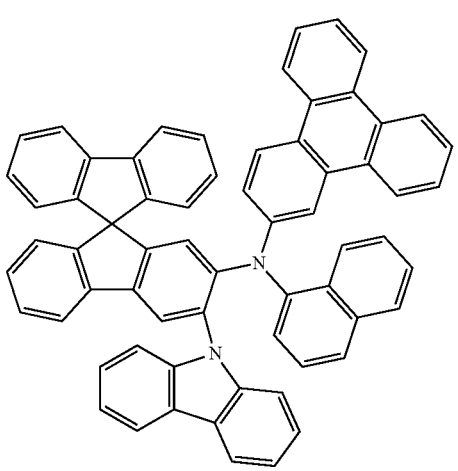
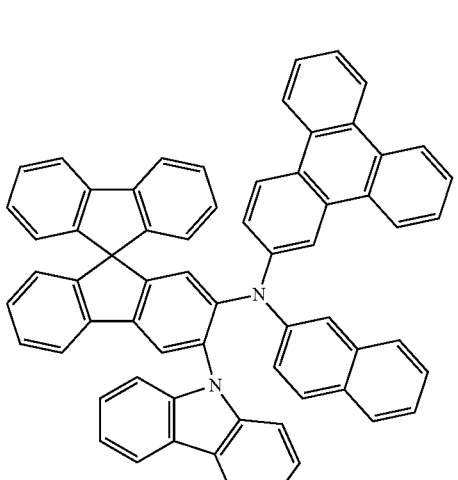

531
-continued
532
-continued
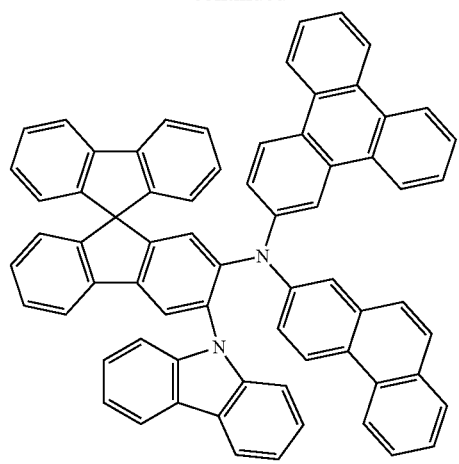
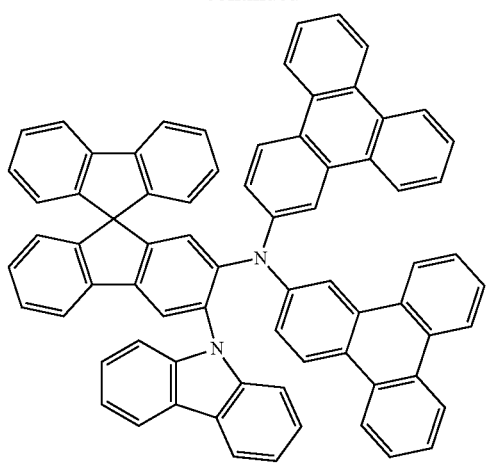
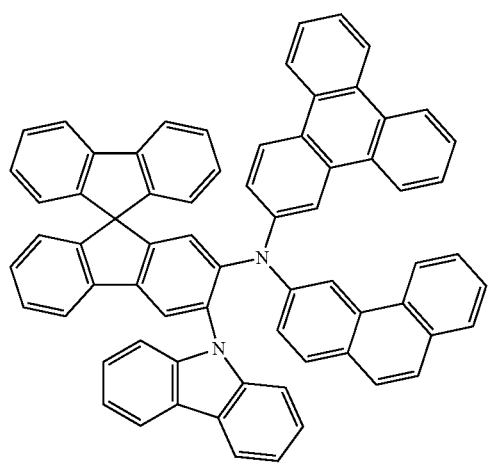
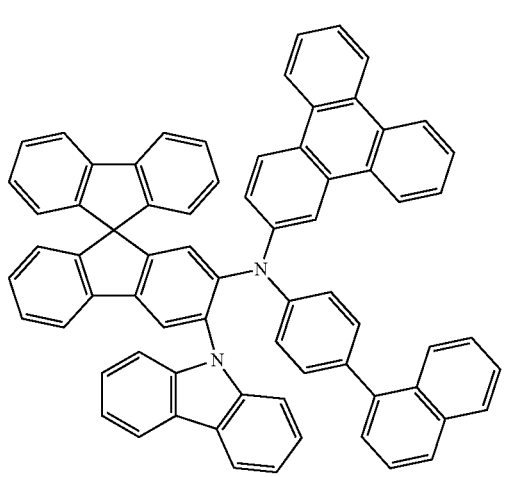
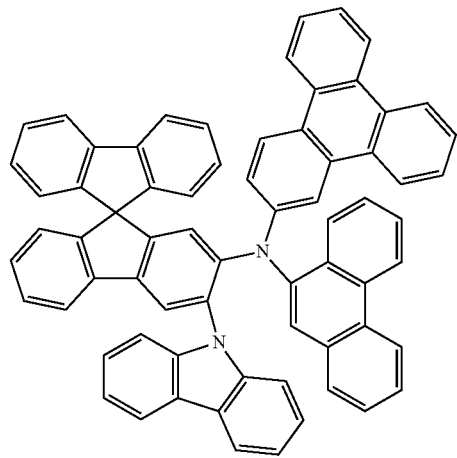
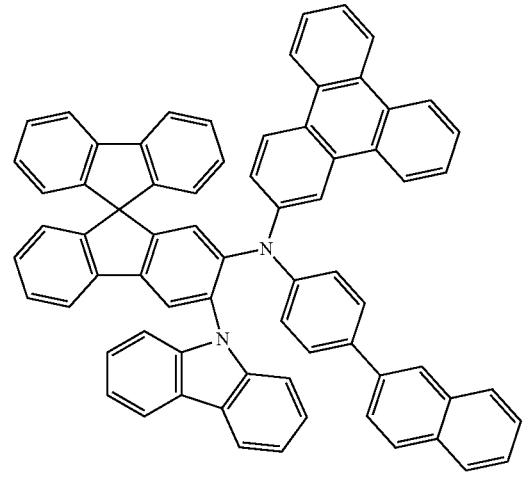

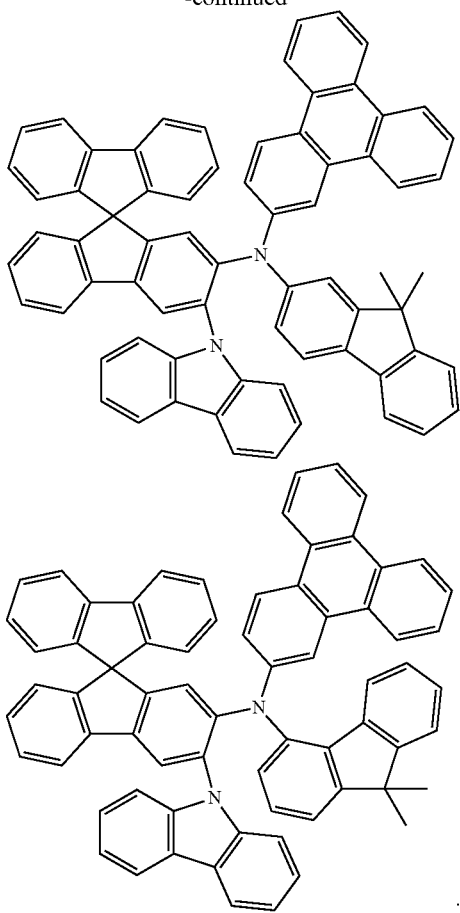

10. An organic light emitting device comprising:
a first electrode;
a second electrode; and
one or more organic material layers disposed between the first electrode and the second electrode,
wherein one or more layers of the one or more organic material layers comprise the compound of claim 1.

11. The organic light emitting device of claim 10, wherein the one or more organic material layers comprise a hole injection layer or a hole transfer layer, and the hole injection layer or the hole transfer layer comprises the compound of Chemical Formula 1.

12. The organic light emitting device of claim 10, wherein the one or more organic material layers comprise a light emitting layer, and the light emitting layer comprises the compound of Chemical Formula 1.

13. The organic light emitting device of claim 10, wherein the one or more organic material layers comprise an electron injection layer or an electron transfer layer, and the electron injection layer or the electron transfer layer comprises the compound of Chemical Formula 1.

14. The organic light emitting device of claim 10, wherein the one or more organic material layers comprise an electron blocking layer, and the electron blocking layer comprises the compound of Chemical Formula 1.

15. The organic light emitting device of claim 10, further comprising one, two or more layers selected from the group consisting of a hole injection layer, a hole transfer layer, an electron transfer layer, an electron injection layer, an electron blocking layer and a hole blocking layer.

* * * * *